US008106026B2

(12) United States Patent
Nabel et al.

(10) Patent No.: US 8,106,026 B2
(45) Date of Patent: Jan. 31, 2012

(54) DEVELOPMENT OF A PREVENTIVE VACCINE FOR FILOVIRUS INFECTION IN PRIMATES

(75) Inventors: Gary J. Nabel, Washington, DC (US); Zhi-yong Yang, Potomac, MD (US); Nancy Sullivan, Kensington, MD (US); Anthony Sanchez, Lilburn, GA (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 185 days.

(21) Appl. No.: 12/612,579

(22) Filed: Nov. 4, 2009

(65) Prior Publication Data

US 2010/0297171 A1 Nov. 25, 2010

Related U.S. Application Data

(62) Division of application No. 10/491,121, filed as application No. PCT/US02/30251 on Sep. 24, 2002, now Pat. No. 7,635,688.

(60) Provisional application No. 60/326,476, filed on Oct. 1, 2001.

(51) Int. Cl.

| | |
|---|---|
| ***A61K 31/70*** | (2006.01) |
| ***A61K 49/00*** | (2006.01) |
| ***A61K 48/00*** | (2006.01) |
| ***A01N 65/00*** | (2009.01) |
| ***C12N 5/00*** | (2006.01) |
| ***C12N 15/00*** | (2006.01) |
| ***C07H 21/02*** | (2006.01) |

(52) U.S. Cl. ......... 514/44; 424/93.1; 424/93.2; 424/9.2; 435/320.1; 435/325; 435/455; 536/23.1

(58) Field of Classification Search ........................ None
See application file for complete search history.

(56) References Cited

U.S. PATENT DOCUMENTS

| | | | |
|---|---|---|---|
| 6,171,596 | B1 | 1/2001 | Earl et al. |
| 6,200,959 | B1 | 3/2001 | Haynes et al. |

FOREIGN PATENT DOCUMENTS

| | | |
|---|---|---|
| WO | WO 97/42320 | 11/1997 |
| WO | WO 99/32147 | 7/1999 |
| WO | WO 01/16183 | 3/2001 |

OTHER PUBLICATIONS

Aoki, K. et al. "Efficient generation of recombinant adenoviral vectors by Cre-lox recombination in vitro," 1999, Mol. Med. 5:224-231.
Australian Patent Office Communication dated Nov. 21, 2006, pursuant to Australia Patent Application No. 2005244541.
Australian Patent Office Communication dated Oct. 25, 2006, pursuant to Australia Patent Application No. 2002327049.
Baize, "Single shot against Ebola and Marburg virus," 2005, Nature Med., 11(7); 720-721.
Baize, S. et al., "Defective humoral responses and extensive intravascular apoptosis are associated with fatal outcome in Ebola virus-infected patients," 1999, Nature Med., 5: 423-426.
Bray, M. et al., "A mouse model for evaluation of prophylaxis and therapy of ebola hemorrhagic fever," 1998, J. infect. Dis. 178: 651-661.
Connolly, B.M. et al., "Pathogenesis of experimental Ebola virus infection in guinea pigs," 1998, J. infect Disc. 179, S203-S217.
Davis, A.R. et al., "Expression of hepatitis B surface antigen with a recombinant adenovirus," 1985, PNAS USA, 82, 7560-7564.
Feldmann, H. et al. "Characterization of filoviruses based on differences in structure and antigenicity fo the virion glycoprotein," 1994, Virology, 199, 469-473.
Fisher-Hoch, S.P. et al., "Pathophysiology of Shock and Hemorrhage in a Fulminating Viral Infection (Ebola)," 1985, J. Infect. Dis., 152, 887-894.
Geisbert, T.W. et al., "Evaluation in nonhuman primates or vaccines against Ebola virus," 2002, 8(5): 503-507.
Hampton, "Vaccines Against Ebola and Marburg Viruses Show Promise in Prime Studies," 2005, JAMA 294(2):163-164.
Hanke, T. et al.,"Enhancement of MHC class I-restricted peptide-specific T cell induction by a DNA prime/MVA boost vaccination regime," 1998, Vaccine, 16, 439-445.
Kiley, M.P. et al., "Ebola virus: identification of virion structural proteins," 1980, J. Gen. Virol., 49, 33-341.
Kreig, A.M. et al., "CpG motifs in bacterial DNA trigger direct B-cell activation," 1995, Nature, 374, 546-549.
Ksiazek, T.G. et al., "Enzyme immunosorbent assay for Ebola virus antigens in tissues of infected primates," 1992, J. Clin. Microbiol., 30, 947-950.
Letvin, N.L. et al., "Potent, protective anti-HIV immune responses generated by bimodal HIV envelope DNA plus protein vaccination," 1997, PNAS USA, 94, 9378-9383.
Maryuama, T. et al., "Ebola virus can be effectively neutralized by antibody produced in natural human infection," 1999, J. Virol. 73, 6024-6030.
Natuk, R.J. et al., "Adenovirus-human immunodeficiency virus (HIV) envelope recombinant vaccines elicit high-titered HIV-neutralizing antibodies in the dog model," 1992, PNAS USA, 89: 7777-7781.
Ohno, T. et al., "Gene therapy for vascular smooth muscle cell proliferation after arterial injury," 1994, Science, 265, 781-784.
Pushko, P. et al., "Individual and bivalent vaccines based on alphavirus replicons protect guinea pigs against infection with Lassa and Ebola viruses," 2001, J. Virol., 75(23): 11677-11685. Robinson, H.L. et al. "Neutralizing antibody-independent containment of immunodeficiency virus challenges by DNA priming and recombinant pox virus booster immunizations," 1999, Nature Med. 5:526-534.
Sanchez A. et al. "Biochemical analysis of the secreted and virion glycoproteins of Ebola virus" 1998, J. Virol. 72:6442-6447.
Sanchez, A. et al. "The virion glycoproteins of Ebola viruses are encoded in two reading frames and are expressed through transcriptional editing," 1996, PNAS USA 93:3602-3607.
Sato, Y. et al. "Immunostimulatory DNA sequences necessary for effective intradermal gene immunization," 1996, Science 273:352-354.

(Continued)

*Primary Examiner* — Sumesh Kaushal
(74) *Attorney, Agent, or Firm* — Kilpatrick Townsend & Stockton LLP

(57) ABSTRACT

The present invention relates generally to viral vaccines and, more specifically, to filovirus vaccines and methods of eliciting an immune response against a filovirus or disease caused by infection with filovirus.

9 Claims, 51 Drawing Sheets

OTHER PUBLICATIONS

Schneider, J. et al. "Enhanced immunogenicity for CD8 + T cell induction and complete protective efficacy of malaria DNA vaccination by boosting with modified vaccinia virus Ankara," 1998, Nature Med. 4:397-402.

Sedegah, M. et al. "Boosting with recombinant vaccinia increases immunogenicity and protective efficacy of malaria DNA vaccine," 1998, PNAS USA 95:7648-7653.

Sedegah, M. et al. "Protection against malaria by immunization with plasmid DNA encoding circumsporozoite protein," 1994, PNAS USA 91:9866-9870.

Sullivan, N.J. et al. "Ebola virus pathogenesis and vaccine development" 2000, Symposium on Marburg and Ebola Viruses, Marburg, Germany, Oct. 1-4, Abstract 23, p. 35.

Sullivan, N.J. et al., "Accelerated vaccination for Ebola virus haemorrhagic fever in non-human primates," 2003, 424: 681-684.

Sullivan, N.J. et al., "Development of a preventive vaccine for Ebola virus infection in primates," 2000, Nature, 408: 605-609.

Tang, D.C. et al. "Genetic immunization is a simple method for eliciting an immune response," 1992, Nature 356:152-154.

Ulmer, J.B. et al. "Heterologous protection against influenza by injection of DNA encoding a viral protein," 1993, Science 259:1745-1749.

Vanderzanden, L. et al. "DNA vaccines expressing either the GP or NP genes of Ebola virus protect mice from lethal challenge," 1998, Virology 246:134-144.

Wang, B. et al. "Gene inoculation generates immune responses against human immunodeficiency virus type 1," 1993, PNAS USA 90:4156-4160.

Wilson, J. et al. "Epitopes involved in antibody-mediated protection from Ebola virus," 2000, Science 287:1664-1666.

Xiang, Z.Q. et al. 1996 "A replication-defective human adenovirus recombinant serves as a highly efficacious vaccine carrier," Virology 219:220-227.

Xu, L. et al. "Immunization for Ebola virus infection," 1998, Nature Med. 4:37-42.

Yang, Z. et al. "Distinct cellular interactions of secreted and transmembrane Ebola virus glycoproteins" 1998, Science 279:1034-1037.

Yang, Z. et al. "Identification of the Ebola virus glycoprotein as the main viral determinant of vascular cell cytotoxicity and injury" 2000, Nature Med. 6:886-889.

Yang, Z.Y. et al., "Overcoming immunity to a viral vaccine by DNA priming before vector boosting," 2003, J. Virol. 77(1): 799-803.

pVR1012-GP(Z)

- Dra III (6952)
- Xho I (6816)
- kanamycin resistance
- Pvu I (6420)
- Hind III (6296)
- Nde I (185)
- Msc I (248)
- Nde I (571)
- CMV enhancer
- Sac II (992)
- CMV IE 5' UTR
- Sph I (1092)
- CMV IE intron
- Hpa I (1755)
- Sal I (1875)
- Pml I (1882)
- Eco RV (1894)
- Not I (1899)
- Xba I (1906)
- Sal I (2081)
- Eco RV (2597)
- Ebola GP Zaire
- Bst XI (4492)
- bovine growth hormone poly A
- Kpn I (4405)
- Sph I (4377)
- Kpn I (4158)
- Bsp MI (3890)
- Bst XI (3780)
- Msc I (3623)

pVRC 6000
7154 bp pVR1012x/s Ebola GP(Z)

Dra III (6986)
Xho I (6850)
Xma I (6576)
Kan r
Pvu I (6454)
Hin d III (6330)
Nde I (185)
Nde I (571)
CMV enhancer
Nco I (697)
Sac II (992)
CMV IE 5' UTR
Sph I (1092)
CMV IE Intron
Hpa I (1755)
Nco I (1848)
Sal I (1875)
Pml I (1882)
Eco RV (1894)
Not I (1899)
Xba I (1906)
Sal I (2081)

VRC6001
7188 bp

Sfi I (4747)
TbGH
Sph I (4377)
Ebola GP (Z)
Eco RV (2597)

pVR1012-GP(Z) delta MUC

- Dra III (6422)
- Xho I (6286)
- kanamycin resistance
- Pvu I (5890)
- Hind III (5766)
- Nde I (185)
- Msc I (248)
- Nde I (571)
- CMV enhancer
- Sac II (992)
- CMV IE 5' UTR
- Sph I (1092)
- Bsp EI (1436)
- CMV IE Intron
- Hpa I (1755)
- Pst I (1865)
- Sal I (1875)
- Pml I (1882)
- Eco RV (1894)
- Not I (1899)
- Xba I (1906)
- Sal I (2081)
- Eco RV (2597)
- Ebola GP Zaire delta MUC
- Earl/Bfal
- Msc I (3093)
- Pst I (3193)
- Bst XI (3250)
- Bsp EI (3314)
- Bsp MI (3360)
- Kpn I (3628)
- Sph I (3847)
- Kpn I (3875)
- bovine growth hormone poly A
- Bst XI (3962)

pVRC 6002
6624 bp pVR1012-GP(Z) delta MUC delta FUR pVRC 6003
6561 bp

- Dra III (6359)
- Xho I (6223)
- kanamycin resistance
- Pvu I (5827)
- Hin dIII (5703)
- Nde I (185)
- Nde I (571)
- CMV enhancer
- Sac II (992)
- CMV IE 5' UTR
- Sph I (1092)
- CMV IE Intron
- Hpa I (1755)
- Pst I (1865)
- Sal I (1875)
- Pml I (1882)
- Bcl I (1886)
- Eco RV (1894)
- Not I (1899)
- Xba I (1906)
- Sal I (2081)
- Eco RV (2597)
- Ebola GP Zaire delta MUC, delta FUR
- Earl/3436bp
- Pst I (3130)
- Bcl I (3215)
- Kpn I (3565)
- Sph I (3784)
- Kpn I (3812)
- bovine growth hormone poly A pVR1012-GP(Z) delta GP2 delta C-term B

Plasmid map of pVRC 6006 (7044 bp) showing the following features and restriction sites:

- Nde I (185)
- Msc I (248)
- Nde I (571)
- CMV enhancer
- Sac II (992)
- CMV IE 5' UTR
- Sph I (1092)
- Bsp EI (1436)
- CMV IE Intron
- Hpa I (1755)
- Pst I (1865)
- Sal I (1875)
- Pml I (1882)
- Bcl I (1886)
- Eco RV (1894)
- Not I (1899)
- Xba I (1906)
- Sal I (2081)
- Eco RV (2597)
- Ebola GP Zaire(BstXI/BspMI)
- Bsp EI (3088)
- Bcl I (3414)
- Msc I (3623)
- BstXI/BspMI
- Bsp MI (3780)
- Kpn I (4048)
- Sph I (4267)
- Kpn I (4295)
- bovine growth hormone poly A
- Bst XI (4382)
- Hind III (6186)
- Pvu I (6310)
- kanamycin resistance
- Xho I (6706)
- Dra III (6842)

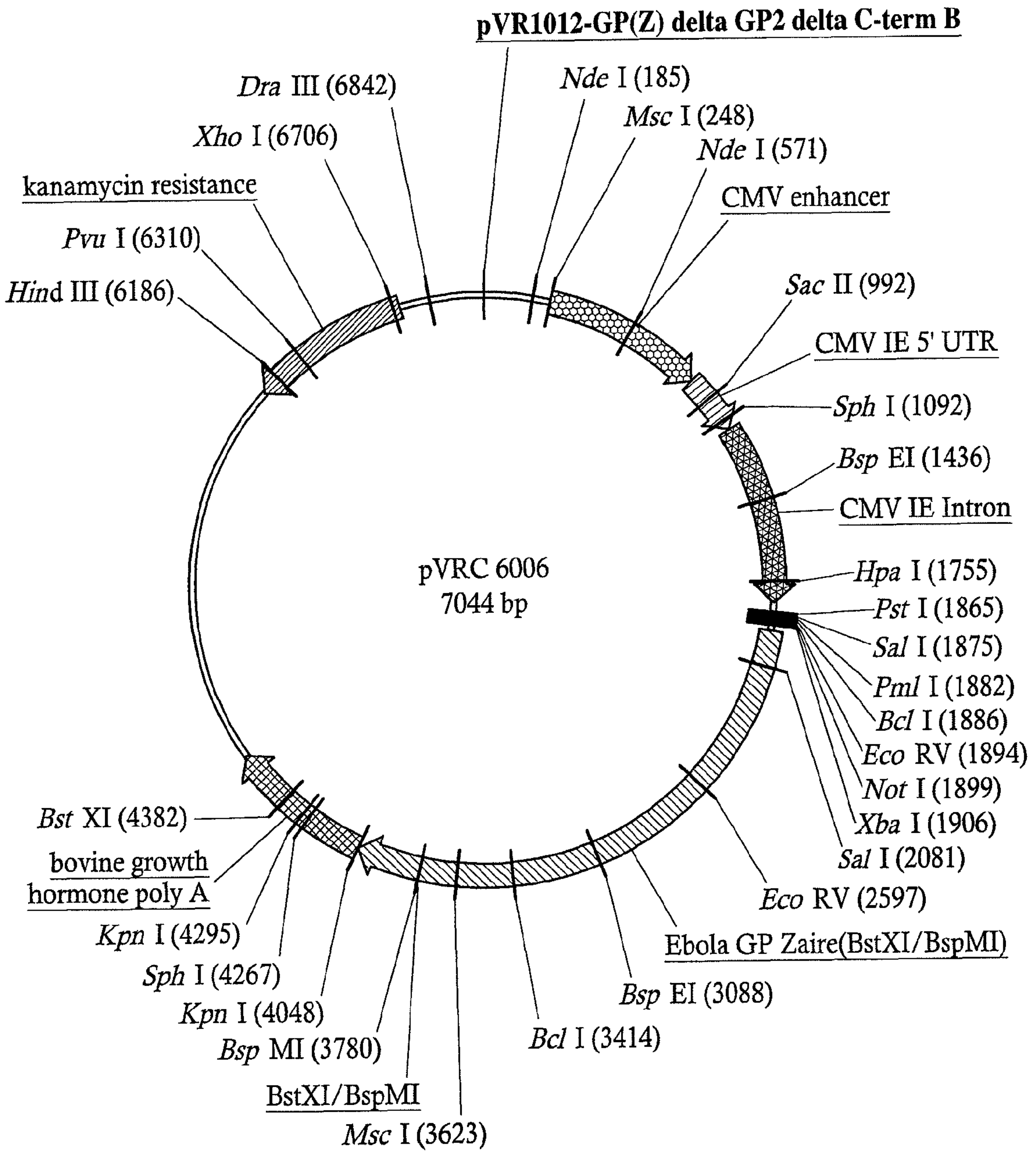

FIG. 7 pAdApt Ebola GP(R) (dTM)

Plasmid map of VRC6110 (8131 bp) with the following features labeled:
- Ad5(bp1-454)
- Nde I (843)
- CMV enhancer
- Pml I (1279)
- Bcl I (1283)
- Eco RV (1291)
- Bcl I (1425)
- Nde I (2001)
- Ebola GP(Reston)(dTM)
- Pvu I (2784)
- Kpn I (3079)
- Xba I (3238)
- Bovine Growth Hormone Poly A
- Kpn I (3494)
- LoxP
- Ad5(bp3511-6093)
- Kas I (5553)
- Nar I (5554)
- Xho I (5823)
- Pml I (6026)
- Amp
- Pvu I (7502)

pVR1012-GP(S)

- Dra III (6880)
- Cla I (6653)
- kanamycin resistance
- Pvu I (6348)
- Hind III (6224)
- Nde I (185)
- Msc I (248)
- Nde I (571)
- CMV enhancer
- Sac II (992)
- CMV IE 5' UTR
- Bsp EI (1436)
- CMV IE Intron
- Hpa I (1755)
- Sal I (1875)
- Pml I (1882)
- Bcl I (1886)
- Not I (1899)
- Not I (1928)
- Xmn I (4650)
- bovine growth hormone poly A
- Kpn I (4333)
- Xba I (4077)
- Hpa I (3491)
- Ebola Glycoprotein Sudan subtype (#U28134)

pVRC 6200
7082 bp pVR1012-GP(S) delta TM pVRC 6202
6940 bp

- Dra III (6738)
- Cla I (6511)
- kanamycin resistance
- Pvu I (6206)
- Hind III (6082)
- Nde I (185)
- Msc I (248)
- Nde I (571)
- CMV enhancer
- Sac II (992)
- CMV IE 5' UTR
- Bsp EI (1436)
- CMV IE Intron
- Hpa I (1755)
- Sal I (1875)
- Not I (1903)
- Eco RV (1922)
- Eco RV (2191)
- Ebola Glycoprotein Sudan Subtype (#U28134)
- Hpa I (3466)
- Kpn I (4191)
- bovine growth hormone poly A
- Xmn I (4508)

pVR1012-GP(IC)

pVRC 6300
7002 bp

- Dra III (6800)
- Nde I (185)
- Xho I (6664)
- Msc I (248)
- Cla I (6573)
- Nde I (571)
- kanamycin resistance
- CMV enhancer
- Pvu I (6268)
- Hind III (6144)
- Sac II (992)
- CMV IE 5' UTR
- Sph I (1092)
- Bsp EI (1436)
- CMV IE Intron
- Hpa I (1755)
- Pst I (1865)
- Sal I (1875)
- Pml I (1882)
- Eco RV (1894)
- Not I (1899)
- Xba I (1906)
- Xho I (2665)
- Ebola Glycoprotein Ivory Coast subtype (#U28006)
- Bst XI (2982)
- Bsp MI (3485)
- Msc I (3619)
- Xba I (3997)
- Bgl II (4018)
- Sph I (4225)
- Kpn I (4253)
- bovine growth hormone poly A
- Bst XI (4340)
- Xmn I (4570)

pVR1012x/s Ebola GP(IC)

- Dra III (6834)
- Xho I (6698)
- Cla I (6607)
- Xma I (6424)
- Kan r
- Pvu I (6302)
- Hin d III (6178)
- Nde I (185)
- Nde I (571)
- CMV enhancer
- Sac II (992)
- CMV IE 5' UTR
- Sph I (1092)
- CMV IE Intron
- Hpa I (1755)
- Pst I (1865)
- Sal I (1875)
- Pml I (1882)
- Eco RV (1894)
- Not I (1899)
- Xba I (1906)
- Eco RI (1910)
- Xho I (2665)
- Ebola GP(IC)
- Sfi I (4595)
- TbGH
- Sph I (4225)
- Bgl II (4018)
- Xba I (3997)
- Eco RI (3993)

VRC6301
7036 bp pVR1012x/s Ebola GP(IC)(dTM)

VRC6303
6889 bp

- Nde I (185)
- Nde I (571)
- CMV Enhancer
- Sac II (992)
- CMV IE 5' UTR
- Sph I (1092)
- CMV IE Intron
- Hpa I (1755)
- Pst I (1865)
- Sal I (1875)
- Pml I (1882)
- Bam HI (2536)
- Xho I (2645)
- Ebola GP(Ivory Coast)(dTM)
- Bam HI (3397)
- Bgl II (3871)
- Sph I (4078)
- Kpn I (4106)
- Bovine Growth Hormone Poly A
- Sfi I (4448)
- Hin d III (6031)
- Pvu I (6155)
- Kan
- Cla I (6460)
- Xho I (6551)
- Dra III (6687)

pVR1012x/s-sGP(IC)

pVRC 6351
7023 bp

- Nde I (185)
- Msc I (248)
- Nde I (571)
- CMV enhancer
- Sac II (992)
- CMV IE 5' UTR
- Sph I (1092)
- Bsp EI (1436)
- CMV IE Intron
- Hpa I (1755)
- Pst I (1865)
- Sal I (1875)
- Pml I (1882)
- Eco RV (1894)
- Not I (1899)
- Xba I (1906)
- Xho I (2665)
- Ebola Secreted Glycoprotein Ivory Coast (#U28006)
- Bst XI (2982)
- Bsp MI (3485)
- Msc I (3619)
- Xba I (3997)
- Bgl II (4018)
- Sph I (4225)
- Kpn I (4253)
- bovine growth hormone poly A
- Bst XI (4340)
- Sfi I (4582)
- Hind III (6165)
- Pvu I (6289)
- kanamycin resistance
- Cla I (6594)
- Xho I (6685)
- Dra III (6821)

pVR1012-NP pVRC 6400
7295 bp

- Dra III (7093)
- Xho I (6957)
- Cla I (6866)
- kanamycin resistance
- Pvu I (6561)
- Hind III (6437)
- CMV enhancer
- Sac II (992)
- CMV IE 5' UTR
- Bsp EI (1436)
- CMV IE Intron
- Pvu II (1701)
- Hpa I (1755)
- Pst I (1865)
- Sal I (1875)
- Pml I (1882)
- Eco RV (1894)
- Not I (1899)
- Xba I (1906)
- BamH I (1921)
- Cla I (1930)
- Kas I (1970)
- Nar I (1971)
- Bgl II (2008)
- Bsp MI (2010)
- Bsp MI (2115)
- Bst XI (2509)
- Ebola Nucleoprotein (#J04337)
- Xba I (3401)
- Kpn I (4546)
- Xmn I (4128)
- bovine growth hormone poly A
- Bst XI (4633)
- Xmn I (4863)

pVR1012x/s Ebola-NP

- Dra III (7127)
- Xho I (6991)
- Cla I (6900)
- Xma I (6717)
- Kan r
- Pvu I (6595)
- Hin d III (6471)
- CMV enhancer
- Sac II (992)
- CMV IE 5' UTR
- CMV IE Intron
- Pvu II (1701)
- Hpa I (1755)
- Pst I (1865)
- MCS
- Sal I (1875)
- Pml I (1882)
- Eco RV (1894)
- Not I (1899)
- Xba I (1906)
- Bam H I (1921)
- Cla I (1930)
- Bgl II (2008)

VRC6401
7329 bp

- Sfi I (4888)
- TbGH
- Untranslated NP
- Ebola NP
- Xba I (3401)

pAdApt Ebola GP(S)(dTM)

- Ad5(1-454)
- Nde I (843)
- CMV Enhancer
- Sal I (1272)
- Pml I (1279)
- Bcl I (1283)
- Not I (1296)
- Eco RI (1323)
- Xho I (1558)
- Ebola GP(Sudan)(dTM)
- Eco RI (2445)
- Hpa I (2859)
- TbGH
- LoxP
- Kpn I (3584)
- Ad5(3511-6093)
- Kas I (5643)
- Nar I (5644)
- Xho I (5913)
- Pml I (6116)
- Sal I (6219)
- Amp
- Pvu I (7592)
- Xmn I (7821)

VRC6602
8221 bp pVR1012x/s Marburg GP(dTM)

Dra III (6803)
Xho I (6667)
Cla I (6576)
Kan
Pvu I (6271)
Hin d III (6147)
CMV Enhancer
Sac II (992)
CMV IE 5' UTR
Sph I (1092)
CMV IE/Intron
Pvu II (1701)
Hpa I (1755)
Pst I (1865)
Sal I (1875)
Pml I (1882)
Bcl I (1886)
Eco RV (1894)
Not I (1899)
Xba I (1906)
Xmn I (1992)
Dra III (2197)
Bam H I (2328)
Kpn I (2592)
Marburg GP(dTM)
Sfi I (4564)
Bovine Growth Hormone Poly A
Kpn I (4222)
Sph I (4194)
Bgl II (3987)
Pst I (3706)

VRC6702
7005 bp pVR1012x/s Lassa GP(dTM)

VRC6801
6258 bp

- Dra III (6056)
- Xho I (5920)
- Cla I (5829)
- Kan
- Pvu I (5524)
- Hin d III (5400)
- Sfi I (3817)
- Bovine Growth Poly A
- Sph I (3460)
- Bgl II (3253)
- Bam H I (3247)
- Nde I (185)
- Nde I (571)
- CMV Enhancer
- Sac II (992)
- CMV IE 5' UTR
- Sph I (1092)
- CMV IE/Intron
- Pvu II (1701)
- Hpa I (1755)
- Pst I (1865)
- Sal I (1875)
- Pml I (1882)
- Eco RV (1894)
- Not I (1899)
- Xba I (1906)
- Eco RI (1950)
- Lassa GP(dTM)(Strain LP)
- Dra III (2785)
- Pvu II (2848)

*PaeR7I* (6530)
*Xho*I (6530)
*Nru*I (6475)
*Bsp*DI (6439)
*Cla*I (6439)
*Sma*I (6258)
*Xma*I (6256)
kanamycin resistance
*Ssp*I (6207)
*Pvu*I (6134)
*Hin*dIII (6010)

*Stu*I (5508)
*Aat*I (5508)

pVR1012x/s
*Spe*I (336)
CMV enhancer
*Sna*BI (677)
*Ecl*136II (903)
*Sac*I (905)
*Sac*II (992)
*Eag*I (992)
*Ecl*XI (992)
*Ksp*I (992)
*Xma*III (992)
CMV IE 5' UTR
*Acc*III (1436)
*Bse*AI (1436)
*Bsp*EI (1436)
*Mro*I (1436)
*Sap*I (1454)
CMV IE intron
*Afl*II (1670)
*Bfr*I (1670)
*Hpa*I (1755)
multiple cloning site
*Sal*I (1875)
*Acc*I (1876)
*Eco*RV (1883)

pVR1012x/s Ebola GP(Z) delta TM/h (P87666)
6868 bp

*Sfi*I (4427)
bovine growth hormone poly A
*Bgl*II (3850)
*Eco*RI (3844)
*Pma*CI (3840)
*Bbr*PI (3840)
*Pml*I (3840)
*Apa*I (3708)
*Bsp*120I (3704)
*Bam*H I (3224)
*Xba*I (2628)
*Xmn*I (2466)
*Asp*700 (2466)
*Bcg*I (2399)
Ebola GP(Z) (P87666)/h

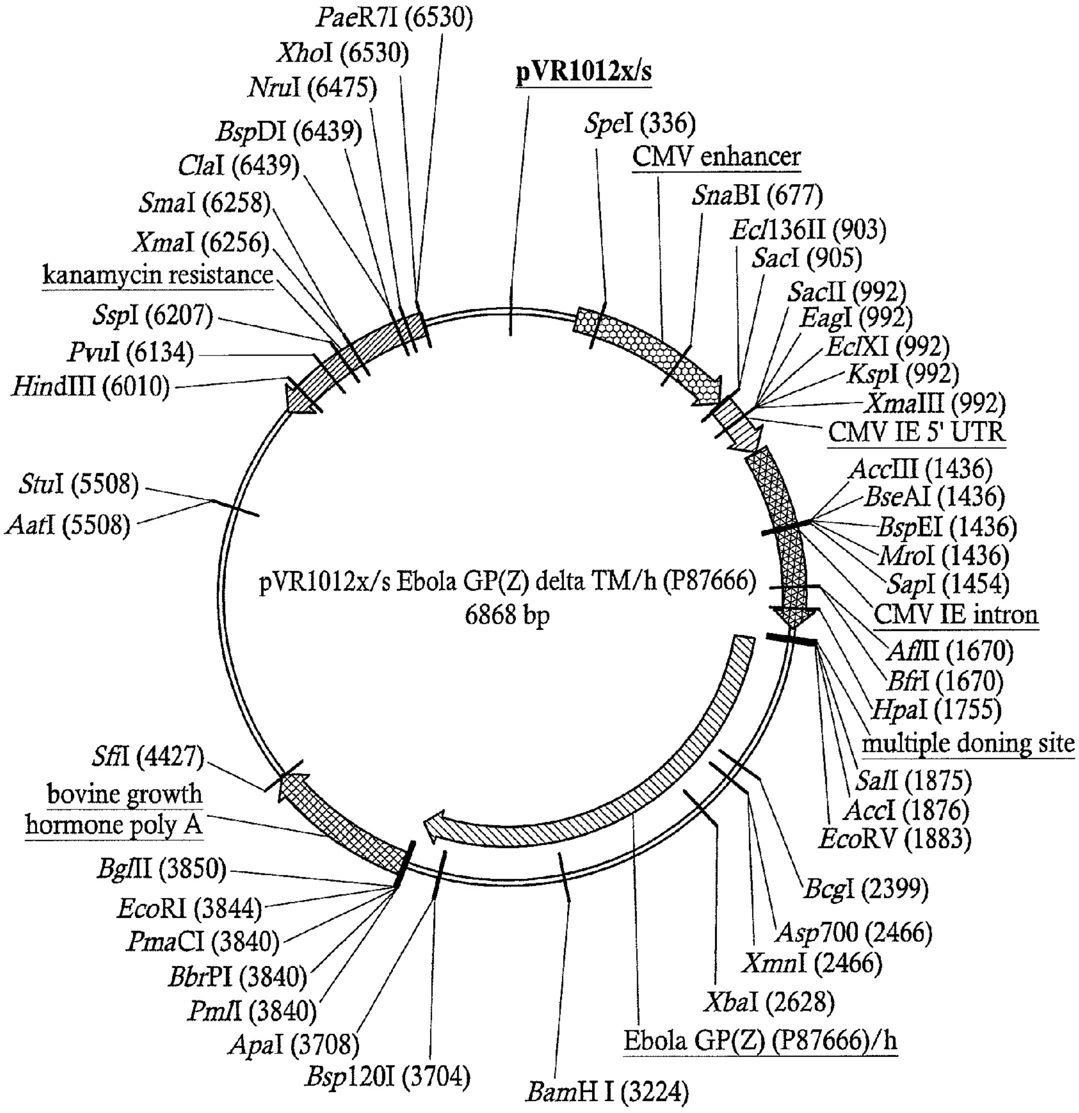

FIG. 38 pVR1012x/s Marburg (codon optimized)

VRC6703
6902 bp

- Nde I (185)
- Nde I (571)
- CMV enhancer
- Nco I (697)
- Sac II (992)
- CMV IE 5' UTR
- CMV IE Intron
- Pvu II (1701)
- Hpa I (1755)
- Nco I (1848)
- Sal I (1875)
- Pml I (1882)
- Eco RV (1894)
- Not I (1899)
- Xba I (1906)
- Eco RV (1914)
- Hpa I (2433)
- Marburg (codon optimized)
- Dra III (3207)
- Pml I (3874)
- Bam HI (3878)
- Bgl II (3884)
- bovine growth hormone poly A
- Sfi I (4461)
- Hin d III (6044)
- Pvu I (6168)
- kanamycin resistance
- Xma I (6290)
- Cla I (6473)
- Xho I (6564)
- Dra III (6700)

A
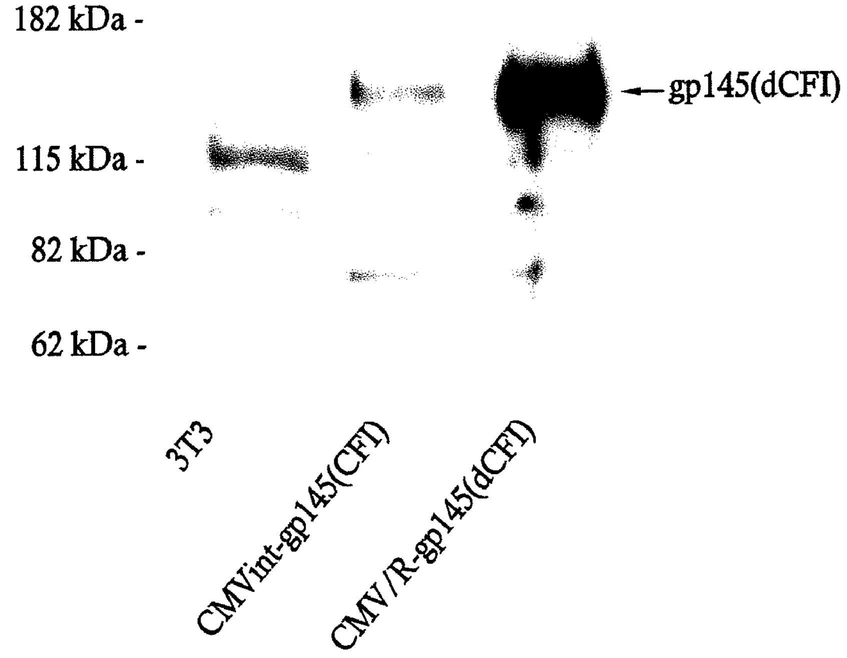
B
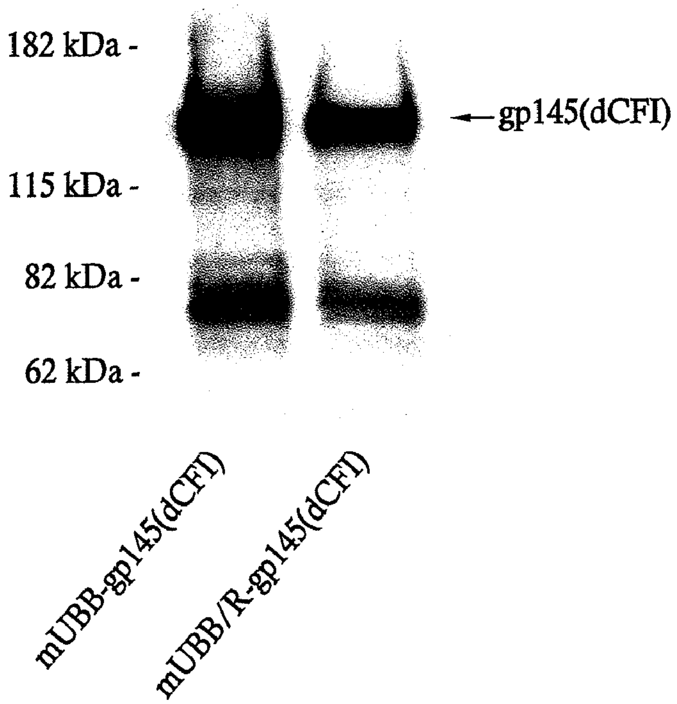
FIG. 50

SEQUENCE LISTING

<160> NUMBER OF SEQ ID NOS: 52

<210> SEQ ID NO 1
<211> LENGTH: 7154
<212> TYPE: DNA
<213> ORGANISM: Artificial Sequence
<220> FEATURE:
<223> OTHER INFORMATION: Synthetic Construct pVR1012 -GP(Z)

<400> SEQUENCE: 1
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcagattgg 240
ctattggcca ttgcatacgt tgtatccata tcataatatg tacatttata ttggctcatg 300
tccaacatta ccgccatgtt gacattgatt attgactagt tattaatagt aatcaattac 360
ggggtcatta gttcatagcc catatatgga gttccgcgtt acataactta cggtaaatgg 420
cccgcctggc tgaccgccca acgacccccg cccattgacg tcaataatga cgtatgttcc 480
catagtaacg ccaataggga ctttccattg acgtcaatgg gtggagtatt tacggtaaac 540
tgcccacttg gcagtacatc aagtgtatca tatgccaagt acgcccccta ttgacgtcaa 600
tgacggtaaa tggcccgcct ggcattatgc ccagtacatg accttatggg actttcctac 660
ttggcagtac atctacgtat tagtcatcgc tattaccatg gtgatgcggt tttggcagta 720
catcaatggg cgtggatagc ggtttgactc acggggattt ccaagtctcc accccattga 780
cgtcaatggg agtttgtttt ggcaccaaaa tcaacgggac tttccaaaat gtcgtaacaa 840
ctccgcccca ttgacgcaaa tgggcggtag gcgtgtacgg tgggaggtct atataagcag 900
agctcgttta gtgaaccgtc agatcgcctg gagacgccat ccacgctgtt ttgacctcca 960
tagaagacac cgggaccgat ccagcctccg cggccgggaa cggtgcattg gaacgcggat 1020
tccccgtgcc aagagtgacg taagtaccgc ctatagactc tataggcaca cccctttggc 1080
tcttatgcat gctatactgt ttttggcttg gggcctatac acccccgctt ccttatgcta 1140
taggtgatgg tatagcttag cctataggtg tgggttattg accattattg accactcccc 1200
tattggtgac gatactttcc attactaatc cataacatgg ctctttgcca caactatctc 1260
tattggctat atgccaatac tctgtccttc agagactgac acggactctg tatttttaca 1320
ggatggggtc ccatttatta tttacaaatt cacatataca acaacgccgt cccccgtgcc 1380

-continued

```
cgcagttttt attaaacata gcgtgggatc tccacgcgaa tctcgggtac gtgttccgga   1440

catgggctct tctccggtag cggcggagct tccacatccg agccctggtc ccatgcctcc   1500

agcggctcat ggtcgctcgg cagctccttg ctcctaacag tggaggccag acttaggcac   1560

agcacaatgc ccaccaccac cagtgtgccg cacaaggccg tggcggtagg gtatgtgtct   1620

gaaaatgagc gtggagattg ggctcgcacg gctgacgcag atggaagact taaggcagcg   1680

gcagaagaag atgcaggcag ctgagttgtt gtattctgat aagagtcaga ggtaactccc   1740

gttgcggtgc tgttaacggt ggagggcagt gtagtctgag cagtactcgt tgctgccgcg   1800

cgcgccacca gacataatag ctgacagact aacagactgt tcctttccat gggtcttttc   1860

tgcagtcacc gtcgtcgaca cgtgtgatca gatatcgcgg ccgctctaga ccaggccctg   1920

gatcgatcca acaacacaat gggcgttaca ggaatattgc agttacctcg tgatcgattc   1980

aagaggacat cattctttct ttgggtaatt atccttttcc aaagaacatt ttccatccca   2040

cttggagtca tccacaatag cacattacag gttagtgatg tcgacaaact agtttgtcgt   2100

gacaaactgt catccacaaa tcaattgaga tcagttggac tgaatctcga agggaatgga   2160

gtggcaactg acgtgccatc tgcaactaaa agatggggct tcaggtccgg tgtcccacca   2220

aaggtggtca attatgaagc tggtgaatgg gctgaaaact gctacaatct tgaaatcaaa   2280

aaacctgacg ggagtgagtg tctaccagca gcgccagacg ggattcgggg cttccccccgg   2340

tgccggtatg tgcacaaagt atcaggaacg ggaccgtgtg ccggagactt tgccttccat   2400

aaagagggtg ctttcttcct gtatgatcga cttgcttcca cagttatcta ccgaggaacg   2460

actttcgctg aaggtgtcgt tgcatttctg atactgcccc aagctaagaa ggacttcttc   2520

agctcacacc ccttgagaga gccggtcaat gcaacggagg acccgtctag tggctactat   2580

tctaccacaa ttagatatca ggctaccggt tttggaacca atgagacaga gtacttgttc   2640

gaggttgaca atttgaccta cgtccaactt gaatcaagat tcacaccaca gtttctgctc   2700

cagctgaatg agacaatata tacaagtggg aaaaggagca ataccacggg aaaactaatt   2760

tggaaggtca accccgaaat tgatacaaca atcggggagt gggccttctg ggaaactaaa   2820

aaaaacctca ctagaaaaat tcgcagtgaa gagttgtctt tcacagttgt atcaaacgga   2880

gccaaaaaca tcagtggtca gagtccggcg cgaacttctt ccgacccagg gaccaacaca   2940

acaactgaag accacaaaat catggcttca gaaaattcct ctgcaatggt tcaagtgcac   3000

agtcaaggaa gggaagctgc agtgtcgcat ctaacaaccc ttgccacaat ctccacgagt   3060

ccccaatccc tcacaaccaa accaggtccg gacaacagca cccataatac acccgtgtat   3120

aaacttgaca tctctgaggc aactcaagtt gaacaacatc accgcagaac agacaacgac   3180

agcacagcct ccgacactcc ctctgccacg accgcagccg gacccccaaa agcagagaac   3240

accaacacga gcaagagcac tgacttcctg gaccccgcca ccacaacaag tccccaaaac   3300

cacagcgaga ccgctggcaa caacaacact catcaccaag ataccggaga agagagtgcc   3360

agcagcggga agctaggctt aattaccaat actattgctg gagtcgcagg actgatcaca   3420

ggcgggagaa gaactcgaag agaagcaatt gtcaatgctc aacccaaatg caaccctaat   3480

ttacattact ggactactca ggatgaaggt gctgcaatcg gactggcctg gataccatat   3540

ttcgggccag cagccgaggg aatttacata gaggggctaa tgcacaatca agatggttta   3600

atctgtgggt tgagacagct ggccaacgag acgactcaag ctcttcaact gttcctgaga   3660

gccacaactg agctacgcac cttttcaatc ctcaaccgta aggcaattga tttcttgctg   3720

cagcgatggg gcggcacatg ccacattctg ggaccggact gctgtatcga accacatgat   3780
```

tggaccaaga acataacaga caaaattgat cagattattc atgattttgt tgataaaacc 3840
cttccggacc agggggacaa tgacaattgg tggacaggat ggagacaatg gataccggca 3900
ggtattggag ttacaggcgt tgtaattgca gttatcgctt tattctgtat atgcaaattt 3960
gtcttttagt tttcttcag attgcttcat ggaaaagctc agcctcaaat caatgaaacc 4020
aggatttaat tatatggatt acttgaatct aagattactt gacaaatgat aatataatac 4080
actggagctt taaacatagc caatgtgatt ctaactcctt taaactcaca gttaatcata 4140
aacaaggttt gaggtaccga gctcgaattg atctgctgtg ccttctagtt gccagccatc 4200
tgttgtttgc ccctcccccg tgccttcctt gaccctggaa ggtgccactc ccactgtcct 4260
ttcctaataa aatgaggaaa ttgcatcgca ttgtctgagt aggtgtcatt ctattctggg 4320
gggtggggtg gggcaggaca gcaaggggga ggattgggaa gacaatagca ggcatgctgg 4380
ggatgcggtg ggctctatgg gtacccaggt gctgaagaat tgacccggtt cctcctgggc 4440
cagaaagaag caggcacatc cccttctctg tgacacaccc tgtccacgcc cctggttctt 4500
agttccagcc ccactcatag gacactcata gctcaggagg gctccgcctt caatcccacc 4560
cgctaaagta cttggagcgg tctctccctc cctcatcagc ccaccaaacc aaacctagcc 4620
tccaagagtg ggaagaaatt aaagcaagat aggctattaa gtgcagaggg agagaaaatg 4680
cctccaacat gtgaggaagt aatgagagaa atcatagaat ttcttccgct tcctcgctca 4740
ctgactcgct gcgctcggtc gttcggctgc ggcgagcggt atcagctcac tcaaaggcgg 4800
taatacggtt atccacagaa tcaggggata acgcaggaaa gaacatgtga gcaaaaggcc 4860
agcaaaaggc caggaaccgt aaaaaggccg cgttgctggc gtttttccat aggctccgcc 4920
cccctgacga gcatcacaaa aatcgacgct caagtcagag gtggcgaaac ccgacaggac 4980
tataaagata ccaggcgttt ccccctggaa gctccctcgt gcgctctcct gttccgaccc 5040
tgccgcttac cggatacctg tccgcctttc tcccttcggg aagcgtggcg ctttctcata 5100
gctcacgctg taggtatctc agttcggtgt aggtcgttcg ctccaagctg ggctgtgtgc 5160
acgaaccccc cgttcagccc gaccgctgcg ccttatccgg taactatcgt cttgagtcca 5220
acccggtaag acacgactta tcgccactgg cagcagccac tggtaacagg attagcagag 5280
cgaggtatgt aggcggtgct acagagttct tgaagtggtg gcctaactac ggctacacta 5340
gaagaacagt atttggtatc tgcgctctgc tgaagccagt taccttcgga aaaagagttg 5400
gtagctcttg atccggcaaa caaaccaccg ctggtagcgg tggttttttt gtttgcaagc 5460
agcagattac gcgcagaaaa aaaggatctc aagaagatcc tttgatcttt tctacggggt 5520
ctgacgctca gtggaacgaa aactcacgtt aagggatttt ggtcatgaga ttatcaaaaa 5580
ggatcttcac ctagatcctt ttaaattaaa aatgaagttt taaatcaatc taaagtatat 5640
atgagtaaac ttggtctgac agttaccaat gcttaatcag tgaggcacct atctcagcga 5700
tctgtctatt tcgttcatcc atagttgcct gactcggggg gggggggcgc tgaggtctgc 5760
ctcgtgaaga aggtgttgct gactcatacc aggcctgaat cgccccatca tccagccaga 5820
aagtgaggga gccacggttg atgagagctt tgttgtaggt ggaccagttg gtgattttga 5880
acttttgctt tgccacggaa cggtctgcgt tgtcgggaag atgcgtgatc tgatccttca 5940
actcagcaaa agttcgattt attcaacaaa gccgccgtcc cgtcaagtca gcgtaatgct 6000
ctgccagtgt tacaaccaat taaccaattc tgattagaaa aactcatcga gcatcaaatg 6060
aaactgcaat ttattcatat caggattatc aataccatat ttttgaaaaa gccgtttctg 6120
taatgaagga gaaaactcac cgaggcagtt ccataggatg gcaagatcct ggtatcggtc 6180
tgcgattccg actcgtccaa catcaataca acctattaat ttcccctcgt caaaaataag 6240
gttatcaagt gagaaatcac catgagtgac gactgaatcc ggtgagaatg gcaaaagctt 6300
atgcatttct ttccagactt gttcaacagg ccagccatta cgctcgtcat caaaatcact 6360
cgcatcaacc aaaccgttat tcattcgtga ttgcgcctga gcgagacgaa atacgcgatc 6420
gctgttaaaa ggacaattac aaacaggaat cgaatgcaac cggcgcagga acactgccag 6480
cgcatcaaca atattttcac ctgaatcagg atattcttct aatacctgga atgctgtttt 6540
cccggggatc gcagtggtga gtaaccatgc atcatcagga gtacggataa aatgcttgat 6600
ggtcggaaga ggcataaatt ccgtcagcca gtttagtctg accatctcat ctgtaacatc 6660
attggcaacg ctacctttgc catgtttcag aaacaactct ggcgcatcgg gcttcccata 6720
caatcgatag attgtcgcac ctgattgccc gacattatcg cgagcccatt tatacccata 6780
taaatcagca tccatgttgg aatttaatcg cggcctcgag caagacgttt cccgttgaat 6840
atggctcata acaccccttg tattactgtt tatgtaagca gacagtttta ttgttcatga 6900
tgatatattt ttatcttgtg caatgtaaca tcagagattt tgagacacaa cgtggctttc 6960
cccccccccc cattattgaa gcatttatca gggttattgt ctcatgagcg gatacatatt 7020
tgaatgtatt tagaaaaata aacaaatagg ggttccgcgc acatttcccc gaaaagtgcc 7080
acctgacgtc taagaaacca ttattatcat gacattaacc tataaaaata ggcgtatcac 7140
gaggcccttt cgtc 7154

<210> SEQ ID NO 2
<211> LENGTH: 7188
<212> TYPE: DNA
<213> ORGANISM: Artificial Sequence
<220> FEATURE:
<223> OTHER INFORMATION: Synthetic Construct pVR1012x/s Ebola GP(Z)

<400> SEQUENCE: 2
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcagattgg 240
ctattggcca ttgcatacgt tgtatccata tcataatatg tacatttata ttggctcatg 300
tccaacatta ccgccatgtt gacattgatt attgactagt tattaatagt aatcaattac 360
ggggtcatta gttcatagcc catatatgga gttccgcgtt acataactta cggtaaatgg 420
cccgcctggc tgaccgccca acgacccccg cccattgacg tcaataatga cgtatgttcc 480
catagtaacg ccaataggga ctttccattg acgtcaatgg gtggagtatt tacggtaaac 540
tgcccacttg gcagtacatc aagtgtatca tatgccaagt acgcccccta ttgacgtcaa 600
tgacggtaaa tggcccgcct ggcattatgc ccagtacatg accttatggg actttcctac 660
ttggcagtac atctacgtat tagtcatcgc tattaccatg gtgatgcggt tttggcagta 720
catcaatggg cgtggatagc ggtttgactc acggggattt ccaagtctcc accccattga 780
cgtcaatggg agtttgtttt ggcaccaaaa tcaacgggac tttccaaaat gtcgtaacaa 840
ctccgcccca ttgacgcaaa tgggcggtag gcgtgtacgg tgggaggtct atataagcag 900
agctcgttta gtgaaccgtc agatcgcctg gagacgccat ccacgctgtt ttgacctcca 960
tagaagacac cgggaccgat ccagcctccg cggccgggaa cggtgcattg gaacgcggat 1020
tccccgtgcc aagagtgacg taagtaccgc ctatagactc tataggcaca cccctttggc 1080

-continued

```
tcttatgcat gctatactgt ttttggcttg gggcctatac acccccgctt ccttatgcta   1140
taggtgatgg tatagcttag cctataggtg tgggttattg accattattg accactcccc   1200
tattggtgac gatactttcc attactaatc cataacatgg ctctttgcca caactatctc   1260
tattggctat atgccaatac tctgtccttc agagactgac acggactctg tatttttaca   1320
ggatggggtc ccatttatta tttacaaatt cacatataca acaacgccgt cccccgtgcc   1380
cgcagttttt attaaacata gcgtgggatc tccacgcgaa tctcgggtac gtgttccgga   1440
catgggctct tctccggtag cggcggagct tccacatccg agccctggtc ccatgcctcc   1500
agcggctcat ggtcgctcgg cagctccttg ctcctaacag tggaggccag acttaggcac   1560
agcacaatgc ccaccaccac cagtgtgccg cacaaggccg tggcggtagg gtatgtgtct   1620
gaaaatgagc gtggagattg ggctcgcacg gctgacgcag atggaagact taaggcagcg   1680
gcagaagaag atgcaggcag ctgagttgtt gtattctgat aagagtcaga ggtaactccc   1740
gttgcggtgc tgttaacggt ggagggcagt gtagtctgag cagtactcgt tgctgccgcg   1800
cgcgccacca gacataatag ctgacagact aacagactgt tcctttccat gggtcttttc   1860
tgcagtcacc gtcgtcgaca cgtgtgatca gatatcgcgg ccgctctaga ccaggccctg   1920
gatcgatcca acaacacaat gggcgttaca ggaatattgc agttacctcg tgatcgattc   1980
aagaggacat cattctttct ttgggtaatt atccttttcc aaagaacatt ttccatccca   2040
cttggagtca tccacaatag cacattacag gttagtgatg tcgacaaact agtttgtcgt   2100
gacaaactgt catccacaaa tcaattgaga tcagttggac tgaatctcga agggaatgga   2160
gtggcaactg acgtgccatc tgcaactaaa agatggggct tcaggtccgg tgtcccacca   2220
aaggtggtca attatgaagc tggtgaatgg gctgaaaact gctacaatct tgaaatcaaa   2280
aaacctgacg ggagtgagtg tctaccagca gcgccagacg ggattcgggg cttccccccgg   2340
tgccggtatg tgcacaaagt atcaggaacg ggaccgtgtg ccggagactt tgccttccat   2400
aaagagggtg ctttcttcct gtatgatcga cttgcttcca cagttatcta ccgaggaacg   2460
actttcgctg aaggtgtcgt tgcatttctg atactgcccc aagctaagaa ggacttcttc   2520
agctcacacc ccttgagaga gccggtcaat gcaacggagg acccgtctag tggctactat   2580
tctaccacaa ttagatatca ggctaccggt tttggaacca atgagacaga gtacttgttc   2640
gaggttgaca atttgaccta cgtccaactt gaatcaagat tcacaccaca gtttctgctc   2700
cagctgaatg agacaatata tacaagtggg aaaaggagca ataccacggg aaaactaatt   2760
tggaaggtca accccgaaat tgatacaaca atcggggagt gggccttctg ggaaactaaa   2820
aaaaacctca ctagaaaaat tcgcagtgaa gagttgtctt tcacagttgt atcaaacgga   2880
gccaaaaaca tcagtggtca gagtccggcg cgaacttctt ccgacccagg gaccaacaca   2940
acaactgaag accacaaaat catggcttca gaaaattcct ctgcaatggt tcaagtgcac   3000
agtcaaggaa gggaagctgc agtgtcgcat ctaacaaccc ttgccacaat ctccacgagt   3060
ccccaatccc tcacaaccaa accaggtccg gacaacagca cccataatac acccgtgtat   3120
aaacttgaca tctctgaggc aactcaagtt gaacaacatc accgcagaac agacaacgac   3180
agcacagcct ccgacactcc ctctgccacg accgcagccg gacccccaaa agcagagaac   3240
accaacacga gcaagagcac tgacttcctg gaccccgcca ccacaacaag tccccaaaac   3300
cacagcgaga ccgctggcaa caacaacact catcaccaag ataccggaga agagagtgcc   3360
agcagcggga agctaggctt aattaccaat actattgctg gagtcgcagg actgatcaca   3420
ggcgggagaa gaactcgaag agaagcaatt gtcaatgctc aacccaaatg caaccctaat   3480
```

-continued

```
ttacattact ggactactca ggatgaaggt gctgcaatcg gactggcctg gataccatat   3540
ttcgggccag cagccgaggg aatttacata gaggggctaa tgcacaatca agatggttta   3600
atctgtgggt tgagacagct ggccaacgag acgactcaag ctcttcaact gttcctgaga   3660
gccacaactg agctacgcac cttttcaatc ctcaaccgta aggcaattga tttcttgctg   3720
cagcgatggg gcggcacatg ccacattctg ggaccggact gctgtatcga accacatgat   3780
tggaccaaga acataacaga caaaattgat cagattattc atgattttgt tgataaaacc   3840
cttccggacc aggggggacaa tgacaattgg tggacaggat ggagacaatg gataccggca   3900
ggtattggag ttacaggcgt tgtaattgca gttatcgctt tattctgtat atgcaaattt   3960
gtcttttagt tttcttcag attgcttcat ggaaaagctc agcctcaaat caatgaaacc   4020
aggatttaat tatatggatt acttgaatct aagattactt gacaaatgat aatataatac   4080
actggagctt taaacatagc caatgtgatt ctaactcctt taaactcaca gttaatcata   4140
aacaaggttt gaggtaccga gctcgaattg atctgctgtg ccttctagtt gccagccatc   4200
tgttgtttgc ccctcccccg tgccttcctt gaccctggaa ggtgccactc ccactgtcct   4260
ttcctaataa aatgaggaaa ttgcatcgca ttgtctgagt aggtgtcatt ctattctggg   4320
gggtggggtg gggcaggaca gcaaggggga ggattgggaa gacaatagca ggcatgctgg   4380
ggatgcggtg ggctctatgg gtacccaggt gctgaagaat tgacccggtt cctcctgggc   4440
cagaaagaag caggcacatc cccttctctg tgacacaccc tgtccacgcc cctggttctt   4500
agttccagcc ccactcatag gacactcata gctcaggagg gctccgcctt caatcccacc   4560
cgctaaagta cttggagcgg tctctccctc cctcatcagc ccaccaaacc aaacctagcc   4620
tccaagagtg ggaagaaatt aaagcaagat aggctattaa gtgcagaggg agagaaaatg   4680
cctccaacat gtgaggaagt aatgagagaa atcatagaat tttaaggcca tgatttaagg   4740
ccatcatggc cttaatcttc cgcttcctcg ctcactgact cgctgcgctc ggtcgttcgg   4800
ctgcggcgag cggtatcagc tcactcaaag gcggtaatac ggttatccac agaatcaggg   4860
gataacgcag gaaagaacat gtgagcaaaa ggccagcaaa aggccaggaa ccgtaaaaag   4920
gccgcgttgc tggcgttttt ccataggctc cgcccccctg acgagcatca caaaaatcga   4980
cgctcaagtc agaggtggcg aaacccgaca ggactataaa gataccaggc gtttccccct   5040
ggaagctccc tcgtgcgctc tcctgttccg accctgccgc ttaccggata cctgtccgcc   5100
tttctccctt cgggaagcgt ggcgctttct catagctcac gctgtaggta tctcagttcg   5160
gtgtaggtcg ttcgctccaa gctgggctgt gtgcacgaac cccccgttca gcccgaccgc   5220
tgcgccttat ccggtaacta tcgtcttgag tccaacccgg taagacacga cttatcgcca   5280
ctggcagcag ccactggtaa caggattagc agagcgaggt atgtaggcgg tgctacagag   5340
ttcttgaagt ggtggcctaa ctacggctac actagaagaa cagtatttgg tatctgcgct   5400
ctgctgaagc cagttacctt cggaaaaaga gttggtagct cttgatccgg caaacaaacc   5460
accgctggta gcggtggttt ttttgtttgc aagcagcaga ttacgcgcag aaaaaaagga   5520
tctcaagaag atcctttgat cttttctacg gggtctgacg ctcagtggaa cgaaaactca   5580
cgttaaggga ttttggtcat gagattatca aaaaggatct tcacctagat ccttttaaat   5640
taaaaatgaa gttttaaatc aatctaaagt atatatgagt aaacttggtc tgacagttac   5700
caatgcttaa tcagtgaggc acctatctca gcgatctgtc tatttcgttc atccatagtt   5760
gcctgactcg gggggggggg gcgctgaggt ctgcctcgtg aagaaggtgt tgctgactca   5820
taccaggcct gaatcgcccc atcatccagc cagaaagtga gggagccacg gttgatgaga   5880
```

-continued gctttgttgt aggtggacca gttggtgatt ttgaactttt gctttgccac ggaacggtct 5940
gcgttgtcgg gaagatgcgt gatctgatcc ttcaactcag caaaagttcg atttattcaa 6000
caaagccgcc gtcccgtcaa gtcagcgtaa tgctctgcca gtgttacaac caattaacca 6060
attctgatta gaaaaactca tcgagcatca aatgaaactg caatttattc atatcaggat 6120
tatcaatacc atatttttga aaaagccgtt tctgtaatga aggagaaaac tcaccgaggc 6180
agttccatag gatggcaaga tcctggtatc ggtctgcgat tccgactcgt ccaacatcaa 6240
tacaacctat taatttcccc tcgtcaaaaa taaggttatc aagtgagaaa tcaccatgag 6300
tgacgactga atccggtgag aatggcaaaa gcttatgcat ttctttccag acttgttcaa 6360
caggccagcc attacgctcg tcatcaaaat cactcgcatc aaccaaaccg ttattcattc 6420
gtgattgcgc ctgagcgaga cgaaatacgc gatcgctgtt aaaaggacaa ttacaaacag 6480
gaatcgaatg caaccggcgc aggaacactg ccagcgcatc aacaatattt tcacctgaat 6540
caggatattc ttctaatacc tggaatgctg ttttcccggg gatcgcagtg gtgagtaacc 6600
atgcatcatc aggagtacgg ataaaatgct tgatggtcgg aagaggcata aattccgtca 6660
gccagtttag tctgaccatc tcatctgtaa catcattggc aacgctacct ttgccatgtt 6720
tcagaaacaa ctctggcgca tcgggcttcc catacaatcg atagattgtc gcacctgatt 6780
gcccgacatt atcgcgagcc catttatacc catataaatc agcatccatg ttggaattta 6840
atcgcggcct cgagcaagac gtttcccgtt gaatatggct cataacaccc cttgtattac 6900
tgtttatgta agcagacagt tttattgttc atgatgatat atttttatct tgtgcaatgt 6960
aacatcagag attttgagac acaacgtggc tttccccccc cccccattat tgaagcattt 7020
atcagggtta ttgtctcatg agcggataca tatttgaatg tatttagaaa aataaacaaa 7080
taggggttcc gcgcacattt ccccgaaaag tgccacctga cgtctaagaa accattatta 7140
tcatgacatt aacctataaa aataggcgta tcacgaggcc ctttcgtc 7188

<210> SEQ ID NO 3
<211> LENGTH: 6624
<212> TYPE: DNA
<213> ORGANISM: Artificial Sequence
<220> FEATURE:
<223> OTHER INFORMATION: Synthetic Construct pVR1012-GP(Z) delta MUC

<400> SEQUENCE: 3
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcagattgg 240
ctattggcca ttgcatacgt tgtatccata tcataatatg tacatttata ttggctcatg 300
tccaacatta ccgccatgtt gacattgatt attgactagt tattaatagt aatcaattac 360
ggggtcatta gttcatagcc catatatgga gttccgcgtt acataactta cggtaaatgg 420
cccgcctggc tgaccgccca acgacccccg cccattgacg tcaataatga cgtatgttcc 480
catagtaacg ccaataggga ctttccattg acgtcaatgg gtggagtatt tacggtaaac 540
tgcccacttg gcagtacatc aagtgtatca tatgccaagt acgcccccta ttgacgtcaa 600
tgacggtaaa tggcccgcct ggcattatgc ccagtacatg accttatggg actttcctac 660
ttggcagtac atctacgtat tagtcatcgc tattaccatg gtgatgcggt tttggcagta 720
catcaatggg cgtggatagc ggtttgactc acggggattt ccaagtctcc accccattga 780

-continued cgtcaatggg agtttgtttt ggcaccaaaa tcaacgggac tttccaaaat gtcgtaacaa 840
ctccgcccca ttgacgcaaa tgggcggtag gcgtgtacgg tgggaggtct atataagcag 900
agctcgttta gtgaaccgtc agatcgcctg gagacgccat ccacgctgtt ttgacctcca 960
tagaagacac cgggaccgat ccagcctccg cggccgggaa cggtgcattg gaacgcggat 1020
tccccgtgcc aagagtgacg taagtaccgc ctatagactc tataggcaca cccctttggc 1080
tcttatgcat gctatactgt ttttggcttg gggcctatac acccccgctt ccttatgcta 1140
taggtgatgg tatagcttag cctataggtg tgggttattg accattattg accactcccc 1200
tattggtgac gatactttcc attactaatc cataacatgg ctctttgcca caactatctc 1260
tattggctat atgccaatac tctgtccttc agagactgac acggactctg tatttttaca 1320
ggatggggtc ccatttatta tttacaaatt cacatataca acaacgccgt cccccgtgcc 1380
cgcagttttt attaaacata gcgtgggatc tccacgcgaa tctcgggtac gtgttccgga 1440
catgggctct tctccggtag cggcggagct tccacatccg agccctggtc ccatgcctcc 1500
agcggctcat ggtcgctcgg cagctccttg ctcctaacag tggaggccag acttaggcac 1560
agcacaatgc ccaccaccac cagtgtgccg cacaaggccg tggcggtagg gtatgtgtct 1620
gaaaatgagc gtggagattg ggctcgcacg gctgacgcag atggaagact taaggcagcg 1680
gcagaagaag atgcaggcag ctgagttgtt gtattctgat aagagtcaga ggtaactccc 1740
gttgcggtgc tgttaacggt ggagggcagt gtagtctgag cagtactcgt tgctgccgcg 1800
cgcgccacca gacataatag ctgacagact aacagactgt tcctttccat gggtcttttc 1860
tgcagtcacc gtcgtcgaca cgtgtgatca gatatcgcgg ccgctctaga ccaggccctg 1920
gatcgatcca acaacacaat gggcgttaca ggaatattgc agttacctcg tgatcgattc 1980
aagaggacat cattctttct ttgggtaatt atccttttcc aaagaacatt ttccatccca 2040
cttggagtca tccacaatag cacattacag gttagtgatg tcgacaaact agtttgtcgt 2100
gacaaactgt catccacaaa tcaattgaga tcagttggac tgaatctcga agggaatgga 2160
gtggcaactg acgtgccatc tgcaactaaa agatggggct tcaggtccgg tgtcccacca 2220
aaggtggtca attatgaagc tggtgaatgg gctgaaaact gctacaatct tgaaatcaaa 2280
aaacctgacg ggagtgagtg tctaccagca gcgccagacg ggattcgggg cttcccccgg 2340
tgccggtatg tgcacaaagt atcaggaacg ggaccgtgtg ccggagactt tgccttccat 2400
aaagagggtg ctttcttcct gtatgatcga cttgcttcca cagttatcta ccgaggaacg 2460
actttcgctg aaggtgtcgt tgcatttctg atactgcccc aagctaagaa ggacttcttc 2520
agctcacacc ccttgagaga gccggtcaat gcaacggagg acccgtctag tggctactat 2580
tctaccacaa ttagatatca ggctaccggt tttggaacca atgagacaga gtacttgttc 2640
gaggttgaca atttgaccta cgtccaactt gaatcaagat tcacaccaca gtttctgctc 2700
cagctgaatg agacaatata tacaagtggg aaaaggagca ataccacggg aaaactaatt 2760
tggaaggtca accccgaaat tgatacaaca atcggggagt gggccttctg ggaaactaaa 2820
aaaaacctca ctagaaaaat tcgtaggctt aattaccaat actattgctg gagtcgcagg 2880
actgatcaca ggcgggagaa gaactcgaag agaagcaatt gtcaatgctc aacccaaatg 2940
caaccctaat ttacattact ggactactca ggatgaaggt gctgcaatcg gactggcctg 3000
gataccatat ttcgggccag cagccgaggg aatttacata gaggggctaa tgcacaatca 3060
agatggttta atctgtgggt tgagacagct ggccaacgag acgactcaag ctcttcaact 3120
gttcctgaga gccacaactg agctacgcac cttttcaatc ctcaaccgta aggcaattga 3180

-continued

```
tttcttgctg cagcgatggg gcggcacatg ccacattctg ggaccggact gctgtatcga   3240
accacatgat tggaccaaga acataacaga caaaattgat cagattattc atgattttgt   3300
tgataaaacc cttccggacc aggggacaa tgacaattgg tggacaggat ggagacaatg   3360
gataccggca ggtattggag ttacaggcgt tgtaattgca gttatcgctt tattctgtat   3420
atgcaaattt gtcttttagt ttttcttcag attgcttcat ggaaaagctc agcctcaaat   3480
caatgaaacc aggatttaat tatatggatt acttgaatct aagattactt gacaaatgat   3540
aatataatac actggagctt taaacatagc caatgtgatt ctaactcctt taaactcaca   3600
gttaatcata aacaaggttt gaggtaccga gctcgaattg atctgctgtg ccttctagtt   3660
gccagccatc tgttgtttgc ccctcccccg tgccttcctt gaccctggaa ggtgccactc   3720
ccactgtcct ttcctaataa aatgaggaaa ttgcatcgca ttgtctgagt aggtgtcatt   3780
ctattctggg gggtggggtg gggcaggaca gcaaggggga ggattgggaa gacaatagca   3840
ggcatgctgg ggatgcggtg ggctctatgg gtacccaggt gctgaagaat tgacccggtt   3900
cctcctgggc cagaaagaag caggcacatc cccttctctg tgacacaccc tgtccacgcc   3960
cctggttctt agttccagcc ccactcatag gacactcata gctcaggagg gctccgcctt   4020
caatcccacc cgctaaagta cttggagcgg tctctccctc cctcatcagc ccaccaaacc   4080
aaacctagcc tccaagagtg ggaagaaatt aaagcaagat aggctattaa gtgcagaggg   4140
agagaaaatg cctccaacat gtgaggaagt aatgagagaa atcatagaat ttcttccgct   4200
tcctcgctca ctgactcgct gcgctcggtc gttcggctgc ggcgagcggt atcagctcac   4260
tcaaaggcgg taatacggtt atccacagaa tcaggggata acgcaggaaa gaacatgtga   4320
gcaaaaggcc agcaaaaggc caggaaccgt aaaaaggccg cgttgctggc gtttttccat   4380
aggctccgcc cccctgacga gcatcacaaa aatcgacgct caagtcagag gtggcgaaac   4440
ccgacaggac tataaagata ccaggcgttt ccccctggaa gctccctcgt gcgctctcct   4500
gttccgaccc tgccgcttac cggatacctg tccgcctttc tcccttcggg aagcgtggcg   4560
ctttctcata gctcacgctg taggtatctc agttcggtgt aggtcgttcg ctccaagctg   4620
ggctgtgtgc acgaaccccc cgttcagccc gaccgctgcg ccttatccgg taactatcgt   4680
cttgagtcca acccggtaag acacgactta tcgccactgg cagcagccac tggtaacagg   4740
attagcagag cgaggtatgt aggcggtgct acagagttct tgaagtggtg gcctaactac   4800
ggctacacta gaagaacagt atttggtatc tgcgctctgc tgaagccagt taccttcgga   4860
aaaagagttg gtagctcttg atccggcaaa caaaccaccg ctggtagcgg tggttttttt   4920
gtttgcaagc agcagattac gcgcagaaaa aaaggatctc aagaagatcc tttgatcttt   4980
tctacggggt ctgacgctca gtggaacgaa aactcacgtt aagggatttt ggtcatgaga   5040
ttatcaaaaa ggatcttcac ctagatcctt ttaaattaaa aatgaagttt taaatcaatc   5100
taaagtatat atgagtaaac ttggtctgac agttaccaat gcttaatcag tgaggcacct   5160
atctcagcga tctgtctatt tcgttcatcc atagttgcct gactcggggg gggggggcgc   5220
tgaggtctgc ctcgtgaaga aggtgttgct gactcatacc aggcctgaat cgccccatca   5280
tccagccaga aagtgaggga gccacggttg atgagagctt tgttgtaggt ggaccagttg   5340
gtgattttga acttttgctt tgccacggaa cggtctgcgt tgtcgggaag atgcgtgatc   5400
tgatccttca actcagcaaa agttcgattt attcaacaaa gccgccgtcc cgtcaagtca   5460
gcgtaatgct ctgccagtgt tacaaccaat taaccaattc tgattagaaa aactcatcga   5520
gcatcaaatg aaactgcaat ttattcatat caggattatc aataccatat ttttgaaaaa   5580
```

gccgtttctg taatgaagga gaaaactcac cgaggcagtt ccataggatg gcaagatcct 5640
ggtatcggtc tgcgattccg actcgtccaa catcaataca acctattaat ttcccctcgt 5700
caaaaataag gttatcaagt gagaaatcac catgagtgac gactgaatcc ggtgagaatg 5760
gcaaaagctt atgcatttct ttccagactt gttcaacagg ccagccatta cgctcgtcat 5820
caaaatcact cgcatcaacc aaaccgttat tcattcgtga ttgcgcctga gcgagacgaa 5880
atacgcgatc gctgttaaaa ggacaattac aaacaggaat cgaatgcaac cggcgcagga 5940
acactgccag cgcatcaaca atattttcac ctgaatcagg atattcttct aatacctgga 6000
atgctgtttt cccggggatc gcagtggtga gtaaccatgc atcatcagga gtacggataa 6060
aatgcttgat ggtcggaaga ggcataaatt ccgtcagcca gtttagtctg accatctcat 6120
ctgtaacatc attggcaacg ctacctttgc catgtttcag aaacaactct ggcgcatcgg 6180
gcttcccata caatcgatag attgtcgcac ctgattgccc gacattatcg cgagcccatt 6240
tatacccata taaatcagca tccatgttgg aatttaatcg cggcctcgag caagacgttt 6300
cccgttgaat atggctcata acaccccttg tattactgtt tatgtaagca gacagtttta 6360
ttgttcatga tgatatattt ttatcttgtg caatgtaaca tcagagattt tgagacacaa 6420
cgtggctttc cccccccccc cattattgaa gcatttatca gggttattgt ctcatgagcg 6480
gatacatatt tgaatgtatt tagaaaaata aacaaatagg ggttccgcgc acatttcccc 6540
gaaaagtgcc acctgacgtc taagaaacca ttattatcat gacattaacc tataaaaata 6600
ggcgtatcac gaggcccttt cgtc 6624

<210> SEQ ID NO 4
<211> LENGTH: 6561
<212> TYPE: DNA
<213> ORGANISM: Artificial Sequence
<220> FEATURE:
<223> OTHER INFORMATION: Synthetic Construct pVR1012-GP(Z) deltaMUC delta FUR

<400> SEQUENCE: 4
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcagattgg 240
ctattggcca ttgcatacgt tgtatccata tcataatatg tacatttata ttggctcatg 300
tccaacatta ccgccatgtt gacattgatt attgactagt tattaatagt aatcaattac 360
ggggtcatta gttcatagcc catatatgga gttccgcgtt acataactta cggtaaatgg 420
cccgcctggc tgaccgccca acgacccccg cccattgacg tcaataatga cgtatgttcc 480
catagtaacg ccaataggga ctttccattg acgtcaatgg gtggagtatt tacggtaaac 540
tgcccacttg gcagtacatc aagtgtatca tatgccaagt acgcccccta ttgacgtcaa 600
tgacggtaaa tggcccgcct ggcattatgc ccagtacatg accttatggg actttcctac 660
ttggcagtac atctacgtat tagtcatcgc tattaccatg gtgatgcggt tttggcagta 720
catcaatggg cgtggatagc ggtttgactc acggggattt ccaagtctcc accccattga 780
cgtcaatggg agtttgtttt ggcaccaaaa tcaacgggac tttccaaaat gtcgtaacaa 840
ctccgcccca ttgacgcaaa tgggcggtag gcgtgtacgg tgggaggtct atataagcag 900
agctcgttta gtgaaccgtc agatcgcctg gagacgccat ccacgctgtt ttgacctcca 960
tagaagacac cgggaccgat ccagcctccg cggccgggaa cggtgcattg gaacgcggat 1020

-continued

```
tccccgtgcc aagagtgacg taagtaccgc ctatagactc tataggcaca cccctttggc   1080
tcttatgcat gctatactgt ttttggcttg gggcctatac acccccgctt ccttatgcta   1140
taggtgatgg tatagcttag cctataggtg tgggttattg accattattg accactcccc   1200
tattggtgac gatactttcc attactaatc cataacatgg ctctttgcca caactatctc   1260
tattggctat atgccaatac tctgtccttc agagactgac acggactctg tatttttaca   1320
ggatggggtc ccatttatta tttacaaatt cacatataca acaacgccgt cccccgtgcc   1380
cgcagttttt attaaacata gcgtgggatc tccacgcgaa tctcgggtac gtgttccgga   1440
catgggctct tctccggtag cggcggagct tccacatccg agccctggtc ccatgcctcc   1500
agcggctcat ggtcgctcgg cagctccttg ctcctaacag tggaggccag acttaggcac   1560
agcacaatgc ccaccaccac cagtgtgccg cacaaggccg tggcggtagg gtatgtgtct   1620
gaaaatgagc gtggagattg ggctcgcacg gctgacgcag atggaagact taaggcagcg   1680
gcagaagaag atgcaggcag ctgagttgtt gtattctgat aagagtcaga ggtaactccc   1740
gttgcggtgc tgttaacggt ggagggcagt gtagtctgag cagtactcgt tgctgccgcg   1800
cgcgccacca gacataatag ctgacagact aacagactgt tcctttccat gggtcttttc   1860
tgcagtcacc gtcgtcgaca cgtgtgatca gatatcgcgg ccgctctaga ccaggccctg   1920
gatcgatcca acaacacaat gggcgttaca ggaatattgc agttacctcg tgatcgattc   1980
aagaggacat cattctttct ttgggtaatt atccttttcc aaagaacatt ttccatccca   2040
cttggagtca tccacaatag cacattacag gttagtgatg tcgacaaact agtttgtcgt   2100
gacaaactgt catccacaaa tcaattgaga tcagttggac tgaatctcga agggaatgga   2160
gtggcaactg acgtgccatc tgcaactaaa agatggggct tcaggtccgg tgtcccacca   2220
aaggtggtca attatgaagc tggtgaatgg gctgaaaact gctacaatct tgaaatcaaa   2280
aaacctgacg ggagtgagtg tctaccagca gcgccagacg ggattcgggg cttcccccgg   2340
tgccggtatg tgcacaaagt atcaggaacg ggaccgtgtg ccggagactt tgccttccat   2400
aaagagggtg ctttcttcct gtatgatcga cttgcttcca cagttatcta ccgaggaacg   2460
actttcgctg aaggtgtcgt tgcatttctg atactgcccc aagctaagaa ggacttcttc   2520
agctcacacc ccttgagaga gccggtcaat gcaacggagg acccgtctag tggctactat   2580
tctaccacaa ttagatatca ggctaccggt tttggaacca atgagacaga gtacttgttc   2640
gaggttgaca atttgaccta cgtccaactt gaatcaagat tcacaccaca gtttctgctc   2700
cagctgaatg agacaatata tacaagtggg aaaaggagca ataccacggg aaaactaatt   2760
tggaaggtca accccgaaat tgatacaaca atcggggagt gggccttctg ggaaactaaa   2820
aaaaacctca ctagaaaaat tcggaagaga agcaattgtc aatgctcaac ccaaatgcaa   2880
ccctaattta cattactgga ctactcagga tgaaggtgct gcaatcggac tggcctggat   2940
accatatttc gggccagcag ccgagggaat ttacatagag gggctaatgc acaatcaaga   3000
tggtttaatc tgtgggttga gacagctggc caacgagacg actcaagctc ttcaactgtt   3060
cctgagagcc acaactgagc tacgcacctt ttcaatcctc aaccgtaagg caattgattt   3120
cttgctgcag cgatggggcg gcacatgcca cattctggga ccggactgct gtatcgaacc   3180
acatgattgg accaagaaca taacagacaa aattgatcag attattcatg attttgttga   3240
taaaaccctt ccggaccagg gggacaatga caattggtgg acaggatgga gacaatggat   3300
accggcaggt attggagtta caggcgttgt aattgcagtt atcgctttat tctgtatatg   3360
caaatttgtc ttttagtttt tcttcagatt gcttcatgga aaagctcagc ctcaaatcaa   3420
```

-continued

```
tgaaaccagg atttaattat atggattact tgaatctaag attacttgac aaatgataat   3480
ataatacact ggagctttaa acatagccaa tgtgattcta actcctttaa actcacagtt   3540
aatcataaac aaggtttgag gtaccgagct cgaattgatc tgctgtgcct tctagttgcc   3600
agccatctgt tgtttgcccc tcccccgtgc cttccttgac cctggaaggt gccactccca   3660
ctgtcctttc ctaataaaat gaggaaattg catcgcattg tctgagtagg tgtcattcta   3720
ttctgggggg tggggtgggg caggacagca agggggagga ttgggaagac aatagcaggc   3780
atgctgggga tgcggtgggc tctatgggta cccaggtgct gaagaattga cccggttcct   3840
cctgggccag aaagaagcag gcacatcccc ttctctgtga cacaccctgt ccacgcccct   3900
ggttcttagt tccagcccca ctcataggac actcatagct caggagggct ccgccttcaa   3960
tcccacccgc taaagtactt ggagcggtct ctccctccct catcagccca ccaaaccaaa   4020
cctagcctcc aagagtggga agaaattaaa gcaagatagg ctattaagtg cagagggaga   4080
gaaaatgcct ccaacatgtg aggaagtaat gagagaaatc atagaatttc ttccgcttcc   4140
tcgctcactg actcgctgcg ctcggtcgtt cggctgcggc gagcggtatc agctcactca   4200
aaggcggtaa tacggttatc cacagaatca ggggataacg caggaaagaa catgtgagca   4260
aaaggccagc aaaaggccag gaaccgtaaa aaggccgcgt tgctggcgtt tttccatagg   4320
ctccgccccc ctgacgagca tcacaaaaat cgacgctcaa gtcagaggtg gcgaaacccg   4380
acaggactat aaagatacca ggcgtttccc cctggaagct ccctcgtgcg ctctcctgtt   4440
ccgaccctgc cgcttaccgg atacctgtcc gcctttctcc cttcgggaag cgtggcgctt   4500
tctcatagct cacgctgtag gtatctcagt tcggtgtagg tcgttcgctc caagctgggc   4560
tgtgtgcacg aaccccccgt tcagcccgac cgctgcgcct tatccggtaa ctatcgtctt   4620
gagtccaacc cggtaagaca cgacttatcg ccactggcag cagccactgg taacaggatt   4680
agcagagcga ggtatgtagg cggtgctaca gagttcttga agtggtggcc taactacggc   4740
tacactagaa gaacagtatt tggtatctgc gctctgctga agccagttac cttcggaaaa   4800
agagttggta gctcttgatc cggcaaacaa accaccgctg gtagcggtgg tttttttgtt   4860
tgcaagcagc agattacgcg cagaaaaaaa ggatctcaag aagatccttt gatcttttct   4920
acggggtctg acgctcagtg gaacgaaaac tcacgttaag ggattttggt catgagatta   4980
tcaaaaagga tcttcaccta gatcctttta aattaaaaat gaagttttaa atcaatctaa   5040
agtatatatg agtaaacttg gtctgacagt taccaatgct taatcagtga ggcacctatc   5100
tcagcgatct gtctatttcg ttcatccata gttgcctgac tcgggggggg ggggcgctga   5160
ggtctgcctc gtgaagaagg tgttgctgac tcataccagg cctgaatcgc cccatcatcc   5220
agccagaaag tgagggagcc acggttgatg agagctttgt tgtaggtgga ccagttggtg   5280
attttgaact tttgctttgc cacggaacgg tctgcgttgt cgggaagatg cgtgatctga   5340
tccttcaact cagcaaaagt tcgatttatt caacaaagcc gccgtcccgt caagtcagcg   5400
taatgctctg ccagtgttac aaccaattaa ccaattctga ttagaaaaac tcatcgagca   5460
tcaaatgaaa ctgcaattta ttcatatcag gattatcaat accatatttt tgaaaaagcc   5520
gtttctgtaa tgaaggagaa aactcaccga ggcagttcca taggatggca agatcctggt   5580
atcggtctgc gattccgact cgtccaacat caatacaacc tattaatttc ccctcgtcaa   5640
aaataaggtt atcaagtgag aaatcaccat gagtgacgac tgaatccggt gagaatggca   5700
aaagcttatg catttctttc cagacttgtt caacaggcca gccattacgc tcgtcatcaa   5760
aatcactcgc atcaaccaaa ccgttattca ttcgtgattg cgcctgagcg agacgaaata   5820
```

```
cgcgatcgct gttaaaagga caattacaaa caggaatcga atgcaaccgg cgcaggaaca   5880

ctgccagcgc atcaacaata ttttcacctg aatcaggata ttcttctaat acctggaatg   5940

ctgttttccc ggggatcgca gtggtgagta accatgcatc atcaggagta cggataaaat   6000

gcttgatggt cggaagaggc ataaattccg tcagccagtt tagtctgacc atctcatctg   6060

taacatcatt ggcaacgcta cctttgccat gtttcagaaa caactctggc gcatcgggct   6120

tcccatacaa tcgatagatt gtcgcacctg attgcccgac attatcgcga gcccatttat   6180

acccatataa atcagcatcc atgttggaat ttaatcgcgg cctcgagcaa gacgtttccc   6240

gttgaatatg gctcataaca ccccttgtat tactgtttat gtaagcagac agttttattg   6300

ttcatgatga tatattttta tcttgtgcaa tgtaacatca gagattttga gacacaacgt   6360

ggctttcccc cccccccat tattgaagca tttatcaggg ttattgtctc atgagcggat   6420

acatatttga atgtatttag aaaaataaac aaataggggt tccgcgcaca tttccccgaa   6480

aagtgccacc tgacgtctaa gaaaccatta ttatcatgac attaacctat aaaaataggc   6540

gtatcacgag gccctttcgt c                                              6561
```

<210> SEQ ID NO 5
<211> LENGTH: 6724
<212> TYPE: DNA
<213> ORGANISM: Artificial Sequence
<220> FEATURE:
<223> OTHER INFORMATION: Synthetic Construct pVR1012-GP(Z) delta GP2

<400> SEQUENCE: 5

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatgcg gtgtgaaata ccgcacagat gcgtaaggag aaaataccgc atcagattgg    240

ctattggcca ttgcatacgt tgtatccata tcataatatg tacatttata ttggctcatg    300

tccaacatta ccgccatgtt gacattgatt attgactagt tattaatagt aatcaattac    360

ggggtcatta gttcatagcc catatatgga gttccgcgtt acataactta cggtaaatgg    420

cccgcctggc tgaccgccca acgacccccg cccattgacg tcaataatga cgtatgttcc    480

catagtaacg ccaataggga ctttccattg acgtcaatgg gtggagtatt tacggtaaac    540

tgcccacttg gcagtacatc aagtgtatca tatgccaagt acgcccccta ttgacgtcaa    600

tgacggtaaa tggcccgcct ggcattatgc ccagtacatg accttatggg actttcctac    660

ttggcagtac atctacgtat tagtcatcgc tattaccatg gtgatgcggt tttggcagta    720

catcaatggg cgtggatagc ggtttgactc acggggattt ccaagtctcc accccattga    780

cgtcaatggg agtttgtttt ggcaccaaaa tcaacgggac tttccaaaat gtcgtaacaa    840

ctccgcccca ttgacgcaaa tgggcggtag gcgtgtacgg tgggaggtct atataagcag    900

agctcgttta gtgaaccgtc agatcgcctg gagacgccat ccacgctgtt ttgacctcca    960

tagaagacac cgggaccgat ccagcctccg cggccgggaa cggtgcattg gaacgcggat   1020

tccccgtgcc aagagtgacg taagtaccgc ctatagactc tataggcaca cccctttggc   1080

tcttatgcat gctatactgt ttttggcttg gggcctatac acccccgctt ccttatgcta   1140

taggtgatgg tatagcttag cctataggtg tgggttattg accattattg accactcccc   1200

tattggtgac gatactttcc attactaatc cataacatgg ctctttgcca caactatctc   1260

tattggctat atgccaatac tctgtccttc agagactgac acggactctg tatttttaca   1320
```

-continued

```
ggatggggtc ccatttatta tttacaaatt cacatataca acaacgccgt cccccgtgcc   1380
cgcagttttt attaaacata gcgtgggatc tccacgcgaa tctcgggtac gtgttccgga   1440
catgggctct tctccggtag cggcggagct tccacatccg agccctggtc ccatgcctcc   1500
agcggctcat ggtcgctcgg cagctccttg ctcctaacag tggaggccag acttaggcac   1560
agcacaatgc ccaccaccac cagtgtgccg cacaaggccg tggcggtagg gtatgtgtct   1620
gaaaatgagc gtggagattg ggctcgcacg gctgacgcag atggaagact taaggcagcg   1680
gcagaagaag atgcaggcag ctgagttgtt gtattctgat aagagtcaga ggtaactccc   1740
gttgcggtgc tgttaacggt ggagggcagt gtagtctgag cagtactcgt tgctgccgcg   1800
cgcgccacca gacataatag ctgacagact aacagactgt tcctttccat gggtcttttc   1860
tgcagtcacc gtcgtcgaca cgtgtgatca gatatcgcgg ccgctctaga ccaggccctg   1920
gatcgatcca acaacacaat gggcgttaca ggaatattgc agttacctcg tgatcgattc   1980
aagaggacat cattctttct ttgggtaatt atccttttcc aaagaacatt ttccatccca   2040
cttggagtca tccacaatag cacattacag gttagtgatg tcgacaaact agtttgtcgt   2100
gacaaactgt catccacaaa tcaattgaga tcagttggac tgaatctcga agggaatgga   2160
gtggcaactg acgtgccatc tgcaactaaa agatggggct tcaggtccgg tgtcccacca   2220
aaggtggtca attatgaagc tggtgaatgg gctgaaaact gctacaatct tgaaatcaaa   2280
aaacctgacg ggagtgagtg tctaccagca gcgccagacg ggattcgggg cttcccccgg   2340
tgccggtatg tgcacaaagt atcaggaacg ggaccgtgtg ccggagactt tgccttccat   2400
aaagagggtg ctttcttcct gtatgatcga cttgcttcca cagttatcta ccgaggaacg   2460
actttcgctg aaggtgtcgt tgcatttctg atactgcccc aagctaagaa ggacttcttc   2520
agctcacacc ccttgagaga gccggtcaat gcaacggagg acccgtctag tggctactat   2580
tctaccacaa ttagatatca ggctaccggt tttggaacca atgagacaga gtacttgttc   2640
gaggttgaca atttgaccta cgtccaactt gaatcaagat tcacaccaca gttctgctc   2700
cagctgaatg agacaatata tacaagtggg aaaaggagca ataccacggg aaaactaatt   2760
tggaaggtca accccgaaat tgatacaaca atcggggagt gggccttctg ggaaactaaa   2820
aaaaacctca ctagaaaaat tcgcagtgaa gagttgtctt tcacagttgt atcaaacgga   2880
gccaaaaaca tcagtggtca gagtccggcg cgaacttctt ccgacccagg gaccaacaca   2940
acaactgaag accacaaaat catggcttca gaaaattcct ctgcaatggt tcaagtgcac   3000
agtcaaggaa gggaagctgc agtgtcgcat ctaacaaccc ttgccacaat ctccacgagt   3060
ccccaatccc tcacaaccaa accaggtccg gacaacagca cccataatac acccgtgtat   3120
aaacttgaca tctctgaggc aactcaagtt gaacaacatc accgcagaac agacaacgac   3180
agcacagcct ccgacactcc ctctgccacg accgcagccg gacccccaaa agcagagaac   3240
accaacacga gcaagagcac tgacttcctg gaccccgcca ccacaacaag tccccaaaac   3300
cacagcgaga ccgctggcaa caacaacact catcaccaag ataccggaga agagagtgcc   3360
agcagcggga agctaggctt aattaccaat actattgctg gagtcgcagg actccggacc   3420
agggggacaa tgacaattgg tggacaggat ggagacaatg gataccggca ggtattggag   3480
ttacaggcgt tgtaattgca gttatcgctt tattctgtat atgcaaattt gtcttttagt   3540
ttttcttcag attgcttcat ggaaaagctc agcctcaaat caatgaaacc aggatttaat   3600
tatatggatt acttgaatct aagattactt gacaaatgat aatataatac actggagctt   3660
taaacatagc caatgtgatt ctaactcctt taaactcaca gttaatcata aacaaggttt   3720
```

-continued

```
gaggtaccga gctcgaattg atctgctgtg ccttctagtt gccagccatc tgttgtttgc   3780
ccctcccccg tgccttcctt gaccctggaa ggtgccactc ccactgtcct ttcctaataa   3840
aatgaggaaa ttgcatcgca ttgtctgagt aggtgtcatt ctattctggg gggtggggtg   3900
gggcaggaca gcaaggggga ggattgggaa gacaatagca ggcatgctgg ggatgcggtg   3960
ggctctatgg gtacccaggt gctgaagaat tgacccggtt cctcctgggc cagaaagaag   4020
caggcacatc cccttctctg tgacacaccc tgtccacgcc cctggttctt agttccagcc   4080
ccactcatag gacactcata gctcaggagg gctccgcctt caatcccacc cgctaaagta   4140
cttggagcgg tctctccctc cctcatcagc ccaccaaacc aaacctagcc tccaagagtg   4200
ggaagaaatt aaagcaagat aggctattaa gtgcagaggg agagaaaatg cctccaacat   4260
gtgaggaagt aatgagagaa atcatagaat ttcttccgct tcctcgctca ctgactcgct   4320
gcgctcggtc gttcggctgc ggcgagcggt atcagctcac tcaaaggcgg taatacggtt   4380
atccacagaa tcaggggata acgcaggaaa gaacatgtga gcaaaaggcc agcaaaaggc   4440
caggaaccgt aaaaaggccg cgttgctggc gtttttccat aggctccgcc cccctgacga   4500
gcatcacaaa aatcgacgct caagtcagag gtggcgaaac ccgacaggac tataaagata   4560
ccaggcgttt ccccctggaa gctccctcgt gcgctctcct gttccgaccc tgccgcttac   4620
cggatacctg tccgcctttc tcccttcggg aagcgtggcg ctttctcata gctcacgctg   4680
taggtatctc agttcggtgt aggtcgttcg ctccaagctg ggctgtgtgc acgaaccccc   4740
cgttcagccc gaccgctgcg ccttatccgg taactatcgt cttgagtcca acccggtaag   4800
acacgactta tcgccactgg cagcagccac tggtaacagg attagcagag cgaggtatgt   4860
aggcggtgct acagagttct tgaagtggtg gcctaactac ggctacacta gaagaacagt   4920
atttggtatc tgcgctctgc tgaagccagt taccttcgga aaaagagttg gtagctcttg   4980
atccggcaaa caaaccaccg ctggtagcgg tggttttttt gtttgcaagc agcagattac   5040
gcgcagaaaa aaaggatctc aagaagatcc tttgatcttt tctacggggt ctgacgctca   5100
gtggaacgaa aactcacgtt aagggatttt ggtcatgaga ttatcaaaaa ggatcttcac   5160
ctagatcctt ttaaattaaa aatgaagttt taaatcaatc taaagtatat atgagtaaac   5220
ttggtctgac agttaccaat gcttaatcag tgaggcacct atctcagcga tctgtctatt   5280
tcgttcatcc atagttgcct gactcggggg gggggggcgc tgaggtctgc ctcgtgaaga   5340
aggtgttgct gactcatacc aggcctgaat cgccccatca tccagccaga aagtgaggga   5400
gccacggttg atgagagctt tgttgtaggt ggaccagttg gtgattttga acttttgctt   5460
tgccacggaa cggtctgcgt tgtcgggaag atgcgtgatc tgatccttca actcagcaaa   5520
agttcgattt attcaacaaa gccgccgtcc cgtcaagtca gcgtaatgct ctgccagtgt   5580
tacaaccaat taaccaattc tgattagaaa aactcatcga gcatcaaatg aaactgcaat   5640
ttattcatat caggattatc aataccatat ttttgaaaaa gccgtttctg taatgaagga   5700
gaaaactcac cgaggcagtt ccataggatg gcaagatcct ggtatcggtc tgcgattccg   5760
actcgtccaa catcaataca acctattaat ttcccctcgt caaaaataag gttatcaagt   5820
gagaaatcac catgagtgac gactgaatcc ggtgagaatg gcaaaagctt atgcatttct   5880
ttccagactt gttcaacagg ccagccatta cgctcgtcat caaaatcact cgcatcaacc   5940
aaaccgttat tcattcgtga ttgcgcctga gcgagacgaa atacgcgatc gctgttaaaa   6000
ggacaattac aaacaggaat cgaatgcaac cggcgcagga acactgccag cgcatcaaca   6060
atattttcac ctgaatcagg atattcttct aatacctgga atgctgtttt cccggggatc   6120
```

```
gcagtggtga gtaaccatgc atcatcagga gtacggataa aatgcttgat ggtcggaaga   6180

ggcataaatt ccgtcagcca gtttagtctg accatctcat ctgtaacatc attggcaacg   6240

ctacctttgc catgtttcag aaacaactct ggcgcatcgg gcttcccata caatcgatag   6300

attgtcgcac ctgattgccc gacattatcg cgagcccatt tatacccata taaatcagca   6360

tccatgttgg aatttaatcg cggcctcgag caagacgttt cccgttgaat atggctcata   6420

acaccccttg tattactgtt tatgtaagca gacagtttta ttgttcatga tgatatattt   6480

ttatcttgtg caatgtaaca tcagagattt tgagacacaa cgtggctttc cccccccccc   6540

cattattgaa gcatttatca gggttattgt ctcatgagcg gatacatatt tgaatgtatt   6600

tagaaaaata aacaaatagg ggttccgcgc acatttcccc gaaaagtgcc acctgacgtc   6660

taagaaacca ttattatcat gacattaacc tataaaaata ggcgtatcac gaggcccttt   6720

cgtc                                                                6724
```

<210> SEQ ID NO 6
<211> LENGTH: 6887
<212> TYPE: DNA
<213> ORGANISM: Artificial Sequence
<220> FEATURE:
<223> OTHER INFORMATION: Synthetic Construct pVR1012-GP(Z) delta GP2 delta C-term A

<400> SEQUENCE: 6

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatgcg gtgtgaaata ccgcacagat gcgtaaggag aaaataccgc atcagattgg    240

ctattggcca ttgcatacgt tgtatccata tcataatatg tacatttata ttggctcatg    300

tccaacatta ccgccatgtt gacattgatt attgactagt tattaatagt aatcaattac    360

ggggtcatta gttcatagcc catatatgga gttccgcgtt acataactta cggtaaatgg    420

cccgcctggc tgaccgccca acgacccccg cccattgacg tcaataatga cgtatgttcc    480

catagtaacg ccaataggga ctttccattg acgtcaatgg gtggagtatt tacggtaaac    540

tgcccacttg gcagtacatc aagtgtatca tatgccaagt acgcccccta ttgacgtcaa    600

tgacggtaaa tggcccgcct ggcattatgc ccagtacatg accttatggg actttcctac    660

ttggcagtac atctacgtat tagtcatcgc tattaccatg gtgatgcggt tttggcagta    720

catcaatggg cgtggatagc ggtttgactc acggggattt ccaagtctcc accccattga    780

cgtcaatggg agtttgtttt ggcaccaaaa tcaacgggac tttccaaaat gtcgtaacaa    840

ctccgcccca ttgacgcaaa tgggcggtag gcgtgtacgg tgggaggtct atataagcag    900

agctcgttta gtgaaccgtc agatcgcctg gagacgccat ccacgctgtt ttgacctcca    960

tagaagacac cgggaccgat ccagcctccg cggccgggaa cggtgcattg gaacgcggat   1020

tccccgtgcc aagagtgacg taagtaccgc ctatagactc tataggcaca cccctttggc   1080

tcttatgcat gctatactgt ttttggcttg gggcctatac acccccgctt ccttatgcta   1140

taggtgatgg tatagcttag cctataggtg tgggttattg accattattg accactcccc   1200

tattggtgac gatactttcc attactaatc cataacatgg ctctttgcca caactatctc   1260

tattggctat atgccaatac tctgtccttc agagactgac acggactctg tatttttaca   1320

ggatggggtc ccatttatta tttacaaatt cacatataca acaacgccgt cccccgtgcc   1380
```

-continued

```
cgcagttttt attaaacata gcgtgggatc tccacgcgaa tctcgggtac gtgttccgga   1440

catgggctct tctccggtag cggcggagct tccacatccg agccctggtc ccatgcctcc   1500

agcggctcat ggtcgctcgg cagctccttg ctcctaacag tggaggccag acttaggcac   1560

agcacaatgc ccaccaccac cagtgtgccg cacaaggccg tggcggtagg gtatgtgtct   1620

gaaaatgagc gtggagattg ggctcgcacg gctgacgcag atggaagact taaggcagcg   1680

gcagaagaag atgcaggcag ctgagttgtt gtattctgat aagagtcaga ggtaactccc   1740

gttgcggtgc tgttaacggt ggagggcagt gtagtctgag cagtactcgt tgctgccgcg   1800

cgcgccacca gacataatag ctgacagact aacagactgt tcctttccat gggtcttttc   1860

tgcagtcacc gtcgtcgaca cgtgtgatca gatatcgcgg ccgctctaga ccaggccctg   1920

gatcgatcca acaacacaat gggcgttaca ggaatattgc agttacctcg tgatcgattc   1980

aagaggacat cattctttct ttgggtaatt atccttttcc aaagaacatt ttccatccca   2040

cttggagtca tccacaatag cacattacag gttagtgatg tcgacaaact agtttgtcgt   2100

gacaaactgt catccacaaa tcaattgaga tcagttggac tgaatctcga agggaatgga   2160

gtggcaactg acgtgccatc tgcaactaaa agatggggct tcaggtccgg tgtcccacca   2220

aaggtggtca attatgaagc tggtgaatgg gctgaaaact gctacaatct tgaaatcaaa   2280

aaacctgacg ggagtgagtg tctaccagca gcgccagacg ggattcgggg cttccccccgg   2340

tgccggtatg tgcacaaagt atcaggaacg ggaccgtgtg ccggagactt tgccttccat   2400

aaagagggtg ctttcttcct gtatgatcga cttgcttcca cagttatcta ccgaggaacg   2460

actttcgctg aaggtgtcgt tgcatttctg atactgcccc aagctaagaa ggacttcttc   2520

agctcacacc ccttgagaga gccggtcaat gcaacggagg acccgtctag tggctactat   2580

tctaccacaa ttagatatca ggctaccggt tttggaacca atgagacaga gtacttgttc   2640

gaggttgaca atttgaccta cgtccaactt gaatcaagat tcacaccaca gtttctgctc   2700

cagctgaatg agacaatata tacaagtggg aaaaggagca ataccacggg aaaactaatt   2760

tggaaggtca accccgaaat tgatacaaca atcggggagt gggccttctg ggaaactaaa   2820

aaaaacctca ctagaaaaat tcgcagtgaa gagttgtctt tcacagttgt atcaaacgga   2880

gccaaaaaca tcagtggtca gagtccggcg cgaacttctt ccgacccagg gaccaacaca   2940

acaactgaag accacaaaat catggcttca gaaaattcct ctgcaatggt tcaagtgcac   3000

agtcaaggaa gggaagctgc agtgtcgcat ctaacaaccc ttgccacaat ctccacgagt   3060

ccccaatccc tcacaaccaa accaggtccg gacaacagca cccataatac acccgtgtat   3120

aaacttgaca tctctgaggc aactcaagtt gaacaacatc accgcagaac agacaacgac   3180

agcacagcct ccgacactcc ctctgccacg accgcagccg gacccccaaa agcagagaac   3240

accaacacga gcaagagcac tgacttcctg gaccccgcca ccacaacaag tccccaaaac   3300

cacagcgaga ccgctggcaa caacaacact catcaccaag ataccggaga agagagtgcc   3360

agcagcggga agctaggctt aattaccaat actattgctg gagtcgcagg actgatcaca   3420

ggcgggagaa gaactcgaag agaagcaatt gtcaatgctc aacccaaatg caaccctaat   3480

ttacattact ggactactca ggatgaaggt gctgcaatcg gactggcctg gataccatat   3540

ttcgggccag cagccgaggg aatttacata gaggggctaa tgcacaatca agatggttta   3600

atctgtgggt tgagacagct ggggataccg gcaggtattg gagttacagg cgttgtaatt   3660

gcagttatcg ctttattctg tatatgcaaa tttgtctttt agtttttctt cagattgctt   3720

catggaaaag ctcagcctca aatcaatgaa accaggattt aattatatgg attacttgaa   3780
```

-continued

```
tctaagatta cttgacaaat gataatataa tacactggag ctttaaacat agccaatgtg   3840
attctaactc ctttaaactc acagttaatc ataaacaagg tttgaggtac cgagctcgaa   3900
ttgatctgct gtgccttcta gttgccagcc atctgttgtt tgcccctccc ccgtgccttc   3960
cttgaccctg gaaggtgcca ctcccactgt cctttcctaa taaaatgagg aaattgcatc   4020
gcattgtctg agtaggtgtc attctattct ggggggtggg gtggggcagg acagcaaggg   4080
ggaggattgg gaagacaata gcaggcatgc tggggatgcg gtgggctcta tgggtaccca   4140
ggtgctgaag aattgacccg gttcctcctg ggccagaaag aagcaggcac atccccttct   4200
ctgtgacaca ccctgtccac gcccctggtt cttagttcca gccccactca taggacactc   4260
atagctcagg agggctccgc cttcaatccc acccgctaaa gtacttggag cggtctctcc   4320
ctccctcatc agcccaccaa accaaaccta gcctccaaga gtgggaagaa attaaagcaa   4380
gataggctat taagtgcaga gggagagaaa atgcctccaa catgtgagga agtaatgaga   4440
gaaatcatag aatttcttcc gcttcctcgc tcactgactc gctgcgctcg gtcgttcggc   4500
tgcggcgagc ggtatcagct cactcaaagg cggtaatacg gttatccaca gaatcagggg   4560
ataacgcagg aaagaacatg tgagcaaaag gccagcaaaa ggccaggaac cgtaaaaagg   4620
ccgcgttgct ggcgtttttc cataggctcc gcccccctga cgagcatcac aaaaatcgac   4680
gctcaagtca gaggtggcga aacccgacag gactataaag ataccaggcg tttccccctg   4740
gaagctccct cgtgcgctct cctgttccga ccctgccgct taccggatac ctgtccgcct   4800
ttctcccttc gggaagcgtg gcgctttctc atagctcacg ctgtaggtat ctcagttcgg   4860
tgtaggtcgt tcgctccaag ctgggctgtg tgcacgaacc ccccgttcag cccgaccgct   4920
gcgccttatc cggtaactat cgtcttgagt ccaacccggt aagacacgac ttatcgccac   4980
tggcagcagc cactggtaac aggattagca gagcgaggta tgtaggcggt gctacagagt   5040
tcttgaagtg gtggcctaac tacggctaca ctagaagaac agtatttggt atctgcgctc   5100
tgctgaagcc agttaccttc ggaaaaagag ttggtagctc ttgatccggc aaacaaacca   5160
ccgctggtag cggtggtttt tttgtttgca agcagcagat tacgcgcaga aaaaaaggat   5220
ctcaagaaga tcctttgatc ttttctacgg ggtctgacgc tcagtggaac gaaaactcac   5280
gttaagggat tttggtcatg agattatcaa aaaggatctt cacctagatc cttttaaatt   5340
aaaaatgaag ttttaaatca atctaaagta tatatgagta aacttggtct gacagttacc   5400
aatgcttaat cagtgaggca cctatctcag cgatctgtct atttcgttca tccatagttg   5460
cctgactcgg gggggggggg cgctgaggtc tgcctcgtga agaaggtgtt gctgactcat   5520
accaggcctg aatcgcccca tcatccagcc agaaagtgag ggagccacgg ttgatgagag   5580
ctttgttgta ggtggaccag ttggtgattt tgaacttttg ctttgccacg gaacggtctg   5640
cgttgtcggg aagatgcgtg atctgatcct tcaactcagc aaaagttcga tttattcaac   5700
aaagccgccg tcccgtcaag tcagcgtaat gctctgccag tgttacaacc aattaaccaa   5760
ttctgattag aaaaactcat cgagcatcaa atgaaactgc aatttattca tatcaggatt   5820
atcaatacca tatttttgaa aaagccgttt ctgtaatgaa ggagaaaact caccgaggca   5880
gttccatagg atggcaagat cctggtatcg gtctgcgatt ccgactcgtc caacatcaat   5940
acaacctatt aatttcccct cgtcaaaaat aaggttatca agtgagaaat caccatgagt   6000
gacgactgaa tccggtgaga atggcaaaag cttatgcatt tctttccaga cttgttcaac   6060
aggccagcca ttacgctcgt catcaaaatc actcgcatca accaaaccgt tattcattcg   6120
tgattgcgcc tgagcgagac gaaatacgcg atcgctgtta aaggacaatt acaaacagg    6180
```

-continued aatcgaatgc aaccggcgca ggaacactgc cagcgcatca acaatatttt cacctgaatc 6240
aggatattct tctaatacct ggaatgctgt tttcccgggg atcgcagtgg tgagtaacca 6300
tgcatcatca ggagtacgga taaaatgctt gatggtcgga agaggcataa attccgtcag 6360
ccagtttagt ctgaccatct catctgtaac atcattggca acgctacctt tgccatgttt 6420
cagaaacaac tctggcgcat cgggcttccc atacaatcga tagattgtcg cacctgattg 6480
cccgacatta tcgcgagccc atttataccc atataaatca gcatccatgt tggaatttaa 6540
tcgcggcctc gagcaagacg tttcccgttg aatatggctc ataacacccc ttgtattact 6600
gtttatgtaa gcagacagtt ttattgttca tgatgatata tttttatctt gtgcaatgta 6660
acatcagaga ttttgagaca caacgtggct ttcccccccc ccccattatt gaagcattta 6720
tcagggttat tgtctcatga gcggatacat atttgaatgt atttagaaaa ataaacaaat 6780
aggggttccg cgcacatttc cccgaaaagt gccacctgac gtctaagaaa ccattattat 6840
catgacatta acctataaaa ataggcgtat cacgaggccc tttcgtc 6887

<210> SEQ ID NO 7
<211> LENGTH: 7044
<212> TYPE: DNA
<213> ORGANISM: Artificial Sequence
<220> FEATURE:
<223> OTHER INFORMATION: Synthetic Construct pVR1012-GP(Z) delta GP2
Delta C-term B

<400> SEQUENCE: 7
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcagattgg 240
ctattggcca ttgcatacgt tgtatccata tcataatatg tacatttata ttggctcatg 300
tccaacatta ccgccatgtt gacattgatt attgactagt tattaatagt aatcaattac 360
ggggtcatta gttcatagcc catatatgga gttccgcgtt acataactta cggtaaatgg 420
cccgcctggc tgaccgccca acgacccccg cccattgacg tcaataatga cgtatgttcc 480
catagtaacg ccaataggga ctttccattg acgtcaatgg gtggagtatt tacggtaaac 540
tgcccacttg gcagtacatc aagtgtatca tatgccaagt acgcccccta ttgacgtcaa 600
tgacggtaaa tggcccgcct ggcattatgc ccagtacatg accttatggg actttcctac 660
ttggcagtac atctacgtat tagtcatcgc tattaccatg gtgatgcggt tttggcagta 720
catcaatggg cgtggatagc ggtttgactc acggggattt ccaagtctcc accccattga 780
cgtcaatggg agtttgtttt ggcaccaaaa tcaacgggac tttccaaaat gtcgtaacaa 840
ctccgcccca ttgacgcaaa tgggcggtag gcgtgtacgg tgggaggtct atataagcag 900
agctcgttta gtgaaccgtc agatcgcctg gagacgccat ccacgctgtt ttgacctcca 960
tagaagacac cgggaccgat ccagcctccg cggccgggaa cggtgcattg gaacgcggat 1020
tccccgtgcc aagagtgacg taagtaccgc ctatagactc tataggcaca cccctttggc 1080
tcttatgcat gctatactgt ttttggcttg gggcctatac acccccgctt ccttatgcta 1140
taggtgatgg tatagcttag cctataggtg tgggttattg accattattg accactcccc 1200
tattggtgac gatactttcc attactaatc cataacatgg ctctttgcca caactatctc 1260
tattggctat atgccaatac tctgtccttc agagactgac acggactctg tatttttaca 1320
ggatggggtc ccatttatta tttacaaatt cacatataca acaacgccgt cccccgtgcc 1380

-continued

```
cgcagttttt attaaacata gcgtgggatc tccacgcgaa tctcgggtac gtgttccgga   1440
catgggctct tctccggtag cggcggagct tccacatccg agccctggtc ccatgcctcc   1500
agcggctcat ggtcgctcgg cagctccttg ctcctaacag tggaggccag acttaggcac   1560
agcacaatgc ccaccaccac cagtgtgccg cacaaggccg tggcggtagg gtatgtgtct   1620
gaaaatgagc gtggagattg ggctcgcacg gctgacgcag atggaagact taaggcagcg   1680
gcagaagaag atgcaggcag ctgagttgtt gtattctgat aagagtcaga ggtaactccc   1740
gttgcggtgc tgttaacggt ggagggcagt gtagtctgag cagtactcgt tgctgccgcg   1800
cgcgccacca gacataatag ctgacagact aacagactgt tcctttccat gggtcttttc   1860
tgcagtcacc gtcgtcgaca cgtgtgatca gatatcgcgg ccgctctaga ccaggccctg   1920
gatcgatcca acaacacaat gggcgttaca ggaatattgc agttacctcg tgatcgattc   1980
aagaggacat cattctttct ttgggtaatt atccttttcc aaagaacatt ttccatccca   2040
cttggagtca tccacaatag cacattacag gttagtgatg tcgacaaact agtttgtcgt   2100
gacaaactgt catccacaaa tcaattgaga tcagttggac tgaatctcga agggaatgga   2160
gtggcaactg acgtgccatc tgcaactaaa agatggggct tcaggtccgg tgtcccacca   2220
aaggtggtca attatgaagc tggtgaatgg gctgaaaact gctacaatct tgaaatcaaa   2280
aaacctgacg ggagtgagtg tctaccagca gcgccagacg ggattcgggg cttcccccgg   2340
tgccggtatg tgcacaaagt atcaggaacg ggaccgtgtg ccggagactt tgccttccat   2400
aaagagggtg ctttcttcct gtatgatcga cttgcttcca cagttatcta ccgaggaacg   2460
actttcgctg aaggtgtcgt tgcatttctg atactgcccc aagctaagaa ggacttcttc   2520
agctcacacc ccttgagaga gccggtcaat gcaacggagg acccgtctag tggctactat   2580
tctaccacaa ttagatatca ggctaccggt tttggaacca atgagacaga gtacttgttc   2640
gaggttgaca atttgaccta cgtccaactt gaatcaagat tcacaccaca gtttctgctc   2700
cagctgaatg agacaatata tacaagtggg aaaaggagca ataccacggg aaaactaatt   2760
tggaaggtca accccgaaat tgatacaaca atcggggagt gggccttctg ggaaactaaa   2820
aaaaacctca ctagaaaaat tcgcagtgaa gagttgtctt tcacagttgt atcaaacgga   2880
gccaaaaaca tcagtggtca gagtccggcg cgaacttctt ccgacccagg gaccaacaca   2940
acaactgaag accacaaaat catggcttca gaaaattcct ctgcaatggt tcaagtgcac   3000
agtcaaggaa gggaagctgc agtgtcgcat ctaacaaccc ttgccacaat ctccacgagt   3060
ccccaatccc tcacaaccaa accaggtccg gacaacagca cccataatac acccgtgtat   3120
aaacttgaca tctctgaggc aactcaagtt gaacaacatc accgcagaac agacaacgac   3180
agcacagcct ccgacactcc ctctgccacg accgcagccg gacccccaaa agcagagaac   3240
accaacacga gcaagagcac tgacttcctg gaccccgcca ccacaacaag tccccaaaac   3300
cacagcgaga ccgctggcaa caacaacact catcaccaag ataccggaga agagagtgcc   3360
agcagcggga agctaggctt aattaccaat actattgctg gagtcgcagg actgatcaca   3420
ggcgggagaa gaactcgaag agaagcaatt gtcaatgctc aacccaaatg caaccctaat   3480
ttacattact ggactactca ggatgaaggt gctgcaatcg gactggcctg gataccatat   3540
ttcgggccag cagccgaggg aatttacata gaggggctaa tgcacaatca agatggttta   3600
atctgtgggt tgagacagct ggccaacgag acgactcaag ctcttcaact gttcctgaga   3660
gccacaactg agctacgcac cttttcaatc ctcaaccgta aggcaattga tttcttgctg   3720
cagcgatggg gcggcacatg ccacattctg ggaccggact gctgtatcga accacatgag   3780
```

```
gataccggca ggtattggag ttacaggcgt tgtaattgca gttatcgctt tattctgtat   3840
atgcaaattt gtcttttagt ttttcttcag attgcttcat ggaaaagctc agcctcaaat   3900
caatgaaacc aggatttaat tatatggatt acttgaatct aagattactt gacaaatgat   3960
aatataatac actggagctt taaacatagc caatgtgatt ctaactcctt taaactcaca   4020
gttaatcata aacaaggttt gaggtaccga gctcgaattg atctgctgtg ccttctagtt   4080
gccagccatc tgttgtttgc ccctcccccg tgccttcctt gaccctggaa ggtgccactc   4140
ccactgtcct ttcctaataa aatgaggaaa ttgcatcgca ttgtctgagt aggtgtcatt   4200
ctattctggg gggtggggtg gggcaggaca gcaaggggga ggattgggaa gacaatagca   4260
ggcatgctgg ggatgcggtg ggctctatgg gtacccaggt gctgaagaat tgacccggtt   4320
cctcctgggc cagaaagaag caggcacatc cccttctctg tgacacaccc tgtccacgcc   4380
cctggttctt agttccagcc ccactcatag gacactcata gctcaggagg gctccgcctt   4440
caatcccacc cgctaaagta cttggagcgg tctctccctc cctcatcagc ccaccaaacc   4500
aaacctagcc tccaagagtg ggaagaaatt aaagcaagat aggctattaa gtgcagaggg   4560
agagaaaatg cctccaacat gtgaggaagt aatgagagaa atcatagaat ttcttccgct   4620
tcctcgctca ctgactcgct gcgctcggtc gttcggctgc ggcgagcggt atcagctcac   4680
tcaaaggcgg taatacggtt atccacagaa tcaggggata acgcaggaaa gaacatgtga   4740
gcaaaaggcc agcaaaaggc caggaaccgt aaaaaggccg cgttgctggc gtttttccat   4800
aggctccgcc cccctgacga gcatcacaaa aatcgacgct caagtcagag gtggcgaaac   4860
ccgacaggac tataaagata ccaggcgttt ccccctggaa gctccctcgt gcgctctcct   4920
gttccgaccc tgccgcttac cggatacctg tccgcctttc tcccttcggg aagcgtggcg   4980
ctttctcata gctcacgctg taggtatctc agttcggtgt aggtcgttcg ctccaagctg   5040
ggctgtgtgc acgaaccccc cgttcagccc gaccgctgcg ccttatccgg taactatcgt   5100
cttgagtcca acccggtaag acacgactta tcgccactgg cagcagccac tggtaacagg   5160
attagcagag cgaggtatgt aggcggtgct acagagttct tgaagtggtg gcctaactac   5220
ggctacacta gaagaacagt atttggtatc tgcgctctgc tgaagccagt taccttcgga   5280
aaaagagttg gtagctcttg atccggcaaa caaaccaccg ctggtagcgg tggttttttt   5340
gtttgcaagc agcagattac gcgcagaaaa aaaggatctc aagaagatcc tttgatcttt   5400
tctacggggt ctgacgctca gtggaacgaa aactcacgtt aagggatttt ggtcatgaga   5460
ttatcaaaaa ggatcttcac ctagatcctt ttaaattaaa aatgaagttt taaatcaatc   5520
taaagtatat atgagtaaac ttggtctgac agttaccaat gcttaatcag tgaggcacct   5580
atctcagcga tctgtctatt tcgttcatcc atagttgcct gactcggggg gggggggcgc   5640
tgaggtctgc ctcgtgaaga aggtgttgct gactcatacc aggcctgaat cgccccatca   5700
tccagccaga aagtgaggga gccacggttg atgagagctt tgttgtaggt ggaccagttg   5760
gtgattttga acttttgctt tgccacggaa cggtctgcgt tgtcgggaag atgcgtgatc   5820
tgatccttca actcagcaaa agttcgattt attcaacaaa gccgccgtcc cgtcaagtca   5880
gcgtaatgct ctgccagtgt tacaaccaat taaccaattc tgattagaaa aactcatcga   5940
gcatcaaatg aaactgcaat ttattcatat caggattatc aataccatat ttttgaaaaa   6000
gccgtttctg taatgaagga gaaaactcac cgaggcagtt ccataggatg gcaagatcct   6060
ggtatcggtc tgcgattccg actcgtccaa catcaataca acctattaat ttcccctcgt   6120
caaaaataag gttatcaagt gagaaatcac catgagtgac gactgaatcc ggtgagaatg   6180
```

```
gcaaaagctt atgcatttct ttccagactt gttcaacagg ccagccatta cgctcgtcat   6240

caaaatcact cgcatcaacc aaaccgttat tcattcgtga ttgcgcctga gcgagacgaa   6300

atacgcgatc gctgttaaaa ggacaattac aaacaggaat cgaatgcaac cggcgcagga   6360

acactgccag cgcatcaaca atattttcac ctgaatcagg atattcttct aatacctgga   6420

atgctgtttt cccggggatc gcagtggtga gtaaccatgc atcatcagga gtacggataa   6480

aatgcttgat ggtcggaaga ggcataaatt ccgtcagcca gtttagtctg accatctcat   6540

ctgtaacatc attggcaacg ctacctttgc catgtttcag aaacaactct ggcgcatcgg   6600

gcttcccata caatcgatag attgtcgcac ctgattgccc gacattatcg cgagcccatt   6660

tatacccata taaatcagca tccatgttgg aatttaatcg cggcctcgag caagacgttt   6720

cccgttgaat atggctcata acaccccttg tattactgtt tatgtaagca gacagtttta   6780

ttgttcatga tgatatattt ttatcttgtg caatgtaaca tcagagattt tgagacacaa   6840

cgtggctttc cccccccccc cattattgaa gcatttatca gggttattgt ctcatgagcg   6900

gatacatatt tgaatgtatt tagaaaaata aacaaatagg ggttccgcgc acatttcccc   6960

gaaaagtgcc acctgacgtc taagaaacca ttattatcat gacattaacc tataaaaata   7020

ggcgtatcac gaggcccttt cgtc                                          7044
```

```
<210> SEQ ID NO 8
<211> LENGTH: 7106
<212> TYPE: DNA
<213> ORGANISM: Artificial Sequence
<220> FEATURE:
<223> OTHER INFORMATION: Synthetic Construct pVR1012-GP(Z) delta GP2
      delta FUS

<400> SEQUENCE: 8

tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatgcg gtgtgaaata ccgcacagat gcgtaaggag aaaataccgc atcagattgg    240

ctattggcca ttgcatacgt tgtatccata tcataatatg tacatttata ttggctcatg    300

tccaacatta ccgccatgtt gacattgatt attgactagt tattaatagt aatcaattac    360

ggggtcatta gttcatagcc catatatgga gttccgcgtt acataactta cggtaaatgg    420

cccgcctggc tgaccgccca acgacccccg cccattgacg tcaataatga cgtatgttcc    480

catagtaacg ccaataggga ctttccattg acgtcaatgg gtggagtatt tacggtaaac    540

tgcccacttg gcagtacatc aagtgtatca tatgccaagt acgcccccta ttgacgtcaa    600

tgacggtaaa tggcccgcct ggcattatgc ccagtacatg accttatggg actttcctac    660

ttggcagtac atctacgtat tagtcatcgc tattaccatg gtgatgcggt tttggcagta    720

catcaatggg cgtggatagc ggtttgactc acggggattt ccaagtctcc accccattga    780

cgtcaatggg agtttgtttt ggcaccaaaa tcaacgggac tttccaaaat gtcgtaacaa    840

ctccgcccca ttgacgcaaa tgggcggtag gcgtgtacgg tgggaggtct atataagcag    900

agctcgttta gtgaaccgtc agatcgcctg gagacgccat ccacgctgtt ttgacctcca    960

tagaagacac cgggaccgat ccagcctccg cggccgggaa cggtgcattg gaacgcggat   1020

tccccgtgcc aagagtgacg taagtaccgc ctatagactc tataggcaca cccctttggc   1080

tcttatgcat gctatactgt ttttggcttg gggcctatac acccccgctt ccttatgcta   1140
```

-continued taggtgatgg tatagcttag cctataggtg tgggttattg accattattg accactcccc 1200
tattggtgac gatactttcc attactaatc cataacatgg ctctttgcca caactatctc 1260
tattggctat atgccaatac tctgtccttc agagactgac acggactctg tatttttaca 1320
ggatggggtc ccatttatta tttacaaatt cacatataca acaacgccgt cccccgtgcc 1380
cgcagttttt attaaacata gcgtgggatc tccacgcgaa tctcgggtac gtgttccgga 1440
catgggctct tctccggtag cggcggagct tccacatccg agccctggtc ccatgcctcc 1500
agcggctcat ggtcgctcgg cagctccttg ctcctaacag tggaggccag acttaggcac 1560
agcacaatgc ccaccaccac cagtgtgccg cacaaggccg tggcggtagg gtatgtgtct 1620
gaaaatgagc gtggagattg ggctcgcacg gctgacgcag atggaagact taaggcagcg 1680
gcagaagaag atgcaggcag ctgagttgtt gtattctgat aagagtcaga ggtaactccc 1740
gttgcggtgc tgttaacggt ggagggcagt gtagtctgag cagtactcgt tgctgccgcg 1800
cgcgccacca gacataatag ctgacagact aacagactgt tcctttccat gggtcttttc 1860
tgcagtcacc gtcgtcgaca cgtgtgatca gatatcgcgg ccgctctaga ccaggccctg 1920
gatcgatcca acaacacaat gggcgttaca ggaatattgc agttacctcg tgatcgattc 1980
aagaggacat cattctttct ttgggtaatt atccttttcc aaagaacatt ttccatccca 2040
cttggagtca tccacaatag cacattacag gttagtgatg tcgacaaact agtttgtcgt 2100
gacaaactgt catccacaaa tcaattgaga tcagttggac tgaatctcga agggaatgga 2160
gtggcaactg acgtgccatc tgcaactaaa agatggggct tcaggtccgg tgtcccacca 2220
aaggtggtca attatgaagc tggtgaatgg gctgaaaact gctacaatct tgaaatcaaa 2280
aaacctgacg ggagtgagtg tctaccagca gcgccagacg ggattcgggg cttcccccgg 2340
tgccggtatg tgcacaaagt atcaggaacg ggaccgtgtg ccggagactt tgccttccat 2400
aaagagggtg ctttcttcct gtatgatcga cttgcttcca cagttatcta ccgaggaacg 2460
actttcgctg aaggtgtcgt tgcatttctg atactgcccc aagctaagaa ggacttcttc 2520
agctcacacc ccttgagaga gccggtcaat gcaacggagg acccgtctag tggctactat 2580
tctaccacaa ttagatatca ggctaccggt tttggaacca atgagacaga gtacttgttc 2640
gaggttgaca atttgaccta cgtccaactt gaatcaagat tcacaccaca gtttctgctc 2700
cagctgaatg agacaatata tacaagtggg aaaaggagca ataccacggg aaaactaatt 2760
tggaaggtca accccgaaat tgatacaaca atcggggagt gggccttctg ggaaactaaa 2820
aaaaacctca ctagaaaaat tcgcagtgaa gagttgtctt tcacagttgt atcaaacgga 2880
gccaaaaaca tcagtggtca gagtccggcg cgaacttctt ccgacccagg gaccaacaca 2940
acaactgaag accacaaaat catggcttca gaaaattcct ctgcaatggt tcaagtgcac 3000
agtcaaggaa gggaagctgc agtgtcgcat ctaacaaccc ttgccacaat ctccacgagt 3060
ccccaatccc tcacaaccaa accaggtccg gacaacagca cccataatac acccgtgtat 3120
aaacttgaca tctctgaggc aactcaagtt gaacaacatc accgcagaac agacaacgac 3180
agcacagcct ccgacactcc ctctgccacg accgcagccg gacccccaaa agcagagaac 3240
accaacacga gcaagagcac tgacttcctg gaccccgcca ccacaacaag tccccaaaac 3300
cacagcgaga ccgctggcaa caacaacact catcaccaag ataccggaga agagagtgcc 3360
agcagcggga agctaggctt aattaccaat actattgctg gagtcgcagg actgatcaca 3420
ggcgggagaa gaactcgaag agaagcaatt gtcaatgctc aacccaaatg caaccctaat 3480
ttacattact ggactactca ggatgaagag ggaatttaca tagaggggct aatgcacaat 3540

-continued

```
caagatggtt taatctgtgg gttgagacag ctggccaacg agacgactca agctcttcaa   3600
ctgttcctga gagccacaac tgagctacgc accttttcaa tcctcaaccg taaggcaatt   3660
gatttcttgc tgcagcgatg gggcggcaca tgccacattc tgggaccgga ctgctgtatc   3720
gaaccacatg attggaccaa gaacataaca gacaaaattg atcagattat tcatgatttt   3780
gttgataaaa cccttccgga ccaggggac aatgacaatt ggtggacagg atggagacaa   3840
tggataccgg caggtattgg agttacaggc gttgtaattg cagttatcgc tttattctgt   3900
atatgcaaat ttgtctttta gtttttcttc agattgcttc atggaaaagc tcagcctcaa   3960
atcaatgaaa ccaggattta attatatgga ttacttgaat ctaagattac ttgacaaatg   4020
ataatataat acactggagc tttaaacata gccaatgtga ttctaactcc tttaaactca   4080
cagttaatca taaacaaggt ttgaggtacc gagctcgaat tgatctgctg tgccttctag   4140
ttgccagcca tctgttgttt gcccctcccc cgtgccttcc ttgaccctgg aaggtgccac   4200
tcccactgtc ctttcctaat aaaatgagga aattgcatcg cattgtctga gtaggtgtca   4260
ttctattctg gggggtgggg tggggcagga cagcaagggg gaggattggg aagacaatag   4320
caggcatgct ggggatgcgg tgggctctat gggtacccag gtgctgaaga attgacccgg   4380
ttcctcctgg gccagaaaga agcaggcaca tccccttctc tgtgacacac cctgtccacg   4440
cccctggttc ttagttccag ccccactcat aggacactca tagctcagga gggctccgcc   4500
ttcaatccca cccgctaaag tacttggagc ggtctctccc tccctcatca gcccaccaaa   4560
ccaaacctag cctccaagag tgggaagaaa ttaaagcaag ataggctatt aagtgcagag   4620
ggagagaaaa tgcctccaac atgtgaggaa gtaatgagag aaatcataga atttcttccg   4680
cttcctcgct cactgactcg ctgcgctcgg tcgttcggct gcggcgagcg gtatcagctc   4740
actcaaaggc ggtaatacgg ttatccacag aatcagggga taacgcagga aagaacatgt   4800
gagcaaaagg ccagcaaaag gccaggaacc gtaaaaaggc cgcgttgctg gcgtttttcc   4860
ataggctccg cccccctgac gagcatcaca aaaatcgacg ctcaagtcag aggtggcgaa   4920
acccgacagg actataaaga taccaggcgt ttccccctgg aagctccctc gtgcgctctc   4980
ctgttccgac cctgccgctt accggatacc tgtccgcctt tctcccttcg ggaagcgtgg   5040
cgctttctca tagctcacgc tgtaggtatc tcagttcggt gtaggtcgtt cgctccaagc   5100
tgggctgtgt gcacgaaccc cccgttcagc ccgaccgctg cgccttatcc ggtaactatc   5160
gtcttgagtc caacccggta agacacgact tatcgccact ggcagcagcc actggtaaca   5220
ggattagcag agcgaggtat gtaggcggtg ctacagagtt cttgaagtgg tggcctaact   5280
acggctacac tagaagaaca gtatttggta tctgcgctct gctgaagcca gttaccttcg   5340
gaaaaagagt tggtagctct tgatccggca aacaaaccac cgctggtagc ggtggttttt   5400
ttgtttgcaa gcagcagatt acgcgcagaa aaaaaggatc tcaagaagat cctttgatct   5460
tttctacggg gtctgacgct cagtggaacg aaaactcacg ttaagggatt ttggtcatga   5520
gattatcaaa aaggatcttc acctagatcc ttttaaatta aaaatgaagt tttaaatcaa   5580
tctaaagtat atatgagtaa acttggtctg acagttacca atgcttaatc agtgaggcac   5640
ctatctcagc gatctgtcta tttcgttcat ccatagttgc ctgactcggg gggggggggc   5700
gctgaggtct gcctcgtgaa gaaggtgttg ctgactcata ccaggcctga atcgccccat   5760
catccagcca gaaagtgagg gagccacggt tgatgagagc tttgttgtag gtggaccagt   5820
tggtgatttt gaacttttgc tttgccacgg aacggtctgc gttgtcggga agatgcgtga   5880
tctgatcctt caactcagca aaagttcgat ttattcaaca aagccgccgt cccgtcaagt   5940
```

-continued cagcgtaatg ctctgccagt gttacaacca attaaccaat tctgattaga aaaactcatc 6000
gagcatcaaa tgaaactgca atttattcat atcaggatta tcaataccat atttttgaaa 6060
aagccgtttc tgtaatgaag gagaaaactc accgaggcag ttccatagga tggcaagatc 6120
ctggtatcgg tctgcgattc cgactcgtcc aacatcaata caacctatta atttcccctc 6180
gtcaaaaata aggttatcaa gtgagaaatc accatgagtg acgactgaat ccggtgagaa 6240
tggcaaaagc ttatgcattt ctttccagac ttgttcaaca ggccagccat tacgctcgtc 6300
atcaaaatca ctcgcatcaa ccaaaccgtt attcattcgt gattgcgcct gagcgagacg 6360
aaatacgcga tcgctgttaa aaggacaatt acaaacagga atcgaatgca accggcgcag 6420
gaacactgcc agcgcatcaa caatattttc acctgaatca ggatattctt ctaatacctg 6480
gaatgctgtt ttcccgggga tcgcagtggt gagtaaccat gcatcatcag gagtacggat 6540
aaaatgcttg atggtcggaa gaggcataaa ttccgtcagc cagtttagtc tgaccatctc 6600
atctgtaaca tcattggcaa cgctaccttt gccatgtttc agaaacaact ctggcgcatc 6660
gggcttccca tacaatcgat agattgtcgc acctgattgc ccgacattat cgcgagccca 6720
tttataccca tataaatcag catccatgtt ggaatttaat cgcggcctcg agcaagacgt 6780
ttcccgttga atatggctca taacacccct tgtattactg tttatgtaag cagacagttt 6840
tattgttcat gatgatatat ttttatcttg tgcaatgtaa catcagagat tttgagacac 6900
aacgtggctt tccccccccc cccattattg aagcatttat cagggttatt gtctcatgag 6960
cggatacata tttgaatgta tttagaaaaa taaacaaata ggggttccgc gcacatttcc 7020
ccgaaaagtg ccacctgacg tctaagaaac cattattatc atgacattaa cctataaaaa 7080
taggcgtatc acgaggccct ttcgtc 7106

<210> SEQ ID NO 9
<211> LENGTH: 6914
<212> TYPE: DNA
<213> ORGANISM: Artificial Sequence
<220> FEATURE:
<223> OTHER INFORMATION: Synthetic Construct pVR1012-GP(Z) delta TM

<400> SEQUENCE: 9
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcagattgg 240
ctattggcca ttgcatacgt tgtatccata tcataatatg tacatttata ttggctcatg 300
tccaacatta ccgccatgtt gacattgatt attgactagt tattaatagt aatcaattac 360
ggggtcatta gttcatagcc catatatgga gttccgcgtt acataactta cggtaaatgg 420
cccgcctggc tgaccgccca acgacccccg cccattgacg tcaataatga cgtatgttcc 480
catagtaacg ccaataggga ctttccattg acgtcaatgg gtggagtatt tacggtaaac 540
tgcccacttg gcagtacatc aagtgtatca tatgccaagt acgcccccta ttgacgtcaa 600
tgacggtaaa tggcccgcct ggcattatgc ccagtacatg accttatggg actttcctac 660
ttggcagtac atctacgtat tagtcatcgc tattaccatg gtgatgcggt tttggcagta 720
catcaatggg cgtggatagc ggtttgactc acggggattt ccaagtctcc accccattga 780
cgtcaatggg agtttgtttt ggcaccaaaa tcaacgggac tttccaaaat gtcgtaacaa 840
ctccgcccca ttgacgcaaa tgggcggtag gcgtgtacgg tgggaggtct atataagcag 900

```
agctcgttta gtgaaccgtc agatcgcctg gagacgccat ccacgctgtt ttgacctcca    960
tagaagacac cgggaccgat ccagcctccg cggccgggaa cggtgcattg gaacgcggat   1020
tccccgtgcc aagagtgacg taagtaccgc ctatagactc tataggcaca cccctttggc   1080
tcttatgcat gctatactgt ttttggcttg gggcctatac acccccgctt ccttatgcta   1140
taggtgatgg tatagcttag cctataggtg tgggttattg accattattg accactcccc   1200
tattggtgac gatactttcc attactaatc cataacatgg ctctttgcca caactatctc   1260
tattggctat atgccaatac tctgtccttc agagactgac acggactctg tatttttaca   1320
ggatggggtc ccatttatta tttacaaatt cacatataca acaacgccgt cccccgtgcc   1380
cgcagttttt attaaacata gcgtgggatc tccacgcgaa tctcgggtac gtgttccgga   1440
catgggctct tctccggtag cggcggagct tccacatccg agccctggtc ccatgcctcc   1500
agcggctcat ggtcgctcgg cagctccttg ctcctaacag tggaggccag acttaggcac   1560
agcacaatgc ccaccaccac cagtgtgccg cacaaggccg tggcggtagg gtatgtgtct   1620
gaaaatgagc gtggagattg ggctcgcacg gctgacgcag atggaagact taaggcagcg   1680
gcagaagaag atgcaggcag ctgagttgtt gtattctgat aagagtcaga ggtaactccc   1740
gttgcggtgc tgttaacggt ggagggcagt gtagtctgag cagtactcgt tgctgccgcg   1800
cgcgccacca gacataatag ctgacagact aacagactgt tcctttccat gggtcttttc   1860
tgcagtcacc gtcgtcgaca cgtgtgatca gatatcgcgg ccgctctaga ccaggccctg   1920
gatcgatcca acaacacaat gggcgttaca ggaatattgc agttacctcg tgatcgattc   1980
aagaggacat cattctttct ttgggtaatt atcctttttcc aaagaacatt ttccatccca   2040
cttggagtca tccacaatag cacattacag gttagtgatg tcgacaaact agtttgtcgt   2100
gacaaactgt catccacaaa tcaattgaga tcagttggac tgaatctcga agggaatgga   2160
gtggcaactg acgtgccatc tgcaactaaa agatggggct tcaggtccgg tgtcccacca   2220
aaggtggtca attatgaagc tggtgaatgg gctgaaaact gctacaatct tgaaatcaaa   2280
aaacctgacg ggagtgagtg tctaccagca gcgccagacg ggattcgggg cttccccccgg   2340
tgccggtatg tgcacaaagt atcaggaacg ggaccgtgtg ccggagactt tgccttccat   2400
aaagagggtg ctttcttcct gtatgatcga cttgcttcca cagttatcta ccgaggaacg   2460
actttcgctg aaggtgtcgt tgcatttctg atactgcccc aagctaagaa ggacttcttc   2520
agctcacacc ccttgagaga gccggtcaat gcaacggagg acccgtctag tggctactat   2580
tctaccacaa ttagatatca ggctaccggt tttggaacca atgagacaga gtacttgttc   2640
gaggttgaca atttgaccta cgtccaactt gaatcaagat tcacaccaca gtttctgctc   2700
cagctgaatg agacaatata tacaagtggg aaaaggagca ataccacggg aaaactaatt   2760
tggaaggtca accccgaaat tgatacaaca atcggggagt gggccttctg ggaaactaaa   2820
aaaaacctca ctagaaaaat tcgcagtgaa gagttgtctt tcacagttgt atcaaacgga   2880
gccaaaaaca tcagtggtca gagtccggcg cgaacttctt ccgacccagg gaccaacaca   2940
acaactgaag accacaaaat catggcttca gaaaattcct ctgcaatggt tcaagtgcac   3000
agtcaaggaa gggaagctgc agtgtcgcat ctaacaaccc ttgccacaat ctccacgagt   3060
ccccaatccc tcacaaccaa accaggtccg gacaacagca cccataatac acccgtgtat   3120
aaacttgaca tctctgaggc aactcaagtt gaacaacatc accgcagaac agacaacgac   3180
agcacagcct ccgacactcc ctctgccacg accgcagccg gacccccaaa agcagagaac   3240
accaacacga gcaagagcac tgacttcctg gaccccgcca ccacaacaag tccccaaaac   3300
```

-continued

```
cacagcgaga ccgctggcaa caacaacact catcaccaag ataccggaga agagagtgcc   3360
agcagcggga agctaggctt aattaccaat actattgctg gagtcgcagg actgatcaca   3420
ggcgggagaa gaactcgaag agaagcaatt gtcaatgctc aacccaaatg caaccctaat   3480
ttacattact ggactactca ggatgaaggt gctgcaatcg gactggcctg gataccatat   3540
ttcgggccag cagccgaggg aatttacata gaggggctaa tgcacaatca agatggttta   3600
atctgtgggt tgagacagct ggccaacgag acgactcaag ctcttcaact gttcctgaga   3660
gccacaactg agctacgcac cttttcaatc ctcaaccgta aggcaattga tttcttgctg   3720
cagcgatggg gcggcacatg ccacattctg ggaccggact gctgtatcga accacatgat   3780
tggaccaaga acataacaga caaaattgat cagattattc atgattttgt tgataaaacc   3840
cttccggacc agggggacaa tgacaattgg tggacaggat ggagacaatg gatggccgca   3900
tcgtgactga ctgacgatct gcctcgcgag atctgctgtg ccttctagtt gccagccatc   3960
tgttgtttgc ccctcccccg tgccttcctt gaccctggaa ggtgccactc ccactgtcct   4020
ttcctaataa aatgaggaaa ttgcatcgca ttgtctgagt aggtgtcatt ctattctggg   4080
gggtggggtg gggcaggaca gcaaggggga ggattgggaa gacaatagca ggcatgctgg   4140
ggatgcggtg ggctctatgg gtacccaggt gctgaagaat tgacccggtt cctcctgggc   4200
cagaaagaag caggcacatc cccttctctg tgacacaccc tgtccacgcc cctggttctt   4260
agttccagcc ccactcatag gacactcata gctcaggagg gctccgcctt caatcccacc   4320
cgctaaagta cttggagcgg tctctccctc cctcatcagc ccaccaaacc aaacctagcc   4380
tccaagagtg ggaagaaatt aaagcaagat aggctattaa gtgcagaggg agagaaaatg   4440
cctccaacat gtgaggaagt aatgagagaa atcatagaat ttcttccgct tcctcgctca   4500
ctgactcgct gcgctcggtc gttcggctgc ggcgagcggt atcagctcac tcaaaggcgg   4560
taatacggtt atccacagaa tcaggggata acgcaggaaa gaacatgtga gcaaaaggcc   4620
agcaaaaggc caggaaccgt aaaaaggccg cgttgctggc gtttttccat aggctccgcc   4680
cccctgacga gcatcacaaa aatcgacgct caagtcagag gtggcgaaac ccgacaggac   4740
tataaagata ccaggcgttt ccccctggaa gctccctcgt gcgctctcct gttccgaccc   4800
tgccgcttac cggatacctg tccgcctttc tcccttcggg aagcgtggcg ctttctcata   4860
gctcacgctg taggtatctc agttcggtgt aggtcgttcg ctccaagctg ggctgtgtgc   4920
acgaaccccc cgttcagccc gaccgctgcg ccttatccgg taactatcgt cttgagtcca   4980
acccggtaag acacgactta tcgccactgg cagcagccac tggtaacagg attagcagag   5040
cgaggtatgt aggcggtgct acagagttct tgaagtggtg gcctaactac ggctacacta   5100
gaagaacagt atttggtatc tgcgctctgc tgaagccagt taccttcgga aaaagagttg   5160
gtagctcttg atccggcaaa caaaccaccg ctggtagcgg tggttttttt gtttgcaagc   5220
agcagattac gcgcagaaaa aaaggatctc aagaagatcc tttgatcttt tctacggggt   5280
ctgacgctca gtggaacgaa aactcacgtt aagggatttt ggtcatgaga ttatcaaaaa   5340
ggatcttcac ctagatcctt ttaaattaaa aatgaagttt taaatcaatc taaagtatat   5400
atgagtaaac ttggtctgac agttaccaat gcttaatcag tgaggcacct atctcagcga   5460
tctgtctatt tcgttcatcc atagttgcct gactcggggg gggggggcgc tgaggtctgc   5520
ctcgtgaaga aggtgttgct gactcatacc aggcctgaat cgccccatca tccagccaga   5580
aagtgaggga gccacggttg atgagagctt tgttgtaggt ggaccagttg gtgattttga   5640
acttttgctt tgccacggaa cggtctgcgt tgtcgggaag atgcgtgatc tgatccttca   5700
```

-continued actcagcaaa agttcgattt attcaacaaa gccgccgtcc cgtcaagtca gcgtaatgct 5760
ctgccagtgt tacaaccaat taaccaattc tgattagaaa aactcatcga gcatcaaatg 5820
aaactgcaat ttattcatat caggattatc aataccatat ttttgaaaaa gccgtttctg 5880
taatgaagga gaaaactcac cgaggcagtt ccataggatg gcaagatcct ggtatcggtc 5940
tgcgattccg actcgtccaa catcaataca acctattaat ttcccctcgt caaaaataag 6000
gttatcaagt gagaaatcac catgagtgac gactgaatcc ggtgagaatg gcaaaagctt 6060
atgcatttct ttccagactt gttcaacagg ccagccatta cgctcgtcat caaaatcact 6120
cgcatcaacc aaaccgttat tcattcgtga ttgcgcctga gcgagacgaa atacgcgatc 6180
gctgttaaaa ggacaattac aaacaggaat cgaatgcaac cggcgcagga acactgccag 6240
cgcatcaaca atattttcac ctgaatcagg atattcttct aatacctgga atgctgtttt 6300
cccggggatc gcagtggtga gtaaccatgc atcatcagga gtacggataa aatgcttgat 6360
ggtcggaaga ggcataaatt ccgtcagcca gtttagtctg accatctcat ctgtaacatc 6420
attggcaacg ctacctttgc catgtttcag aaacaactct ggcgcatcgg gcttcccata 6480
caatcgatag attgtcgcac ctgattgccc gacattatcg cgagcccatt tatacccata 6540
taaatcagca tccatgttgg aatttaatcg cggcctcgag caagacgttt cccgttgaat 6600
atggctcata acaccccttg tattactgtt tatgtaagca gacagtttta ttgttcatga 6660
tgatatattt ttatcttgtg caatgtaaca tcagagattt tgagacacaa cgtggctttc 6720
cccccccccc cattattgaa gcatttatca gggttattgt ctcatgagcg gatacatatt 6780
tgaatgtatt tagaaaaata aacaaatagg ggttccgcgc acatttcccc gaaaagtgcc 6840
acctgacgtc taagaaacca ttattatcat gacattaacc tataaaaata ggcgtatcac 6900
gaggcccttt cgtc 6914

<210> SEQ ID NO 10
<211> LENGTH: 6467
<212> TYPE: DNA
<213> ORGANISM: Artificial Sequence
<220> FEATURE:
<223> OTHER INFORMATION: Synthetic Construct pVR1012-GP(Z) delta SGP

<400> SEQUENCE: 10
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcagattgg 240
ctattggcca ttgcatacgt tgtatccata tcataatatg tacatttata ttggctcatg 300
tccaacatta ccgccatgtt gacattgatt attgactagt tattaatagt aatcaattac 360
ggggtcatta gttcatagcc catatatgga gttccgcgtt acataactta cggtaaatgg 420
cccgcctggc tgaccgccca acgacccccg cccattgacg tcaataatga cgtatgttcc 480
catagtaacg ccaataggga ctttccattg acgtcaatgg gtggagtatt tacggtaaac 540
tgcccacttg gcagtacatc aagtgtatca tatgccaagt acgcccccta ttgacgtcaa 600
tgacggtaaa tggcccgcct ggcattatgc ccagtacatg accttatggg actttcctac 660
ttggcagtac atctacgtat tagtcatcgc tattaccatg gtgatgcggt tttggcagta 720
catcaatggg cgtggatagc ggtttgactc acggggattt ccaagtctcc accccattga 780
cgtcaatggg agtttgtttt ggcaccaaaa tcaacgggac tttccaaaat gtcgtaacaa 840

-continued

```
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctccg cggccgggaa cggtgcattg gaacgcggat   1020
tccccgtgcc aagagtgacg taagtaccgc ctatagactc tataggcaca cccctttggc   1080
tcttatgcat gctatactgt ttttggcttg gggcctatac acccccgctt ccttatgcta   1140
taggtgatgg tatagcttag cctataggtg tgggttattg accattattg accactcccc   1200
tattggtgac gatactttcc attactaatc cataacatgg ctctttgcca caactatctc   1260
tattggctat atgccaatac tctgtccttc agagactgac acggactctg tatttttaca   1320
ggatggggtc ccatttatta tttacaaatt cacatataca acaacgccgt cccccgtgcc   1380
cgcagttttt attaaacata gcgtgggatc tccacgcgaa tctcgggtac gtgttccgga   1440
catgggctct tctccggtag cggcggagct tccacatccg agccctggtc ccatgcctcc   1500
agcggctcat ggtcgctcgg cagctccttg ctcctaacag tggaggccag acttaggcac   1560
agcacaatgc ccaccaccac cagtgtgccg cacaaggccg tggcggtagg gtatgtgtct   1620
gaaaatgagc gtggagattg ggctcgcacg gctgacgcag atggaagact taaggcagcg   1680
gcagaagaag atgcaggcag ctgagttgtt gtattctgat aagagtcaga ggtaactccc   1740
gttgcggtgc tgttaacggt ggagggcagt gtagtctgag cagtactcgt tgctgccgcg   1800
cgcgccacca gacataatag ctgacagact aacagactgt tcctttccat gggtcttttc   1860
tgcagtcacc gtcgtcgaca cgtgtgatca gatatcgcgg ccgctctaga ccaggccctg   1920
gatcgatcca acaacacaat gggcgttaca ggaatattgc agttacctcg tgatcgattc   1980
aagaggacat cattctttct ttgggtaatt atccttttcc aaagaacatt ttccatccca   2040
cttggagtca tccacaatag cacattacag gttagtgatg tcaaccccga aattgataca   2100
acaatcgggg agtgggcctt ctgggaaact aaaaaaaacc tcactagaaa aattcgcagt   2160
gaagagttgt ctttcacagt tgtatcaaac ggagccaaaa acatcagtgg tcagagtccg   2220
gcgcgaactt cttccgaccc agggaccaac acaacaactg aagaccacaa aatcatggct   2280
tcagaaaatt cctctgcaat ggttcaagtg cacagtcaag gaagggaagc tgcagtgtcg   2340
catctaacaa cccttgccac aatctccacg agtccccaat ccctcacaac caaaccaggt   2400
ccggacaaca gcacccataa tacacccgtg tataaacttg acatctctga ggcaactcaa   2460
gttgaacaac atcaccgcag aacagacaac gacagcacag cctccgacac tccctctgcc   2520
acgaccgcag ccggaccccc aaaagcagag aacaccaaca cgagcaagag cactgacttc   2580
ctggaccccg ccaccacaac aagtccccaa aaccacagcg agaccgctgg caacaacaac   2640
actcatcacc aagataccgg agaagagagt gccagcagcg ggaagctagg cttaattacc   2700
aatactattg ctggagtcgc aggactgatc acaggcggga gaagaactcg aagagaagca   2760
attgtcaatg ctcaacccaa atgcaaccct aatttacatt actggactac tcaggatgaa   2820
ggtgctgcaa tcggactggc ctggatacca tatttcgggc cagcagccga gggaatttac   2880
atagaggggc taatgcacaa tcaagatggt ttaatctgtg ggttgagaca gctggccaac   2940
gagacgactc aagctcttca actgttcctg agagccacaa ctgagctacg cacctttca    3000
atcctcaacc gtaaggcaat tgatttcttg ctgcagcgat ggggcggcac atgccacatt   3060
ctgggaccgg actgctgtat cgaaccacat gattggacca agaacataac agacaaaatt   3120
gatcagatta ttcatgattt tgttgataaa acccttccgg accagggga caatgacaat    3180
tggtggacag gatggagaca atggataccg gcaggtattg gagttacagg cgttgtaatt   3240
```

-continued

```
gcagttatcg ctttattctg tatatgcaaa tttgtctttt agtttttctt cagattgctt   3300
catggaaaag ctcagcctca aatcaatgaa accaggattt aattatatgg attacttgaa   3360
tctaagatta cttgacaaat gataatataa tacactggag ctttaaacat agccaatgtg   3420
attctaactc ctttaaactc acagttaatc ataaacaagg tttgaggtac cgagctcgaa   3480
ttgatctgct gtgccttcta gttgccagcc atctgttgtt tgcccctccc ccgtgccttc   3540
cttgaccctg gaaggtgcca ctcccactgt cctttcctaa taaaatgagg aaattgcatc   3600
gcattgtctg agtaggtgtc attctattct ggggggtggg gtggggcagg acagcaaggg   3660
ggaggattgg gaagacaata gcaggcatgc tggggatgcg gtgggctcta tgggtaccca   3720
ggtgctgaag aattgacccg gttcctcctg ggccagaaag aagcaggcac atccccttct   3780
ctgtgacaca ccctgtccac gcccctggtt cttagttcca gccccactca taggacactc   3840
atagctcagg agggctccgc cttcaatccc acccgctaaa gtacttggag cggtctctcc   3900
ctccctcatc agcccaccaa accaaaccta gcctccaaga gtgggaagaa attaaagcaa   3960
gataggctat taagtgcaga gggagagaaa atgcctccaa catgtgagga agtaatgaga   4020
gaaatcatag aatttcttcc gcttcctcgc tcactgactc gctgcgctcg gtcgttcggc   4080
tgcggcgagc ggtatcagct cactcaaagg cggtaatacg gttatccaca gaatcagggg   4140
ataacgcagg aaagaacatg tgagcaaaag gccagcaaaa ggccaggaac cgtaaaaagg   4200
ccgcgttgct ggcgtttttc cataggctcc gcccccctga cgagcatcac aaaaatcgac   4260
gctcaagtca gaggtggcga aacccgacag gactataaag ataccaggcg tttccccctg   4320
gaagctccct cgtgcgctct cctgttccga ccctgccgct taccggatac ctgtccgcct   4380
ttctcccttc gggaagcgtg gcgctttctc atagctcacg ctgtaggtat ctcagttcgg   4440
tgtaggtcgt tcgctccaag ctgggctgtg tgcacgaacc ccccgttcag cccgaccgct   4500
gcgccttatc cggtaactat cgtcttgagt ccaacccggt aagacacgac ttatcgccac   4560
tggcagcagc cactggtaac aggattagca gagcgaggta tgtaggcggt gctacagagt   4620
tcttgaagtg gtggcctaac tacggctaca ctagaagaac agtatttggt atctgcgctc   4680
tgctgaagcc agttaccttc ggaaaaagag ttggtagctc ttgatccggc aaacaaacca   4740
ccgctggtag cggtggtttt tttgtttgca agcagcagat tacgcgcaga aaaaaaggat   4800
ctcaagaaga tcctttgatc ttttctacgg ggtctgacgc tcagtggaac gaaaactcac   4860
gttaagggat tttggtcatg agattatcaa aaaggatctt cacctagatc cttttaaatt   4920
aaaaatgaag ttttaaatca atctaaagta tatatgagta aacttggtct gacagttacc   4980
aatgcttaat cagtgaggca cctatctcag cgatctgtct atttcgttca tccatagttg   5040
cctgactcgg gggggggggg cgctgaggtc tgcctcgtga agaaggtgtt gctgactcat   5100
accaggcctg aatcgcccca tcatccagcc agaaagtgag ggagccacgg ttgatgagag   5160
ctttgttgta ggtggaccag ttggtgattt tgaacttttg ctttgccacg gaacggtctg   5220
cgttgtcggg aagatgcgtg atctgatcct tcaactcagc aaaagttcga tttattcaac   5280
aaagccgccg tcccgtcaag tcagcgtaat gctctgccag tgttacaacc aattaaccaa   5340
ttctgattag aaaaactcat cgagcatcaa atgaaactgc aatttattca tatcaggatt   5400
atcaatacca tatttttgaa aaagccgttt ctgtaatgaa ggagaaaact caccgaggca   5460
gttccatagg atggcaagat cctggtatcg gtctgcgatt ccgactcgtc caacatcaat   5520
acaacctatt aatttcccct cgtcaaaaat aaggttatca agtgagaaat caccatgagt   5580
gacgactgaa tccggtgaga atggcaaaag cttatgcatt tctttccaga cttgttcaac   5640
```

aggccagcca ttacgctcgt catcaaaatc actcgcatca accaaaccgt tattcattcg 5700
tgattgcgcc tgagcgagac gaaatacgcg atcgctgtta aaaggacaat tacaaacagg 5760
aatcgaatgc aaccggcgca ggaacactgc cagcgcatca acaatatttt cacctgaatc 5820
aggatattct tctaatacct ggaatgctgt tttcccgggg atcgcagtgg tgagtaacca 5880
tgcatcatca ggagtacgga taaaatgctt gatggtcgga agaggcataa attccgtcag 5940
ccagtttagt ctgaccatct catctgtaac atcattggca acgctacctt tgccatgttt 6000
cagaaacaac tctggcgcat cgggcttccc atacaatcga tagattgtcg cacctgattg 6060
cccgacatta tcgcgagccc atttataccc atataaatca gcatccatgt tggaatttaa 6120
tcgcggcctc gagcaagacg tttcccgttg aatatggctc ataacacccc ttgtattact 6180
gtttatgtaa gcagacagtt ttattgttca tgatgatata tttttatctt gtgcaatgta 6240
acatcagaga ttttgagaca caacgtggct ttcccccccc ccccattatt gaagcattta 6300
tcagggttat tgtctcatga gcggatacat atttgaatgt atttagaaaa ataaacaaat 6360
aggggttccg cgcacatttc cccgaaaagt gccacctgac gtctaagaaa ccattattat 6420
catgacatta acctataaaa ataggcgtat cacgaggccc tttcgtc 6467

<210> SEQ ID NO 11
<211> LENGTH: 6913
<212> TYPE: DNA
<213> ORGANISM: Artificial Sequence
<220> FEATURE:
<223> OTHER INFORMATION: Synthetic Construct pVR1012x/s Ebola GP(R)
(dTM)

<400> SEQUENCE: 11
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcagattgg 240
ctattggcca ttgcatacgt tgtatccata tcataatatg tacatttata ttggctcatg 300
tccaacatta ccgccatgtt gacattgatt attgactagt tattaatagt aatcaattac 360
ggggtcatta gttcatagcc catatatgga gttccgcgtt acataactta cggtaaatgg 420
cccgcctggc tgaccgccca acgacccccg cccattgacg tcaataatga cgtatgttcc 480
catagtaacg ccaataggga ctttccattg acgtcaatgg gtggagtatt tacggtaaac 540
tgcccacttg gcagtacatc aagtgtatca tatgccaagt acgcccccta ttgacgtcaa 600
tgacggtaaa tggcccgcct ggcattatgc ccagtacatg accttatggg actttcctac 660
ttggcagtac atctacgtat tagtcatcgc tattaccatg gtgatgcggt tttggcagta 720
catcaatggg cgtggatagc ggtttgactc acggggattt ccaagtctcc accccattga 780
cgtcaatggg agtttgtttt ggcaccaaaa tcaacgggac tttccaaaat gtcgtaacaa 840
ctccgcccca ttgacgcaaa tgggcggtag gcgtgtacgg tgggaggtct atataagcag 900
agctcgttta gtgaaccgtc agatcgcctg gagacgccat ccacgctgtt ttgacctcca 960
tagaagacac cgggaccgat ccagcctccg cggccgggaa cggtgcattg gaacgcggat 1020
tccccgtgcc aagagtgacg taagtaccgc ctatagactc tataggcaca cccctttggc 1080
tcttatgcat gctatactgt ttttggcttg gggcctatac acccccgctt ccttatgcta 1140
taggtgatgg tatagcttag cctataggtg tgggttattg accattattg accactcccc 1200
tattggtgac gatactttcc attactaatc cataacatgg ctctttgcca caactatctc 1260

-continued tattggctat atgccaatac tctgtccttc agagactgac acggactctg tatttttaca 1320
ggatggggtc ccatttatta tttacaaatt cacatataca acaacgccgt cccccgtgcc 1380
cgcagttttt attaaacata gcgtgggatc tccacgcgaa tctcgggtac gtgttccgga 1440
catgggctct tctccggtag cggcggagct tccacatccg agccctggtc ccatgcctcc 1500
agcggctcat ggtcgctcgg cagctccttg ctcctaacag tggaggccag acttaggcac 1560
agcacaatgc ccaccaccac cagtgtgccg cacaaggccg tggcggtagg gtatgtgtct 1620
gaaaatgagc gtggagattg ggctcgcacg gctgacgcag atggaagact taaggcagcg 1680
gcagaagaag atgcaggcag ctgagttgtt gtattctgat aagagtcaga ggtaactccc 1740
gttgcggtgc tgttaacggt ggagggcagt gtagtctgag cagtactcgt tgctgccgcg 1800
cgcgccacca gacataatag ctgacagact aacagactgt tcctttccat gggtcttttc 1860
tgcagtcacc gtcgtcgaca cgtgtgatca gatccccaaa ttacctatac aacatggggt 1920
caggatatca acttctccaa ttgcctcggg aacgttttcg taaaacttcg ttcttagtat 1980
gggtaatcat cctcttccag cgagcaatct ccatgccgct tggtatagtg acaaatagca 2040
ctctcaaagc aacagaaatt gatcaattgg tttgtcggga caaactgtca tcaaccagtc 2100
agctcaagtc tgtggggctg aatctggaag gaaatggaat tgcaaccgat gtcccatcag 2160
caacaaaacg ctggggattt cgttcaggtg tgcctcccaa ggtggtcagc tatgaagccg 2220
gagaatgggc agaaaattgc tacaatctgg agatcaaaaa gtcagacgga agtgaatgcc 2280
tccctctccc tcccgacggt gtacgaggat tccctagatg tcgctatgtc cacaaagttc 2340
aaggaacagg tccttgtccc ggtgacttag ctttccataa aaatggggct tttttcttgt 2400
atgatagatt ggcctcaact gtcatctacc gagggacaac ttttgctgaa ggtgtcgtag 2460
ctttttttaat tctgtcagag cccaagaagc atttttggaa ggctacacca gctcatgaac 2520
cggtgaacac aacagatgat tccacaagct actacatgac cctgacactc agctacgaga 2580
tgtcaaattt tgggggcaat gaaagtaaca ccctttttaa ggtagacaac cacacatatg 2640
tgcaactaga tcgtccacac actccgcagt tccttgttca gctcaatgaa acacttcgaa 2700
gaaataatcg ccttagcaac agtacaggga gattgacttg gacattggat cctaaaattg 2760
aaccagatgt tggtgagtgg gccttctggg aaactaaaaa aactttttccc aacaacttca 2820
tggagaaaac ttgcatttcc aaattctatc aacccacacc aacaactcct cagatcagag 2880
cccggcggga actgtccaag gaaaaattag ctaccaccca cccgccaaca actccgagct 2940
ggttccaacg gattcccctc cagtggtttc agtgctcact gcaggacgga cagaggaaat 3000
gtcgacccaa ggtctaacca acggagagac aatcacaggt ttcaccgcga acccaatgac 3060
aaccaccatt gccccaagtc caaccatgac aagcgaggtt gataacaatg taccaagtga 3120
acaaccgaac aacacagcat ccattgaaga ctccccccca tcggcaagca acgagacaat 3180
ttaccactcc gagatggatc cgatccaagg ctcgaacaac tccgcccaga gcccacagac 3240
caagaccacg ccagcaccca caacatcccc gatgacccag gacccgcaag agacggccaa 3300
cagcagcaaa ccaggaacca gcccaggaag cgcagccgga ccaagtcagc ccggactcac 3360
tataaataca gtaagtaagg tagctgattc actgagtccc accaggaaac aaaagcgatc 3420
ggttcgacaa aacaccgcta ataaatgtaa cccagatctt tactattgga cagctgttga 3480
tgagggggca gcagtaggat tggcatggat tccatatttc ggacctgcag cagaaggcat 3540
ctacattgag ggtgtaatgc ataatcagaa tgggcttatt tgcgggctac gtcagctagc 3600
caatgaaact acccaggctc ttcaattatt tctgcgggcc acaacagaac tgaggactta 3660

-continued

```
ctcacttctt aacagaaaag ctattgattt tcttcttcaa cgatggggag gtacctgtcg   3720

aatcctagga ccatcttgtt gcattgagcc acatgattgg acaaaaaata ttactgatga   3780

aattaaccaa attaaacatg actttattga caatccccta ccagaccacg gagatgatct   3840

taatctatgg acaggttgga gacaatggtg aatctagacc aggccctgga tccagatctg   3900

ctgtgccttc tagttgccag ccatctgttg tttgcccctc ccccgtgcct tccttgaccc   3960

tggaaggtgc cactcccact gtcctttcct aataaaatga ggaaattgca tcgcattgtc   4020

tgagtaggtg tcattctatt ctggggggtg gggtggggca ggacagcaag ggggaggatt   4080

gggaagacaa tagcaggcat gctggggatg cggtgggctc tatgggtacc caggtgctga   4140

agaattgacc cggttcctcc tgggccagaa agaagcaggc acatcccctt ctctgtgaca   4200

caccctgtcc acgcccctgg ttcttagttc cagccccact cataggacac tcatagctca   4260

ggagggctcc gccttcaatc ccacccgcta aagtacttgg agcggtctct ccctccctca   4320

tcagcccacc aaaccaaacc tagcctccaa gagtgggaag aaattaaagc aagataggct   4380

attaagtgca gagggagaga aaatgcctcc aacatgtgag gaagtaatga gagaaatcat   4440

agaattttaa ggccatgatt taaggccatc atggccttaa tcttccgctt cctcgctcac   4500

tgactcgctg cgctcggtcg ttcggctgcg gcgagcggta tcagctcact caaaggcggt   4560

aatacggtta tccacagaat caggggataa cgcaggaaag aacatgtgag caaaaggcca   4620

gcaaaaggcc aggaaccgta aaaaggccgc gttgctggcg tttttccata ggctccgccc   4680

ccctgacgag catcacaaaa atcgacgctc aagtcagagg tggcgaaacc cgacaggact   4740

ataaagatac caggcgtttc cccctggaag ctccctcgtg cgctctcctg ttccgaccct   4800

gccgcttacc ggatacctgt ccgcctttct cccttcggga agcgtggcgc tttctcatag   4860

ctcacgctgt aggtatctca gttcggtgta ggtcgttcgc tccaagctgg gctgtgtgca   4920

cgaacccccc gttcagcccg accgctgcgc cttatccggt aactatcgtc ttgagtccaa   4980

cccggtaaga cacgacttat cgccactggc agcagccact ggtaacagga ttagcagagc   5040

gaggtatgta ggcggtgcta cagagttctt gaagtggtgg cctaactacg gctacactag   5100

aagaacagta tttggtatct gcgctctgct gaagccagtt accttcggaa aaagagttgg   5160

tagctcttga tccggcaaac aaaccaccgc tggtagcggt ggtttttttg tttgcaagca   5220

gcagattacg cgcagaaaaa aaggatctca agaagatcct ttgatctttt ctacggggtc   5280

tgacgctcag tggaacgaaa actcacgtta agggattttg gtcatgagat tatcaaaaag   5340

gatcttcacc tagatccttt taaattaaaa atgaagtttt aaatcaatct aaagtatata   5400

tgagtaaact tggtctgaca gttaccaatg cttaatcagt gaggcaccta tctcagcgat   5460

ctgtctattt cgttcatcca tagttgcctg actcgggggg ggggggcgct gaggtctgcc   5520

tcgtgaagaa ggtgttgctg actcatacca ggcctgaatc gccccatcat ccagccagaa   5580

agtgagggag ccacggttga tgagagcttt gttgtaggtg gaccagttgg tgattttgaa   5640

cttttgcttt gccacggaac ggtctgcgtt gtcgggaaga tgcgtgatct gatccttcaa   5700

ctcagcaaaa gttcgattta ttcaacaaag ccgccgtccc gtcaagtcag cgtaatgctc   5760

tgccagtgtt acaaccaatt aaccaattct gattagaaaa actcatcgag catcaaatga   5820

aactgcaatt tattcatatc aggattatca ataccatatt tttgaaaaag ccgtttctgt   5880

aatgaaggag aaaactcacc gaggcagttc cataggatgg caagatcctg gtatcggtct   5940

gcgattccga ctcgtccaac atcaatacaa cctattaatt tcccctcgtc aaaaataagg   6000

ttatcaagtg agaaatcacc atgagtgacg actgaatccg gtgagaatgg caaaagctta   6060
```

```
tgcatttctt tccagacttg ttcaacaggc cagccattac gctcgtcatc aaaatcactc   6120

gcatcaacca aaccgttatt cattcgtgat tgcgcctgag cgagacgaaa tacgcgatcg   6180

ctgttaaaag gacaattaca aacaggaatc gaatgcaacc ggcgcaggaa cactgccagc   6240

gcatcaacaa tattttcacc tgaatcagga tattcttcta atacctggaa tgctgttttc   6300

ccggggatcg cagtggtgag taaccatgca tcatcaggag tacggataaa atgcttgatg   6360

gtcggaagag gcataaattc cgtcagccag tttagtctga ccatctcatc tgtaacatca   6420

ttggcaacgc tacctttgcc atgtttcaga aacaactctg gcgcatcggg cttcccatac   6480

aatcgataga ttgtcgcacc tgattgcccg acattatcgc gagcccattt atacccatat   6540

aaatcagcat ccatgttgga atttaatcgc ggcctcgagc aagacgtttc ccgttgaata   6600

tggctcataa caccccttgt attactgttt atgtaagcag acagttttat tgttcatgat   6660

gatatatttt tatcttgtgc aatgtaacat cagagatttt gagacacaac gtggctttcc   6720

cccccccccc attattgaag catttatcag ggttattgtc tcatgagcgg atacatattt   6780

gaatgtattt agaaaaataa acaaataggg gttccgcgca catttccccg aaaagtgcca   6840

cctgacgtct aagaaaccat tattatcatg acattaacct ataaaaatag gcgtatcacg   6900

aggccctttc gtc                                                      6913
```

<210> SEQ ID NO 12
<211> LENGTH: 8131
<212> TYPE: DNA
<213> ORGANISM: Artificial Sequence
<220> FEATURE:
<223> OTHER INFORMATION: Synthetic Construct pAdApt Ebola GP(R)(dTM)

<400> SEQUENCE: 12

```
ttaattaacc gcaattctca tgtttgacag cttatcatca tcaataatat accttatttt     60

ggattgaagc caatatgata atgagggggt ggagtttgtg acgtggcgcg gggcgtggga    120

acggggcggg tgacgtagta gtgtggcgga agtgtgatgt tgcaagtgtg gcggaacaca    180

tgtaagcgac ggatgtggca aaagtgacgt ttttggtgtg cgccggtgta cacaggaagt    240

gacaattttc gcgcggtttt aggcggatgt tgtagtaaat ttgggcgtaa ccgagtaaga    300

tttggccatt ttcgcgggaa aactgaataa gaggaagtga aatctgaata attttgtgtt    360

actcatagcg cgtaatattt gtctagggcc gcggggactt tgaccgttta cgtggagact    420

cgcccaggtg tttttctcag gtgttttccg cgttccgggt caaagttggc gttttattat    480

tatagtcagt acgtaccagt gcactggcct agagcggccc cattgcatac gttgtatcca    540

tatcataata tgtacattta tattggctca tgtccaacat taccgccatg ttgacattga    600

ttattgacta gttattaata gtaatcaatt acggggtcat tagttcatag cccatatatg    660

gagttccgcg ttacataact tacggtaaat ggcccgcctg gctgaccgcc caacgacccc    720

cgcccattga cgtcaataat gacgtatgtt cccatagtaa cgccaatagg gactttccat    780

tgacgtcaat gggtggagta tttacggtaa actgcccact tggcagtaca tcaagtgtat    840

catatgccaa gtacgccccc tattgacgtc aatgacggta aatggcccgc ctggcattat    900

gcccagtaca tgaccttatg ggactttcct acttggcagt acatctacgt attagtcatc    960

gctattacca tggtgatgcg gttttggcag tacatcaatg ggcgtggata gcggtttgac   1020

tcacggggat ttccaagtct ccaccccatt gacgtcaatg ggagtttgtt ttggcaccaa   1080

aatcaacggg actttccaaa atgtcgtaac aactccgccc cattgacgca aatgggcggt   1140

aggcgtgtac ggtgggaggt ctatataagc agagctcgtt tagtgaaccg tcagatcgcc   1200
```

-continued

```
tggagacgcc atccacgctg ttttgacctc catagaagac accgggaccg atccagcctc   1260
cgtcaccgtc gtcgacacgt gtgatcagat atcaacttct ccaattgcct cgggaacgtt   1320
ttcgtaaaac ttcgttctta gtatgggtaa tcatcctctt ccagcgagca atctccatgc   1380
cgcttggtat agtgacaaat agcactctca aagcaacaga aattgatcaa ttggtttgtc   1440
gggacaaact gtcatcaacc agtcagctca agtctgtggg gctgaatctg gaaggaaatg   1500
gaattgcaac cgatgtccca tcagcaacaa aacgctgggg atttcgttca ggtgtgcctc   1560
ccaaggtggt cagctatgaa gccggagaat gggcagaaaa ttgctacaat ctggagatca   1620
aaaagtcaga cggaagtgaa tgcctccctc tccctcccga cggtgtacga ggattcccta   1680
gatgtcgcta tgtccacaaa gttcaaggaa caggtccttg tcccggtgac ttagctttcc   1740
ataaaaatgg ggcttttttc ttgtatgata gattggcctc aactgtcatc taccgaggga   1800
caacttttgc tgaaggtgtc gtagcttttt taattctgtc agagcccaag aagcattttt   1860
ggaaggctac accagctcat gaaccggtga acacaacaga tgattccaca agctactaca   1920
tgaccctgac actcagctac gagatgtcaa attttggggg caatgaaagt aacacccttt   1980
ttaaggtaga caaccacaca tatgtgcaac tagatcgtcc acacactccg cagttccttg   2040
ttcagctcaa tgaaacactt cgaagaaata atcgccttag caacagtaca gggagattga   2100
cttggacatt ggatcctaaa attgaaccag atgttggtga gtgggccttc tgggaaacta   2160
aaaaaacttt tcccaacaac ttcatggaga aaacttgcat ttccaaattc tatcaaccca   2220
caccaacaac tcctcagatc agagcccggc gggaactgtc caaggaaaaa ttagctacca   2280
cccacccgcc aacaactccg agctggttcc aacggattcc cctccagtgg tttcagtgct   2340
cactgcagga cggacagagg aaatgtcgac ccaaggtcta accaacggag agacaatcac   2400
aggtttcacc gcgaacccaa tgacaaccac cattgcccca agtccaacca tgacaagcga   2460
ggttgataac aatgtaccaa gtgaacaacc gaacaacaca gcatccattg aagactcccc   2520
cccatcggca agcaacgaga caatttacca ctccgagatg gatccgatcc aaggctcgaa   2580
caactccgcc cagagcccac agaccaagac cacgccagca cccacaacat ccccgatgac   2640
ccaggacccg caagagacgg ccaacagcag caaaccagga accagcccag gaagcgcagc   2700
cggaccaagt cagcccggac tcactataaa tacagtaagt aaggtagctg attcactgag   2760
tcccaccagg aaacaaaagc gatcggttcg acaaaacacc gctaataaat gtaacccaga   2820
tctttactat tggacagctg ttgatgaggg ggcagcagta ggattggcat ggattccata   2880
tttcggacct gcagcagaag gcatctacat tgagggtgta atgcataatc agaatgggct   2940
tatttgcggg ctacgtcagc tagccaatga aactacccag gctcttcaat tatttctgcg   3000
ggccacaaca gaactgagga cttactcact tcttaacaga aaagctattg attttcttct   3060
tcaacgatgg ggaggtacct gtcgaatcct aggaccatct tgttgcattg agccacatga   3120
ttggacaaaa aatattactg atgaaattaa ccaaattaaa catgacttta ttgacaatcc   3180
cctaccagac cacggagatg atcttaatct atggacaggt tggagacaat ggtgaatcta   3240
gaccaggccc tggatccaga tctgctgtgc cttctagttg ccagccatct gttgtttgcc   3300
cctcccccgt gccttccttg accctggaag gtgccactcc cactgtcctt tcctaataaa   3360
atgaggaaat tgcatcgcat tgtctgagta ggtgtcattc tattctgggg ggtggggtgg   3420
ggcagcacag caagggggag gattgggaag acaatagcag gcatgctggg gatgcggtgg   3480
gctctatggg tacccagggc cgcataactt cgtataatgt atgctatacg aagttataag   3540
atctgtactg aaatgtgtgg gcgtggctta agggtgggaa agaatatata aggtgggggt   3600
```

-continued

```
cttatgtagt tttgtatctg ttttgcagca gccgccgccg ccatgagcac caactcgttt   3660
gatggaagca ttgtgagctc atatttgaca acgcgcatgc ccccatgggc cggggtgcgt   3720
cagaatgtga tgggctccag cattgatggt cgccccgtcc tgcccgcaaa ctctactacc   3780
ttgacctacg agaccgtgtc tggaacgccg ttggagactg cagcctccgc cgccgcttca   3840
gccgctgcag ccaccgcccg cgggattgtg actgactttg ctttcctgag cccgcttgca   3900
agcagtgcag cttcccgttc atccgcccgc gatgacaagt tgacggctct tttggcacaa   3960
ttggattctt tgacccggga acttaatgtc gtttctcagc agctgttgga tctgcgccag   4020
caggtttctg ccctgaaggc ttcctcccct cccaatgcgg tttaaaacat aaataaaaaa   4080
ccagactctg tttggatttg gatcaagcaa gtgtcttgct gtctttattt aggggttttg   4140
cgcgcgcggt aggcccggga ccagcggtct cggtcgttga gggtcctgtg tatttttcc   4200
aggacgtggt aaaggtgact ctggatgttc agatacatgg gcataagccc gtctctgggg   4260
tggaggtagc accactgcag agcttcatgc tgcggggtgg tgttgtagat gatccagtcg   4320
tagcaggagc gctgggcgtg gtgcctaaaa atgtctttca gtagcaagct gattgccagg   4380
ggcaggccct tggtgtaagt gtttacaaag cggttaagct gggatgggtg catacgtggg   4440
gatatgagat gcatcttgga ctgtattttt aggttggcta tgttcccagc catatccctc   4500
cggggattca tgttgtgcag aaccaccagc acagtgtatc cggtgcactt gggaaatttg   4560
tcatgtagct tagaaggaaa tgcgtggaag aacttggaga cgcccttgtg acctccaaga   4620
ttttccatgc attcgtccat aatgatggca atgggcccac gggcggcggc ctgggcgaag   4680
atatttctgg gatcactaac gtcatagttg tgttccagga tgagatcgtc ataggccatt   4740
tttacaaagc gcgggcggag ggtgccagac tgcggtataa tggttccatc cggcccaggg   4800
gcgtagttac cctcacagat ttgcatttcc cacgctttga gttcagatgg ggggatcatg   4860
tctacctgcg gggcgatgaa gaaaacggtt tccggggtag gggagatcag ctgggaagaa   4920
agcaggttcc tgagcagctg cgacttaccg cagccggtgg gcccgtaaat cacacctatt   4980
accggctgca actggtagtt aagagagctg cagctgccgt catccctgag caggggggcc   5040
acttcgttaa gcatgtccct gactcgcatg ttttccctga ccaaatccgc cagaaggcgc   5100
tcgccgccca gcgatagcag ttcttgcaag gaagcaaagt ttttcaacgg tttgagaccg   5160
tccgccgtag gcatgctttt gagcgtttga ccaagcagtt ccaggcggtc ccacagctcg   5220
gtcacctgct ctacggcatc tcgatccagc atatctcctc gtttcgcggg ttggggcggc   5280
tttcgctgta cggcagtagt cggtgctcgt ccagacgggc cagggtcatg tctttccacg   5340
ggcgcagggt cctcgtcagc gtagtctggg tcacggtgaa ggggtgcgct ccgggctgcg   5400
cgctggccag ggtgcgcttg aggctggtcc tgctggtgct gaagcgctgc cggtcttcgc   5460
cctgcgcgtc ggccaggtag catttgacca tggtgtcata gtccagcccc tccgcggcgt   5520
ggcccttggc gcgcagcttg cccttggagg aggcgccgca cgaggggcag tgcagacttt   5580
tgagggcgta gagcttgggc gcgagaaata ccgattccgg ggagtaggca tccgcgccgc   5640
aggccccgca gacggtctcg cattccacga gccaggtgag ctctggccgt tcggggtcaa   5700
aaaccaggtt tcccccatgc tttttgatgc gtttcttacc tctggtttcc atgagccggt   5760
gtccacgctc ggtgacgaaa aggctgtccg tgtccccgta tacagacttg agaggcctgt   5820
cctcgagcgg tgttccgcgg tcctcctcgt atagaaactc ggaccactct gagacaaagg   5880
ctcgcgtcca ggccagcacg aaggaggcta agtgggaggg gtagcggtcg ttgtccacta   5940
gggggtccac tcgctccagg gtgtgaagac acatgtcgcc ctcttcggca tcaaggaagg   6000
```

-continued

```
tgattggttt gtaggtgtag gccacgtgac cgggtgttcc tgaagggggg ctataaaagg   6060
gggtgggggc gcgttcgtcc tcactctctt ccgcatcgct gtctgcgagg gccagctgtt   6120
ggggtgagtc gacgcgaggc tggatggcct tccccattat gattcttctc gcttccggcg   6180
gcatcgggat gcccgcgttg caggccatgc tgtccaggca ggtagatgac gaccatcagg   6240
gacagcttca aggccagcaa aaggccagga accgtaaaaa ggccgcgttg ctggcgtttt   6300
tccataggct ccgcccccct gacgagcatc acaaaaatcg acgctcaagt cagaggtggc   6360
gaaacccgac aggactataa agataccagg cgtttccccc tggaagctcc ctcgtgcgct   6420
ctcctgttcc gaccctgccg cttaccggat acctgtccgc ctttctccct tcgggaagcg   6480
tggcgctttc tcatagctca cgctgtaggt atctcagttc ggtgtaggtc gttcgctcca   6540
agctgggctg tgtgcacgaa ccccccgttc agcccgaccg ctgcgcctta tccggtaact   6600
atcgtcttga gtccaacccg gtaagacacg acttatcgcc actggcagca gccactggta   6660
acaggattag cagagcgagg tatgtaggcg gtgctacaga gttcttgaag tggtggccta   6720
actacggcta cactagaagg acagtatttg gtatctgcgc tctgctgaag ccagttacct   6780
tcggaaaaag agttggtagc tcttgatccg gcaaacaaac caccgctggt agcggtggtt   6840
tttttgtttg caagcagcag attacgcgca gaaaaaaagg atctcaagaa gatcctttga   6900
tcttttctac ggggtctgac gctcagtgga acgaaaactc acgttaaggg attttggtca   6960
tgagattatc aaaaaggatc ttcacctaga tccttttaaa ttaaaaatga agttttaaat   7020
caatctaaag tatatatgag taaacttggt ctgacagtta ccaatgctta atcagtgagg   7080
cacctatctc agcgatctgt ctatttcgtt catccatagt tgcctgactc cccgtcgtgt   7140
agataactac gatacgggag ggcttaccat ctggccccag tgctgcaatg ataccgcgag   7200
acccacgctc accggctcca gatttatcag caataaacca gccagccgga agggccgagc   7260
gcagaagtgg tcctgcaact ttatccgcct ccatccagtc tattaattgt tgccgggaag   7320
ctagagtaag tagttcgcca gttaatagtt tgcgcaacgt tgttgccatt gctgcaggca   7380
tcgtggtgtc acgctcgtcg tttggtatgg cttcattcag ctccggttcc caacgatcaa   7440
ggcgagttac atgatccccc atgttgtgca aaaaagcggt tagctccttc ggtcctccga   7500
tcgttgtcag aagtaagttg gccgcagtgt tatcactcat ggttatggca gcactgcata   7560
attctcttac tgtcatgcca tccgtaagat gcttttctgt gactggtgag tactcaacca   7620
agtcattctg agaatagtgt atgcggcgac cgagttgctc ttgcccggcg tcaacacggg   7680
ataataccgc gccacatagc agaactttaa aagtgctcat cattggaaaa cgttcttcgg   7740
ggcgaaaact ctcaaggatc ttaccgctgt tgagatccag ttcgatgtaa cccactcgtg   7800
cacccaactg atcttcagca tcttttactt tcaccagcgt ttctgggtga gcaaaaacag   7860
gaaggcaaaa tgccgcaaaa aagggaataa gggcgacacg gaaatgttga atactcatac   7920
tcttcctttt tcaatattat tgaagcattt atcagggtta ttgtctcatg agcggataca   7980
tatttgaatg tatttagaaa aataaacaaa taggggttcc gcgcacattt ccccgaaaag   8040
tgccacctga cgtctaagaa accattatta tcatgacatt aacctataaa aataggcgta   8100
tcacgaggcc ctttcgtctt caagaattgt t                                  8131
```

<210> SEQ ID NO 13
<211> LENGTH: 7082
<212> TYPE: DNA
<213> ORGANISM: Artificial Sequence
<220> FEATURE:
<223> OTHER INFORMATION: Synthetic Construct pVR1012-GP(S)

<400> SEQUENCE: 13
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcagattgg 240
ctattggcca ttgcatacgt tgtatccata tcataatatg tacatttata ttggctcatg 300
tccaacatta ccgccatgtt gacattgatt attgactagt tattaatagt aatcaattac 360
ggggtcatta gttcatagcc catatatgga gttccgcgtt acataactta cggtaaatgg 420
cccgcctggc tgaccgccca acgacccccg cccattgacg tcaataatga cgtatgttcc 480
catagtaacg ccaataggga ctttccattg acgtcaatgg gtggagtatt tacggtaaac 540
tgcccacttg gcagtacatc aagtgtatca tatgccaagt acgcccccta ttgacgtcaa 600
tgacggtaaa tggcccgcct ggcattatgc ccagtacatg accttatggg actttcctac 660
ttggcagtac atctacgtat tagtcatcgc tattaccatg gtgatgcggt tttggcagta 720
catcaatggg cgtggatagc ggtttgactc acggggattt ccaagtctcc accccattga 780
cgtcaatggg agtttgtttt ggcaccaaaa tcaacgggac tttccaaaat gtcgtaacaa 840
ctccgcccca ttgacgcaaa tgggcggtag gcgtgtacgg tgggaggtct atataagcag 900
agctcgttta gtgaaccgtc agatcgcctg gagacgccat ccacgctgtt ttgacctcca 960
tagaagacac cgggaccgat ccagcctccg cggccgggaa cggtgcattg gaacgcggat 1020
tccccgtgcc aagagtgacg taagtaccgc ctatagactc tataggcaca cccctttggc 1080
tcttatgcat gctatactgt ttttggcttg gggcctatac acccccgctt ccttatgcta 1140
taggtgatgg tatagcttag cctataggtg tgggttattg accattattg accactcccc 1200
tattggtgac gatactttcc attactaatc cataacatgg ctctttgcca caactatctc 1260
tattggctat atgccaatac tctgtccttc agagactgac acggactctg tatttttaca 1320
ggatggggtc ccatttatta tttacaaatt cacatataca acaacgccgt cccccgtgcc 1380
cgcagttttt attaaacata gcgtgggatc tccacgcgaa tctcgggtac gtgttccgga 1440
catgggctct tctccggtag cggcggagct tccacatccg agccctggtc ccatgcctcc 1500
agcggctcat ggtcgctcgg cagctccttg ctcctaacag tggaggccag acttaggcac 1560
agcacaatgc ccaccaccac cagtgtgccg cacaaggccg tggcggtagg gtatgtgtct 1620
gaaaatgagc gtggagattg ggctcgcacg gctgacgcag atggaagact taaggcagcg 1680
gcagaagaag atgcaggcag ctgagttgtt gtattctgat aagagtcaga ggtaactccc 1740
gttgcggtgc tgttaacggt ggagggcagt gtagtctgag cagtactcgt tgctgccgcg 1800
cgcgccacca gacataatag ctgacagact aacagactgt tcctttccat gggtcttttc 1860
tgcagtcacc gtcgtcgaca cgtgtgatca gatatcgcgg ccgctctagc tagatgcatg 1920
ctcgagcggc cgccagtgtg atggatatct gcagaattcg gcttatcttc aggatctcgc 1980
catggagggt cttagcctac tccaattgcc cagagataaa tttcgaaaaa gctctttctt 2040
tgtttgggtc atcatcttat ttcaaaaggc cttttccatg cctttgggtg ttgtgaccaa 2100
cagcacttta gaagtaacag agattgacca gctagtctgc aaggatcatc ttgcatccac 2160
tgaccagctg aaatcagttg gtctcaacct cgaggggagc ggagtatcta ctgatatccc 2220
atctgcgaca aagcgttggg gcttcagatc tggtgtgcct cccaaggtgg tcagctatga 2280
agcaggagaa tggctgaaaa ttgctacaa tcttgaaata aagaagccgg acgggagcga 2340

-continued

```
atgcttaccc ccaccgccgg atggtgtcag aggctttcca aggtgccgct atgttcacaa   2400
agcccaagga accgggccct gcccgggtga ctatgccttt cacaaggatg gagctttctt   2460
cctctatgac aggctggctt caactgtaat ttacagagga gtcaattttg ctgagggggt   2520
aattgcattc ttgatattgg ctaaaccaaa ggaaacgttc cttcaatcac cccccattcg   2580
agaggcagta aactacactg aaaatacatc aagttactat gccacatcct acttggagta   2640
cgaaatcgaa aattttggtg ctcaacactc cacgaccctt ttcaaaatta acaataatac   2700
ttttgttctt ctggacaggc cccacacgcc tcagttcctt ttccagctga atgataccat   2760
tcaccttcac caacagttga gcaacacaac tgggaaacta atttggacac tagatgctaa   2820
tatcaatgct gatattggtg aatgggcttt ttgggaaaat aaaaaaaatc tctccgaaca   2880
actacgtgga gaagagctgt ctttcgaaac tttatcgctc aacgagacag aagacgatga   2940
tgcgacatcg tcgagaacta caaagggaag aatctccgac cgggccacca ggaagtattc   3000
ggacctggtt ccaaaggatt cccctgggat ggtttcattg cacgtaccag aaggggaaac   3060
aacattgccg tctcagaatt cgacagaagg tcgaagagta gatgtgaata ctcaggaaac   3120
tatcacagag acaactgcaa caatcatagg cactaacggt aacaacatgc agatctccac   3180
catcgggaca ggactgagct ccagccaaat cctgagttcc tcaccgacca tggcaccaag   3240
ccctgagact cagacctcca caacctacac accaaaacta ccagtgatga ccaccgagga   3300
accaacaaca ccaccgagaa actctcctgg ctcaacaaca gaagcaccca ctctcaccac   3360
cccagagaat ataacaacag cggttaaaac tgttttgcca caagagtcca caagcaacgg   3420
tctaataact tcaacagtaa cagggattct tgggagcctt ggacttcgaa aacgcagcag   3480
aagacaagtt aacaccaggg ccacgggtaa atgcaatccc aacttacact actggactgc   3540
acaagaacaa cataatgctg ctgggattgc ctggatcccg tactttggac cgggtgcaga   3600
aggcatatac actgaaggcc ttatgcacaa ccaaaatgcc ttagtctgtg gactcagaca   3660
acttgcaaat gaaacaactc aagctctgca gcttttctta agggccacga cggagctgcg   3720
gacatatacc atactcaata ggaaggccat agatttcctt ctgcgacgat ggggcgggac   3780
atgtaggatc ctgggaccag attgttgcat tgagccacat gattggacca aaaacatcac   3840
tgataaaatc aaccaaatca tccatgattt catcgacaac cctttaccca atcaggataa   3900
tgatgataat tggtggacgg gctggagaca gtggatccct gcaggaatag gcattactgg   3960
aattattatt gcaatcattg ctcttctttg cgtctgcaag ctgctttgtt gaatatcaag   4020
ccgaattcca gcacactggc ggccgttact agtggatccg agctcggatc caagctctag   4080
accaggccct ggatccagat ctgctgtgcc ttctagttgc cagccatctg ttgtttgccc   4140
ctcccccgtg ccttccttga ccctggaagg tgccactccc actgtccttt cctaataaaa   4200
tgaggaaatt gcatcgcatt gtctgagtag gtgtcattct attctggggg gtggggtggg   4260
gcaggacagc aagggggagg attgggaaga caatagcagg catgctgggg atgcggtggg   4320
ctctatgggt acccaggtgc tgaagaattg acccggttcc tcctgggcca gaaagaagca   4380
ggcacatccc cttctctgtg acacaccctg tccacgcccc tggttcttag ttccagcccc   4440
actcatagga cactcatagc tcaggagggc tccgccttca atcccacccg ctaaagtact   4500
tggagcggtc tctccctccc tcatcagccc accaaaccaa acctagcctc caagagtggg   4560
aagaaattaa agcaagatag gctattaagt gcagagggag agaaaatgcc tccaacatgt   4620
gaggaagtaa tgagagaaat catagaattt cttccgcttc ctcgctcact gactcgctgc   4680
gctcggtcgt tcggctgcgg cgagcggtat cagctcactc aaaggcggta atacggttat   4740
```

-continued

```
ccacagaatc aggggataac gcaggaaaga acatgtgagc aaaaggccag caaaaggcca   4800
ggaaccgtaa aaaggccgcg ttgctggcgt ttttccatag gctccgcccc cctgacgagc   4860
atcacaaaaa tcgacgctca agtcagaggt ggcgaaaccc gacaggacta taaagatacc   4920
aggcgtttcc ccctggaagc tccctcgtgc gctctcctgt tccgaccctg ccgcttaccg   4980
gatacctgtc cgcctttctc ccttcgggaa gcgtggcgct ttctcatagc tcacgctgta   5040
ggtatctcag ttcggtgtag gtcgttcgct ccaagctggg ctgtgtgcac gaaccccccg   5100
ttcagcccga ccgctgcgcc ttatccggta actatcgtct tgagtccaac ccggtaagac   5160
acgacttatc gccactggca gcagccactg gtaacaggat tagcagagcg aggtatgtag   5220
gcggtgctac agagttcttg aagtggtggc ctaactacgg ctacactaga agaacagtat   5280
ttggtatctg cgctctgctg aagccagtta ccttcggaaa aagagttggt agctcttgat   5340
ccggcaaaca aaccaccgct ggtagcggtg gtttttttgt ttgcaagcag cagattacgc   5400
gcagaaaaaa aggatctcaa gaagatcctt tgatcttttc tacggggtct gacgctcagt   5460
ggaacgaaaa ctcacgttaa gggattttgg tcatgagatt atcaaaaagg atcttcacct   5520
agatcctttt aaattaaaaa tgaagtttta aatcaatcta aagtatatat gagtaaactt   5580
ggtctgacag ttaccaatgc ttaatcagtg aggcacctat ctcagcgatc tgtctatttc   5640
gttcatccat agttgcctga ctcggggggg gggggcgctg aggtctgcct cgtgaagaag   5700
gtgttgctga ctcataccag gcctgaatcg ccccatcatc cagccagaaa gtgagggagc   5760
cacggttgat gagagctttg ttgtaggtgg accagttggt gattttgaac ttttgctttg   5820
ccacggaacg gtctgcgttg tcgggaagat gcgtgatctg atccttcaac tcagcaaaag   5880
ttcgatttat tcaacaaagc cgccgtcccg tcaagtcagc gtaatgctct gccagtgtta   5940
caaccaatta accaattctg attagaaaaa ctcatcgagc atcaaatgaa actgcaattt   6000
attcatatca ggattatcaa taccatattt ttgaaaaagc cgtttctgta atgaaggaga   6060
aaactcaccg aggcagttcc ataggatggc aagatcctgg tatcggtctg cgattccgac   6120
tcgtccaaca tcaatacaac ctattaattt cccctcgtca aaaataaggt tatcaagtga   6180
gaaatcacca tgagtgacga ctgaatccgg tgagaatggc aaaagcttat gcatttcttt   6240
ccagacttgt tcaacaggcc agccattacg ctcgtcatca aaatcactcg catcaaccaa   6300
accgttattc attcgtgatt gcgcctgagc gagacgaaat acgcgatcgc tgttaaaagg   6360
acaattacaa acaggaatcg aatgcaaccg gcgcaggaac actgccagcg catcaacaat   6420
attttcacct gaatcaggat attcttctaa tacctggaat gctgttttcc cggggatcgc   6480
agtggtgagt aaccatgcat catcaggagt acggataaaa tgcttgatgg tcggaagagg   6540
cataaattcc gtcagccagt ttagtctgac catctcatct gtaacatcat tggcaacgct   6600
acctttgcca tgtttcagaa acaactctgg cgcatcgggc ttcccataca atcgatagat   6660
tgtcgcacct gattgcccga cattatcgcg agcccattta tacccatata aatcagcatc   6720
catgttggaa tttaatcgcg gcctcgagca agacgtttcc cgttgaatat ggctcataac   6780
accccttgta ttactgttta tgtaagcaga cagttttatt gttcatgatg atatattttt   6840
atcttgtgca atgtaacatc agagattttg agacacaacg tggctttccc ccccccccca   6900
ttattgaagc atttatcagg gttattgtct catgagcgga tacatatttg aatgtattta   6960
gaaaaataaa caaatagggg ttccgcgcac atttccccga aaagtgccac ctgacgtcta   7020
agaaaccatt attatcatga cattaaccta taaaaatagg cgtatcacga ggccctttcg   7080
tc                                                                  7082
```

<210> SEQ ID NO 14
<211> LENGTH: 7087
<212> TYPE: DNA
<213> ORGANISM: Artificial Sequence
<220> FEATURE:
<223> OTHER INFORMATION: Synthetic Construct pVR1012x/s Ebola GP(S)

<400> SEQUENCE: 14

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatgcg gtgtgaaata ccgcacagat gcgtaaggag aaaataccgc atcagattgg    240

ctattggcca ttgcatacgt tgtatccata tcataatatg tacatttata ttggctcatg    300

tccaacatta ccgccatgtt gacattgatt attgactagt tattaatagt aatcaattac    360

ggggtcatta gttcatagcc catatatgga gttccgcgtt acataactta cggtaaatgg    420

cccgcctggc tgaccgccca acgacccccg cccattgacg tcaataatga cgtatgttcc    480

catagtaacg ccaataggga ctttccattg acgtcaatgg gtggagtatt tacggtaaac    540

tgcccacttg gcagtacatc aagtgtatca tatgccaagt acgcccccta ttgacgtcaa    600

tgacggtaaa tggcccgcct ggcattatgc ccagtacatg accttatggg actttcctac    660

ttggcagtac atctacgtat tagtcatcgc tattaccatg gtgatgcggt tttggcagta    720

catcaatggg cgtggatagc ggtttgactc acggggattt ccaagtctcc accccattga    780

cgtcaatggg agtttgtttt ggcaccaaaa tcaacgggac tttccaaaat gtcgtaacaa    840

ctccgcccca ttgacgcaaa tgggcggtag gcgtgtacgg tgggaggtct atataagcag    900

agctcgttta gtgaaccgtc agatcgcctg gagacgccat ccacgctgtt ttgacctcca    960

tagaagacac cgggaccgat ccagcctccg cggccgggaa cggtgcattg gaacgcggat   1020

tccccgtgcc aagagtgacg taagtaccgc ctatagactc tataggcaca cccctttggc   1080

tcttatgcat gctatactgt ttttggcttg gggcctatac acccccgctt ccttatgcta   1140

taggtgatgg tatagcttag cctataggtg tgggttattg accattattg accactcccc   1200

tattggtgac gatactttcc attactaatc cataacatgg ctctttgcca caactatctc   1260

tattggctat atgccaatac tctgtccttc agagactgac acggactctg tatttttaca   1320

ggatggggtc ccatttatta tttacaaatt cacatataca acaacgccgt cccccgtgcc   1380

cgcagttttt attaaacata gcgtgggatc tccacgcgaa tctcgggtac gtgttccgga   1440

catgggctct tctccggtag cggcggagct tccacatccg agccctggtc ccatgcctcc   1500

agcggctcat ggtcgctcgg cagctccttg ctcctaacag tggaggccag acttaggcac   1560

agcacaatgc ccaccaccac cagtgtgccg cacaaggccg tggcggtagg gtatgtgtct   1620

gaaaatgagc gtggagattg ggctcgcacg gctgacgcag atggaagact taaggcagcg   1680

gcagaagaag atgcaggcag ctgagttgtt gtattctgat aagagtcaga ggtaactccc   1740

gttgcggtgc tgttaacggt ggagggcagt gtagtctgag cagtactcgt tgctgccgcg   1800

cgcgccacca gacataatag ctgacagact aacagactgt tcctttccat gggtcttttc   1860

tgcagtcacc gtcgtcgaca cgtgtgatca gatatcgcgg ccgccagtgt gatggatatc   1920

tgcagaattc ggcttatctt caggatctcg ccatggaggg tcttagccta ctccaattgc   1980

ccagagataa atttcgaaaa agctctttct ttgtttgggt catcatctta tttcaaaagg   2040

ccttttccat gcctttgggt gttgtgacca acagcacttt agaagtaaca gagattgacc   2100
```

-continued agctagtctg caaggatcat cttgcatcca ctgaccagct gaaatcagtt ggtctcaacc 2160
tcgaggggag cggagtatct actgatatcc catctgcgac aaagcgttgg ggcttcagat 2220
ctggtgtgcc tcccaaggtg gtcagctatg aagcaggaga atgggctgaa aattgctaca 2280
atcttgaaat aaagaagccg gacgggagcg aatgcttacc cccaccgccg gatggtgtca 2340
gaggctttcc aaggtgccgc tatgttcaca aagcccaagg aaccgggccc tgcccgggtg 2400
actatgcctt tcacaaggat ggagctttct tcctctatga caggctggct tcaactgtaa 2460
tttacagagg agtcaatttt gctgaggggg taattgcatt cttgatattg gctaaaccaa 2520
aggaaacgtt ccttcaatca ccccccattc gagaggcagt aaactacact gaaaatacat 2580
caagttacta tgccacatcc tacttggagt acgaaatcga aattttggt gctcaacact 2640 ccacgaccct tttcaaaatt aacaataata cttttgttct tctggacagg ccccacacgc 2700
ctcagttcct tttccagctg aatgatacca ttcaccttca ccaacagttg agcaacacaa 2760
ctgggaaact aatttggaca ctagatgcta atatcaatgc tgatattggt gaatgggctt 2820
tttgggaaaa taaaaaaaat ctctccgaac aactacgtgg agaagagctg tctttcgaaa 2880
ctttatcgct caacgagaca gaagacgatg atgcgacatc gtcgagaact acaaagggaa 2940
gaatctccga ccgggccacc aggaagtatt cggacctggt tccaaaggat tcccctggga 3000
tggtttcatt gcacgtacca gaaggggaaa caacattgcc gtctcagaat tcgacagaag 3060
gtcgaagagt agatgtgaat actcaggaaa ctatcacaga gacaactgca acaatcatag 3120
gcactaacgg taacaacatg cagatctcca ccatcgggac aggactgagc tccagccaaa 3180
tcctgagttc ctcaccgacc atggcaccaa gccctgagac tcagacctcc acaacctaca 3240
caccaaaact accagtgatg accaccgagg aatcaacaac accaccgaga aactctcctg 3300
gctcaacaac agaagcaccc actctcacca ccccagagaa tataacaaca gcggttaaaa 3360
ctgttttgcc acaagagtcc acaagcaacg gtctaataac ttcaacagta acagggattc 3420
ttgggagcct tggacttcga aaacgcagca gaagacaagt taacaccagg gccacgggta 3480
aatgcaatcc caacttacac tactggactg cacaagaaca acataatgct gctgggattg 3540
cctggatccc gtactttgga ccgggtgcag aaggcatata cactgaaggc cttatgcaca 3600
accaaaatgc cttagtctgt ggactcagac aacttgcaaa tgaaacaact caagctctgc 3660
agcttttctt aagggccacg acggagctgc ggacatatac catactcaat aggaaggcca 3720
tagatttcct tctgcgacga tggggcggga catgtaggat cctgggacca gattgttgca 3780
ttgagccaca tgattggacc aaaaacatca ctgataaaat caaccaaatc atccatgatt 3840
tcatcgacaa ccctttaccc aatcaggata atgatgataa ttggtggacg ggctggagac 3900
agtggatccc tgcaggaata ggcattactg gaattattat tgcaatcatt gctcttcttt 3960
gcgtctgcaa gctgctttgt tgaatatcaa gccgaattcc agcacactgg cggccgttac 4020
tagtggatcc gagctcggta ccaagctcta gaccaggccc tggatccaga tctgctgtgc 4080
cttctagttg ccagccatct gttgtttgcc cctcccccgt gccttccttg accctggaag 4140
gtgccactcc cactgtcctt tcctaataaa atgaggaaat tgcatcgcat tgtctgagta 4200
ggtgtcattc tattctgggg ggtggggtgg ggcaggacag caagggggag gattgggaag 4260
acaatagcag gcatgctggg gatgcggtgg gctctatggg tacccaggtg ctgaagaatt 4320
gacccggttc ctcctgggcc agaaagaagc aggcacatcc ccttctctgt gacacaccct 4380
gtccacgccc ctggttctta gttccagccc cactcatagg acactcatag ctcaggaggg 4440
ctccgccttc aatcccaccc gctaaagtac ttggagcggt ctctccctcc ctcatcagcc 4500

```
caccaaacca aacctagcct ccaagagtgg gaagaaatta aagcaagata ggctattaag   4560
tgcagaggga gagaaaatgc ctccaacatg tgaggaagta atgagagaaa tcatagaatt   4620
ttaaggccat gatttaaggc catcatggcc ttaatcttcc gcttcctcgc tcactgactc   4680
gctgcgctcg gtcgttcggc tgcggcgagc ggtatcagct cactcaaagg cggtaatacg   4740
gttatccaca gaatcagggg ataacgcagg aaagaacatg tgagcaaaag gccagcaaaa   4800
ggccaggaac cgtaaaaagg ccgcgttgct ggcgtttttc cataggctcc gcccccctga   4860
cgagcatcac aaaaatcgac gctcaagtca gaggtggcga aacccgacag gactataaag   4920
ataccaggcg tttccccctg gaagctccct cgtgcgctct cctgttccga ccctgccgct   4980
taccggatac ctgtccgcct ttctcccttc gggaagcgtg gcgctttctc atagctcacg   5040
ctgtaggtat ctcagttcgg tgtaggtcgt tcgctccaag ctgggctgtg tgcacgaacc   5100
ccccgttcag cccgaccgct gcgccttatc cggtaactat cgtcttgagt ccaacccggt   5160
aagacacgac ttatcgccac tggcagcagc cactggtaac aggattagca gagcgaggta   5220
tgtaggcggt gctacagagt tcttgaagtg gtggcctaac tacggctaca ctagaagaac   5280
agtatttggt atctgcgctc tgctgaagcc agttaccttc ggaaaaagag ttggtagctc   5340
ttgatccggc aaacaaacca ccgctggtag cggtggtttt tttgtttgca agcagcagat   5400
tacgcgcaga aaaaaaggat ctcaagaaga tcctttgatc ttttctacgg ggtctgacgc   5460
tcagtggaac gaaaactcac gttaagggat tttggtcatg agattatcaa aaaggatctt   5520
cacctagatc cttttaaatt aaaaatgaag ttttaaatca atctaaagta tatatgagta   5580
aacttggtct gacagttacc aatgcttaat cagtgaggca cctatctcag cgatctgtct   5640
atttcgttca tccatagttg cctgactcgg gggggggggg cgctgaggtc tgcctcgtga   5700
agaaggtgtt gctgactcat accaggcctg aatcgcccca tcatccagcc agaaagtgag   5760
ggagccacgg ttgatgagag ctttgttgta ggtggaccag ttggtgattt tgaacttttg   5820
ctttgccacg gaacggtctg cgttgtcggg aagatgcgtg atctgatcct tcaactcagc   5880
aaaagttcga tttattcaac aaagccgccg tcccgtcaag tcagcgtaat gctctgccag   5940
tgttacaacc aattaaccaa ttctgattag aaaaactcat cgagcatcaa atgaaactgc   6000
aatttattca tatcaggatt atcaatacca tatttttgaa aaagccgttt ctgtaatgaa   6060
ggagaaaact caccgaggca gttccatagg atggcaagat cctggtatcg gtctgcgatt   6120
ccgactcgtc caacatcaat acaacctatt aatttcccct cgtcaaaaat aaggttatca   6180
agtgagaaat caccatgagt gacgactgaa tccggtgaga atggcaaaag cttatgcatt   6240
tctttccaga cttgttcaac aggccagcca ttacgctcgt catcaaaatc actcgcatca   6300
accaaaccgt tattcattcg tgattgcgcc tgagcgagac gaaatacgcg atcgctgtta   6360
aaaggacaat tacaaacagg aatcgaatgc aaccggcgca ggaacactgc cagcgcatca   6420
acaatatttt cacctgaatc aggatattct tctaatacct ggaatgctgt tttcccgggg   6480
atcgcagtgg tgagtaacca tgcatcatca ggagtacgga taaaatgctt gatggtcgga   6540
agaggcataa attccgtcag ccagtttagt ctgaccatct catctgtaac atcattggca   6600
acgctacctt tgccatgttt cagaaacaac tctggcgcat cgggcttccc atacaatcga   6660
tagattgtcg cacctgattg cccgacatta tcgcgagccc atttataccc atataaatca   6720
gcatccatgt tggaatttaa tcgcggcctc gagcaagacg tttcccgttg aatatggctc   6780
ataacacccc ttgtattact gtttatgtaa gcagacagtt ttattgttca tgatgatata   6840
tttttatctt gtgcaatgta acatcagaga ttttgagaca caacgtggct ttcccccccc   6900
```

ccccattatt gaagcattta tcagggttat tgtctcatga gcggatacat atttgaatgt 6960
atttagaaaa ataaacaaat aggggttccg cgcacatttc cccgaaaagt gccacctgac 7020
gtctaagaaa ccattattat catgacatta acctataaaa ataggcgtat cacgaggccc 7080
tttcgtc 7087

<210> SEQ ID NO 15
<211> LENGTH: 6940
<212> TYPE: DNA
<213> ORGANISM: Artificial Sequence
<220> FEATURE:
<223> OTHER INFORMATION: Synthetic Construct pVR1012-GP(S) delta TM

<400> SEQUENCE: 15
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcagattgg 240
ctattggcca ttgcatacgt tgtatccata tcataatatg tacatttata ttggctcatg 300
tccaacatta ccgccatgtt gacattgatt attgactagt tattaatagt aatcaattac 360
ggggtcatta gttcatagcc catatatgga gttccgcgtt acataactta cggtaaatgg 420
cccgcctggc tgaccgccca acgacccccg cccattgacg tcaataatga cgtatgttcc 480
catagtaacg ccaataggga ctttccattg acgtcaatgg gtggagtatt tacggtaaac 540
tgcccacttg gcagtacatc aagtgtatca tatgccaagt acgcccccta ttgacgtcaa 600
tgacggtaaa tggcccgcct ggcattatgc ccagtacatg accttatggg actttcctac 660
ttggcagtac atctacgtat tagtcatcgc tattaccatg gtgatgcggt tttggcagta 720
catcaatggg cgtggatagc ggtttgactc acggggattt ccaagtctcc accccattga 780
cgtcaatggg agtttgtttt ggcaccaaaa tcaacgggac tttccaaaat gtcgtaacaa 840
ctccgcccca ttgacgcaaa tgggcggtag gcgtgtacgg tgggaggtct atataagcag 900
agctcgttta gtgaaccgtc agatcgcctg gagacgccat ccacgctgtt ttgacctcca 960
tagaagacac cgggaccgat ccagcctccg cggccgggaa cggtgcattg gaacgcggat 1020
tccccgtgcc aagagtgacg taagtaccgc ctatagactc tataggcaca cccctttggc 1080
tcttatgcat gctatactgt ttttggcttg gggcctatac acccccgctt ccttatgcta 1140
taggtgatgg tatagcttag cctataggtg tgggttattg accattattg accactcccc 1200
tattggtgac gatactttcc attactaatc cataacatgg ctctttgcca caactatctc 1260
tattggctat atgccaatac tctgtccttc agagactgac acggactctg tatttttaca 1320
ggatggggtc ccatttatta tttacaaatt cacatataca acaacgccgt cccccgtgcc 1380
cgcagttttt attaaacata gcgtgggatc tccacgcgaa tctcgggtac gtgttccgga 1440
catgggctct tctccggtag cggcggagct tccacatccg agccctggtc ccatgcctcc 1500
agcggctcat ggtcgctcgg cagctccttg ctcctaacag tggaggccag acttaggcac 1560
agcacaatgc ccaccaccac cagtgtgccg cacaaggccg tggcggtagg gtatgtgtct 1620
gaaaatgagc gtggagattg ggctcgcacg gctgacgcag atggaagact taaggcagcg 1680
gcagaagaag atgcaggcag ctgagttgtt gtattctgat aagagtcaga ggtaactccc 1740
gttgcggtgc tgttaacggt ggagggcagt gtagtctgag cagtactcgt tgctgccgcg 1800
cgcgccacca gacataatag ctgacagact aacagactgt tcctttccat gggtcttttc 1860

-continued

```
tgcagtcacc gtcgtcgact ctagctagat gcatgctcga gcggccgcca gtgtgatgga   1920
tatctgcaga attcggctta tcttcaggat ctcgccatgg agggtcttag cctactccaa   1980
ttgcccagag ataaatttcg aaaaagctct ttctttgttt gggtcatcat cttatttcaa   2040
aaggcctttt ccatgccttt gggtgttgtg accaacagca ctttagaagt aacagagatt   2100
gaccagctag tctgcaagga tcatcttgca tccactgacc agctgaaatc agttggtctc   2160
aacctcgagg ggagcggagt atctactgat atcccatctg cgacaaagcg ttggggcttc   2220
agatctggtg tgcctcccaa ggtggtcagc tatgaagcag gagaatgggc tgaaaattgc   2280
tacaatcttg aaataaagaa gccggacggg agcgaatgct tacccccacc gccggatggt   2340
gtcagaggct ttccaaggtg ccgctatgtt cacaaagccc aaggaaccgg gccctgcccg   2400
ggtgactatg cctttcacaa ggatggagct ttcttcctct atgacaggct ggcttcaact   2460
gtaatttaca gaggagtcaa ttttgctgag gggtaattg cattcttgat attggctaaa   2520
ccaaaggaaa cgttccttca atcacccccc attcgagagg cagtaaacta cactgaaaat   2580
acatcaagtt actatgccac atcctacttg gagtacgaaa tcgaaaattt tggtgctcaa   2640
cactccacga ccctttcaa aattaacaat aatactttg ttcttctgga caggccccac   2700
acgcctcagt tcctttcca gctgaatgat accattcacc ttcaccaaca gttgagcaac   2760
acaactggga aactaatttg gacactagat gctaatatca atgctgatat tggtgaatgg   2820
gctttttggg aaaataaaaa aaatctctcc gaacaactac gtggagaaga gctgtctttc   2880
gaaactttat cgctcaacga gacagaagac gatgatgcga catcgtcgag aactacaaag   2940
ggaagaatct ccgaccgggc caccaggaag tattcggacc tggttccaaa ggattcccct   3000
gggatggttt cattgcacgt accagaaggg gaaacaacat tgccgtctca gaattcgaca   3060
gaaggtcgaa gagtagatgt gaatactcag gaaactatca cagagacaac tgcaacaatc   3120
ataggcacta acggtaacaa catgcagatc tccaccatcg ggacaggact gagctccagc   3180
caaatcctga gttcctcacc gaccatggca ccaagccctg agactcagac ctccacaacc   3240
tacacaccaa aactaccagt gatgaccacc gaggaaccaa caacaccacc gagaaactct   3300
cctggctcaa caacagaagc acccactctc accaccccag agaatataac aacagcggtt   3360
aaaactgttt tgccacaaga gtccacaagc aacggtctaa taacttcaac agtaacaggg   3420
attcttggga gccttggact tcgaaaacgc agcagaagac aagttaacac cagggccacg   3480
ggtaaatgca atcccaactt acactactgg actgcacaag aacaacataa tgctgctggg   3540
attgcctgga tcccgtactt tggaccgggt gcagaaggca tatacactga aggccttatg   3600
cacaaccaaa atgccttagt ctgtggactc agacaacttg caaatgaaac aactcaagct   3660
ctgcagcttt tcttaagggc cacgacggag ctgcggacat ataccatact caataggaag   3720
gccatagatt tccttctgcg acgatggggc gggacatgta ggatcctggg accagattgt   3780
tgcattgagc cacatgattg gaccaaaaac atcactgata aaatcaacca aatcatccat   3840
gatttcatcg acaacccttt acccaatcag gataatgatg ataattggtg gacgggctgg   3900
agacagtgga tcccggccgc atcgtgactg actgacgatc tgcctcgcgg atccagatct   3960
gctgtgcctt ctagttgcca gccatctgtt gtttgcccct cccccgtgcc ttccttgacc   4020
ctggaaggtg ccactcccac tgtcctttcc taataaaatg aggaaattgc atcgcattgt   4080
ctgagtaggt gtcattctat tctgggggt ggggtggggc aggacagcaa gggggaggat   4140
tgggaagaca atagcaggca tgctggggat gcggtgggct ctatgggtac ccaggtgctg   4200
aagaattgac ccggttcctc ctgggccaga aagaagcagg cacatcccct tctctgtgac   4260
```

-continued

```
acaccctgtc cacgcccctg gttcttagtt ccagccccac tcataggaca ctcatagctc   4320
aggagggctc cgccttcaat cccacccgct aaagtacttg gagcggtctc tccctccctc   4380
atcagcccac caaaccaaac ctagcctcca agagtgggaa gaaattaaag caagataggc   4440
tattaagtgc agagggagag aaaatgcctc caacatgtga ggaagtaatg agagaaatca   4500
tagaatttct tccgcttcct cgctcactga ctcgctgcgc tcggtcgttc ggctgcggcg   4560
agcggtatca gctcactcaa aggcggtaat acggttatcc acagaatcag gggataacgc   4620
aggaaagaac atgtgagcaa aaggccagca aaaggccagg aaccgtaaaa aggccgcgtt   4680
gctggcgttt ttccataggc tccgcccccc tgacgagcat cacaaaaatc gacgctcaag   4740
tcagaggtgg cgaaacccga caggactata aagataccag gcgtttcccc ctggaagctc   4800
cctcgtgcgc tctcctgttc cgaccctgcc gcttaccgga tacctgtccg cctttctccc   4860
ttcgggaagc gtggcgcttt ctcatagctc acgctgtagg tatctcagtt cggtgtaggt   4920
cgttcgctcc aagctgggct gtgtgcacga accccccgtt cagcccgacc gctgcgcctt   4980
atccggtaac tatcgtcttg agtccaaccc ggtaagacac gacttatcgc cactggcagc   5040
agccactggt aacaggatta gcagagcgag gtatgtaggc ggtgctacag agttcttgaa   5100
gtggtggcct aactacggct acactagaag aacagtattt ggtatctgcg ctctgctgaa   5160
gccagttacc ttcggaaaaa gagttggtag ctcttgatcc ggcaaacaaa ccaccgctgg   5220
tagcggtggt ttttttgttt gcaagcagca gattacgcgc agaaaaaaag gatctcaaga   5280
agatcctttg atcttttcta cggggtctga cgctcagtgg aacgaaaact cacgttaagg   5340
gattttggtc atgagattat caaaaaggat cttcacctag atccttttaa attaaaaatg   5400
aagttttaaa tcaatctaaa gtatatatga gtaaacttgg tctgacagtt accaatgctt   5460
aatcagtgag gcacctatct cagcgatctg tctatttcgt tcatccatag ttgcctgact   5520
cggggggggg gggcgctgag gtctgcctcg tgaagaaggt gttgctgact cataccaggc   5580
ctgaatcgcc ccatcatcca gccagaaagt gagggagcca cggttgatga gagctttgtt   5640
gtaggtggac cagttggtga ttttgaactt ttgctttgcc acggaacggt ctgcgttgtc   5700
gggaagatgc gtgatctgat ccttcaactc agcaaaagtt cgatttattc aacaaagccg   5760
ccgtcccgtc aagtcagcgt aatgctctgc cagtgttaca accaattaac caattctgat   5820
tagaaaaact catcgagcat caaatgaaac tgcaatttat tcatatcagg attatcaata   5880
ccatattttt gaaaaagccg tttctgtaat gaaggagaaa actcaccgag gcagttccat   5940
aggatggcaa gatcctggta tcggtctgcg attccgactc gtccaacatc aatacaacct   6000
attaatttcc cctcgtcaaa aataaggtta tcaagtgaga aatcaccatg agtgacgact   6060
gaatccggtg agaatggcaa aagcttatgc atttctttcc agacttgttc aacaggccag   6120
ccattacgct cgtcatcaaa atcactcgca tcaaccaaac cgttattcat tcgtgattgc   6180
gcctgagcga gacgaaatac gcgatcgctg ttaaaaggac aattacaaac aggaatcgaa   6240
tgcaaccggc gcaggaacac tgccagcgca tcaacaatat tttcacctga atcaggatat   6300
tcttctaata cctggaatgc tgttttcccg gggatcgcag tggtgagtaa ccatgcatca   6360
tcaggagtac ggataaaatg cttgatggtc ggaagaggca taaattccgt cagccagttt   6420
agtctgacca tctcatctgt aacatcattg gcaacgctac ctttgccatg tttcagaaac   6480
aactctggcg catcgggctt cccatacaat cgatagattg tcgcacctga ttgcccgaca   6540
ttatcgcgag cccatttata cccatataaa tcagcatcca tgttggaatt taatcgcggc   6600
ctcgagcaag acgtttcccg ttgaatatgg ctcataacac cccttgtatt actgtttatg   6660
```

taagcagaca gttttattgt tcatgatgat atatttttat cttgtgcaat gtaacatcag 6720
agattttgag acacaacgtg gctttccccc cccccccatt attgaagcat ttatcagggt 6780
tattgtctca tgagcggata catatttgaa tgtatttaga aaaataaaca aataggggtt 6840
ccgcgcacat ttccccgaaa agtgccacct gacgtctaag aaaccattat tatcatgaca 6900
ttaacctata aaaataggcg tatcacgagg ccctttcgtc 6940

<210> SEQ ID NO 16
<211> LENGTH: 7002
<212> TYPE: DNA
<213> ORGANISM: Artificial Sequence
<220> FEATURE:
<223> OTHER INFORMATION: Synthetic Construct pVR1012-GP(IC)

<400> SEQUENCE: 16
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcagattgg 240
ctattggcca ttgcatacgt tgtatccata tcataatatg tacatttata ttggctcatg 300
tccaacatta ccgccatgtt gacattgatt attgactagt tattaatagt aatcaattac 360
ggggtcatta gttcatagcc catatatgga gttccgcgtt acataactta cggtaaatgg 420
cccgcctggc tgaccgccca acgacccccg cccattgacg tcaataatga cgtatgttcc 480
catagtaacg ccaataggga ctttccattg acgtcaatgg gtggagtatt tacggtaaac 540
tgcccacttg gcagtacatc aagtgtatca tatgccaagt acgcccccta ttgacgtcaa 600
tgacggtaaa tggcccgcct ggcattatgc ccagtacatg accttatggg actttcctac 660
ttggcagtac atctacgtat tagtcatcgc tattaccatg gtgatgcggt tttggcagta 720
catcaatggg cgtggatagc ggtttgactc acggggattt ccaagtctcc accccattga 780
cgtcaatggg agtttgtttt ggcaccaaaa tcaacgggac tttccaaaat gtcgtaacaa 840
ctccgcccca ttgacgcaaa tgggcggtag gcgtgtacgg tgggaggtct atataagcag 900
agctcgttta gtgaaccgtc agatcgcctg gagacgccat ccacgctgtt ttgacctcca 960
tagaagacac cgggaccgat ccagcctccg cggccgggaa cggtgcattg gaacgcggat 1020
tccccgtgcc aagagtgacg taagtaccgc ctatagactc tataggcaca cccctttggc 1080
tcttatgcat gctatactgt ttttggcttg gggcctatac acccccgctt ccttatgcta 1140
taggtgatgg tatagcttag cctataggtg tgggttattg accattattg accactcccc 1200
tattggtgac gatactttcc attactaatc cataacatgg ctctttgcca caactatctc 1260
tattggctat atgccaatac tctgtccttc agagactgac acggactctg tatttttaca 1320
ggatggggtc ccatttatta tttacaaatt cacatataca acaacgccgt cccccgtgcc 1380
cgcagttttt attaaacata gcgtgggatc tccacgcgaa tctcgggtac gtgttccgga 1440
catgggctct tctccggtag cggcggagct tccacatccg agccctggtc ccatgcctcc 1500
agcggctcat ggtcgctcgg cagctccttg ctcctaacag tggaggccag acttaggcac 1560
agcacaatgc ccaccaccac cagtgtgccg cacaaggccg tggcggtagg gtatgtgtct 1620
gaaaatgagc gtggagattg ggctcgcacg gctgacgcag atggaagact taaggcagcg 1680
gcagaagaag atgcaggcag ctgagttgtt gtattctgat aagagtcaga ggtaactccc 1740
gttgcggtgc tgttaacggt ggagggcagt gtagtctgag cagtactcgt tgctgccgcg 1800

-continued

```
cgcgccacca gacataatag ctgacagact aacagactgt tcctttccat gggtcttttc   1860
tgcagtcacc gtcgtcgaca cgtgtgatca gatatcgcgg ccgctctaga attcggcttc   1920
taatcacagt caccatggga gcgtcaggga ttctgcaatt gccccgtgag cgcttcagga   1980
aaacatcttt ctttgtttgg gtaataatcc tattccataa agtcttttca atcccgttgg   2040
gggttgtaca caacaatacc ctacaagtga gtgatattga caagtttgtg tgccgagaca   2100
aactctcttc aactagccaa ttgaagtcag tcgggttgaa cttggagggc aatggagtag   2160
caactgatgt accaacggca accaaaagat ggggttttcg agctggtgtt ccaccaaagg   2220
tggtaaattg cgaagctgga gaatgggctg agaactgtta taacctggct ataaagaaag   2280
ttgatggtag tgagtgccta ccagaagccc ctgagggagt gagggatttt ccccgttgcc   2340
gctatgtaca caaagtctca ggaactggac catgcccagg aggactcgcc tttcacaaag   2400
aaggagcctt cttcctgtat gaccgactcg catcaacaat catttatcgg ggtacaacct   2460
ttgccgaagg agttattgca tttctgatct tgcctaaggc gcgaaaggat tttttccagt   2520
ctcctccatt gcatgagcct gccaacatga ccacggatcc ctccagttac tatcacacga   2580
caacaataaa ctacgtggtt gataattttg gaaccaacac cacagagttt ctgttccaag   2640
tcgatcattt gacgtatgtg cagctcgagg caagattcac accacaattc cttgtcctcc   2700
taaatgaaac catctactct gataaccgca gaagtaacac aacaggaaaa ctaatctgga   2760
aaataaatcc cactgttgat accagcatgg gtgagtgggc tttctgggaa aataaaaaaa   2820
acttcacaaa aaccctttca agtgaagagt tgtctttcgt acctgtacca gaaacccaga   2880
accaggtcct tgacacgaca gcgacggtct ctcctcccat ctccgcccac aaccacgcag   2940
ccgaagacca caaagaattg gtttcagagg attccactcc agtggttcag atgcaaaaca   3000
tcaagggaaa ggacacaatg ccaaccacag tgacgggtgt accaacaacc acaccctctc   3060
catttccaat caatgctcgc aacactgatc ataccaaatc atttatcggc ctggaggggc   3120
cccaagaaga ccacagcacc acacagcctg ccaagaccac cagccaacca accaacagca   3180
cagaatcgac gacactaaac ccaacatcag agccctccag tagaggcacg ggaccatcca   3240
gccccacggt ccccaacacc acagaaagcc acgccgaact tggcaagaca accccaacca   3300
cactcccaga acagcacact gccgccagtg ccattccaag agccgtgcac cccgacgaac   3360
tcagtggacc tggcttcctg acgaacacaa tacgggggt tacaaatctc ctgacaggat    3420
ccagaagaaa gcgaagggat gtcactccca atacacaacc caaatgcaac ccaaacctgc   3480
actattggac agccttggat gagggtgctg ccataggttt agcctggata ccatacttcg   3540
ggccagcagc tgagggaatt tacactgaag gcataatgga gaatcaaaat ggattgatct   3600
gtggattgag gcagctggcc aacgaaacga cacaagctct tcaattgttc ttaagggcaa   3660
ctactgagtt gcgtacattc tctatactaa atcggaaagc aatagacttc ttgctccaaa   3720
gatggggagg aacatgtcac attctagggc ctgattgttg cattgaaccc caagattgga   3780
ccaaaaatat cactgataaa attgatcaaa taatccatga ctttgtcgat aataatcttc   3840
caaatcagaa tgatggcagc aactggtgga ctggatggaa acaatgggtt cctgctggaa   3900
taggaatcac aggagtaatc attgctatta ttgctttgct gtgcatttgc aaattcatgc   3960
tttgaactaa tatagcatca tactttaagc cgaattctag accaggccct ggatccagat   4020
ctgctgtgcc ttctagttgc cagccatctg ttgtttgccc ctcccccgtg ccttccttga   4080
ccctggaagg tgccactccc actgtccttt cctaataaaa tgaggaaatt gcatcgcatt   4140
gtctgagtag gtgtcattct attctggggg gtggggtggg gcaggacagc aagggggagg   4200
```

```
attgggaaga caatagcagg catgctgggg atgcggtggg ctctatgggt acccaggtgc   4260
tgaagaattg acccggttcc tcctgggcca gaaagaagca ggcacatccc cttctctgtg   4320
acacaccctg tccacgcccc tggttcttag ttccagcccc actcatagga cactcatagc   4380
tcaggagggc tccgccttca atcccacccg ctaaagtact tggagcggtc tctccctccc   4440
tcatcagccc accaaaccaa acctagcctc caagagtggg aagaaattaa agcaagatag   4500
gctattaagt gcagagggag agaaaatgcc tccaacatgt gaggaagtaa tgagagaaat   4560
catagaattt cttccgcttc ctcgctcact gactcgctgc gctcggtcgt tcggctgcgg   4620
cgagcggtat cagctcactc aaaggcggta atacggttat ccacagaatc aggggataac   4680
gcaggaaaga acatgtgagc aaaaggccag caaaaggcca ggaaccgtaa aaaggccgcg   4740
ttgctggcgt ttttccatag gctccgcccc cctgacgagc atcacaaaaa tcgacgctca   4800
agtcagaggt ggcgaaaccc gacaggacta taaagatacc aggcgtttcc ccctggaagc   4860
tccctcgtgc gctctcctgt tccgaccctg ccgcttaccg gatacctgtc cgcctttctc   4920
ccttcgggaa gcgtggcgct ttctcatagc tcacgctgta ggtatctcag ttcggtgtag   4980
gtcgttcgct ccaagctggg ctgtgtgcac gaaccccccg ttcagcccga ccgctgcgcc   5040
ttatccggta actatcgtct tgagtccaac ccggtaagac acgacttatc gccactggca   5100
gcagccactg gtaacaggat tagcagagcg aggtatgtag gcggtgctac agagttcttg   5160
aagtggtggc ctaactacgg ctacactaga agaacagtat ttggtatctg cgctctgctg   5220
aagccagtta ccttcggaaa aagagttggt agctcttgat ccggcaaaca aaccaccgct   5280
ggtagcggtg gtttttttgt ttgcaagcag cagattacgc gcagaaaaaa aggatctcaa   5340
gaagatcctt tgatcttttc tacggggtct gacgctcagt ggaacgaaaa ctcacgttaa   5400
gggattttgg tcatgagatt atcaaaaagg atcttcacct agatcctttt aaattaaaaa   5460
tgaagtttta aatcaatcta aagtatatat gagtaaactt ggtctgacag ttaccaatgc   5520
ttaatcagtg aggcacctat ctcagcgatc tgtctatttc gttcatccat agttgcctga   5580
ctcggggggg gggggcgctg aggtctgcct cgtgaagaag gtgttgctga ctcataccag   5640
gcctgaatcg ccccatcatc cagccagaaa gtgagggagc cacggttgat gagagctttg   5700
ttgtaggtgg accagttggt gattttgaac ttttgctttg ccacggaacg gtctgcgttg   5760
tcgggaagat gcgtgatctg atccttcaac tcagcaaaag ttcgatttat tcaacaaagc   5820
cgccgtcccg tcaagtcagc gtaatgctct gccagtgtta caaccaatta accaattctg   5880
attagaaaaa ctcatcgagc atcaaatgaa actgcaattt attcatatca ggattatcaa   5940
taccatattt ttgaaaaagc cgtttctgta atgaaggaga aaactcaccg aggcagttcc   6000
ataggatggc aagatcctgg tatcggtctg cgattccgac tcgtccaaca tcaatacaac   6060
ctattaattt cccctcgtca aaaataaggt tatcaagtga gaaatcacca tgagtgacga   6120
ctgaatccgg tgagaatggc aaaagcttat gcatttcttt ccagacttgt tcaacaggcc   6180
agccattacg ctcgtcatca aaatcactcg catcaaccaa accgttattc attcgtgatt   6240
gcgcctgagc gagacgaaat acgcgatcgc tgttaaaagg acaattacaa acaggaatcg   6300
aatgcaaccg gcgcaggaac actgccagcg catcaacaat attttcacct gaatcaggat   6360
attcttctaa tacctggaat gctgttttcc cggggatcgc agtggtgagt aaccatgcat   6420
catcaggagt acggataaaa tgcttgatgg tcggaagagg cataaattcc gtcagccagt   6480
ttagtctgac catctcatct gtaacatcat tggcaacgct acctttgcca tgtttcagaa   6540
acaactctgg cgcatcgggc ttcccataca atcgatagat tgtcgcacct gattgcccga   6600
```

```
cattatcgcg agcccattta tacccatata aatcagcatc catgttggaa tttaatcgcg   6660

gcctcgagca agacgtttcc cgttgaatat ggctcataac accccttgta ttactgttta   6720

tgtaagcaga cagttttatt gttcatgatg atatattttt atcttgtgca atgtaacatc   6780

agagattttg agacacaacg tggctttccc ccccccccca ttattgaagc atttatcagg   6840

gttattgtct catgagcgga tacatatttg aatgtattta gaaaaataaa caaatagggg   6900

ttccgcgcac atttccccga aaagtgccac ctgacgtcta agaaaccatt attatcatga   6960

cattaaccta taaaaatagg cgtatcacga ggccctttcg tc                      7002
```

<210> SEQ ID NO 17
<211> LENGTH: 7036
<212> TYPE: DNA
<213> ORGANISM: Artificial Sequence
<220> FEATURE:
<223> OTHER INFORMATION: Synthetic Construct pVR1012 x/s Ebola GP(IC)

<400> SEQUENCE: 17

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatgcg gtgtgaaata ccgcacagat gcgtaaggag aaaataccgc atcagattgg    240

ctattggcca ttgcatacgt tgtatccata tcataatatg tacatttata ttggctcatg    300

tccaacatta ccgccatgtt gacattgatt attgactagt tattaatagt aatcaattac    360

ggggtcatta gttcatagcc catatatgga gttccgcgtt acataactta cggtaaatgg    420

cccgcctggc tgaccgccca acgacccccg cccattgacg tcaataatga cgtatgttcc    480

catagtaacg ccaataggga ctttccattg acgtcaatgg gtggagtatt tacggtaaac    540

tgcccacttg gcagtacatc aagtgtatca tatgccaagt acgcccccta ttgacgtcaa    600

tgacggtaaa tggcccgcct ggcattatgc ccagtacatg accttatggg actttcctac    660

ttggcagtac atctacgtat tagtcatcgc tattaccatg gtgatgcggt tttggcagta    720

catcaatggg cgtggatagc ggtttgactc acggggattt ccaagtctcc accccattga    780

cgtcaatggg agtttgtttt ggcaccaaaa tcaacgggac tttccaaaat gtcgtaacaa    840

ctccgcccca ttgacgcaaa tgggcggtag gcgtgtacgg tgggaggtct atataagcag    900

agctcgttta gtgaaccgtc agatcgcctg gagacgccat ccacgctgtt ttgacctcca    960

tagaagacac cgggaccgat ccagcctccg cggccgggaa cggtgcattg gaacgcggat   1020

tccccgtgcc aagagtgacg taagtaccgc ctatagactc tataggcaca cccctttggc   1080

tcttatgcat gctatactgt ttttggcttg gggcctatac acccccgctt ccttatgcta   1140

taggtgatgg tatagcttag cctataggtg tgggttattg accattattg accactcccc   1200

tattggtgac gatactttcc attactaatc cataacatgg ctctttgcca caactatctc   1260

tattggctat atgccaatac tctgtccttc agagactgac acggactctg tatttttaca   1320

ggatggggtc ccatttatta tttacaaatt cacatataca acaacgccgt cccccgtgcc   1380

cgcagttttt attaaacata gcgtgggatc tccacgcgaa tctcgggtac gtgttccgga   1440

catgggctct tctccggtag cggcggagct tccacatccg agccctggtc ccatgcctcc   1500

agcggctcat ggtcgctcgg cagctccttg ctcctaacag tggaggccag acttaggcac   1560

agcacaatgc ccaccaccac cagtgtgccg cacaaggccg tggcggtagg gtatgtgtct   1620

gaaaatgagc gtggagattg ggctcgcacg gctgacgcag atggaagact taaggcagcg   1680
```

-continued

```
gcagaagaag atgcaggcag ctgagttgtt gtattctgat aagagtcaga ggtaactccc   1740
gttgcggtgc tgttaacggt ggagggcagt gtagtctgag cagtactcgt tgctgccgcg   1800
cgcgccacca gacataatag ctgacagact aacagactgt tcctttccat gggtcttttc   1860
tgcagtcacc gtcgtcgaca cgtgtgatca gatatcgcgg ccgctctaga attcggcttc   1920
taatcacagt caccatggga gcgtcaggga ttctgcaatt gccccgtgag cgcttcagga   1980
aaacatcttt ctttgtttgg gtaataatcc tattccataa agtcttttca atcccgttgg   2040
gggttgtaca caacaatacc ctacaagtga gtgatattga caagtttgtg tgccgagaca   2100
aactctcttc aactagccaa ttgaagtcag tcgggttgaa cttggagggc aatggagtag   2160
caactgatgt accaacggca accaaaagat ggggttttcg agctggtgtt ccaccaaagg   2220
tggtaaattg cgaagctgga gaatgggctg agaactgtta taacctggct ataaagaaag   2280
ttgatggtag tgagtgccta ccagaagccc ctgagggagt gagggatttt ccccgttgcc   2340
gctatgtaca caaagtctca ggaactggac catgcccagg aggactcgcc tttcacaaag   2400
aaggagcctt cttcctgtat gaccgactcg catcaacaat catttatcgg ggtacaacct   2460
ttgccgaagg agttattgca tttctgatct tgcctaaggc gcgaaaggat tttttccagt   2520
ctcctccatt gcatgagcct gccaacatga ccacggatcc ctccagttac tatcacacga   2580
caacaataaa ctacgtggtt gataattttg gaaccaacac cacagagttt ctgttccaag   2640
tcgatcattt gacgtatgtg cagctcgagg caagattcac accacaattc cttgtcctcc   2700
taaatgaaac catctactct gataaccgca gaagtaacac aacaggaaaa ctaatctgga   2760
aaataaatcc cactgttgat accagcatgg gtgagtgggc tttctgggaa aataaaaaaa   2820
acttcacaaa aacccttca agtgaagagt tgtctttcgt acctgtacca gaaacccaga   2880
accaggtcct tgacacgaca gcgacggtct ctcctcccat ctccgcccac aaccacgcag   2940
ccgaagacca caaagaattg gtttcagagg attccactcc agtggttcag atgcaaaaca   3000
tcaagggaaa ggacacaatg ccaaccacag tgacgggtgt accaacaacc acaccctctc   3060
catttccaat caatgctcgc aacactgatc ataccaaatc atttatcggc ctggaggggc   3120
cccaagaaga ccacagcacc acacagcctg ccaagaccac cagccaacca accaacagca   3180
cagaatcgac gacactaaac ccaacatcag agccctccag tagaggcacg ggaccatcca   3240
gccccacggt ccccaacacc acagaaagcc acgccgaact tggcaagaca accccaacca   3300
cactcccaga acagcacact gccgccagtg ccattccaag agccgtgcac cccgacgaac   3360
tcagtggacc tggcttcctg acgaacacaa tacggggggt tacaaatctc ctgacaggat   3420
ccagaagaaa gcgaagggat gtcactccca atacacaacc caaatgcaac ccaaacctgc   3480
actattggac agccttggat gagggtgctg ccataggttt agcctggata ccatacttcg   3540
ggccagcagc tgagggaatt tacactgaag gcataatgga gaatcaaaat ggattgatct   3600
gtggattgag gcagctggcc aacgaaacga cacaagctct tcaattgttc ttaagggcaa   3660
ctactgagtt gcgtacattc tctatactaa atcggaaagc aatagacttc ttgctccaaa   3720
gatggggagg aacatgtcac attctagggc ctgattgttg cattgaaccc caagattgga   3780
ccaaaaatat cactgataaa attgatcaaa taatccatga ctttgtcgat aataatcttc   3840
caaatcagaa tgatggcagc aactggtgga ctggatggaa acaatgggtt cctgctggaa   3900
taggaatcac aggagtaatc attgctatta ttgctttgct gtgcatttgc aaattcatgc   3960
tttgaactaa tatagcatca tactttaagc cgaattctag accaggccct ggatccagat   4020
ctgctgtgcc ttctagttgc cagccatctg ttgtttgccc ctcccccgtg ccttccttga   4080
```

```
ccctggaagg tgccactccc actgtccttt cctaataaaa tgaggaaatt gcatcgcatt   4140
gtctgagtag gtgtcattct attctggggg gtggggtggg gcaggacagc aagggggagg   4200
attgggaaga caatagcagg catgctgggg atgcggtggg ctctatgggt acccaggtgc   4260
tgaagaattg acccggttcc tcctgggcca gaaagaagca ggcacatccc cttctctgtg   4320
acacaccctg tccacgcccc tggttcttag ttccagcccc actcatagga cactcatagc   4380
tcaggagggc tccgccttca atcccacccg ctaaagtact tggagcggtc tctccctccc   4440
tcatcagccc accaaaccaa acctagcctc caagagtggg aagaaattaa agcaagatag   4500
gctattaagt gcagagggag agaaaatgcc tccaacatgt gaggaagtaa tgagagaaat   4560
catagaattt taaggccatg atttaaggcc atcatggcct taatcttccg cttcctcgct   4620
cactgactcg ctgcgctcgg tcgttcggct gcggcgagcg gtatcagctc actcaaaggc   4680
ggtaatacgg ttatccacag aatcagggga taacgcagga aagaacatgt gagcaaaagg   4740
ccagcaaaag gccaggaacc gtaaaaaggc cgcgttgctg gcgtttttcc ataggctccg   4800
cccccctgac gagcatcaca aaaatcgacg ctcaagtcag aggtggcgaa acccgacagg   4860
actataaaga taccaggcgt ttccccctgg aagctccctc gtgcgctctc ctgttccgac   4920
cctgccgctt accggatacc tgtccgcctt tctcccttcg ggaagcgtgg cgctttctca   4980
tagctcacgc tgtaggtatc tcagttcggt gtaggtcgtt cgctccaagc tgggctgtgt   5040
gcacgaaccc cccgttcagc ccgaccgctg cgccttatcc ggtaactatc gtcttgagtc   5100
caacccggta agacacgact tatcgccact ggcagcagcc actggtaaca ggattagcag   5160
agcgaggtat gtaggcggtg ctacagagtt cttgaagtgg tggcctaact acggctacac   5220
tagaagaaca gtatttggta tctgcgctct gctgaagcca gttaccttcg gaaaaagagt   5280
tggtagctct tgatccggca aacaaaccac cgctggtagc ggtggttttt ttgtttgcaa   5340
gcagcagatt acgcgcagaa aaaaaggatc tcaagaagat cctttgatct tttctacggg   5400
gtctgacgct cagtggaacg aaaactcacg ttaagggatt ttggtcatga gattatcaaa   5460
aaggatcttc acctagatcc ttttaaatta aaaatgaagt tttaaatcaa tctaaagtat   5520
atatgagtaa acttggtctg acagttacca atgcttaatc agtgaggcac ctatctcagc   5580
gatctgtcta tttcgttcat ccatagttgc ctgactcggg gggggggggc gctgaggtct   5640
gcctcgtgaa gaaggtgttg ctgactcata ccaggcctga atcgccccat catccagcca   5700
gaaagtgagg gagccacggt tgatgagagc tttgttgtag gtggaccagt tggtgatttt   5760
gaacttttgc tttgccacgg aacggtctgc gttgtcggga agatgcgtga tctgatcctt   5820
caactcagca aaagttcgat ttattcaaca aagccgccgt cccgtcaagt cagcgtaatg   5880
ctctgccagt gttacaacca attaaccaat tctgattaga aaaactcatc gagcatcaaa   5940
tgaaactgca atttattcat atcaggatta tcaataccat atttttgaaa aagccgtttc   6000
tgtaatgaag gagaaaactc accgaggcag ttccatagga tggcaagatc ctggtatcgg   6060
tctgcgattc cgactcgtcc aacatcaata caacctatta atttcccctc gtcaaaaata   6120
aggttatcaa gtgagaaatc accatgagtg acgactgaat ccggtgagaa tggcaaaagc   6180
ttatgcattt ctttccagac ttgttcaaca ggccagccat tacgctcgtc atcaaaatca   6240
ctcgcatcaa ccaaaccgtt attcattcgt gattgcgcct gagcgagacg aaatacgcga   6300
tcgctgttaa aaggacaatt acaaacagga atcgaatgca accggcgcag gaacactgcc   6360
agcgcatcaa caatattttc acctgaatca ggatattctt ctaatacctg gaatgctgtt   6420
ttcccgggga tcgcagtggt gagtaaccat gcatcatcag gagtacggat aaaatgcttg   6480
```

atggtcggaa gaggcataaa ttccgtcagc cagtttagtc tgaccatctc atctgtaaca 6540
tcattggcaa cgctaccttt gccatgtttc agaaacaact ctggcgcatc gggcttccca 6600
tacaatcgat agattgtcgc acctgattgc ccgacattat cgcgagccca tttataccca 6660
tataaatcag catccatgtt ggaatttaat cgcggcctcg agcaagacgt ttcccgttga 6720
atatggctca taacacccct tgtattactg tttatgtaag cagacagttt tattgttcat 6780
gatgatatat ttttatcttg tgcaatgtaa catcagagat tttgagacac aacgtggctt 6840
tccccccccc cccattattg aagcatttat cagggttatt gtctcatgag cggatacata 6900
tttgaatgta tttagaaaaa taaacaaata ggggttccgc gcacatttcc ccgaaaagtg 6960
ccacctgacg tctaagaaac cattattatc atgacattaa cctataaaaa taggcgtatc 7020
acgaggccct ttcgtc 7036

<210> SEQ ID NO 18
<211> LENGTH: 6885
<212> TYPE: DNA
<213> ORGANISM: Artificial Sequence
<220> FEATURE:
<223> OTHER INFORMATION: Synthetic Construct pVR1012-GP(IC) delta TM

<400> SEQUENCE: 18
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcagattgg 240
ctattggcca ttgcatacgt tgtatccata tcataatatg tacatttata ttggctcatg 300
tccaacatta ccgccatgtt gacattgatt attgactagt tattaatagt aatcaattac 360
ggggtcatta gttcatagcc catatatgga gttccgcgtt acataactta cggtaaatgg 420
cccgcctggc tgaccgccca acgacccccg cccattgacg tcaataatga cgtatgttcc 480
catagtaacg ccaataggga ctttccattg acgtcaatgg gtggagtatt tacggtaaac 540
tgcccacttg gcagtacatc aagtgtatca tatgccaagt acgcccccta ttgacgtcaa 600
tgacggtaaa tggcccgcct ggcattatgc ccagtacatg accttatggg actttcctac 660
ttggcagtac atctacgtat tagtcatcgc tattaccatg gtgatgcggt tttggcagta 720
catcaatggg cgtggatagc ggtttgactc acggggattt ccaagtctcc accccattga 780
cgtcaatggg agtttgtttt ggcaccaaaa tcaacgggac tttccaaaat gtcgtaacaa 840
ctccgcccca ttgacgcaaa tgggcggtag gcgtgtacgg tgggaggtct atataagcag 900
agctcgttta gtgaaccgtc agatcgcctg gagacgccat ccacgctgtt ttgacctcca 960
tagaagacac cgggaccgat ccagcctccg cggccgggaa cggtgcattg gaacgcggat 1020
tccccgtgcc aagagtgacg taagtaccgc ctatagactc tataggcaca cccctttggc 1080
tcttatgcat gctatactgt ttttggcttg gggcctatac acccccgctt ccttatgcta 1140
taggtgatgg tatagcttag cctataggtg tgggttattg accattattg accactcccc 1200
tattggtgac gatactttcc attactaatc cataacatgg ctctttgcca caactatctc 1260
tattggctat atgccaatac tctgtccttc agagactgac acggactctg tatttttaca 1320
ggatggggtc ccatttatta tttacaaatt cacatataca acaacgccgt cccccgtgcc 1380
cgcagttttt attaaacata gcgtgggatc tccacgcgaa tctcgggtac gtgttccgga 1440
catgggctct tctccggtag cggcggagct tccacatccg agccctggtc ccatgcctcc 1500

-continued agcggctcat ggtcgctcgg cagctccttg ctcctaacag tggaggccag acttaggcac 1560
agcacaatgc ccaccaccac cagtgtgccg cacaaggccg tggcggtagg gtatgtgtct 1620
gaaaatgagc gtggagattg ggctcgcacg gctgacgcag atggaagact taaggcagcg 1680
gcagaagaag atgcaggcag ctgagttgtt gtattctgat aagagtcaga ggtaactccc 1740
gttgcggtgc tgttaacggt ggagggcagt gtagtctgag cagtactcgt tgctgccgcg 1800
cgcgccacca gacataatag ctgacagact aacagactgt tcctttccat gggtcttttc 1860
tgcagtcacc gtcgtcgaca cgtgtgatca gatatcgcgg ccgctctaga attcggcttc 1920
taatcacagt caccatggga gcgtcaggga ttctgcaatt gccccgtgag cgcttcagga 1980
aaacatcttt ctttgtttgg gtaataatcc tattccataa agtcttttca atcccgttgg 2040
gggttgtaca caacaatacc ctacaagtga gtgatattga caagtttgtg tgccgagaca 2100
aactctcttc aactagccaa ttgaagtcag tcgggttgaa cttggagggc aatggagtag 2160
caactgatgt accaacggca accaaaagat ggggttttcg agctggtgtt ccaccaaagg 2220
tggtaaattg cgaagctgga gaatgggctg agaactgtta taacctggct ataaagaaag 2280
ttgatggtag tgagtgccta ccagaagccc ctgagggagt gagggatttt ccccgttgcc 2340
gctatgtaca caaagtctca ggaactggac catgcccagg aggactcgcc tttcacaaag 2400
aaggagcctt cttcctgtat gaccgactcg catcaacaat catttatcgg ggtacaacct 2460
ttgccgaagg agttattgca tttctgatct tgcctaaggc gcgaaaggat tttttccagt 2520
ctcctccatt gcatgagcct gccaacatga ccacggatcc ctccagttac tatcacacga 2580
caacaataaa ctacgtggtt gataattttg gaaccaacac cacagagttt ctgttccaag 2640
tcgatcattt gacgtatgtg cagctcgagg caagattcac accacaattc cttgtcctcc 2700
taaatgaaac catctactct gataaccgca gaagtaacac aacaggaaaa ctaatctgga 2760
aaataaatcc cactgttgat accagcatgg gtgagtgggc tttctgggaa aataaaaaaa 2820
acttcacaaa aaccctttca agtgaagagt tgtctttcgt acctgtacca gaaacccaga 2880
accaggtcct tgacacgaca gcgacggtct ctcctcccat ctccgcccac aaccacgcag 2940
ccgaagacca caaagaattg gtttcagagg attccactcc agtggttcag atgcaaaaca 3000
tcaagggaaa ggacacaatg ccaaccacag tgacgggtgt accaacaacc acaccctctc 3060
catttccaat caatgctcgc aacactgatc ataccaaatc atttatcggc ctggaggggc 3120
cccaagaaga ccacagcacc acacagcctg ccaagaccac cagccaacca accaacagca 3180
cagaatcgac gacactaaac ccaacatcag agccctccag tagaggcacg ggaccatcca 3240
gccccacggt ccccaacacc acagaaagcc acgccgaact tggcaagaca accccaacca 3300
cactcccaga acagcacact gccgccagtg ccattccaag agccgtgcac cccgacgaac 3360
tcagtggacc tggcttcctg acgaacacaa tacggggggt tacaaatctc ctgacaggat 3420
ccagaagaaa gcgaagggat gtcactccca atacacaacc caaatgcaac ccaaacctgc 3480
actattggac agccttggat gagggtgctg ccataggttt agcctggata ccatacttcg 3540
ggccagcagc tgagggaatt tacactgaag gcataatgga gaatcaaaat ggattgatct 3600
gtggattgag gcagctggcc aacgaaacga cacaagctct tcaattgttc ttaagggcaa 3660
ctactgagtt gcgtacattc tctatactaa atcggaaagc aatagacttc ttgctccaaa 3720
gatggggagg aacatgtcac attctagggc ctgattgttg cattgaaccc caagattgga 3780
ccaaaaatat cactgataaa attgatcaaa taatccatga ctttgtcgat aataatcttc 3840
caaatcagaa tgatggcagg gccgcatcgt gactgactga cgatctgcct cgcggatcca 3900

```
gatctgctgt gccttctagt tgccagccat ctgttgtttg cccctccccc gtgccttcct   3960
tgaccctgga aggtgccact cccactgtcc tttcctaata aaatgaggaa attgcatcgc   4020
attgtctgag taggtgtcat tctattctgg ggggtggggt ggggcaggac agcaaggggg   4080
aggattggga agacaatagc aggcatgctg gggatgcggt gggctctatg ggtacccagg   4140
tgctgaagaa ttgacccggt tcctcctggg ccagaaagaa gcaggcacat ccccttctct   4200
gtgacacacc ctgtccacgc ccctggttct tagttccagc cccactcata ggacactcat   4260
agctcaggag ggctccgcct tcaatcccac ccgctaaagt acttggagcg gtctctccct   4320
ccctcatcag cccaccaaac caaacctagc ctccaagagt gggaagaaat taaagcaaga   4380
taggctatta agtgcagagg gagagaaaat gcctccaaca tgtgaggaag taatgagaga   4440
aatcatagaa tttcttccgc ttcctcgctc actgactcgc tgcgctcggt cgttcggctg   4500
cggcgagcgg tatcagctca ctcaaaggcg gtaatacggt tatccacaga atcaggggat   4560
aacgcaggaa agaacatgtg agcaaaaggc cagcaaaagg ccaggaaccg taaaaaggcc   4620
gcgttgctgg cgtttttcca taggctccgc ccccctgacg agcatcacaa aaatcgacgc   4680
tcaagtcaga ggtggcgaaa cccgacagga ctataaagat accaggcgtt tccccctgga   4740
agctccctcg tgcgctctcc tgttccgacc ctgccgctta ccggatacct gtccgccttt   4800
ctcccttcgg gaagcgtggc gctttctcat agctcacgct gtaggtatct cagttcggtg   4860
taggtcgttc gctccaagct gggctgtgtg cacgaacccc ccgttcagcc cgaccgctgc   4920
gccttatccg gtaactatcg tcttgagtcc aacccggtaa gacacgactt atcgccactg   4980
gcagcagcca ctggtaacag gattagcaga gcgaggtatg taggcggtgc tacagagttc   5040
ttgaagtggt ggcctaacta cggctacact agaagaacag tatttggtat ctgcgctctg   5100
ctgaagccag ttaccttcgg aaaaagagtt ggtagctctt gatccggcaa acaaaccacc   5160
gctggtagcg gtggtttttt tgtttgcaag cagcagatta cgcgcagaaa aaaaggatct   5220
caagaagatc ctttgatctt ttctacgggg tctgacgctc agtggaacga aaactcacgt   5280
taagggattt tggtcatgag attatcaaaa aggatcttca cctagatcct tttaaattaa   5340
aaatgaagtt ttaaatcaat ctaaagtata tatgagtaaa cttggtctga cagttaccaa   5400
tgcttaatca gtgaggcacc tatctcagcg atctgtctat ttcgttcatc catagttgcc   5460
tgactcgggg gggggggcg ctgaggtctg cctcgtgaag aaggtgttgc tgactcatac   5520
caggcctgaa tcgccccatc atccagccag aaagtgaggg agccacggtt gatgagagct   5580
ttgttgtagg tggaccagtt ggtgattttg aacttttgct ttgccacgga acggtctgcg   5640
ttgtcgggaa gatgcgtgat ctgatccttc aactcagcaa aagttcgatt tattcaacaa   5700
agccgccgtc ccgtcaagtc agcgtaatgc tctgccagtg ttacaaccaa ttaaccaatt   5760
ctgattagaa aaactcatcg agcatcaaat gaaactgcaa tttattcata tcaggattat   5820
caataccata tttttgaaaa agccgtttct gtaatgaagg agaaaactca ccgaggcagt   5880
tccataggat ggcaagatcc tggtatcggt ctgcgattcc gactcgtcca acatcaatac   5940
aacctattaa tttcccctcg tcaaaaataa ggttatcaag tgagaaatca ccatgagtga   6000
cgactgaatc cggtgagaat ggcaaaagct tatgcatttc tttccagact tgttcaacag   6060
gccagccatt acgctcgtca tcaaaatcac tcgcatcaac caaaccgtta ttcattcgtg   6120
attgcgcctg agcgagacga aatacgcgat cgctgttaaa aggacaatta caaacaggaa   6180
tcgaatgcaa ccggcgcagg aacactgcca gcgcatcaac aatattttca cctgaatcag   6240
gatattcttc taatacctgg aatgctgttt tcccggggat cgcagtggtg agtaaccatg   6300
```

catcatcagg agtacggata aaatgcttga tggtcggaag aggcataaat tccgtcagcc 6360
agtttagtct gaccatctca tctgtaacat cattggcaac gctacctttg ccatgtttca 6420
gaaacaactc tggcgcatcg ggcttcccat acaatcgata gattgtcgca cctgattgcc 6480
cgacattatc gcgagcccat ttatacccat ataaatcagc atccatgttg gaatttaatc 6540
gcggcctcga gcaagacgtt tcccgttgaa tatggctcat aacacccctt gtattactgt 6600
ttatgtaagc agacagtttt attgttcatg atgatatatt tttatcttgt gcaatgtaac 6660
atcagagatt ttgagacaca acgtggcttt cccccccccc ccattattga agcatttatc 6720
agggttattg tctcatgagc ggatacatat ttgaatgtat ttagaaaaat aaacaaatag 6780
gggttccgcg cacatttccc cgaaaagtgc cacctgacgt ctaagaaacc attattatca 6840
tgacattaac ctataaaaat aggcgtatca cgaggccctt tcgtc 6885

<210> SEQ ID NO 19
<211> LENGTH: 6889
<212> TYPE: DNA
<213> ORGANISM: Artificial Sequence
<220> FEATURE:
<223> OTHER INFORMATION: Synthetic Construct pVR1012x/s Ebola GP(IC) (dTM)

<400> SEQUENCE: 19
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcagattgg 240
ctattggcca ttgcatacgt tgtatccata tcataatatg tacatttata ttggctcatg 300
tccaacatta ccgccatgtt gacattgatt attgactagt tattaatagt aatcaattac 360
ggggtcatta gttcatagcc catatatgga gttccgcgtt acataactta cggtaaatgg 420
cccgcctggc tgaccgccca acgacccccg cccattgacg tcaataatga cgtatgttcc 480
catagtaacg ccaataggga ctttccattg acgtcaatgg gtggagtatt tacggtaaac 540
tgcccacttg gcagtacatc aagtgtatca tatgccaagt acgcccccta ttgacgtcaa 600
tgacggtaaa tggcccgcct ggcattatgc ccagtacatg accttatggg actttcctac 660
ttggcagtac atctacgtat tagtcatcgc tattaccatg gtgatgcggt tttggcagta 720
catcaatggg cgtggatagc ggtttgactc acggggattt ccaagtctcc accccattga 780
cgtcaatggg agtttgtttt ggcaccaaaa tcaacgggac tttccaaaat gtcgtaacaa 840
ctccgcccca ttgacgcaaa tgggcggtag gcgtgtacgg tgggaggtct atataagcag 900
agctcgttta gtgaaccgtc agatcgcctg gagacgccat ccacgctgtt ttgacctcca 960
tagaagacac cgggaccgat ccagcctccg cggccgggaa cggtgcattg gaacgcggat 1020
tccccgtgcc aagagtgacg taagtaccgc ctatagactc tataggcaca cccctttggc 1080
tcttatgcat gctatactgt ttttggcttg gggcctatac acccccgctt ccttatgcta 1140
taggtgatgg tatagcttag cctataggtg tgggttattg accattattg accactcccc 1200
tattggtgac gatactttcc attactaatc cataacatgg ctctttgcca caactatctc 1260
tattggctat atgccaatac tctgtccttc agagactgac acggactctg tatttttaca 1320
ggatggggtc ccatttatta tttacaaatt cacatataca acaacgccgt cccccgtgcc 1380
cgcagttttt attaaacata gcgtgggatc tccacgcgaa tctcgggtac gtgttccgga 1440

-continued

```
catgggctct tctccggtag cggcggagct tccacatccg agccctggtc ccatgcctcc   1500
agcggctcat ggtcgctcgg cagctccttg ctcctaacag tggaggccag acttaggcac   1560
agcacaatgc ccaccaccac cagtgtgccg cacaaggccg tggcggtagg gtatgtgtct   1620
gaaaatgagc gtggagattg ggctcgcacg gctgacgcag atggaagact taaggcagcg   1680
gcagaagaag atgcaggcag ctgagttgtt gtattctgat aagagtcaga ggtaactccc   1740
gttgcggtgc tgttaacggt ggagggcagt gtagtctgag cagtactcgt tgctgccgcg   1800
cgcgccacca gacataatag ctgacagact aacagactgt tcctttccat gggtcttttc   1860
tgcagtcacc gtcgtcgaca cgtgtgatca gataattctc taatcacagt catcatggga   1920
gcgtcaggga ttctgcaatt gccccgtgag cgcttcagga aaacatcttt ctttgtttgg   1980
gtaataatcc tattccataa agtcttttca atcccgttgg gggttgtaca caacaatacc   2040
ctacaagtga gtgatattga caagtttgtg tgccgagaca aactctcttc aactagccaa   2100
ttgaagtcag tcgggttgaa cttggagggc aatggagtag caactgatgt accaacggca   2160
accaaaagat ggggttttcg agctggtgtt ccaccaaagg tggtaaatta cgaagctgga   2220
gaatgggctg agaactgtta taacctggct ataaagaaag ttgatggtag tgagtgccta   2280
ccagaagccc ctgagggagt gagggatttt ccccgttgcc gctatgtaca caaagtctca   2340
ggaactggac catgcccagg aggactcgcc tttcacaaag aaggagcctt cttcctgtat   2400
gaccgactcg catcaacaat catttatcgg ggtacaacct ttgccgaagg agttattgca   2460
tttctgatct tgcctaaggc gcgaaaggat tttttccagt ctcctccatt gcatgagcct   2520
gccaacatga ccacggatcc ctccagttac tatcacacga caacaataaa ctacgtggtt   2580
gataattttg gaaccaacac cacagagttt ctgttccaag tcgatcattt gacgtatgtg   2640
cagctcgagg caagattcac accacaattc cttgtcctcc taaatgaaac catctactct   2700
gataaccgca gaagtaacac aacaggaaaa ctaatctgga aataaatcc cactgttgat    2760
accagcatgg gtgagtgggc tttctgggaa aataaaaaaa cttcacaaaa accctttcaa   2820
gtgaagagtt gtctttcgta cctgtaccag aaacccagaa ccaggtcctt gacacgacag   2880
cgacggtctc tcctcccatc tccgcccaca accacgcagg cgaagaccac aaagaattgg   2940
tttcagagga ttccactcca gtggttcaga tgcaaaacat caagggaaag gacacaatgc   3000
caaccacagt gacgggtgta ccaacaacca caccctctcc atttccaatc aatgctcgca   3060
acactgatca taccaaatca tttatcggcc tggaggggcc ccaagaagac cacagcacca   3120
cacagcctgc caagaccacc agccaaccaa ccaacagcac agaatcgacg acactaaacc   3180
caacatcaga gccctccagt agaggcacgg gaccatccag ccccacggtc cccaacacca   3240
cagaaagcca cgccgaactt ggcaagacaa ccccaaccac actcccagaa cagcacactg   3300
ccgccagtgc cattccaaga gccgtgcacc ccgacgaact cagtggacct ggcttcctga   3360
cgaacacaat acgggggggtg acaaatctcc tgacaggatc cagaagaaag cgaagggatg  3420
tcactcccaa tacacaaccc aaatgcaacc caaacctgca ctattggaca gccttggatg   3480
agggtgctgc catagggtta gcctggatac catacttcgg gccagcagct gagggaattt   3540
acactgaagg cataatggag aatcaaaatg gattgatctg tggattgagg cagctggcca   3600
acgaaacgac acaagctctt caattgttct taagggcaac tactgagttg cgtacattct   3660
ctatactaaa tcggaaagca atagacttct tgctccaaag atggggagga acatgtcaca   3720
ttctagggcc tgattgttgc attgaacccc aagattggac caaaaatatc actgataaaa   3780
ttgatcaaat aatccatgac tttgtcgata ataatcttcc aaatcagaat gatggcagca   3840
```

-continued

```
actggtggac tggatggaaa caatggtgaa gatctgctgt gccttctagt tgccagccat   3900
ctgttgtttg cccctccccc gtgccttcct tgaccctgga aggtgccact cccactgtcc   3960
tttcctaata aaatgaggaa attgcatcgc attgtctgag taggtgtcat tctattctgg   4020
ggggtggggt ggggcaggac agcaaggggg aggattggga agacaatagc aggcatgctg   4080
gggatgcggt gggctctatg ggtacccagg tgctgaagaa ttgacccggt tcctcctggg   4140
ccagaaagaa gcaggcacat ccccttctct gtgacacacc ctgtccacgc ccctggttct   4200
tagttccagc cccactcata ggacactcat agctcaggag ggctccgcct tcaatcccac   4260
ccgctaaagt acttggagcg gtctctccct ccctcatcag cccaccaaac caaacctagc   4320
ctccaagagt gggaagaaat taaagcaaga taggctatta agtgcagagg gagagaaaat   4380
gcctccaaca tgtgaggaag taatgagaga aatcatagaa ttttaaggcc atgatttaag   4440
gccatcatgg ccttaatctt ccgcttcctc gctcactgac tcgctgcgct cggtcgttcg   4500
gctgcggcga gcggtatcag ctcactcaaa ggcggtaata cggttatcca cagaatcagg   4560
ggataacgca ggaaagaaca tgtgagcaaa aggccagcaa aaggccagga accgtaaaaa   4620
ggccgcgttg ctggcgtttt tccataggct ccgcccccct gacgagcatc acaaaaatcg   4680
acgctcaagt cagaggtggc gaaacccgac aggactataa agataccagg cgtttccccc   4740
tggaagctcc ctcgtgcgct ctcctgttcc gaccctgccg cttaccggat acctgtccgc   4800
ctttctccct tcgggaagcg tggcgctttc tcatagctca cgctgtaggt atctcagttc   4860
ggtgtaggtc gttcgctcca agctgggctg tgtgcacgaa ccccccgttc agcccgaccg   4920
ctgcgcctta tccggtaact atcgtcttga gtccaacccg gtaagacacg acttatcgcc   4980
actggcagca gccactggta acaggattag cagagcgagg tatgtaggcg gtgctacaga   5040
gttcttgaag tggtggccta actacggcta cactagaaga acagtatttg gtatctgcgc   5100
tctgctgaag ccagttacct tcggaaaaag agttggtagc tcttgatccg gcaaacaaac   5160
caccgctggt agcggtggtt tttttgtttg caagcagcag attacgcgca gaaaaaaagg   5220
atctcaagaa gatcctttga tcttttctac ggggtctgac gctcagtgga acgaaaactc   5280
acgttaaggg attttggtca tgagattatc aaaaaggatc ttcacctaga tccttttaaa   5340
ttaaaaatga agttttaaat caatctaaag tatatatgag taaacttggt ctgacagtta   5400
ccaatgctta atcagtgagg cacctatctc agcgatctgt ctatttcgtt catccatagt   5460
tgcctgactc gggggggggg ggcgctgagg tctgcctcgt gaagaaggtg ttgctgactc   5520
ataccaggcc tgaatcgccc catcatccag ccagaaagtg agggagccac ggttgatgag   5580
agctttgttg taggtggacc agttggtgat tttgaacttt tgctttgcca cggaacggtc   5640
tgcgttgtcg ggaagatgcg tgatctgatc cttcaactca gcaaaagttc gatttattca   5700
acaaagccgc cgtcccgtca agtcagcgta atgctctgcc agtgttacaa ccaattaacc   5760
aattctgatt agaaaaactc atcgagcatc aaatgaaact gcaatttatt catatcagga   5820
ttatcaatac catatttttg aaaaagccgt ttctgtaatg aaggagaaaa ctcaccgagg   5880
cagttccata ggatggcaag atcctggtat cggtctgcga ttccgactcg tccaacatca   5940
atacaaccta ttaatttccc ctcgtcaaaa ataaggttat caagtgagaa atcaccatga   6000
gtgacgactg aatccggtga gaatggcaaa agcttatgca tttctttcca gacttgttca   6060
acaggccagc cattacgctc gtcatcaaaa tcactcgcat caaccaaacc gttattcatt   6120
cgtgattgcg cctgagcgag acgaaatacg cgatcgctgt taaaaggaca attacaaaca   6180
ggaatcgaat gcaaccggcg caggaacact gccagcgcat caacaatatt ttcacctgaa   6240
```

```
tcaggatatt cttctaatac ctggaatgct gttttcccgg ggatcgcagt ggtgagtaac   6300

catgcatcat caggagtacg gataaaatgc ttgatggtcg gaagaggcat aaattccgtc   6360

agccagttta gtctgaccat ctcatctgta acatcattgg caacgctacc tttgccatgt   6420

ttcagaaaca actctggcgc atcgggcttc ccatacaatc gatagattgt cgcacctgat   6480

tgcccgacat tatcgcgagc ccatttatac ccatataaat cagcatccat gttggaattt   6540

aatcgcggcc tcgagcaaga cgtttcccgt tgaatatggc tcataacacc ccttgtatta   6600

ctgtttatgt aagcagacag ttttattgtt catgatgata tatttttatc ttgtgcaatg   6660

taacatcaga gattttgaga cacaacgtgg ctttcccccc cccccatta ttgaagcatt   6720

tatcagggtt attgtctcat gagcggatac atatttgaat gtatttagaa aaataaacaa   6780

ataggggttc cgcgcacatt tccccgaaaa gtgccacctg acgtctaaga aaccattatt   6840

atcatgacat taacctataa aaataggcgt atcacgaggc cctttcgtc              6889
```

<210> SEQ ID NO 20
<211> LENGTH: 8146
<212> TYPE: DNA
<213> ORGANISM: Artificial Sequence
<220> FEATURE:
<223> OTHER INFORMATION: Synthetic Construct pAdApt EbolaGP(IC)(dTM)

<400> SEQUENCE: 20

```
ttaattaacc gcaattctca tgtttgacag cttatcatca tcaataatat accttatttt     60

ggattgaagc caatatgata atgagggggt ggagtttgtg acgtggcgcg gggcgtggga    120

acggggcggg tgacgtagta gtgtggcgga agtgtgatgt tgcaagtgtg gcggaacaca    180

tgtaagcgac ggatgtggca aaagtgacgt ttttggtgtg cgccggtgta cacaggaagt    240

gacaattttc gcgcggtttt aggcggatgt tgtagtaaat ttgggcgtaa ccgagtaaga    300

tttggccatt ttcgcgggaa aactgaataa gaggaagtga aatctgaata attttgtgtt    360

actcatagcg cgtaatattt gtctagggcc gcggggactt tgaccgttta cgtggagact    420

cgcccaggtg tttttctcag gtgttttccg cgttccgggt caaagttggc gttttattat    480

tatagtcagt acgtaccagt gcactggcct agagcggccc cattgcatac gttgtatcca    540

tatcataata tgtacattta tattggctca tgtccaacat taccgccatg ttgacattga    600

ttattgacta gttattaata gtaatcaatt acggggtcat tagttcatag cccatatatg    660

gagttccgcg ttacataact tacggtaaat ggcccgcctg gctgaccgcc caacgacccc    720

cgcccattga cgtcaataat gacgtatgtt cccatagtaa cgccaatagg gactttccat    780

tgacgtcaat gggtggagta tttacggtaa actgcccact tggcagtaca tcaagtgtat    840

catatgccaa gtacgccccc tattgacgtc aatgacggta aatggcccgc ctggcattat    900

gcccagtaca tgaccttatg ggactttcct acttggcagt acatctacgt attagtcatc    960

gctattacca tggtgatgcg gttttggcag tacatcaatg ggcgtggata gcggtttgac   1020

tcacggggat ttccaagtct ccaccccatt gacgtcaatg ggagtttgtt ttggcaccaa   1080

aatcaacggg actttccaaa atgtcgtaac aactccgccc cattgacgca aatgggcggt   1140

aggcgtgtac ggtgggaggt ctatataagc agagctcgtt tagtgaaccg tcagatcgcc   1200

tggagacgcc atccacgctg ttttgacctc catagaagac accgggaccg atccagcctc   1260

cgtcaccgtc gtcgacacgt gtgatcagat aattctctaa tcacagtcat catgggagcg   1320

tcagggattc tgcaattgcc ccgtgagcgc ttcaggaaaa catctttctt tgtttgggta   1380

ataatcctat tccataaagt cttttcaatc ccgttggggg ttgtacacaa caataccta    1440
```

caagtgagtg atattgacaa gtttgtgtgc cgagacaaac tctcttcaac tagccaattg 1500
aagtcagtcg ggttgaactt ggagggcaat ggagtagcaa ctgatgtacc aacggcaacc 1560
aaaagatggg gttttcgagc tggtgttcca ccaaaggtgg taaattacga agctggagaa 1620
tgggctgaga actgttataa cctggctata aagaaagttg atggtagtga gtgcctacca 1680
gaagcccctg agggagtgag ggattttccc cgttgccgct atgtacacaa agtctcagga 1740
actggaccat gcccaggagg actcgccttt cacaaagaag gagccttctt cctgtatgac 1800
cgactcgcat caacaatcat ttatcggggt acaacctttg ccgaaggagt tattgcattt 1860
ctgatcttgc ctaaggcgcg aaaggatttt ttccagtctc ctccattgca tgagcctgcc 1920
aacatgacca cggatccctc cagttactat cacacgacaa caataaacta cgtggttgat 1980
aattttggaa ccaacaccac agagtttctg ttccaagtcg atcatttgac gtatgtgcag 2040
ctcgaggcaa gattcacacc acaattcctt gtcctcctaa atgaaaccat ctactctgat 2100
aaccgcagaa gtaacacaac aggaaaacta atctggaaaa taaatcccac tgttgatacc 2160
agcatgggtg agtgggcttt ctgggaaaat aaaaaaactt cacaaaaacc ctttcaagtg 2220
aagagttgtc tttcgtacct gtaccagaaa cccagaacca ggtccttgac acgacagcga 2280
cggtctctcc tcccatctcc gcccacaacc acgcaggcga agaccacaaa gaattggttt 2340
cagaggattc cactccagtg gttcagatgc aaaacatcaa gggaaaggac acaatgccaa 2400
ccacagtgac gggtgtacca acaaccacac cctctccatt tccaatcaat gctcgcaaca 2460
ctgatcatac caaatcattt atcggcctgg aggggcccca agaagaccac agcaccacac 2520
agcctgccaa gaccaccagc caaccaacca acagcacaga atcgacgaca ctaaacccaa 2580
catcagagcc ctccagtaga ggcacgggac catccagccc cacggtcccc aacaccacag 2640
aaagccacgc cgaacttggc aagacaaccc caaccacact cccagaacag cacactgccg 2700
ccagtgccat tccaagagcc gtgcaccccg acgaactcag tggacctggc ttcctgacga 2760
acacaatacg gggggtgaca aatctcctga caggatccag aagaaagcga agggatgtca 2820
ctcccaatac acaacccaaa tgcaacccaa acctgcacta ttggacagcc ttggatgagg 2880
gtgctgccat aggtttagcc tggataccat acttcgggcc agcagctgag ggaatttaca 2940
ctgaaggcat aatggagaat caaaatggat tgatctgtgg attgaggcag ctggccaacg 3000
aaacgacaca agctcttcaa ttgttcttaa gggcaactac tgagttgcgt acattctcta 3060
tactaaatcg gaaagcaata gacttcttgc tccaaagatg gggaggaaca tgtcacattc 3120
tagggcctga ttgttgcatt gaaccccaag attggaccaa aaatatcact gataaaattg 3180
atcaaataat ccatgacttt gtcgataata atcttccaaa tcagaatgat ggcagcaact 3240
ggtggactgg atggaaacaa tggtgaagat ccagatctgc tgtgccttct agttgccagc 3300
catctgttgt ttgcccctcc cccgtgcctt ccttgaccct ggaaggtgcc actcccactg 3360
tcctttccta ataaaatgag gaaattgcat cgcattgtct gagtaggtgt cattctattc 3420
tggggggtgg ggtggggcag cacagcaagg gggaggattg ggaagacaat agcaggcatg 3480
ctggggatgc ggtgggctct atgggtaccc agggccgcat aacttcgtat aatgtatgct 3540
atacgaagtt ataagatctg tactgaaatg tgtgggcgtg gcttaagggt gggaaagaat 3600
atataaggtg gggtcttat gtagttttgt atctgttttg cagcagccgc cgccgccatg 3660
agcaccaact cgtttgatgg aagcattgtg agctcatatt tgacaacgcg catgccccca 3720
tgggccgggg tgcgtcagaa tgtgatgggc tccagcattg atggtcgccc cgtcctgccc 3780
gcaaactcta ctaccttgac ctacgagacc gtgtctggaa cgccgttgga gactgcagcc 3840

-continued

```
tccgccgccg cttcagccgc tgcagccacc gcccgcggga ttgtgactga ctttgctttc   3900

ctgagcccgc ttgcaagcag tgcagcttcc cgttcatccg cccgcgatga caagttgacg   3960

gctcttttgg cacaattgga ttctttgacc cgggaactta atgtcgtttc tcagcagctg   4020

ttggatctgc gccagcaggt ttctgccctg aaggcttcct cccctcccaa tgcggtttaa   4080

aacataaata aaaaaccaga ctctgtttgg atttggatca agcaagtgtc ttgctgtctt   4140

tatttagggg ttttgcgcgc gcggtaggcc cgggaccagc ggtctcggtc gttgagggtc   4200

ctgtgtattt tttccaggac gtggtaaagg tgactctgga tgttcagata catgggcata   4260

agcccgtctc tggggtggag gtagcaccac tgcagagctt catgctgcgg ggtggtgttg   4320

tagatgatcc agtcgtagca ggagcgctgg gcgtggtgcc taaaaatgtc tttcagtagc   4380

aagctgattg ccaggggcag gcccttggtg taagtgttta caaagcggtt aagctgggat   4440

gggtgcatac gtggggatat gagatgcatc ttggactgta tttttaggtt ggctatgttc   4500

ccagccatat ccctccgggg attcatgttg tgcagaacca ccagcacagt gtatccggtg   4560

cacttgggaa atttgtcatg tagcttagaa ggaaatgcgt ggaagaactt ggagacgccc   4620

ttgtgacctc caagattttc catgcattcg tccataatga tggcaatggg cccacgggcg   4680

gcggcctggg cgaagatatt tctgggatca ctaacgtcat agttgtgttc caggatgaga   4740

tcgtcatagg ccatttttac aaagcgcggg cggagggtgc cagactgcgg tataatggtt   4800

ccatccggcc caggggcgta gttaccctca cagatttgca tttcccacgc tttgagttca   4860

gatgggggga tcatgtctac ctgcggggcg atgaagaaaa cggtttccgg ggtaggggag   4920

atcagctggg aagaaagcag gttcctgagc agctgcgact taccgcagcc ggtgggcccg   4980

taaatcacac ctattaccgg ctgcaactgg tagttaagag agctgcagct gccgtcatcc   5040

ctgagcaggg gggccacttc gttaagcatg tccctgactc gcatgttttc cctgaccaaa   5100

tccgccagaa ggcgctcgcc gcccagcgat agcagttctt gcaaggaagc aaagtttttc   5160

aacggtttga gaccgtccgc cgtaggcatg cttttgagcg tttgaccaag cagttccagg   5220

cggtcccaca gctcggtcac ctgctctacg gcatctcgat ccagcatatc tcctcgtttc   5280

gcgggttggg gcggctttcg ctgtacggca gtagtcggtg ctcgtccaga cgggccaggg   5340

tcatgtcttt ccacgggcgc agggtcctcg tcagcgtagt ctgggtcacg gtgaaggggt   5400

gcgctccggg ctgcgcgctg gccagggtgc gcttgaggct ggtcctgctg gtgctgaagc   5460

gctgccggtc ttcgccctgc gcgtcggcca ggtagcattt gaccatggtg tcatagtcca   5520

gcccctccgc ggcgtggccc ttggcgcgca gcttgccctt ggaggaggcg ccgcacgagg   5580

ggcagtgcag acttttgagg gcgtagagct tgggcgcgag aaataccgat tccggggagt   5640

aggcatccgc gccgcaggcc ccgcagacgg tctcgcattc cacgagccag gtgagctctg   5700

gccgttcggg gtcaaaaacc aggtttcccc catgcttttt gatgcgtttc ttacctctgg   5760

tttccatgag ccggtgtcca cgctcggtga cgaaaaggct gtccgtgtcc ccgtatacag   5820

acttgagagg cctgtcctcg agcggtgttc cgcggtcctc ctcgtataga aactcggacc   5880

actctgagac aaaggctcgc gtccaggcca gcacgaagga ggctaagtgg gaggggtagc   5940

ggtcgttgtc cactaggggg tccactcgct ccagggtgtg aagacacatg tcgccctctt   6000

cggcatcaag gaaggtgatt ggtttgtagg tgtaggccac gtgaccgggt gttcctgaag   6060

gggggctata aaagggggtg ggggcgcgtt cgtcctcact ctcttccgca tcgctgtctg   6120

cgagggccag ctgttggggt gagtcgacgc gaggctggat ggccttcccc attatgattc   6180

ttctcgcttc cggcggcatc gggatgcccg cgttgcaggc catgctgtcc aggcaggtag   6240
```

-continued

```
atgacgacca tcagggacag cttcaaggcc agcaaaaggc caggaaccgt aaaaaggccg   6300

cgttgctggc gtttttccat aggctccgcc cccctgacga gcatcacaaa aatcgacgct   6360

caagtcagag gtggcgaaac ccgacaggac tataaagata ccaggcgttt ccccctggaa   6420

gctccctcgt gcgctctcct gttccgaccc tgccgcttac cggatacctg tccgcctttc   6480

tcccttcggg aagcgtggcg ctttctcata gctcacgctg taggtatctc agttcggtgt   6540

aggtcgttcg ctccaagctg ggctgtgtgc acgaaccccc cgttcagccc gaccgctgcg   6600

ccttatccgg taactatcgt cttgagtcca acccggtaag acacgactta tcgccactgg   6660

cagcagccac tggtaacagg attagcagag cgaggtatgt aggcggtgct acagagttct   6720

tgaagtggtg gcctaactac ggctacacta gaaggacagt atttggtatc tgcgctctgc   6780

tgaagccagt taccttcgga aaaagagttg gtagctcttg atccggcaaa caaaccaccg   6840

ctggtagcgg tggttttttt gtttgcaagc agcagattac gcgcagaaaa aaaggatctc   6900

aagaagatcc tttgatcttt tctacggggt ctgacgctca gtggaacgaa aactcacgtt   6960

aagggatttt ggtcatgaga ttatcaaaaa ggatcttcac ctagatcctt ttaaattaaa   7020

aatgaagttt taaatcaatc taaagtatat atgagtaaac ttggtctgac agttaccaat   7080

gcttaatcag tgaggcacct atctcagcga tctgtctatt tcgttcatcc atagttgcct   7140

gactccccgt cgtgtagata actacgatac gggagggctt accatctggc cccagtgctg   7200

caatgatacc gcgagaccca cgctcaccgg ctccagattt atcagcaata aaccagccag   7260

ccggaagggc cgagcgcaga agtggtcctg caactttatc cgcctccatc cagtctatta   7320

attgttgccg ggaagctaga gtaagtagtt cgccagttaa tagtttgcgc aacgttgttg   7380

ccattgctgc aggcatcgtg gtgtcacgct cgtcgtttgg tatggcttca ttcagctccg   7440

gttcccaacg atcaaggcga gttacatgat cccccatgtt gtgcaaaaaa gcggttagct   7500

ccttcggtcc tccgatcgtt gtcagaagta agttggccgc agtgttatca ctcatggtta   7560

tggcagcact gcataattct cttactgtca tgccatccgt aagatgcttt tctgtgactg   7620

gtgagtactc aaccaagtca ttctgagaat agtgtatgcg gcgaccgagt tgctcttgcc   7680

cggcgtcaac acgggataat accgcgccac atagcagaac tttaaaagtg ctcatcattg   7740

gaaaacgttc ttcggggcga aaactctcaa ggatcttacc gctgttgaga tccagttcga   7800

tgtaacccac tcgtgcaccc aactgatctt cagcatcttt tactttcacc agcgtttctg   7860

ggtgagcaaa aacaggaagg caaaatgccg caaaaaaggg aataagggcg acacggaaat   7920

gttgaatact catactcttc ctttttcaat attattgaag catttatcag ggttattgtc   7980

tcatgagcgg atacatattt gaatgtattt agaaaaataa acaaataggg gttccgcgca   8040

catttccccg aaaagtgcca cctgacgtct aagaaaccat tattatcatg acattaacct   8100

ataaaaatag gcgtatcacg aggccctttc gtcttcaaga attgtt                  8146
```

<210> SEQ ID NO 21
<211> LENGTH: 7023
<212> TYPE: DNA
<213> ORGANISM: Artificial Sequence
<220> FEATURE:
<223> OTHER INFORMATION: Synthetic Construct pVR1012x/s-SGP(IC)

<400> SEQUENCE: 21

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180
```

-continued

```
accatatgcg gtgtgaaata ccgcacagat gcgtaaggag aaaataccgc atcagattgg    240
ctattggcca ttgcatacgt tgtatccata tcataatatg tacatttata ttggctcatg    300
tccaacatta ccgccatgtt gacattgatt attgactagt tattaatagt aatcaattac    360
ggggtcatta gttcatagcc catatatgga gttccgcgtt acataactta cggtaaatgg    420
cccgcctggc tgaccgccca acgacccccg cccattgacg tcaataatga cgtatgttcc    480
catagtaacg ccaataggga ctttccattg acgtcaatgg gtggagtatt tacggtaaac    540
tgcccacttg gcagtacatc aagtgtatca tatgccaagt acgcccccta ttgacgtcaa    600
tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctccg cggccgggaa cggtgcattg gaacgcggat   1020
tccccgtgcc aagagtgacg taagtaccgc ctatagactc tataggcaca cccctttggc   1080
tcttatgcat gctatactgt ttttggcttg gggcctatac acccccgctt ccttatgcta   1140
taggtgatgg tatagcttag cctataggtg tgggttattg accattattg accactcccc   1200
tattggtgac gatactttcc attactaatc cataacatgg ctctttgcca caactatctc   1260
tattggctat atgccaatac tctgtccttc agagactgac acggactctg tatttttaca   1320
ggatggggtc ccatttatta tttacaaatt cacatataca acaacgccgt cccccgtgcc   1380
cgcagttttt attaaacata gcgtgggatc tccacgcgaa tctcgggtac gtgttccgga   1440
catgggctct tctccggtag cggcggagct tccacatccg agccctggtc ccatgcctcc   1500
agcggctcat ggtcgctcgg cagctccttg ctcctaacag tggaggccag acttaggcac   1560
agcacaatgc ccaccaccac cagtgtgccg cacaaggccg tggcggtagg gtatgtgtct   1620
gaaaatgagc gtggagattg ggctcgcacg gctgacgcag atggaagact taaggcagcg   1680
gcagaagaag atgcaggcag ctgagttgtt gtattctgat aagagtcaga ggtaactccc   1740
gttgcggtgc tgttaacggt ggagggcagt gtagtctgag cagtactcgt tgctgccgcg   1800
cgcgccacca gacataatag ctgacagact aacagactgt tcctttccat gggtcttttc   1860
tgcagtcacc gtcgtcgaca cgtgtgatca gatatcgcgg ccgctctaga attcggcttc   1920
taatcacagt caccatggga gcgtcaggga ttctgcaatt gccccgtgag cgcttcagga   1980
aaacatcttt ctttgtttgg gtaataatcc tattccataa agtcttttca atcccgttgg   2040
gggttgtaca caacaatacc ctacaagtga gtgatattga caagtttgtg tgccgagaca   2100
aactctcttc aactagccaa ttgaagtcag tcgggttgaa cttggagggc aatggagtag   2160
caactgatgt accaacggca accaaaagat ggggttttcg agctggtgtt ccaccaaagg   2220
tggtaaattg cgaagctgga gaatgggctg agaactgtta taacctggct ataaagaaag   2280
ttgatggtag tgagtgccta ccagaagccc ctgagggagt gagggatttt ccccgttgcc   2340
gctatgtaca caaagtctca ggaactggac catgcccagg aggactcgcc tttcacaaag   2400
aaggagcctt cttcctgtat gaccgactcg catcaacaat catttatcgg ggtacaacct   2460
ttgccgaagg agttattgca tttctgatct tgcctaaggc gcgaaaggat tttttccagt   2520
ctcctccatt gcatgagcct gccaacatga ccacggatcc ctccagttac tatcacacga   2580
```

-continued caacaataaa ctacgtggtt gataattttg gaaccaacac cacagagttt ctgttccaag 2640
tcgatcattt gacgtatgtg cagctcgagg caagattcac accacaattc cttgtcctcc 2700
taaatgaaac catctactct gataaccgca gaagtaacac aacaggaaaa ctaatctgga 2760
aaataaatcc cactgttgat accagcatgg gtgagtgggc tttctgggaa aataaaaaaa 2820
acttcacaaa aaccctttca agtgaagagt tgtctttcgt acctgtacca gaaacccaga 2880
accaggtcct tgacacgaca gcgacggtct ctcctcccat ctccgcccac aaccacgcag 2940
ccgaagacca caaagaattg gtttcagagg attccactcc agtggttcag atgcaaaaca 3000
tcaagggaaa ggacacaatg ccaaccacag tgacgggtgt accaacaacc acaccctctc 3060
catttccaat caatgctcgc aacactgatc ataccaaatc atttatcggc ctggaggggc 3120
cccaagaaga ccacagcacc acacagcctg ccaagaccac cagccaacca accaacagca 3180
cagaatcgac gacactaaac ccaacatcag agccctccag tagaggcacg ggaccatcca 3240
gccccacggt ccccaacacc acagaaagcc acgccgaact tggcaagaca accccaacca 3300
cactcccaga acagcacact gccgccagtg ccattccaag agccgtgcac cccgacgaac 3360
tcagtggacc tggcttcctg acgaacacaa tacggggggt tacaaatctc ctgacaggat 3420
ccagaagaaa gcgaagggat gtcactccca atacacaacc caaatgcaac ccaaacctgc 3480
actattggac agccttggat gagggtgctg ccataggttt agcctggata ccatacttcg 3540
ggccagcagc tgagggaatt tacactgaag gcataatgga gaatcaaaat ggattgatct 3600
gtggattgag gcagctggcc aacgaaacga cacaagctct tcaattgttc ttaagggcaa 3660
ctactgagtt gcgtacattc tctatactaa atcggaaagc aatagacttc ttgctccaaa 3720
gatggggagg aacatgtcac attctagggc ctgattgttg cattgaaccc caagattgga 3780
ccaaaaatat cactgataaa attgatcaaa taatccatga ctttgtcgat aataatcttc 3840
caaatcagaa tgatggcagc aactggtgga ctggatggaa acaatgggtt cctgctggaa 3900
taggaatcac aggagtaatc attgctatta ttgctttgct gtgcatttgc aaattcatgc 3960
tttgaactaa tatagcatca tactttaagc cgaattctag accaggccct ggatccagat 4020
ctgctgtgcc ttctagttgc cagccatctg ttgtttgccc ctcccccgtg ccttccttga 4080
ccctggaagg tgccactccc actgtccttt cctaataaaa tgaggaaatt gcatcgcatt 4140
gtctgagtag gtgtcattct attctggggg gtggggtggg gcaggacagc aagggggagg 4200
attgggaaga caatagcagg catgctgggg atgcggtggg ctctatgggt acccaggtgc 4260
tgaagaattg acccggttcc tcctgggcca gaaagaagca ggcacatccc cttctctgtg 4320
acacaccctg tccacgcccc tggttcttag ttccagcccc actcatagga cactcatagc 4380
tcaggagggc tccgccttca atcccacccg ctaaagtact tggagcggtc tctccctccc 4440
tcatcagccc accaaaccaa acctagcctc caagagtggg aagaaattaa agcaagatag 4500
gctattaagt gcagagggag agaaaatgcc tccaacatgt gaggaagtaa tgagagaaat 4560
catagaattt taaggccatc atggccttaa tcttccgctt cctcgctcac tgactcgctg 4620
cgctcggtcg ttcggctgcg gcgagcggta tcagctcact caaaggcggt aatacggtta 4680
tccacagaat caggggataa cgcaggaaag aacatgtgag caaaaggcca gcaaaaggcc 4740
aggaaccgta aaaaggccgc gttgctggcg tttttccata ggctccgccc ccctgacgag 4800
catcacaaaa atcgacgctc aagtcagagg tggcgaaacc cgacaggact ataaagatac 4860
caggcgtttc cccctggaag ctccctcgtg cgctctcctg ttccgaccct gccgcttacc 4920
ggatacctgt ccgcctttct cccttcggga agcgtggcgc tttctcatag ctcacgctgt 4980

-continued aggtatctca gttcggtgta ggtcgttcgc tccaagctgg gctgtgtgca cgaacccccc 5040
gttcagcccg accgctgcgc cttatccggt aactatcgtc ttgagtccaa cccggtaaga 5100
cacgacttat cgccactggc agcagccact ggtaacagga ttagcagagc gaggtatgta 5160
ggcggtgcta cagagttctt gaagtggtgg cctaactacg gctacactag aagaacagta 5220
tttggtatct gcgctctgct gaagccagtt accttcggaa aaagagttgg tagctcttga 5280
tccggcaaac aaaccaccgc tggtagcggt ggtttttttg tttgcaagca gcagattacg 5340
cgcagaaaaa aaggatctca agaagatcct ttgatctttt ctacggggtc tgacgctcag 5400
tggaacgaaa actcacgtta agggattttg gtcatgagat tatcaaaaag gatcttcacc 5460
tagatccttt taaattaaaa atgaagtttt aaatcaatct aaagtatata tgagtaaact 5520
tggtctgaca gttaccaatg cttaatcagt gaggcaccta tctcagcgat ctgtctattt 5580
cgttcatcca tagttgcctg actcgggggg ggggggcgct gaggtctgcc tcgtgaagaa 5640
ggtgttgctg actcatacca ggcctgaatc gccccatcat ccagccagaa agtgagggag 5700
ccacggttga tgagagcttt gttgtaggtg gaccagttgg tgattttgaa cttttgcttt 5760
gccacggaac ggtctgcgtt gtcgggaaga tgcgtgatct gatccttcaa ctcagcaaaa 5820
gttcgattta ttcaacaaag ccgccgtccc gtcaagtcag cgtaatgctc tgccagtgtt 5880
acaaccaatt aaccaattct gattagaaaa actcatcgag catcaaatga aactgcaatt 5940
tattcatatc aggattatca ataccatatt tttgaaaaag ccgtttctgt aatgaaggag 6000
aaaactcacc gaggcagttc cataggatgg caagatcctg gtatcggtct gcgattccga 6060
ctcgtccaac atcaatacaa cctattaatt tcccctcgtc aaaaataagg ttatcaagtg 6120
agaaatcacc atgagtgacg actgaatccg gtgagaatgg caaaagctta tgcatttctt 6180
tccagacttg ttcaacaggc cagccattac gctcgtcatc aaaatcactc gcatcaacca 6240
aaccgttatt cattcgtgat tgcgcctgag cgagacgaaa tacgcgatcg ctgttaaaag 6300
gacaattaca aacaggaatc gaatgcaacc ggcgcaggaa cactgccagc gcatcaacaa 6360
tattttcacc tgaatcagga tattcttcta atacctggaa tgctgttttc ccggggatcg 6420
cagtggtgag taaccatgca tcatcaggag tacggataaa atgcttgatg gtcggaagag 6480
gcataaattc cgtcagccag tttagtctga ccatctcatc tgtaacatca ttggcaacgc 6540
tacctttgcc atgtttcaga aacaactctg gcgcatcggg cttcccatac aatcgataga 6600
ttgtcgcacc tgattgcccg acattatcgc gagcccattt atacccatat aaatcagcat 6660
ccatgttgga atttaatcgc ggcctcgagc aagacgtttc ccgttgaata tggctcataa 6720
caccccttgt attactgttt atgtaagcag acagttttat tgttcatgat gatatatttt 6780
tatcttgtgc aatgtaacat cagagatttt gagacacaac gtggctttcc cccccccccc 6840
attattgaag catttatcag ggttattgtc tcatgagcgg atacatattt gaatgtattt 6900
agaaaaataa acaaataggg gttccgcgca catttccccg aaaagtgcca cctgacgtct 6960
aagaaaccat tattatcatg acattaacct ataaaaatag gcgtatcacg aggccctttc 7020
gtc 7023

<210> SEQ ID NO 22
<211> LENGTH: 7295
<212> TYPE: DNA
<213> ORGANISM: Artificial Sequence
<220> FEATURE:
<223> OTHER INFORMATION: Synthetic Construct pVR1012-NP

<400> SEQUENCE: 22

-continued

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcagattgg    240
ctattggcca ttgcatacgt tgtatccata tcataatatg tacatttata ttggctcatg    300
tccaacatta ccgccatgtt gacattgatt attgactagt tattaatagt aatcaattac    360
ggggtcatta gttcatagcc catatatgga gttccgcgtt acataactta cggtaaatgg    420
cccgcctggc tgaccgccca acgacccccg cccattgacg tcaataatga cgtatgttcc    480
catagtaacg ccaataggga ctttccattg acgtcaatgg gtggagtatt tacggtaaac    540
tgcccacttg gcagtacatc aagtgtatca tatgccaagt acgcccccta ttgacgtcaa    600
tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctccg cggccgggaa cggtgcattg gaacgcggat   1020
tccccgtgcc aagagtgacg taagtaccgc ctatagactc tataggcaca cccctttggc   1080
tcttatgcat gctatactgt ttttggcttg gggcctatac acccccgctt ccttatgcta   1140
taggtgatgg tatagcttag cctataggtg tgggttattg accattattg accactcccc   1200
tattggtgac gatactttcc attactaatc cataacatgg ctctttgcca caactatctc   1260
tattggctat atgccaatac tctgtccttc agagactgac acggactctg tatttttaca   1320
ggatggggtc ccatttatta tttacaaatt cacatataca acaacgccgt cccccgtgcc   1380
cgcagttttt attaaacata gcgtgggatc tccacgcgaa tctcgggtac gtgttccgga   1440
catgggctct tctccggtag cggcggagct tccacatccg agccctggtc ccatgcctcc   1500
agcggctcat ggtcgctcgg cagctccttg ctcctaacag tggaggccag acttaggcac   1560
agcacaatgc ccaccaccac cagtgtgccg cacaaggccg tggcggtagg gtatgtgtct   1620
gaaaatgagc gtggagattg ggctcgcacg gctgacgcag atggaagact taaggcagcg   1680
gcagaagaag atgcaggcag ctgagttgtt gtattctgat aagagtcaga ggtaactccc   1740
gttgcggtgc tgttaacggt ggagggcagt gtagtctgag cagtactcgt tgctgccgcg   1800
cgcgccacca gacataatag ctgacagact aacagactgt tcctttccat gggtcttttc   1860
tgcagtcacc gtcgtcgaca cgtgtgatca gatatcgcgg ccgctctaga ccaggccctg   1920
gatccagatc gatccgagta tggattctcg tcctcagaaa atctggatgg cgccgagtct   1980
cactgaatct gacatggatt accacaagat cttgacagca ggtctgtccg ttcaacaggg   2040
gattgttcgg caaagagtca tcccagtgta tcaagtaaac aatcttgaag aaatttgcca   2100
acttatcata caggcctttg aagcaggtgt tgattttcaa gagagtgcgg acagtttcct   2160
tctcatgctt tgtcttcatc atgcgtacca gggagattac aaacttttct tggaaagtgg   2220
cgcagtcaag tatttggaag ggcacgggtt ccgttttgaa gtcaagaagc gtgatggagt   2280
gaagcgcctt gaggaattgc tgccagcagt atctagtgga aaaaacatta agagaacact   2340
tgctgccatg ccggaagagg agacaactga agctaatgcc ggtcagtttc tctcctttgc   2400
```

-continued

```
aagtctattc cttccgaaat tggtagtagg agaaaaggct tgccttgaga aggttcaaag   2460
gcaaattcaa gtacatgcag agcaaggact gatacaatat ccaacagctt ggcaatcagt   2520
aggacacatg atggtgattt tccgtttgat gcgaacaaat tttctgatca aatttctcct   2580
aatacaccaa gggatgcaca tggttgccgg gcatgatgcc aacgatgctg tgatttcaaa   2640
ttcagtggct caagctcgtt tttcaggctt attgattgtc aaaacagtac ttgatcatat   2700
cctacaaaag acagaacgag gagttcgtct ccatcctctt gcaaggaccg ccaaggtaaa   2760
aaatgaggtg aactccttta aggctgcact cagctccctg gccaagcatg gagagtatgc   2820
tcctttcgcc cgacttttga acctttctgg agtaaataat cttgagcatg gtcttttccc   2880
tcaactatcg gcaattgcac tcggagtcgc cacagcacac gggagtaccc tcgcaggagt   2940
aaatgttgga gaacagtatc aacaactcag agaggctgcc actgaggctg agaagcaact   3000
ccaacaatat gcagagtctc gcgaacttga ccatcttgga cttgatgatc aggaaaagaa   3060
aattcttatg aacttccatc agaaaaagaa cgaaatcagc ttccagcaaa caaacgctat   3120
ggtaactcta agaaaagagc gcctggccaa gctgacagaa gctatcactg ctgcgtcact   3180
gcccaaaaca agtggacatt acgatgatga tgacgacatt ccctttccag gacccatcaa   3240
tgatgacgac aatcctggcc atcaagatga tgatccgact gactcacagg atacgaccat   3300
tcccgatgtg gtggttgatc ccgatgatgg aagctacggc gaataccaga gttactcgga   3360
aaacggcatg aatgcaccag atgacttggt cctattcgat ctagacgagg acgacgagga   3420
cactaagcca gtgcctaata gatcgaccaa gggtggacaa cagaagaaca gtcaaaaggg   3480
ccagcatata gagggcagac agacacaatc caggccaatt caaaatgtcc caggccctca   3540
cagaacaatc caccacgcca gtgcgccact cacggacaat gacagaagaa atgaaccctc   3600
cggctcaacc agccctcgca tgctgacacc aattaacgaa gaggcagacc cactggacga   3660
tgccgacgac gagacgtcta gccttccgcc cttggagtca gatgatgaag agcaggacag   3720
ggacggaact tccaaccgca cacccactgt cgccccaccg gctcccgtat acagagatca   3780
ctctgaaaag aaagaactcc cgcaagacga gcaacaagat caggaccaca ctcaagaggc   3840
caggaaccag gacagtgaca acacccagtc agaacactct tttgaggaga tgtatcgcca   3900
cattctaaga tcacaggggc catttgatgc tgttttgtat tatcatatga tgaaggatga   3960
gcctgtagtt ttcagtacca gtgatggcaa agagtacacg tatccagact ccccttgaaga   4020
ggaatatcca ccatggctca ctgaaaaaga ggctatgaat gaagagaata gatttgttac   4080
attggatggt caacaatttt attggccggt gatgaatcac aagaataaat tcatggcaat   4140
cctgcaacat catcagtgaa tgagcatgga acaatgggat gattcaaccg acaaatagct   4200
aacattaagt agtcaaggaa cgaaaacagg aagaattttt gatgtctaag gtgtgaatta   4260
ttatcacaat aaaagtgatt cttatttttg aatttgggcg agctcgaatt gatctgctgt   4320
gccttctagt tgccagccat ctgttgtttg cccctccccc gtgccttcct tgaccctgga   4380
aggtgccact cccactgtcc tttcctaata aaatgaggaa attgcatcgc attgtctgag   4440
taggtgtcat tctattctgg ggggtggggt ggggcaggac agcaaggggg aggattggga   4500
agacaatagc aggcatgctg gggatgcggt gggctctatg ggtacccagg tgctgaagaa   4560
ttgacccggt tcctcctggg ccagaaagaa gcaggcacat ccccttctct gtgacacacc   4620
ctgtccacgc ccctggttct tagttccagc cccactcata ggacactcat agctcaggag   4680
ggctccgcct tcaatcccac ccgctaaagt acttggagcg gtctctccct ccctcatcag   4740
cccaccaaac caaacctagc ctccaagagt gggaagaaat taaagcaaga taggctatta   4800
```

-continued

```
agtgcagagg gagagaaaat gcctccaaca tgtgaggaag taatgagaga aatcatagaa   4860
tttcttccgc ttcctcgctc actgactcgc tgcgctcggt cgttcggctg cggcgagcgg   4920
tatcagctca ctcaaaggcg gtaatacggt tatccacaga atcaggggat aacgcaggaa   4980
agaacatgtg agcaaaaggc cagcaaaagg ccaggaaccg taaaaaggcc gcgttgctgg   5040
cgtttttcca taggctccgc ccccctgacg agcatcacaa aaatcgacgc tcaagtcaga   5100
ggtggcgaaa cccgacagga ctataaagat accaggcgtt tccccctgga agctccctcg   5160
tgcgctctcc tgttccgacc ctgccgctta ccggatacct gtccgccttt ctcccttcgg   5220
gaagcgtggc gctttctcat agctcacgct gtaggtatct cagttcggtg taggtcgttc   5280
gctccaagct gggctgtgtg cacgaacccc ccgttcagcc cgaccgctgc gccttatccg   5340
gtaactatcg tcttgagtcc aacccggtaa gacacgactt atcgccactg gcagcagcca   5400
ctggtaacag gattagcaga gcgaggtatg taggcggtgc tacagagttc ttgaagtggt   5460
ggcctaacta cggctacact agaagaacag tatttggtat ctgcgctctg ctgaagccag   5520
ttaccttcgg aaaaagagtt ggtagctctt gatccggcaa acaaaccacc gctggtagcg   5580
gtggtttttt tgtttgcaag cagcagatta cgcgcagaaa aaaaggatct caagaagatc   5640
ctttgatctt ttctacgggg tctgacgctc agtggaacga aaactcacgt taagggattt   5700
tggtcatgag attatcaaaa aggatcttca cctagatcct tttaaattaa aaatgaagtt   5760
ttaaatcaat ctaaagtata tatgagtaaa cttggtctga cagttaccaa tgcttaatca   5820
gtgaggcacc tatctcagcg atctgtctat ttcgttcatc catagttgcc tgactcgggg   5880
gggggggcg ctgaggtctg cctcgtgaag aaggtgttgc tgactcatac caggcctgaa   5940
tcgccccatc atccagccag aaagtgaggg agccacggtt gatgagagct ttgttgtagg   6000
tggaccagtt ggtgattttg aacttttgct ttgccacgga acggtctgcg ttgtcgggaa   6060
gatgcgtgat ctgatccttc aactcagcaa aagttcgatt tattcaacaa agccgccgtc   6120
ccgtcaagtc agcgtaatgc tctgccagtg ttacaaccaa ttaaccaatt ctgattagaa   6180
aaactcatcg agcatcaaat gaaactgcaa tttattcata tcaggattat caataccata   6240
tttttgaaaa agccgtttct gtaatgaagg agaaaactca ccgaggcagt tccataggat   6300
ggcaagatcc tggtatcggt ctgcgattcc gactcgtcca acatcaatac aacctattaa   6360
tttcccctcg tcaaaaataa ggttatcaag tgagaaatca ccatgagtga cgactgaatc   6420
cggtgagaat ggcaaaagct tatgcatttc tttccagact tgttcaacag gccagccatt   6480
acgctcgtca tcaaaatcac tcgcatcaac caaaccgtta ttcattcgtg attgcgcctg   6540
agcgagacga aatacgcgat cgctgttaaa aggacaatta caaacaggaa tcgaatgcaa   6600
ccggcgcagg aacactgcca gcgcatcaac aatattttca cctgaatcag gatattcttc   6660
taatacctgg aatgctgttt tcccggggat cgcagtggtg agtaaccatg catcatcagg   6720
agtacggata aaatgcttga tggtcggaag aggcataaat tccgtcagcc agtttagtct   6780
gaccatctca tctgtaacat cattggcaac gctacctttg ccatgtttca gaaacaactc   6840
tggcgcatcg ggcttcccat acaatcgata gattgtcgca cctgattgcc cgacattatc   6900
gcgagcccat ttatacccat ataaatcagc atccatgttg gaatttaatc gcggcctcga   6960
gcaagacgtt tcccgttgaa tatggctcat aacacccctt gtattactgt ttatgtaagc   7020
agacagtttt attgttcatg atgatatatt tttatcttgt gcaatgtaac atcagagatt   7080
ttgagacaca acgtggcttt cccccccccc ccattattga agcatttatc agggttattg   7140
tctcatgagc ggatacatat ttgaatgtat ttagaaaaat aaacaaatag gggttccgcg   7200
```

```
cacatttccc cgaaaagtgc cacctgacgt ctaagaaacc attattatca tgacattaac   7260

ctataaaaat aggcgtatca cgaggccctt tcgtc                              7295


<210> SEQ ID NO 23
<211> LENGTH: 7329
<212> TYPE: DNA
<213> ORGANISM: Artificial Sequence
<220> FEATURE:
<223> OTHER INFORMATION: Synthetic Construct pVR1012x/s Ebola-NP

<400> SEQUENCE: 23

tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatgcg gtgtgaaata ccgcacagat gcgtaaggag aaaataccgc atcagattgg    240

ctattggcca ttgcatacgt tgtatccata tcataatatg tacatttata ttggctcatg    300

tccaacatta ccgccatgtt gacattgatt attgactagt tattaatagt aatcaattac    360

ggggtcatta gttcatagcc catatatgga gttccgcgtt acataactta cggtaaatgg    420

cccgcctggc tgaccgccca acgacccccg cccattgacg tcaataatga cgtatgttcc    480

catagtaacg ccaataggga ctttccattg acgtcaatgg gtggagtatt tacggtaaac    540

tgcccacttg gcagtacatc aagtgtatca tatgccaagt acgcccccta ttgacgtcaa    600

tgacggtaaa tggcccgcct ggcattatgc ccagtacatg accttatggg actttcctac    660

ttggcagtac atctacgtat tagtcatcgc tattaccatg gtgatgcggt tttggcagta    720

catcaatggg cgtggatagc ggtttgactc acggggattt ccaagtctcc accccattga    780

cgtcaatggg agtttgtttt ggcaccaaaa tcaacgggac tttccaaaat gtcgtaacaa    840

ctccgcccca ttgacgcaaa tgggcggtag gcgtgtacgg tgggaggtct atataagcag    900

agctcgttta gtgaaccgtc agatcgcctg gagacgccat ccacgctgtt ttgacctcca    960

tagaagacac cgggaccgat ccagcctccg cggccgggaa cggtgcattg gaacgcggat   1020

tccccgtgcc aagagtgacg taagtaccgc ctatagactc tataggcaca cccctttggc   1080

tcttatgcat gctatactgt ttttggcttg gggcctatac acccccgctt ccttatgcta   1140

taggtgatgg tatagcttag cctataggtg tgggttattg accattattg accactcccc   1200

tattggtgac gatactttcc attactaatc cataacatgg ctctttgcca caactatctc   1260

tattggctat atgccaatac tctgtccttc agagactgac acggactctg tatttttaca   1320

ggatggggtc ccatttatta tttacaaatt cacatataca acaacgccgt cccccgtgcc   1380

cgcagttttt attaaacata gcgtgggatc tccacgcgaa tctcgggtac gtgttccgga   1440

catgggctct tctccggtag cggcggagct tccacatccg agccctggtc ccatgcctcc   1500

agcggctcat ggtcgctcgg cagctccttg ctcctaacag tggaggccag acttaggcac   1560

agcacaatgc ccaccaccac cagtgtgccg cacaaggccg tggcggtagg gtatgtgtct   1620

gaaaatgagc gtggagattg ggctcgcacg gctgacgcag atggaagact taaggcagcg   1680

gcagaagaag atgcaggcag ctgagttgtt gtattctgat aagagtcaga ggtaactccc   1740

gttgcggtgc tgttaacggt ggagggcagt gtagtctgag cagtactcgt tgctgccgcg   1800

cgcgccacca gacataatag ctgacagact aacagactgt tcctttccat gggtcttttc   1860

tgcagtcacc gtcgtcgaca cgtgtgatca gatatcgcgg ccgctctaga ccaggccctg   1920

gatccagatc gatccgagta tggattctcg tcctcagaaa atctggatgg cgccgagtct   1980
```

-continued

```
cactgaatct gacatggatt accacaagat cttgacagca ggtctgtccg ttcaacaggg   2040

gattgttcgg caaagagtca tcccagtgta tcaagtaaac aatcttgaag aaatttgcca   2100

acttatcata caggcctttg aagcaggtgt tgattttcaa gagagtgcgg acagtttcct   2160

tctcatgctt tgtcttcatc atgcgtacca gggagattac aaacttttct tggaaagtgg   2220

cgcagtcaag tatttggaag ggcacgggtt ccgttttgaa gtcaagaagc gtgatggagt   2280

gaagcgcctt gaggaattgc tgccagcagt atctagtgga aaaaacatta agagaacact   2340

tgctgccatg ccggaagagg agacaactga agctaatgcc ggtcagtttc tctcctttgc   2400

aagtctattc cttccgaaat tggtagtagg agaaaaggct tgccttgaga aggttcaaag   2460

gcaaattcaa gtacatgcag agcaaggact gatacaatat ccaacagctt ggcaatcagt   2520

aggacacatg atggtgattt tccgtttgat gcgaacaaat tttctgatca aatttctcct   2580

aatacaccaa gggatgcaca tggttgccgg gcatgatgcc aacgatgctg tgatttcaaa   2640

ttcagtggct caagctcgtt tttcaggctt attgattgtc aaaacagtac ttgatcatat   2700

cctacaaaag acagaacgag gagttcgtct ccatcctctt gcaaggaccg ccaaggtaaa   2760

aaatgaggtg aactccttta aggctgcact cagctccctg gccaagcatg gagagtatgc   2820

tcctttcgcc cgacttttga acctttctgg agtaaataat cttgagcatg gtcttttccc   2880

tcaactatcg gcaattgcac tcggagtcgc cacagcacac gggagtaccc tcgcaggagt   2940

aaatgttgga gaacagtatc aacaactcag agaggctgcc actgaggctg agaagcaact   3000

ccaacaatat gcagagtctc gcgaacttga ccatcttgga cttgatgatc aggaaaagaa   3060

aattcttatg aacttccatc agaaaaagaa cgaaatcagc ttccagcaaa caaacgctat   3120

ggtaactcta agaaaagagc gcctggccaa gctgacagaa gctatcactg ctgcgtcact   3180

gcccaaaaca agtggacatt acgatgatga tgacgacatt ccctttccag gacccatcaa   3240

tgatgacgac aatcctggcc atcaagatga tgatccgact gactcacagg atacgaccat   3300

tcccgatgtg gtggttgatc ccgatgatgg aagctacggc gaataccaga gttactcgga   3360

aaacggcatg aatgcaccag atgacttggt cctattcgat ctagacgagg acgacgagga   3420

cactaagcca gtgcctaata gatcgaccaa gggtggacaa cagaagaaca gtcaaaaggg   3480

ccagcatata gagggcagac agacacaatc caggccaatt caaaatgtcc caggccctca   3540

cagaacaatc caccacgcca gtgcgccact cacggacaat gacagaagaa atgaaccctc   3600

cggctcaacc agccctcgca tgctgacacc aattaacgaa gaggcagacc cactggacga   3660

tgccgacgac gagacgtcta gccttccgcc cttggagtca gatgatgaag agcaggacag   3720

ggacggaact tccaaccgca cacccactgt cgccccaccg gctcccgtat acagagatca   3780

ctctgaaaag aaagaactcc cgcaagacga gcaacaagat caggaccaca ctcaagaggc   3840

caggaaccag gacagtgaca acacccagtc agaacactct tttgaggaga tgtatcgcca   3900

cattctaaga tcacaggggc catttgatgc tgttttgtat tatcatatga tgaaggatga   3960

gcctgtagtt ttcagtacca gtgatggcaa agagtacacg tatccagact cccttgaaga   4020

ggaatatcca ccatggctca ctgaaaaaga ggctatgaat gaagagaata gatttgttac   4080

attggatggt caacaatttt attggccggt gatgaatcac aagaataaat tcatggcaat   4140

cctgcaacat catcagtgaa tgagcatgga acaatgggat gattcaaccg acaaatagct   4200

aacattaagt agtcaaggaa cgaaaacagg aagaattttt gatgtctaag gtgtgaatta   4260

ttatcacaat aaaagtgatt cttatttttg aatttgggcg agctcgaatt gatctgctgt   4320

gccttctagt tgccagccat ctgttgtttg cccctccccc gtgccttcct tgaccctgga   4380
```

-continued

```
aggtgccact cccactgtcc tttcctaata aaatgaggaa attgcatcgc attgtctgag   4440
taggtgtcat tctattctgg ggggtggggt ggggcaggac agcaaggggg aggattggga   4500
agacaatagc aggcatgctg gggatgcggt gggctctatg ggtacccagg tgctgaagaa   4560
ttgacccggt tcctcctggg ccagaaagaa gcaggcacat ccccttctct gtgacacacc   4620
ctgtccacgc ccctggttct tagttccagc cccactcata ggacactcat agctcaggag   4680
ggctccgcct tcaatcccac ccgctaaagt acttggagcg gtctctccct ccctcatcag   4740
cccaccaaac caaacctagc ctccaagagt gggaagaaat taaagcaaga taggctatta   4800
agtgcagagg gagagaaaat gcctccaaca tgtgaggaag taatgagaga aatcatagaa   4860
ttttaaggcc atgatttaag gccatcatgg ccttaatctt ccgcttcctc gctcactgac   4920
tcgctgcgct cggtcgttcg gctgcggcga gcggtatcag ctcactcaaa ggcggtaata   4980
cggttatcca cagaatcagg ggataacgca ggaaagaaca tgtgagcaaa aggccagcaa   5040
aaggccagga accgtaaaaa ggccgcgttg ctggcgtttt tccataggct ccgcccccct   5100
gacgagcatc acaaaaatcg acgctcaagt cagaggtggc gaaacccgac aggactataa   5160
agataccagg cgtttccccc tggaagctcc ctcgtgcgct ctcctgttcc gaccctgccg   5220
cttaccggat acctgtccgc ctttctccct tcgggaagcg tggcgctttc tcatagctca   5280
cgctgtaggt atctcagttc ggtgtaggtc gttcgctcca agctgggctg tgtgcacgaa   5340
ccccccgttc agcccgaccg ctgcgcctta tccggtaact atcgtcttga gtccaacccg   5400
gtaagacacg acttatcgcc actggcagca gccactggta acaggattag cagagcgagg   5460
tatgtaggcg gtgctacaga gttcttgaag tggtggccta actacggcta cactagaaga   5520
acagtatttg gtatctgcgc tctgctgaag ccagttacct tcggaaaaag agttggtagc   5580
tcttgatccg gcaaacaaac caccgctggt agcggtggtt tttttgtttg caagcagcag   5640
attacgcgca gaaaaaaagg atctcaagaa gatcctttga tcttttctac ggggtctgac   5700
gctcagtgga acgaaaactc acgttaaggg attttggtca tgagattatc aaaaaggatc   5760
ttcacctaga tccttttaaa ttaaaaatga agttttaaat caatctaaag tatatatgag   5820
taaacttggt ctgacagtta ccaatgctta atcagtgagg cacctatctc agcgatctgt   5880
ctatttcgtt catccatagt tgcctgactc gggggggggg ggcgctgagg tctgcctcgt   5940
gaagaaggtg ttgctgactc ataccaggcc tgaatcgccc catcatccag ccagaaagtg   6000
agggagccac ggttgatgag agctttgttg taggtggacc agttggtgat tttgaacttt   6060
tgctttgcca cggaacggtc tgcgttgtcg ggaagatgcg tgatctgatc cttcaactca   6120
gcaaaagttc gatttattca acaaagccgc cgtcccgtca agtcagcgta atgctctgcc   6180
agtgttacaa ccaattaacc aattctgatt agaaaaactc atcgagcatc aaatgaaact   6240
gcaatttatt catatcagga ttatcaatac catatttttg aaaaagccgt ttctgtaatg   6300
aaggagaaaa ctcaccgagg cagttccata ggatggcaag atcctggtat cggtctgcga   6360
ttccgactcg tccaacatca atacaaccta ttaatttccc ctcgtcaaaa ataaggttat   6420
caagtgagaa atcaccatga gtgacgactg aatccggtga gaatggcaaa agcttatgca   6480
tttctttcca gacttgttca acaggccagc cattacgctc gtcatcaaaa tcactcgcat   6540
caaccaaacc gttattcatt cgtgattgcg cctgagcgag acgaaatacg cgatcgctgt   6600
taaaaggaca attacaaaca ggaatcgaat gcaaccggcg caggaacact gccagcgcat   6660
caacaatatt ttcacctgaa tcaggatatt cttctaatac ctggaatgct gttttcccgg   6720
ggatcgcagt ggtgagtaac catgcatcat caggagtacg gataaaatgc ttgatggtcg   6780
```

-continued gaagaggcat aaattccgtc agccagttta gtctgaccat ctcatctgta acatcattgg 6840
caacgctacc tttgccatgt ttcagaaaca actctggcgc atcgggcttc ccatacaatc 6900
gatagattgt cgcacctgat tgcccgacat tatcgcgagc ccatttatac ccatataaat 6960
cagcatccat gttggaattt aatcgcggcc tcgagcaaga cgtttcccgt tgaatatggc 7020
tcataacacc ccttgtatta ctgtttatgt aagcagacag ttttattgtt catgatgata 7080
tatttttatc ttgtgcaatg taacatcaga gattttgaga cacaacgtgg ctttcccccc 7140
ccccccatta ttgaagcatt tatcagggtt attgtctcat gagcggatac atatttgaat 7200
gtatttagaa aaataaacaa ataggggttc cgcgcacatt tccccgaaaa gtgccacctg 7260
acgtctaaga aaccattatt atcatgacat taacctataa aaataggcgt atcacgaggc 7320
cctttcgtc 7329

<210> SEQ ID NO 24
<211> LENGTH: 6148
<212> TYPE: DNA
<213> ORGANISM: Artificial Sequence
<220> FEATURE:
<223> OTHER INFORMATION: Synthetic Construct pVR1012-VP35

<400> SEQUENCE: 24
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcagattgg 240
ctattggcca ttgcatacgt tgtatccata tcataatatg tacatttata ttggctcatg 300
tccaacatta ccgccatgtt gacattgatt attgactagt tattaatagt aatcaattac 360
ggggtcatta gttcatagcc catatatgga gttccgcgtt acataactta cggtaaatgg 420
cccgcctggc tgaccgccca acgacccccg cccattgacg tcaataatga cgtatgttcc 480
catagtaacg ccaataggga ctttccattg acgtcaatgg gtggagtatt tacggtaaac 540
tgcccacttg gcagtacatc aagtgtatca tatgccaagt acgcccccta ttgacgtcaa 600
tgacggtaaa tggcccgcct ggcattatgc ccagtacatg accttatggg actttcctac 660
ttggcagtac atctacgtat tagtcatcgc tattaccatg gtgatgcggt tttggcagta 720
catcaatggg cgtggatagc ggtttgactc acggggattt ccaagtctcc accccattga 780
cgtcaatggg agtttgtttt ggcaccaaaa tcaacgggac tttccaaaat gtcgtaacaa 840
ctccgcccca ttgacgcaaa tgggcggtag gcgtgtacgg tgggaggtct atataagcag 900
agctcgttta gtgaaccgtc agatcgcctg gagacgccat ccacgctgtt ttgacctcca 960
tagaagacac cgggaccgat ccagcctccg cggccgggaa cggtgcattg gaacgcggat 1020
tccccgtgcc aagagtgacg taagtaccgc ctatagactc tataggcaca cccctttggc 1080
tcttatgcat gctatactgt ttttggcttg gggcctatac acccccgctt ccttatgcta 1140
taggtgatgg tatagcttag cctataggtg tgggttattg accattattg accactcccc 1200
tattggtgac gatactttcc attactaatc cataacatgg ctctttgcca caactatctc 1260
tattggctat atgccaatac tctgtccttc agagactgac acggactctg tatttttaca 1320
ggatggggtc ccatttatta tttacaaatt cacatataca acaacgccgt cccccgtgcc 1380
cgcagttttt attaaacata gcgtgggatc tccacgcgaa tctcgggtac gtgttccgga 1440
catgggctct tctccggtag cggcggagct tccacatccg agccctggtc ccatgcctcc 1500

-continued

```
agcggctcat ggtcgctcgg cagctccttg ctcctaacag tggaggccag acttaggcac   1560
agcacaatgc ccaccaccac cagtgtgccg cacaaggccg tggcggtagg gtatgtgtct   1620
gaaaatgagc gtggagattg ggctcgcacg gctgacgcag atggaagact taaggcagcg   1680
gcagaagaag atgcaggcag ctgagttgtt gtattctgat aagagtcaga ggtaactccc   1740
gttgcggtgc tgttaacggt ggagggcagt gtagtctgag cagtactcgt tgctgccgcg   1800
cgcgccacca gacataatag ctgacagact aacagactgt tcctttccat gggtcttttc   1860
tgcagtcacc gtcgaattct ctagcactcg aagcttattg tcttcaatgt aaaagaaaag   1920
ctggtctaac aagatgacaa ctagaacaaa gggcaggggc catactgcgg ccacgactca   1980
aaacgacaga atgccaggcc ctgagctttc gggctggatc tctgagcagc taatgaccgg   2040
aagaattcct gtaagcgaca tcttctgtga tattgagaac aatccaggat tatgctacgc   2100
atcccaaatg caacaaacga agccaaaccc gaagacgcgc aacagtcaaa cccaaacgga   2160
cccaatttgc aatcatagtt ttgaggaggt agtacaaaca ttggcttcat tggctactgt   2220
tgtgcaacaa caaaccatcg catcagaatc attagaacaa cgcattacga gtcttgagaa   2280
tggtctaaag ccagtttatg atatggcaaa aacaatctcc tcattgaaca gggtttgtgc   2340
tgagatggtt gcaaaatatg atcttctggt gatgacaacc ggtcgggcaa cagcaaccgc   2400
tgcggcaact gaggcttatt gggccgaaca tggtcaacca ccacctggac catcacttta   2460
tgaagaaagt gcgattcggg gtaagattga atctagagat gagaccgtcc ctcaaagtgt   2520
tagggaggca ttcaacaatc taaacagtac cacttcacta actgaggaaa attttgggaa   2580
acctgacatt tcggcaaagg atttgagaaa cattatgtat gatcacttgc ctggttttgg   2640
aactgctttc caccaattag tacaagtgat ttgtaaattg ggaaaagata gcaactcatt   2700
ggacatcatt catgctgagt tccaggccag cctggctgaa ggagactctc ctcaatgtgc   2760
cctaattcaa attacaaaaa gagttccaat cttccaagat gctgctccat ctgtcatcca   2820
catccgcttt cgaggtgaca ttccccgagc ttgccagaaa agcttgcgtc cagtcccacc   2880
atcgcccaag attgatcgag gttgggatgt gtttttcagc ttcaagatgg taaaacactt   2940
ggactcaaaa tttgagccaa tctcccttcc ctccgaaaga ggcgaataat agcagaggct   3000
tcaactgctg aactataggg tacgttacat taatgataca cttgtgagta tcagccctgg   3060
ataatataag tcaattaaac gaccaagata aaattgttca tatctcgcta gcagcttaaa   3120
atataaatgt aataggagct atatctctga caggggggatc cagatctgct gtgccttcta   3180
gttgccagcc atctgttgtt tgcccctccc ccgtgccttc cttgaccctg gaaggtgcca   3240
ctcccactgt cctttcctaa taaaatgagg aaattgcatc gcattgtctg agtaggtgtc   3300
attctattct ggggggtggg gtggggcagc acagcaaggg ggaggattgg gaagacaata   3360
gcaggcatgc tggggatgcg gtgggctcta tgggtaccca ggtgctgaag aattgacccg   3420
gttcctcctg ggccagaaag aagcaggcac atccccttct ctgtgacaca ccctgtccac   3480
gcccctggtt cttagttcca gccccactca taggacactc atagctcagg agggctccgc   3540
cttcaatccc acccgctaaa gtacttggag cggtctctcc ctccctcatc agcccaccaa   3600
accaaaccta gcctccaaga gtgggaagaa attaaagcaa gataggctat taagtgcaga   3660
gggagagaaa atgcctccaa catgtgagga agtaatgaga gaaatcatag aatttcttcc   3720
gcttcctcgc tcactgactc gctgcgctcg gtcgttcggc tgcggcgagc ggtatcagct   3780
cactcaaagg cggtaatacg gttatccaca gaatcagggg ataacgcagg aaagaacatg   3840
tgagcaaaag gccagcaaaa ggccaggaac cgtaaaaagg ccgcgttgct ggcgtttttc   3900
```

-continued cataggctcc gcccccctga cgagcatcac aaaaatcgac gctcaagtca gaggtggcga 3960
aacccgacag gactataaag ataccaggcg tttccccctg gaagctccct cgtgcgctct 4020
cctgttccga ccctgccgct taccggatac ctgtccgcct ttctcccttc gggaagcgtg 4080
gcgctttctc aatgctcacg ctgtaggtat ctcagttcgg tgtaggtcgt tcgctccaag 4140
ctgggctgtg tgcacgaacc ccccgttcag cccgaccgct gcgccttatc cggtaactat 4200
cgtcttgagt ccaacccggt aagacacgac ttatcgccac tggcagcagc cactggtaac 4260
aggattagca gagcgaggta tgtaggcggt gctacagagt tcttgaagtg gtggcctaac 4320
tacggctaca ctagaaggac agtatttggt atctgcgctc tgctgaagcc agttaccttc 4380
ggaaaaagag ttggtagctc ttgatccggc aaacaaacca ccgctggtag cggtggtttt 4440
tttgtttgca agcagcagat tacgcgcaga aaaaaaggat ctcaagaaga tcctttgatc 4500
ttttctacgg ggtctgacgc tcagtggaac gaaaactcac gttaagggat tttggtcatg 4560
agattatcaa aaaggatctt cacctagatc cttttaaatt aaaaatgaag ttttaaatca 4620
atctaaagta tatatgagta aacttggtct gacagttacc aatgcttaat cagtgaggca 4680
cctatctcag cgatctgtct atttcgttca tccatagttg cctgactccg gggggggggg 4740
gcgctgaggt ctgcctcgtg aagaaggtgt tgctgactca taccaggcct gaatcgcccc 4800
atcatccagc cagaaagtga gggagccacg gttgatgaga gctttgttgt aggtggacca 4860
gttggtgatt ttgaactttt gctttgccac ggaacggtct gcgttgtcgg gaagatgcgt 4920
gatctgatcc ttcaactcag caaaagttcg atttattcaa caaagccgcc gtcccgtcaa 4980
gtcagcgtaa tgctctgcca gtgttacaac caattaacca attctgatta gaaaaactca 5040
tcgagcatca aatgaaactg caatttattc atatcaggat tatcaatacc atatttttga 5100
aaaagccgtt tctgtaatga aggagaaaac tcaccgaggc agttccatag gatggcaaga 5160
tcctggtatc ggtctgcgat tccgactcgt ccaacatcaa tacaacctat taatttcccc 5220
tcgtcaaaaa taaggttatc aagtgagaaa tcaccatgag tgacgactga atccggtgag 5280
aatggcaaaa gcttatgcat ttctttccag acttgttcaa caggccagcc attacgctcg 5340
tcatcaaaat cactcgcatc aaccaaaccg ttattcattc gtgattgcgc ctgagcgaga 5400
cgaaatacgc gatcgctgtt aaaaggacaa ttacaaacag gaatcgaatg caaccggcgc 5460
aggaacactg ccagcgcatc aacaatattt tcacctgaat caggatattc ttctaatacc 5520
tggaatgctg ttttcccggg gatcgcagtg gtgagtaacc atgcatcatc aggagtacgg 5580
ataaaatgct tgatggtcgg aagaggcata aattccgtca gccagtttag tctgaccatc 5640
tcatctgtaa catcattggc aacgctacct ttgccatgtt tcagaaacaa ctctggcgca 5700
tcgggcttcc catacaatcg atagattgtc gcacctgatt gcccgacatt atcgcgagcc 5760
catttatacc catataaatc agcatccatg ttggaattta atcgcggcct cgagcaagac 5820
gtttcccgtt gaatatggct cataacaccc cttgtattac tgtttatgta agcagacagt 5880
tttattgttc atgatgatat atttttatct tgtgcaatgt aacatcagag attttgagac 5940
acaacgtggc tttccccccc cccccattat tgaagcattt atcagggtta ttgtctcatg 6000
agcggataca tatttgaatg tatttagaaa aataaacaaa taggggttcc gcgcacattt 6060
ccccgaaaag tgccacctga cgtctaagaa accattatta tcatgacatt aacctataaa 6120
aataggcgta tcacgaggcc ctttcgtc 6148

<210> SEQ ID NO 25
<211> LENGTH: 10783
<212> TYPE: DNA

<213> ORGANISM: Artificial Sequence
<220> FEATURE:
<223> OTHER INFORMATION: Synthetic Construct pAD/CMV-GP(dTM)(Z-CITE-S)

<400> SEQUENCE: 25
ttaattaacc gcaattctca tgtttgacag cttatcatca tcaataatat accttatttt 60
ggattgaagc caatatgata atgagggggt ggagtttgtg acgtggcgcg gggcgtggga 120
acggggcggg tgacgtagta gtgtggcgga agtgtgatgt tgcaagtgtg gcggaacaca 180
tgtaagcgac ggatgtggca aaagtgacgt ttttggtgtg cgccggtgta cacaggaagt 240
gacaattttc gcgcggtttt aggcggatgt tgtagtaaat ttgggcgtaa ccgagtaaga 300
tttggccatt ttcgcgggaa aactgaataa gaggaagtga aatctgaata attttgtgtt 360
actcatagcg cgtaatattt gtctagggcc gcggggactt tgaccgttta cgtggagact 420
cgcccaggtg tttttctcag gtgttttccg cgttccgggt caaagttggc gttttattat 480
tatagtcagt acgtaccagt gcactggcct agagcggccc cattgcatac gttgtatcca 540
tatcataata tgtacattta tattggctca tgtccaacat taccgccatg ttgacattga 600
ttattgacta gttattaata gtaatcaatt acggggtcat tagttcatag cccatatatg 660
gagttccgcg ttacataact tacggtaaat ggcccgcctg gctgaccgcc caacgacccc 720
cgcccattga cgtcaataat gacgtatgtt cccatagtaa cgccaatagg gactttccat 780
tgacgtcaat gggtggagta tttacggtaa actgcccact tggcagtaca tcaagtgtat 840
catatgccaa gtacgccccc tattgacgtc aatgacggta aatggcccgc ctggcattat 900
gcccagtaca tgaccttatg ggactttcct acttggcagt acatctacgt attagtcatc 960
gctattacca tggtgatgcg gttttggcag tacatcaatg ggcgtggata gcggtttgac 1020
tcacggggat ttccaagtct ccaccccatt gacgtcaatg ggagtttgtt ttggcaccaa 1080
aatcaacggg actttccaaa atgtcgtaac aactccgccc cattgacgca aatgggcggt 1140
aggcgtgtac ggtgggaggt ctatataagc agagctcgtt tagtgaaccg tcagatcgcc 1200
tggagacgcc atccacgctg ttttgacctc catagaagac accgggaccg atccagcctc 1260
cgtcaccgtc gtcgacacgt gtgatcagat ctagaccagg ccctggatcg atccaacaac 1320
acaatgggcg ttacaggaat attgcagtta cctcgtgatc gattcaagag gacatcattc 1380
tttctttggg taattatcct tttccaaaga acattttcca tcccacttgg agtcatccac 1440
aatagcacat tacaggttag tgatgtcgac aaactagttt gtcgtgacaa actgtcatcc 1500
acaaatcaat tgagatcagt tggactgaat ctcgaaggga atggagtggc aactgacgtg 1560
ccatctgcaa ctaaaagatg ggcttcagg tccggtgtcc caccaaaggt ggtcaattat 1620
gaagctggtg aatgggctga aaactgctac aatcttgaaa tcaaaaaacc tgacgggagt 1680
gagtgtctac cagcagcgcc agacgggatt cggggcttcc cccggtgccg gtatgtgcac 1740
aaagtatcag gaacgggacc gtgtgccgga gactttgcct tccataaaga gggtgctttc 1800
ttcctgtatg atcgacttgc ttccacagtt atctaccgag gaacgacttt cgctgaaggt 1860
gtcgttgcat ttctgatact gccccaagct aagaaggact tcttcagctc acaccccttg 1920
agagagccgg tcaatgcaac ggaggacccg tctagtggct actattctac cacaattaga 1980
tatcaggcta ccggttttgg aaccaatgag acagagtact tgttcgaggt tgacaatttg 2040
acctacgtcc aacttgaatc aagattcaca ccacagtttc tgctccagct gaatgagaca 2100
atatatacaa gtgggaaaag gagcaatacc acgggaaaac taatttggaa ggtcaacccc 2160
gaaattgata caacaatcgg ggagtgggcc ttctgggaaa ctaaaaaaaa cctcactaga 2220

-continued

```
aaaattcgca gtgaagagtt gtctttcaca gttgtatcaa acggagccaa aaacatcagt   2280
ggtcagagtc cggcgcgaac ttcttccgac ccagggacca acacaacaac tgaagaccac   2340
aaaatcatgg cttcagaaaa ttcctctgca atggttcaag tgcacagtca aggaagggaa   2400
gctgcagtgt cgcatctaac aacccttgcc acaatctcca cgagtcccca atccctcaca   2460
accaaaccag gtccggacaa cagcacccat aatacacccg tgtataaact tgacatctct   2520
gaggcaactc aagttgaaca acatcaccgc agaacagaca acgacagcac agcctccgac   2580
actccctctg ccacgaccgc agccggaccc ccaaaagcag agaacaccaa cacgagcaag   2640
agcactgact tcctggaccc cgccaccaca acaagtcccc aaaaccacag cgagaccgct   2700
ggcaacaaca acactcatca ccaagatacc ggagaagaga gtgccagcag cgggaagcta   2760
ggcttaatta ccaatactat tgctggagtc gcaggactga tcacaggcgg gagaagaact   2820
cgaagagaag caattgtcaa tgctcaaccc aaatgcaacc ctaatttaca ttactggact   2880
actcaggatg aaggtgctgc aatcggactg gcctggatac catatttcgg gccagcagcc   2940
gagggaattt acatagaggg gctaatgcac aatcaagatg gtttaatctg tgggttgaga   3000
cagctggcca acgagacgac tcaagctctt caactgttcc tgagagccac aactgagcta   3060
cgcacctttt caatcctcaa ccgtaaggca attgatttct tgctgcagcg atggggcggc   3120
acatgccaca ttctgggacc ggactgctgt atcgaaccac atgattggac caagaacata   3180
acagacaaaa ttgatcagat tattcatgat tttgttgata aaacccttcc ggaccagggg   3240
gacaatgaca attggtggac aggatggaga caatggatgg ccgcatcgtg actgactgac   3300
gatctgcctc gcgagatcaa ttccgcccct ctccctcccc ccccccctaac gttactggcc   3360
gaagccgctt ggaataaggc cggtgtgcgt ttgtctatat gttattttcc accatattgc   3420
cgtcttttgg caatgtgagg gcccggaaac ctggccctgt cttcttgacg agcattccta   3480
ggggtctttc ccctctcgcc aaaggaatgc aaggtctgtt gaatgtcgtg aaggaagcag   3540
ttcctctgga agcttcttga agacaaacaa cgtctgtagc gaccctttgc aggcagcgga   3600
acccccacc tggcgacagg tgcctctgcg gccaaaagcc acgtgtataa gatacacctg   3660
caaaggcggc acaaccccag tgccacgttg tgagttggat agttgtggaa agagtcaaat   3720
ggctctcctc aagcgtattc aacaaggggc tgaaggatgc ccagaaggta ccccattgta   3780
tgggatctga tctggggcct cggtgcacat gctttacatg tgtttagtcg aggttaaaaa   3840
acgtctaggc cccccgaacc acggggacgt ggttttcctt tgaaaaacac gatgataata   3900
tggccacaac catggagggt cttagcctac tccaattgcc cagagataaa tttcgaaaaa   3960
gctctttctt tgtttgggtc atcatcttat ttcaaaaggc cttttccatg cctttgggtg   4020
ttgtgaccaa cagcacttta gaagtaacag agattgacca gctagtctgc aaggatcatc   4080
ttgcatccac tgaccagctg aaatcagttg gtctcaacct cgaggggagc ggagtatcta   4140
ctgatatccc atctgcgaca aagcgttggg gcttcagatc tggtgtgcct cccaaggtgg   4200
tcagctatga agcaggagaa tgggctgaaa attgctacaa tcttgaaata aagaagccgg   4260
acgggagcga atgcttaccc ccaccgccgg atggtgtcag aggctttcca aggtgccgct   4320
atgttcacaa agcccaagga accgggccct gcccgggtga ctatgccttt cacaaggatg   4380
gagctttctt cctctatgac aggctggctt caactgtaat ttacagagga gtcaattttg   4440
ctgagggggt aattgcattc ttgatattgg ctaaaccaaa ggaaacgttc cttcaatcac   4500
cccccattcg agaggcagta aactacactg aaaatacatc aagttactat gccacatcct   4560
acttggagta cgaaatcgaa aattttggtg ctcaacactc cacgaccctt ttcaaaatta   4620
```

-continued

```
acaataatac ttttgttctt ctggacaggc cccacacgcc tcagttcctt ttccagctga   4680
atgataccat tcaccttcac caacagttga gcaacacaac tgggaaacta atttggacac   4740
tagatgctaa tatcaatgct gatattggtg aatgggcttt ttgggaaaat aaaaaaaatc   4800
tctccgaaca actacgtgga gaagagctgt ctttcgaaac tttatcgctc aacgagacag   4860
aagacgatga tgcgacatcg tcgagaacta caaagggaag aatctccgac cgggccacca   4920
ggaagtattc ggacctggtt ccaaaggatt cccctgggat ggtttcattg cacgtaccag   4980
aaggggaaac aacattgccg tctcagaatt cgacagaagg tcgaagagta gatgtgaata   5040
ctcaggaaac tatcacagag acaactgcaa caatcatagg cactaacggt aacaacatgc   5100
agatctccac catcgggaca ggactgagct ccagccaaat cctgagttcc tcaccgacca   5160
tggcaccaag ccctgagact cagacctcca caacctacac accaaaacta ccagtgatga   5220
ccaccgagga accaacaaca ccaccgagaa actctcctgg ctcaacaaca gaagcaccca   5280
ctctcaccac cccagagaat ataacaacag cggttaaaac tgttttgcca caagagtcca   5340
caagcaacgg tctaataact tcaacagtaa cagggattct tgggagcctt ggacttcgaa   5400
aacgcagcag aagacaagtt aacaccaggg ccacgggtaa atgcaatccc aacttacact   5460
actggactgc acaagaacaa cataatgctg ctgggattgc ctggatcccg tactttggac   5520
cgggtgcaga aggcatatac actgaaggcc ttatgcacaa ccaaaatgcc ttagtctgtg   5580
gactcagaca acttgcaaat gaaacaactc aagctctgca gcttttctta agggccacga   5640
cggagctgcg gacatatacc atactcaata ggaaggccat agatttcctt ctgcgacgat   5700
ggggcgggac atgtaggatc ctgggaccag attgttgcat tgagccacat gattggacca   5760
aaaacatcac tgataaaatc aaccaaatca tccatgattt catcgacaac cctttaccca   5820
atcaggataa tgatgataat tggtggacgg gctggagaca gtggatcccg gccgcatcgt   5880
gactgactga cgatctgcct cgcggatcca gatctgctgt gccttctagt tgccagccat   5940
ctgttgtttg cccctccccc gtgccttcct tgaccctgga aggtgccact cccactgtcc   6000
tttcctaata aaatgaggaa attgcatcgc attgtctgag taggtgtcat tctattctgg   6060
ggggtggggt ggggcagcac agcaaggggg aggattggga agacaatagc aggcatgctg   6120
gggatgcggt gggctctatg ggtacccagg gccgcataac ttcgtataat gtatgctata   6180
cgaagttata agatctgtac tgaaatgtgt gggcgtggct taagggtggg aaagaatata   6240
taaggtgggg gtcttatgta gttttgtatc tgttttgcag cagccgccgc cgccatgagc   6300
accaactcgt ttgatggaag cattgtgagc tcatatttga caacgcgcat gccccatgg    6360
gccggggtgc gtcagaatgt gatgggctcc agcattgatg gtcgccccgt cctgcccgca   6420
aactctacta ccttgaccta cgagaccgtg tctggaacgc cgttggagac tgcagcctcc   6480
gccgccgctt cagccgctgc agccaccgcc cgcgggattg tgactgactt tgctttcctg   6540
agcccgcttg caagcagtgc agcttcccgt tcatccgccc gcgatgacaa gttgacggct   6600
cttttggcac aattggattc tttgacccgg gaacttaatg tcgtttctca gcagctgttg   6660
gatctgcgcc agcaggtttc tgccctgaag gcttcctccc ctcccaatgc ggtttaaaac   6720
ataaataaaa aaccagactc tgtttggatt tggatcaagc aagtgtcttg ctgtctttat   6780
ttaggggttt tgcgcgcgcg gtaggcccgg gaccagcggt ctcggtcgtt gagggtcctg   6840
tgtatttttt ccaggacgtg gtaaaggtga ctctggatgt tcagatacat gggcataagc   6900
ccgtctctgg ggtggaggta gcaccactgc agagcttcat gctgcggggt ggtgttgtag   6960
atgatccagt cgtagcagga gcgctgggcg tggtgcctaa aaatgtcttt cagtagcaag   7020
```

-continued ctgattgcca ggggcaggcc cttggtgtaa gtgtttacaa agcggttaag ctgggatggg 7080
tgcatacgtg gggatatgag atgcatcttg gactgtattt ttaggttggc tatgttccca 7140
gccatatccc tccggggatt catgttgtgc agaaccacca gcacagtgta tccggtgcac 7200
ttgggaaatt tgtcatgtag cttagaagga aatgcgtgga agaacttgga gacgcccttg 7260
tgacctccaa gattttccat gcattcgtcc ataatgatgg caatgggccc acgggcggcg 7320
gcctgggcga agatatttct gggatcacta acgtcatagt tgtgttccag gatgagatcg 7380
tcataggcca tttttacaaa gcgcgggcgg agggtgccag actgcggtat aatggttcca 7440
tccggcccag gggcgtagtt accctcacag atttgcattt cccacgcttt gagttcagat 7500
ggggggatca tgtctacctg cggggcgatg aagaaaacgg tttccggggt aggggagatc 7560
agctgggaag aaagcaggtt cctgagcagc tgcgacttac cgcagccggt gggcccgtaa 7620
atcacaccta ttaccggctg caactggtag ttaagagagc tgcagctgcc gtcatccctg 7680
agcagggggg ccacttcgtt aagcatgtcc ctgactcgca tgttttccct gaccaaatcc 7740
gccagaaggc gctcgccgcc cagcgatagc agttcttgca aggaagcaaa gtttttcaac 7800
ggtttgagac cgtccgccgt aggcatgctt ttgagcgttt gaccaagcag ttccaggcgg 7860
tcccacagct cggtcacctg ctctacggca tctcgatcca gcatatctcc tcgtttcgcg 7920
ggttggggcg gctttcgctg tacggcagta gtcggtgctc gtccagacgg gccagggtca 7980
tgtctttcca cgggcgcagg gtcctcgtca gcgtagtctg ggtcacggtg aaggggtgcg 8040
ctccgggctg cgcgctggcc agggtgcgct tgaggctggt cctgctggtg ctgaagcgct 8100
gccggtcttc gccctgcgcg tcggccaggt agcatttgac catggtgtca tagtccagcc 8160
cctccgcggc gtggcccttg gcgcgcagct tgcccttgga ggaggcgccg cacgaggggc 8220
agtgcagact tttgagggcg tagagcttgg gcgcgagaaa taccgattcc ggggagtagg 8280
catccgcgcc gcaggccccg cagacggtct cgcattccac gagccaggtg agctctggcc 8340
gttcggggtc aaaaaccagg tttcccccat gctttttgat gcgtttctta cctctggttt 8400
ccatgagccg gtgtccacgc tcggtgacga aaaggctgtc cgtgtccccg tatacagact 8460
tgagaggcct gtcctcgagc ggtgttccgc ggtcctcctc gtatagaaac tcggaccact 8520
ctgagacaaa ggctcgcgtc caggccagca cgaaggaggc taagtgggag gggtagcggt 8580
cgttgtccac tagggggtcc actcgctcca gggtgtgaag acacatgtcg ccctcttcgg 8640
catcaaggaa ggtgattggt ttgtaggtgt aggccacgtg accgggtgtt cctgaagggg 8700
ggctataaaa gggggtgggg gcgcgttcgt cctcactctc ttccgcatcg ctgtctgcga 8760
gggccagctg ttggggtgag tcgacgcgag gctggatggc cttccccatt atgattcttc 8820
tcgcttccgg cggcatcggg atgcccgcgt tgcaggccat gctgtccagg caggtagatg 8880
acgaccatca gggacagctt caaggccagc aaaaggccag gaaccgtaaa aaggccgcgt 8940
tgctggcgtt tttccatagg ctccgccccc ctgacgagca tcacaaaaat cgacgctcaa 9000
gtcagaggtg gcgaaacccg acaggactat aaagatacca ggcgtttccc cctggaagct 9060
ccctcgtgcg ctctcctgtt ccgaccctgc cgcttaccgg atacctgtcc gcctttctcc 9120
cttcgggaag cgtggcgctt tctcatagct cacgctgtag gtatctcagt tcggtgtagg 9180
tcgttcgctc caagctgggc tgtgtgcacg aaccccccgt tcagcccgac cgctgcgcct 9240
tatccggtaa ctatcgtctt gagtccaacc cggtaagaca cgacttatcg ccactggcag 9300
cagccactgg taacaggatt agcagagcga ggtatgtagg cggtgctaca gagttcttga 9360
agtggtggcc taactacggc tacactagaa ggacagtatt tggtatctgc gctctgctga 9420

-continued

```
agccagttac cttcggaaaa agagttggta gctcttgatc cggcaaacaa accaccgctg   9480

gtagcggtgg tttttttgtt tgcaagcagc agattacgcg cagaaaaaaa ggatctcaag   9540

aagatccttt gatcttttct acggggtctg acgctcagtg gaacgaaaac tcacgttaag   9600

ggattttggt catgagatta tcaaaaagga tcttcaccta gatcctttta aattaaaaat   9660

gaagttttaa atcaatctaa agtatatatg agtaaacttg gtctgacagt taccaatgct   9720

taatcagtga ggcacctatc tcagcgatct gtctatttcg ttcatccata gttgcctgac   9780

tccccgtcgt gtagataact acgatacggg agggcttacc atctggcccc agtgctgcaa   9840

tgataccgcg agacccacgc tcaccggctc cagatttatc agcaataaac cagccagccg   9900

gaagggccga gcgcagaagt ggtcctgcaa ctttatccgc ctccatccag tctattaatt   9960

gttgccggga agctagagta agtagttcgc cagttaatag tttgcgcaac gttgttgcca  10020

ttgctgcagg catcgtggtg tcacgctcgt cgtttggtat ggcttcattc agctccggtt  10080

cccaacgatc aaggcgagtt acatgatccc ccatgttgtg caaaaaagcg gttagctcct  10140

tcggtcctcc gatcgttgtc agaagtaagt tggccgcagt gttatcactc atggttatgg  10200

cagcactgca taattctctt actgtcatgc catccgtaag atgcttttct gtgactggtg  10260

agtactcaac caagtcattc tgagaatagt gtatgcggcg accgagttgc tcttgcccgg  10320

cgtcaacacg ggataatacc gcgccacata gcagaacttt aaaagtgctc atcattggaa  10380

aacgttcttc ggggcgaaaa ctctcaagga tcttaccgct gttgagatcc agttcgatgt  10440

aacccactcg tgcacccaac tgatcttcag catcttttac tttcaccagc gtttctgggt  10500

gagcaaaaac aggaaggcaa aatgccgcaa aaaagggaat aagggcgaca cggaaatgtt  10560

gaatactcat actcttcctt tttcaatatt attgaagcat ttatcagggt tattgtctca  10620

tgagcggata catatttgaa tgtatttaga aaaataaaca aataggggtt ccgcgcacat  10680

ttccccgaaa agtgccacct gacgtctaag aaaccattat tatcatgaca ttaacctata  10740

aaaataggcg tatcacgagg ccctttcgtc ttcaagaatt gtt                    10783
```

<210> SEQ ID NO 26
<211> LENGTH: 8338
<212> TYPE: DNA
<213> ORGANISM: Artificial Sequence
<220> FEATURE:
<223> OTHER INFORMATION: Synthetic Construct pAdApt Ebola GP(S)

<400> SEQUENCE: 26

```
ttaattaacc gcaattctca tgtttgacag cttatcatca tcaataatat accttatttt     60

ggattgaagc caatatgata atgagggggt ggagtttgtg acgtggcgcg gggcgtggga    120

acggggcggg tgacgtagta gtgtggcgga agtgtgatgt tgcaagtgtg gcggaacaca    180

tgtaagcgac ggatgtggca aaagtgacgt ttttggtgtg cgccggtgta cacaggaagt    240

gacaattttc gcgcggtttt aggcggatgt tgtagtaaat ttgggcgtaa ccgagtaaga    300

tttggccatt ttcgcgggaa aactgaataa gaggaagtga aatctgaata attttgtgtt    360

actcatagcg cgtaatattt gtctagggcc gcggggactt tgaccgttta cgtggagact    420

cgcccaggtg tttttctcag gtgttttccg cgttccgggt caaagttggc gttttattat    480

tatagtcagt acgtaccagt gcactggcct agagcggccc cattgcatac gttgtatcca    540

tatcataata tgtacattta tattggctca tgtccaacat taccgccatg ttgacattga    600

ttattgacta gttattaata gtaatcaatt acggggtcat tagttcatag cccatatatg    660

gagttccgcg ttacataact tacggtaaat ggcccgcctg gctgaccgcc caacgacccc    720
```

-continued

```
cgcccattga cgtcaataat gacgtatgtt cccatagtaa cgccaatagg gactttccat    780
tgacgtcaat gggtggagta tttacggtaa actgcccact tggcagtaca tcaagtgtat    840
catatgccaa gtacgccccc tattgacgtc aatgacggta aatggcccgc ctggcattat    900
gcccagtaca tgaccttatg ggactttcct acttggcagt acatctacgt attagtcatc    960
gctattacca tggtgatgcg gttttggcag tacatcaatg ggcgtggata gcggtttgac   1020
tcacggggat ttccaagtct ccaccccatt gacgtcaatg ggagtttgtt ttggcaccaa   1080
aatcaacggg actttccaaa atgtcgtaac aactccgccc cattgacgca aatgggcggt   1140
aggcgtgtac ggtgggaggt ctatataagc agagctcgtt tagtgaaccg tcagatcgcc   1200
tggagacgcc atccacgctg ttttgacctc catagaagac accgggaccg atccagcctc   1260
cgtcaccgtc gtcgacacgt gtgatcagat atcgcggccg ccagtgtgat ggatatctgc   1320
agaattcggc ttatcttcag gatctcgcca tggagggtct tagcctactc caattgccca   1380
gagataaatt tcgaaaaagc tctttctttg tttgggtcat catcttattt caaaaggcct   1440
tttccatgcc tttgggtgtt gtgaccaaca gcactttaga agtaacagag attgaccagc   1500
tagtctgcaa ggatcatctt gcatccactg accagctgaa atcagttggt ctcaacctcg   1560
aggggagcgg agtatctact gatatcccat ctgcgacaaa gcgttggggc ttcagatctg   1620
gtgtgcctcc caaggtggtc agctatgaag caggagaatg ggctgaaaat tgctacaatc   1680
ttgaaataaa gaagccggac gggagcgaat gcttaccccc accgccggat ggtgtcagag   1740
gctttccaag gtgccgctat gttcacaaag cccaaggaac cgggccctgc ccgggtgact   1800
atgcctttca caaggatgga gctttcttcc tctatgacag gctggcttca actgtaattt   1860
acagaggagt caattttgct gagggggtaa ttgcattctt gatattggct aaaccaaagg   1920
aaacgttcct tcaatcaccc cccattcgag aggcagtaaa ctacactgaa aatacatcaa   1980
gttactatgc cacatcctac ttggagtacg aaatcgaaaa ttttggtgct caacactcca   2040
cgaccctttt caaaattaac aataatactt ttgttcttct ggacaggccc cacacgcctc   2100
agttcctttt ccagctgaat gataccattc accttcacca acagttgagc aacacaactg   2160
ggaaactaat ttggacacta gatgctaata tcaatgctga tattggtgaa tgggcttttt   2220
gggaaaataa aaaaaatctc tccgaacaac tacgtggaga agagctgtct ttcgaaactt   2280
tatcgctcaa cgagacagaa gacgatgatg cgacatcgtc gagaactaca aagggaagaa   2340
tctccgaccg ggccaccagg aagtattcgg acctggttcc aaaggattcc cctgggatgg   2400
tttcattgca cgtaccagaa ggggaaacaa cattgccgtc tcagaattcg acagaaggtc   2460
gaagagtaga tgtgaatact caggaaacta tcacagagac aactgcaaca atcataggca   2520
ctaacggtaa caacatgcag atctccacca tcgggacagg actgagctcc agccaaatcc   2580
tgagttcctc accgaccatg gcaccaagcc ctgagactca gacctccaca acctacacac   2640
caaaactacc agtgatgacc accgaggaac caacaacacc accgagaaac tctcctggct   2700
caacaacaga agcacccact ctcaccaccc cagagaatat aacaacagcg gttaaaactg   2760
ttttgccaca agagtccaca agcaacggtc taataacttc aacagtaaca gggattcttg   2820
ggagccttgg acttcgaaaa cgcagcagaa gacaagttaa caccagggcc acgggtaaat   2880
gcaatcccaa cttacactac tggactgcac aagaacaaca taatgctgct gggattgcct   2940
ggatcccgta ctttggaccg ggtgcagaag gcatatacac tgaaggcctt atgcacaacc   3000
aaaatgcctt agtctgtgga ctcagacaac ttgcaaatga aacaactcaa gctctgcagc   3060
ttttcttaag ggccacgacg gagctgcgga catataccat actcaatagg aaggccatag   3120
```

-continued

```
atttccttct gcgacgatgg ggcgggacat gtaggatcct gggaccagat tgttgcattg   3180
agccacatga ttggaccaaa aacatcactg ataaaatcaa ccaaatcatc catgatttca   3240
tcgacaaccc tttacccaat caggataatg atgataattg gtggacgggc tggagacagt   3300
ggatccctgc aggaataggc attactggaa ttattattgc aatcattgct cttctttgcg   3360
tctgcaagct gctttgttga atatcaagcc gaattccagc acactggcgg ccgttactag   3420
tggatccgag ctcggatcca agctctagac caggccctgg atccagatct gctgtgcctt   3480
ctagttgcca gccatctgtt gtttgcccct cccccgtgcc ttccttgacc ctggaaggtg   3540
ccactcccac tgtcctttcc taataaaatg aggaaattgc atcgcattgt ctgagtaggt   3600
gtcattctat tctggggggt ggggtggggc aggacagcaa gggggaggat tgggaagaca   3660
atagcaggca tgctggggat gcggtgggct ctatgggtac ccagggccgc ataacttcgt   3720
ataatgtatg ctatacgaag ttataagatc tgtactgaaa tgtgtgggcg tggcttaagg   3780
gtgggaaaga atatataagg tgggggtctt atgtagtttt gtatctgttt tgcagcagcc   3840
gccgccgcca tgagcaccaa ctcgtttgat ggaagcattg tgagctcata tttgacaacg   3900
cgcatgcccc catgggccgg ggtgcgtcag aatgtgatgg gctccagcat tgatggtcgc   3960
cccgtcctgc ccgcaaactc tactaccttg acctacgaga ccgtgtctgg aacgccgttg   4020
gagactgcag cctccgccgc cgcttcagcc gctgcagcca ccgcccgcgg gattgtgact   4080
gactttgctt tcctgagccc gcttgcaagc agtgcagctt cccgttcatc cgcccgcgat   4140
gacaagttga cggctctttt ggcacaattg gattctttga cccgggaact taatgtcgtt   4200
tctcagcagc tgttggatct gcgccagcag gtttctgccc tgaaggcttc ctcccctccc   4260
aatgcggttt aaaacataaa taaaaaacca gactctgttt ggatttggat caagcaagtg   4320
tcttgctgtc tttatttagg ggttttgcgc gcgcggtagg cccgggacca gcggtctcgg   4380
tcgttgaggg tcctgtgtat tttttccagg acgtggtaaa ggtgactctg gatgttcaga   4440
tacatgggca taagcccgtc tctggggtgg aggtagcacc actgcagagc ttcatgctgc   4500
ggggtggtgt tgtagatgat ccagtcgtag caggagcgct gggcgtggtg cctaaaaatg   4560
tctttcagta gcaagctgat tgccaggggc aggcccttgg tgtaagtgtt tacaaagcgg   4620
ttaagctggg atgggtgcat acgtggggat atgagatgca tcttggactg tatttttagg   4680
ttggctatgt tcccagccat atccctccgg ggattcatgt tgtgcagaac caccagcaca   4740
gtgtatccgg tgcacttggg aaatttgtca tgtagcttag aaggaaatgc gtggaagaac   4800
ttggagacgc ccttgtgacc tccaagattt tccatgcatt cgtccataat gatggcaatg   4860
ggcccacggg cggcggcctg ggcgaagata tttctgggat cactaacgtc atagttgtgt   4920
tccaggatga gatcgtcata ggccattttt acaaagcgcg ggcggagggt gccagactgc   4980
ggtataatgg ttccatccgg cccaggggcg tagttaccct cacagatttg catttcccac   5040
gctttgagtt cagatggggg gatcatgtct acctgcgggg cgatgaagaa aacggtttcc   5100
ggggtagggg agatcagctg ggaagaaagc aggttcctga gcagctgcga cttaccgcag   5160
ccggtgggcc cgtaaatcac acctattacc ggctgcaact ggtagttaag agagctgcag   5220
ctgccgtcat ccctgagcag gggggccact tcgttaagca tgtccctgac tcgcatgttt   5280
tccctgacca aatccgccag aaggcgctcg ccgcccagcg atagcagttc ttgcaaggaa   5340
gcaaagtttt tcaacggttt gagaccgtcc gccgtaggca tgcttttgag cgtttgacca   5400
agcagttcca ggcggtccca cagctcggtc acctgctcta cggcatctcg atccagcata   5460
tctcctcgtt tcgcgggttg ggcggctttt cgctgtacgg cagtagtcgg tgctcgtcca   5520
```

-continued

```
gacgggccag ggtcatgtct ttccacgggc gcagggtcct cgtcagcgta gtctgggtca   5580
cggtgaaggg gtgcgctccg ggctgcgcgc tggccagggt gcgcttgagg ctggtcctgc   5640
tggtgctgaa gcgctgccgg tcttcgccct gcgcgtcggc caggtagcat ttgaccatgg   5700
tgtcatagtc cagcccctcc gcggcgtggc ccttggcgcg cagcttgccc ttggaggagg   5760
cgccgcacga ggggcagtgc agacttttga gggcgtagag cttgggcgcg agaaataccg   5820
attccgggga gtaggcatcc gcgccgcagg ccccgcagac ggtctcgcat tccacgagcc   5880
aggtgagctc tggccgttcg gggtcaaaaa ccaggtttcc cccatgcttt ttgatgcgtt   5940
tcttacctct ggtttccatg agccggtgtc cacgctcggt gacgaaaagg ctgtccgtgt   6000
ccccgtatac agacttgaga ggcctgtcct cgagcggtgt tccgcggtcc tcctcgtata   6060
gaaactcgga ccactctgag acaaaggctc gcgtccaggc cagcacgaag gaggctaagt   6120
gggaggggta gcggtcgttg tccactaggg ggtccactcg ctccagggtg tgaagacaca   6180
tgtcgccctc ttcggcatca aggaaggtga ttggtttgta ggtgtaggcc acgtgaccgg   6240
gtgttcctga aggggggcta taaaaggggg tgggggcgcg ttcgtcctca ctctcttccg   6300
catcgctgtc tgcgagggcc agctgttggg gtgagtcgac gcgaggctgg atggccttcc   6360
ccattatgat tcttctcgct tccggcggca tcgggatgcc cgcgttgcag gccatgctgt   6420
ccaggcaggt agatgacgac catcagggac agcttcaagg ccagcaaaag gccaggaacc   6480
gtaaaaaggc cgcgttgctg gcgtttttcc ataggctccg cccccctgac gagcatcaca   6540
aaaatcgacg ctcaagtcag aggtggcgaa acccgacagg actataaaga taccaggcgt   6600
ttccccctgg aagctccctc gtgcgctctc ctgttccgac cctgccgctt accggatacc   6660
tgtccgcctt tctcccttcg ggaagcgtgg cgctttctca tagctcacgc tgtaggtatc   6720
tcagttcggt gtaggtcgtt cgctccaagc tgggctgtgt gcacgaaccc cccgttcagc   6780
ccgaccgctg cgccttatcc ggtaactatc gtcttgagtc caacccggta agacacgact   6840
tatcgccact ggcagcagcc actggtaaca ggattagcag agcgaggtat gtaggcggtg   6900
ctacagagtt cttgaagtgg tggcctaact acggctacac tagaaggaca gtatttggta   6960
tctgcgctct gctgaagcca gttaccttcg gaaaaagagt tggtagctct tgatccggca   7020
aacaaaccac cgctggtagc ggtggttttt ttgtttgcaa gcagcagatt acgcgcagaa   7080
aaaaaggatc tcaagaagat cctttgatct tttctacggg gtctgacgct cagtggaacg   7140
aaaactcacg ttaagggatt ttggtcatga gattatcaaa aaggatcttc acctagatcc   7200
ttttaaatta aaaatgaagt tttaaatcaa tctaaagtat atatgagtaa acttggtctg   7260
acagttacca atgcttaatc agtgaggcac ctatctcagc gatctgtcta tttcgttcat   7320
ccatagttgc ctgactcccc gtcgtgtaga taactacgat acgggagggc ttaccatctg   7380
gccccagtgc tgcaatgata ccgcgagacc cacgctcacc ggctccagat ttatcagcaa   7440
taaaccagcc agccggaagg gccgagcgca gaagtggtcc tgcaacttta tccgcctcca   7500
tccagtctat taattgttgc cgggaagcta gagtaagtag ttcgccagtt aatagtttgc   7560
gcaacgttgt tgccattgct gcaggcatcg tggtgtcacg ctcgtcgttt ggtatggctt   7620
cattcagctc cggttcccaa cgatcaaggc gagttacatg atcccccatg ttgtgcaaaa   7680
aagcggttag ctccttcggt cctccgatcg ttgtcagaag taagttggcc gcagtgttat   7740
cactcatggt tatggcagca ctgcataatt ctcttactgt catgccatcc gtaagatgct   7800
tttctgtgac tggtgagtac tcaaccaagt cattctgaga atagtgtatg cggcgaccga   7860
gttgctcttg cccggcgtca acacgggata ataccgcgcc acatagcaga actttaaaag   7920
```

tgctcatcat tggaaaacgt tcttcggggc gaaaactctc aaggatctta ccgctgttga 7980
gatccagttc gatgtaaccc actcgtgcac ccaactgatc ttcagcatct tttactttca 8040
ccagcgtttc tgggtgagca aaaacaggaa ggcaaaatgc cgcaaaaaag ggaataaggg 8100
cgacacggaa atgttgaata ctcatactct tcctttttca atattattga agcatttatc 8160
agggttattg tctcatgagc ggatacatat ttgaatgtat ttagaaaaat aaacaaatag 8220
gggttccgcg cacatttccc cgaaaagtgc cacctgacgt ctaagaaacc attattatca 8280
tgacattaac ctataaaaat aggcgtatca cgaggccctt tcgtcttcaa gaattgtt 8338

<210> SEQ ID NO 27
<211> LENGTH: 8221
<212> TYPE: DNA
<213> ORGANISM: Artificial Sequence
<220> FEATURE:
<223> OTHER INFORMATION: Synthetic Construct pAdApt Ebola GP(S)(dTM)

<400> SEQUENCE: 27
ttaattaacc gcaattctca tgtttgacag cttatcatca tcaataatat accttatttt 60
ggattgaagc caatatgata atgagggggt ggagtttgtg acgtggcgcg gggcgtggga 120
acggggcggg tgacgtagta gtgtggcgga agtgtgatgt tgcaagtgtg gcggaacaca 180
tgtaagcgac ggatgtggca aaagtgacgt ttttggtgtg cgccggtgta cacaggaagt 240
gacaattttc gcgcggtttt aggcggatgt tgtagtaaat ttgggcgtaa ccgagtaaga 300
tttggccatt ttcgcgggaa aactgaataa gaggaagtga aatctgaata attttgtgtt 360
actcatagcg cgtaatattt gtctagggcc gcggggactt tgaccgttta cgtggagact 420
cgcccaggtg tttttctcag gtgttttccg cgttccgggt caaagttggc gttttattat 480
tatagtcagt acgtaccagt gcactggcct agagcggccc cattgcatac gttgtatcca 540
tatcataata tgtacattta tattggctca tgtccaacat taccgccatg ttgacattga 600
ttattgacta gttattaata gtaatcaatt acggggtcat tagttcatag cccatatatg 660
gagttccgcg ttacataact tacggtaaat ggcccgcctg gctgaccgcc caacgacccc 720
cgcccattga cgtcaataat gacgtatgtt cccatagtaa cgccaatagg gactttccat 780
tgacgtcaat gggtggagta tttacggtaa actgcccact tggcagtaca tcaagtgtat 840
catatgccaa gtacgccccc tattgacgtc aatgacggta aatggcccgc ctggcattat 900
gcccagtaca tgaccttatg ggactttcct acttggcagt acatctacgt attagtcatc 960
gctattacca tggtgatgcg gttttggcag tacatcaatg ggcgtggata gcggtttgac 1020
tcacggggat ttccaagtct ccaccccatt gacgtcaatg ggagtttgtt ttggcaccaa 1080
aatcaacggg actttccaaa atgtcgtaac aactccgccc cattgacgca aatgggcggt 1140
aggcgtgtac ggtgggaggt ctatataagc agagctcgtt tagtgaaccg tcagatcgcc 1200
tggagacgcc atccacgctg ttttgacctc catagaagac accgggaccg atccagcctc 1260
cgtcaccgtc gtcgacacgt gtgatcagat atcgcggccg ccagtgtgat ggatatctgc 1320
agaattcggc ttatcttcag gatctcgcca tggagggtct tagcctactc caattgccca 1380
gagataaatt tcgaaaaagc tctttctttg tttgggtcat catcttattt caaaaggcct 1440
tttccatgcc tttgggtgtt gtgaccaaca gcactttaga agtaacagag attgaccagc 1500
tagtctgcaa ggatcatctt gcatccactg accagctgaa atcagttggt ctcaacctcg 1560
aggggagcgg agtatctact gatatcccat ctgcgacaaa gcgttggggc ttcagatctg 1620
gtgtgcctcc caaggtggtc agctatgaag caggagaatg ggctgaaaat tgctacaatc 1680

-continued

```
ttgaaataaa gaagccggac gggagcgaat gcttaccccc accgccggat ggtgtcagag   1740
gctttccaag gtgccgctat gttcacaaag cccaaggaac cgggccctgc ccgggtgact   1800
atgcctttca caaggatgga gctttcttcc tctatgacag gctggcttca actgtaattt   1860
acagaggagt caattttgct gagggggtaa ttgcattctt gatattggct aaaccaaagg   1920
aaacgttcct tcaatcaccc cccattcgag aggcagtaaa ctacactgaa aatacatcaa   1980
gttactatgc cacatcctac ttggagtacg aaatcgaaaa ttttggtgct caacactcca   2040
cgaccctttt caaaattaac aataatactt ttgttcttct ggacaggccc cacacgcctc   2100
agttcctttt ccagctgaat gataccattc accttcacca acagttgagc aacacaactg   2160
ggaaactaat ttggacacta gatgctaata tcaatgctga tattggtgaa tgggcttttt   2220
gggaaaataa aaaaaatctc tccgaacaac tacgtggaga agagctgtct ttcgaaactt   2280
tatcgctcaa cgagacagaa gacgatgatg cgacatcgtc gagaactaca aagggaagaa   2340
tctccgaccg ggccaccagg aagtattcgg acctggttcc aaaggattcc cctgggatgg   2400
tttcattgca cgtaccagaa ggggaaacaa cattgccgtc tcagaattcg acagaaggtc   2460
gaagagtaga tgtgaatact caggaaacta tcacagagac aactgcaaca atcataggca   2520
ctaacggtaa caacatgcag atctccacca tcgggacagg actgagctcc agccaaatcc   2580
tgagttcctc accgaccatg gcaccaagcc ctgagactca gacctccaca acctacacac   2640
caaaactacc agtgatgacc accgaggaac caacaacacc accgagaaac tctcctggct   2700
caacaacaga agcacccact ctcaccaccc cagagaatat aacaacagcg gttaaaactg   2760
ttttgccaca agagtccaca agcaacggtc taataacttc aacagtaaca gggattcttg   2820
ggagccttgg acttcgaaaa cgcagcagaa gacaagttaa caccagggcc acgggtaaat   2880
gcaatcccaa cttacactac tggactgcac aagaacaaca taatgctgct gggattgcct   2940
ggatcccgta ctttggaccg ggtgcagaag gcatatacac tgaaggcctt atgcacaacc   3000
aaaatgcctt agtctgtgga ctcagacaac ttgcaaatga aacaactcaa gctctgcagc   3060
ttttcttaag ggccacgacg gagctgcgga catataccat actcaatagg aaggccatag   3120
atttccttct gcgacgatgg ggcgggacat gtaggatcct gggaccagat tgttgcattg   3180
agccacatga ttggaccaaa aacatcactg ataaaatcaa ccaaatcatc catgatttca   3240
tcgacaaccc tttacccaat caggataatg atgataattg gtggacgggc tggagacagt   3300
ggatcccggc cgcatcgtga ctgactgacg atctgcctcg cggatccaga tctgctgtgc   3360
cttctagttg ccagccatct gttgtttgcc cctcccccgt gccttccttg accctggaag   3420
gtgccactcc cactgtcctt tcctaataaa atgaggaaat tgcatcgcat tgtctgagta   3480
ggtgtcattc tattctgggg ggtggggtgg ggcaggacag caagggggag gattgggaag   3540
acaatagcag gcatgctggg gatgcggtgg gctctatggg tacccagggc cgcataactt   3600
cgtataatgt atgctatacg aagttataag atctgtactg aaatgtgtgg gcgtggctta   3660
agggtgggaa agaatatata aggtgggggt cttatgtagt tttgtatctg ttttgcagca   3720
gccgccgccg ccatgagcac caactcgttt gatggaagca ttgtgagctc atatttgaca   3780
acgcgcatgc ccccatgggc cggggtgcgt cagaatgtga tgggctccag cattgatggt   3840
cgccccgtcc tgcccgcaaa ctctactacc ttgacctacg agaccgtgtc tggaacgccg   3900
ttggagactg cagcctccgc cgccgcttca gccgctgcag ccaccgcccg cgggattgtg   3960
actgactttg ctttcctgag cccgcttgca agcagtgcag cttcccgttc atccgcccgc   4020
gatgacaagt tgacggctct tttggcacaa ttggattctt tgacccggga acttaatgtc   4080
```

-continued

```
gtttctcagc agctgttgga tctgcgccag caggtttctg ccctgaaggc ttcctcccct   4140
cccaatgcgg tttaaaacat aaataaaaaa ccagactctg tttggatttg gatcaagcaa   4200
gtgtcttgct gtctttattt aggggttttg cgcgcgcggt aggcccggga ccagcggtct   4260
cggtcgttga gggtcctgtg tatttttttcc aggacgtggt aaaggtgact ctggatgttc   4320
agatacatgg gcataagccc gtctctgggg tggaggtagc accactgcag agcttcatgc   4380
tgcggggtgg tgttgtagat gatccagtcg tagcaggagc gctgggcgtg gtgcctaaaa   4440
atgtctttca gtagcaagct gattgccagg ggcaggccct tggtgtaagt gtttacaaag   4500
cggttaagct gggatgggtg catacgtggg gatatgagat gcatcttgga ctgtattttt   4560
aggttggcta tgttcccagc catatccctc cggggattca tgttgtgcag aaccaccagc   4620
acagtgtatc cggtgcactt gggaaatttg tcatgtagct tagaaggaaa tgcgtggaag   4680
aacttggaga cgcccttgtg acctccaaga ttttccatgc attcgtccat aatgatggca   4740
atgggcccac gggcggcggc ctgggcgaag atatttctgg gatcactaac gtcatagttg   4800
tgttccagga tgagatcgtc ataggccatt tttacaaagc gcgggcggag ggtgccagac   4860
tgcggtataa tggttccatc cggcccaggg gcgtagttac cctcacagat ttgcatttcc   4920
cacgctttga gttcagatgg ggggatcatg tctacctgcg gggcgatgaa gaaaacggtt   4980
tccggggtag gggagatcag ctgggaagaa agcaggttcc tgagcagctg cgacttaccg   5040
cagccggtgg gcccgtaaat cacacctatt accggctgca actggtagtt aagagagctg   5100
cagctgccgt catccctgag caggggggcc acttcgttaa gcatgtccct gactcgcatg   5160
ttttccctga ccaaatccgc cagaaggcgc tcgccgccca gcgatagcag ttcttgcaag   5220
gaagcaaagt ttttcaacgg tttgagaccg tccgccgtag gcatgctttt gagcgtttga   5280
ccaagcagtt ccaggcggtc ccacagctcg gtcacctgct ctacggcatc tcgatccagc   5340
atatctcctc gtttcgcggg ttggggcggc tttcgctgta cggcagtagt cggtgctcgt   5400
ccagacgggc cagggtcatg tctttccacg ggcgcagggt cctcgtcagc gtagtctggg   5460
tcacggtgaa ggggtgcgct ccgggctgcg cgctggccag ggtgcgcttg aggctggtcc   5520
tgctggtgct gaagcgctgc cggtcttcgc cctgcgcgtc ggccaggtag catttgacca   5580
tggtgtcata gtccagcccc tccgcggcgt ggcccttggc gcgcagcttg cccttggagg   5640
aggcgccgca cgaggggcag tgcagacttt tgagggcgta gagcttgggc gcgagaaata   5700
ccgattccgg ggagtaggca tccgcgccgc aggccccgca gacggtctcg cattccacga   5760
gccaggtgag ctctggccgt tcggggtcaa aaaccaggtt tcccccatgc tttttgatgc   5820
gtttcttacc tctggtttcc atgagccggt gtccacgctc ggtgacgaaa aggctgtccg   5880
tgtccccgta tacagacttg agaggcctgt cctcgagcgg tgttccgcgg tcctcctcgt   5940
atagaaactc ggaccactct gagacaaagg ctcgcgtcca ggccagcacg aaggaggcta   6000
agtgggaggg gtagcggtcg ttgtccacta gggggtccac tcgctccagg gtgtgaagac   6060
acatgtcgcc ctcttcggca tcaaggaagg tgattggttt gtaggtgtag gccacgtgac   6120
cgggtgttcc tgaagggggg ctataaaagg gggtgggggc gcgttcgtcc tcactctctt   6180
ccgcatcgct gtctgcgagg gccagctgtt ggggtgagtc gacgcgaggc tggatggcct   6240
tccccattat gattcttctc gcttccggcg gcatcgggat gcccgcgttg caggccatgc   6300
tgtccaggca ggtagatgac gaccatcagg gacagcttca aggccagcaa aaggccagga   6360
accgtaaaaa ggccgcgttg ctggcgtttt tccataggct ccgcccccct gacgagcatc   6420
acaaaaatcg acgctcaagt cagaggtggc gaaacccgac aggactataa agataccagg   6480
```

cgtttccccc tggaagctcc ctcgtgcgct ctcctgttcc gaccctgccg cttaccggat 6540
acctgtccgc ctttctccct tcgggaagcg tggcgctttc tcatagctca cgctgtaggt 6600
atctcagttc ggtgtaggtc gttcgctcca agctgggctg tgtgcacgaa ccccccgttc 6660
agcccgaccg ctgcgcctta tccggtaact atcgtcttga gtccaacccg gtaagacacg 6720
acttatcgcc actggcagca gccactggta acaggattag cagagcgagg tatgtaggcg 6780
gtgctacaga gttcttgaag tggtggccta actacggcta cactagaagg acagtatttg 6840
gtatctgcgc tctgctgaag ccagttacct tcggaaaaag agttggtagc tcttgatccg 6900
gcaaacaaac caccgctggt agcggtggtt tttttgtttg caagcagcag attacgcgca 6960
gaaaaaaagg atctcaagaa gatcctttga tcttttctac ggggtctgac gctcagtgga 7020
acgaaaactc acgttaaggg attttggtca tgagattatc aaaaaggatc ttcacctaga 7080
tccttttaaa ttaaaaatga agttttaaat caatctaaag tatatatgag taaacttggt 7140
ctgacagtta ccaatgctta atcagtgagg cacctatctc agcgatctgt ctatttcgtt 7200
catccatagt tgcctgactc cccgtcgtgt agataactac gatacgggag ggcttaccat 7260
ctggccccag tgctgcaatg ataccgcgag acccacgctc accggctcca gatttatcag 7320
caataaacca gccagccgga agggccgagc gcagaagtgg tcctgcaact ttatccgcct 7380
ccatccagtc tattaattgt tgccgggaag ctagagtaag tagttcgcca gttaatagtt 7440
tgcgcaacgt tgttgccatt gctgcaggca tcgtggtgtc acgctcgtcg tttggtatgg 7500
cttcattcag ctccggttcc caacgatcaa ggcgagttac atgatccccc atgttgtgca 7560
aaaaagcggt tagctccttc ggtcctccga tcgttgtcag aagtaagttg gccgcagtgt 7620
tatcactcat ggttatggca gcactgcata attctcttac tgtcatgcca tccgtaagat 7680
gcttttctgt gactggtgag tactcaacca agtcattctg agaatagtgt atgcggcgac 7740
cgagttgctc ttgcccggcg tcaacacggg ataataccgc gccacatagc agaactttaa 7800
aagtgctcat cattggaaaa cgttcttcgg ggcgaaaact ctcaaggatc ttaccgctgt 7860
tgagatccag ttcgatgtaa cccactcgtg cacccaactg atcttcagca tcttttactt 7920
tcaccagcgt ttctgggtga gcaaaaacag gaaggcaaaa tgccgcaaaa aagggaataa 7980
gggcgacacg gaaatgttga atactcatac tcttcctttt tcaatattat tgaagcattt 8040
atcagggtta ttgtctcatg agcggataca tatttgaatg tatttagaaa aataaacaaa 8100
taggggttcc gcgcacattt ccccgaaaag tgccacctga cgtctaagaa accattatta 8160
tcatgacatt aacctataaa aataggcgta tcacgaggcc ctttcgtctt caagaattgt 8220
t 8221

<210> SEQ ID NO 28
<211> LENGTH: 8439
<212> TYPE: DNA
<213> ORGANISM: Artificial Sequence
<220> FEATURE:
<223> OTHER INFORMATION: Synthetic Construct pAdApt Ebola GP(Z)

<400> SEQUENCE: 28
ttaattaacc gcaattctca tgtttgacag cttatcatca tcaataatat accttatttt 60
ggattgaagc caatatgata atgagggggt ggagtttgtg acgtggcgcg gggcgtggga 120
acggggcggg tgacgtagta gtgtggcgga agtgtgatgt tgcaagtgtg gcggaacaca 180
tgtaagcgac ggatgtggca aaagtgacgt ttttggtgtg cgccggtgta cacaggaagt 240
gacaattttc gcgcggtttt aggcggatgt tgtagtaaat ttgggcgtaa ccgagtaaga 300

-continued

```
tttggccatt ttcgcgggaa aactgaataa gaggaagtga aatctgaata attttgtgtt    360
actcatagcg cgtaatattt gtctagggcc gcggggactt tgaccgttta cgtggagact    420
cgcccaggtg tttttctcag gtgttttccg cgttccgggt caaagttggc gttttattat    480
tatagtcagt acgtaccagt gcactggcct agagcggccc cattgcatac gttgtatcca    540
tatcataata tgtacattta tattggctca tgtccaacat taccgccatg ttgacattga    600
ttattgacta gttattaata gtaatcaatt acggggtcat tagttcatag cccatatatg    660
gagttccgcg ttacataact tacggtaaat ggcccgcctg gctgaccgcc caacgacccc    720
cgcccattga cgtcaataat gacgtatgtt cccatagtaa cgccaatagg gactttccat    780
tgacgtcaat gggtggagta tttacggtaa actgcccact tggcagtaca tcaagtgtat    840
catatgccaa gtacgccccc tattgacgtc aatgacggta aatggcccgc ctggcattat    900
gcccagtaca tgaccttatg ggactttcct acttggcagt acatctacgt attagtcatc    960
gctattacca tggtgatgcg gttttggcag tacatcaatg ggcgtggata gcggtttgac   1020
tcacggggat ttccaagtct ccaccccatt gacgtcaatg ggagtttgtt ttggcaccaa   1080
aatcaacggg actttccaaa atgtcgtaac aactccgccc cattgacgca aatgggcggt   1140
aggcgtgtac ggtgggaggt ctatataagc agagctcgtt tagtgaaccg tcagatcgcc   1200
tggagacgcc atccacgctg ttttgacctc catagaagac accgggaccg atccagcctc   1260
cgtcaccgtc gtcgacacgt gtgatcagat atcgcggccg ctctagacca ggccctggat   1320
cgatccaaca acacaatggg cgttacagga atattgcagt tacctcgtga tcgattcaag   1380
aggacatcat tctttctttg ggtaattatc cttttccaaa gaacattttc catcccactt   1440
ggagtcatcc acaatagcac attacaggtt agtgatgtcg acaaactagt ttgtcgtgac   1500
aaactgtcat ccacaaatca attgagatca gttggactga atctcgaagg gaatggagtg   1560
gcaactgacg tgccatctgc aactaaaaga tggggcttca ggtccggtgt cccaccaaag   1620
gtggtcaatt atgaagctgg tgaatgggct gaaaactgct acaatcttga aatcaaaaaa   1680
cctgacggga gtgagtgtct accagcagcg ccagacggga ttcggggctt cccccggtgc   1740
cggtatgtgc acaaagtatc aggaacggga ccgtgtgccg gagactttgc cttccataaa   1800
gagggtgctt tcttcctgta tgatcgactt gcttccacag ttatctaccg aggaacgact   1860
ttcgctgaag gtgtcgttgc atttctgata ctgccccaag ctaagaagga cttcttcagc   1920
tcacacccct tgagagagcc ggtcaatgca acggaggacc cgtctagtgg ctactattct   1980
accacaatta gatatcaggc taccggtttt ggaaccaatg agacagagta cttgttcgag   2040
gttgacaatt tgacctacgt ccaacttgaa tcaagattca caccacagtt tctgctccag   2100
ctgaatgaga caatatatac aagtgggaaa aggagcaata ccacgggaaa actaatttgg   2160
aaggtcaacc ccgaaattga tacaacaatc ggggagtggg ccttctggga aactaaaaaa   2220
aacctcacta gaaaaattcg cagtgaagag ttgtctttca cagttgtatc aaacggagcc   2280
aaaaacatca gtggtcagag tccggcgcga acttcttccg acccagggac caacacaaca   2340
actgaagacc acaaaatcat ggcttcagaa aattcctctg caatggttca agtgcacagt   2400
caaggaaggg aagctgcagt gtcgcatcta acaacccttg ccacaatctc cacgagtccc   2460
caatccctca caaccaaacc aggtccggac aacagcaccc ataatacacc cgtgtataaa   2520
cttgacatct ctgaggcaac tcaagttgaa caacatcacc gcagaacaga caacgacagc   2580
acagcctccg acactccctc tgccacgacc gcagccggac ccccaaaagc agagaacacc   2640
aacacgagca agagcactga cttcctggac cccgccacca caacaagtcc ccaaaaccac   2700
```

agcgagaccg ctggcaacaa caacactcat caccaagata ccggagaaga gagtgccagc 2760
agcgggaagc taggcttaat taccaatact attgctggag tcgcaggact gatcacaggc 2820
gggagaagaa ctcgaagaga agcaattgtc aatgctcaac ccaaatgcaa ccctaattta 2880
cattactgga ctactcagga tgaaggtgct gcaatcggac tggcctggat accatatttc 2940
gggccagcag ccgagggaat ttacatagag ggctaatgc acaatcaaga tggtttaatc 3000
tgtgggttga gacagctggc caacgagacg actcaagctc ttcaactgtt cctgagagcc 3060
acaactgagc tacgcacctt ttcaatcctc aaccgtaagg caattgattt cttgctgcag 3120
cgatggggcg gcacatgcca cattctggga ccggactgct gtatcgaacc acatgattgg 3180
accaagaaca taacagacaa aattgatcag attattcatg attttgttga taaaaccctt 3240
ccggaccagg gggacaatga caattggtgg acaggatgga gacaatggat accggcaggt 3300
attggagtta caggcgttgt aattgcagtt atcgctttat tctgtatatg caaatttgtc 3360
ttttagtttt tcttcagatt gcttcatgga aaagctcagc ctcaaatcaa tgaaaccagg 3420
atttaattat atggattact tgaatctaag attacttgac aaatgataat ataatacact 3480
ggagctttaa acatagccaa tgtgattcta actcctttaa actcacagtt aatcataaac 3540
aaggtttgag gtaccgagct cgaattgatc tgctgtgcct tctagttgcc agccatctgt 3600
tgtttgcccc tcccccgtgc cttccttgac cctggaaggt gccactccca ctgtcctttc 3660
ctaataaaat gaggaaattg catcgcattg tctgagtagg tgtcattcta ttctgggggg 3720
tggggtgggg caggacagca agggggagga ttgggaagac aatagcaggc atgctgggga 3780
tgcggtgggc tctatgggta cccagggccg cataacttcg tataatgtat gctatacgaa 3840
gttataagat ctgtactgaa atgtgtgggc gtggcttaag ggtgggaaag aatatataag 3900
gtgggggtct tatgtagttt tgtatctgtt ttgcagcagc cgccgccgcc atgagcacca 3960
actcgtttga tggaagcatt gtgagctcat atttgacaac gcgcatgccc ccatgggccg 4020
gggtgcgtca gaatgtgatg ggctccagca ttgatggtcg ccccgtcctg cccgcaaact 4080
ctactacctt gacctacgag accgtgtctg gaacgccgtt ggagactgca gcctccgccg 4140
ccgcttcagc cgctgcagcc accgcccgcg ggattgtgac tgactttgct ttcctgagcc 4200
cgcttgcaag cagtgcagct tcccgttcat ccgcccgcga tgacaagttg acggctcttt 4260
tggcacaatt ggattctttg acccgggaac ttaatgtcgt ttctcagcag ctgttggatc 4320
tgcgccagca ggtttctgcc ctgaaggctt cctcccctcc caatgcggtt taaaacataa 4380
ataaaaaacc agactctgtt tggatttgga tcaagcaagt gtcttgctgt ctttatttag 4440
gggttttgcg cgcgcggtag gcccgggacc agcggtctcg gtcgttgagg gtcctgtgta 4500
ttttttccag gacgtggtaa aggtgactct ggatgttcag atacatgggc ataagcccgt 4560
ctctggggtg gaggtagcac cactgcagag cttcatgctg cggggtggtg ttgtagatga 4620
tccagtcgta gcaggagcgc tgggcgtggt gcctaaaaat gtctttcagt agcaagctga 4680
ttgccagggg caggcccttg gtgtaagtgt ttacaaagcg gttaagctgg gatgggtgca 4740
tacgtgggga tatgagatgc atcttggact gtatttttag gttggctatg ttcccagcca 4800
tatccctccg ggattcatg ttgtgcagaa ccaccagcac agtgtatccg gtgcacttgg 4860
gaaatttgtc atgtagctta gaaggaaatg cgtggaagaa cttggagacg cccttgtgac 4920
ctccaagatt ttccatgcat tcgtccataa tgatggcaat gggcccacgg gcggcggcct 4980
gggcgaagat atttctggga tcactaacgt catagttgtg ttccaggatg agatcgtcat 5040
aggccatttt tacaaagcgc gggcggaggg tgccagactg cggtataatg gttccatccg 5100

-continued

```
gcccaggggc gtagttaccc tcacagattt gcatttccca cgctttgagt tcagatgggg   5160
ggatcatgtc tacctgcggg gcgatgaaga aaacggtttc cggggtaggg gagatcagct   5220
gggaagaaag caggttcctg agcagctgcg acttaccgca gccggtgggc ccgtaaatca   5280
cacctattac cggctgcaac tggtagttaa gagagctgca gctgccgtca tccctgagca   5340
ggggggccac ttcgttaagc atgtccctga ctcgcatgtt ttccctgacc aaatccgcca   5400
gaaggcgctc gccgcccagc gatagcagtt cttgcaagga agcaaagttt ttcaacggtt   5460
tgagaccgtc cgccgtaggc atgcttttga gcgtttgacc aagcagttcc aggcggtccc   5520
acagctcggt cacctgctct acggcatctc gatccagcat atctcctcgt ttcgcgggtt   5580
ggggcggctt tcgctgtacg gcagtagtcg gtgctcgtcc agacgggcca gggtcatgtc   5640
tttccacggg cgcagggtcc tcgtcagcgt agtctgggtc acggtgaagg ggtgcgctcc   5700
gggctgcgcg ctggccaggg tgcgcttgag gctggtcctg ctggtgctga agcgctgccg   5760
gtcttcgccc tgcgcgtcgg ccaggtagca tttgaccatg gtgtcatagt ccagcccctc   5820
cgcggcgtgg cccttggcgc gcagcttgcc cttggaggag gcgccgcacg aggggcagtg   5880
cagacttttg agggcgtaga gcttgggcgc gagaaatacc gattccgggg agtaggcatc   5940
cgcgccgcag gccccgcaga cggtctcgca ttccacgagc caggtgagct ctggccgttc   6000
ggggtcaaaa accaggtttc ccccatgctt tttgatgcgt ttcttacctc tggtttccat   6060
gagccggtgt ccacgctcgg tgacgaaaag gctgtccgtg tccccgtata cagacttgag   6120
aggcctgtcc tcgagcggtg ttccgcggtc ctcctcgtat agaaactcgg accactctga   6180
gacaaaggct cgcgtccagg ccagcacgaa ggaggctaag tgggaggggt agcggtcgtt   6240
gtccactagg gggtccactc gctccagggt gtgaagacac atgtcgccct cttcggcatc   6300
aaggaaggtg attggtttgt aggtgtaggc cacgtgaccg ggtgttcctg aaggggggct   6360
ataaaagggg gtgggggcgc gttcgtcctc actctcttcc gcatcgctgt ctgcgagggc   6420
cagctgttgg ggtgagtcga cgcgaggctg gatggccttc cccattatga ttcttctcgc   6480
ttccggcggc atcgggatgc ccgcgttgca ggccatgctg tccaggcagg tagatgacga   6540
ccatcaggga cagcttcaag gccagcaaaa ggccaggaac cgtaaaaagg ccgcgttgct   6600
ggcgtttttc cataggctcc gcccccctga cgagcatcac aaaaatcgac gctcaagtca   6660
gaggtggcga aacccgacag gactataaag ataccaggcg tttccccctg gaagctccct   6720
cgtgcgctct cctgttccga ccctgccgct taccggatac ctgtccgcct ttctcccttc   6780
gggaagcgtg gcgctttctc atagctcacg ctgtaggtat ctcagttcgg tgtaggtcgt   6840
tcgctccaag ctgggctgtg tgcacgaacc ccccgttcag cccgaccgct gcgccttatc   6900
cggtaactat cgtcttgagt ccaacccggt aagacacgac ttatcgccac tggcagcagc   6960
cactggtaac aggattagca gagcgaggta tgtaggcggt gctacagagt tcttgaagtg   7020
gtggcctaac tacggctaca ctagaaggac agtatttggt atctgcgctc tgctgaagcc   7080
agttaccttc ggaaaaagag ttggtagctc ttgatccggc aaacaaacca ccgctggtag   7140
cggtggtttt tttgtttgca agcagcagat tacgcgcaga aaaaaaggat ctcaagaaga   7200
tcctttgatc ttttctacgg ggtctgacgc tcagtggaac gaaaactcac gttaagggat   7260
tttggtcatg agattatcaa aaaggatctt cacctagatc cttttaaatt aaaaatgaag   7320
ttttaaatca atctaaagta tatatgagta aacttggtct gacagttacc aatgcttaat   7380
cagtgaggca cctatctcag cgatctgtct atttcgttca tccatagttg cctgactccc   7440
cgtcgtgtag ataactacga tacgggaggg cttaccatct ggccccagtg ctgcaatgat   7500
```

-continued accgcgagac ccacgctcac cggctccaga tttatcagca ataaaccagc cagccggaag 7560
ggccgagcgc agaagtggtc ctgcaacttt atccgcctcc atccagtcta ttaattgttg 7620
ccgggaagct agagtaagta gttcgccagt taatagtttg cgcaacgttg ttgccattgc 7680
tgcaggcatc gtggtgtcac gctcgtcgtt tggtatggct tcattcagct ccggttccca 7740
acgatcaagg cgagttacat gatcccccat gttgtgcaaa aaagcggtta gctccttcgg 7800
tcctccgatc gttgtcagaa gtaagttggc cgcagtgtta tcactcatgg ttatggcagc 7860
actgcataat tctcttactg tcatgccatc cgtaagatgc ttttctgtga ctggtgagta 7920
ctcaaccaag tcattctgag aatagtgtat gcggcgaccg agttgctctt gcccggcgtc 7980
aacacgggat aataccgcgc cacatagcag aactttaaaa gtgctcatca ttggaaaacg 8040
ttcttcgggg cgaaaactct caaggatctt accgctgttg agatccagtt cgatgtaacc 8100
cactcgtgca cccaactgat cttcagcatc ttttactttc accagcgttt ctgggtgagc 8160
aaaaacagga aggcaaaatg ccgcaaaaaa gggaataagg gcgacacgga aatgttgaat 8220
actcatactc ttcctttttc aatattattg aagcatttat cagggttatt gtctcatgag 8280
cggatacata tttgaatgta tttagaaaaa taaacaaata ggggttccgc gcacatttcc 8340
ccgaaaagtg ccacctgacg tctaagaaac cattattatc atgacattaa cctataaaaa 8400
taggcgtatc acgaggccct ttcgtcttca agaattgtt 8439

<210> SEQ ID NO 29
<211> LENGTH: 8199
<212> TYPE: DNA
<213> ORGANISM: Artificial Sequence
<220> FEATURE:
<223> OTHER INFORMATION: Synthetic Construct pAdApt Ebola GP(Z)(dTM)

<400> SEQUENCE: 29
ttaattaacc gcaattctca tgtttgacag cttatcatca tcaataatat accttatttt 60
ggattgaagc caatatgata atgagggggt ggagtttgtg acgtggcgcg gggcgtggga 120
acggggcggg tgacgtagta gtgtggcgga agtgtgatgt tgcaagtgtg gcggaacaca 180
tgtaagcgac ggatgtggca aaagtgacgt ttttggtgtg cgccggtgta cacaggaagt 240
gacaattttc gcgcggtttt aggcggatgt tgtagtaaat ttgggcgtaa ccgagtaaga 300
tttggccatt ttcgcgggaa aactgaataa gaggaagtga aatctgaata attttgtgtt 360
actcatagcg cgtaatattt gtctagggcc gcggggactt tgaccgttta cgtggagact 420
cgcccaggtg tttttctcag gtgttttccg cgttccgggt caaagttggc gttttattat 480
tatagtcagt acgtaccagt gcactggcct agagcggccc cattgcatac gttgtatcca 540
tatcataata tgtacattta tattggctca tgtccaacat taccgccatg ttgacattga 600
ttattgacta gttattaata gtaatcaatt acggggtcat tagttcatag cccatatatg 660
gagttccgcg ttacataact tacggtaaat ggcccgcctg gctgaccgcc caacgacccc 720
cgcccattga cgtcaataat gacgtatgtt cccatagtaa cgccaatagg gactttccat 780
tgacgtcaat gggtggagta tttacggtaa actgcccact tggcagtaca tcaagtgtat 840
catatgccaa gtacgccccc tattgacgtc aatgacggta aatggcccgc ctggcattat 900
gcccagtaca tgaccttatg ggactttcct acttggcagt acatctacgt attagtcatc 960
gctattacca tggtgatgcg gttttggcag tacatcaatg ggcgtggata gcggtttgac 1020
tcacggggat ttccaagtct ccaccccatt gacgtcaatg ggagtttgtt ttggcaccaa 1080
aatcaacggg actttccaaa atgtcgtaac aactccgccc cattgacgca aatgggcggt 1140

-continued

```
aggcgtgtac ggtgggaggt ctatataagc agagctcgtt tagtgaaccg tcagatcgcc   1200
tggagacgcc atccacgctg ttttgacctc catagaagac accgggaccg atccagcctc   1260
cgtcaccgtc gtcgacacgt gtgatcagat atcgcggccg ctctagacca ggccctggat   1320
cgatccaaca acacaatggg cgttacagga atattgcagt tacctcgtga tcgattcaag   1380
aggacatcat tctttctttg ggtaattatc cttttccaaa gaacattttc catcccactt   1440
ggagtcatcc acaatagcac attacaggtt agtgatgtcg acaaactagt ttgtcgtgac   1500
aaactgtcat ccacaaatca attgagatca gttggactga atctcgaagg gaatggagtg   1560
gcaactgacg tgccatctgc aactaaaaga tggggcttca ggtccggtgt cccaccaaag   1620
gtggtcaatt atgaagctgg tgaatgggct gaaaactgct acaatcttga aatcaaaaaa   1680
cctgacggga gtgagtgtct accagcagcg ccagacggga ttcggggctt cccccggtgc   1740
cggtatgtgc acaaagtatc aggaacggga ccgtgtgccg gagactttgc cttccataaa   1800
gagggtgctt tcttcctgta tgatcgactt gcttccacag ttatctaccg aggaacgact   1860
ttcgctgaag gtgtcgttgc atttctgata ctgccccaag ctaagaagga cttcttcagc   1920
tcacacccct tgagagagcc ggtcaatgca acggaggacc cgtctagtgg ctactattct   1980
accacaatta gatatcaggc taccggtttt ggaaccaatg agacagagta cttgttcgag   2040
gttgacaatt tgacctacgt ccaacttgaa tcaagattca caccacagtt tctgctccag   2100
ctgaatgaga caatatatac aagtgggaaa aggagcaata ccacgggaaa actaatttgg   2160
aaggtcaacc ccgaaattga tacaacaatc ggggagtggg ccttctggga aactaaaaaa   2220
aacctcacta gaaaaattcg cagtgaagag ttgtctttca cagttgtatc aaacggagcc   2280
aaaaacatca gtggtcagag tccggcgcga acttcttccg acccagggac caacacaaca   2340
actgaagacc acaaaatcat ggcttcagaa aattcctctg caatggttca agtgcacagt   2400
caaggaaggg aagctgcagt gtcgcatcta acaacccttg ccacaatctc cacgagtccc   2460
caatccctca caaccaaacc aggtccggac aacagcaccc ataatacacc cgtgtataaa   2520
cttgacatct ctgaggcaac tcaagttgaa caacatcacc gcagaacaga caacgacagc   2580
acagcctccg acactccctc tgccacgacc gcagccggac ccccaaaagc agagaacacc   2640
aacacgagca agagcactga cttcctggac cccgccacca caacaagtcc ccaaaaccac   2700
agcgagaccg ctggcaacaa caacactcat caccaagata ccggagaaga gagtgccagc   2760
agcgggaagc taggcttaat taccaatact attgctggag tcgcaggact gatcacaggc   2820
gggagaagaa ctcgaagaga agcaattgtc aatgctcaac ccaaatgcaa ccctaattta   2880
cattactgga ctactcagga tgaaggtgct gcaatcggac tggcctggat accatatttc   2940
gggccagcag ccgagggaat ttacatagag gggctaatgc acaatcaaga tggtttaatc   3000
tgtgggttga gacagctggc caacgagacg actcaagctc ttcaactgtt cctgagagcc   3060
acaactgagc tacgcacctt ttcaatcctc aaccgtaagg caattgattt cttgctgcag   3120
cgatggggcg gcacatgcca cattctggga ccggactgct gtatcgaacc acatgattgg   3180
accaagaaca taacagacaa aattgatcag attattcatg attttgttga taaaaccctt   3240
ccggaccagg gggacaatga caattggtgg acaggatgga gacaatggat ggccgcatcg   3300
tgactgactg acgatctgcc tcgcgagatc tgctgtgcct tctagttgcc agccatctgt   3360
tgtttgcccc tcccccgtgc cttccttgac cctggaaggt gccactccca ctgtcctttc   3420
ctaataaaat gaggaaattg catcgcattg tctgagtagg tgtcattcta ttctgggggg   3480
tggggtgggg caggacagca agggggagga ttgggaagac aatagcaggc atgctgggga   3540
```

-continued tgcggtgggc tctatgggta cccagggccg cataacttcg tataatgtat gctatacgaa 3600
gttataagat ctgtactgaa atgtgtgggc gtggcttaag ggtgggaaag aatatataag 3660
gtgggggtct tatgtagttt tgtatctgtt ttgcagcagc cgccgccgcc atgagcacca 3720
actcgtttga tggaagcatt gtgagctcat atttgacaac gcgcatgccc ccatgggccg 3780
gggtgcgtca gaatgtgatg ggctccagca ttgatggtcg ccccgtcctg cccgcaaact 3840
ctactacctt gacctacgag accgtgtctg gaacgccgtt ggagactgca gcctccgccg 3900
ccgcttcagc cgctgcagcc accgcccgcg ggattgtgac tgactttgct ttcctgagcc 3960
cgcttgcaag cagtgcagct tcccgttcat ccgcccgcga tgacaagttg acggctcttt 4020
tggcacaatt ggattctttg acccgggaac ttaatgtcgt ttctcagcag ctgttggatc 4080
tgcgccagca ggtttctgcc ctgaaggctt cctcccctcc caatgcggtt taaaacataa 4140
ataaaaaacc agactctgtt tggatttgga tcaagcaagt gtcttgctgt ctttatttag 4200
gggttttgcg cgcgcggtag gcccgggacc agcggtctcg gtcgttgagg gtcctgtgta 4260
tttttccag gacgtggtaa aggtgactct ggatgttcag atacatgggc ataagcccgt 4320
ctctggggtg gaggtagcac cactgcagag cttcatgctg cggggtggtg ttgtagatga 4380
tccagtcgta gcaggagcgc tgggcgtggt gcctaaaaat gtctttcagt agcaagctga 4440
ttgccagggg caggcccttg gtgtaagtgt ttacaaagcg gttaagctgg gatgggtgca 4500
tacgtgggga tatgagatgc atcttggact gtatttttag gttggctatg ttcccagcca 4560
tatccctccg gggattcatg ttgtgcagaa ccaccagcac agtgtatccg gtgcacttgg 4620
gaaatttgtc atgtagctta gaaggaaatg cgtggaagaa cttggagacg cccttgtgac 4680
ctccaagatt ttccatgcat tcgtccataa tgatggcaat gggcccacgg gcggcggcct 4740
gggcgaagat atttctggga tcactaacgt catagttgtg ttccaggatg agatcgtcat 4800
aggccatttt tacaaagcgc gggcggaggg tgccagactg cggtataatg gttccatccg 4860
gcccaggggc gtagttaccc tcacagattt gcatttccca cgctttgagt tcagatgggg 4920
ggatcatgtc tacctgcggg gcgatgaaga aaacggtttc cggggtaggg gagatcagct 4980
gggaagaaag caggttcctg agcagctgcg acttaccgca gccggtgggc ccgtaaatca 5040
cacctattac cggctgcaac tggtagttaa gagagctgca gctgccgtca tccctgagca 5100
ggggggccac ttcgttaagc atgtccctga ctcgcatgtt ttccctgacc aaatccgcca 5160
gaaggcgctc gccgcccagc gatagcagtt cttgcaagga agcaaagttt ttcaacggtt 5220
tgagaccgtc cgccgtaggc atgcttttga gcgtttgacc aagcagttcc aggcggtccc 5280
acagctcggt cacctgctct acggcatctc gatccagcat atctcctcgt ttcgcgggtt 5340
ggggcggctt tcgctgtacg gcagtagtcg gtgctcgtcc agacgggcca gggtcatgtc 5400
tttccacggg cgcagggtcc tcgtcagcgt agtctgggtc acggtgaagg ggtgcgctcc 5460
gggctgcgcg ctggccaggg tgcgcttgag gctggtcctg ctggtgctga agcgctgccg 5520
gtcttcgccc tgcgcgtcgg ccaggtagca tttgaccatg gtgtcatagt ccagcccctc 5580
cgcggcgtgg cccttggcgc gcagcttgcc cttggaggag gcgccgcacg aggggcagtg 5640
cagacttttg agggcgtaga gcttgggcgc gagaaatacc gattccgggg agtaggcatc 5700
cgcgccgcag gccccgcaga cggtctcgca ttccacgagc caggtgagct ctggccgttc 5760
ggggtcaaaa accaggtttc ccccatgctt tttgatgcgt ttcttacctc tggtttccat 5820
gagccggtgt ccacgctcgg tgacgaaaag gctgtccgtg tccccgtata cagacttgag 5880
aggcctgtcc tcgagcggtg ttccgcggtc ctcctcgtat agaaactcgg accactctga 5940

```
gacaaaggct cgcgtccagg ccagcacgaa ggaggctaag tgggaggggt agcggtcgtt   6000

gtccactagg gggtccactc gctccagggt gtgaagacac atgtcgccct cttcggcatc   6060

aaggaaggtg attggtttgt aggtgtaggc cacgtgaccg ggtgttcctg aagggggct    6120

ataaaagggg gtgggggcgc gttcgtcctc actctcttcc gcatcgctgt ctgcgagggc   6180

cagctgttgg ggtgagtcga cgcgaggctg gatggccttc cccattatga ttcttctcgc   6240

ttccggcggc atcgggatgc ccgcgttgca ggccatgctg tccaggcagg tagatgacga   6300

ccatcaggga cagcttcaag gccagcaaaa ggccaggaac cgtaaaaagg ccgcgttgct   6360

ggcgtttttc cataggctcc gcccccctga cgagcatcac aaaaatcgac gctcaagtca   6420

gaggtggcga aacccgacag gactataaag ataccaggcg tttccccctg gaagctccct   6480

cgtgcgctct cctgttccga ccctgccgct taccggatac ctgtccgcct ttctcccttc   6540

gggaagcgtg gcgctttctc atagctcacg ctgtaggtat ctcagttcgg tgtaggtcgt   6600

tcgctccaag ctgggctgtg tgcacgaacc ccccgttcag cccgaccgct gcgccttatc   6660

cggtaactat cgtcttgagt ccaacccggt aagacacgac ttatcgccac tggcagcagc   6720

cactggtaac aggattagca gagcgaggta tgtaggcggt gctacagagt tcttgaagtg   6780

gtggcctaac tacggctaca ctagaaggac agtatttggt atctgcgctc tgctgaagcc   6840

agttaccttc ggaaaaagag ttggtagctc ttgatccggc aaacaaacca ccgctggtag   6900

cggtggtttt tttgtttgca agcagcagat tacgcgcaga aaaaaaggat ctcaagaaga   6960

tcctttgatc ttttctacgg ggtctgacgc tcagtggaac gaaaactcac gttaagggat   7020

tttggtcatg agattatcaa aaaggatctt cacctagatc cttttaaatt aaaaatgaag   7080

ttttaaatca atctaaagta tatatgagta aacttggtct gacagttacc aatgcttaat   7140

cagtgaggca cctatctcag cgatctgtct atttcgttca tccatagttg cctgactccc   7200

cgtcgtgtag ataactacga tacgggaggg cttaccatct ggccccagtg ctgcaatgat   7260

accgcgagac ccacgctcac cggctccaga tttatcagca ataaaccagc cagccggaag   7320

ggccgagcgc agaagtggtc ctgcaacttt atccgcctcc atccagtcta ttaattgttg   7380

ccgggaagct agagtaagta gttcgccagt taatagtttg cgcaacgttg ttgccattgc   7440

tgcaggcatc gtggtgtcac gctcgtcgtt tggtatggct tcattcagct ccggttccca   7500

acgatcaagg cgagttacat gatcccccat gttgtgcaaa aaagcggtta gctccttcgg   7560

tcctccgatc gttgtcagaa gtaagttggc cgcagtgtta tcactcatgg ttatggcagc   7620

actgcataat tctcttactg tcatgccatc cgtaagatgc ttttctgtga ctggtgagta   7680

ctcaaccaag tcattctgag aatagtgtat gcggcgaccg agttgctctt gcccggcgtc   7740

aacacgggat aataccgcgc cacatagcag aactttaaaa gtgctcatca ttggaaaacg   7800

ttcttcgggg cgaaaactct caaggatctt accgctgttg agatccagtt cgatgtaacc   7860

cactcgtgca cccaactgat cttcagcatc ttttactttc accagcgttt ctgggtgagc   7920

aaaaacagga aggcaaaatg ccgcaaaaaa gggaataagg gcgacacgga aatgttgaat   7980

actcatactc ttcctttttc aatattattg aagcatttat cagggttatt gtctcatgag   8040

cggatacata tttgaatgta tttagaaaaa taaacaaata ggggttccgc gcacatttcc   8100

ccgaaaagtg ccacctgacg tctaagaaac cattattatc atgacattaa cctataaaaa   8160

taggcgtatc acgaggccct ttcgtcttca agaattgtt                          8199
```

<210> SEQ ID NO 30
<211> LENGTH: 7778
<212> TYPE: DNA

<213> ORGANISM: Artificial Sequence
<220> FEATURE:
<223> OTHER INFORMATION: Synthetic Construct pVR1012 Marburg

<400> SEQUENCE: 30
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcagattgg 240
ctattggcca ttgcatacgt tgtatccata tcataatatg tacatttata ttggctcatg 300
tccaacatta ccgccatgtt gacattgatt attgactagt tattaatagt aatcaattac 360
ggggtcatta gttcatagcc catatatgga gttccgcgtt acataactta cggtaaatgg 420
cccgcctggc tgaccgccca acgacccccg cccattgacg tcaataatga cgtatgttcc 480
catagtaacg ccaataggga ctttccattg acgtcaatgg gtggagtatt tacggtaaac 540
tgcccacttg gcagtacatc aagtgtatca tatgccaagt acgcccccta ttgacgtcaa 600
tgacggtaaa tggcccgcct ggcattatgc ccagtacatg accttatggg actttcctac 660
ttggcagtac atctacgtat tagtcatcgc tattaccatg gtgatgcggt tttggcagta 720
catcaatggg cgtggatagc ggtttgactc acggggattt ccaagtctcc accccattga 780
cgtcaatggg agtttgtttt ggcaccaaaa tcaacgggac tttccaaaat gtcgtaacaa 840
ctccgcccca ttgacgcaaa tgggcggtag gcgtgtacgg tgggaggtct atataagcag 900
agctcgttta gtgaaccgtc agatcgcctg gagacgccat ccacgctgtt ttgacctcca 960
tagaagacac cgggaccgat ccagcctccg cggccgggaa cggtgcattg gaacgcggat 1020
tccccgtgcc aagagtgacg taagtaccgc ctatagactc tataggcaca cccctttggc 1080
tcttatgcat gctatactgt ttttggcttg gggcctatac acccccgctt ccttatgcta 1140
taggtgatgg tatagcttag cctataggtg tgggttattg accattattg accactcccc 1200
tattggtgac gatactttcc attactaatc cataacatgg ctctttgcca caactatctc 1260
tattggctat atgccaatac tctgtccttc agagactgac acggactctg tatttttaca 1320
ggatggggtc ccatttatta tttacaaatt cacatataca acaacgccgt cccccgtgcc 1380
cgcagttttt attaaacata gcgtgggatc tccacgcgaa tctcgggtac gtgttccgga 1440
catgggctct tctccggtag cggcggagct tccacatccg agccctggtc ccatgcctcc 1500
agcggctcat ggtcgctcgg cagctccttg ctcctaacag tggaggccag acttaggcac 1560
agcacaatgc ccaccaccac cagtgtgccg cacaaggccg tggcggtagg gtatgtgtct 1620
gaaaatgagc gtggagattg ggctcgcacg gctgacgcag atggaagact taaggcagcg 1680
gcagaagaag atgcaggcag ctgagttgtt gtattctgat aagagtcaga ggtaactccc 1740
gttgcggtgc tgttaacggt ggagggcagt gtagtctgag cagtactcgt tgctgccgcg 1800
cgcgccacca gacataatag ctgacagact aacagactgt tcctttccat gggtcttttc 1860
tgcagtcacc gtcgtcgaca cgtgtgatca gatatcgcgg ccgctctaga gtcgaatgaa 1920
gaacattaat tgctgggtaa aagtgattaa tttctttaaa tttgaccaga ataatatttt 1980
gtcagtgaat atattctcat atcacttgat taaaaacaga aaattaccct aacatgaaga 2040
ccacatgttt ccttatcagt cttatcttaa ttcaagggac aaaaaatctc cccattttag 2100
agatagctag taataatcaa ccccaaaatg tggattcggt atgctccgga actctccaga 2160
agacagaaga cgtccatctg atgggattca cactgagtgg gcaaaaagtt gctgattccc 2220

-continued

```
ctttggaggc atccaagcga tgggctttca ggacaggtgt acctcccaag aatgttgagt   2280
acacagaggg ggaggaagcc aaaacatgct acaatataag tgtaacggat ccctctggaa   2340
aatccttgct gttagatcct cctaccaaca tccgtgacta tcctaaatgc aaaactatcc   2400
atcatattca aggtcaaaac cctcatgcac aggggatcgc ccttcattta tggggagcat   2460
tttttctgta tgatcgcatt gcctccacaa caatgtaccg aggcaaagtc ttcactgaag   2520
ggaacatagc agctatgatt gtcaataaga cagtgcacaa aatgattttc tcgcggcaag   2580
gacaagggta ccgtcatatg aatctgactt ctactaataa atattggaca agtagtaacg   2640
gaacgcaaac gaatgacact ggatgtttcg gcgctcttca agaatacaat tctacaaaga   2700
accaaacatg tgctccgtcc aaaatacctc caccactgcc cacagcccgt ccggagatca   2760
aactcacaag caccccaact gatgccacca aactcaatac cacggaccca agcagtgatg   2820
atgaggacct cgcaacatcc ggctcagggt ccggagaacg agaaccccac acaacttctg   2880
atgcggtcac caagcaaggg ctttcatcaa caatgccacc cactccctca ccacaaccaa   2940
gcacgccaca gcaaggagga aacaacacaa accattccca agatgctgtg actgaactag   3000
acaaaaataa cacaactgca caaccgtcca tgcccccctca taacactacc acaatctcta   3060
ctaacaacac ctccaaacac aacttcagca ctctctctgc accattacaa aacaccacca   3120
atgacaacac acagagcaca atcactgaaa atgagcaaac cagtgccccc tcgataacaa   3180
ccctgcctcc aacgggaaat cccaccacag caaagagcac cagcagcaaa aaaggccccg   3240
ccacaacggc accaaacacg acaaatgagc atttcaccag tcctcccccc acccccagct   3300
cgactgcaca acatcttgta tatttcagaa gaaagcgaag tatcctctgg agggaaggcg   3360
acatgttccc ttttctggat gggttaataa atgctccaat tgattttgac ccagttccaa   3420
atacaaaaac aatctttgat gaatcctcta gttctggtgc ctcggctgag gaagatcaac   3480
atgcctcccc caatattagt ttaactttat cttattttcc taatataaat gagaacactg   3540
cctactctgg agaaaatgag aatgattgtg atgcagagtt aagaatttgg agcgttcagg   3600
aggatgacct ggccgcaggg ctcagttgga taccgttttt tggccctgga attgaaggac   3660
tttacactgc tgttttaatt aaaaatcaaa acaatttggt ctgcaggttg aggcgtctag   3720
ccaatcaaac tgccaaatcc ttggaactct tattgagagt cacaactgag gaaagaacat   3780
tctccttaat caatagacat gctattgact ttctactcac aagatgggga ggaacatgca   3840
aagtgcttgg acctgattgt tgcatcggga tagaagactt gtccaaaaat atttcagagc   3900
aaattgacca aattaaaaag gacgaacaaa aagaggggac tggttggggt ctgggtggta   3960
aatggtggac atccgactgg ggtgttctta ctaacttggg cattttgcta ctattatcca   4020
tagctgtctt gattgctcta tcctgtattt gtcgtatctt tactaaatat atcggataac   4080
gttaaatgtg taatgattag gactttagga caattgctac tgagcccttt tctaatctac   4140
tgaaatcaac ttgggagatt tttaagaagc tgataactta atgtgaatca atagtttatg   4200
tattatcgat tattatggtt tgatattcaa ttgttattat tgtcaggagt gaccttttct   4260
atttgatgca ttaatgtttt aaactacctc ttaagccttt gagggcgtcc caatatgtgc   4320
gtaggggtta atttaaaggg atttcttatt gtacagtttt ctgtattact tatttgggct   4380
tgaagacata gttaagattt gccgaaatgc tctccagtca attccatccc ctctcagaaa   4440
agacgtgctg ttcaaagagt cttaatttat aaccaactat tgcaagaatt aatttacttt   4500
ttccgttata cttagttaca ttaatctttt gactgttcag cattattaac gacttgtctt   4560
aattcaatcg ttcggatgaa attcataagg aaaaatgagc ctccttcccc ctattctggg   4620
```

-continued

```
ctgagaaaat ttctcttatc cgcctaaaat cagatctgtt aggtcatggg tccttcataa   4680
tctgtttgag catgaatatt gatgaaatga ccaaatgata gtgcatttgt atagactcaa   4740
ttatccttta ttaagaaaaa tcgacctgca ggcatgcaag cttcaggatc cagatctgct   4800
gtgccttcta gttgccagcc atctgttgtt tgcccctccc ccgtgccttc cttgaccctg   4860
gaaggtgcca ctcccactgt cctttcctaa taaaatgagg aaattgcatc gcattgtctg   4920
agtaggtgtc attctattct ggggggtggg gtggggcagc acagcaaggg ggaggattgg   4980
gaagacaata gcaggcatgc tggggatgcg gtgggctcta tgggtaccca ggtgctgaag   5040
aattgacccg gttcctcctg ggccagaaag aagcaggcac atccccttct ctgtgacaca   5100
ccctgtccac gcccctggtt cttagttcca gccccactca taggacactc atagctcagg   5160
agggctccgc cttcaatccc acccgctaaa gtacttggag cggtctctcc ctccctcatc   5220
agcccaccaa accaaaccta gcctccaaga gtgggaagaa attaaagcaa gataggctat   5280
taagtgcaga gggagagaaa atgcctccaa catgtgagga agtaatgaga gaaatcatag   5340
aatttcttcc gcttcctcgc tcactgactc gctgcgctcg gtcgttcggc tgcggcgagc   5400
ggtatcagct cactcaaagg cggtaatacg gttatccaca gaatcagggg ataacgcagg   5460
aaagaacatg tgagcaaaag gccagcaaaa ggccaggaac cgtaaaaagg ccgcgttgct   5520
ggcgtttttc cataggctcc gcccccctga cgagcatcac aaaaatcgac gctcaagtca   5580
gaggtggcga aacccgacag gactataaag ataccaggcg tttccccctg gaagctccct   5640
cgtgcgctct cctgttccga ccctgccgct taccggatac ctgtccgcct ttctcccttc   5700
gggaagcgtg gcgctttctc aatgctcacg ctgtaggtat ctcagttcgg tgtaggtcgt   5760
tcgctccaag ctgggctgtg tgcacgaacc ccccgttcag cccgaccgct gcgccttatc   5820
cggtaactat cgtcttgagt ccaacccggt aagacacgac ttatcgccac tggcagcagc   5880
cactggtaac aggattagca gagcgaggta tgtaggcggt gctacagagt tcttgaagtg   5940
gtggcctaac tacggctaca ctagaaggac agtatttggt atctgcgctc tgctgaagcc   6000
agttaccttc ggaaaaagag ttggtagctc ttgatccggc aaacaaacca ccgctggtag   6060
cggtggtttt tttgtttgca agcagcagat tacgcgcaga aaaaaaggat ctcaagaaga   6120
tcctttgatc ttttctacgg ggtctgacgc tcagtggaac gaaaactcac gttaagggat   6180
tttggtcatg agattatcaa aaaggatctt cacctagatc cttttaaatt aaaaatgaag   6240
ttttaaatca atctaaagta tatatgagta aacttggtct gacagttacc aatgcttaat   6300
cagtgaggca cctatctcag cgatctgtct atttcgttca tccatagttg cctgactccg   6360
gggggggggg gcgctgaggt ctgcctcgtg aagaaggtgt tgctgactca taccaggcct   6420
gaatcgcccc atcatccagc cagaaagtga gggagccacg gttgatgaga gctttgttgt   6480
aggtggacca gttggtgatt ttgaactttt gctttgccac ggaacggtct gcgttgtcgg   6540
gaagatgcgt gatctgatcc ttcaactcag caaaagttcg atttattcaa caaagccgcc   6600
gtcccgtcaa gtcagcgtaa tgctctgcca gtgttacaac caattaacca attctgatta   6660
gaaaaactca tcgagcatca aatgaaactg caatttattc atatcaggat tatcaatacc   6720
atatttttga aaaagccgtt tctgtaatga aggagaaaac tcaccgaggc agttccatag   6780
gatggcaaga tcctggtatc ggtctgcgat tccgactcgt ccaacatcaa tacaacctat   6840
taatttcccc tcgtcaaaaa taaggttatc aagtgagaaa tcaccatgag tgacgactga   6900
atccggtgag aatggcaaaa gcttatgcat ttctttccag acttgttcaa caggccagcc   6960
attacgctcg tcatcaaaat cactcgcatc aaccaaaccg ttattcattc gtgattgcgc   7020
```

ctgagcgaga cgaaatacgc gatcgctgtt aaaaggacaa ttacaaacag gaatcgaatg 7080
caaccggcgc aggaacactg ccagcgcatc aacaatattt tcacctgaat caggatattc 7140
ttctaatacc tggaatgctg ttttcccggg gatcgcagtg gtgagtaacc atgcatcatc 7200
aggagtacgg ataaaatgct tgatggtcgg aagaggcata aattccgtca gccagtttag 7260
tctgaccatc tcatctgtaa catcattggc aacgctacct ttgccatgtt tcagaaacaa 7320
ctctggcgca tcgggcttcc catacaatcg atagattgtc gcacctgatt gcccgacatt 7380
atcgcgagcc catttatacc catataaatc agcatccatg ttggaattta atcgcggcct 7440
cgagcaagac gtttcccgtt gaatatggct cataacaccc cttgtattac tgtttatgta 7500
agcagacagt tttattgttc atgatgatat atttttatct tgtgcaatgt aacatcagag 7560
attttgagac acaacgtggc tttccccccc cccccattat tgaagcattt atcagggtta 7620
ttgtctcatg agcggataca tatttgaatg tatttagaaa aataaacaaa taggggttcc 7680
gcgcacattt ccccgaaaag tgccacctga cgtctaagaa accattatta tcatgacatt 7740
aacctataaa aataggcgta tcacgaggcc ctttcgtc 7778

<210> SEQ ID NO 31
<211> LENGTH: 7005
<212> TYPE: DNA
<213> ORGANISM: Artificial Sequence
<220> FEATURE:
<223> OTHER INFORMATION: Synthetic Construct pVR1012x/s Marburg GP(dTM)

<400> SEQUENCE: 31
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcagattgg 240
ctattggcca ttgcatacgt tgtatccata tcataatatg tacatttata ttggctcatg 300
tccaacatta ccgccatgtt gacattgatt attgactagt tattaatagt aatcaattac 360
ggggtcatta gttcatagcc catatatgga gttccgcgtt acataactta cggtaaatgg 420
cccgcctggc tgaccgccca acgacccccg cccattgacg tcaataatga cgtatgttcc 480
catagtaacg ccaataggga ctttccattg acgtcaatgg gtggagtatt tacggtaaac 540
tgcccacttg gcagtacatc aagtgtatca tatgccaagt acgcccccta ttgacgtcaa 600
tgacggtaaa tggcccgcct ggcattatgc ccagtacatg accttatggg actttcctac 660
ttggcagtac atctacgtat tagtcatcgc tattaccatg gtgatgcggt tttggcagta 720
catcaatggg cgtggatagc ggtttgactc acggggattt ccaagtctcc accccattga 780
cgtcaatggg agtttgtttt ggcaccaaaa tcaacgggac tttccaaaat gtcgtaacaa 840
ctccgcccca ttgacgcaaa tgggcggtag gcgtgtacgg tgggaggtct atataagcag 900
agctcgttta gtgaaccgtc agatcgcctg gagacgccat ccacgctgtt ttgacctcca 960
tagaagacac cgggaccgat ccagcctccg cggccgggaa cggtgcattg gaacgcggat 1020
tccccgtgcc aagagtgacg taagtaccgc ctatagactc tataggcaca cccctttggc 1080
tcttatgcat gctatactgt ttttggcttg gggcctatac acccccgctt ccttatgcta 1140
taggtgatgg tatagcttag cctataggtg tgggttattg accattattg accactcccc 1200
tattggtgac gatactttcc attactaatc cataacatgg ctctttgcca caactatctc 1260
tattggctat atgccaatac tctgtccttc agagactgac acggactctg tatttttaca 1320

-continued ggatggggtc ccatttatta tttacaaatt cacatataca acaacgccgt cccccgtgcc 1380
cgcagttttt attaaacata gcgtgggatc tccacgcgaa tctcgggtac gtgttccgga 1440
catgggctct tctccggtag cggcggagct tccacatccg agccctggtc ccatgcctcc 1500
agcggctcat ggtcgctcgg cagctccttg ctcctaacag tggaggccag acttaggcac 1560
agcacaatgc ccaccaccac cagtgtgccg cacaaggccg tggcggtagg gtatgtgtct 1620
gaaaatgagc gtggagattg ggctcgcacg gctgacgcag atggaagact taaggcagcg 1680
gcagaagaag atgcaggcag ctgagttgtt gtattctgat aagagtcaga ggtaactccc 1740
gttgcggtgc tgttaacggt ggagggcagt gtagtctgag cagtactcgt tgctgccgcg 1800
cgcgccacca gacataatag ctgacagact aacagactgt tcctttccat gggtcttttc 1860
tgcagtcacc gtcgtcgaca cgtgtgatca gatatcgcgg ccgctctaga gtcgaatgaa 1920
gaacattaat tgctgggtaa aagtgattaa tttctttaaa tttgaccaga ataatatttt 1980
gtcagtgaat atattctcat atcacttgat taaaaacaga aaattaccct aacatgaaga 2040
ccacatgttt ccttatcagt cttatcttaa ttcaagggac aaaaaatctc cccattttag 2100
agatagctag taataatcaa ccccaaaatg tggattcggt atgctccgga actctccaga 2160
agacagaaga cgtccatctg atgggattca cactgagtgg gcaaaaagtt gctgattccc 2220
ctttggaggc atccaagcga tgggctttca ggacaggtgt acctcccaag aatgttgagt 2280
acacagaggg ggaggaagcc aaaacatgct acaatataag tgtaacggat ccctctggaa 2340
aatccttgct gttagatcct cctaccaaca tccgtgacta tcctaaatgc aaaactatcc 2400
atcatattca aggtcaaaac cctcatgcac aggggatcgc ccttcattta tggggagcat 2460
tttttctgta tgatcgcatt gcctccacaa caatgtaccg aggcaaagtc ttcactgaag 2520
ggaacatagc agctatgatt gtcaataaga cagtgcacaa aatgattttc tcgcggcaag 2580
gacaagggta ccgtcatatg aatctgactt ctactaataa atattggaca agtagtaacg 2640
gaacgcaaac gaatgacact ggatgtttcg gcgctcttca agaatacaat tctacaaaga 2700
accaaacatg tgctccgtcc aaaatacctc caccactgcc cacagcccgt ccggagatca 2760
aactcacaag caccccaact gatgccacca aactcaatac cacggaccca agcagtgatg 2820
atgaggacct cgcaacatcc ggctcagggt ccggagaacg agaaccccac acaacttctg 2880
atgcggtcac caagcaaggg ctttcatcaa caatgccacc cactccctca ccacaaccaa 2940
gcacgccaca gcaaggagga aacaacacaa accattccca agatgctgtg actgaactag 3000
acaaaaataa cacaactgca caaccgtcca tgccccctca taacactacc acaatctcta 3060
ctaacaacac ctccaaacac aacttcagca ctctctctgc accattacaa aacaccacca 3120
atgacaacac acagagcaca atcactgaaa atgagcaaac cagtgccccc tcgataacaa 3180
ccctgcctcc aacgggaaat cccaccacag caaagagcac cagcagcaaa aaaggccccg 3240
ccacaacggc accaaacacg acaaatgagc atttcaccag tcctcccccc acccccagct 3300
cgactgcaca acatcttgta tatttcagaa gaaagcgaag tatcctctgg agggaaggcg 3360
acatgttccc ttttctggat gggttaataa atgctccaat tgattttgac ccagttccaa 3420
atacaaaaac aatctttgat gaatcctcta gttctggtgc ctcggctgag gaagatcaac 3480
atgcctcccc caatattagt ttaactttat cttattttcc taatataaat gagaacactg 3540
cctactctgg agaaaatgag aatgattgtg atgcagagtt aagaatttgg agcgttcagg 3600
aggatgacct ggccgcaggg ctcagttgga taccgttttt tggccctgga attgaaggac 3660
tttacactgc tgttttaatt aaaaatcaaa acaatttggt ctgcaggttg aggcgtctag 3720

-continued ccaatcaaac tgccaaatcc ttggaactct tattgagagt cacaactgag gaaagaacat 3780
tctccttaat caatagacat gctattgact ttctactcac aagatgggga ggaacatgca 3840
aagtgcttgg acctgattgt tgcatcggga tagaagactt gtccaaaaat atttcagagc 3900
aaattgacca aattaaaaag gacgaacaaa aagaggggac tggttggggt ctgggtggta 3960
aatggtggac atccgactgg ggttaagatc tgctgtgcct tctagttgcc agccatctgt 4020
tgtttgcccc tcccccgtgc cttccttgac cctggaaggt gccactccca ctgtcctttc 4080
ctaataaaat gaggaaattg catcgcattg tctgagtagg tgtcattcta ttctgggggg 4140
tggggtgggg caggacagca agggggagga ttgggaagac aatagcaggc atgctgggga 4200
tgcggtgggc tctatgggta cccaggtgct gaagaattga cccggttcct cctgggccag 4260
aaagaagcag gcacatcccc ttctctgtga cacaccctgt ccacgcccct ggttcttagt 4320
tccagcccca ctcataggac actcatagct caggagggct ccgccttcaa tcccacccgc 4380
taaagtactt ggagcggtct ctccctccct catcagccca ccaaaccaaa cctagcctcc 4440
aagagtggga agaaattaaa gcaagatagg ctattaagtg cagagggaga gaaaatgcct 4500
ccaacatgtg aggaagtaat gagagaaatc atagaatttt aaggccatga tttaaggcca 4560
tcatggcctt aatcttccgc ttcctcgctc actgactcgc tgcgctcggt cgttcggctg 4620
cggcgagcgg tatcagctca ctcaaaggcg gtaatacggt tatccacaga atcaggggat 4680
aacgcaggaa agaacatgtg agcaaaaggc cagcaaaagg ccaggaaccg taaaaaggcc 4740
gcgttgctgg cgtttttcca taggctccgc ccccctgacg agcatcacaa aaatcgacgc 4800
tcaagtcaga ggtggcgaaa cccgacagga ctataaagat accaggcgtt tccccctgga 4860
agctccctcg tgcgctctcc tgttccgacc ctgccgctta ccggatacct gtccgccttt 4920
ctcccttcgg gaagcgtggc gctttctcat agctcacgct gtaggtatct cagttcggtg 4980
taggtcgttc gctccaagct gggctgtgtg cacgaacccc ccgttcagcc cgaccgctgc 5040
gccttatccg gtaactatcg tcttgagtcc aacccggtaa gacacgactt atcgccactg 5100
gcagcagcca ctggtaacag gattagcaga gcgaggtatg taggcggtgc tacagagttc 5160
ttgaagtggt ggcctaacta cggctacact agaagaacag tatttggtat ctgcgctctg 5220
ctgaagccag ttaccttcgg aaaaagagtt ggtagctctt gatccggcaa acaaaccacc 5280
gctggtagcg gtggtttttt tgtttgcaag cagcagatta cgcgcagaaa aaaaggatct 5340
caagaagatc ctttgatctt ttctacgggg tctgacgctc agtggaacga aaactcacgt 5400
taagggattt tggtcatgag attatcaaaa aggatcttca cctagatcct tttaaattaa 5460
aaatgaagtt ttaaatcaat ctaaagtata tatgagtaaa cttggtctga cagttaccaa 5520
tgcttaatca gtgaggcacc tatctcagcg atctgtctat ttcgttcatc catagttgcc 5580
tgactcgggg gggggggcg ctgaggtctg cctcgtgaag aaggtgttgc tgactcatac 5640
caggcctgaa tcgccccatc atccagccag aaagtgaggg agccacggtt gatgagagct 5700
ttgttgtagg tggaccagtt ggtgattttg aacttttgct ttgccacgga acggtctgcg 5760
ttgtcgggaa gatgcgtgat ctgatccttc aactcagcaa aagttcgatt tattcaacaa 5820
agccgccgtc ccgtcaagtc agcgtaatgc tctgccagtg ttacaaccaa ttaaccaatt 5880
ctgattagaa aaactcatcg agcatcaaat gaaactgcaa tttattcata tcaggattat 5940
caataccata tttttgaaaa agccgtttct gtaatgaagg agaaaactca ccgaggcagt 6000
tccataggat ggcaagatcc tggtatcggt ctgcgattcc gactcgtcca acatcaatac 6060
aacctattaa tttcccctcg tcaaaaataa ggttatcaag tgagaaatca ccatgagtga 6120

-continued

```
cgactgaatc cggtgagaat ggcaaaagct tatgcatttc tttccagact tgttcaacag   6180

gccagccatt acgctcgtca tcaaaatcac tcgcatcaac caaaccgtta ttcattcgtg   6240

attgcgcctg agcgagacga aatacgcgat cgctgttaaa aggacaatta caaacaggaa   6300

tcgaatgcaa ccggcgcagg aacactgcca gcgcatcaac aatattttca cctgaatcag   6360

gatattcttc taatacctgg aatgctgttt tcccggggat cgcagtggtg agtaaccatg   6420

catcatcagg agtacggata aaatgcttga tggtcggaag aggcataaat tccgtcagcc   6480

agtttagtct gaccatctca tctgtaacat cattggcaac gctacctttg ccatgtttca   6540

gaaacaactc tggcgcatcg ggcttcccat acaatcgata gattgtcgca cctgattgcc   6600

cgacattatc gcgagcccat ttatacccat ataaatcagc atccatgttg gaatttaatc   6660

gcggcctcga gcaagacgtt tcccgttgaa tatggctcat aacacccctt gtattactgt   6720

ttatgtaagc agacagtttt attgttcatg atgatatatt tttatcttgt gcaatgtaac   6780

atcagagatt ttgagacaca acgtggcttt cccccccccc ccattattga agcatttatc   6840

agggttattg tctcatgagc ggatacatat ttgaatgtat ttagaaaaat aaacaaatag   6900

gggttccgcg cacatttccc cgaaaagtgc cacctgacgt ctaagaaacc attattatca   6960

tgacattaac ctataaaaat aggcgtatca cgaggccctt tcgtc                    7005
```

<210> SEQ ID NO 32
<211> LENGTH: 8256
<212> TYPE: DNA
<213> ORGANISM: Artificial Sequence
<220> FEATURE:
<223> OTHER INFORMATION: Synthetic Construct pAdApt Marburg GP(dTM)

<400> SEQUENCE: 32

```
ttaattaacc gcaattctca tgtttgacag cttatcatca tcaataatat accttatttt     60

ggattgaagc caatatgata atgagggggt ggagtttgtg acgtggcgcg gggcgtggga    120

acggggcggg tgacgtagta gtgtggcgga agtgtgatgt tgcaagtgtg gcggaacaca    180

tgtaagcgac ggatgtggca aaagtgacgt ttttggtgtg cgccggtgta cacaggaagt    240

gacaattttc gcgcggtttt aggcggatgt tgtagtaaat ttgggcgtaa ccgagtaaga    300

tttggccatt ttcgcgggaa aactgaataa gaggaagtga aatctgaata attttgtgtt    360

actcatagcg cgtaatattt gtctagggcc gcggggactt tgaccgttta cgtggagact    420

cgcccaggtg tttttctcag gtgttttccg cgttccgggt caaagttggc gttttattat    480

tatagtcagt acgtaccagt gcactggcct agagcggccc cattgcatac gttgtatcca    540

tatcataata tgtacattta tattggctca tgtccaacat taccgccatg ttgacattga    600

ttattgacta gttattaata gtaatcaatt acggggtcat tagttcatag cccatatatg    660

gagttccgcg ttacataact tacggtaaat ggcccgcctg gctgaccgcc caacgacccc    720

cgcccattga cgtcaataat gacgtatgtt cccatagtaa cgccaatagg gactttccat    780

tgacgtcaat gggtggagta tttacggtaa actgcccact tggcagtaca tcaagtgtat    840

catatgccaa gtacgccccc tattgacgtc aatgacggta aatggcccgc ctggcattat    900

gcccagtaca tgaccttatg ggactttcct acttggcagt acatctacgt attagtcatc    960

gctattacca tggtgatgcg gttttggcag tacatcaatg ggcgtggata gcggtttgac   1020

tcacggggat ttccaagtct ccaccccatt gacgtcaatg ggagtttgtt ttggcaccaa   1080

aatcaacggg actttccaaa atgtcgtaac aactccgccc cattgacgca aatgggcggt   1140

aggcgtgtac ggtgggaggt ctatataagc agagctcgtt tagtgaaccg tcagatcgcc   1200
```

-continued

```
tggagacgcc atccacgctg ttttgacctc catagaagac accgggaccg atccagcctc   1260
cgtcaccgtc gtcgacacgt gtgatcagat atcgcggccg ctctagagtc gaatgaagaa   1320
cattaattgc tgggtaaaag tgattaattt ctttaaattt gaccagaata atattttgtc   1380
agtgaatata ttctcatatc acttgattaa aaacagaaaa ttaccctaac atgaagacca   1440
catgtttcct tatcagtctt atcttaattc aagggacaaa aaatctcccc attttagaga   1500
tagctagtaa taatcaaccc caaaatgtgg attcggtatg ctccggaact ctccagaaga   1560
cagaagacgt ccatctgatg ggattcacac tgagtgggca aaaagttgct gattcccctt   1620
tggaggcatc caagcgatgg gctttcagga caggtgtacc tcccaagaat gttgagtaca   1680
cagaggggga ggaagccaaa acatgctaca atataagtgt aacggatccc tctggaaaat   1740
ccttgctgtt agatcctcct accaacatcc gtgactatcc taaatgcaaa actatccatc   1800
atattcaagg tcaaaaccct catgcacagg ggatcgccct tcatttatgg ggagcatttt   1860
ttctgtatga tcgcattgcc tccacaacaa tgtaccgagg caaagtcttc actgaaggga   1920
acatagcagc tatgattgtc aataagacag tgcacaaaat gattttctcg cggcaaggac   1980
aagggtaccg tcatatgaat ctgacttcta ctaataaata ttggacaagt agtaacggaa   2040
cgcaaacgaa tgacactgga tgtttcggcg ctcttcaaga atacaattct acaaagaacc   2100
aaacatgtgc tccgtccaaa atacctccac cactgcccac agcccgtccg gagatcaaac   2160
tcacaagcac cccaactgat gccaccaaac tcaataccac ggacccaagc agtgatgatg   2220
aggacctcgc aacatccggc tcagggtccg gagaacgaga accccacaca acttctgatg   2280
cggtcaccaa gcaagggctt tcatcaacaa tgccacccac tccctcacca caaccaagca   2340
cgccacagca aggaggaaac aacacaaacc attcccaaga tgctgtgact gaactagaca   2400
aaaataacac aactgcacaa ccgtccatgc cccctcataa cactaccaca atctctacta   2460
acaacacctc caaacacaac ttcagcactc tctctgcacc attacaaaac accaccaatg   2520
acaacacaca gagcacaatc actgaaaatg agcaaaccag tgccccctcg ataacaaccc   2580
tgcctccaac gggaaatccc accacagcaa agagcaccag cagcaaaaaa ggccccgcca   2640
caacggcacc aaacacgaca aatgagcatt tcaccagtcc tccccccacc cccagctcga   2700
ctgcacaaca tcttgtatat ttcagaagaa agcgaagtat cctctggagg gaaggcgaca   2760
tgttcccttt tctggatggg ttaataaatg ctccaattga ttttgaccca gttccaaata   2820
caaaaacaat ctttgatgaa tcctctagtt ctggtgcctc ggctgaggaa gatcaacatg   2880
cctcccccaa tattagttta actttatctt attttcctaa tataaatgag aacactgcct   2940
actctggaga aaatgagaat gattgtgatg cagagttaag aatttggagc gttcaggagg   3000
atgacctggc cgcagggctc agttggatac cgtttttttgg ccctggaatt gaaggacttt   3060
acactgctgt tttaattaaa aatcaaaaca atttggtctg caggttgagg cgtctagcca   3120
atcaaactgc caaatccttg gaactcttat tgagagtcac aactgaggaa agaacattct   3180
ccttaatcaa tagacatgct attgactttc tactcacaag atggggagga acatgcaaag   3240
tgcttggacc tgattgttgc atcgggatag aagacttgtc caaaaatatt tcagagcaaa   3300
ttgaccaaat taaaaaggac gaacaaaaag aggggactgg ttggggtctg ggtggtaaat   3360
ggtggacatc cgactggggt taagatctgc tgtgccttct agttgccagc catctgttgt   3420
ttgcccctcc cccgtgcctt ccttgaccct ggaaggtgcc actcccactg tcctttccta   3480
ataaaatgag gaaattgcat cgcattgtct gagtaggtgt cattctattc tggggggtgg   3540
ggtggggcag cacagcaagg gggaggattg ggaagacaat agcaggcatg ctggggatgc   3600
```

-continued

```
ggtgggctct atgggtaccc agggccgcat aacttcgtat aatgtatgct atacgaagtt   3660
ataagatctg tactgaaatg tgtgggcgtg gcttaagggt gggaaagaat atataaggtg   3720
ggggtcttat gtagttttgt atctgttttg cagcagccgc cgccgccatg agcaccaact   3780
cgtttgatgg aagcattgtg agctcatatt tgacaacgcg catgccccca tgggccgggg   3840
tgcgtcagaa tgtgatgggc tccagcattg atggtcgccc cgtcctgccc gcaaactcta   3900
ctaccttgac ctacgagacc gtgtctggaa cgccgttgga gactgcagcc tccgccgccg   3960
cttcagccgc tgcagccacc gcccgcggga ttgtgactga ctttgctttc ctgagcccgc   4020
ttgcaagcag tgcagcttcc cgttcatccg cccgcgatga caagttgacg gctcttttgg   4080
cacaattgga ttctttgacc cgggaactta atgtcgtttc tcagcagctg ttggatctgc   4140
gccagcaggt ttctgccctg aaggcttcct cccctcccaa tgcggtttaa aacataaata   4200
aaaaaccaga ctctgtttgg atttggatca agcaagtgtc ttgctgtctt tatttagggg   4260
ttttgcgcgc gcggtaggcc cgggaccagc ggtctcggtc gttgagggtc ctgtgtattt   4320
tttccaggac gtggtaaagg tgactctgga tgttcagata catgggcata agcccgtctc   4380
tggggtggag gtagcaccac tgcagagctt catgctgcgg ggtggtgttg tagatgatcc   4440
agtcgtagca ggagcgctgg gcgtggtgcc taaaaatgtc tttcagtagc aagctgattg   4500
ccaggggcag gcccttggtg taagtgttta caaagcggtt aagctgggat gggtgcatac   4560
gtggggatat gagatgcatc ttggactgta tttttaggtt ggctatgttc ccagccatat   4620
ccctccgggg attcatgttg tgcagaacca ccagcacagt gtatccggtg cacttgggaa   4680
atttgtcatg tagcttagaa ggaaatgcgt ggaagaactt ggagacgccc ttgtgacctc   4740
caagattttc catgcattcg tccataatga tggcaatggg cccacgggcg gcggcctggg   4800
cgaagatatt tctgggatca ctaacgtcat agttgtgttc caggatgaga tcgtcatagg   4860
ccatttttac aaagcgcggg cggagggtgc cagactgcgg tataatggtt ccatccggcc   4920
caggggcgta gttaccctca cagatttgca tttcccacgc tttgagttca gatgggggga   4980
tcatgtctac ctgcggggcg atgaagaaaa cggtttccgg ggtaggggag atcagctggg   5040
aagaaagcag gttcctgagc agctgcgact taccgcagcc ggtgggcccg taaatcacac   5100
ctattaccgg ctgcaactgg tagttaagag agctgcagct gccgtcatcc ctgagcaggg   5160
gggccacttc gttaagcatg tccctgactc gcatgttttc cctgaccaaa tccgccagaa   5220
ggcgctcgcc gcccagcgat agcagttctt gcaaggaagc aaagtttttc aacggtttga   5280
gaccgtccgc cgtaggcatg cttttgagcg tttgaccaag cagttccagg cggtcccaca   5340
gctcggtcac ctgctctacg gcatctcgat ccagcatatc tcctcgtttc gcgggttggg   5400
gcggctttcg ctgtacggca gtagtcggtg ctcgtccaga cgggccaggg tcatgtcttt   5460
ccacgggcgc agggtcctcg tcagcgtagt ctgggtcacg gtgaaggggt gcgctccggg   5520
ctgcgcgctg gccagggtgc gcttgaggct ggtcctgctg gtgctgaagc gctgccggtc   5580
ttcgccctgc gcgtcggcca ggtagcattt gaccatggtg tcatagtcca gcccctccgc   5640
ggcgtggccc ttggcgcgca gcttgccctt ggaggaggcg ccgcacgagg ggcagtgcag   5700
acttttgagg gcgtagagct tgggcgcgag aaataccgat tccggggagt aggcatccgc   5760
gccgcaggcc ccgcagacgg tctcgcattc cacgagccag gtgagctctg gccgttcggg   5820
gtcaaaaacc aggtttcccc catgcttttt gatgcgtttc ttacctctgg tttccatgag   5880
ccggtgtcca cgctcggtga cgaaaaggct gtccgtgtcc ccgtatacag acttgagagg   5940
cctgtcctcg agcggtgttc cgcggtcctc ctcgtataga aactcggacc actctgagac   6000
```

-continued aaaggctcgc gtccaggcca gcacgaagga ggctaagtgg gaggggtagc ggtcgttgtc 6060
cactaggggg tccactcgct ccagggtgtg aagacacatg tcgccctctt cggcatcaag 6120
gaaggtgatt ggtttgtagg tgtaggccac gtgaccgggt gttcctgaag gggggctata 6180
aaagggggtg ggggcgcgtt cgtcctcact ctcttccgca tcgctgtctg cgagggccag 6240
ctgttggggt gagtcgacgc gaggctggat ggccttcccc attatgattc ttctcgcttc 6300
cggcggcatc gggatgcccg cgttgcaggc catgctgtcc aggcaggtag atgacgacca 6360
tcagggacag cttcaaggcc agcaaaaggc caggaaccgt aaaaaggccg cgttgctggc 6420
gtttttccat aggctccgcc cccctgacga gcatcacaaa aatcgacgct caagtcagag 6480
gtggcgaaac ccgacaggac tataaagata ccaggcgttt ccccctggaa gctccctcgt 6540
gcgctctcct gttccgaccc tgccgcttac cggatacctg tccgcctttc tcccttcggg 6600
aagcgtggcg ctttctcata gctcacgctg taggtatctc agttcggtgt aggtcgttcg 6660
ctccaagctg ggctgtgtgc acgaaccccc cgttcagccc gaccgctgcg ccttatccgg 6720
taactatcgt cttgagtcca acccggtaag acacgactta tcgccactgg cagcagccac 6780
tggtaacagg attagcagag cgaggtatgt aggcggtgct acagagttct tgaagtggtg 6840
gcctaactac ggctacacta gaaggacagt atttggtatc tgcgctctgc tgaagccagt 6900
taccttcgga aaaagagttg gtagctcttg atccggcaaa caaaccaccg ctggtagcgg 6960
tggttttttt gtttgcaagc agcagattac gcgcagaaaa aaaggatctc aagaagatcc 7020
tttgatcttt tctacggggt ctgacgctca gtggaacgaa aactcacgtt aagggatttt 7080
ggtcatgaga ttatcaaaaa ggatcttcac ctagatcctt ttaaattaaa aatgaagttt 7140
taaatcaatc taaagtatat atgagtaaac ttggtctgac agttaccaat gcttaatcag 7200
tgaggcacct atctcagcga tctgtctatt tcgttcatcc atagttgcct gactccccgt 7260
cgtgtagata actacgatac gggagggctt accatctggc cccagtgctg caatgatacc 7320
gcgagaccca cgctcaccgg ctccagattt atcagcaata aaccagccag ccggaagggc 7380
cgagcgcaga agtggtcctg caactttatc cgcctccatc cagtctatta attgttgccg 7440
ggaagctaga gtaagtagtt cgccagttaa tagtttgcgc aacgttgttg ccattgctgc 7500
aggcatcgtg gtgtcacgct cgtcgtttgg tatggcttca ttcagctccg gttcccaacg 7560
atcaaggcga gttacatgat cccccatgtt gtgcaaaaaa gcggttagct ccttcggtcc 7620
tccgatcgtt gtcagaagta agttggccgc agtgttatca ctcatggtta tggcagcact 7680
gcataattct cttactgtca tgccatccgt aagatgcttt tctgtgactg gtgagtactc 7740
aaccaagtca ttctgagaat agtgtatgcg gcgaccgagt tgctcttgcc cggcgtcaac 7800
acgggataat accgcgccac atagcagaac tttaaaagtg ctcatcattg gaaaacgttc 7860
ttcggggcga aaactctcaa ggatcttacc gctgttgaga tccagttcga tgtaacccac 7920
tcgtgcaccc aactgatctt cagcatcttt tactttcacc agcgtttctg ggtgagcaaa 7980
aacaggaagg caaaatgccg caaaaaaggg aataagggcg acacggaaat gttgaatact 8040
catactcttc ctttttcaat attattgaag catttatcag ggttattgtc tcatgagcgg 8100
atacatattt gaatgtattt agaaaaataa acaaataggg gttccgcgca catttccccg 8160
aaaagtgcca cctgacgtct aagaaaccat tattatcatg acattaacct ataaaaatag 8220
gcgtatcacg aggccctttc gtcttcaaga attgtt 8256

<210> SEQ ID NO 33
<211> LENGTH: 6447
<212> TYPE: DNA

<213> ORGANISM: Artificial Sequence
<220> FEATURE:
<223> OTHER INFORMATION: Synthetic Construct pVR1012x/s Lassa GP

<400> SEQUENCE: 33

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcagattgg    240
ctattggcca ttgcatacgt tgtatccata tcataatatg tacatttata ttggctcatg    300
tccaacatta ccgccatgtt gacattgatt attgactagt tattaatagt aatcaattac    360
ggggtcatta gttcatagcc catatatgga gttccgcgtt acataactta cggtaaatgg    420
cccgcctggc tgaccgccca acgacccccg cccattgacg tcaataatga cgtatgttcc    480
catagtaacg ccaataggga ctttccattg acgtcaatgg gtggagtatt tacggtaaac    540
tgcccacttg gcagtacatc aagtgtatca tatgccaagt acgcccccta ttgacgtcaa    600
tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctccg cggccgggaa cggtgcattg gaacgcggat   1020
tccccgtgcc aagagtgacg taagtaccgc ctatagactc tataggcaca cccctttggc   1080
tcttatgcat gctatactgt ttttggcttg gggcctatac acccccgctt ccttatgcta   1140
taggtgatgg tatagcttag cctataggtg tgggttattg accattattg accactcccc   1200
tattggtgac gatactttcc attactaatc cataacatgg ctctttgcca caactatctc   1260
tattggctat atgccaatac tctgtccttc agagactgac acggactctg tatttttaca   1320
ggatggggtc ccatttatta tttacaaatt cacatataca acaacgccgt cccccgtgcc   1380
cgcagttttt attaaacata gcgtgggatc tccacgcgaa tctcgggtac gtgttccgga   1440
catgggctct tctccggtag cggcggagct tccacatccg agccctggtc ccatgcctcc   1500
agcggctcat ggtcgctcgg cagctccttg ctcctaacag tggaggccag acttaggcac   1560
agcacaatgc ccaccaccac cagtgtgccg cacaaggccg tggcggtagg gtatgtgtct   1620
gaaaatgagc gtggagattg ggctcgcacg gctgacgcag atggaagact taaggcagcg   1680
gcagaagaag atgcaggcag ctgagttgtt gtattctgat aagagtcaga ggtaactccc   1740
gttgcggtgc tgttaacggt ggagggcagt gtagtctgag cagtactcgt tgctgccgcg   1800
cgcgccacca gacataatag ctgacagact aacagactgt tcctttccat gggtcttttc   1860
tgcagtcacc gtcgtcgaca cgtgtgatca gatatcgcgg ccgctctaga atttaggatt   1920
gcgcttttag agattcacta ctagttagga attcctaaat catggggcag attattacat   1980
tctttcaaga agtgccacat gtaatagagg aagtcatgaa cattgtgcta attgcgcttt   2040
ctctattggc aatcttgaag ggcttgtata acatcgctac atgtgggatt attggattgg   2100
ttgccttttt attcttgtgt ggcaagtctt gttccctaac ccttaaaggg ggatatgagc   2160
tgcaaacctt agaattaaat atggagaccc taaacatgac catgccctta tcatgcacca   2220
```

-continued agaacagcag tcatcattac ataagagtgg gcaatgagac tggattagaa ttgactttaa 2280
ctaacaccag cattataaat cacaaatttt gcaacttatc cgatgctcac aaaaagaatc 2340
tttatgatca tgctctcatg agcatcatct caacattcca tctatccatt ccaaacttca 2400
atcagtatga agccatgagt tgtgatttca atggagggaa aatcagtgtg caatacaacc 2460
tctctcattc ctatgctggg gatgcggccg aacactgtgg gacagttgcc aacggagtgt 2520
tgcaaacatt tatgagaatg gcctggggtg gaagatacat tgcattagac tcaggaaagg 2580
gaaactggga ctgtataatg accagctacc agtacctgat aattcaaaat acaacatggg 2640
aggaccactg ccaattctca agaccgtctc ctatcgggta ccttggcctt ttgtcacaaa 2700
ggacaagaga tatatatata agtaggaggc tcttggggac cttcacctgg acattgtcag 2760
attctgaggg caatgaaaca ccaggtggtt attgtttaac caggtggatg ctaattgaag 2820
cagaactcaa gtgttttggg aatacagctg tggcaaaatg caatgagaag catgatgagg 2880
agttttgtga catgctgaga ttgtttgatt tcaacaagca agcaatccgt aggttgaagg 2940
ctgaggccca gatgagtatt caattaataa ataaagccgt gaatgcctta atcaatgatc 3000
aattaatcat gaagaaccat ttaagagaca tcatgggcat tccctactgc aattacagca 3060
agtattggta ccttaatcat actagtagcg ggagaacatc actaccaaag tgttggctta 3120
tatccaatgg gtcatatcta aatgaaaccc agttctctga tgacatagaa cagcaagccg 3180
acaatatgat cacagagatg cttcagaaag aatacattga aagacaaggg aaaacgccct 3240
tgggactagt ggacattttc atctttagca caagctttta tctgatcagc attttcttgc 3300
atttaattaa aatccctaca catcgacaca tcgttgggaa accctgtccc aaacccccata 3360 gactaaatca catgggagta tgttcctgtg gactgtacaa acaccctggt gttccaacaa 3420
agtggaagag atagggatcc agatctgctg tgccttctag ttgccagcca tctgttgttt 3480
gcccctcccc cgtgccttcc ttgaccctgg aaggtgccac tcccactgtc ctttcctaat 3540
aaaatgagga aattgcatcg cattgtctga gtaggtgtca ttctattctg gggggtgggg 3600
tggggcagga cagcaagggg gaggattggg aagacaatag caggcatgct ggggatgcgg 3660
tgggctctat gggtacccag gtgctgaaga attgacccgg ttcctcctgg gccagaaaga 3720
agcaggcaca tccccttctc tgtgacacac cctgtccacg cccctggttc ttagttccag 3780
ccccactcat aggacactca tagctcagga gggctccgcc ttcaatccca cccgctaaag 3840
tacttggagc ggtctctccc tccctcatca gcccaccaaa ccaaacctag cctccaagag 3900
tgggaagaaa ttaaagcaag ataggctatt aagtgcagag ggagagaaaa tgcctccaac 3960
atgtgaggaa gtaatgagag aaatcataga attttaaggc catcatggcc ttaatcttcc 4020
gcttcctcgc tcactgactc gctgcgctcg gtcgttcggc tgcggcgagc ggtatcagct 4080
cactcaaagg cggtaatacg gttatccaca gaatcagggg ataacgcagg aaagaacatg 4140
tgagcaaaag gccagcaaaa ggccaggaac cgtaaaaagg ccgcgttgct ggcgtttttc 4200
cataggctcc gcccccctga cgagcatcac aaaaatcgac gctcaagtca gaggtggcga 4260
aacccgacag gactataaag ataccaggcg tttccccctg gaagctccct cgtgcgctct 4320
cctgttccga ccctgccgct taccggatac ctgtccgcct ttctcccttc gggaagcgtg 4380
gcgctttctc atagctcacg ctgtaggtat ctcagttcgg tgtaggtcgt tcgctccaag 4440
ctgggctgtg tgcacgaacc ccccgttcag cccgaccgct gcgccttatc cggtaactat 4500
cgtcttgagt ccaacccggt aagacacgac ttatcgccac tggcagcagc cactggtaac 4560
aggattagca gagcgaggta tgtaggcggt gctacagagt tcttgaagtg gtggcctaac 4620

-continued

```
tacggctaca ctagaagaac agtatttggt atctgcgctc tgctgaagcc agttaccttc   4680

ggaaaaagag ttggtagctc ttgatccggc aaacaaacca ccgctggtag cggtggtttt   4740

tttgtttgca agcagcagat tacgcgcaga aaaaaaggat ctcaagaaga tcctttgatc   4800

ttttctacgg ggtctgacgc tcagtggaac gaaaactcac gttaagggat tttggtcatg   4860

agattatcaa aaaggatctt cacctagatc cttttaaatt aaaaatgaag ttttaaatca   4920

atctaaagta tatatgagta aacttggtct gacagttacc aatgcttaat cagtgaggca   4980

cctatctcag cgatctgtct atttcgttca tccatagttg cctgactcgg gggggggggg   5040

cgctgaggtc tgcctcgtga agaaggtgtt gctgactcat accaggcctg aatcgcccca   5100

tcatccagcc agaaagtgag ggagccacgg ttgatgagag ctttgttgta ggtggaccag   5160

ttggtgattt tgaacttttg ctttgccacg gaacggtctg cgttgtcggg aagatgcgtg   5220

atctgatcct tcaactcagc aaaagttcga tttattcaac aaagccgccg tcccgtcaag   5280

tcagcgtaat gctctgccag tgttacaacc aattaaccaa ttctgattag aaaaactcat   5340

cgagcatcaa atgaaactgc aatttattca tatcaggatt atcaatacca tatttttgaa   5400

aaagccgttt ctgtaatgaa ggagaaaact caccgaggca gttccatagg atggcaagat   5460

cctggtatcg gtctgcgatt ccgactcgtc caacatcaat acaacctatt aatttcccct   5520

cgtcaaaaat aaggttatca agtgagaaat caccatgagt gacgactgaa tccggtgaga   5580

atggcaaaag cttatgcatt tctttccaga cttgttcaac aggccagcca ttacgctcgt   5640

catcaaaatc actcgcatca accaaaccgt tattcattcg tgattgcgcc tgagcgagac   5700

gaaatacgcg atcgctgtta aaaggacaat tacaaacagg aatcgaatgc aaccggcgca   5760

ggaacactgc cagcgcatca acaatatttt cacctgaatc aggatattct tctaatacct   5820

ggaatgctgt tttcccgggg atcgcagtgg tgagtaacca tgcatcatca ggagtacgga   5880

taaaatgctt gatggtcgga agaggcataa attccgtcag ccagtttagt ctgaccatct   5940

catctgtaac atcattggca acgctacctt tgccatgttt cagaaacaac tctggcgcat   6000

cgggcttccc atacaatcga tagattgtcg cacctgattg cccgacatta tcgcgagccc   6060

atttataccc atataaatca gcatccatgt tggaatttaa tcgcggcctc gagcaagacg   6120

tttcccgttg aatatggctc ataacacccc ttgtattact gtttatgtaa gcagacagtt   6180

ttattgttca tgatgatata tttttatctt gtgcaatgta acatcagaga ttttgagaca   6240

caacgtggct ttcccccccc ccccattatt gaagcattta tcagggttat tgtctcatga   6300

gcggatacat atttgaatgt atttagaaaa ataaacaaat aggggttccg cgcacatttc   6360

cccgaaaagt gccacctgac gtctaagaaa ccattattat catgacatta acctataaaa   6420

ataggcgtat cacgaggccc tttcgtc                                        6447
```

<210> SEQ ID NO 34
<211> LENGTH: 6258
<212> TYPE: DNA
<213> ORGANISM: Artificial Sequence
<220> FEATURE:
<223> OTHER INFORMATION: Synthetic Construct pVR1012x/s Lassa GP(dTM)

<400> SEQUENCE: 34

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatgcg gtgtgaaata ccgcacagat gcgtaaggag aaaataccgc atcagattgg    240
```

-continued

```
ctattggcca ttgcatacgt tgtatccata tcataatatg tacatttata ttggctcatg    300
tccaacatta ccgccatgtt gacattgatt attgactagt tattaatagt aatcaattac    360
ggggtcatta gttcatagcc catatatgga gttccgcgtt acataactta cggtaaatgg    420
cccgcctggc tgaccgccca acgacccccg cccattgacg tcaataatga cgtatgttcc    480
catagtaacg ccaataggga ctttccattg acgtcaatgg gtggagtatt tacggtaaac    540
tgcccacttg gcagtacatc aagtgtatca tatgccaagt acgcccccta ttgacgtcaa    600
tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctccg cggccgggaa cggtgcattg gaacgcggat   1020
tccccgtgcc aagagtgacg taagtaccgc ctatagactc tataggcaca cccctttggc   1080
tcttatgcat gctatactgt ttttggcttg gggcctatac acccccgctt ccttatgcta   1140
taggtgatgg tatagcttag cctataggtg tgggttattg accattattg accactcccc   1200
tattggtgac gatactttcc attactaatc cataacatgg ctctttgcca caactatctc   1260
tattggctat atgccaatac tctgtccttc agagactgac acggactctg tatttttaca   1320
ggatggggtc ccatttatta tttacaaatt cacatataca acaacgccgt cccccgtgcc   1380
cgcagttttt attaaacata gcgtgggatc tccacgcgaa tctcgggtac gtgttccgga   1440
catgggctct tctccggtag cggcggagct tccacatccg agccctggtc ccatgcctcc   1500
agcggctcat ggtcgctcgg cagctccttg ctcctaacag tggaggccag acttaggcac   1560
agcacaatgc ccaccaccac cagtgtgccg cacaaggccg tggcggtagg gtatgtgtct   1620
gaaaatgagc gtggagattg ggctcgcacg gctgacgcag atggaagact taaggcagcg   1680
gcagaagaag atgcaggcag ctgagttgtt gtattctgat aagagtcaga ggtaactccc   1740
gttgcggtgc tgttaacggt ggagggcagt gtagtctgag cagtactcgt tgctgccgcg   1800
cgcgccacca gacataatag ctgacagact aacagactgt tcctttccat gggtcttttc   1860
tgcagtcacc gtcgtcgaca cgtgtgatca gatatcgcgg ccgctctaga atttaggatt   1920
gcgcttttag agattcacta ctagttagga attcctaaat catggggcag attattacat   1980
tctttcaaga agtgccacat gtaatagagg aagtcatgaa cattgtgcta attgcgcttt   2040
ctctattggc aatcttgaag ggcttgtata acatcgctac atgtgggatt attggattgg   2100
ttgccttttt attcttgtgt ggcaagtctt gttccctaac ccttaaaggg ggatatgagc   2160
tgcaaacctt agaattaaat atggagaccc taaacatgac catgccctta tcatgcacca   2220
agaacagcag tcatcattac ataagagtgg gcaatgagac tggattagaa ttgactttaa   2280
ctaacaccag cattataaat cacaaatttt gcaacttatc cgatgctcac aaaaagaatc   2340
tttatgatca tgctctcatg agcatcatct caacattcca tctatccatt ccaaacttca   2400
atcagtatga agccatgagt tgtgatttca atggagggaa aatcagtgtg caatacaacc   2460
tctctcattc ctatgctggg gatgcggccg aacactgtgg gacagttgcc aacggagtgt   2520
tgcaaacatt tatgagaatg gcctggggtg gaagatacat tgcattagac tcaggaaagg   2580
gaaactggga ctgtataatg accagctacc agtacctgat aattcaaaat acaacatggg   2640
```

-continued

```
aggaccactg ccaattctca agaccgtctc ctatcgggta ccttggcctt ttgtcacaaa   2700
ggacaagaga tatatatata agtaggaggc tcttggggac cttcacctgg acattgtcag   2760
attctgaggg caatgaaaca ccaggtggtt attgtttaac caggtggatg ctaattgaag   2820
cagaactcaa gtgttttggg aatacagctg tggcaaaatg caatgagaag catgatgagg   2880
agttttgtga catgctgaga ttgtttgatt tcaacaagca agcaatccgt aggttgaagg   2940
ctgaggccca gatgagtatt caattaataa ataaagccgt gaatgcctta atcaatgatc   3000
aattaatcat gaagaaccat ttaagagaca tcatgggcat tccctactgc aattacagca   3060
agtattggta ccttaatcat actagtagcg ggagaacatc actaccaaag tgttggctta   3120
tatccaatgg gtcatatcta aatgaaaccc agttctctga tgacatagaa cagcaagccg   3180
acaatatgat cacagagatg cttcagaaag aatacattga aagacaaggg aaaacgccct   3240
tgtagggatc cagatctgct gtgccttcta gttgccagcc atctgttgtt tgcccctccc   3300
ccgtgccttc cttgaccctg gaaggtgcca ctcccactgt cctttcctaa taaaatgagg   3360
aaattgcatc gcattgtctg agtaggtgtc attctattct ggggggtggg gtggggcagg   3420
acagcaaggg ggaggattgg gaagacaata gcaggcatgc tggggatgcg gtgggctcta   3480
tgggtaccca ggtgctgaag aattgacccg gttcctcctg ggccagaaag aagcaggcac   3540
atccccttct ctgtgacaca ccctgtccac gcccctggtt cttagttcca gccccactca   3600
taggacactc atagctcagg agggctccgc cttcaatccc acccgctaaa gtacttggag   3660
cggtctctcc ctccctcatc agcccaccaa accaaaccta gcctccaaga gtgggaagaa   3720
attaaagcaa gataggctat taagtgcaga gggagagaaa atgcctccaa catgtgagga   3780
agtaatgaga gaaatcatag aattttaagg ccatcatggc cttaatcttc cgcttcctcg   3840
ctcactgact cgctgcgctc ggtcgttcgg ctgcggcgag cggtatcagc tcactcaaag   3900
gcggtaatac ggttatccac agaatcaggg gataacgcag gaaagaacat gtgagcaaaa   3960
ggccagcaaa aggccaggaa ccgtaaaaag gccgcgttgc tggcgttttt ccataggctc   4020
cgcccccctg acgagcatca caaaaatcga cgctcaagtc agaggtggcg aaacccgaca   4080
ggactataaa gataccaggc gtttccccct ggaagctccc tcgtgcgctc tcctgttccg   4140
accctgccgc ttaccggata cctgtccgcc tttctccctt cgggaagcgt ggcgctttct   4200
catagctcac gctgtaggta tctcagttcg gtgtaggtcg ttcgctccaa gctgggctgt   4260
gtgcacgaac cccccgttca gcccgaccgc tgcgccttat ccggtaacta tcgtcttgag   4320
tccaacccgg taagacacga cttatcgcca ctggcagcag ccactggtaa caggattagc   4380
agagcgaggt atgtaggcgg tgctacagag ttcttgaagt ggtggcctaa ctacggctac   4440
actagaagaa cagtatttgg tatctgcgct ctgctgaagc cagttacctt cggaaaaaga   4500
gttggtagct cttgatccgg caaacaaacc accgctggta gcggtggttt ttttgtttgc   4560
aagcagcaga ttacgcgcag aaaaaaagga tctcaagaag atcctttgat cttttctacg   4620
gggtctgacg ctcagtggaa cgaaaactca cgttaaggga ttttggtcat gagattatca   4680
aaaaggatct tcacctagat ccttttaaat taaaaatgaa gttttaaatc aatctaaagt   4740
atatatgagt aaacttggtc tgacagttac caatgcttaa tcagtgaggc acctatctca   4800
gcgatctgtc tatttcgttc atccatagtt gcctgactcg gggggggggg gcgctgaggt   4860
ctgcctcgtg aagaaggtgt tgctgactca taccaggcct gaatcgcccc atcatccagc   4920
cagaaagtga gggagccacg gttgatgaga gctttgttgt aggtggacca gttggtgatt   4980
ttgaactttt gctttgccac ggaacggtct gcgttgtcgg gaagatgcgt gatctgatcc   5040
```

-continued

```
ttcaactcag caaaagttcg atttattcaa caaagccgcc gtcccgtcaa gtcagcgtaa   5100

tgctctgcca gtgttacaac caattaacca attctgatta gaaaaactca tcgagcatca   5160

aatgaaactg caatttattc atatcaggat tatcaatacc atatttttga aaaagccgtt   5220

tctgtaatga aggagaaaac tcaccgaggc agttccatag gatggcaaga tcctggtatc   5280

ggtctgcgat tccgactcgt ccaacatcaa tacaacctat taatttcccc tcgtcaaaaa   5340

taaggttatc aagtgagaaa tcaccatgag tgacgactga atccggtgag aatggcaaaa   5400

gcttatgcat ttctttccag acttgttcaa caggccagcc attacgctcg tcatcaaaat   5460

cactcgcatc aaccaaaccg ttattcattc gtgattgcgc ctgagcgaga cgaaatacgc   5520

gatcgctgtt aaaaggacaa ttacaaacag gaatcgaatg caaccggcgc aggaacactg   5580

ccagcgcatc aacaatattt tcacctgaat caggatattc ttctaatacc tggaatgctg   5640

ttttcccggg gatcgcagtg gtgagtaacc atgcatcatc aggagtacgg ataaaatgct   5700

tgatggtcgg aagaggcata aattccgtca gccagtttag tctgaccatc tcatctgtaa   5760

catcattggc aacgctacct ttgccatgtt tcagaaacaa ctctggcgca tcgggcttcc   5820

catacaatcg atagattgtc gcacctgatt gcccgacatt atcgcgagcc catttatacc   5880

catataaatc agcatccatg ttggaattta atcgcggcct cgagcaagac gtttcccgtt   5940

gaatatggct cataacaccc cttgtattac tgtttatgta agcagacagt tttattgttc   6000

atgatgatat atttttatct tgtgcaatgt aacatcagag attttgagac acaacgtggc   6060

tttccccccc cccccattat tgaagcattt atcagggtta ttgtctcatg agcggataca   6120

tatttgaatg tatttagaaa aataaacaaa taggggttcc gcgcacattt ccccgaaaag   6180

tgccacctga cgtctaagaa accattatta tcatgacatt aacctataaa aataggcgta   6240

tcacgaggcc ctttcgtc                                                 6258
```

<210> SEQ ID NO 35
<211> LENGTH: 7711
<212> TYPE: DNA
<213> ORGANISM: Artificial Sequence
<220> FEATURE:
<223> OTHER INFORMATION: Synthetic Construct pAdApt Lassa GP

<400> SEQUENCE: 35

```
ttaattaacc gcaattctca tgtttgacag cttatcatca tcaataatat accttatttt     60

ggattgaagc caatatgata atgagggggt ggagtttgtg acgtggcgcg gggcgtggga    120

acggggcggg tgacgtagta gtgtggcgga agtgtgatgt tgcaagtgtg gcggaacaca    180

tgtaagcgac ggatgtggca aaagtgacgt ttttggtgtg cgccggtgta cacaggaagt    240

gacaattttc gcgcggtttt aggcggatgt tgtagtaaat ttgggcgtaa ccgagtaaga    300

tttggccatt ttcgcgggaa aactgaataa gaggaagtga aatctgaata attttgtgtt    360

actcatagcg cgtaatattt gtctagggcc gcggggactt tgaccgttta cgtggagact    420

cgcccaggtg tttttctcag gtgttttccg cgttccgggt caaagttggc gttttattat    480

tatagtcagt acgtaccagt gcactggcct agagcggccc cattgcatac gttgtatcca    540

tatcataata tgtacattta tattggctca tgtccaacat taccgccatg ttgacattga    600

ttattgacta gttattaata gtaatcaatt acggggtcat tagttcatag cccatatatg    660

gagttccgcg ttacataact tacggtaaat ggcccgcctg gctgaccgcc caacgacccc    720

cgcccattga cgtcaataat gacgtatgtt cccatagtaa cgccaatagg gactttccat    780

tgacgtcaat gggtggagta tttacggtaa actgcccact tggcagtaca tcaagtgtat    840
```

-continued

```
catatgccaa gtacgccccc tattgacgtc aatgacggta aatggcccgc ctggcattat    900
gcccagtaca tgaccttatg ggactttcct acttggcagt acatctacgt attagtcatc    960
gctattacca tggtgatgcg gttttggcag tacatcaatg ggcgtggata gcggtttgac   1020
tcacggggat ttccaagtct ccaccccatt gacgtcaatg ggagtttgtt ttggcaccaa   1080
aatcaacggg actttccaaa atgtcgtaac aactccgccc cattgacgca aatgggcggt   1140
aggcgtgtac ggtgggaggt ctatataagc agagctcgtt tagtgaaccg tcagatcgcc   1200
tggagacgcc atccacgctg ttttgacctc catagaagac accgggaccg atccagcctc   1260
cgtcaccgtc gtcgacacgt gtgatcagat atcgcggccg ctctagaatt taggattgcg   1320
cttttagaga ttcactacta gttaggaatt cctaaatcat ggggcagatt attacattct   1380
ttcaagaagt gccacatgta atagaggaag tcatgaacat tgtgctaatt gcgctttctc   1440
tattggcaat cttgaagggc ttgtataaca tcgctacatg tgggattatt ggattggttg   1500
ccttttttatt cttgtgtggc aagtcttgtt ccctaaccct taaaggggga tatgagctgc   1560
aaaccttaga attaaatatg gagaccctaa acatgaccat gcccttatca tgcaccaaga   1620
acagcagtca tcattacata agagtgggca atgagactgg attagaattg actttaacta   1680
acaccagcat tataaatcac aaattttgca acttatccga tgctcacaaa aagaatcttt   1740
atgatcatgc tctcatgagc atcatctcaa cattccatct atccattcca aacttcaatc   1800
agtatgaagc catgagttgt gatttcaatg gagggaaaat cagtgtgcaa tacaacctct   1860
ctcattccta tgctggggat gcggccgaac actgtgggac agttgccaac ggagtgttgc   1920
aaacatttat gagaatggcc tggggtggaa gatacattgc attagactca ggaaagggaa   1980
actgggactg tataatgacc agctaccagt acctgataat tcaaaataca acatgggagg   2040
accactgcca attctcaaga ccgtctccta tcgggtacct tggccttttg tcacaaagga   2100
caagagatat atatataagt aggaggctct tggggacctt cacctggaca ttgtcagatt   2160
ctgagggcaa tgaaacacca ggtggttatt gtttaaccag gtggatgcta attgaagcag   2220
aactcaagtg ttttgggaat acagctgtgg caaaatgcaa tgagaagcat gatgaggagt   2280
tttgtgacat gctgagattg tttgatttca acaagcaagc aatccgtagg ttgaaggctg   2340
aggcccagat gagtattcaa ttaataaata aagccgtgaa tgccttaatc aatgatcaat   2400
taatcatgaa gaaccattta agagacatca tgggcattcc ctactgcaat tacagcaagt   2460
attggtacct taatcatact agtagcggga gaacatcact accaaagtgt tggcttatat   2520
ccaatgggtc atatctaaat gaaacccagt tctctgatga catagaacag caagccgaca   2580
atatgatcac agagatgctt cagaaagaat acattgaaag acaagggaaa acgcccttgg   2640
gactagtgga cattttcatc tttagcacaa gcttttatct gatcagcatt ttcttgcatt   2700
taattaaaat ccctacacat cgacacatcg ttgggaaacc ctgtcccaaa ccccatagac   2760
taaatcacat gggagtatgt tcctgtggac tgtacaaaca ccctggtgtt ccaacaaagt   2820
ggaagagata gggatccaga tctgctgtgc cttctagttg ccagccatct gttgtttgcc   2880
cctcccccgt gccttccttg accctggaag gtgccactcc cactgtcctt tcctaataaa   2940
atgaggaaat tgcatcgcat tgtctgagta ggtgtcattc tattctgggg ggtggggtgg   3000
ggcagcacag caagggggag gattgggaag acaatagcag gcatgctggg gatgcggtgg   3060
gctctatggg tacccagggc cgcataactt cgtataatgt atgctatacg aagttataag   3120
atctgtactg aaatgtgtgg gcgtggctta agggtgggaa agaatatata aggtgggggt   3180
cttatgtagt tttgtatctg ttttgcagca gccgccgccg ccatgagcac caactcgttt   3240
```

-continued gatggaagca ttgtgagctc atatttgaca acgcgcatgc ccccatgggc cggggtgcgt 3300
cagaatgtga tgggctccag cattgatggt cgccccgtcc tgcccgcaaa ctctactacc 3360
ttgacctacg agaccgtgtc tggaacgccg ttggagactg cagcctccgc cgccgcttca 3420
gccgctgcag ccaccgcccg cgggattgtg actgactttg ctttcctgag cccgcttgca 3480
agcagtgcag cttcccgttc atccgcccgc gatgacaagt tgacggctct tttggcacaa 3540
ttggattctt tgacccggga acttaatgtc gtttctcagc agctgttgga tctgcgccag 3600
caggtttctg ccctgaaggc ttcctcccct cccaatgcgg tttaaaacat aaataaaaaa 3660
ccagactctg tttggatttg gatcaagcaa gtgtcttgct gtctttattt aggggttttg 3720
cgcgcgcggt aggcccggga ccagcggtct cggtcgttga gggtcctgtg tatttttttcc 3780 aggacgtggt aaaggtgact ctggatgttc agatacatgg gcataagccc gtctctgggg 3840
tggaggtagc accactgcag agcttcatgc tgcggggtgg tgttgtagat gatccagtcg 3900
tagcaggagc gctgggcgtg gtgcctaaaa atgtctttca gtagcaagct gattgccagg 3960
ggcaggccct tggtgtaagt gtttacaaag cggttaagct gggatgggtg catacgtggg 4020
gatatgagat gcatcttgga ctgtattttt aggttggcta tgttcccagc catatccctc 4080
cggggattca tgttgtgcag aaccaccagc acagtgtatc cggtgcactt gggaaatttg 4140
tcatgtagct tagaaggaaa tgcgtggaag aacttggaga cgcccttgtg acctccaaga 4200
ttttccatgc attcgtccat aatgatggca atgggcccac gggcggcggc ctgggcgaag 4260
atatttctgg gatcactaac gtcatagttg tgttccagga tgagatcgtc ataggccatt 4320
tttacaaagc gcgggcggag ggtgccagac tgcggtataa tggttccatc cggcccaggg 4380
gcgtagttac cctcacagat ttgcatttcc cacgctttga gttcagatgg ggggatcatg 4440
tctacctgcg gggcgatgaa gaaaacggtt tccggggtag gggagatcag ctgggaagaa 4500
agcaggttcc tgagcagctg cgacttaccg cagccggtgg gcccgtaaat cacacctatt 4560
accggctgca actggtagtt aagagagctg cagctgccgt catccctgag caggggggcc 4620
acttcgttaa gcatgtccct gactcgcatg ttttccctga ccaaatccgc cagaaggcgc 4680
tcgccgccca gcgatagcag ttcttgcaag gaagcaaagt ttttcaacgg tttgagaccg 4740
tccgccgtag gcatgctttt gagcgtttga ccaagcagtt ccaggcggtc ccacagctcg 4800
gtcacctgct ctacggcatc tcgatccagc atatctcctc gtttcgcggg ttggggcggc 4860
tttcgctgta cggcagtagt cggtgctcgt ccagacgggc cagggtcatg tctttccacg 4920
ggcgcagggt cctcgtcagc gtagtctggg tcacggtgaa ggggtgcgct ccgggctgcg 4980
cgctggccag ggtgcgcttg aggctggtcc tgctggtgct gaagcgctgc cggtcttcgc 5040
cctgcgcgtc ggccaggtag catttgacca tggtgtcata gtccagcccc tccgcggcgt 5100
ggcccttggc gcgcagcttg cccttggagg aggcgccgca cgaggggcag tgcagacttt 5160
tgagggcgta gagcttgggc gcgagaaata ccgattccgg ggagtaggca tccgcgccgc 5220
aggccccgca gacggtctcg cattccacga gccaggtgag ctctggccgt tcggggtcaa 5280
aaaccaggtt tcccccatgc tttttgatgc gtttcttacc tctggtttcc atgagccggt 5340
gtccacgctc ggtgacgaaa aggctgtccg tgtccccgta tacagacttg agaggcctgt 5400
cctcgagcgg tgttccgcgg tcctcctcgt atagaaactc ggaccactct gagacaaagg 5460
ctcgcgtcca ggccagcacg aaggaggcta agtgggaggg gtagcggtcg ttgtccacta 5520
gggggtccac tcgctccagg gtgtgaagac acatgtcgcc ctcttcggca tcaaggaagg 5580
tgattggttt gtaggtgtag gccacgtgac cgggtgttcc tgaagggggg ctataaaagg 5640
gggtgggggc gcgttcgtcc tcactctctt ccgcatcgct gtctgcgagg gccagctgtt 5700
ggggtgagtc gacgcgaggc tggatggcct tccccattat gattcttctc gcttccggcg 5760
gcatcgggat gcccgcgttg caggccatgc tgtccaggca ggtagatgac gaccatcagg 5820
gacagcttca aggccagcaa aaggccagga accgtaaaaa ggccgcgttg ctggcgtttt 5880
tccataggct ccgcccccct gacgagcatc acaaaaatcg acgctcaagt cagaggtggc 5940
gaaacccgac aggactataa agataccagg cgtttccccc tggaagctcc ctcgtgcgct 6000
ctcctgttcc gaccctgccg cttaccggat acctgtccgc ctttctccct tcgggaagcg 6060
tggcgctttc tcatagctca cgctgtaggt atctcagttc ggtgtaggtc gttcgctcca 6120
agctgggctg tgtgcacgaa ccccccgttc agcccgaccg ctgcgcctta tccggtaact 6180
atcgtcttga gtccaacccg gtaagacacg acttatcgcc actggcagca gccactggta 6240
acaggattag cagagcgagg tatgtaggcg gtgctacaga gttcttgaag tggtggccta 6300
actacggcta cactagaagg acagtatttg gtatctgcgc tctgctgaag ccagttacct 6360
tcggaaaaag agttggtagc tcttgatccg gcaaacaaac caccgctggt agcggtggtt 6420
tttttgtttg caagcagcag attacgcgca gaaaaaaagg atctcaagaa gatcctttga 6480
tcttttctac ggggtctgac gctcagtgga acgaaaactc acgttaaggg attttggtca 6540
tgagattatc aaaaaggatc ttcacctaga tccttttaaa ttaaaaatga agttttaaat 6600
caatctaaag tatatatgag taaacttggt ctgacagtta ccaatgctta atcagtgagg 6660
cacctatctc agcgatctgt ctatttcgtt catccatagt tgcctgactc cccgtcgtgt 6720
agataactac gatacgggag ggcttaccat ctggccccag tgctgcaatg ataccgcgag 6780
acccacgctc accggctcca gatttatcag caataaacca gccagccgga agggccgagc 6840
gcagaagtgg tcctgcaact ttatccgcct ccatccagtc tattaattgt tgccgggaag 6900
ctagagtaag tagttcgcca gttaatagtt tgcgcaacgt tgttgccatt gctgcaggca 6960
tcgtggtgtc acgctcgtcg tttggtatgg cttcattcag ctccggttcc caacgatcaa 7020
ggcgagttac atgatccccc atgttgtgca aaaaagcggt tagctccttc ggtcctccga 7080
tcgttgtcag aagtaagttg gccgcagtgt tatcactcat ggttatggca gcactgcata 7140
attctcttac tgtcatgcca tccgtaagat gcttttctgt gactggtgag tactcaacca 7200
agtcattctg agaatagtgt atgcggcgac cgagttgctc ttgcccggcg tcaacacggg 7260
ataataccgc gccacatagc agaactttaa aagtgctcat cattggaaaa cgttcttcgg 7320
ggcgaaaact ctcaaggatc ttaccgctgt tgagatccag ttcgatgtaa cccactcgtg 7380
cacccaactg atcttcagca tcttttactt tcaccagcgt ttctgggtga gcaaaaacag 7440
gaaggcaaaa tgccgcaaaa aagggaataa gggcgacacg gaaatgttga atactcatac 7500
tcttcctttt tcaatattat tgaagcattt atcagggtta ttgtctcatg agcggataca 7560
tatttgaatg tatttagaaa aataaacaaa taggggttcc gcgcacattt ccccgaaaag 7620
tgccacctga cgtctaagaa accattatta tcatgacatt aacctataaa aataggcgta 7680
tcacgaggcc ctttcgtctt caagaattgt t 7711

<210> SEQ ID NO 36
<211> LENGTH: 7522
<212> TYPE: DNA
<213> ORGANISM: Artificial Sequence
<220> FEATURE:
<223> OTHER INFORMATION: Synthetic Construct pAdApt Lassa GP(dTM)

<400> SEQUENCE: 36

-continued

```
ttaattaacc gcaattctca tgtttgacag cttatcatca tcaataatat accttatttt     60
ggattgaagc caatatgata atgagggggt ggagtttgtg acgtggcgcg gggcgtggga    120
acggggcggg tgacgtagta gtgtggcgga agtgtgatgt tgcaagtgtg gcggaacaca    180
tgtaagcgac ggatgtggca aaagtgacgt ttttggtgtg cgccggtgta cacaggaagt    240
gacaattttc gcgcggtttt aggcggatgt tgtagtaaat ttgggcgtaa ccgagtaaga    300
tttggccatt ttcgcgggaa aactgaataa gaggaagtga aatctgaata attttgtgtt    360
actcatagcg cgtaatattt gtctagggcc gcggggactt tgaccgttta cgtggagact    420
cgcccaggtg tttttctcag gtgttttccg cgttccgggt caaagttggc gttttattat    480
tatagtcagt acgtaccagt gcactggcct agagcggccc cattgcatac gttgtatcca    540
tatcataata tgtacattta tattggctca tgtccaacat taccgccatg ttgacattga    600
ttattgacta gttattaata gtaatcaatt acggggtcat tagttcatag cccatatatg    660
gagttccgcg ttacataact tacggtaaat ggcccgcctg gctgaccgcc caacgacccc    720
cgcccattga cgtcaataat gacgtatgtt cccatagtaa cgccaatagg gactttccat    780
tgacgtcaat gggtggagta tttacggtaa actgcccact tggcagtaca tcaagtgtat    840
catatgccaa gtacgccccc tattgacgtc aatgacggta aatggcccgc ctggcattat    900
gcccagtaca tgaccttatg ggactttcct acttggcagt acatctacgt attagtcatc    960
gctattacca tggtgatgcg gttttggcag tacatcaatg ggcgtggata gcggtttgac   1020
tcacggggat ttccaagtct ccaccccatt gacgtcaatg ggagtttgtt ttggcaccaa   1080
aatcaacggg actttccaaa atgtcgtaac aactccgccc cattgacgca aatgggcggt   1140
aggcgtgtac ggtgggaggt ctatataagc agagctcgtt tagtgaaccg tcagatcgcc   1200
tggagacgcc atccacgctg ttttgacctc catagaagac accgggaccg atccagcctc   1260
cgtcaccgtc gtcgacacgt gtgatcagat atcgcggccg ctctagaatt taggattgcg   1320
cttttagaga ttcactacta gttaggaatt cctaaatcat ggggcagatt attacattct   1380
ttcaagaagt gccacatgta atagaggaag tcatgaacat tgtgctaatt gcgctttctc   1440
tattggcaat cttgaagggc ttgtataaca tcgctacatg tgggattatt ggattggttg   1500
cctttttatt cttgtgtggc aagtcttgtt ccctaaccct taaaggggga tatgagctgc   1560
aaaccttaga attaaatatg gagaccctaa acatgaccat gcccttatca tgcaccaaga   1620
acagcagtca tcattacata agagtgggca atgagactgg attagaattg actttaacta   1680
acaccagcat tataaatcac aaattttgca acttatccga tgctcacaaa aagaatcttt   1740
atgatcatgc tctcatgagc atcatctcaa cattccatct atccattcca aacttcaatc   1800
agtatgaagc catgagttgt gatttcaatg gagggaaaat cagtgtgcaa tacaacctct   1860
ctcattccta tgctggggat gcggccgaac actgtgggac agttgccaac ggagtgttgc   1920
aaacatttat gagaatggcc tggggtggaa gatacattgc attagactca ggaaagggaa   1980
actgggactg tataatgacc agctaccagt acctgataat tcaaaataca acatgggagg   2040
accactgcca attctcaaga ccgtctccta tcgggtacct tggccttttg tcacaaagga   2100
caagagatat atatataagt aggaggctct tggggacctt cacctggaca ttgtcagatt   2160
ctgagggcaa tgaaacacca ggtggttatt gtttaaccag gtggatgcta attgaagcag   2220
aactcaagtg ttttgggaat acagctgtgg caaaatgcaa tgagaagcat gatgaggagt   2280
tttgtgacat gctgagattg tttgatttca acaagcaagc aatccgtagg ttgaaggctg   2340
aggcccagat gagtattcaa ttaataaata aagccgtgaa tgccttaatc aatgatcaat   2400
```

-continued

```
taatcatgaa gaaccattta agagacatca tgggcattcc ctactgcaat tacagcaagt   2460
attggtacct taatcatact agtagcggga gaacatcact accaaagtgt tggcttatat   2520
ccaatgggtc atatctaaat gaaacccagt tctctgatga catagaacag caagccgaca   2580
atatgatcac agagatgctt cagaaagaat acattgaaag acaagggaaa acgcccttgt   2640
agggatccag atctgctgtg ccttctagtt gccagccatc tgttgtttgc cctcccccg    2700
tgccttcctt gaccctggaa ggtgccactc ccactgtcct ttcctaataa aatgaggaaa   2760
ttgcatcgca ttgtctgagt aggtgtcatt ctattctggg gggtggggtg gggcagcaca   2820
gcaaggggga ggattgggaa gacaatagca ggcatgctgg ggatgcggtg ggctctatgg   2880
gtacccaggg ccgcataact tcgtataatg tatgctatac gaagttataa gatctgtact   2940
gaaatgtgtg ggcgtggctt aagggtggga aagaatatat aaggtggggg tcttatgtag   3000
ttttgtatct gttttgcagc agccgccgcc gccatgagca ccaactcgtt tgatggaagc   3060
attgtgagct catatttgac aacgcgcatg cccccatggg ccggggtgcg tcagaatgtg   3120
atgggctcca gcattgatgg tcgccccgtc ctgcccgcaa actctactac cttgacctac   3180
gagaccgtgt ctggaacgcc gttggagact gcagcctccg ccgccgcttc agccgctgca   3240
gccaccgccc gcgggattgt gactgacttt gctttcctga gcccgcttgc aagcagtgca   3300
gcttcccgtt catccgcccg cgatgacaag ttgacggctc ttttggcaca attggattct   3360
ttgacccggg aacttaatgt cgtttctcag cagctgttgg atctgcgcca gcaggtttct   3420
gccctgaagg cttcctcccc tcccaatgcg gtttaaaaca taaataaaaa accagactct   3480
gtttggattt ggatcaagca agtgtcttgc tgtctttatt taggggtttt gcgcgcgcgg   3540
taggcccggg accagcggtc tcggtcgttg agggtcctgt gtattttttc caggacgtgg   3600
taaaggtgac tctggatgtt cagatacatg ggcataagcc cgtctctggg gtggaggtag   3660
caccactgca gagcttcatg ctgcggggtg gtgttgtaga tgatccagtc gtagcaggag   3720
cgctgggcgt ggtgcctaaa aatgtctttc agtagcaagc tgattgccag gggcaggccc   3780
ttggtgtaag tgtttacaaa gcggttaagc tgggatgggt gcatacgtgg ggatatgaga   3840
tgcatcttgg actgtatttt taggttggct atgttcccag ccatatccct ccggggattc   3900
atgttgtgca gaaccaccag cacagtgtat ccggtgcact tgggaaattt gtcatgtagc   3960
ttagaaggaa atgcgtggaa gaacttggag acgcccttgt gacctccaag attttccatg   4020
cattcgtcca taatgatggc aatgggccca cgggcggcgg cctgggcgaa gatatttctg   4080
ggatcactaa cgtcatagtt gtgttccagg atgagatcgt cataggccat ttttacaaag   4140
cgcgggcgga gggtgccaga ctgcggtata atggttccat ccggcccagg ggcgtagtta   4200
ccctcacaga tttgcatttc ccacgctttg agttcagatg gggggatcat gtctacctgc   4260
ggggcgatga agaaaacggt ttccggggta ggggagatca gctgggaaga aagcaggttc   4320
ctgagcagct gcgacttacc gcagccggtg ggcccgtaaa tcacacctat taccggctgc   4380
aactggtagt taagagagct gcagctgccg tcatccctga gcaggggggc cacttcgtta   4440
agcatgtccc tgactcgcat gttttccctg accaaatccg ccagaaggcg ctcgccgccc   4500
agcgatagca gttcttgcaa ggaagcaaag tttttcaacg gtttgagacc gtccgccgta   4560
ggcatgcttt tgagcgtttg accaagcagt tccaggcggt cccacagctc ggtcacctgc   4620
tctacggcat ctcgatccag catatctcct cgtttcgcgg gttggggcgg ctttcgctgt   4680
acggcagtag tcggtgctcg tccagacggg ccagggtcat gtctttccac gggcgcaggg   4740
tcctcgtcag cgtagtctgg gtcacggtga aggggtgcgc tccgggctgc gcgctggcca   4800
```

-continued gggtgcgctt gaggctggtc ctgctggtgc tgaagcgctg ccggtcttcg ccctgcgcgt 4860
cggccaggta gcatttgacc atggtgtcat agtccagccc ctccgcggcg tggcccttgg 4920
cgcgcagctt gcccttggag gaggcgccgc acgaggggca gtgcagactt ttgagggcgt 4980
agagcttggg cgcgagaaat accgattccg gggagtaggc atccgcgccg caggccccgc 5040
agacggtctc gcattccacg agccaggtga gctctggccg ttcggggtca aaaaccaggt 5100
ttcccccatg ctttttgatg cgtttcttac ctctggtttc catgagccgg tgtccacgct 5160
cggtgacgaa aaggctgtcc gtgtccccgt atacagactt gagaggcctg tcctcgagcg 5220
gtgttccgcg gtcctcctcg tatagaaact cggaccactc tgagacaaag gctcgcgtcc 5280
aggccagcac gaaggaggct aagtgggagg ggtagcggtc gttgtccact agggggtcca 5340
ctcgctccag ggtgtgaaga cacatgtcgc cctcttcggc atcaaggaag gtgattggtt 5400
tgtaggtgta ggccacgtga ccgggtgttc ctgaaggggg gctataaaag ggggtggggg 5460
cgcgttcgtc ctcactctct tccgcatcgc tgtctgcgag ggccagctgt tggggtgagt 5520
cgacgcgagg ctggatggcc ttccccatta tgattcttct cgcttccggc ggcatcggga 5580
tgcccgcgtt gcaggccatg ctgtccaggc aggtagatga cgaccatcag ggacagcttc 5640
aaggccagca aaaggccagg aaccgtaaaa aggccgcgtt gctggcgttt ttccataggc 5700
tccgcccccc tgacgagcat cacaaaaatc gacgctcaag tcagaggtgg cgaaacccga 5760
caggactata aagataccag gcgtttcccc ctggaagctc cctcgtgcgc tctcctgttc 5820
cgaccctgcc gcttaccgga tacctgtccg cctttctccc ttcgggaagc gtggcgcttt 5880
ctcatagctc acgctgtagg tatctcagtt cggtgtaggt cgttcgctcc aagctgggct 5940
gtgtgcacga accccccgtt cagcccgacc gctgcgcctt atccggtaac tatcgtcttg 6000
agtccaaccc ggtaagacac gacttatcgc cactggcagc agccactggt aacaggatta 6060
gcagagcgag gtatgtaggc ggtgctacag agttcttgaa gtggtggcct aactacggct 6120
acactagaag gacagtattt ggtatctgcg ctctgctgaa gccagttacc ttcggaaaaa 6180
gagttggtag ctcttgatcc ggcaaacaaa ccaccgctgg tagcggtggt ttttttgttt 6240
gcaagcagca gattacgcgc agaaaaaaag gatctcaaga agatcctttg atcttttcta 6300
cggggtctga cgctcagtgg aacgaaaact cacgttaagg gattttggtc atgagattat 6360
caaaaaggat cttcacctag atccttttaa attaaaaatg aagttttaaa tcaatctaaa 6420
gtatatatga gtaaacttgg tctgacagtt accaatgctt aatcagtgag gcacctatct 6480
cagcgatctg tctatttcgt tcatccatag ttgcctgact ccccgtcgtg tagataacta 6540
cgatacggga gggcttacca tctggcccca gtgctgcaat gataccgcga gacccacgct 6600
caccggctcc agatttatca gcaataaacc agccagccgg aagggccgag cgcagaagtg 6660
gtcctgcaac tttatccgcc tccatccagt ctattaattg ttgccgggaa gctagagtaa 6720
gtagttcgcc agttaatagt ttgcgcaacg ttgttgccat tgctgcaggc atcgtggtgt 6780
cacgctcgtc gtttggtatg gcttcattca gctccggttc ccaacgatca aggcgagtta 6840
catgatcccc catgttgtgc aaaaaagcgg ttagctcctt cggtcctccg atcgttgtca 6900
gaagtaagtt ggccgcagtg ttatcactca tggttatggc agcactgcat aattctctta 6960
ctgtcatgcc atccgtaaga tgcttttctg tgactggtga gtactcaacc aagtcattct 7020
gagaatagtg tatgcggcga ccgagttgct cttgcccggc gtcaacacgg gataataccg 7080
cgccacatag cagaacttta aaagtgctca tcattggaaa acgttcttcg gggcgaaaac 7140
tctcaaggat cttaccgctg ttgagatcca gttcgatgta acccactcgt gcacccaact 7200
gatcttcagc atcttttact ttcaccagcg tttctgggtg agcaaaaaca ggaaggcaaa 7260
atgccgcaaa aaagggaata agggcgacac ggaaatgttg aatactcata ctcttccttt 7320
ttcaatatta ttgaagcatt tatcagggtt attgtctcat gagcggatac atatttgaat 7380
gtatttagaa aaataaacaa ataggggttc cgcgcacatt tccccgaaaa gtgccacctg 7440
acgtctaaga aaccattatt atcatgacat taacctataa aaataggcgt atcacgaggc 7500 ccctttcgtct tcaagaattg tt 7522

<210> SEQ ID NO 37
<211> LENGTH: 6324
<212> TYPE: DNA
<213> ORGANISM: Artificial Sequence
<220> FEATURE:
<223> OTHER INFORMATION: Synthetic Construct CMV/R Ebola GP(Z) delta TM/h

<400> SEQUENCE: 37
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcagattgg 240
ctattggcca ttgcatacgt tgtatccata tcataatatg tacatttata ttggctcatg 300
tccaacatta ccgccatgtt gacattgatt attgactagt tattaatagt aatcaattac 360
ggggtcatta gttcatagcc catatatgga gttccgcgtt acataactta cggtaaatgg 420
cccgcctggc tgaccgccca acgacccccg cccattgacg tcaataatga cgtatgttcc 480
catagtaacg ccaataggga ctttccattg acgtcaatgg gtggagtatt tacggtaaac 540
tgcccacttg gcagtacatc aagtgtatca tatgccaagt acgcccccta ttgacgtcaa 600
tgacggtaaa tggcccgcct ggcattatgc ccagtacatg accttatggg actttcctac 660
ttggcagtac atctacgtat tagtcatcgc tattaccatg gtgatgcggt tttggcagta 720
catcaatggg cgtggatagc ggtttgactc acggggattt ccaagtctcc accccattga 780
cgtcaatggg agtttgtttt ggcaccaaaa tcaacgggac tttccaaaat gtcgtaacaa 840
ctccgcccca ttgacgcaaa tgggcggtag gcgtgtacgg tgggaggtct atataagcag 900
agctcgttta gtgaaccgtc agatcgcctg gagacgccat ccacgctgtt ttgacctcca 960
tagaagacac cgggaccgat ccagcctcca tcggctcgca tctctccttc acgcgcccgc 1020
cgccttacct gaggccgcca tccacgccgg ttgagtcgcg ttctgccgcc tcccgcctgt 1080
ggtgcctcct gaactacgtc cgccgtctag gtaagtttag agctcaggtc gagaccgggc 1140
ctttgtccgg cgctcccttg gagcctacct agactcagcc ggctctccac gctttgcctg 1200
accctgcttg ctcaactcta gttaacggtg gagggcagtg tagtctgagc agtactcgtt 1260
gctgccgcgc gcgccaccag acataatagc tgacagacta acagactgtt cctttccatg 1320
ggtcttttct gcagtcaccg tcgtcgacga tatcgccgcc atgggcgtga ccggcatcct 1380
gcagctgccc agggacaggt tcaagaggac cagcttcttc ctgtgggtga tcatcctgtt 1440
ccagaggacc ttcagcatcc ccctgggcgt gatccacaac agcaccctgc aggtgagcga 1500
cgtggacaag ctggtgtgca gggacaagct gagcagcacc aaccagctga ggagcgtggg 1560
cctgaacctg gagggcaacg gcgtggccac cgacgtgccc agcgccacca agaggtgggg 1620
cttcaggagc ggcgtgcctc ccaaggtggt gaactacgag gccggcgagt gggccgagaa 1680
ctgctacaac ctggagatca agaagcccga cggcagcgag tgcctgcccg ccgcccctga 1740

-continued

```
cggcatcagg ggcttcccca ggtgcaggta cgtgcacaag gtgagcggca ccggcccctg   1800
cgccggcgac ttcgccttcc acaaggaggg cgccttcttc ctgtacgaca ggctggccag   1860
caccgtgatc tacaggggca ccaccttcgc cgagggcgtg gtggccttcc tgatcctgcc   1920
ccaggccaag aaggacttct tcagcagcca ccctctgagg gagcccgtga acgccaccga   1980
ggaccccagc agcggctact acagcaccac catcaggtac caggccaccg gcttcggcac   2040
caacgagacc gagtacctgt tcgaggtgga caacctgacc tacgtgcagc tggagtctag   2100
attcacccct cagttcctgc tgcagctgaa cgagaccatc tacaccagcg gcaagaggag   2160
caacaccacc ggcaagctga tctggaaggt gaaccccgag atcgacacca ccatcggcga   2220
gtgggccttc tgggagacca agaagaacct gaccaggaag atcaggagcg aggagctgag   2280
cttcaccgtc gtgagcaacg gggccaagaa catcagcggc cagagccccg ccaggaccag   2340
cagcgacccc ggcaccaaca ccaccaccga ggaccacaag atcatggcca gcgagaacag   2400
cagcgccatg gtgcaggtgc acagccaggg cagggaggcc gccgtgagcc acctgaccac   2460
cctggccacc atcagcacca gccctcagtc tttaaccacc aagcccggcc ccgacaacag   2520
cacccacaac acccctgtgt acaagctgga catcagcgag gccacccagg tggagcagca   2580
ccacaggagg accgacaacg acagcaccgc cagcgacacc ccttccgcca ccaccgccgc   2640
cggccctccg aaggccgaga acaccaacac cagcaagagc accgactttc tggatcccgc   2700
caccaccacc agccctcaga accacagcga gaccgccggc aacaacaaca cccaccacca   2760
ggacaccggc gaggagagcg ccagcagcgg caagctgggc ctgatcacca acaccatcgc   2820
cggcgtggcc ggcctgatca ccggcggcag gaggaccagg agggaggcca tcgtgaacgc   2880
ccagcccaag tgcaacccca acctgcacta ctggaccacc caggacgagg gcgccgccat   2940
cggcctggcc tggattccct acttcggccc cgccgccgag ggcatctaca tcgagggcct   3000
gatgcacaac caggacggcc tgatctgcgg cctgaggcag ctggccaacg agaccaccca   3060
ggccctgcag ctgttcctga gggccaccac cgagctgagg accttcagca tcctgaacag   3120
gaaggccatc gacttcctgc tgcagaggtg gggcggcacc tgccacatcc tgggccccga   3180
ctgctgcatc gagccccacg actggaccaa gaacatcacc gacaagatcg accagatcat   3240
ccacgacttc gtggacaaga ccctgcccga ccagggcgac aacgacaact ggtggaccgg   3300
ctgaacacgt ggaattcaga tctgctgtgc cttctagttg ccagccatct gttgtttgcc   3360
cctcccccgt gccttccttg accctggaag gtgccactcc cactgtcctt tcctaataaa   3420
atgaggaaat tgcatcgcat tgtctgagta ggtgtcattc tattctgggg ggtggggtgg   3480
ggcaggacag caagggggag gattgggaag acaatagcag gcatgctggg gatgcggtgg   3540
gctctatggg tacccaggtg ctgaagaatt gacccggttc ctcctgggcc agaaagaagc   3600
aggcacatcc ccttctctgt gacacaccct gtccacgccc ctggttctta gttccagccc   3660
cactcatagg acactcatag ctcaggaggg ctccgccttc aatcccaccc gctaaagtac   3720
ttggagcggt ctctccctcc ctcatcagcc caccaaacca aacctagcct ccaagagtgg   3780
gaagaaatta aagcaagata ggctattaag tgcagaggga gagaaaatgc ctccaacatg   3840
tgaggaagta atgagagaaa tcatagaatt ttaaggccat catggcctta atcttccgct   3900
tcctcgctca ctgactcgct gcgctcggtc gttcggctgc ggcgagcggt atcagctcac   3960
tcaaaggcgg taatacggtt atccacagaa tcaggggata acgcaggaaa gaacatgtga   4020
gcaaaaggcc agcaaaaggc caggaaccgt aaaaaggccg cgttgctggc gtttttccat   4080
aggctccgcc cccctgacga gcatcacaaa aatcgacgct caagtcagag gtggcgaaac   4140
```

ccgacaggac tataaagata ccaggcgttt ccccctggaa gctccctcgt gcgctctcct 4200
gttccgaccc tgccgcttac cggatacctg tccgcctttc tcccttcggg aagcgtggcg 4260
ctttctcata gctcacgctg taggtatctc agttcggtgt aggtcgttcg ctccaagctg 4320
ggctgtgtgc acgaaccccc cgttcagccc gaccgctgcg ccttatccgg taactatcgt 4380
cttgagtcca acccggtaag acacgactta tcgccactgg cagcagccac tggtaacagg 4440
attagcagag cgaggtatgt aggcggtgct acagagttct tgaagtggtg gcctaactac 4500
ggctacacta gaagaacagt atttggtatc tgcgctctgc tgaagccagt taccttcgga 4560
aaaagagttg gtagctcttg atccggcaaa caaaccaccg ctggtagcgg tggttttttt 4620
gtttgcaagc agcagattac gcgcagaaaa aaaggatctc aagaagatcc tttgatcttt 4680
tctacggggt ctgacgctca gtggaacgaa aactcacgtt aagggatttt ggtcatgaga 4740
ttatcaaaaa ggatcttcac ctagatcctt ttaaattaaa aatgaagttt taaatcaatc 4800
taaagtatat atgagtaaac ttggtctgac agttaccaat gcttaatcag tgaggcacct 4860
atctcagcga tctgtctatt tcgttcatcc atagttgcct gactcggggg gggggggcgc 4920
tgaggtctgc ctcgtgaaga aggtgttgct gactcatacc aggcctgaat cgccccatca 4980
tccagccaga aagtgaggga gccacggttg atgagagctt tgttgtaggt ggaccagttg 5040
gtgattttga acttttgctt tgccacggaa cggtctgcgt tgtcgggaag atgcgtgatc 5100
tgatccttca actcagcaaa agttcgattt attcaacaaa gccgccgtcc cgtcaagtca 5160
gcgtaatgct ctgccagtgt tacaaccaat taaccaattc tgattagaaa aactcatcga 5220
gcatcaaatg aaactgcaat ttattcatat caggattatc aataccatat ttttgaaaaa 5280
gccgtttctg taatgaagga gaaaactcac cgaggcagtt ccataggatg gcaagatcct 5340
ggtatcggtc tgcgattccg actcgtccaa catcaataca acctattaat ttcccctcgt 5400
caaaaataag gttatcaagt gagaaatcac catgagtgac gactgaatcc ggtgagaatg 5460
gcaaaagctt atgcatttct ttccagactt gttcaacagg ccagccatta cgctcgtcat 5520
caaaatcact cgcatcaacc aaaccgttat tcattcgtga ttgcgcctga gcgagacgaa 5580
atacgcgatc gctgttaaaa ggacaattac aaacaggaat cgaatgcaac cggcgcagga 5640
acactgccag cgcatcaaca atattttcac ctgaatcagg atattcttct aatacctgga 5700
atgctgtttt cccggggatc gcagtggtga gtaaccatgc atcatcagga gtacggataa 5760
aatgcttgat ggtcggaaga ggcataaatt ccgtcagcca gtttagtctg accatctcat 5820
ctgtaacatc attggcaacg ctacctttgc catgtttcag aaacaactct ggcgcatcgg 5880
gcttcccata caatcgatag attgtcgcac ctgattgccc gacattatcg cgagcccatt 5940
tatacccata taaatcagca tccatgttgg aatttaatcg cggcctcgag caagacgttt 6000
cccgttgaat atggctcata acaccccttg tattactgtt tatgtaagca gacagtttta 6060
ttgttcatga tgatatattt ttatcttgtg caatgtaaca tcagagattt tgagacacaa 6120
cgtggctttc cccccccccc cattattgaa gcatttatca gggttattgt ctcatgagcg 6180
gatacatatt tgaatgtatt tagaaaaata aacaaatagg ggttccgcgc acatttcccc 6240
gaaaagtgcc acctgacgtc taagaaacca ttattatcat gacattaacc tataaaaata 6300
ggcgtatcac gaggcccttt cgtc 6324

<210> SEQ ID NO 38
<211> LENGTH: 6868
<212> TYPE: DNA
<213> ORGANISM: Artificial Sequence
<220> FEATURE:
<223> OTHER INFORMATION: Synthetic Construct pVR1012x/s Ebola GP(Z)
delta TM/h (P87666)

<400> SEQUENCE: 38

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcagattgg    240
ctattggcca ttgcatacgt tgtatccata tcataatatg tacatttata ttggctcatg    300
tccaacatta ccgccatgtt gacattgatt attgactagt tattaatagt aatcaattac    360
ggggtcatta gttcatagcc catatatgga gttccgcgtt acataactta cggtaaatgg    420
cccgcctggc tgaccgccca acgacccccg cccattgacg tcaataatga cgtatgttcc    480
catagtaacg ccaataggga ctttccattg acgtcaatgg gtggagtatt tacggtaaac    540
tgcccacttg gcagtacatc aagtgtatca tatgccaagt acgcccccta ttgacgtcaa    600
tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctccg cggccgggaa cggtgcattg gaacgcggat   1020
tccccgtgcc aagagtgacg taagtaccgc ctatagactc tataggcaca cccctttggc   1080
tcttatgcat gctatactgt ttttggcttg gggcctatac acccccgctt ccttatgcta   1140
taggtgatgg tatagcttag cctataggtg tgggttattg accattattg accactcccc   1200
tattggtgac gatactttcc attactaatc cataacatgg ctctttgcca caactatctc   1260
tattggctat atgccaatac tctgtccttc agagactgac acggactctg tatttttaca   1320
ggatggggtc ccatttatta tttacaaatt cacatataca acaacgccgt cccccgtgcc   1380
cgcagttttt attaaacata gcgtgggatc tccacgcgaa tctcgggtac gtgttccgga   1440
catgggctct tctccggtag cggcggagct tccacatccg agccctggtc ccatgcctcc   1500
agcggctcat ggtcgctcgg cagctccttg ctcctaacag tggaggccag acttaggcac   1560
agcacaatgc ccaccaccac cagtgtgccg cacaaggccg tggcggtagg gtatgtgtct   1620
gaaaatgagc gtggagattg ggctcgcacg gctgacgcag atggaagact taaggcagcg   1680
gcagaagaag atgcaggcag ctgagttgtt gtattctgat aagagtcaga ggtaactccc   1740
gttgcggtgc tgttaacggt ggagggcagt gtagtctgag cagtactcgt tgctgccgcg   1800
cgcgccacca gacataatag ctgacagact aacagactgt tcctttccat gggtcttttc   1860
tgcagtcacc gtcgtcgacg atatcgccgc catggagggc ctgagcctgc tgcagctgcc   1920
cagggacaag ttcaggaaga gcagcttctt cgtgtgggtg atcatcctgt tccagaaggc   1980
cttcagcatg cccctgggcg tggtgaccaa cagcaccctg gaggtgaccg agatcgacca   2040
gctggtgtgc aaggaccacc tggccagcac cgaccagctg aagagcgtgg gcctgaacct   2100
ggagggcagc ggcgtgagca ccgacatccc cagcgccacc aagaggtggg gcttcaggag   2160
cggcgtgcct ccccaggtgg tgagctacga ggccggcgag tgggccgaga actgctacaa   2220
```

-continued

```
cctggagatc aagaagcccg acggcagcga gtgcctgcct cctcctcctg acggcgtgag   2280
gggcttcccc aggtgcaggt acgtgcacaa ggcccagggc accggcccct gccccggcga   2340
ctacgccttc cacaaggacg gcgccttctt cctgtacgac aggctggcca gcaccgtgat   2400
ctacaggggc gtgaacttcg ccgagggcgt gatcgccttc ctgatcctgg ccaagcccaa   2460
ggagaccttc ctgcagagcc ctcccatcag ggaggccgcc aactacaccg agaacaccag   2520
cagctactac gccaccagct atctagagta cgagatcgag aacttcggcg cccagcacag   2580
caccaccctg ttcaagatca acaacaacac cttcgtgctg ctggacaggc cccacacccc   2640
tcagttcctg ttccagctga acgacaccat ccagctgcac cagcagctga gcaacaccac   2700
cggcaagctg atctggaccc tggacgccaa catcaacgcc gacatcggcg agtgggcctt   2760
ctgggagaac aagaagaacc tgagcgagca gctgaggggc gaggagctga gcttcgagac   2820
cctgagcctg aacgagaccg aggacgacga cgccaccagc agcaggacca ccaagggcag   2880
gatcagcgac agggccacca ggaagtacag cgacctggtg cccaaggaca gccccggcat   2940
ggtgagcctg cacgtgcccg agggcgagac caccctgccc agccagaaca gcaccgaggg   3000
caggagggtg gacgtgaaca cccaggagac catcaccgag accaccgcca ccatcatcgg   3060
caccaacggc aacaacatgc agatcagcac catcggcacc ggcctgagca gcagccagat   3120
cctgagcagc agccccacca tggcccctag ccccgagacc cagaccagca ccacctacac   3180
ccctaagctg cccgtgatga ccaccgagga gcccaccacc cctcccagga acagccccgg   3240
atccaccacc gaggccccta ccctgaccac ccctgagaac atcaccaccg ccgtgaagac   3300
cgtgtgggcc caggagagca ccagcaacgg cctgatcacc agcaccgtga ccggcatcct   3360
gggcagcctg ggcctgagga agaggagcag gaggcaggtg aacaccaggg ccaccggcaa   3420
gtgcaacccc aacctgcact actggaccgc ccaggagcag cacaacgccg ccggcatcgc   3480
ctggattccc tacttcggcc ccggcgccga gggcatctac accgagggcc tgatgcacaa   3540
ccagaacgcc ctggtgtgcg gcctgaggca gctggccaac gagaccaccc aggccctgca   3600
gctgttcctg agggccacca ccgagctgag gacctacacc atcctgaaca ggaaggccat   3660
cgacttcctg ctgaggaggt ggggcggcac ctgcaggatt ctgggccccg actgctgcat   3720
cgagccccac gactggacca agaacatcac cgacaagatc aaccagatca tccacgactt   3780
catcgacaac cctctgccca accaggacaa cgacgacaac tggtggaccg gctgaacacg   3840
tggaattcag atctgctgtg ccttctagtt gccagccatc tgttgtttgc ccctcccccg   3900
tgccttcctt gaccctggaa ggtgccactc ccactgtcct ttcctaataa aatgaggaaa   3960
ttgcatcgca ttgtctgagt aggtgtcatt ctattctggg gggtggggtg gggcaggaca   4020
gcaaggggga ggattgggaa gacaatagca ggcatgctgg ggatgcggtg ggctctatgg   4080
gtacccaggt gctgaagaat tgacccggtt cctcctgggc cagaaagaag caggcacatc   4140
cccttctctg tgacacaccc tgtccacgcc cctggttctt agttccagcc ccactcatag   4200
gacactcata gctcaggagg gctccgcctt caatcccacc cgctaaagta cttggagcgg   4260
tctctccctc cctcatcagc ccaccaaacc aaacctagcc tccaagagtg ggaagaaatt   4320
aaagcaagat aggctattaa gtgcagaggg agagaaaatg cctccaacat gtgaggaagt   4380
aatgagagaa atcatagaat tttaaggcca tgatttaagg ccatcatggc cttaatcttc   4440
cgcttcctcg ctcactgact cgctgcgctc ggtcgttcgg ctgcggcgag cggtatcagc   4500
tcactcaaag gcggtaatac ggttatccac agaatcaggg gataacgcag gaaagaacat   4560
gtgagcaaaa ggccagcaaa aggccaggaa ccgtaaaaag gccgcgttgc tggcgttttt   4620
```

ccataggctc cgcccccctg acgagcatca caaaaatcga cgctcaagtc agaggtggcg 4680
aaacccgaca ggactataaa gataccaggc gtttccccct ggaagctccc tcgtgcgctc 4740
tcctgttccg accctgccgc ttaccggata cctgtccgcc tttctccctt cgggaagcgt 4800
ggcgctttct catagctcac gctgtaggta tctcagttcg gtgtaggtcg ttcgctccaa 4860
gctgggctgt gtgcacgaac cccccgttca gcccgaccgc tgcgccttat ccggtaacta 4920
tcgtcttgag tccaacccgg taagacacga cttatcgcca ctggcagcag ccactggtaa 4980
caggattagc agagcgaggt atgtaggcgg tgctacagag ttcttgaagt ggtggcctaa 5040
ctacggctac actagaagaa cagtatttgg tatctgcgct ctgctgaagc cagttacctt 5100
cggaaaaaga gttggtagct cttgatccgg caaacaaacc accgctggta gcggtggttt 5160
ttttgtttgc aagcagcaga ttacgcgcag aaaaaaagga tctcaagaag atcctttgat 5220
cttttctacg gggtctgacg ctcagtggaa cgaaaactca cgttaaggga ttttggtcat 5280
gagattatca aaaaggatct tcacctagat ccttttaaat taaaaatgaa gttttaaatc 5340
aatctaaagt atatatgagt aaacttggtc tgacagttac caatgcttaa tcagtgaggc 5400
acctatctca gcgatctgtc tatttcgttc atccatagtt gcctgactcg gggggggggg 5460
gcgctgaggt ctgcctcgtg aagaaggtgt tgctgactca taccaggcct gaatcgcccc 5520
atcatccagc cagaaagtga gggagccacg gttgatgaga gctttgttgt aggtggacca 5580
gttggtgatt ttgaactttt gctttgccac ggaacggtct gcgttgtcgg gaagatgcgt 5640
gatctgatcc ttcaactcag caaaagttcg atttattcaa caaagccgcc gtcccgtcaa 5700
gtcagcgtaa tgctctgcca gtgttacaac caattaacca attctgatta gaaaaactca 5760
tcgagcatca aatgaaactg caatttattc atatcaggat tatcaatacc atatttttga 5820
aaaagccgtt tctgtaatga aggagaaaac tcaccgaggc agttccatag gatggcaaga 5880
tcctggtatc ggtctgcgat tccgactcgt ccaacatcaa tacaacctat taatttcccc 5940
tcgtcaaaaa taaggttatc aagtgagaaa tcaccatgag tgacgactga atccggtgag 6000
aatggcaaaa gcttatgcat ttctttccag acttgttcaa caggccagcc attacgctcg 6060
tcatcaaaat cactcgcatc aaccaaaccg ttattcattc gtgattgcgc ctgagcgaga 6120
cgaaatacgc gatcgctgtt aaaaggacaa ttacaaacag gaatcgaatg caaccggcgc 6180
aggaacactg ccagcgcatc aacaatattt tcacctgaat caggatattc ttctaatacc 6240
tggaatgctg ttttcccggg gatcgcagtg gtgagtaacc atgcatcatc aggagtacgg 6300
ataaaatgct tgatggtcgg aagaggcata aattccgtca gccagtttag tctgaccatc 6360
tcatctgtaa catcattggc aacgctacct ttgccatgtt tcagaaacaa ctctggcgca 6420
tcgggcttcc catacaatcg atagattgtc gcacctgatt gcccgacatt atcgcgagcc 6480
catttatacc catataaatc agcatccatg ttggaattta atcgcggcct cgagcaagac 6540
gtttcccgtt gaatatggct cataacaccc cttgtattac tgtttatgta agcagacagt 6600
tttattgttc atgatgatat atttttatct tgtgcaatgt aacatcagag attttgagac 6660
acaacgtggc tttccccccc cccccattat tgaagcattt atcagggtta ttgtctcatg 6720
agcggataca tatttgaatg tatttagaaa aataaacaaa taggggttcc gcgcacattt 6780
ccccgaaaag tgccacctga cgtctaagaa accattatta tcatgacatt aacctataaa 6840
aataggcgta tcacgaggcc ctttcgtc 6868

<210> SEQ ID NO 39
<211> LENGTH: 6322
<212> TYPE: DNA

<213> ORGANISM: Artificial Sequence
<220> FEATURE:
<223> OTHER INFORMATION: Synthetic Construct CMV/R-GP(S/G)(deltaTM)/h

<400> SEQUENCE: 39
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcagattgg 240
ctattggcca ttgcatacgt tgtatccata tcataatatg tacatttata ttggctcatg 300
tccaacatta ccgccatgtt gacattgatt attgactagt tattaatagt aatcaattac 360
ggggtcatta gttcatagcc catatatgga gttccgcgtt acataactta cggtaaatgg 420
cccgcctggc tgaccgccca acgacccccg cccattgacg tcaataatga cgtatgttcc 480
catagtaacg ccaataggga ctttccattg acgtcaatgg gtggagtatt tacggtaaac 540
tgcccacttg gcagtacatc aagtgtatca tatgccaagt acgcccccta ttgacgtcaa 600
tgacggtaaa tggcccgcct ggcattatgc ccagtacatg accttatggg actttcctac 660
ttggcagtac atctacgtat tagtcatcgc tattaccatg gtgatgcggt tttggcagta 720
catcaatggg cgtggatagc ggtttgactc acggggattt ccaagtctcc accccattga 780
cgtcaatggg agtttgtttt ggcaccaaaa tcaacgggac tttccaaaat gtcgtaacaa 840
ctccgcccca ttgacgcaaa tgggcggtag gcgtgtacgg tgggaggtct atataagcag 900
agctcgttta gtgaaccgtc agatcgcctg gagacgccat ccacgctgtt ttgacctcca 960
tagaagacac cgggaccgat ccagcctcca tcggctcgca tctctccttc acgcgcccgc 1020
cgccttacct gaggccgcca tccacgccgg ttgagtcgcg ttctgccgcc tcccgcctgt 1080
ggtgcctcct gaactacgtc cgccgtctag gtaagtttag agctcaggtc gagaccgggc 1140
ctttgtccgg cgctcccttg gagcctacct agactcagcc ggctctccac gctttgcctg 1200
accctgcttg ctcaactcta gttaacggtg gagggcagtg tagtctgagc agtactcgtt 1260
gctgccgcgc gcgccaccag acataatagc tgacagacta acagactgtt cctttccatg 1320
ggtcttttct gcagtcaccg tcgtcgacga tatcgccgcc atggagggcc tgagcctgct 1380
gcagctgccc agggacaagt tcaggaagag cagcttcttc gtgtgggtga tcatcctgtt 1440
ccagaaggcc ttcagcatgc ccctgggcgt ggtgaccaac agcaccctgg aggtgaccga 1500
gatcgaccag ctggtgtgca aggaccacct ggccagcacc gaccagctga agagcgtggg 1560
cctgaacctg gagggcagcg gcgtgagcac cgacatcccc agcgccacca agaggtgggg 1620
cttcaggagc ggcgtgcctc ccaaggtggt gagctacgag gccggcgagt gggccgagaa 1680
ctgctacaac ctggagatca agaagcccga cggcagcgag tgcctgcctc ctcctcctga 1740
cggcgtgagg ggcttcccca ggtgcaggta cgtgcacaag gcccagggca ccggcccctg 1800
ccccggcgac tacgccttcc acaaggacgg cgccttcttc ctgtacgaca ggctggccag 1860
caccgtgatc tacaggggcg tgaacttcgc cgagggcgtg atcgccttcc tgatcctggc 1920
caagcccaag gagaccttcc tgcagagccc tcccatcagg gaggccgtga actacaccga 1980
gaacaccagc agctactacg ccaccagcta tctagagtac gagatcgaga acttcggcgc 2040
ccagcacagc accaccctgt tcaagatcga caacaacacc ttcgtgaggc tggacaggcc 2100
ccacacccct cagttcctgt tccagctgaa cgacaccatc cacctgcacc agcagctgag 2160
caacaccacc ggcaggctga tctggaccct ggacgccaac atcaacgccg acatcggcga 2220

-continued

```
gtgggccttc tgggagaaca agaagaacct gagcgagcag ctgaggggcg aggagctgag   2280
cttcgaggcc ctgagcctga acgagaccga ggacgacgac gccgccagca gcaggatcac   2340
caagggcagg atcagcgaca gggccaccag gaagtacagc gacctggtgc ccaagaacag   2400
ccccggcatg gtgcccctgc acatccccga gggcgagacc accctgccca gccagaacag   2460
caccgagggc aggagggtgg gcgtgaacac ccaggagacc atcaccgaga ccgccgccac   2520
catcatcggc accaacggca accacatgca gatcagcacc atcggcatca ggcccagcag   2580
cagccagatc cccagcagca gccccaccac cgcccctagc cccgaggccc agacccccac   2640
cacccacacc agcggaccca gcgtgatggc caccgaggag cccaccaccc ctcccggcag   2700
cagccccgga cccaccaccg aggcccctac cctgaccacc cctgagaaca tcaccaccgc   2760
cgtgaagacc gtgctgcccc aggagagcac cagcaacggc ctgatcacca gcaccgtgac   2820
cggcatcctg ggcagcctgg gcctgaggaa gaggagcagg aggcagacca acaccaaggc   2880
caccggcaag tgcaacccca acctgcacta ctggaccgcc caggagcagc acaacgccgc   2940
cggcatcgcc tggattccct acttcggccc cggcgccgag ggcatctaca ccgagggcct   3000
gatgcacaac cagaacgccc tggtgtgcgg cctgaggcag ctggccaacg agaccaccca   3060
ggccctgcag ctgttcctga gggccaccac cgagctgagg acctacacca tcctgaacag   3120
gaaggccatc gacttcctgc tgaggaggtg gggcggcacc tgcaggattc tgggccccga   3180
ctgctgcatc gagccccacg actggaccaa gaacatcacc gacaagatca accagatcat   3240
ccacgacttc atcgacaacc ctctgcccaa ccaggacaac gacgacaact ggtggaccgg   3300
ctgaacacgt ggaattgatc tgctgtgcct tctagttgcc agccatctgt tgtttgcccc   3360
tcccccgtgc cttccttgac cctggaaggt gccactccca ctgtcctttc ctaataaaat   3420
gaggaaattg catcgcattg tctgagtagg tgtcattcta ttctgggggg tggggtgggg   3480
caggacagca agggggagga ttgggaagac aatagcaggc atgctgggga tgcggtgggc   3540
tctatgggta cccaggtgct gaagaattga cccggttcct cctgggccag aaagaagcag   3600
gcacatcccc ttctctgtga cacaccctgt ccacgcccct ggttcttagt tccagcccca   3660
ctcataggac actcatagct caggagggct ccgccttcaa tcccacccgc taaagtactt   3720
ggagcggtct ctccctccct catcagccca ccaaaccaaa cctagcctcc aagagtggga   3780
agaaattaaa gcaagatagg ctattaagtg cagagggaga gaaaatgcct ccaacatgtg   3840
aggaagtaat gagagaaatc atagaatttt aaggccatca tggccttaat cttccgcttc   3900
ctcgctcact gactcgctgc gctcggtcgt tcggctgcgg cgagcggtat cagctcactc   3960
aaaggcggta atacggttat ccacagaatc aggggataac gcaggaaaga acatgtgagc   4020
aaaaggccag caaaaggcca ggaaccgtaa aaaggccgcg ttgctggcgt ttttccatag   4080
gctccgcccc cctgacgagc atcacaaaaa tcgacgctca agtcagaggt ggcgaaaccc   4140
gacaggacta taaagatacc aggcgtttcc ccctggaagc tccctcgtgc gctctcctgt   4200
tccgaccctg ccgcttaccg gatacctgtc cgcctttctc ccttcgggaa gcgtggcgct   4260
ttctcatagc tcacgctgta ggtatctcag ttcggtgtag gtcgttcgct ccaagctggg   4320
ctgtgtgcac gaaccccccg ttcagcccga ccgctgcgcc ttatccggta actatcgtct   4380
tgagtccaac ccggtaagac acgacttatc gccactggca gcagccactg gtaacaggat   4440
tagcagagcg aggtatgtag gcggtgctac agagttcttg aagtggtggc ctaactacgg   4500
ctacactaga agaacagtat ttggtatctg cgctctgctg aagccagtta ccttcggaaa   4560
aagagttggt agctcttgat ccggcaaaca aaccaccgct ggtagcggtg gtttttttgt   4620
```

-continued

```
ttgcaagcag cagattacgc gcagaaaaaa aggatctcaa gaagatcctt tgatcttttc   4680

tacggggtct gacgctcagt ggaacgaaaa ctcacgttaa gggattttgg tcatgagatt   4740

atcaaaaagg atcttcacct agatcctttt aaattaaaaa tgaagtttta aatcaatcta   4800

aagtatatat gagtaaactt ggtctgacag ttaccaatgc ttaatcagtg aggcacctat   4860

ctcagcgatc tgtctatttc gttcatccat agttgcctga ctcggggggg gggggcgctg   4920

aggtctgcct cgtgaagaag gtgttgctga ctcataccag gcctgaatcg ccccatcatc   4980

cagccagaaa gtgagggagc cacggttgat gagagctttg ttgtaggtgg accagttggt   5040

gattttgaac ttttgctttg ccacggaacg gtctgcgttg tcgggaagat gcgtgatctg   5100

atccttcaac tcagcaaaag ttcgatttat tcaacaaagc cgccgtcccg tcaagtcagc   5160

gtaatgctct gccagtgtta caaccaatta accaattctg attagaaaaa ctcatcgagc   5220

atcaaatgaa actgcaattt attcatatca ggattatcaa taccatattt ttgaaaaagc   5280

cgtttctgta atgaaggaga aaactcaccg aggcagttcc ataggatggc aagatcctgg   5340

tatcggtctg cgattccgac tcgtccaaca tcaatacaac ctattaattt cccctcgtca   5400

aaaataaggt tatcaagtga gaaatcacca tgagtgacga ctgaatccgg tgagaatggc   5460

aaaagcttat gcatttcttt ccagacttgt tcaacaggcc agccattacg ctcgtcatca   5520

aaatcactcg catcaaccaa accgttattc attcgtgatt gcgcctgagc gagacgaaat   5580

acgcgatcgc tgttaaaagg acaattacaa acaggaatcg aatgcaaccg gcgcaggaac   5640

actgccagcg catcaacaat attttcacct gaatcaggat attcttctaa tacctggaat   5700

gctgttttcc cggggatcgc agtggtgagt aaccatgcat catcaggagt acggataaaa   5760

tgcttgatgg tcggaagagg cataaattcc gtcagccagt ttagtctgac catctcatct   5820

gtaacatcat tggcaacgct acctttgcca tgtttcagaa acaactctgg cgcatcgggc   5880

ttcccataca atcgatagat tgtcgcacct gattgcccga cattatcgcg agcccattta   5940

tacccatata aatcagcatc catgttggaa tttaatcgcg gcctcgagca agacgtttcc   6000

cgttgaatat ggctcataac accccttgta ttactgttta tgtaagcaga cagttttatt   6060

gttcatgatg atatattttt atcttgtgca atgtaacatc agagattttg agacacaacg   6120

tggctttccc ccccccccca ttattgaagc atttatcagg gttattgtct catgagcgga   6180

tacatatttg aatgtattta gaaaaataaa caaatagggg ttccgcgcac atttccccga   6240

aaagtgccac ctgacgtcta agaaaccatt attatcatga cattaaccta taaaaatagg   6300

cgtatcacga ggccctttcg tc                                            6322
```

```
<210> SEQ ID NO 40
<211> LENGTH: 6324
<212> TYPE: DNA
<213> ORGANISM: Artificial Sequence
<220> FEATURE:
<223> OTHER INFORMATION: Synthetic Construct CMV/R-GP(S, Q66798)(dTM)/h

<400> SEQUENCE: 40

tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatgcg gtgtgaaata ccgcacagat gcgtaaggag aaaataccgc atcagattgg    240

ctattggcca ttgcatacgt tgtatccata tcataatatg tacatttata ttggctcatg    300

tccaacatta ccgccatgtt gacattgatt attgactagt tattaatagt aatcaattac    360
```

-continued

```
ggggtcatta gttcatagcc catatatgga gttccgcgtt acataactta cggtaaatgg    420
cccgcctggc tgaccgccca acgacccccg cccattgacg tcaataatga cgtatgttcc    480
catagtaacg ccaataggga ctttccattg acgtcaatgg gtggagtatt tacggtaaac    540
tgcccacttg gcagtacatc aagtgtatca tatgccaagt acgcccccta ttgacgtcaa    600
tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctcca tcggctcgca tctctccttc acgcgcccgc   1020
cgccttacct gaggccgcca tccacgccgg ttgagtcgcg ttctgccgcc tcccgcctgt   1080
ggtgcctcct gaactacgtc cgccgtctag gtaagtttag agctcaggtc gagaccgggc   1140
ctttgtccgg cgctcccttg gagcctacct agactcagcc ggctctccac gctttgcctg   1200
accctgcttg ctcaactcta gttaacggtg gagggcagtg tagtctgagc agtactcgtt   1260
gctgccgcgc gcgccaccag acataatagc tgacagacta acagactgtt cctttccatg   1320
ggtcttttct gcagtcaccg tcgtcgacga tatcgccgcc atggagggcc tgagcctgct   1380
gcagctgccc agggacaagt tcaggaagag cagcttcttc gtgtgggtga tcatcctgtt   1440
ccagaaggcc ttcagcatgc cctgggcgt ggtgaccaac agcaccctgg aggtgaccga   1500
gatcgaccag ctggtgtgca aggaccacct ggccagcacc gaccagctga agagcgtggg   1560
cctgaacctg gagggcagcg gcgtgagcac cgacatcccc agcgccacca agaggtgggg   1620
cttcaggagc ggcgtgcctc cccaggtggt gagctacgag gccggcgagt gggccgagaa   1680
ctgctacaac ctggagatca agaagcccga cggcagcgag tgcctgcctc ctcctcctga   1740
cggcgtgagg ggcttcccca ggtgcaggta cgtgcacaag gcccagggca ccggcccctg   1800
ccccggcgac tacgccttcc acaaggacgg cgccttcttc ctgtacgaca ggctggccag   1860
caccgtgatc tacaggggcg tgaacttcgc cgagggcgtg atcgccttcc tgatcctggc   1920
caagcccaag gagaccttcc tgcagagccc tcccatcagg gaggccgcca actacaccga   1980
gaacaccagc agctactacg ccaccagcta tctagagtac gagatcgaga acttcggcgc   2040
ccagcacagc accaccctgt tcaagatcaa caacaacacc ttcgtgctgc tggacaggcc   2100
ccacacccct cagttcctgt tccagctgaa cgacaccatc cagctgcacc agcagctgag   2160
caacaccacc ggcaagctga tctggaccct ggacgccaac atcaacgccg acatcggcga   2220
gtgggccttc tgggagaaca agaagaacct gagcgagcag ctgaggggcg aggagctgag   2280
cttcgagacc ctgagcctga acgagaccga ggacgacgac gccaccagca gcaggaccac   2340
caagggcagg atcagcgaca gggccaccag gaagtacagc gacctggtgc ccaaggacag   2400
ccccggcatg gtgagcctgc acgtgcccga gggcgagacc accctgccca gccagaacag   2460
caccgagggc aggagggtgg acgtgaacac ccaggagacc atcaccgaga ccaccgccac   2520
catcatcggc accaacggca acaacatgca gatcagcacc atcggcaccg gcctgagcag   2580
cagccagatc ctgagcagca gccccaccat ggcccctagc cccgagaccc agaccagcac   2640
cacctacacc cctaagctgc ccgtgatgac caccgaggag cccaccaccc ctcccaggaa   2700
cagccccgga tccaccaccg aggcccctac cctgaccacc cctgagaaca tcaccaccgc   2760
```

-continued

```
cgtgaagacc gtgtgggccc aggagagcac cagcaacggc ctgatcacca gcaccgtgac   2820
cggcatcctg ggcagcctgg gcctgaggaa gaggagcagg aggcaggtga acaccagggc   2880
caccggcaag tgcaacccca acctgcacta ctggaccgcc caggagcagc acaacgccgc   2940
cggcatcgcc tggattccct acttcggccc cggcgccgag ggcatctaca ccgagggcct   3000
gatgcacaac cagaacgccc tggtgtgcgg cctgaggcag ctggccaacg agaccaccca   3060
ggccctgcag ctgttcctga gggccaccac cgagctgagg acctacacca tcctgaacag   3120
gaaggccatc gacttcctgc tgaggaggtg gggcggcacc tgcaggattc tgggccccga   3180
ctgctgcatc gagccccacg actggaccaa gaacatcacc gacaagatca accagatcat   3240
ccacgacttc atcgacaacc ctctgcccaa ccaggacaac gacgacaact ggtggaccgg   3300
ctgaacacgt ggaattcaga tctgctgtgc cttctagttg ccagccatct gttgtttgcc   3360
cctcccccgt gccttccttg accctggaag gtgccactcc cactgtcctt tcctaataaa   3420
atgaggaaat tgcatcgcat tgtctgagta ggtgtcattc tattctgggg ggtggggtgg   3480
ggcaggacag caagggggag gattgggaag acaatagcag gcatgctggg gatgcggtgg   3540
gctctatggg tacccaggtg ctgaagaatt gacccggttc ctcctgggcc agaaagaagc   3600
aggcacatcc ccttctctgt gacacaccct gtccacgccc ctggttctta gttccagccc   3660
cactcatagg acactcatag ctcaggaggg ctccgccttc aatcccaccc gctaaagtac   3720
ttggagcggt ctctccctcc ctcatcagcc caccaaacca aacctagcct ccaagagtgg   3780
gaagaaatta aagcaagata ggctattaag tgcagaggga gagaaaatgc ctccaacatg   3840
tgaggaagta atgagagaaa tcatagaatt ttaaggccat catggcctta atcttccgct   3900
tcctcgctca ctgactcgct gcgctcggtc gttcggctgc ggcgagcggt atcagctcac   3960
tcaaaggcgg taatacggtt atccacagaa tcaggggata acgcaggaaa gaacatgtga   4020
gcaaaaggcc agcaaaaggc caggaaccgt aaaaaggccg cgttgctggc gtttttccat   4080
aggctccgcc cccctgacga gcatcacaaa aatcgacgct caagtcagag gtggcgaaac   4140
ccgacaggac tataaagata ccaggcgttt ccccctggaa gctccctcgt gcgctctcct   4200
gttccgaccc tgccgcttac cggatacctg tccgcctttc tcccttcggg aagcgtggcg   4260
ctttctcata gctcacgctg taggtatctc agttcggtgt aggtcgttcg ctccaagctg   4320
ggctgtgtgc acgaaccccc cgttcagccc gaccgctgcg ccttatccgg taactatcgt   4380
cttgagtcca acccggtaag acacgactta tcgccactgg cagcagccac tggtaacagg   4440
attagcagag cgaggtatgt aggcggtgct acagagttct tgaagtggtg gcctaactac   4500
ggctacacta gaagaacagt atttggtatc tgcgctctgc tgaagccagt taccttcgga   4560
aaaagagttg gtagctcttg atccggcaaa caaaccaccg ctggtagcgg tggttttttt   4620
gtttgcaagc agcagattac gcgcagaaaa aaaggatctc aagaagatcc tttgatcttt   4680
tctacggggt ctgacgctca gtggaacgaa aactcacgtt aagggatttt ggtcatgaga   4740
ttatcaaaaa ggatcttcac ctagatcctt ttaaattaaa aatgaagttt taaatcaatc   4800
taaagtatat atgagtaaac ttggtctgac agttaccaat gcttaatcag tgaggcacct   4860
atctcagcga tctgtctatt tcgttcatcc atagttgcct gactcggggg gggggggcgc   4920
tgaggtctgc ctcgtgaaga aggtgttgct gactcatacc aggcctgaat cgccccatca   4980
tccagccaga aagtgaggga gccacggttg atgagagctt tgttgtaggt ggaccagttg   5040
gtgattttga acttttgctt tgccacggaa cggtctgcgt tgtcgggaag atgcgtgatc   5100
tgatccttca actcagcaaa agttcgattt attcaacaaa gccgccgtcc cgtcaagtca   5160
```

gcgtaatgct ctgccagtgt tacaaccaat taaccaattc tgattagaaa aactcatcga 5220
gcatcaaatg aaactgcaat ttattcatat caggattatc aataccatat ttttgaaaaa 5280
gccgtttctg taatgaagga gaaaactcac cgaggcagtt ccataggatg gcaagatcct 5340
ggtatcggtc tgcgattccg actcgtccaa catcaataca acctattaat ttcccctcgt 5400
caaaaataag gttatcaagt gagaaatcac catgagtgac gactgaatcc ggtgagaatg 5460
gcaaaagctt atgcatttct ttccagactt gttcaacagg ccagccatta cgctcgtcat 5520
caaaatcact cgcatcaacc aaaccgttat tcattcgtga ttgcgcctga gcgagacgaa 5580
atacgcgatc gctgttaaaa ggacaattac aaacaggaat cgaatgcaac cggcgcagga 5640
acactgccag cgcatcaaca atattttcac ctgaatcagg atattcttct aatacctgga 5700
atgctgtttt cccggggatc gcagtggtga gtaaccatgc atcatcagga gtacggataa 5760
aatgcttgat ggtcggaaga ggcataaatt ccgtcagcca gtttagtctg accatctcat 5820
ctgtaacatc attggcaacg ctacctttgc catgtttcag aaacaactct ggcgcatcgg 5880
gcttcccata caatcgatag attgtcgcac ctgattgccc gacattatcg cgagcccatt 5940
tatacccata taaatcagca tccatgttgg aatttaatcg cggcctcgag caagacgttt 6000
cccgttgaat atggctcata acaccccttg tattactgtt tatgtaagca gacagtttta 6060
ttgttcatga tgatatattt ttatcttgtg caatgtaaca tcagagattt tgagacacaa 6120
cgtggctttc cccccccccc cattattgaa gcatttatca gggttattgt ctcatgagcg 6180
gatacatatt tgaatgtatt tagaaaaata aacaaatagg ggttccgcgc acatttcccc 6240
gaaaagtgcc acctgacgtc taagaaacca ttattatcat gacattaacc tataaaaata 6300
ggcgtatcac gaggcccttt cgtc 6324

<210> SEQ ID NO 41
<211> LENGTH: 6236
<212> TYPE: DNA
<213> ORGANISM: Artificial Sequence
<220> FEATURE:
<223> OTHER INFORMATION: Synthetic Construct pVR1012x/s Lassa (codon optimized)

<400> SEQUENCE: 41
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcagattgg 240
ctattggcca ttgcatacgt tgtatccata tcataatatg tacatttata ttggctcatg 300
tccaacatta ccgccatgtt gacattgatt attgactagt tattaatagt aatcaattac 360
ggggtcatta gttcatagcc catatatgga gttccgcgtt acataactta cggtaaatgg 420
cccgcctggc tgaccgccca acgacccccg cccattgacg tcaataatga cgtatgttcc 480
catagtaacg ccaataggga ctttccattg acgtcaatgg gtggagtatt tacggtaaac 540
tgcccacttg gcagtacatc aagtgtatca tatgccaagt acgcccccta ttgacgtcaa 600
tgacggtaaa tggcccgcct ggcattatgc ccagtacatg accttatggg actttcctac 660
ttggcagtac atctacgtat tagtcatcgc tattaccatg gtgatgcggt tttggcagta 720
catcaatggg cgtggatagc ggtttgactc acggggattt ccaagtctcc accccattga 780
cgtcaatggg agtttgtttt ggcaccaaaa tcaacgggac tttccaaaat gtcgtaacaa 840
ctccgcccca ttgacgcaaa tgggcggtag gcgtgtacgg tgggaggtct atataagcag 900

-continued

```
agctcgttta gtgaaccgtc agatcgcctg gagacgccat ccacgctgtt ttgacctcca    960
tagaagacac cgggaccgat ccagcctccg cggccgggaa cggtgcattg gaacgcggat   1020
tccccgtgcc aagagtgacg taagtaccgc ctatagactc tataggcaca cccctttggc   1080
tcttatgcat gctatactgt ttttggcttg gggcctatac acccccgctt ccttatgcta   1140
taggtgatgg tatagcttag cctataggtg tgggttattg accattattg accactcccc   1200
tattggtgac gatactttcc attactaatc cataacatgg ctctttgcca caactatctc   1260
tattggctat atgccaatac tctgtccttc agagactgac acggactctg tatttttaca   1320
ggatggggtc ccatttatta tttacaaatt cacatataca acaacgccgt cccccgtgcc   1380
cgcagttttt attaaacata gcgtgggatc tccacgcgaa tctcgggtac gtgttccgga   1440
catgggctct tctccggtag cggcggagct tccacatccg agccctggtc ccatgcctcc   1500
agcggctcat ggtcgctcgg cagctccttg ctcctaacag tggaggccag acttaggcac   1560
agcacaatgc ccaccaccac cagtgtgccg cacaaggccg tggcggtagg gtatgtgtct   1620
gaaaatgagc gtggagattg ggctcgcacg gctgacgcag atggaagact taaggcagcg   1680
gcagaagaag atgcaggcag ctgagttgtt gtattctgat aagagtcaga ggtaactccc   1740
gttgcggtgc tgttaacggt ggagggcagt gtagtctgag cagtactcgt tgctgccgcg   1800
cgcgccacca gacataatag ctgacagact aacagactgt tcctttccat gggtcttttc   1860
tgcagtcacc gtcgtcgaca cgtgtgatca gatatcgcgg ccgctctaga gatatcgccg   1920
ccatgggcca gatcgtgacc ttcttccagg aggtgcccca tgtgatcgag gaggtgatga   1980
acatcgtgct gatcgccctg agcgtgctgg ccgtgctgaa gggcctgtac aacttcgcca   2040
cctgcggcct ggtgggcctg gtgaccttcc tgctgctgtg cggcaggagc tgcaccacca   2100
gcctgtacaa gggcgtgtac gagctgcaga ccctggagct gaacatggag accctgaaca   2160
tgaccatgcc cctgagctgc accaagaaca acagccacca ctacatcatg gtgggcaacg   2220
agaccggcct ggagctaacc ctgaccaaca ccagcatcat caaccacaag ttctgcaacc   2280
tgagcgacgc ccacaagaag aacctgtacg accacgccct gatgagcatc atcagcacct   2340
tccacctgag catccccaac ttcaaccagt acgaggccat gagctgcgac ttcaacggcg   2400
gcaagatcag cgtgcagtac aacctgagcc acagctacgc cggcgacgcc gccaaccact   2460
gcggcaccgt ggccaacggc gtgctgcaga ccttcatgag gatggcctgg ggcggcagct   2520
acatcgccct ggacagcggc aggggcaact gggactgcat catgaccagc taccagtacc   2580
tgatcatcca gaacaccacc tgggaggacc actgccagtt cagcaggccc agccccatcg   2640
gctacctggg cctgctgagc cagaggacca gggacatcta catcagcagg aggctgctgg   2700
gcaccttcac ctggaccctg agcgacagcg agggcaagga cacacccggc ggctactgcc   2760
tgaccaggtg gatgctgatc gaggccgagc tgaagtgctt cggcaacacc gccgtggcca   2820
agtgcaacga gaagcacgac gaggagttct gcgacatgct gaggctgttc gacttcaaca   2880
agcaggccat ccagaggctg aaggccgagg cccagatgag catccagctg atcaacaagg   2940
ccgtgaacgc cctgatcaac gaccagctga tcatgaagaa ccacctgagg gacatcatgg   3000
gcatccccta ctgcaactac agcaagtact ggtacctgaa ccacaccacc accggcagga   3060
ccagcctgcc caagtgctgg ctggtgagca acggcagcta cctgaacgag acccacttca   3120
gcgacgacat cgagcagcag gccgacaaca tgatcaccga gatgctgcag aaggagtaca   3180
tggagaggca gggcaagacc tgaacacgtg ggatccagat ctgctgtgcc ttctagttgc   3240
cagccatctg ttgtttgccc ctcccccgtg ccttccttga ccctggaagg tgccactccc   3300
```

```
actgtccttt cctaataaaa tgaggaaatt gcatcgcatt gtctgagtag gtgtcattct   3360
attctggggg gtggggtggg gcaggacagc aagggggagg attgggaaga caatagcagg   3420
catgctgggg atgcggtggg ctctatgggt acccaggtgc tgaagaattg acccggttcc   3480
tcctgggcca gaaagaagca ggcacatccc cttctctgtg acacaccctg tccacgcccc   3540
tggttcttag ttccagcccc actcatagga cactcatagc tcaggagggc tccgccttca   3600
atcccacccg ctaaagtact tggagcggtc tctccctccc tcatcagccc accaaaccaa   3660
acctagcctc caagagtggg aagaaattaa agcaagatag gctattaagt gcagagggag   3720
agaaaatgcc tccaacatgt gaggaagtaa tgagagaaat catagaattt taaggccatg   3780
atttaaggcc atcatggcct taatcttccg cttcctcgct cactgactcg ctgcgctcgg   3840
tcgttcggct gcggcgagcg gtatcagctc actcaaaggc ggtaatacgg ttatccacag   3900
aatcagggga taacgcagga aagaacatgt gagcaaaagg ccagcaaaag gccaggaacc   3960
gtaaaaaggc cgcgttgctg gcgtttttcc ataggctccg cccccctgac gagcatcaca   4020
aaaatcgacg ctcaagtcag aggtggcgaa acccgacagg actataaaga taccaggcgt   4080
ttccccctgg aagctccctc gtgcgctctc ctgttccgac cctgccgctt accggatacc   4140
tgtccgcctt tctcccttcg ggaagcgtgg cgctttctca tagctcacgc tgtaggtatc   4200
tcagttcggt gtaggtcgtt cgctccaagc tgggctgtgt gcacgaaccc cccgttcagc   4260
ccgaccgctg cgccttatcc ggtaactatc gtcttgagtc caacccggta agacacgact   4320
tatcgccact ggcagcagcc actggtaaca ggattagcag agcgaggtat gtaggcggtg   4380
ctacagagtt cttgaagtgg tggcctaact acggctacac tagaagaaca gtatttggta   4440
tctgcgctct gctgaagcca gttaccttcg gaaaaagagt tggtagctct tgatccggca   4500
aacaaaccac cgctggtagc ggtggttttt ttgtttgcaa gcagcagatt acgcgcagaa   4560
aaaaaggatc tcaagaagat cctttgatct tttctacggg gtctgacgct cagtggaacg   4620
aaaactcacg ttaagggatt ttggtcatga gattatcaaa aaggatcttc acctagatcc   4680
ttttaaatta aaaatgaagt tttaaatcaa tctaaagtat atatgagtaa acttggtctg   4740
acagttacca atgcttaatc agtgaggcac ctatctcagc gatctgtcta tttcgttcat   4800
ccatagttgc ctgactcggg gggggggggc gctgaggtct gcctcgtgaa gaaggtgttg   4860
ctgactcata ccaggcctga atcgccccat catccagcca gaaagtgagg gagccacggt   4920
tgatgagagc tttgttgtag gtggaccagt tggtgatttt gaacttttgc tttgccacgg   4980
aacggtctgc gttgtcggga agatgcgtga tctgatcctt caactcagca aaagttcgat   5040
ttattcaaca aagccgccgt cccgtcaagt cagcgtaatg ctctgccagt gttacaacca   5100
attaaccaat tctgattaga aaaactcatc gagcatcaaa tgaaactgca atttattcat   5160
atcaggatta tcaataccat atttttgaaa aagccgtttc tgtaatgaag gagaaaactc   5220
accgaggcag ttccatagga tggcaagatc ctggtatcgg tctgcgattc cgactcgtcc   5280
aacatcaata caacctatta atttcccctc gtcaaaaata aggttatcaa gtgagaaatc   5340
accatgagtg acgactgaat ccggtgagaa tggcaaaagc ttatgcattt ctttccagac   5400
ttgttcaaca ggccagccat tacgctcgtc atcaaaatca ctcgcatcaa ccaaaccgtt   5460
attcattcgt gattgcgcct gagcgagacg aaatacgcga tcgctgttaa aaggacaatt   5520
acaaacagga atcgaatgca accggcgcag gaacactgcc agcgcatcaa caatattttc   5580
acctgaatca ggatattctt ctaatacctg gaatgctgtt ttcccgggga tcgcagtggt   5640
gagtaaccat gcatcatcag gagtacggat aaaatgcttg atggtcggaa gaggcataaa   5700
```

-continued

```
ttccgtcagc cagtttagtc tgaccatctc atctgtaaca tcattggcaa cgctaccttt   5760

gccatgtttc agaaacaact ctggcgcatc gggcttccca tacaatcgat agattgtcgc   5820

acctgattgc ccgacattat cgcgagccca tttataccca tataaatcag catccatgtt   5880

ggaatttaat cgcggcctcg agcaagacgt ttcccgttga atatggctca taacacccct   5940

tgtattactg tttatgtaag cagacagttt tattgttcat gatgatatat ttttatcttg   6000

tgcaatgtaa catcagagat tttgagacac aacgtggctt tccccccccc cccattattg   6060

aagcatttat cagggttatt gtctcatgag cggatacata tttgaatgta tttagaaaaa   6120

taaacaaata ggggttccgc gcacatttcc ccgaaaagtg ccacctgacg tctaagaaac   6180

cattattatc atgacattaa cctataaaaa taggcgtatc acgaggccct ttcgtc       6236
```

<210> SEQ ID NO 42
<211> LENGTH: 6902
<212> TYPE: DNA
<213> ORGANISM: Artificial Sequence
<220> FEATURE:
<223> OTHER INFORMATION: Synthetic Construct pVR1012x/s Marburg (codon optimized)

<400> SEQUENCE: 42

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatgcg gtgtgaaata ccgcacagat gcgtaaggag aaaataccgc atcagattgg    240

ctattggcca ttgcatacgt tgtatccata tcataatatg tacatttata ttggctcatg    300

tccaacatta ccgccatgtt gacattgatt attgactagt tattaatagt aatcaattac    360

ggggtcatta gttcatagcc catatatgga gttccgcgtt acataactta cggtaaatgg    420

cccgcctggc tgaccgccca acgacccccg cccattgacg tcaataatga cgtatgttcc    480

catagtaacg ccaataggga ctttccattg acgtcaatgg gtggagtatt tacggtaaac    540

tgcccacttg gcagtacatc aagtgtatca tatgccaagt acgcccccta ttgacgtcaa    600

tgacggtaaa tggcccgcct ggcattatgc ccagtacatg accttatggg actttcctac    660

ttggcagtac atctacgtat tagtcatcgc tattaccatg gtgatgcggt tttggcagta    720

catcaatggg cgtggatagc ggtttgactc acggggattt ccaagtctcc accccattga    780

cgtcaatggg agtttgtttt ggcaccaaaa tcaacgggac tttccaaaat gtcgtaacaa    840

ctccgcccca ttgacgcaaa tgggcggtag gcgtgtacgg tgggaggtct atataagcag    900

agctcgttta gtgaaccgtc agatcgcctg gagacgccat ccacgctgtt ttgacctcca    960

tagaagacac cgggaccgat ccagcctccg cggccgggaa cggtgcattg gaacgcggat   1020

tccccgtgcc aagagtgacg taagtaccgc ctatagactc tataggcaca cccctttggc   1080

tcttatgcat gctatactgt ttttggcttg gggcctatac acccccgctt ccttatgcta   1140

taggtgatgg tatagcttag cctataggtg tgggttattg accattattg accactcccc   1200

tattggtgac gatactttcc attactaatc cataacatgg ctctttgcca caactatctc   1260

tattggctat atgccaatac tctgtccttc agagactgac acggactctg tatttttaca   1320

ggatggggtc ccatttatta tttacaaatt cacatataca acaacgccgt cccccgtgcc   1380

cgcagttttt attaaacata gcgtgggatc tccacgcgaa tctcgggtac gtgttccgga   1440

catgggctct tctccggtag cggcggagct tccacatccg agccctggtc ccatgcctcc   1500
```

-continued

```
agcggctcat ggtcgctcgg cagctccttg ctcctaacag tggaggccag acttaggcac   1560
agcacaatgc ccaccaccac cagtgtgccg cacaaggccg tggcggtagg gtatgtgtct   1620
gaaaatgagc gtggagattg ggctcgcacg gctgacgcag atggaagact taaggcagcg   1680
gcagaagaag atgcaggcag ctgagttgtt gtattctgat aagagtcaga ggtaactccc   1740
gttgcggtgc tgttaacggt ggagggcagt gtagtctgag cagtactcgt tgctgccgcg   1800
cgcgccacca gacataatag ctgacagact aacagactgt tcctttccat gggtcttttc   1860
tgcagtcacc gtcgtcgaca cgtgtgatca gatatcgcgg ccgctctaga gatatcgccg   1920
ccatgaagac cacctgcctg ttcatcagcc tgatcctgat ccagggcatc aagaccctgc   1980
ccatcctgga gatcgccagc aacaaccagc cccagaacgt ggacagcgtg tgcagcggca   2040
ccctgcagaa gaccgaggac gtgcacctga tgggcttcac cctgagcggc cagaaggtgg   2100
ccgacagccc tctggaggcc agcaagaggt gggccttcag gaccggcgtg ccccccaaga   2160
acgtggagta caccgagggc gaggaggcca agacctgcta caacatcagc gtgaccgacc   2220
ccagcggcaa gagcctgctg ctggaccctc ccaccaacat cagggactac cctaagtgca   2280
agaccatcca ccacatccag ggccagaacc ctcacgccca gggcatcgcc ctgcacctgt   2340
ggggcgcctt cttcctgtac gacaggatcg ccagcaccac catgtacagg ggcagggtgt   2400
tcaccgaggg caacatcgcc gccatgatcg ttaacaagac cgtgcacaag atgatcttca   2460
gcaggcaggg ccagggctac aggcacatga acctgaccag caccaacaag tactggacca   2520
gcaacaacgg cacccagacc aacgacaccg gctgcttcgg cgccctgcag gagtacaaca   2580
gcaccaagaa ccagacctgc gcccccagca agatccccag cccccctgccc accgccaggc  2640
ccgagatcaa gcccaccagc acccccaccg acgccaccac cctgaacacc accgacccca   2700
acaacgacga cgaggacctg atcaccagcg gcagcggcag cggcgagcag gagccctaca   2760
ccaccagcga cgccgtgacc aagcagggcc tgagcagcac catgcctcct accccctagcc  2820
ctcagcccag caccccctcag caggagggca acaacaccga ccacagccag ggcaccgtga  2880
ccgagcccaa caagaccaac accaccgccc agcccagcat gcctcctcac aacaccaccg   2940
ccatcagcac caacaacacc agcaagaaca acttcagcac cctgagcgtg agcctgcaga   3000
acaccaccaa ctacgacacc cagagcaccg ccaccgagaa cgagcagacc agcgcccccta  3060
gcaagaccac cctgcctccc accggcaacc tgaccaccgc caagagcacc aacaacacca   3120
agggccccac caccaccgcc cctaacatga ccaacggcca cctgaccagc cccagcccca   3180
cccccaaccc caccacccag cacctggtgt acttcaggaa gaagaggagc atcctgtgga   3240
gggagggcga tatgttcccc ttcctggacg gcctgatcaa cgcccctatc gacttcgacc   3300
ccgtgcccaa caccaagacc atcttcgacg agagcagcag cagcggcgcc agcgccgagg   3360
aggaccagca cgccagcccc aacatcagcc tgaccctgag ctacttcccc aacatcaacg   3420
agaacaccgc ctacagcggc gagaacgaga acgactgcga cgccgagctg aggatctgga   3480
gcgtgcagga ggacgacctg gccgccggcc tgagctggat tcccttcttc ggccccggca   3540
tcgagggcct gtacaccgcc ggcctgatca agaaccagaa caacctggtg tgcaggctga   3600
ggaggctggc caaccagacc gccaagagcc tggagctgct gctgagggtg accaccgagg   3660
agaggacctt cagcctgatc aacaggcacg ccatcgactt cctgctgacc aggtggggcg   3720
gcacctgcaa ggtgctgggc cccgactgct gcatcggcat cgaggacctg agcaggaaca   3780
tcagcgagca gatcgaccag atcaagaagg acgagcagaa ggagggcacc ggctggggcc   3840
tgggcggcaa gtggtggacc agcgactgaa cacgtgggat ccagatctgc tgtgccttct   3900
```

agttgccagc catctgttgt ttgcccctcc cccgtgcctt ccttgaccct ggaaggtgcc 3960
actcccactg tcctttccta ataaaatgag gaaattgcat cgcattgtct gagtaggtgt 4020
cattctattc tggggggtgg ggtggggcag gacagcaagg gggaggattg ggaagacaat 4080
agcaggcatg ctggggatgc ggtgggctct atgggtaccc aggtgctgaa gaattgaccc 4140
ggttcctcct gggccagaaa gaagcaggca catccccttc tctgtgacac accctgtcca 4200
cgcccctggt tcttagttcc agccccactc ataggacact catagctcag gagggctccg 4260
ccttcaatcc cacccgctaa agtacttgga gcggtctctc cctccctcat cagcccacca 4320
aaccaaacct agcctccaag agtgggaaga aattaaagca agataggcta ttaagtgcag 4380
agggagagaa aatgcctcca acatgtgagg aagtaatgag agaaatcata gaattttaag 4440
gccatgattt aaggccatca tggccttaat cttccgcttc ctcgctcact gactcgctgc 4500
gctcggtcgt tcggctgcgg cgagcggtat cagctcactc aaaggcggta atacggttat 4560
ccacagaatc aggggataac gcaggaaaga acatgtgagc aaaaggccag caaaaggcca 4620
ggaaccgtaa aaaggccgcg ttgctggcgt ttttccatag gctccgcccc cctgacgagc 4680
atcacaaaaa tcgacgctca agtcagaggt ggcgaaaccc gacaggacta taaagatacc 4740
aggcgtttcc ccctggaagc tccctcgtgc gctctcctgt tccgaccctg ccgcttaccg 4800
gatacctgtc cgcctttctc ccttcgggaa gcgtggcgct ttctcatagc tcacgctgta 4860
ggtatctcag ttcggtgtag gtcgttcgct ccaagctggg ctgtgtgcac gaaccccccg 4920
ttcagcccga ccgctgcgcc ttatccggta actatcgtct tgagtccaac ccggtaagac 4980
acgacttatc gccactggca gcagccactg gtaacaggat tagcagagcg aggtatgtag 5040
gcggtgctac agagttcttg aagtggtggc ctaactacgg ctacactaga agaacagtat 5100
ttggtatctg cgctctgctg aagccagtta ccttcggaaa aagagttggt agctcttgat 5160
ccggcaaaca aaccaccgct ggtagcggtg gtttttttgt ttgcaagcag cagattacgc 5220
gcagaaaaaa aggatctcaa gaagatcctt tgatcttttc tacggggtct gacgctcagt 5280
ggaacgaaaa ctcacgttaa gggattttgg tcatgagatt atcaaaaagg atcttcacct 5340
agatcctttt aaattaaaaa tgaagtttta aatcaatcta aagtatatat gagtaaactt 5400
ggtctgacag ttaccaatgc ttaatcagtg aggcacctat ctcagcgatc tgtctatttc 5460
gttcatccat agttgcctga ctcggggggg gggggcgctg aggtctgcct cgtgaagaag 5520
gtgttgctga ctcataccag gcctgaatcg ccccatcatc cagccagaaa gtgagggagc 5580
cacggttgat gagagctttg ttgtaggtgg accagttggt gattttgaac ttttgctttg 5640
ccacggaacg gtctgcgttg tcgggaagat gcgtgatctg atccttcaac tcagcaaaag 5700
ttcgatttat tcaacaaagc cgccgtcccg tcaagtcagc gtaatgctct gccagtgtta 5760
caaccaatta accaattctg attagaaaaa ctcatcgagc atcaaatgaa actgcaattt 5820
attcatatca ggattatcaa taccatattt ttgaaaaagc cgtttctgta atgaaggaga 5880
aaactcaccg aggcagttcc ataggatggc aagatcctgg tatcggtctg cgattccgac 5940
tcgtccaaca tcaatacaac ctattaattt cccctcgtca aaaataaggt tatcaagtga 6000
gaaatcacca tgagtgacga ctgaatccgg tgagaatggc aaaagcttat gcatttcttt 6060
ccagacttgt tcaacaggcc agccattacg ctcgtcatca aaatcactcg catcaaccaa 6120
accgttattc attcgtgatt gcgcctgagc gagacgaaat acgcgatcgc tgttaaaagg 6180
acaattacaa acaggaatcg aatgcaaccg gcgcaggaac actgccagcg catcaacaat 6240
attttcacct gaatcaggat attcttctaa tacctggaat gctgttttcc cggggatcgc 6300

-continued

```
agtggtgagt aaccatgcat catcaggagt acggataaaa tgcttgatgg tcggaagagg   6360
cataaattcc gtcagccagt ttagtctgac catctcatct gtaacatcat tggcaacgct   6420
acctttgcca tgtttcagaa acaactctgg cgcatcgggc ttcccataca atcgatagat   6480
tgtcgcacct gattgcccga cattatcgcg agcccattta tacccatata aatcagcatc   6540
catgttggaa tttaatcgcg gcctcgagca agacgtttcc cgttgaatat ggctcataac   6600
accccttgta ttactgttta tgtaagcaga cagttttatt gttcatgatg atatattttt   6660
atcttgtgca atgtaacatc agagattttg agacacaacg tggctttccc cccccccca    6720
ttattgaagc atttatcagg gttattgtct catgagcgga tacatatttg aatgtattta   6780
gaaaaataaa caaatagggg ttccgcgcac atttccccga aaagtgccac ctgacgtcta   6840
agaaaccatt attatcatga cattaaccta taaaaatagg cgtatcacga ggccctttcg   6900
tc                                                                  6902
```

<210> SEQ ID NO 43
<211> LENGTH: 6625
<212> TYPE: DNA
<213> ORGANISM: Artificial Sequence
<220> FEATURE:
<223> OTHER INFORMATION: Synthetic Construct CMV/R Ebola NP

<400> SEQUENCE: 43

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcagattgg    240
ctattggcca ttgcatacgt tgtatccata tcataatatg tacatttata ttggctcatg    300
tccaacatta ccgccatgtt gacattgatt attgactagt tattaatagt aatcaattac    360
ggggtcatta gttcatagcc catatatgga gttccgcgtt acataactta cggtaaatgg    420
cccgcctggc tgaccgccca acgacccccg cccattgacg tcaataatga cgtatgttcc    480
catagtaacg ccaataggga ctttccattg acgtcaatgg gtggagtatt tacggtaaac    540
tgcccacttg gcagtacatc aagtgtatca tatgccaagt acgcccccta ttgacgtcaa    600
tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctcca tcggctcgca tctctccttc acgcgcccgc   1020
cgccttacct gaggccgcca tccacgccgg ttgagtcgcg ttctgccgcc tcccgcctgt   1080
ggtgcctcct gaactacgtc cgccgtctag gtaagtttag agctcaggtc gagaccgggc   1140
ctttgtccgg cgctcccttg gagcctacct agactcagcc ggctctccac gctttgcctg   1200
accctgcttg ctcaactcta gttaacggtg gagggcagtg tagtctgagc agtactcgtt   1260
gctgccgcgc gcgccaccag acataatagc tgacagacta acagactgtt cctttccatg   1320
ggtcttttct gcagtcaccg tcgtcgacac gtgtgatcag atatcgcggc cgctctagac   1380
caggccctgg atccagatcg atccgagtat ggattctcgt cctcagaaaa tctggatggc   1440
```

-continued

```
gccgagtctc actgaatctg acatggatta ccacaagatc ttgacagcag gtctgtccgt   1500
tcaacagggg attgttcggc aaagagtcat cccagtgtat caagtaaaca atcttgaaga   1560
aatttgccaa cttatcatac aggcctttga agcaggtgtt gattttcaag agagtgcgga   1620
cagtttcctt ctcatgcttt gtcttcatca tgcgtaccag ggagattaca aacttttctt   1680
ggaaagtggc gcagtcaagt atttggaagg gcacgggttc cgttttgaag tcaagaagcg   1740
tgatggagtg aagcgccttg aggaattgct gccagcagta tctagtggaa aaaacattaa   1800
gagaacactt gctgccatgc cggaagagga gacaactgaa gctaatgccg gtcagtttct   1860
ctcctttgca agtctattcc ttccgaaatt ggtagtagga gaaaaggctt gccttgagaa   1920
ggttcaaagg caaattcaag tacatgcaga gcaaggactg atacaatatc caacagcttg   1980
gcaatcagta ggacacatga tggtgatttt ccgtttgatg cgaacaaatt ttctgatcaa   2040
atttctccta atacaccaag ggatgcacat ggttgccggg catgatgcca acgatgctgt   2100
gatttcaaat tcagtggctc aagctcgttt ttcaggctta ttgattgtca aaacagtact   2160
tgatcatatc ctacaaaaga cagaacgagg agttcgtctc catcctcttg caaggaccgc   2220
caaggtaaaa aatgaggtga actcctttaa ggctgcactc agctccctgg ccaagcatgg   2280
agagtatgct cctttcgccc gacttttgaa cctttctgga gtaaataatc ttgagcatgg   2340
tcttttccct caactatcgg caattgcact cggagtcgcc acagcacacg ggagtaccct   2400
cgcaggagta aatgttggag aacagtatca acaactcaga gaggctgcca ctgaggctga   2460
gaagcaactc caacaatatg cagagtctcg cgaacttgac catcttggac ttgatgatca   2520
ggaaaagaaa attcttatga acttccatca gaaaaagaac gaaatcagct tccagcaaac   2580
aaacgctatg gtaactctaa gaaaagagcg cctggccaag ctgacagaag ctatcactgc   2640
tgcgtcactg cccaaaacaa gtggacatta cgatgatgat gacgacattc cctttccagg   2700
acccatcaat gatgacgaca atcctggcca tcaagatgat gatccgactg actcacagga   2760
tacgaccatt cccgatgtgg tggttgatcc cgatgatgga agctacggcg aataccagag   2820
ttactcggaa aacggcatga atgcaccaga tgacttggtc ctattcgatc tagacgagga   2880
cgacgaggac actaagccag tgcctaatag atcgaccaag ggtggacaac agaagaacag   2940
tcaaaagggc cagcatatag agggcagaca gacacaatcc aggccaattc aaaatgtccc   3000
aggccctcac agaacaatcc accacgccag tgcgccactc acggacaatg acagaagaaa   3060
tgaaccctcc ggctcaacca gccctcgcat gctgacacca attaacgaag aggcagaccc   3120
actggacgat gccgacgacg agacgtctag ccttccgccc ttggagtcag atgatgaaga   3180
gcaggacagg gacggaactt ccaaccgcac acccactgtc gccccaccgg ctcccgtata   3240
cagagatcac tctgaaaaga aagaactccc gcaagacgag caacaagatc aggaccacac   3300
tcaagaggcc aggaaccagg acagtgacaa cacccagtca gaacactctt ttgaggagat   3360
gtatcgccac attctaagat cacaggggcc atttgatgct gttttgtatt atcatatgat   3420
gaaggatgag cctgtagttt tcagtaccag tgatggcaaa gagtacacgt atccagactc   3480
ccttgaagag gaatatccac catggctcac tgaaaaagag gctatgaatg aagagaatag   3540
atttgttaca ttggatggtc aacaatttta ttggccggtg atgaatcaca agaataaatt   3600
catggcaatc ctgcaacatc atcagctgtg ccttctagtt gccagccatc tgttgtttgc   3660
ccctcccccg tgccttcctt gaccctggaa ggtgccactc ccactgtcct ttcctaataa   3720
aatgaggaaa ttgcatcgca ttgtctgagt aggtgtcatt ctattctggg gggtggggtg   3780
gggcaggaca gcaaggggga ggattgggaa gacaatagca ggcatgctgg ggatgcggtg   3840
```

-continued

```
ggctctatgg gtacccaggt gctgaagaat tgacccggtt cctcctgggc cagaaagaag   3900
caggcacatc cccttctctg tgacacaccc tgtccacgcc cctggttctt agttccagcc   3960
ccactcatag gacactcata gctcaggagg gctccgcctt caatcccacc cgctaaagta   4020
cttggagcgg tctctccctc cctcatcagc ccaccaaacc aaacctagcc tccaagagtg   4080
ggaagaaatt aaagcaagat aggctattaa gtgcagaggg agagaaaatg cctccaacat   4140
gtgaggaagt aatgagagaa atcatagaat tttaaggcca tcatggcctt aatcttccgc   4200
ttcctcgctc actgactcgc tgcgctcggt cgttcggctg cggcgagcgg tatcagctca   4260
ctcaaaggcg gtaatacggt tatccacaga atcaggggat aacgcaggaa agaacatgtg   4320
agcaaaaggc cagcaaaagg ccaggaaccg taaaaaggcc gcgttgctgg cgtttttcca   4380
taggctccgc ccccctgacg agcatcacaa aaatcgacgc tcaagtcaga ggtggcgaaa   4440
cccgacagga ctataaagat accaggcgtt tccccctgga agctccctcg tgcgctctcc   4500
tgttccgacc ctgccgctta ccggatacct gtccgccttt ctcccttcgg gaagcgtggc   4560
gctttctcat agctcacgct gtaggtatct cagttcggtg taggtcgttc gctccaagct   4620
gggctgtgtg cacgaacccc ccgttcagcc cgaccgctgc gccttatccg gtaactatcg   4680
tcttgagtcc aacccggtaa gacacgactt atcgccactg gcagcagcca ctggtaacag   4740
gattagcaga gcgaggtatg taggcggtgc tacagagttc ttgaagtggt ggcctaacta   4800
cggctacact agaagaacag tatttggtat ctgcgctctg ctgaagccag ttaccttcgg   4860
aaaaagagtt ggtagctctt gatccggcaa acaaaccacc gctggtagcg gtggtttttt   4920
tgtttgcaag cagcagatta cgcgcagaaa aaaaggatct caagaagatc ctttgatctt   4980
ttctacgggg tctgacgctc agtggaacga aaactcacgt taagggattt tggtcatgag   5040
attatcaaaa aggatcttca cctagatcct tttaaattaa aaatgaagtt ttaaatcaat   5100
ctaaagtata tatgagtaaa cttggtctga cagttaccaa tgcttaatca gtgaggcacc   5160
tatctcagcg atctgtctat ttcgttcatc catagttgcc tgactcgggg ggggggggcg   5220
ctgaggtctg cctcgtgaag aaggtgttgc tgactcatac caggcctgaa tcgccccatc   5280
atccagccag aaagtgaggg agccacggtt gatgagagct ttgttgtagg tggaccagtt   5340
ggtgattttg aacttttgct ttgccacgga acggtctgcg ttgtcgggaa gatgcgtgat   5400
ctgatccttc aactcagcaa aagttcgatt tattcaacaa agccgccgtc ccgtcaagtc   5460
agcgtaatgc tctgccagtg ttacaaccaa ttaaccaatt ctgattagaa aaactcatcg   5520
agcatcaaat gaaactgcaa tttattcata tcaggattat caataccata tttttgaaaa   5580
agccgtttct gtaatgaagg agaaaactca ccgaggcagt tccataggat ggcaagatcc   5640
tggtatcggt ctgcgattcc gactcgtcca acatcaatac aacctattaa tttcccctcg   5700
tcaaaaataa ggttatcaag tgagaaatca ccatgagtga cgactgaatc cggtgagaat   5760
ggcaaaagct tatgcatttc tttccagact tgttcaacag gccagccatt acgctcgtca   5820
tcaaaatcac tcgcatcaac caaaccgtta ttcattcgtg attgcgcctg agcgagacga   5880
aatacgcgat cgctgttaaa aggacaatta caaacaggaa tcgaatgcaa ccggcgcagg   5940
aacactgcca gcgcatcaac aatattttca cctgaatcag gatattcttc taatacctgg   6000
aatgctgttt tcccggggat cgcagtggtg agtaaccatg catcatcagg agtacggata   6060
aaatgcttga tggtcggaag aggcataaat tccgtcagcc agtttagtct gaccatctca   6120
tctgtaacat cattggcaac gctacctttg ccatgtttca gaaacaactc tggcgcatcg   6180
ggcttcccat acaatcgata gattgtcgca cctgattgcc cgacattatc gcgagcccat   6240
```

-continued

```
ttatacccat ataaatcagc atccatgttg gaatttaatc gcggcctcga gcaagacgtt   6300

tcccgttgaa tatggctcat aacacccctt gtattactgt ttatgtaagc agacagtttt   6360

attgttcatg atgatatatt tttatcttgt gcaatgtaac atcagagatt ttgagacaca   6420

acgtggcttt cccccccccc ccattattga agcatttatc agggttattg tctcatgagc   6480

ggatacatat ttgaatgtat ttagaaaaat aaacaaatag gggttccgcg cacatttccc   6540

cgaaaagtgc cacctgacgt ctaagaaacc attattatca tgacattaac ctataaaaat   6600

aggcgtatca cgaggccctt tcgtc                                         6625


<210> SEQ ID NO 44
<211> LENGTH: 22
<212> TYPE: DNA
<213> ORGANISM: Artificial Sequence
<220> FEATURE:
<223> OTHER INFORMATION: Ebola Sudan GP primer

<400> SEQUENCE: 44

atcttcagga tctcgccatg ga                                              22


<210> SEQ ID NO 45
<211> LENGTH: 24
<212> TYPE: DNA
<213> ORGANISM: Artificial Sequence
<220> FEATURE:
<223> OTHER INFORMATION: Ebola Sudan GP primer

<400> SEQUENCE: 45

gatattcaac aaagcagctt gcag                                            24


<210> SEQ ID NO 46
<211> LENGTH: 21
<212> TYPE: DNA
<213> ORGANISM: Artificial Sequence
<220> FEATURE:
<223> OTHER INFORMATION: Ebola Ivory Coast GP primer

<400> SEQUENCE: 46

ctaatcacag tcaccatggg a                                               21


<210> SEQ ID NO 47
<211> LENGTH: 24
<212> TYPE: DNA
<213> ORGANISM: Artificial Sequence
<220> FEATURE:
<223> OTHER INFORMATION: Ebola Ivory Coast GP primer

<400> SEQUENCE: 47

aaagtatgat gctatattag ttca                                            24


<210> SEQ ID NO 48
<211> LENGTH: 10
<212> TYPE: PRT
<213> ORGANISM: Ebola Virus

<400> SEQUENCE: 48

Gln Arg Thr Phe Ser Ile Pro Leu Gly Val
 1               5                  10


<210> SEQ ID NO 49
<211> LENGTH: 10
<212> TYPE: PRT
<213> ORGANISM: Ebola Virus

<400> SEQUENCE: 49
```

-continued

Arg Arg Thr Arg Arg Glu Ala Ile Val Asn
1 5 10

<210> SEQ ID NO 50
<211> LENGTH: 16
<212> TYPE: PRT
<213> ORGANISM: Ebola Virus

<400> SEQUENCE: 50

Gly Ala Ala Ile Gly Leu Ala Trp Ile Pro Tyr Phe Gly Pro Ala Ala
1 5 10 15

<210> SEQ ID NO 51
<211> LENGTH: 5
<212> TYPE: PRT
<213> ORGANISM: Ebola Virus

<400> SEQUENCE: 51

Arg Arg Thr Arg Arg
1 5

<210> SEQ ID NO 52
<211> LENGTH: 1087
<212> TYPE: DNA
<213> ORGANISM: Artificial Sequence
<220> FEATURE:
<223> OTHER INFORMATION: The CMV Enhancer/Promoter, R Region (HTVL-1), CMV IE Splicing Acceptor sequence

<400> SEQUENCE: 52
ccattgcata cgttgtatcc atatcataat atgtacattt atattggctc atgtccaaca 60
ttaccgccat gttgacattg attattgact agttattaat agtaatcaat tacggggtca 120
ttagttcata gcccatatat ggagttccgc gttacataac ttacggtaaa tggcccgcct 180
ggctgaccgc ccaacgaccc ccgcccattg acgtcaataa tgacgtatgt tcccatagta 240
acgccaatag ggactttcca ttgacgtcaa tgggtggagt atttacggta aactgcccac 300
ttggcagtac atcaagtgta tcatatgcca agtacgcccc ctattgacgt caatgacggt 360
aaatggcccg cctggcatta tgcccagtac atgaccttat gggactttcc tacttggcag 420
tacatctacg tattagtcat cgctattacc atggtgatgc ggttttggca gtacatcaat 480
gggcgtggat agcggtttga ctcacgggga tttccaagtc tccaccccat tgacgtcaat 540
gggagtttgt tttggcacca aaatcaacgg gactttccaa aatgtcgtaa caactccgcc 600
ccattgacgc aaatgggcgg taggcgtgta cggtgggagg tctatataag cagagctcgt 660
ttagtgaacc gtcagatcgc ctggagacgc catccacgct gttttgacct ccatagaaga 720
caccgggacc gatccagcct ccatcggctc gcatctctcc ttcacgcgcc cgccgcctta 780
cctgaggccg ccatccacgc cggttgagtc gcgttctgcc gcctcccgcc tgtggtgcct 840
cctgaactac gtccgccgtc taggtaagtt tagagctcag gtcgagaccg ggcctttgtc 900
cggcgctccc ttggagccta cctagactca gccggctctc cacgctttgc ctgaccctgc 960
ttgctcaact ctagttaacg gtggagggca gtgtagtctg agcagtactc gttgctgccg 1020
cgcgcgccac cagacataat agctgacaga ctaacagact gttcctttcc atgggtcttt 1080
tctgcag 1087

DEVELOPMENT OF A PREVENTIVE VACCINE FOR FILOVIRUS INFECTION IN PRIMATES

This application is a division of U.S. patent application Ser. No. 10/491,121, filed Aug. 23, 2004, which is a 371 national phase of PCT/US02/30251, filed Sep. 24, 2002, which claims priority to U.S. Provisional Patent Application No. 60/326, 476, filed Oct. 1, 2001, the contents of both are incorporated herein in the entirety for all purposes.

FIELD OF THE INVENTION

The present invention relates generally to viral vaccines and, more particularly, to filovirus vaccines and methods of eliciting an immune response against a filovirus or a disease caused by infection with filovirus.

BACKGROUND OF THE INVENTION

The Ebola viruses, and the genetically-related Marburg virus, are filoviruses associated with outbreaks of highly lethal hemorrhagic fever in humans and primates in North America, Europe, and Africa (Peters, C. J. et al. in: *Fields Virology*, eds. Fields, B. N. et al. 1161-1176, Philadelphia, Lippincott-Raven, 1996; Peters, C. J. et al. 1994 *Semin Virol* 5:147-154). Ebola viruses are negative-stranded RNA viruses comprised of four subtypes, including those described in the Zaire, Sudan, Reston, and Ivory Coast episodes (Sanchez, A. et al. 1996 *PNAS USA* 93:3602-3607). Although several subtypes have been defined, the genetic organization of these viruses is similar, each containing seven linearly arrayed genes. Among the viral proteins, the envelope glycoprotein exists in two alternative forms, a 50-70 kilodalton (kDa) secreted protein of unknown function encoded by the viral genome and a 130 kDa transmembrane glycoprotein generated by RNA editing that mediates viral entry (Peters, C. J. et al. in: *Fields Virology*, eds. Fields, B. N. et al. 1161-1176, Philadelphia, Lippincott-Raven, 1996; Sanchez, A. et al. 1996 *PNAS USA* 93:3602-3607). Other structural gene products include the nucleoprotein (NP), matrix proteins VP24 and VP40, presumed nonstructural proteins VP30 and VP35, and the viral polymerase (reviewed in Peters, C. J. et al. in: *Fields Virology*, eds. Fields, B. N. et al. 1161-1176, Philadelphia, Lippincott-Raven, 1996). Although spontaneous variation of its RNA sequence does occur in nature, there appears to be less nucleotide polymorphism within Ebola subtypes than among other RNA viruses (Sanchez, A. et al. 1996 *PNAS* USA 93:3602-3607), suggesting that immunization may be useful in protecting against this disease. Previous attempts to elicit protective immune responses against Ebola virus using traditional active and passive immunization approaches have, however, not succeeded in primates (Peters, C. J. et al. in: *Fields Virology*, eds. Fields, B. N. et al. 1161-1176, Philadelphia, Lippincott-Raven, 1996; Clegg, J. C. S. et al. 1997 *New Generation Vaccines*, eds.: Levine, M. M. et al. 749-765, New York, N.Y. Marcel Dekker, Inc.; Jahrling, P. B. et al. 1996 *Arch Virol Suppl* 11:135-140). It would thus be desirable to provide a vaccine to elicit an immune response against a filovirus or disease caused by infection with filovirus. It would further be desirable to provide methods of making and using said vaccine.

SUMMARY OF THE INVENTION

Outbreaks of hemorrhagic fever caused by the Ebola virus are associated with high mortality rates that are a distinguishing feature of this human pathogen. The highest lethality is associated with the Zaire subtype, one of four strains identified to date (Feldmann, H. et al. 1994 *Virology* 199:469-473; Sanchez, A. et al. 1996 *PNAS* USA 93:3602-3607). Its rapid progression allows little opportunity to develop natural immunity, and there is currently no effective anti-viral therapy. Therefore, vaccination offers a promising intervention to prevent infection and limit spread. Here we describe a highly effective vaccine strategy for Ebola virus infection in primates. A combination of DNA immunization and boosting with adenoviral vectors that encode viral proteins generated cellular and humoral immunity in cynomolgus macaques. Challenge with a lethal dose of the highly pathogenic, wild-type, 1976 Maying a strain of Ebola Zaire virus resulted in uniform infection in controls, who progressed to a moribund state and death in less than one week. In contrast, all vaccinated animals were asymptomatic for more than six months, with no detectable virus after the initial challenge. These findings demonstrate that it is possible to develop a preventive vaccine against Ebola virus infection in primates.

BRIEF DESCRIPTION OF THE DRAWINGS

FIG. 7 shows VRC6006 (pVR1012-GP(Z) delta GP2 delta C-term B) construct map (see, Ebola/Marburg/Lassa Plasmids, and Recombinant Adenoviruses in Table 2).

FIG. 38 shows pVR1012 Ebola GP (Z, P87666) delta TM/h (codon optimized) construct map (see, Ebola/Marburg/Lassa Plasmids, and Recombinant Adenoviruses in Table 2).

FIG. 50 (A-B) shows enhanced expression of modified CMV expression vector, CMV/R.

TABLE 1

Figure 1:
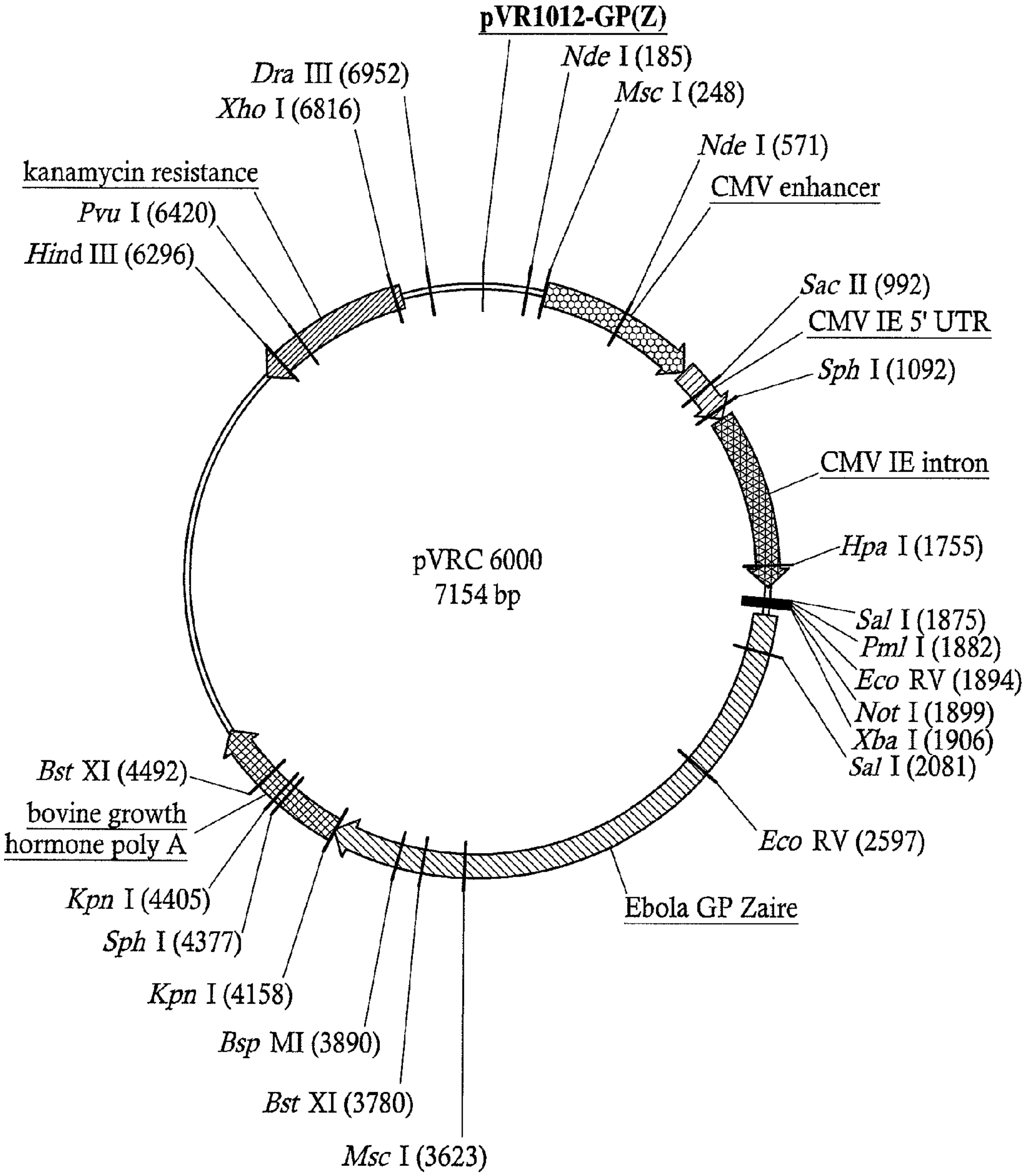
FIG. 1 shows VRC6000 (pVR1012-GP(Z)) construct map (see, Ebola/Marburg/Lassa Plasmids, and Recombinant Adenoviruses in Table 2).
Figure 2:
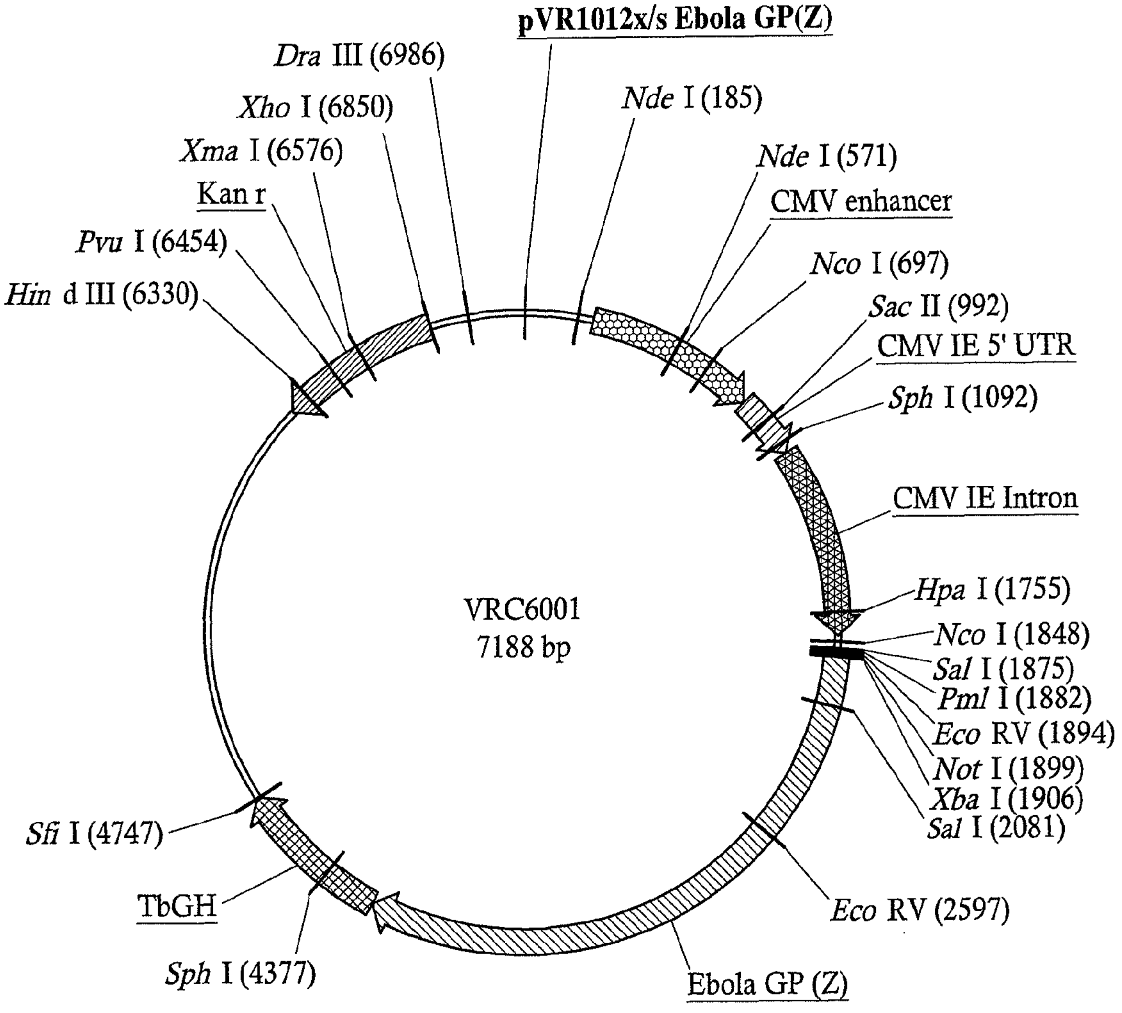
FIG. 2 shows VRC6001 (pVR1012x/s-GP(Z)) construct map (see, Ebola/Marburg/Lassa Plasmids, and Recombinant Adenoviruses in Table 2).
Figure 3:
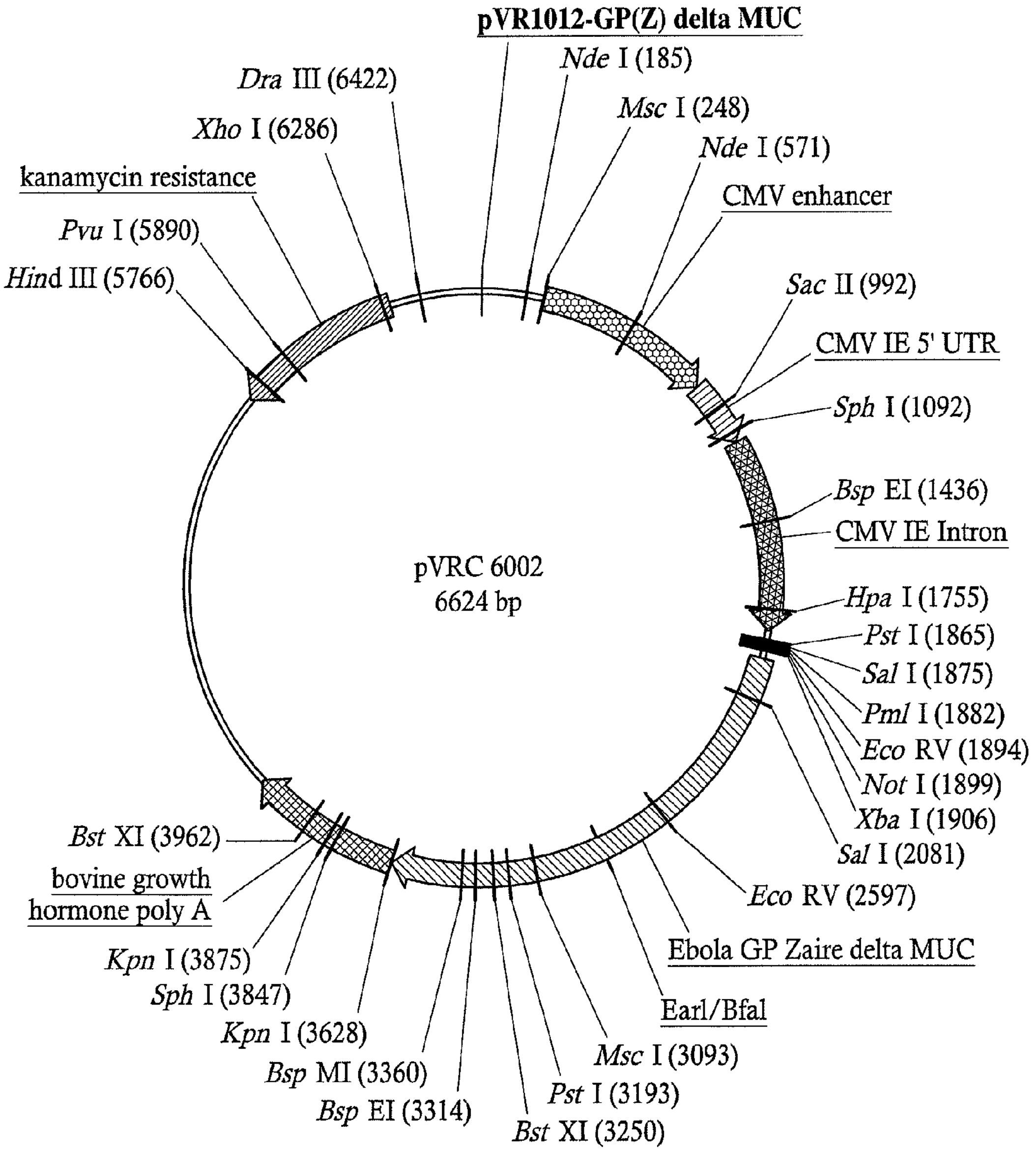
FIG. 3 shows VRC6002 (pVR1012-GP(Z) delta MUC) construct map (see, Ebola/Marburg/Lassa Plasmids, and Recombinant Adenoviruses in Table 2).
Figure 4:
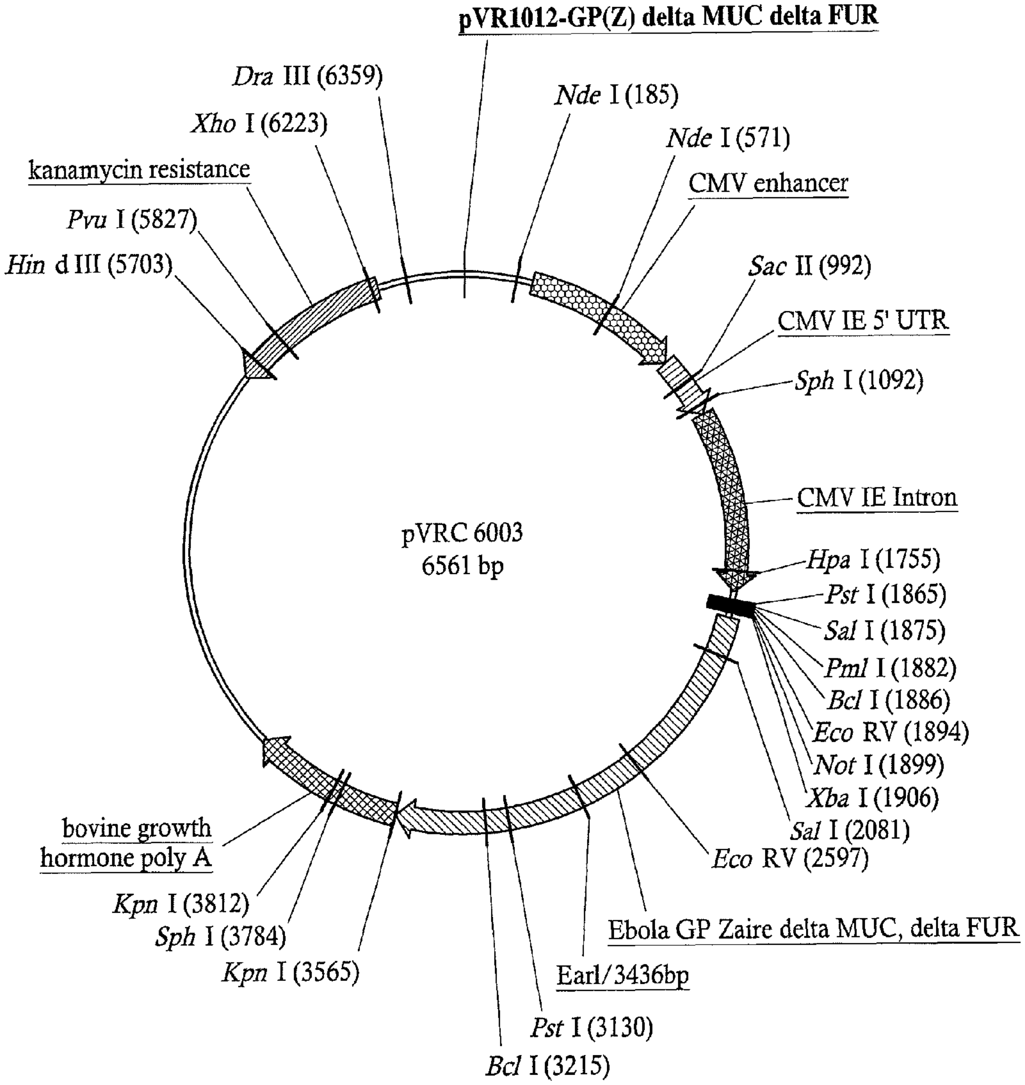
FIG. 4 shows VRC6003 (pVR1012-GP(Z) delta MUC delta FUR) construct map (see, Ebola/Marburg/Lassa Plasmids, and Recombinant Adenoviruses in Table 2).
Figure 5:
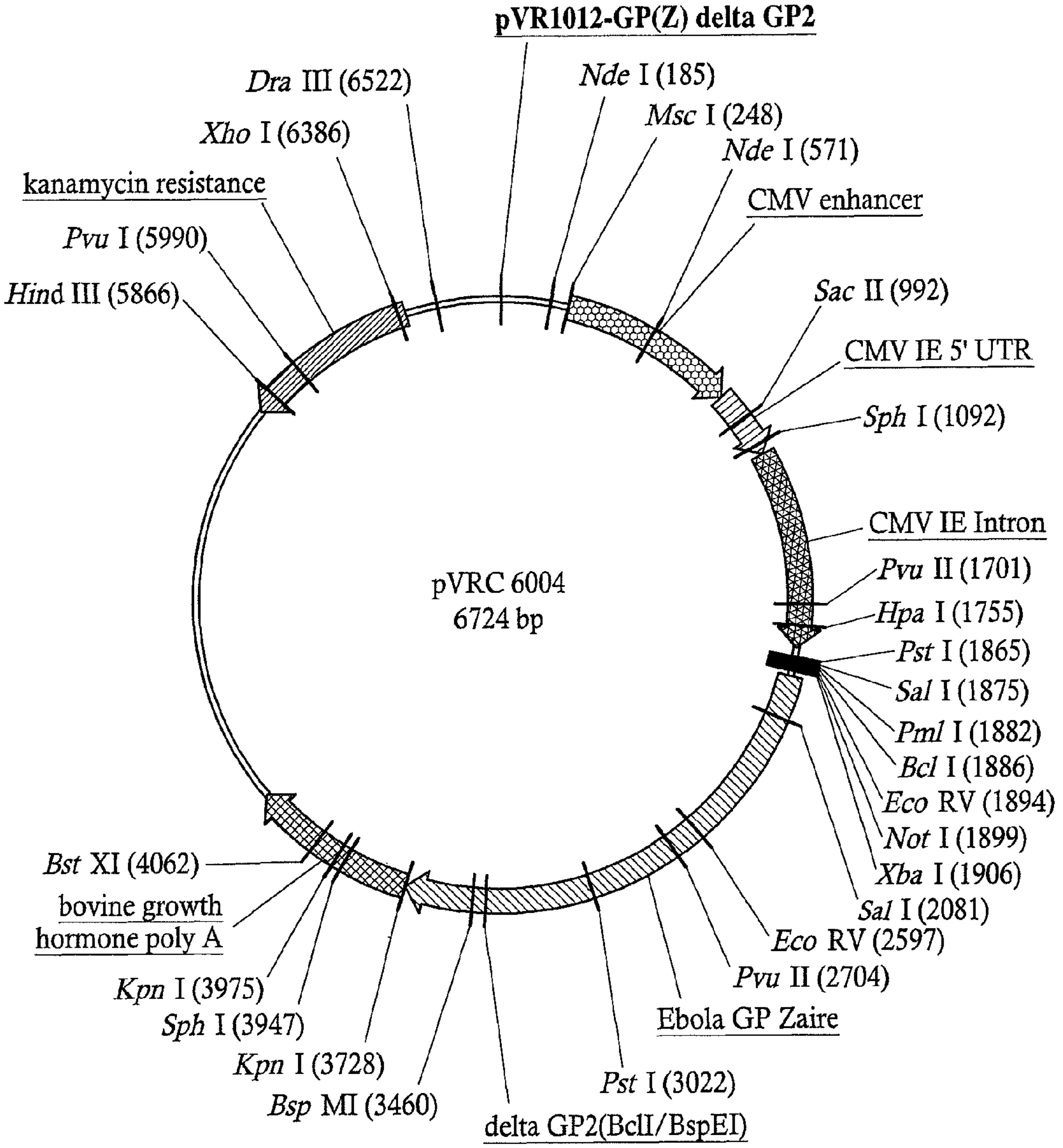
FIG. 5 shows VRC6004 (pVR1012-GP(Z) delta GP2) construct map (see, Ebola/Marburg/Lassa Plasmids, and Recombinant Adenoviruses in Table 2).
Figure 6:
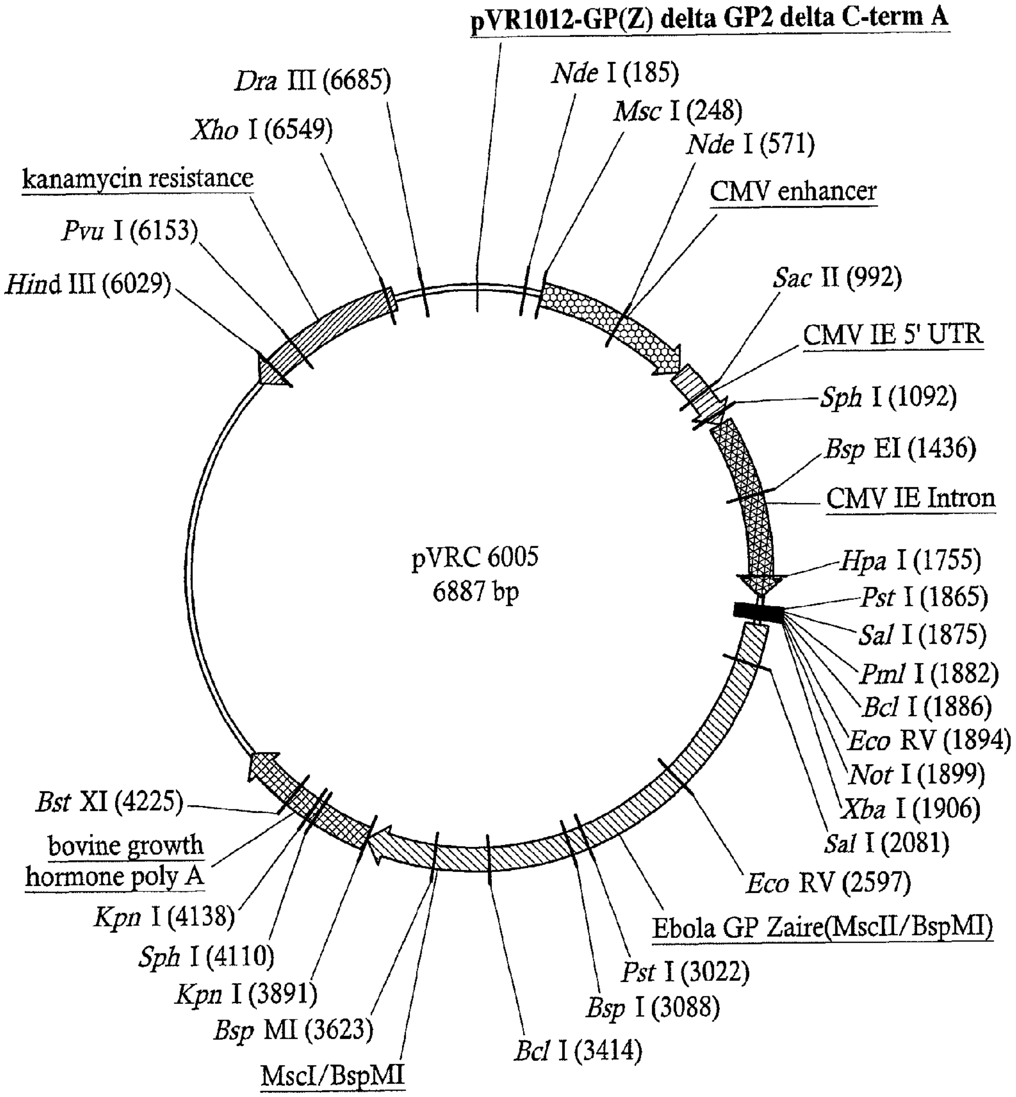
FIG. 6 shows VRC6005 (pVR1012-GP(Z) delta GP2 delta C-term A) construct map (see, Ebola/Marburg/Lassa Plasmids, and Recombinant Adenoviruses in Table 2).
Figure 8:
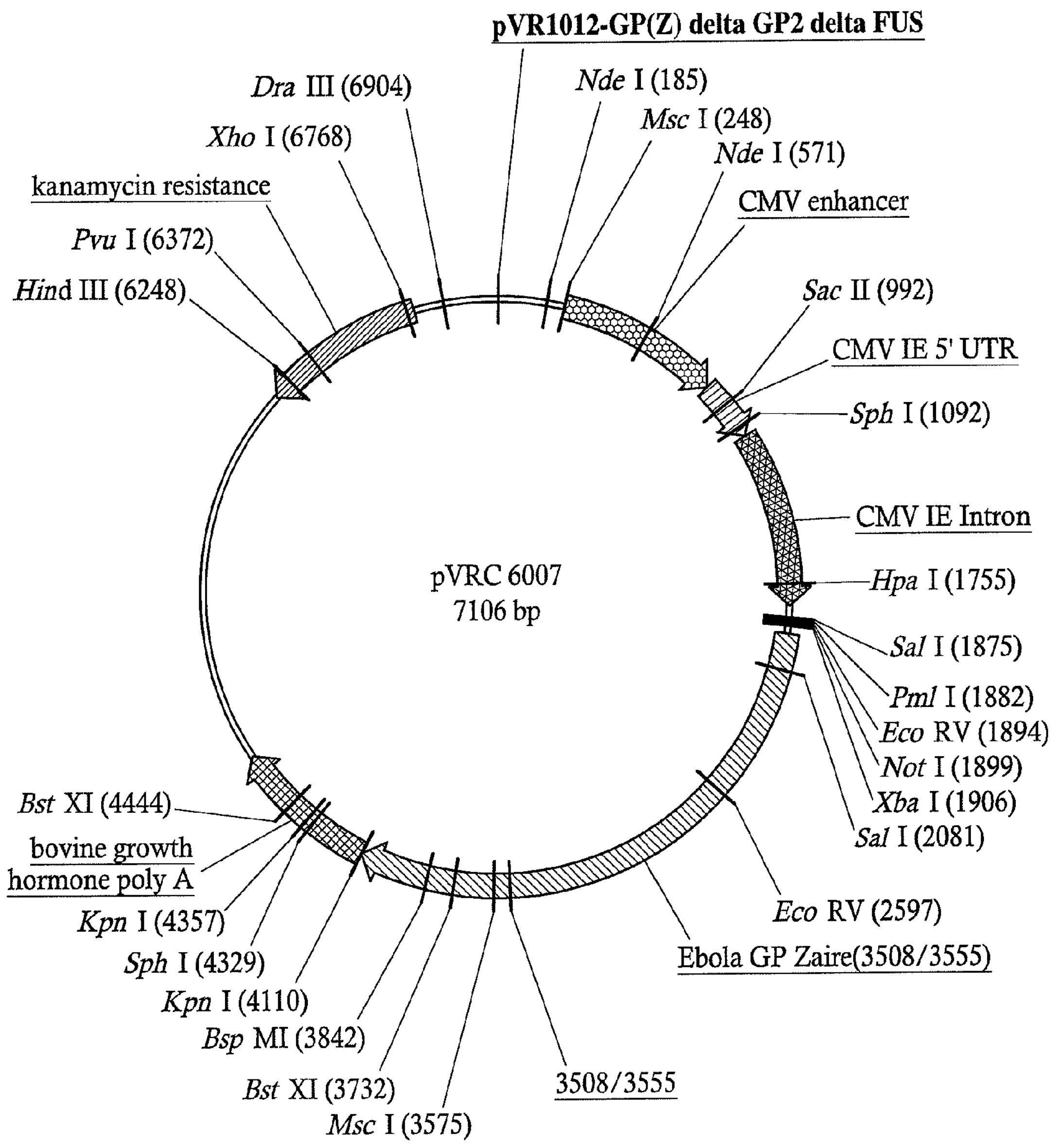
FIG. 8 shows VRC6007 (pVR1012-GP(Z) delta GP2 delta FUS) construct map (see, Ebola/Marburg/Lassa Plasmids, and Recombinant Adenoviruses in Table 2).
Figure 9:
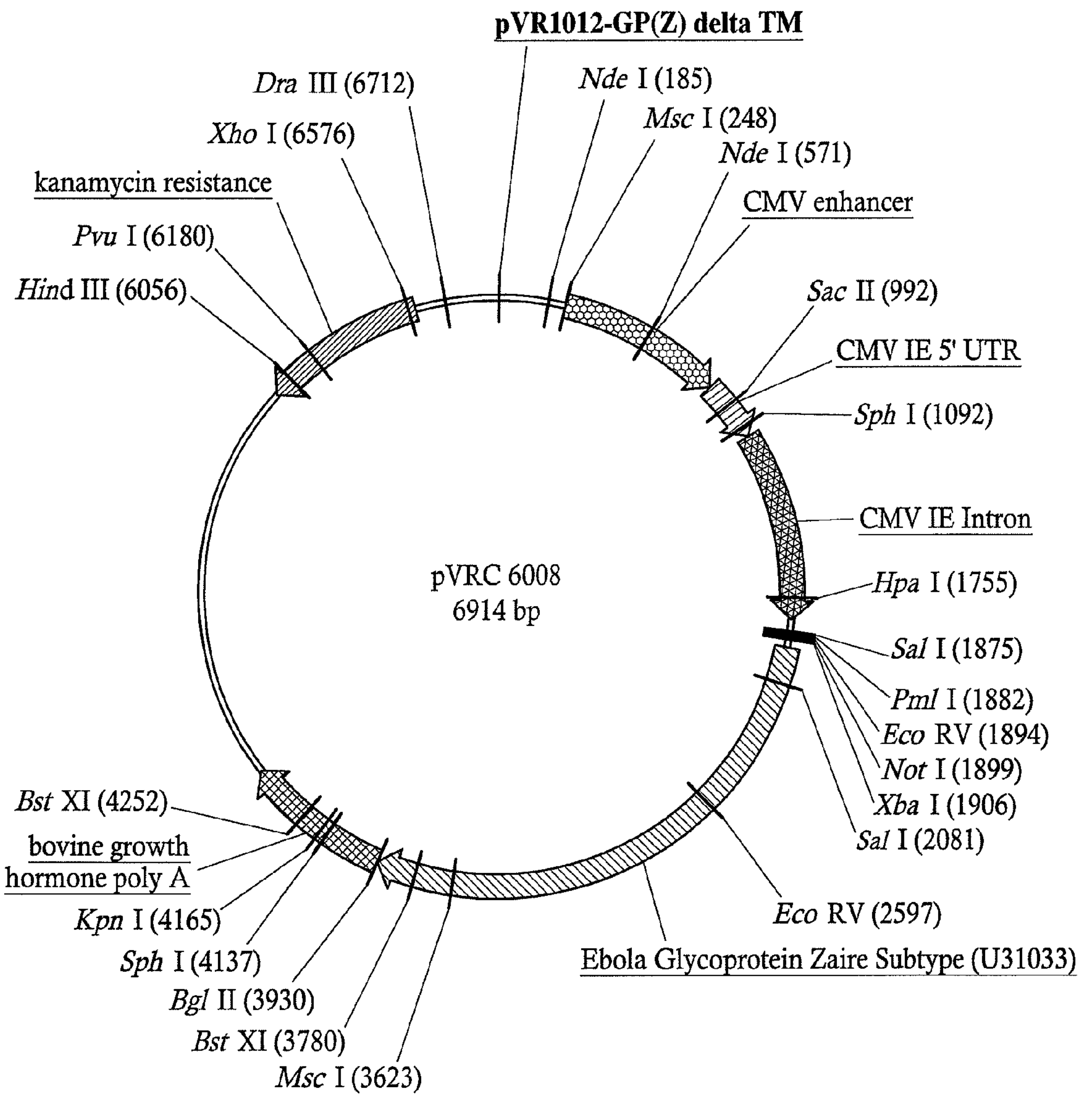
FIG. 9 shows VRC6008 (pVR1012-GP(Z) delta TM) construct map (see, Ebola/Marburg/Lassa Plasmids, and Recombinant Adenoviruses in Table 2).
Figure 10:
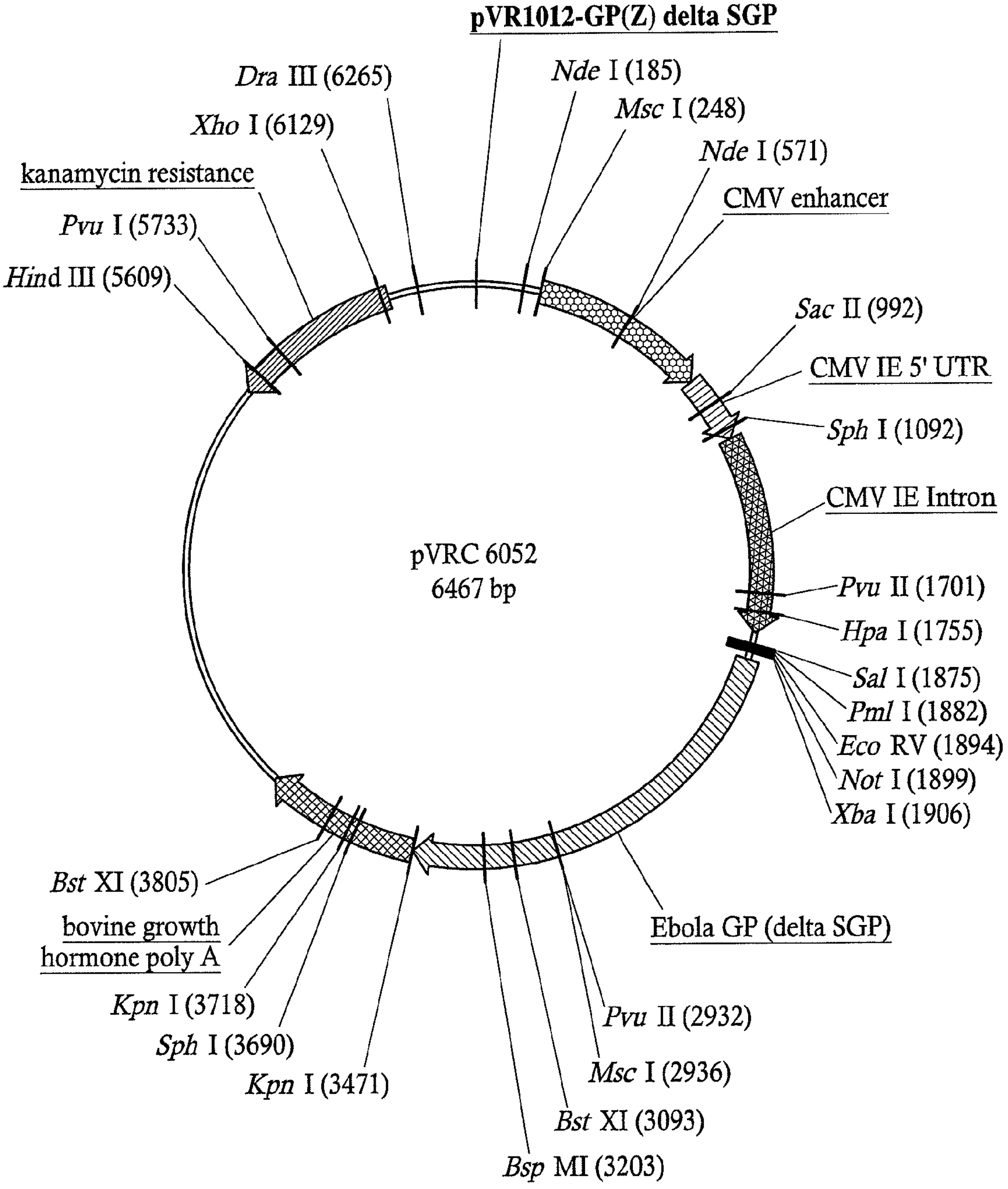
FIG. 10 shows VRC 6052 (pVR1012-GP(Z) delta SGP) construct map (see, Ebola/Marburg/Lassa Plasmids, and Recombinant Adenoviruses in Table 2).
Figure 11:
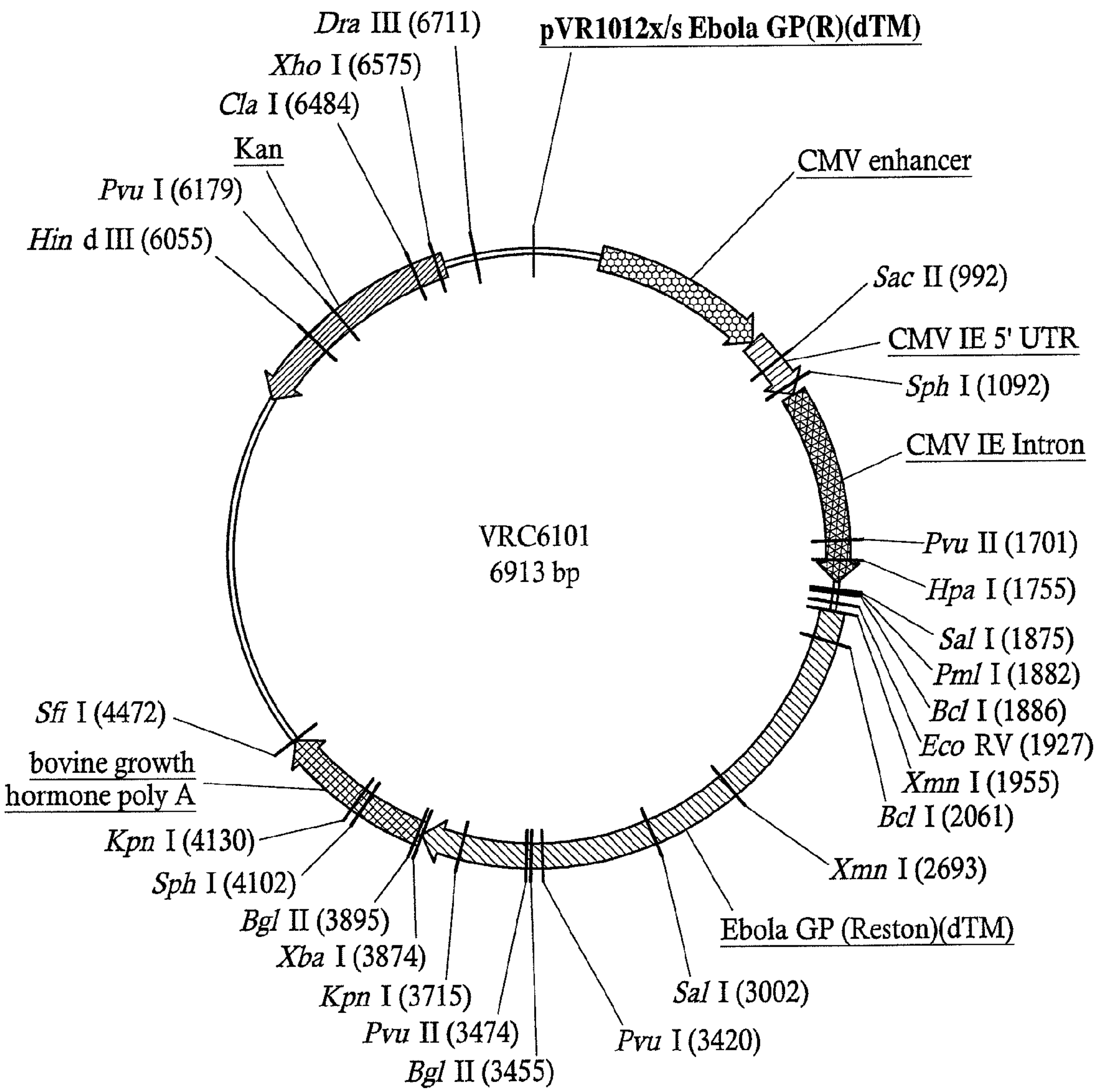
FIG. 11 shows VRC 6101 (pVR1012x/s Ebola GP(R) (dTM)) construct map (see, Ebola/Marburg/Lassa Plasmids, and Recombinant Adenoviruses in Table 2).
Figure 12:
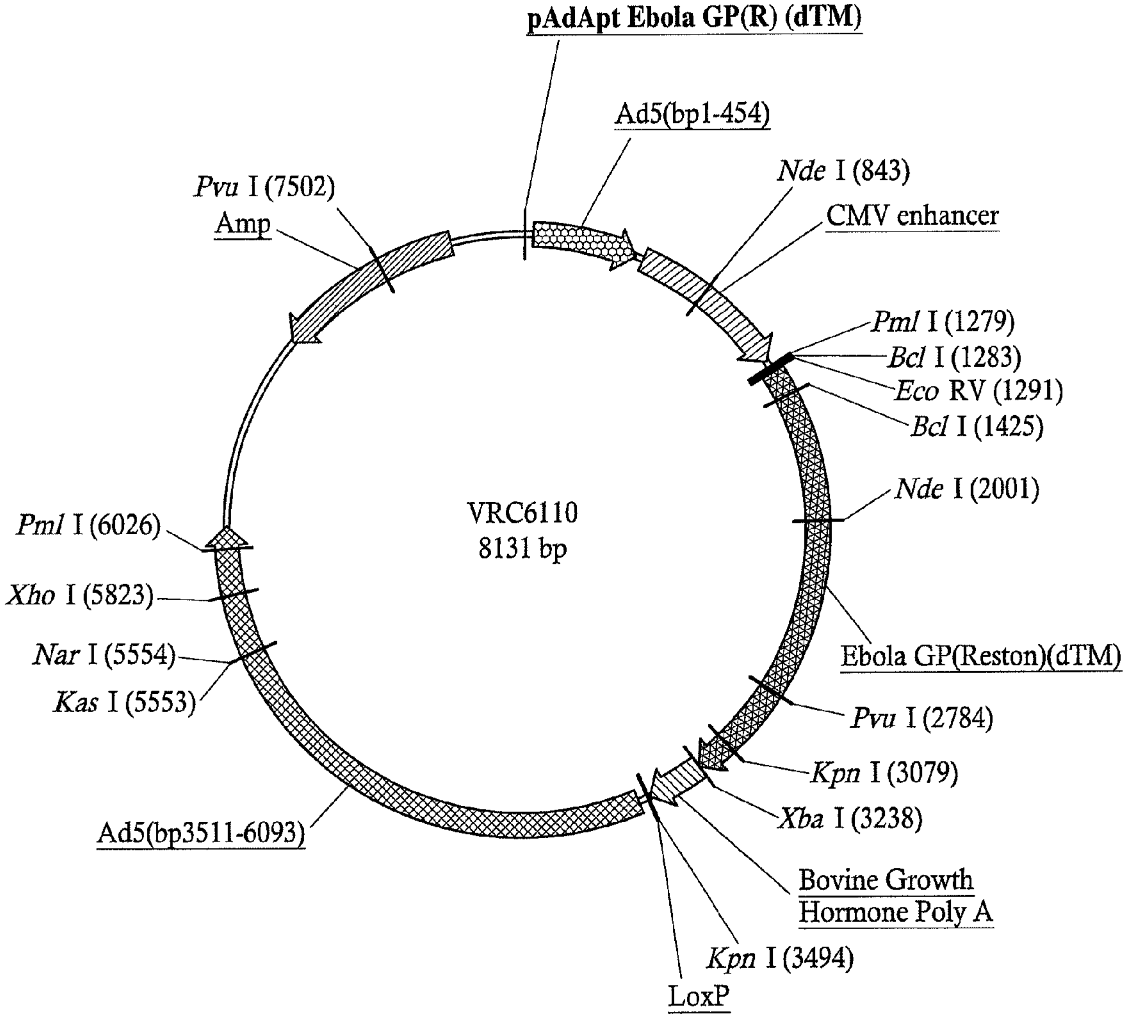
FIG. 12 shows VRC 6110 (pAdApt Ebola GP(R) (dTM)) construct map (see, Ebola/Marburg/Lassa Plasmids, and Recombinant Adenoviruses in Table 2).
Figure 13:
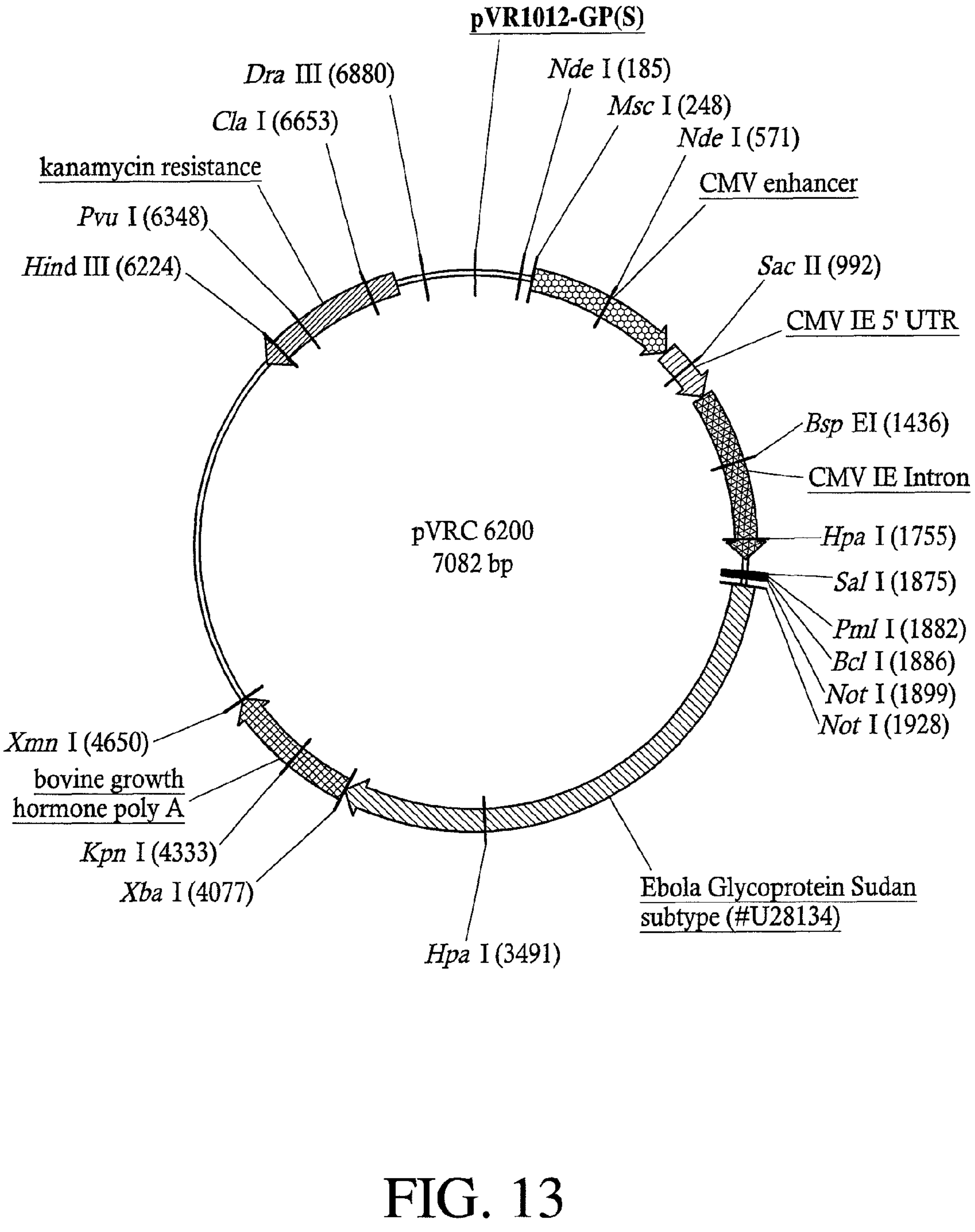
FIG. 13 shows VRC6200 (pVR1012-GP(S)) construct map (see, Ebola/Marburg/Lassa Plasmids, and Recombinant Adenoviruses in Table 2).
Figure 14:
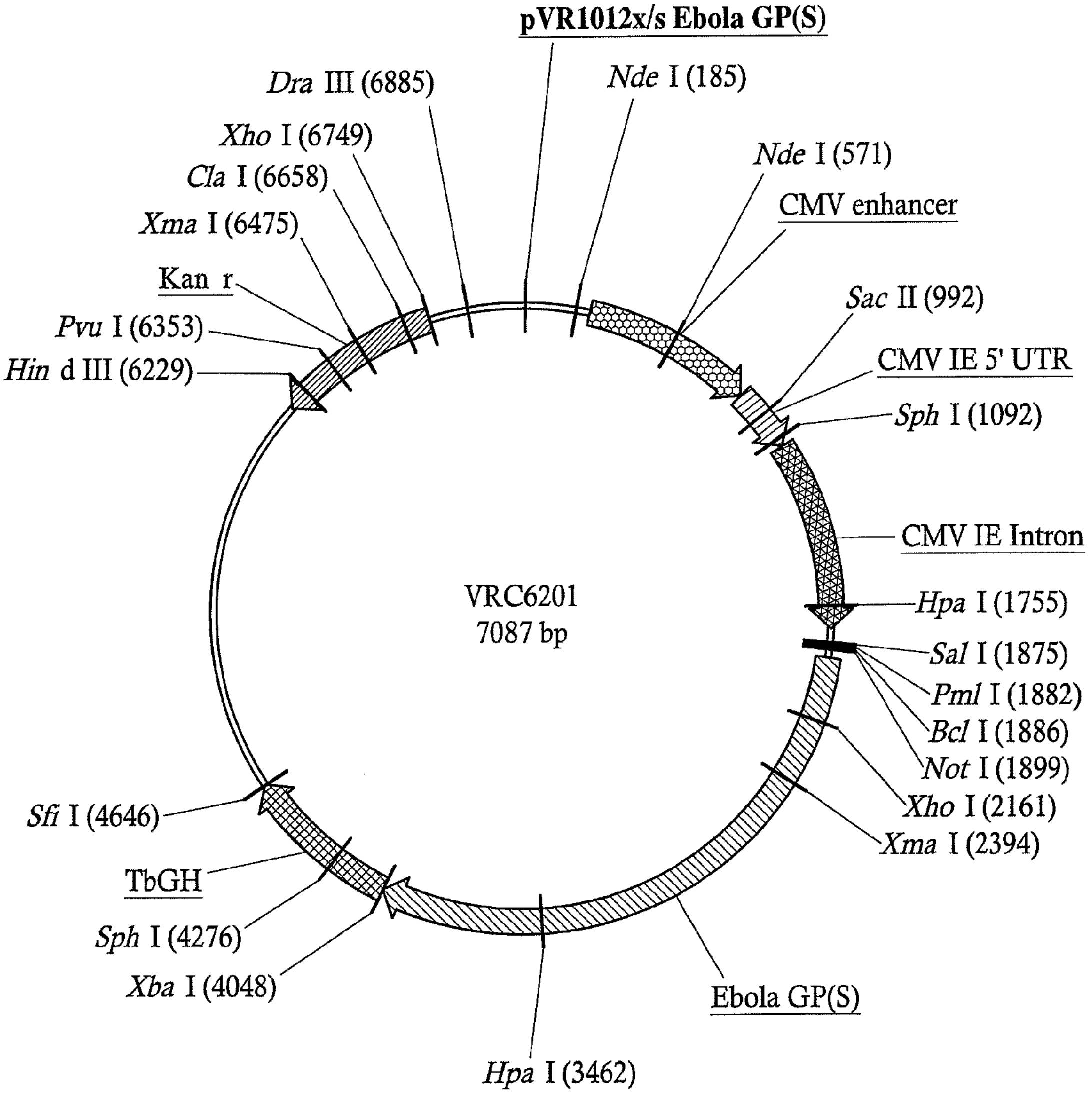
FIG. 14 shows VRC 6201 (pVR1012x/s Ebola GP(S)) construct map (see, Ebola/Marburg/Lassa Plasmids, and Recombinant Adenoviruses in Table 2).
Figure 15:
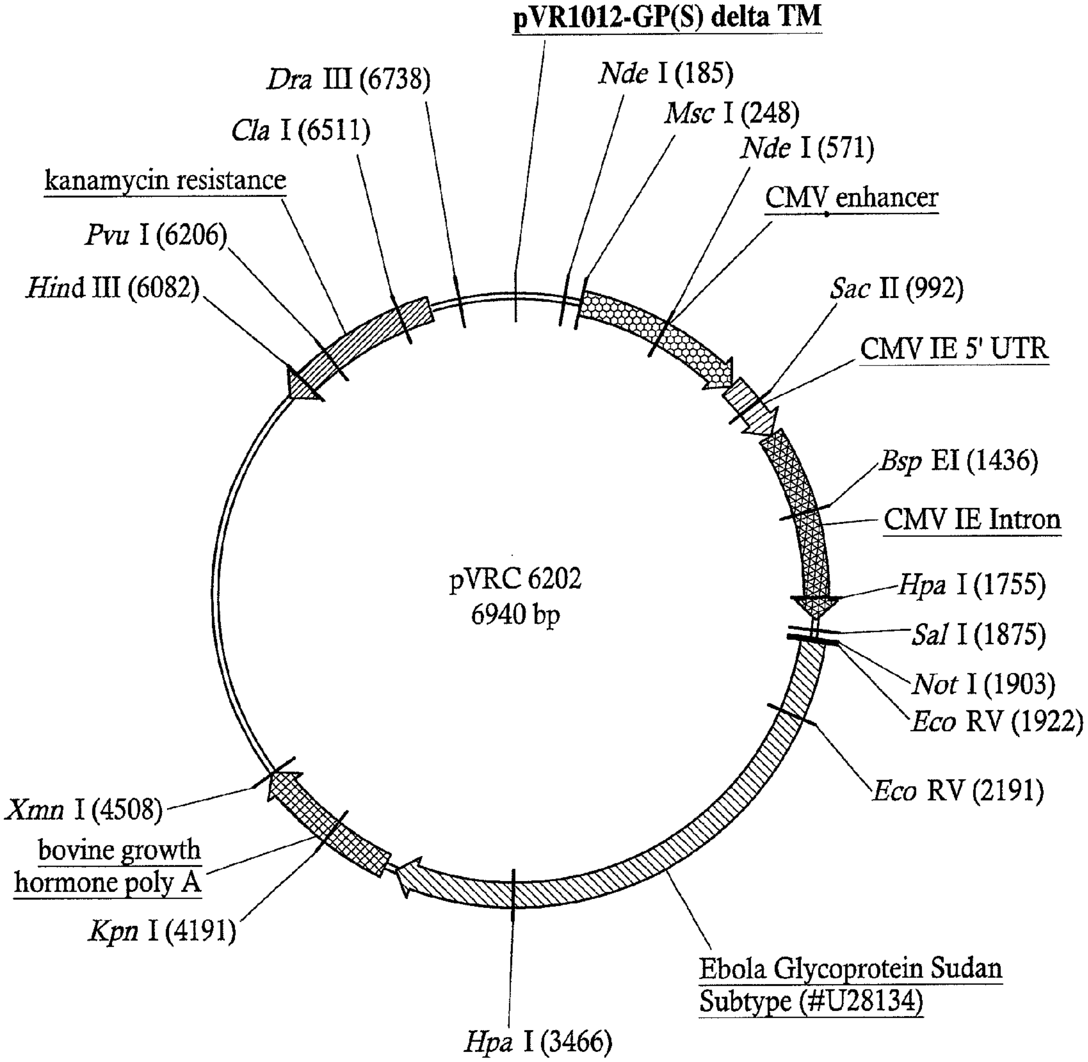
FIG. 15 shows VRC6202 (pVR1012-GP(S) delta TM) construct map (see, Ebola/Marburg/Lassa Plasmids, and Recombinant Adenoviruses in Table 2).
Figure 16:
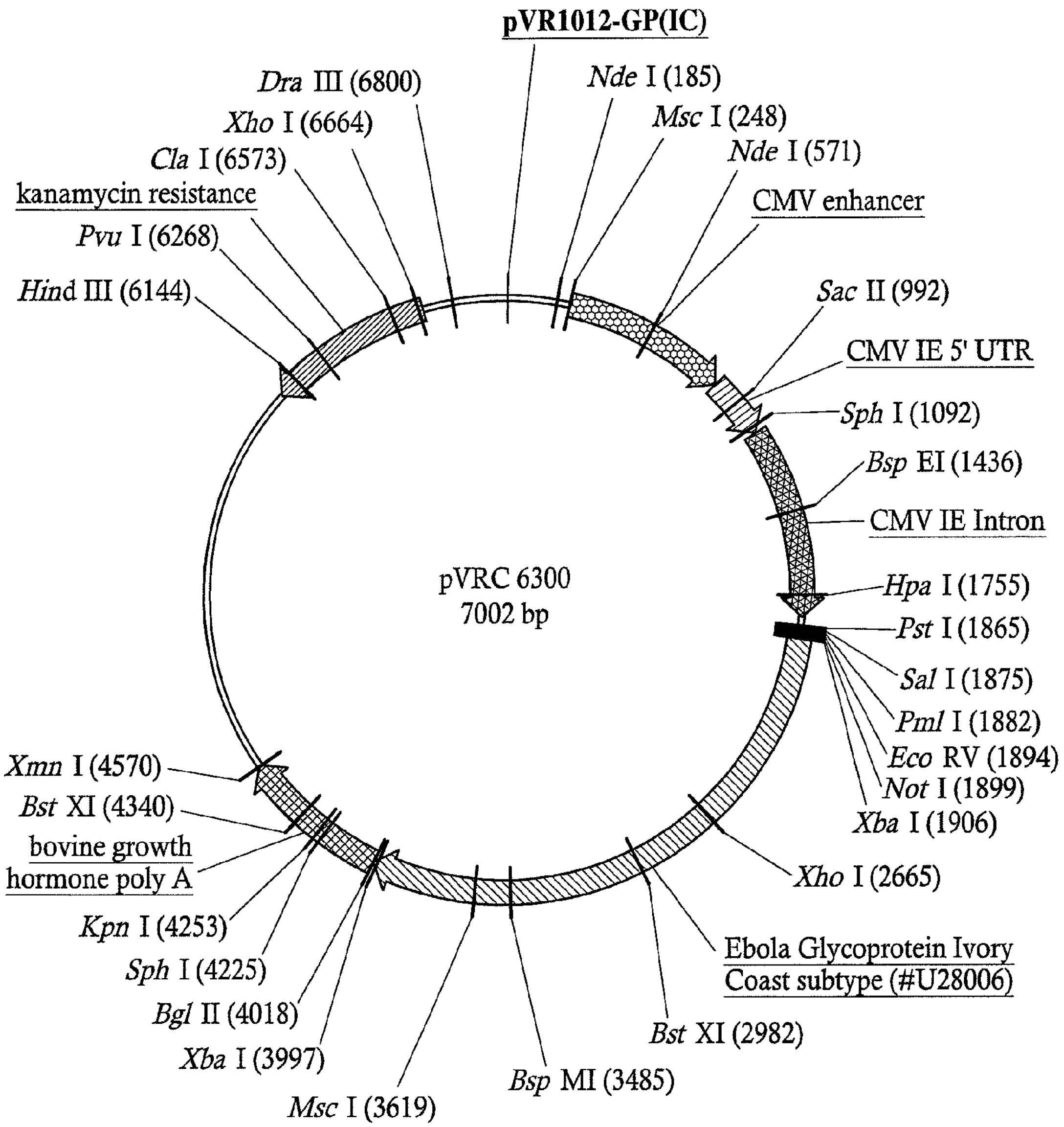
FIG. 16 shows VRC6300 (pVR1012-GP(IC)) construct map (see, Ebola/Marburg/Lassa Plasmids, and Recombinant Adenoviruses in Table 2).
Figure 17:
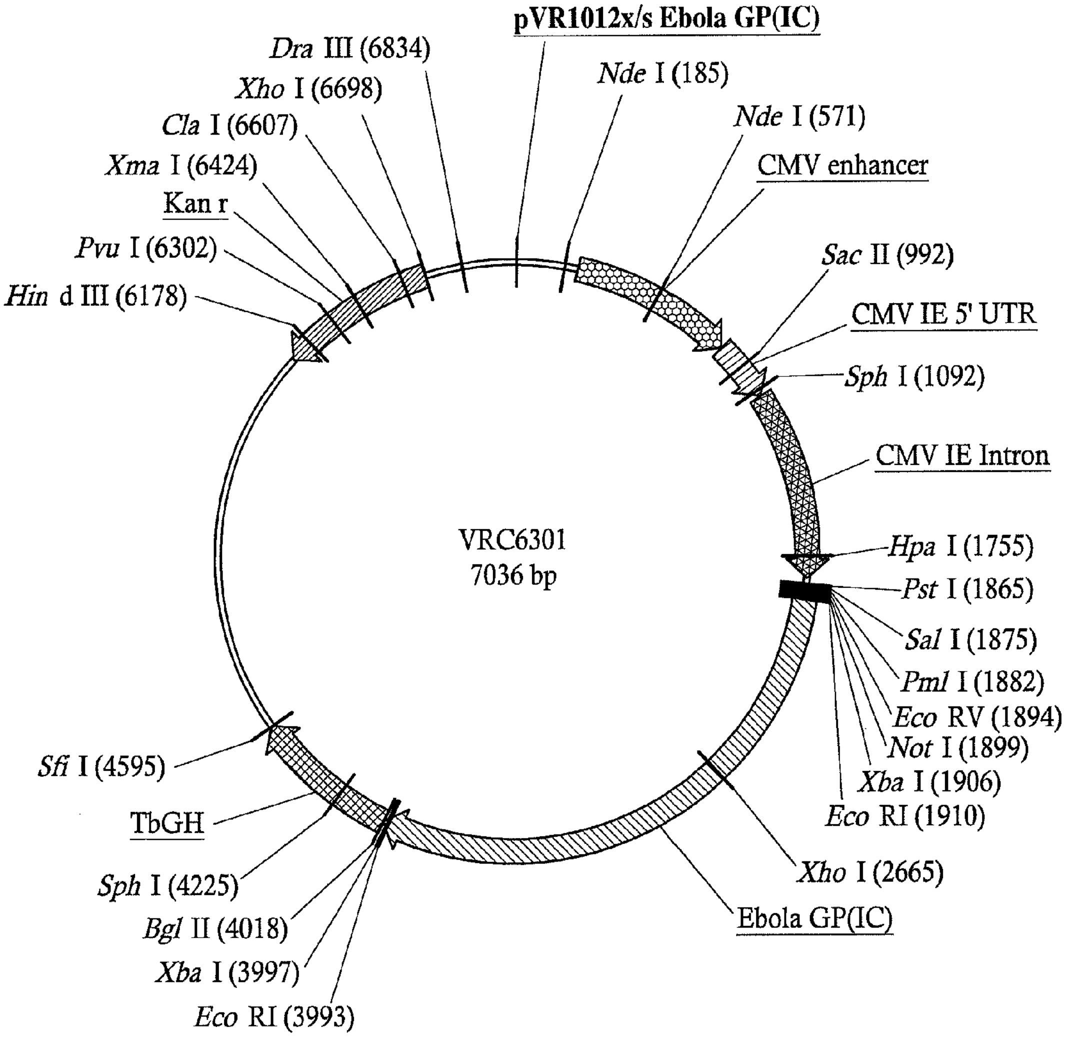
FIG. 17 shows VRC6301 (pVR1012x/s-GP(IC)) construct map (see, Ebola/Marburg/Lassa Plasmids, and Recombinant Adenoviruses in Table 2).
Figure 18:
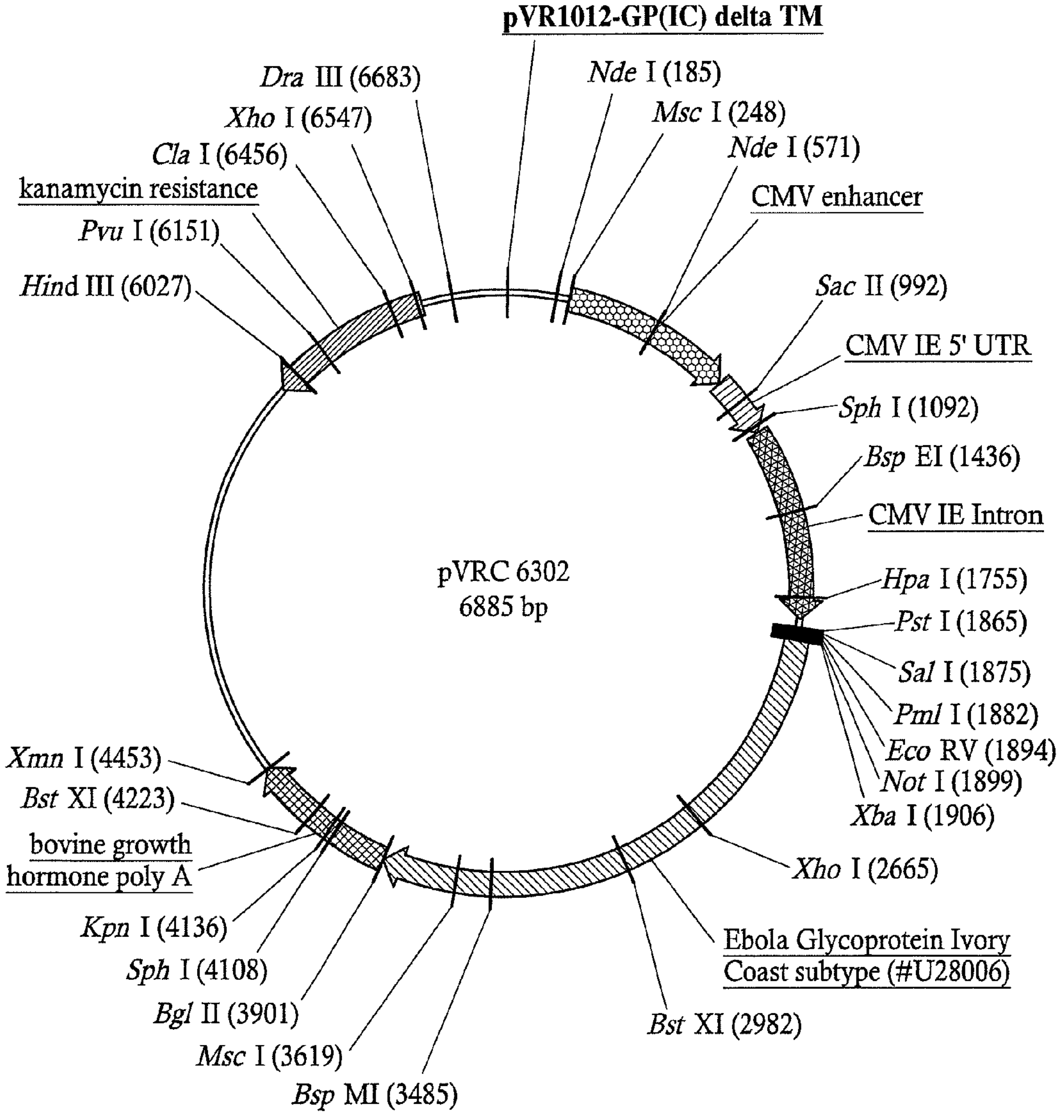
FIG. 18 shows VRC6302 (pVR1012-GP(IC) delta TM) construct map (see, Ebola/Marburg/Lassa Plasmids, and Recombinant Adenoviruses in Table 2).
Figure 19:
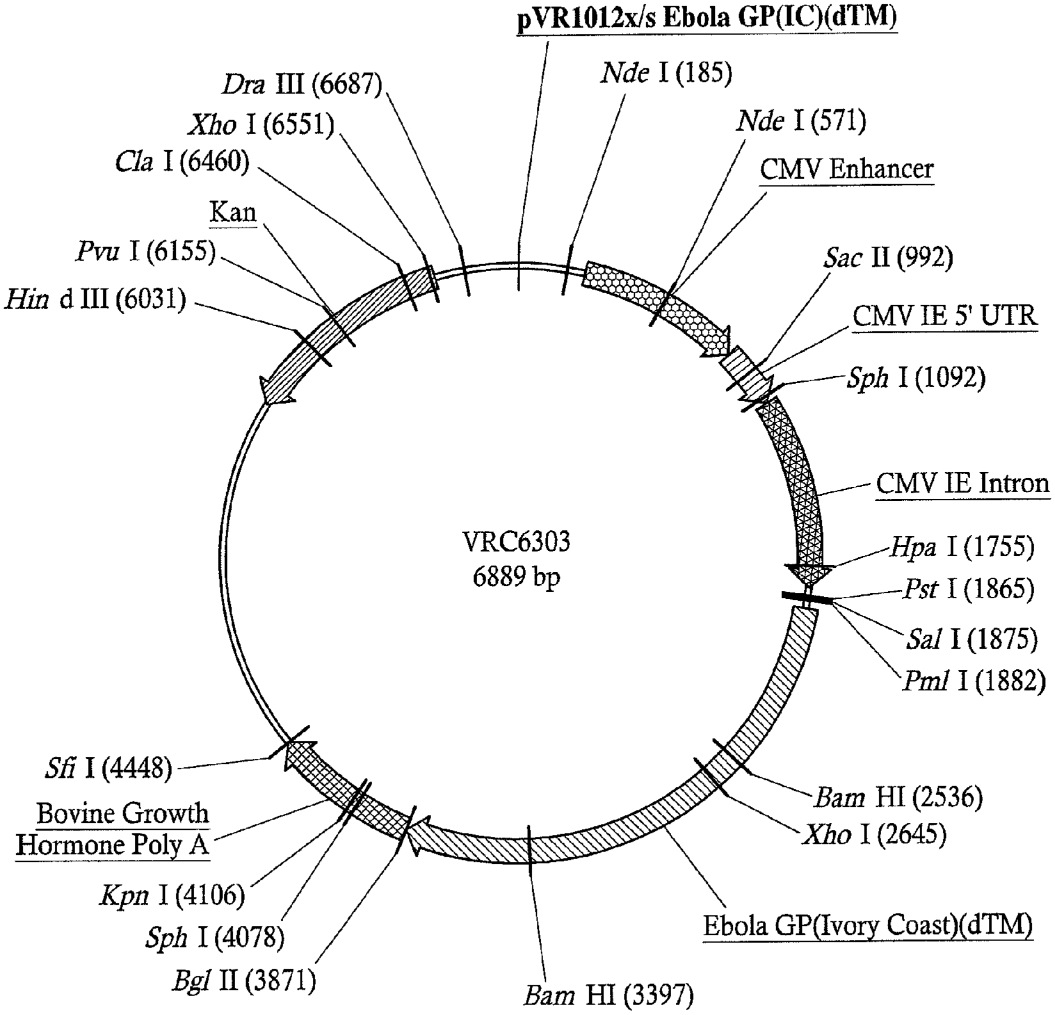
FIG. 19 shows VRC 6303 (pVR1012x/s Ebola GP (IC) (dTM)) construct map (see, Ebola/Marburg/Lassa Plasmids, and Recombinant Adenoviruses in Table 2).
Figure 20:
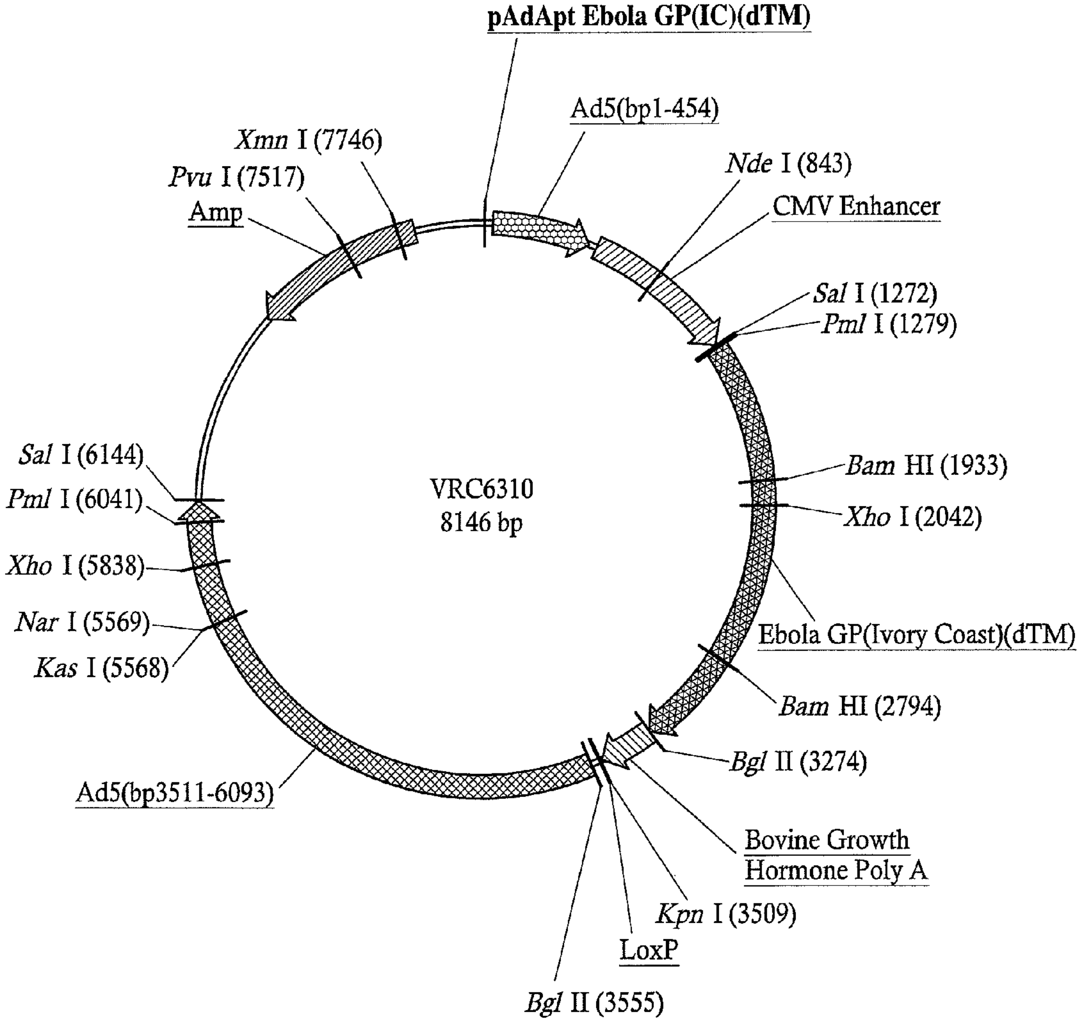
FIG. 20 shows VRC 6310 (pAdApt Ebola GP (IC) (dTM)) construct map (see, Ebola/Marburg/Lassa Plasmids, and Recombinant Adenoviruses in Table 2).
Figure 21:
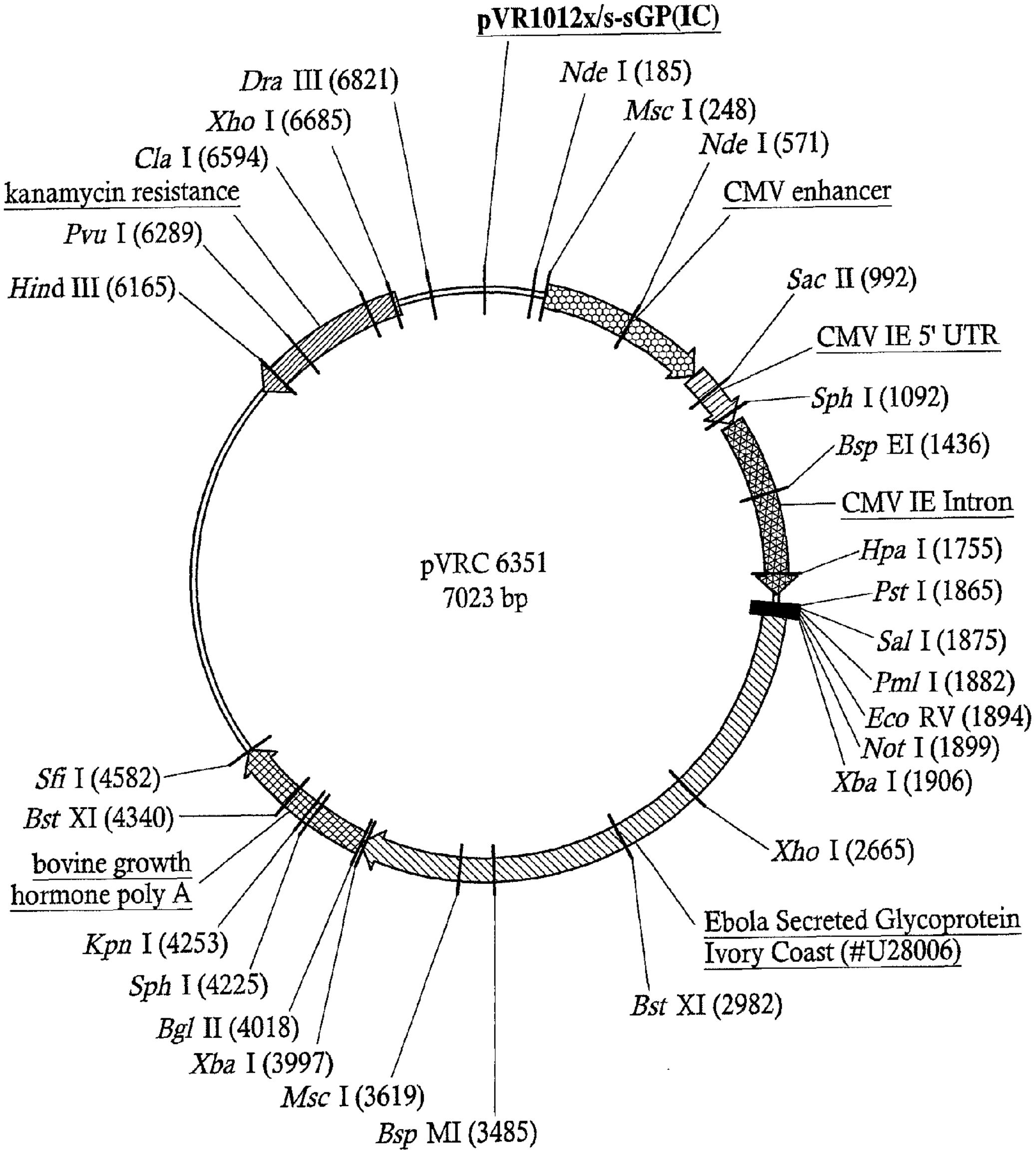
FIG. 21 shows VRC6351 (pVR1012x/s-SGP(IC)) construct map (see, Ebola/Marburg/Lassa Plasmids, and Recombinant Adenoviruses in Table 2).
Figure 22:
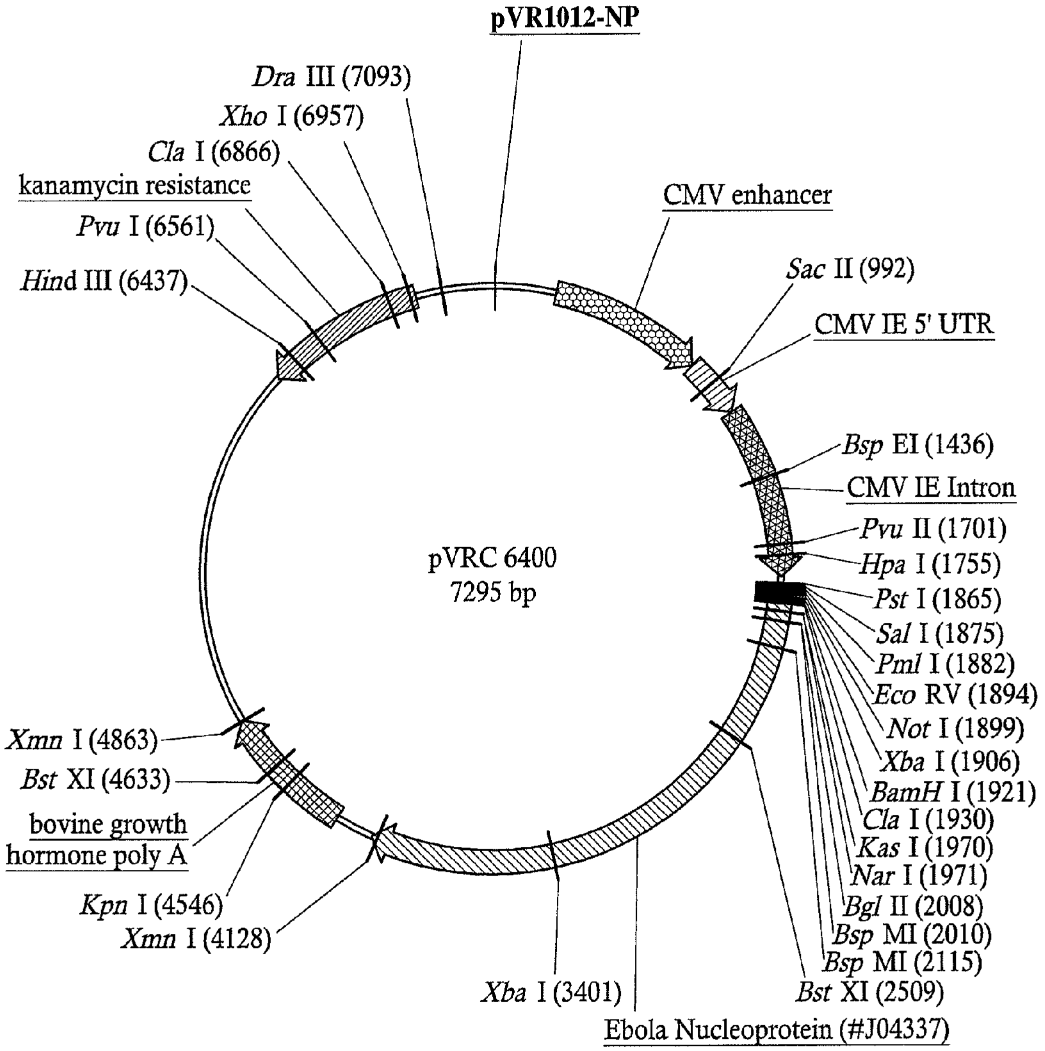
FIG. 22 shows VRC6400 (pVR1012-NP) construct map (see, Ebola/Marburg/Lassa Plasmids, and Recombinant Adenoviruses in Table 2).
Figure 23:
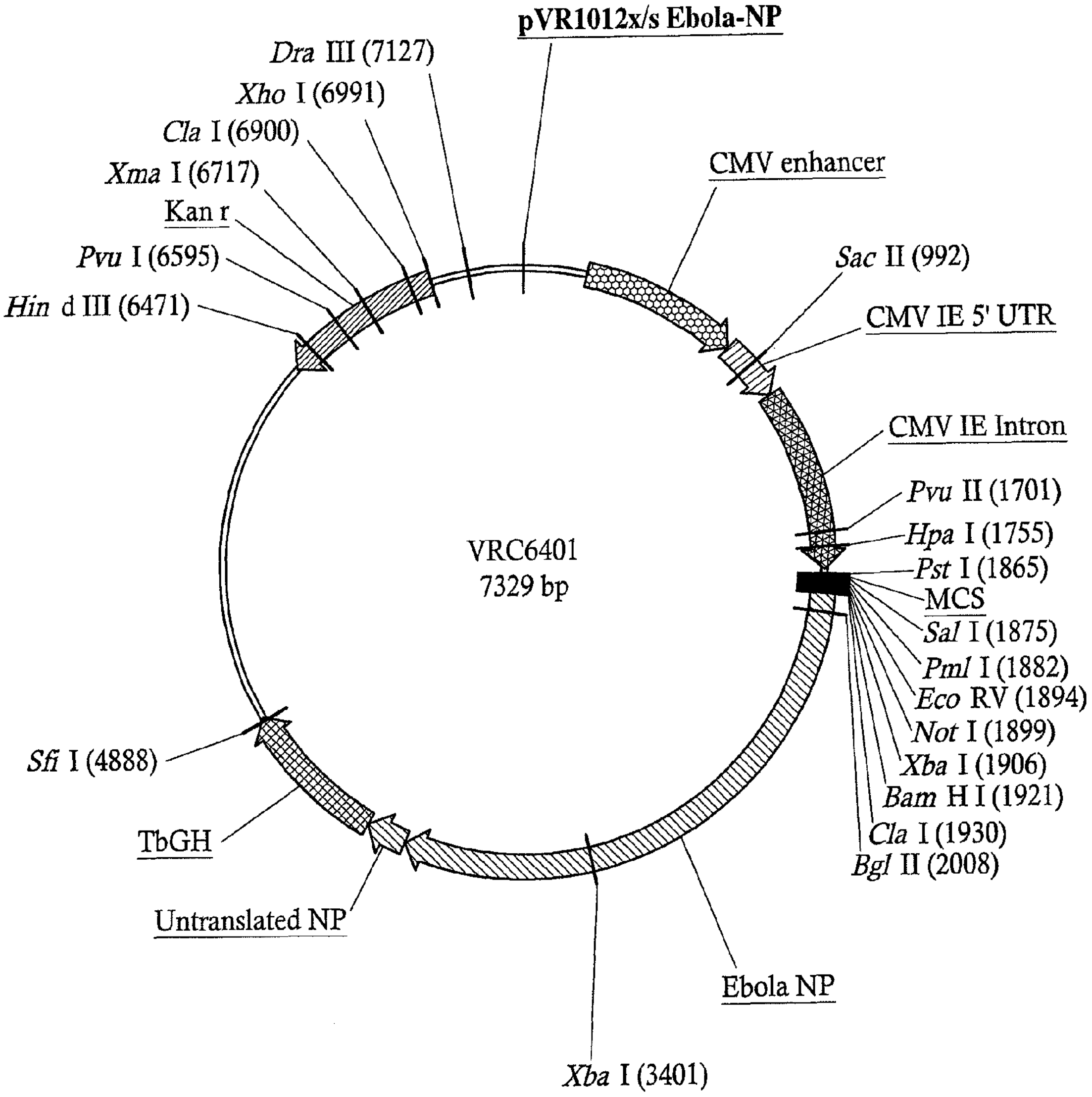
FIG. 23 shows VRC6401 (pVR1012x/s-NP) construct map (see, Ebola/Marburg/Lassa Plasmids, and Recombinant Adenoviruses in Table 2).
Figure 24:
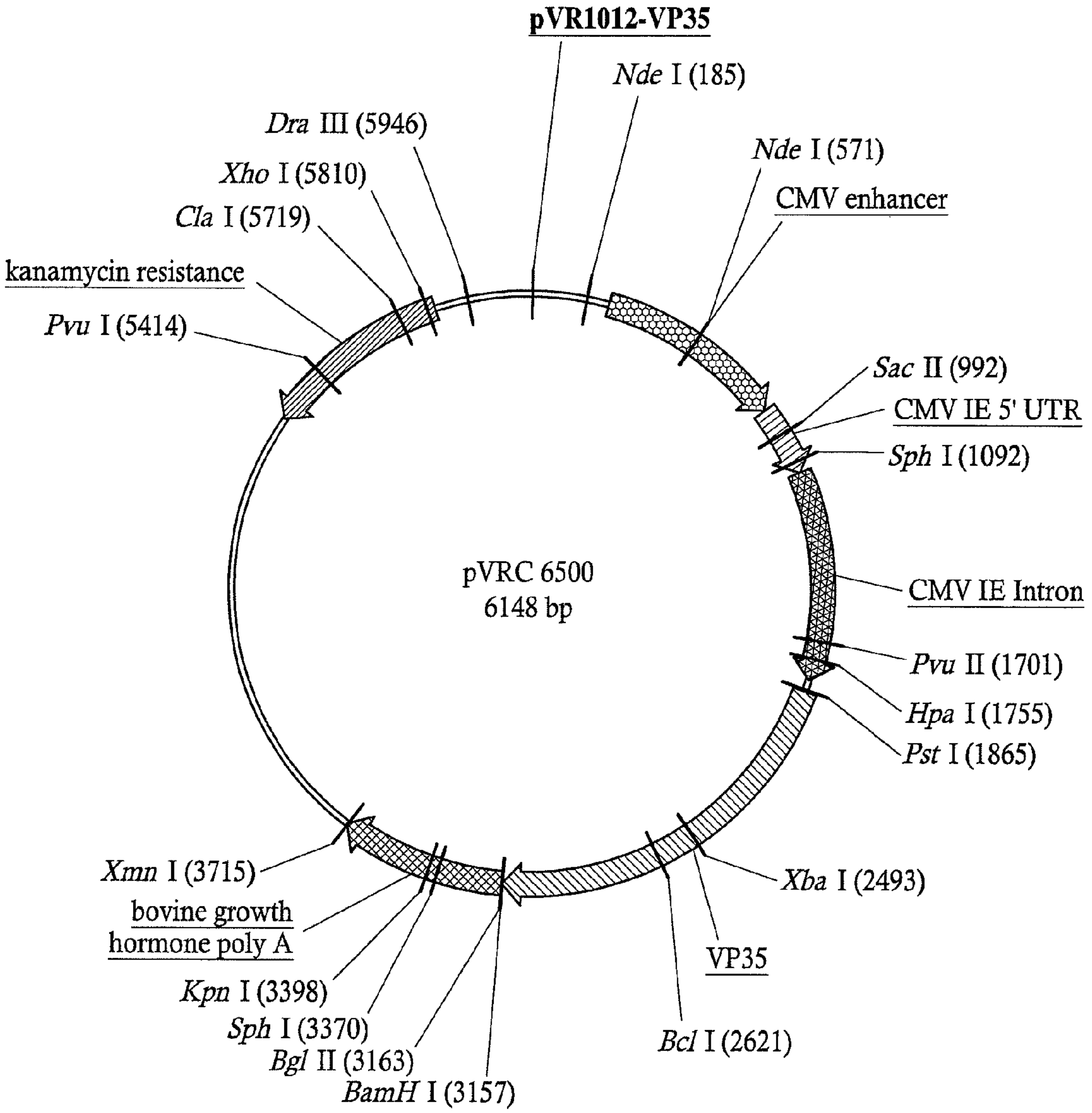
FIG. 24 shows VRC6500 (pVR1012-VP35) construct map (see, Ebola/Marburg/Lassa Plasmids, and Recombinant Adenoviruses in Table 2).
Figure 25:
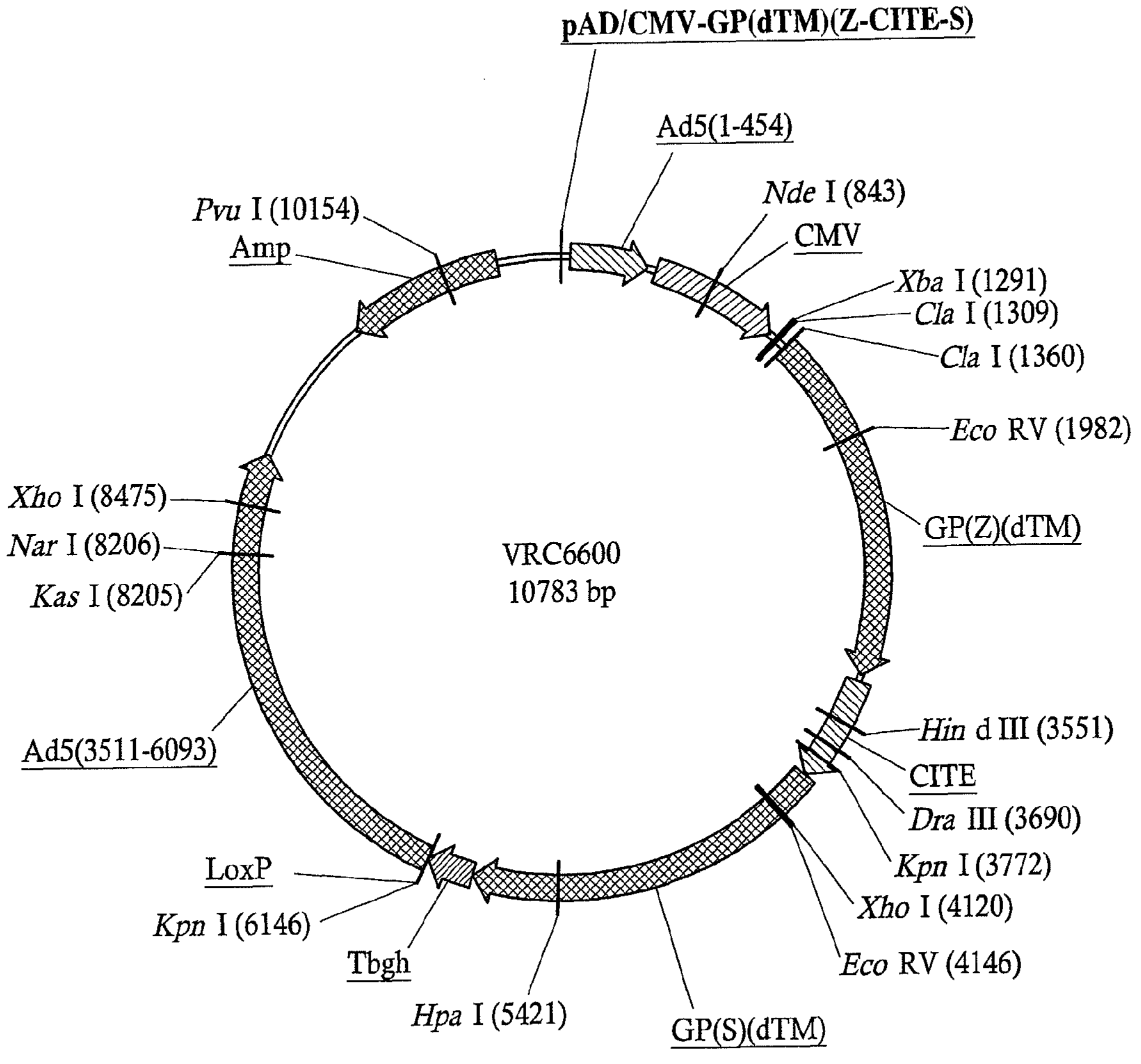
FIG. 25 shows VRC6600 (pAD/CMV-GP(dTM)(Z-CITE-S) construct map (see, Ebola/Marburg/Lassa Plasmids, and Recombinant Adenoviruses in Table 2).
Figure 26:
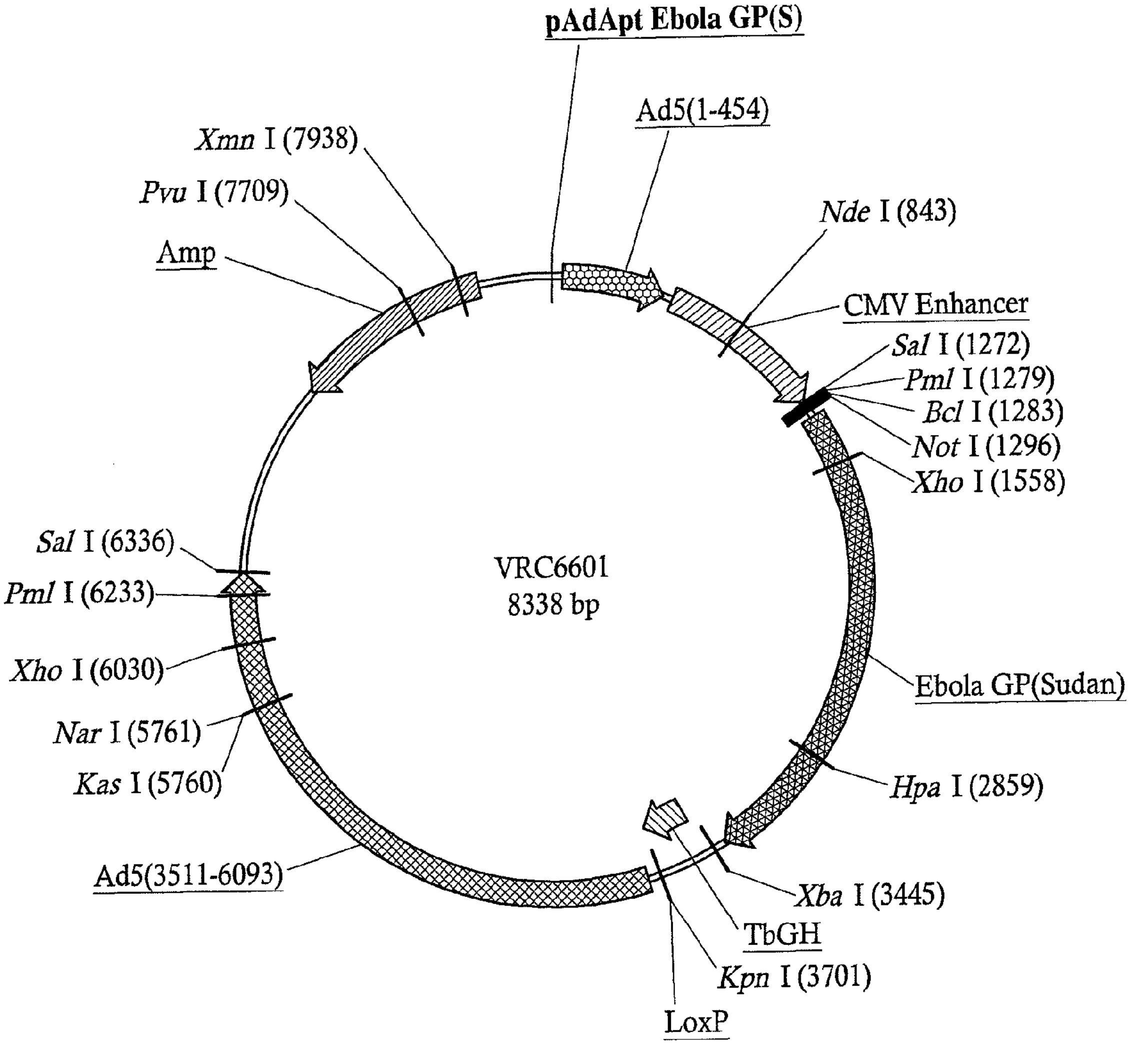
FIG. 26 shows VRC6601 (pAdApt Ebola GP(S)) construct map (see, Ebola/Marburg/Lassa Plasmids, and Recombinant Adenoviruses in Table 2).
Figure 27:
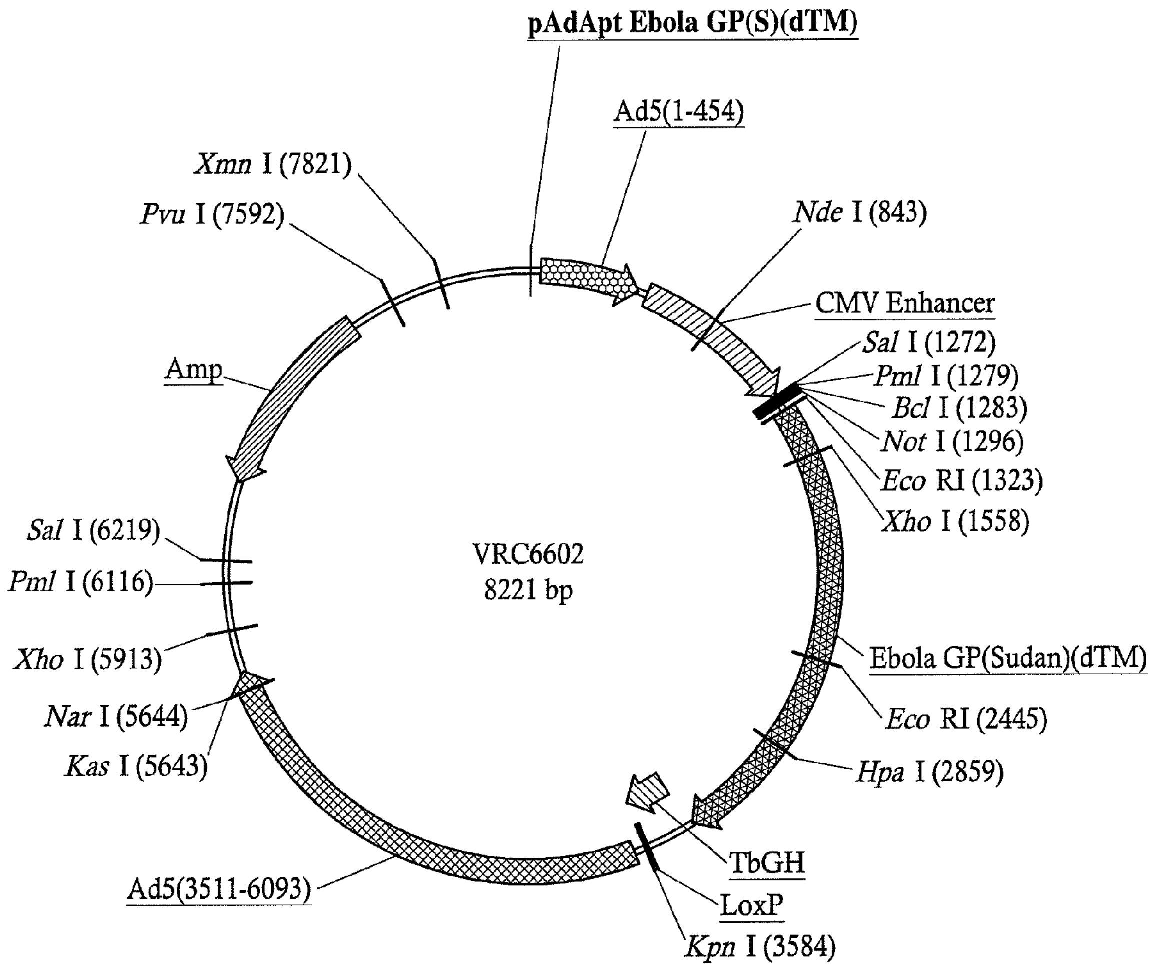
FIG. 27 shows VRC 6602 (pAdApt Ebola GP(S)(dTM)) construct map (see, Ebola/Marburg/Lassa Plasmids, and Recombinant Adenoviruses in Table 2).
Figure 28:
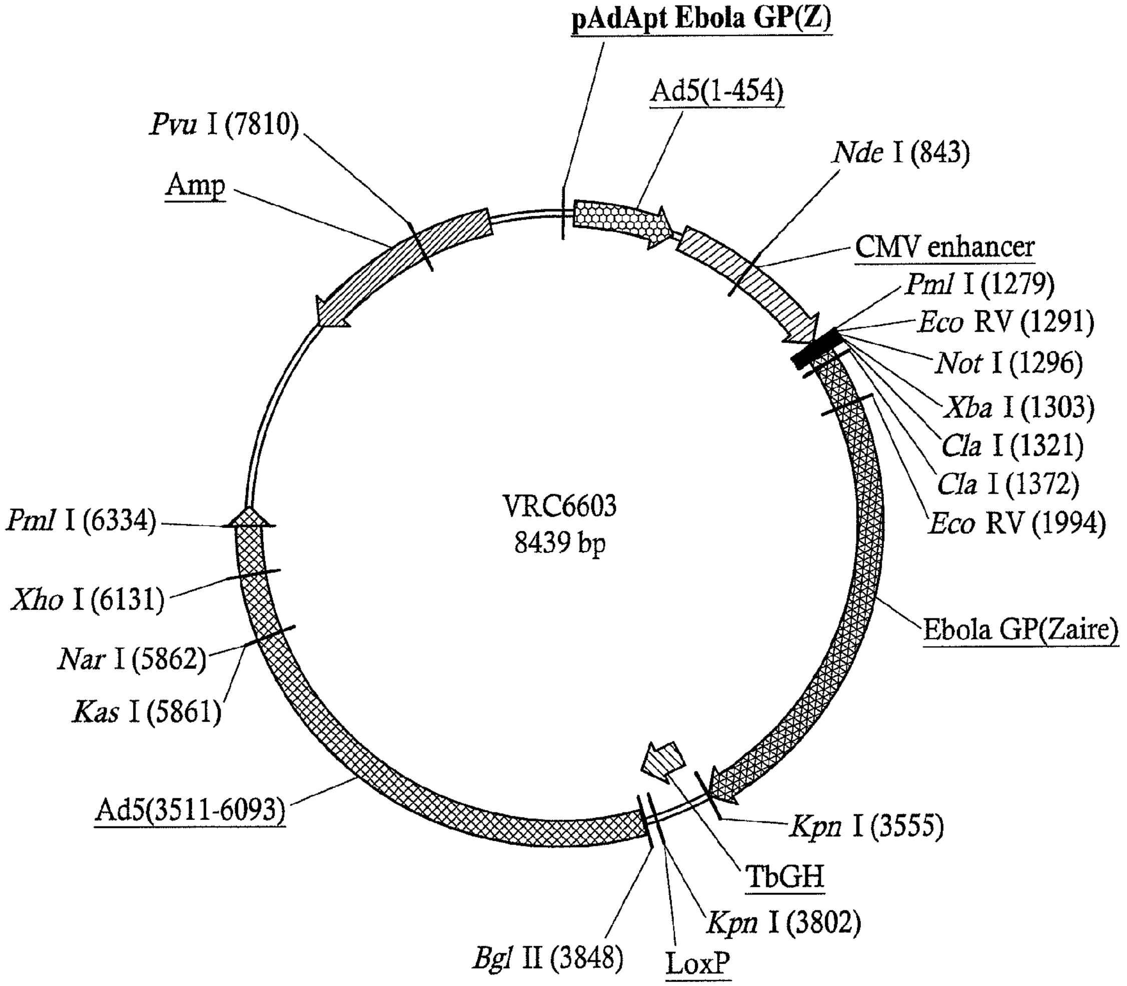
FIG. 28 shows VRC6603 (pAdApt Ebola GP(Z)) construct map (see, Ebola/Marburg/Lassa Plasmids, and Recombinant Adenoviruses in Table 2).
Figure 29:
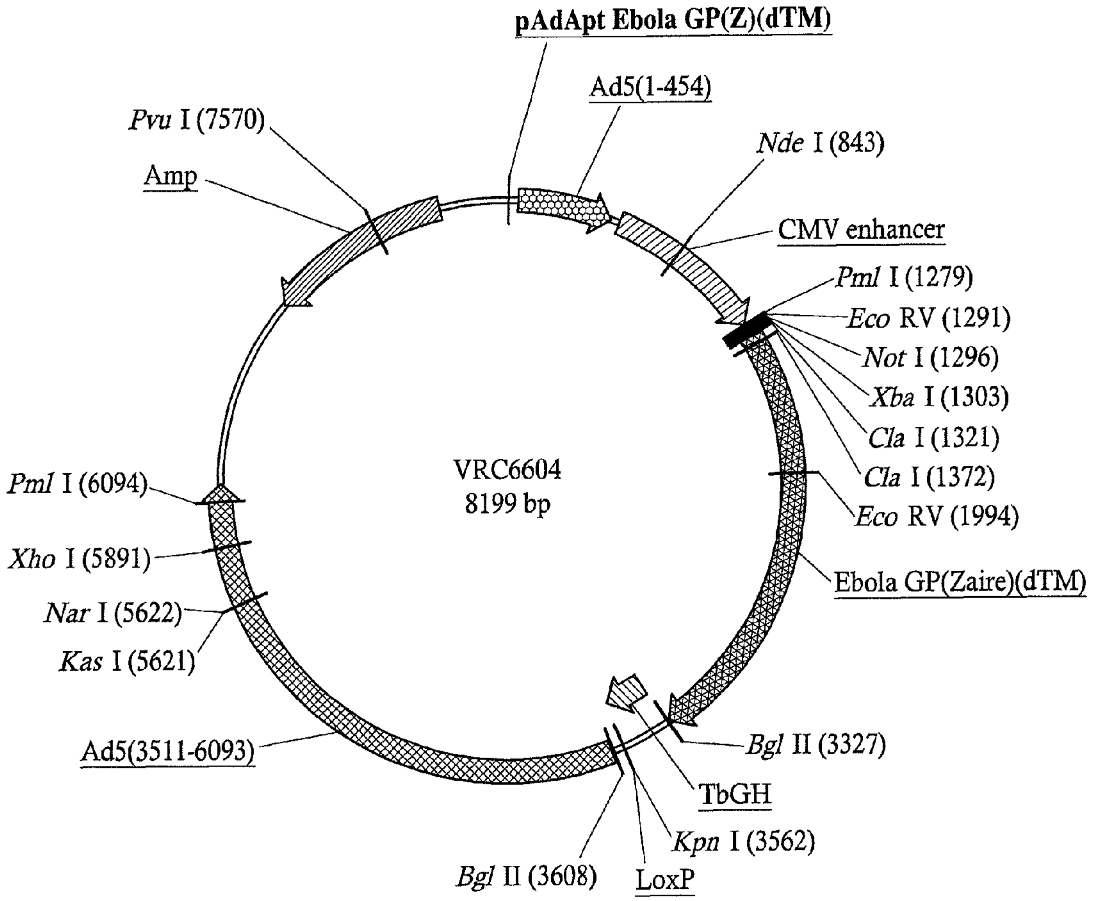
FIG. 29 shows VRC 6604 (pAdApt Ebola GP(Z)(dTM)) construct map (see, Ebola/Marburg/Lassa Plasmids, and Recombinant Adenoviruses in Table 2).
Figure 30:
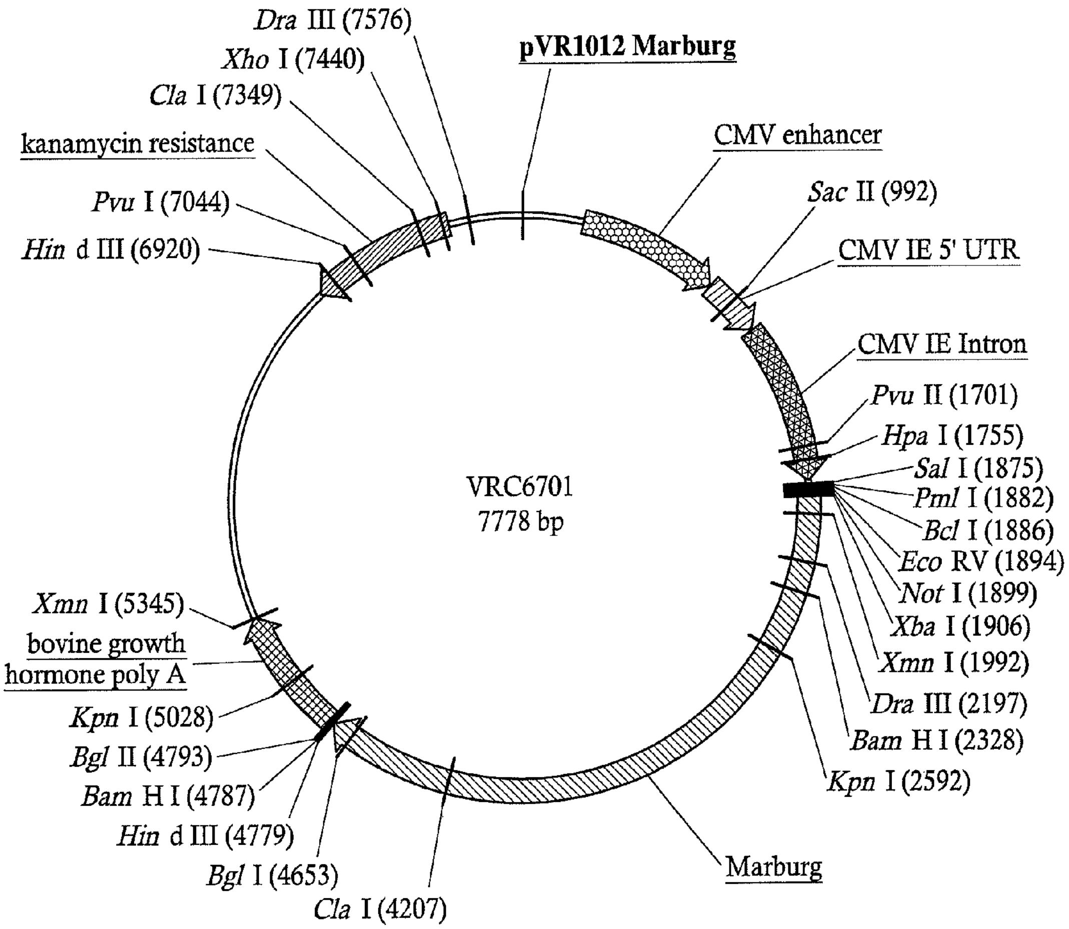
FIG. 30 shows VRC6701 (pVR1012-Marburg) construct map (see, Ebola/Marburg/Lassa Plasmids, and Recombinant Adenoviruses in Table 2).
Figure 31:
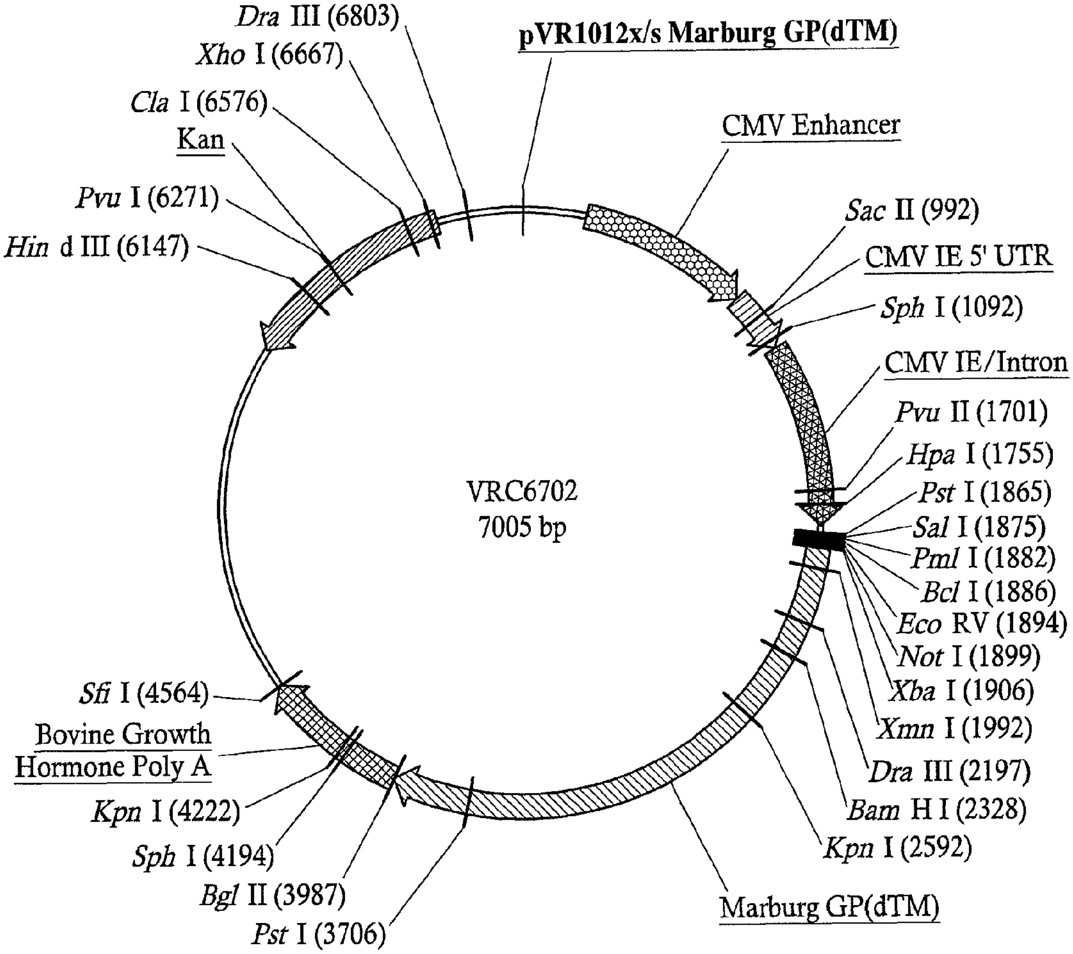
FIG. 31 shows VRC 6702 (pVR1012x/s Marburg GP (dTM)) construct map (see, Ebola/Marburg/Lassa Plasmids, and Recombinant Adenoviruses in Table 2).
Figure 32:
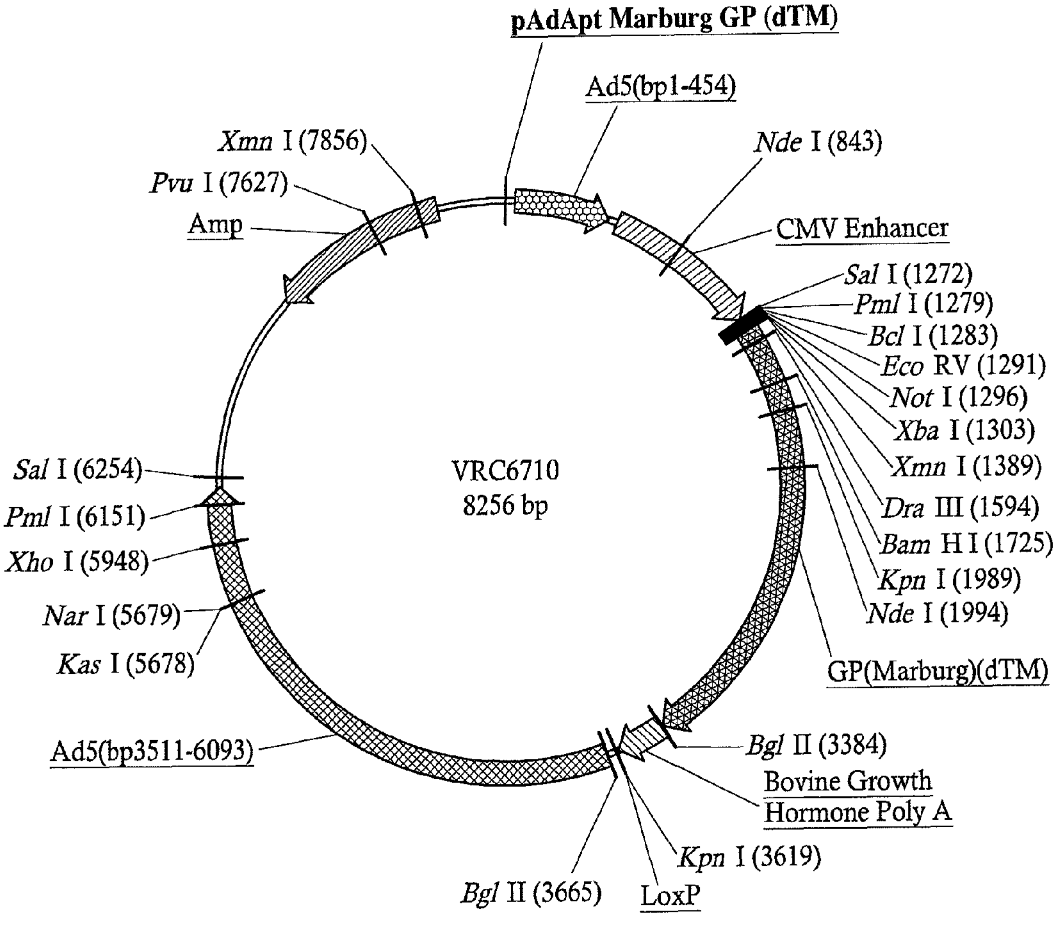
FIG. 32 shows VRC 6710 (pAdApt Marburg GP (dTM)) construct map (see, Ebola/Marburg/Lassa Plasmids, and Recombinant Adenoviruses in Table 2).
Figure 33:
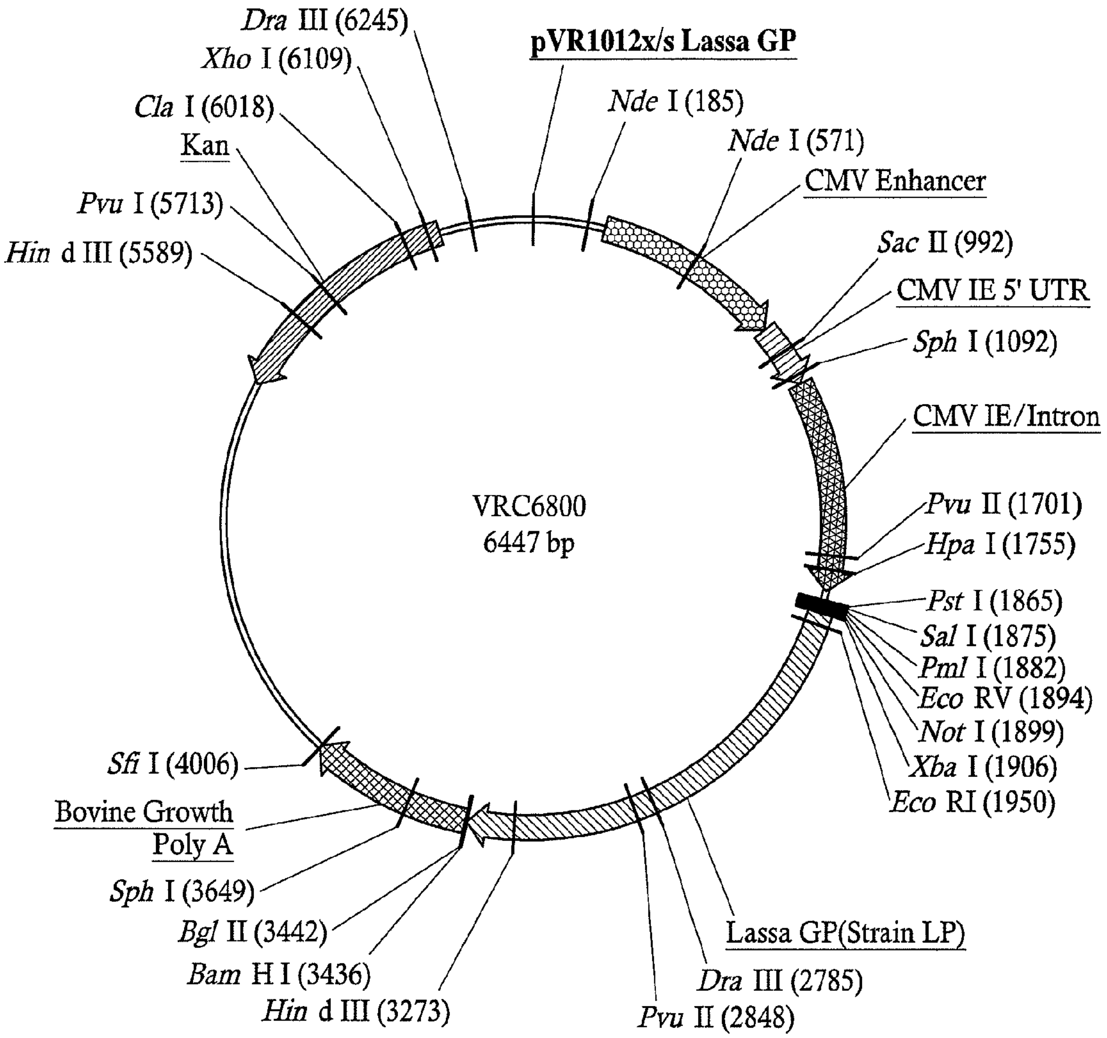
FIG. 33 shows VRC6800 (pVR1012x/s Lassa GP) construct map (see, Ebola/Marburg/Lassa Plasmids, and Recombinant Adenoviruses in Table 2).
Figure 34:
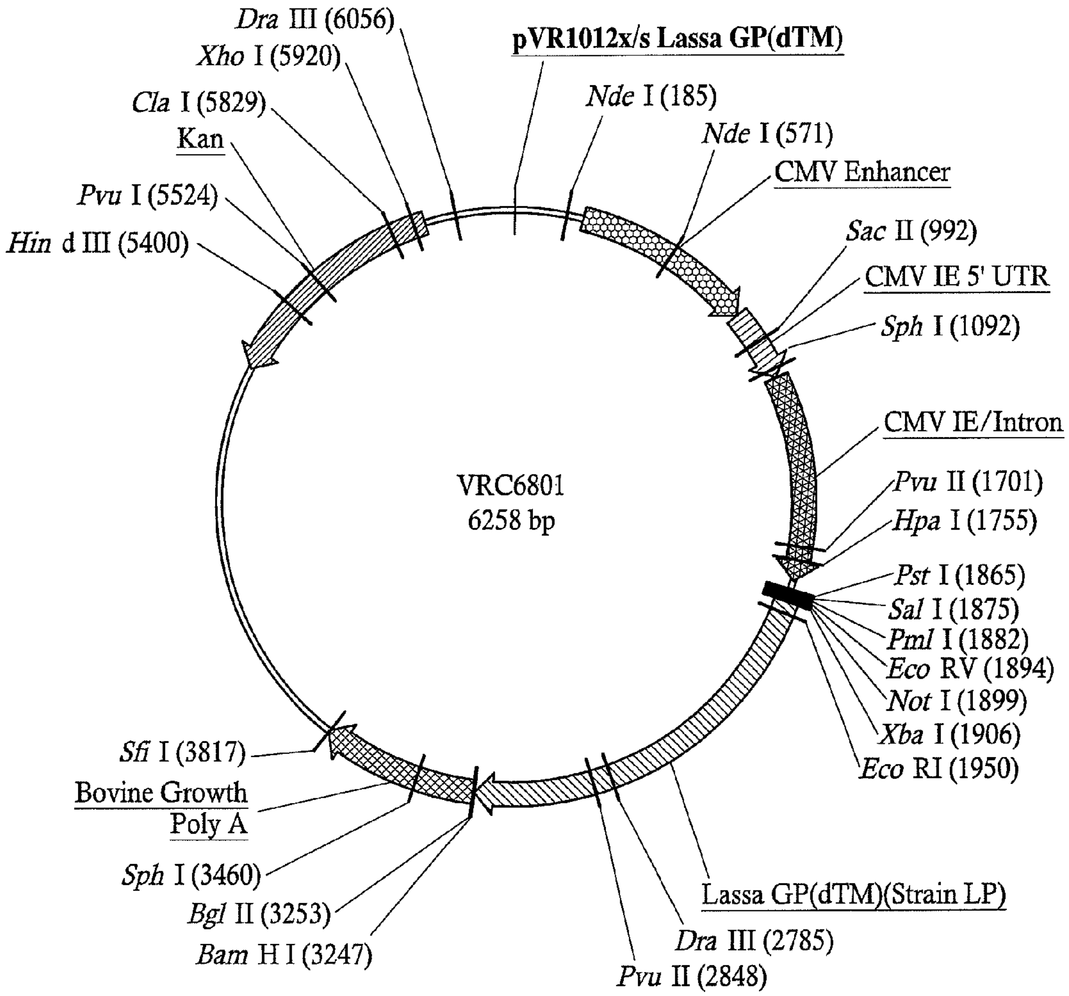
FIG. 34 shows VRC6801 (pVR1012x/s Lassa GP (dTM) construct map (see, Ebola/Marburg/Lassa Plasmids, and Recombinant Adenoviruses in Table 2).
Figure 35:
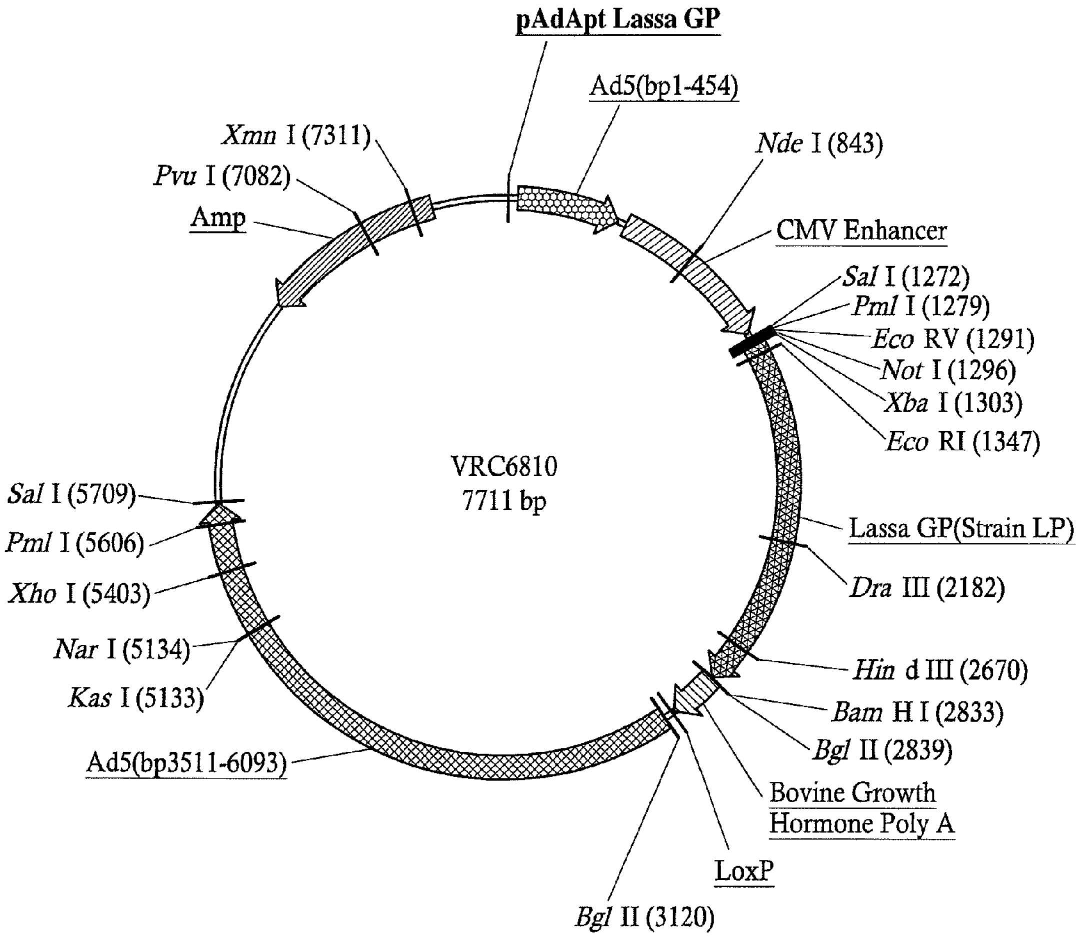
FIG. 35 shows VRC6810 (pAdApt Lassa GP) construct map (see, Ebola/Marburg/Lassa Plasmids, and Recombinant Adenoviruses in Table 2).
Figure 36:
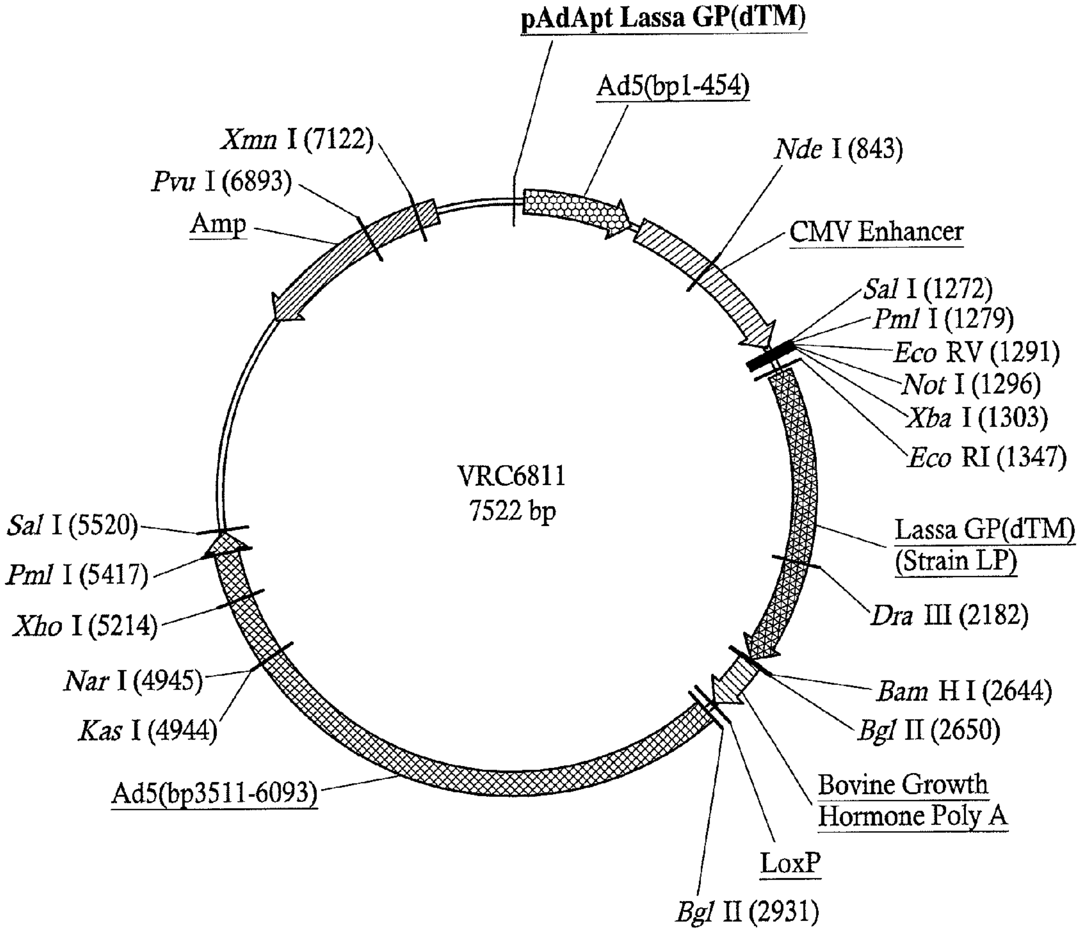
FIG. 36 shows VRC6811 (pAdApt Lassa GP (dTM)) construct map (see, Ebola/Marburg/Lassa Plasmids, and Recombinant Adenoviruses in Table 2).
Figure 37:
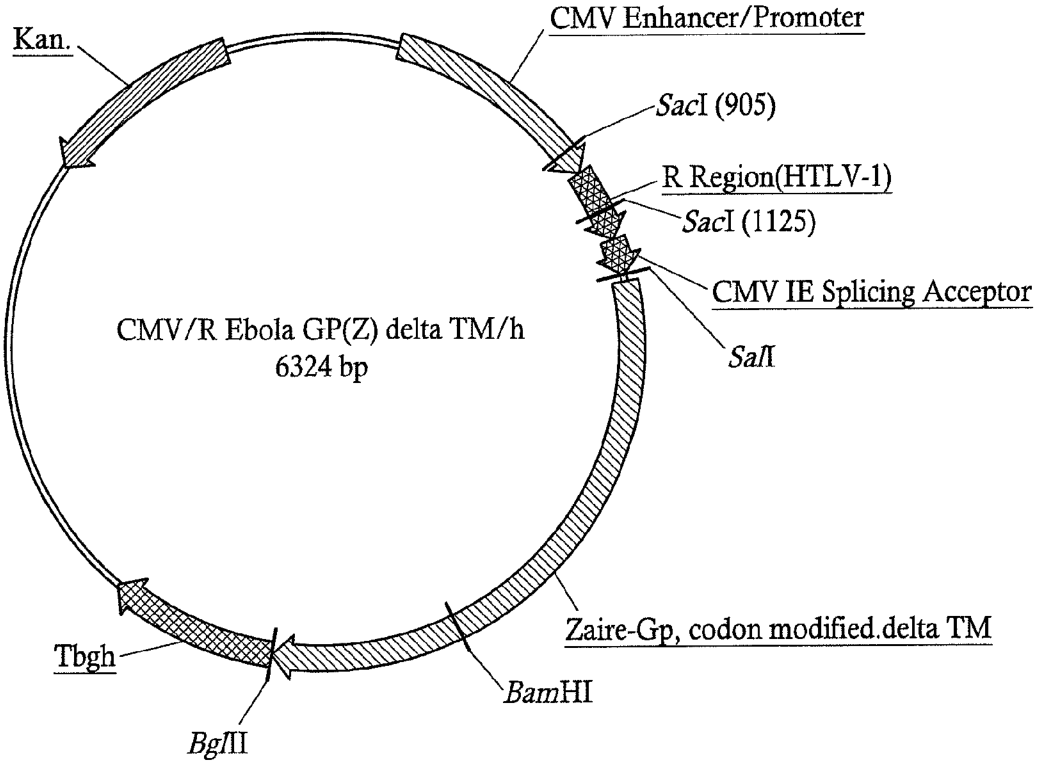
FIG. 37 shows CMV/R Ebola GP (Z) delta™/h (codon optimized) construct map (see, Ebola/Marburg/Lassa Plasmids, and Recombinant Adenoviruses in Table 2).
Figure 39:
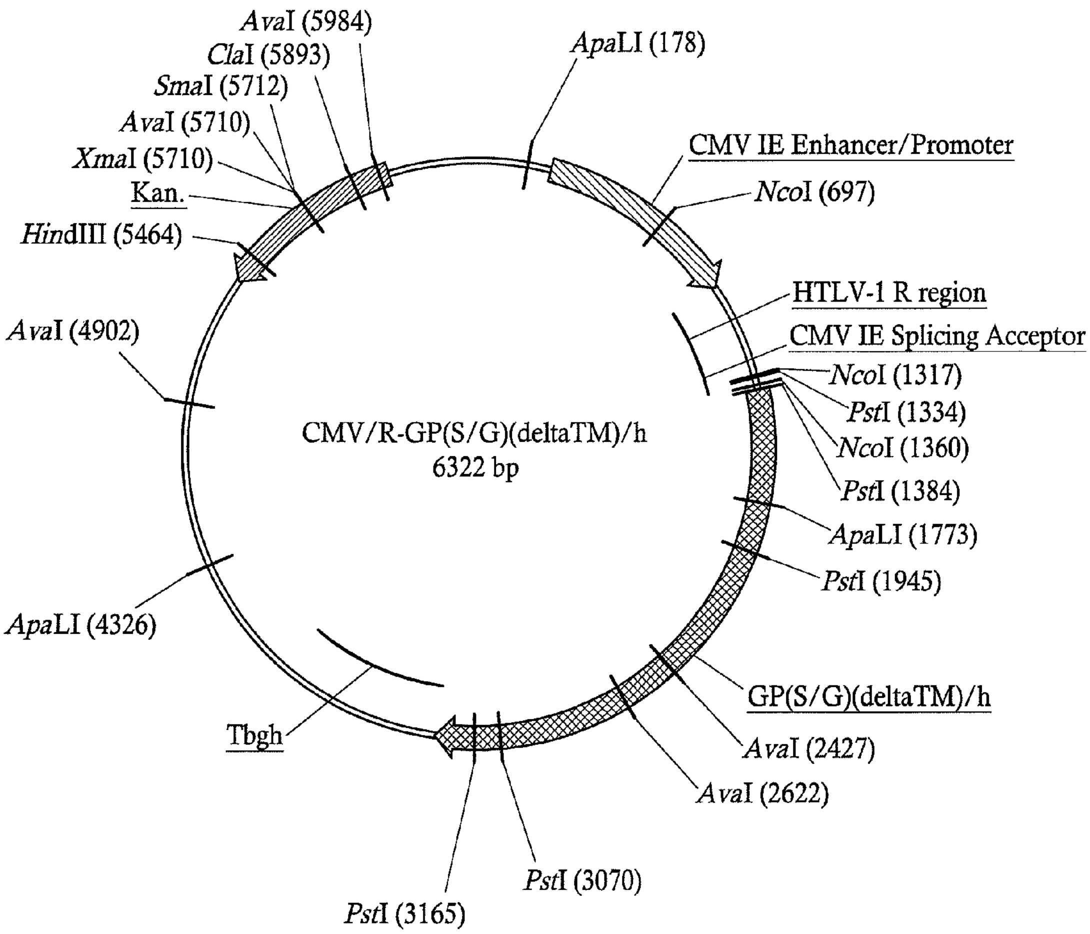
FIG. 39 shows CMV/R Ebola GP (S/Gulu) delta TM/h (codon optimized) construct map (see, Ebola/Marburg/Lassa Plasmids, and Recombinant Adenoviruses in Table 2).
Figure 40:
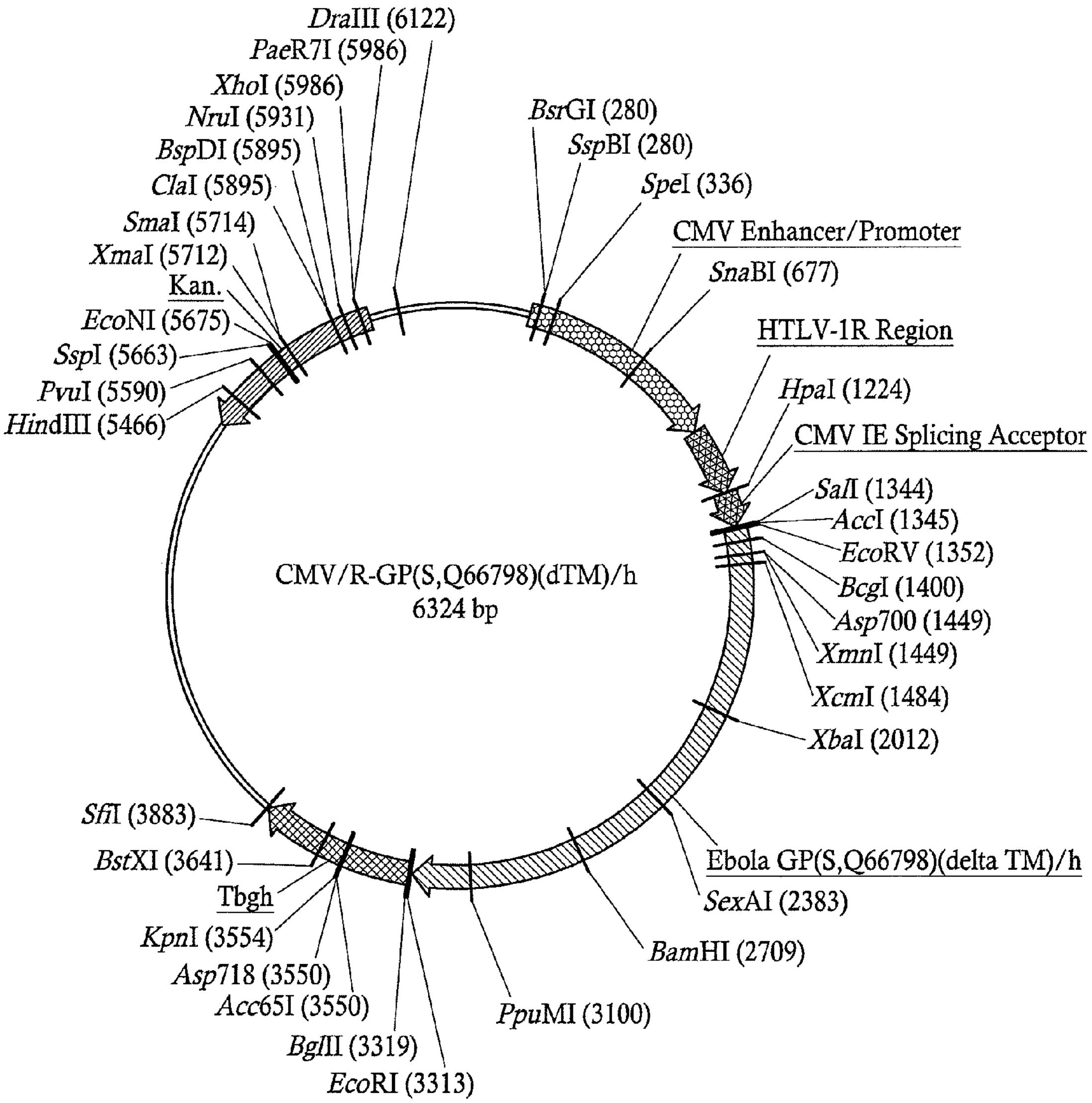
FIG. 40 shows CMV/R Ebola GP (S,Q66798) delta TM/h (codon optimized) construct map (see, Ebola/Marburg/Lassa Plasmids, and Recombinant Adenoviruses in Table 2).
Figure 41:
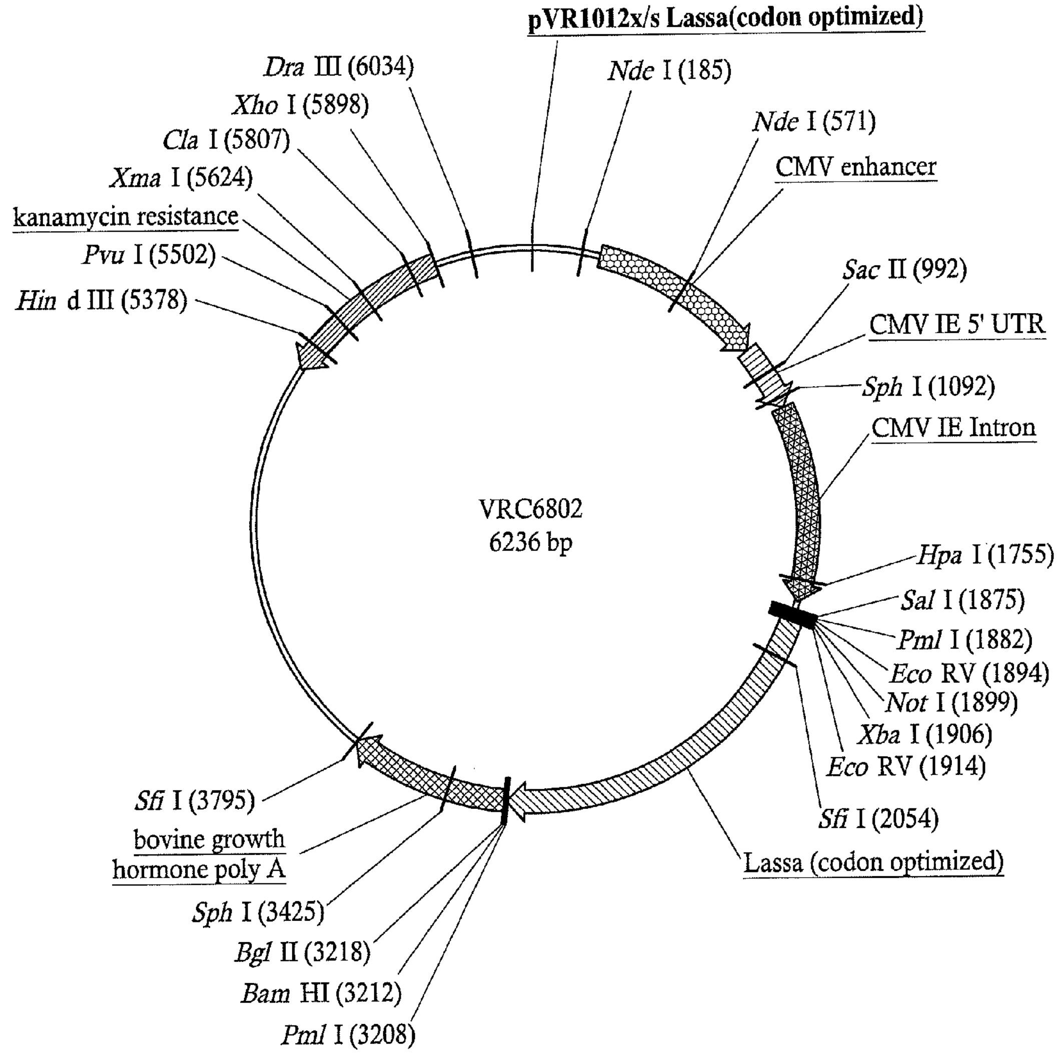
FIG. 41 shows VRC6802, pVR1012x/s Lassa delta TM/h (codon optimized) construct map (see, Ebola/Marburg/Lassa Plasmids, and Recombinant Adenoviruses in Table 2).
Figure 42:
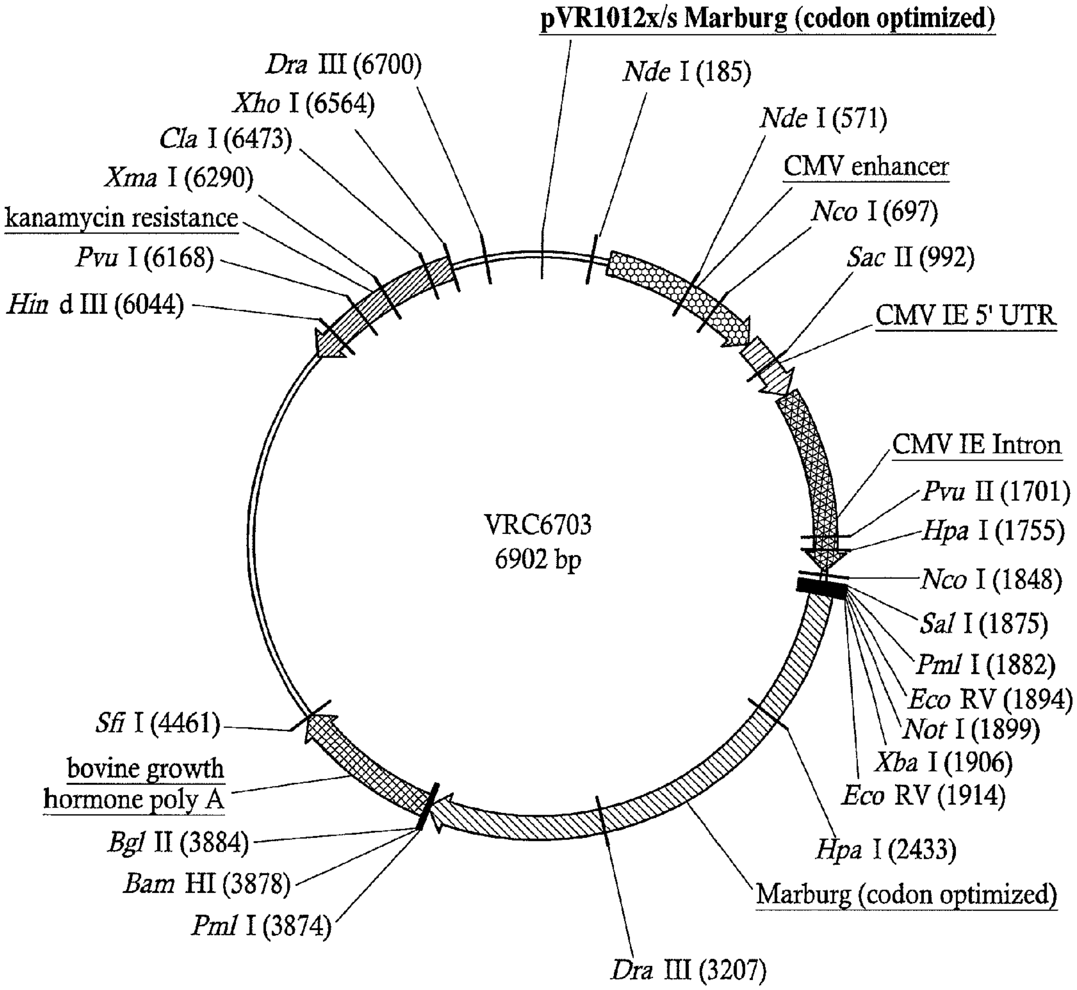
FIG. 42 shows VRC6703, pVR1012x/s Marburg delta TM/h (codon optimized) construct map (see, Ebola/Marburg/Lassa Plasmids, and Recombinant Adenoviruses in Table 2).
Figure 43:
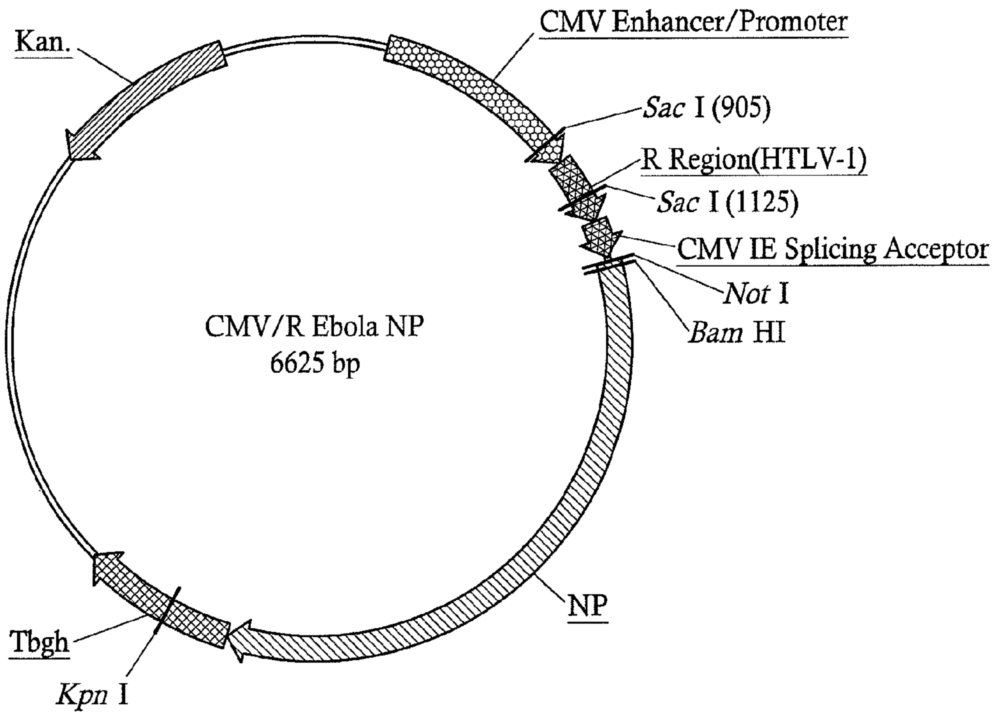
FIG. 43 shows CMV/R Ebola NP construct map (see, Ebola/Marburg/Lassa Plasmids, and Recombinant Adenoviruses in Table 2).

Ebola/Marburg/Lassa GenBank Accession Numbers.

| Gene | GenBank Accession number |
|---|---|
| Ebola Zaire GP | U23187, P87666 |
| Ebola Zaire NP | J04337 |
| Ebola Sudan GP | U28134, Q66798 |
| Ebola Sudan NP | AF173836 |
| Ebola Ivory Coast GP | U28006 |
| Ebola Ivory Coast NP | JO4336 |
| Ebola Reston GP | U23152 |
| Ebola Reston NP | |
| Marburg GP | Z12132 |
| Marburg NP | X68495 |
| Lassa GP | AF181853 |
| Lassa NP | AF246121 |

TABLE 2

Ebola/Marburg/Lassa Plasmids, and Recombinant Adenoviruses

| Construct | Construct Name/Description | Construct Map Name | SEQ ID NO | Figure |
|---|---|---|---|---|
| VRC6000 | VRC6000 (pVR1012-GP(Z)) | pVR1012-GP(Z) | 1 | 1 |
| VRC6001 | VRC6001 (pVR1012x/s-GP(Z)) | pVR1012x/s Ebola GP(Z) | 2 | 2 |
| VRC6002 | VRC6002 (pVR1012-GP(Z) delta MUC) | pVR1012-GP(Z) delta MUC | 3 | 3 |
| VRC6003 | VRC6003 (pVR1012-GP(Z) delta MUC delta FUR) | pVR1012-GP(Z) delta MUC delta FUR | 4 | 4 |
| VRC6004 | VRC6004 (pVR1012-GP(Z) delta GP2) | pVR1012-GP(Z) delta GP2 | 5 | 5 |
| VRC6005 | VRC6005 (pVR1012-GP(Z) delta GP2 delta C-term A) | pVR1012-GP(Z) delta GP2 delta C-term A | 6 | 6 |
| VRC6006 | VRC6006 (pVR1012-GP(Z) delta GP2 delta C-term B) | pVR1012-GP(Z) delta GP2 delta C-term B | 7 | 7 |
| VRC6007 | VRC6007 (pVR1012-GP(Z) delta GP2 delta FUS) | pVR1012-GP(Z) delta GP2 delta FUS | 8 | 8 |
| VRC6008 | VRC6008 (pVR1012-GP(Z) delta TM) | pVR1012-GP(Z) delta TM | 9 | 9 |
| VRC6052 | VRC 6052 (pVR1012-GP(Z) delta SGP) | pVR1012-GP(Z) delta SGP | 10 | 10 |
| VRC6101 | VRC 6101 (pVR1012x/s Ebola GP(R) (dTM)) | pVR1012x/s Ebola GP(R)(dTM) | 11 | 11 |
| VRC6110 | VRC 6110 (pAdApt Ebola GP(R) (dTM)) | pAdApt Ebola GP(R) (dTM) | 12 | 12 |
| VRC6200 | VRC6200 (pVR1012-GP(S)) | pVR1012-GP(S) | 13 | 13 |
| VRC6201 | VRC 6201 (pVR1012x/s Ebola GP(S)) | pVR1012x/s Ebola GP(S) | 14 | 14 |
| VRC6202 | VRC6202 (pVR1012-GP(S) delta TM) | pVR1012-GP(S) delta TM | 15 | 15 |
| VRC6300 | VRC6300 (pVR1012-GP(IC)) | pVR1012-GP(IC) | 16 | 16 |
| VRC6301 | VRC6301 (pVR1012x/s-GP(IC)) | pVR1012x/s Ebola GP(IC) | 17 | 17 |
| VRC6302 | VRC6302 (pVR1012-GP(IC) delta TM) | pVR1012-GP(IC) delta TM | 18 | 18 |
| VRC6303 | VRC 6303 (pVR1012x/s Ebola GP (IC) (dTM)) | pVR1012x/s Ebola GP(IC)(dTM) | 19 | 19 |
| VRC6310 | VRC 6310 (pAdApt Ebola GP (IC) (dTM)) | pAdApt Ebola GP(IC)(dTM) | 20 | 20 |
| VRC6351 | VRC6351 (pVR1012x/s-sGP(IC)) | pVR1012x/s-sGP(IC) | 21 | 21 |
| VRC6400 | VRC6400 (pVR1012-NP) | pVR1012-NP | 22 | 22 |
| VRC6401 | VRC6401 (pVR1012x/s-NP) | pVR1012x/s Ebola-NP | 23 | 23 |
| VRC6500 | VRC6500 (pVR1012-VP35) | pVR1012-VP35 | 24 | 24 |
| VRC6600 | VRC6600 (pAD/CMV-GP(dTM)(Z-CITE-S) | pAD/CMV-GP(dTM)(Z-CITE-S) | 25 | 25 |
| VRC6601 | VRC6601 (pAdApt Ebola GP(S)) | pAdApt Ebola GP(S) | 26 | 26 |
| VRC6602 | VRC 6602 (pAdApt Ebola GP(S)(dTM)) | pAdApt Ebola GP(S)(dTM) | 27 | 27 |
| VRC6603 | VRC6603 (pAdApt Ebola GP(Z)) | pAdApt Ebola GP(Z) | 28 | 28 |
| VRC6604 | VRC 6604 (pAdApt Ebola GP(Z)(dTM)) | pAdApt Ebola GP(Z)(dTM) | 29 | 29 |
| VRC6701 | VRC6701 (pVR1012-Marburg) | pVR1012 Marburg | 30 | 30 |
| VRC6702 | VRC 6702 (pVR1012x/s Marburg GP (dTM)) | pVR1012x/s Marburg GP(dTM) | 31 | 31 |
| VRC6710 | VRC 6710 (pAdApt Marburg GP (dTM)) | pAdApt Marburg GP (dTM) | 32 | 32 |
| VRC6800 | VRC6800 (pVR1012x/s Lassa GP) | pVR1012x/s Lassa GP | 33 | 33 |
| VRC6801 | VRC6801 (pVR1012x/s Lassa GP (dTM) | pVR1012x/s Lassa GP (dTM) | 34 | 34 |
| VRC6810 | VRC6810 (pAdApt Lassa GP) | pAdApt Lassa GP | 35 | 35 |
| VRC6811 | VRC6811 (pAdApt Lassa GP (dTM)) | pAdApt Lassa GP (dTM) | 36 | 36 |
| | CMV/R Ebola GP (Z) deltaTM/h (codon optimized) | CMV/R Ebola GP(Z) delta TM/h | 37 | 37 |
| | pVR1012 EbolaGP(Z, P87666)delta TM/h (codon optimized) | pVR1012x/s Ebola GP(Z) delta TM/h (P87666) | 38 | 38 |
| | CMV/R Ebola GP (S/Gulu) delta TM/h (codon optimized) | CMV/R-GP(S/G)(deltaTM)/h | 39 | 39 |
| | CMV/R Ebola GP (S,Q66798) delta TM/h (codon optimized) | CMV/R-GP(S,Q66798)(dTM)/h | 40 | 40 |

TABLE 2-continued

| Ebola/Marburg/Lassa Plasmids, and Recombinant Adenoviruses | | | | |
|---|---|---|---|---|
| Construct | Construct Name/Description | Construct Map Name | SEQ ID NO | Figure |
| VRC6802 | VRC6802, pVR1012x/s Lassa delta TM/h (codon optimized) | pVR1012x/s Lassa (codon optimized) | 41 | 41 |
| VRC6703 | VRC6703, pVR1012x/sMarburgdeltaTM/h (codon optimized) | PVR1012x/s Marburg (codon optimized) | 42 | 42 |
| | CMV/R Ebola NP | CMV/R Ebola NP | 43 | 43 |

DETAILED DESCRIPTION OF THE INVENTION

Filovirus vaccines are provided comprising a nucleic acid molecule encoding a filoviral structural protein operatively-linked to a control sequence in a pharmaceutically acceptable excipient. In one embodiment, the nucleic acid molecule encodes the transmembrane form of the viral glycoprotein (GP). In another embodiment, the nucleic acid molecule encodes the secreted form of the viral glycoprotein (SGP). In yet another embodiment, the nucleic acid molecule encodes the viral nucleoprotein (NP).

The present invention further includes vaccines comprising nucleic acid molecules encoding filoviral structural proteins other than GP, SGP, and NP, e.g., other structural gene products which elicit an immune response against a filovirus or disease caused by infection with filovirus. The nucleic acid molecules of the vaccines of the present invention encode structural gene products of any Ebola viral strain including the Zaire, Sudan, Ivory Coast and Reston strains. Nucleic acid molecules encoding structural gene products of the genetically-related Marburg virus strains may also be employed. Moreover, the nucleic acid molecules of the present invention may be modified, e.g., the nucleic acid molecules set forth herein may be mutated, as long as the modified expressed protein elicits an immune response against a pathogen or disease. For example, the nucleic acid molecule may be mutated so that the expressed protein is less toxic to cells. The present invention also includes vaccines comprising a combination of nucleic acid molecules. For example, and without limitation, nucleic acid molecules encoding GP, SGP and NP of the Zaire, Sudan and Ivory Coast Ebola strains may be combined in any combination, in one vaccine composition.

The present invention also provides methods for immunizing a subject against disease caused by infection with filovirus comprising administering to the subject an immunoeffective amount of a filovirus vaccine. Methods of making and using filovirus vaccines are also provided by the present invention including the preparation of pharmaceutical compositions.

Biochemical Analysis of Secreted and Virion Glycoproteins of Ebola Virus.

Ebola (EBO) viruses are members of the Filoviridae and cause a severe, often fatal form of hemorrhagic fever disease in human and/or non-human primates. The glycoprotein (GP) gene of filoviruses is the fourth gene (of seven) from the 3' end of the negative-strand RNA genome. All EBO viruses characterized thus far have the same unconventional type of GP gene organization that results in the expression of a secreted, nonstructural glycoprotein (SGP) in preference to the structural GP. The SGP is encoded in a single frame (0 frame), while the GP is encoded in two frames (0 and −1 frames). Expression of the GP occurs when the two frames are connected through a transcriptional editing event that results in the insertion of a single extra adenosine (added to a run of seven adenosines).

Figure 44:
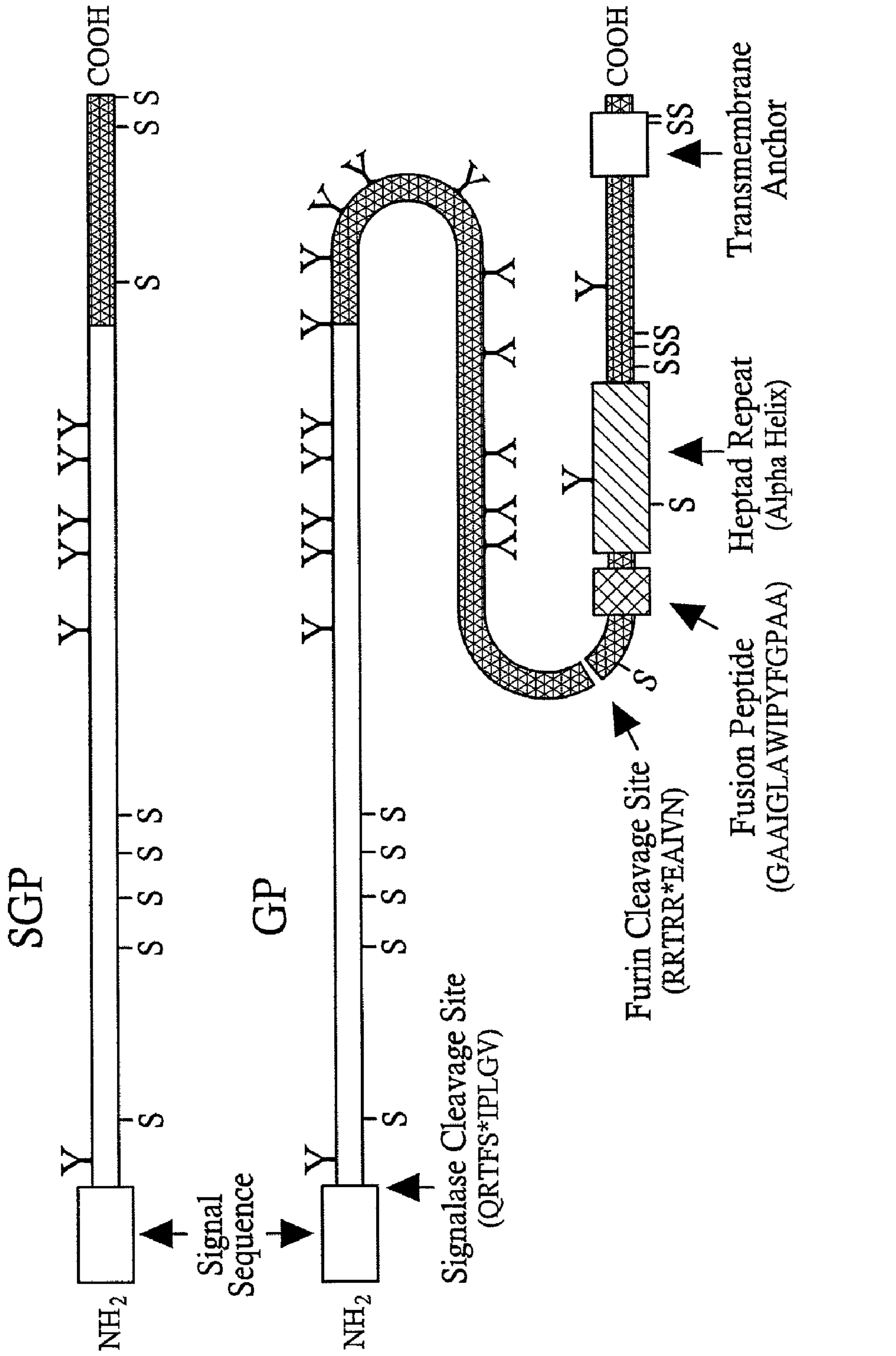
FIG. 44 is a diagrammatic representation of secreted glycoprotein (SGP) and glycoprotein (GP) molecules of Ebola virus (Zaire species isolated in 1976) showing important structural features. The white N-terminal regions of SGP and GP correspond to identical (shared) sequences, while the black C termini identify sequences unique to GP or SGP molecules. The common signalase cleavage sites for both SGP and GP and the furin cleavage site for GP0 (uncleaved form of GP) (↓) were determined by N-terminal sequencing. Also shown are cysteine residues (S), predicted N-linked glycosylation sites (Y-shaped projections), a predicted fusion peptide, a heptad repeat sequence, and a transmembrane anchor sequence. In Ebola viruses, the positions of these structures are conserved and their sequences are very similar or, in the case of N-linked glycosylation sites, are at least concentrated in the central region of GP. Signalase cleavage site is SEQ ID NO: 48, Furin cleavage site is SEQ ID NO: 49, and Fusion peptide is SEQ ID NO: 50.

Referring to FIG. 44, for Zaire species of EBO virus, the N-terminal 295 residues (including signal sequence) of the SGP (364 total residues) and GP (676 total residues) are identical, but the length and composition of their C-terminal sequences are unique. The GP, a type 1 transmembrane protein, is found on the surface of the infectious virion and functions in attachment structure in the binding and entry of the virus into susceptible cells. Comparisons of GP predicted amino acid sequences for all species of EBO virus show a general conservation in the N-terminal and C-terminal regions (each approximately one-third of the total sequence) and are separated by a highly variable middle section. This protein is highly glycosylated, containing large amounts of N- and O-linked glycans, and for Marburg (MBG) virus (another type of filovirus) has been shown to form trimers. Just N terminal to the transmembrane anchor sequence of the GP (residues 650 to 672) is a motif (residues 585 to 609) that is highly conserved in filoviruses. This sequence also has a high degree of homology with a motif in the glycoproteins of oncogenic retroviruses that has been shown to be immunosuppressive in vitro. Partially overlapping this motif is a heptad repeat sequence (53 residues; positions 541 to 593) that is thought to function in the formation of intermolecular coiled coils in the assembly of trimers, similar to structures predicted for the surface glycoproteins of other viruses. Immediately N terminal to this sequence is a predicted fusion peptide followed closely by a putative multibasic cleavage site for a subtilisin/kexin-like convertase, furin. Cleavage by furin has been indirectly demonstrated by use of specific inhibitors and is predicted to occur at the last arginine in the sequence RRTRR↓ (position 501 from the beginning of the open reading frame [ORF]). Although the role of the SGP is less defined, recent studies have shown that SGP can bind to neutrophils, while GP binds to endothelial cells. The different binding patterns of SGP and GP suggest that despite having identical N-terminal amino acid sequences (~280 residues), these glycoproteins are structurally very distinct from one another.

Figure 45:
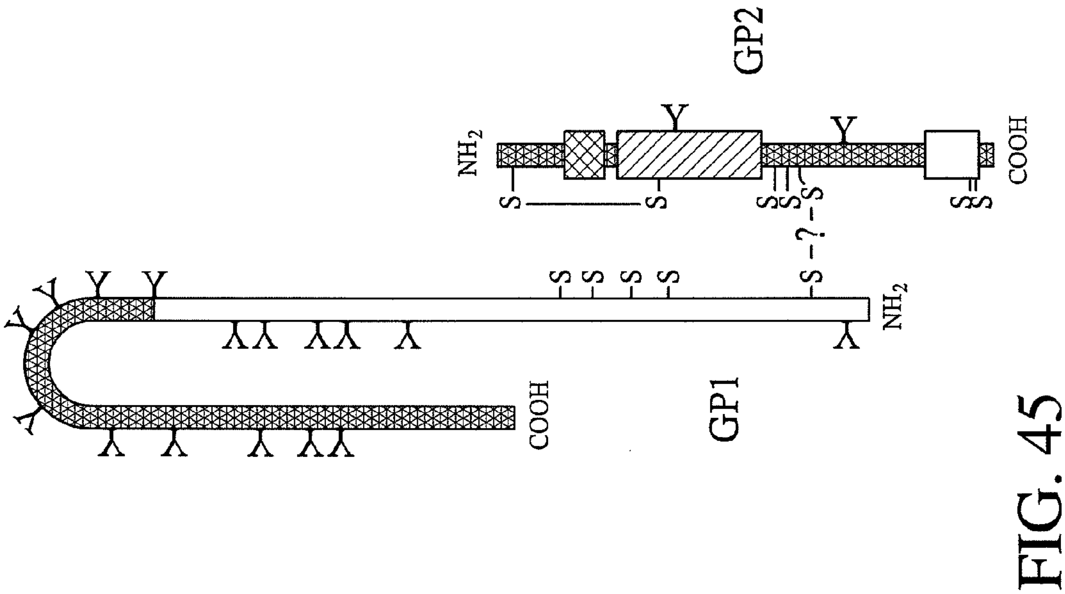
FIG. 45 is a diagrammatic representation of the structural GP. Shown is the predicted orientation of the GP1-GP2 heterodimer linked by undetermined disulfide bonding (indicated by the question mark). Intramolecular disulfide bonds that are shown come from prior predictions based on similarities to retrovirus glycoprotein structures. See FIG. 44 for other features of the amino acid sequence.

Referring to FIG. 45, the glycoproteins expressed by a Zaire species of Ebola virus were analyzed for cleavage, oligomerization, and other structural properties to better define their functions. The 50- to 70-kDa secreted and 150-kDa virion/structural glycoproteins (SGP and GP, respectively), which share the 295 N-terminal residues, are cleaved near the N terminus by signalase. A second cleavage event, occurring in GP at a multibasic site (RRTRR↓) (SEQ ID NO: 51) that is likely mediated by furin, results in two glycoproteins (GP1 and GP2) linked by disulfide bonding. This furin cleavage site is present in the same position in the GPs of all Ebola viruses (R[R/K]X[R/K]R↓), and one is predicted for Marburg viruses (R[R/K]KR↓), although in a different location. Based on the results of cross-linking studies, investigators were able to determine that Ebola virion peplomers are composed of trimers of GP1-GP2 heterodimers and that aspects of their structure are similar to those of retroviruses (including lentiviruses like HIV-1 and HIV-2), paramyxoviruses, and influenza viruses. Investigators also determined that SGP is secreted from infected cells almost exclusively in the form of a homodimer that is joined by disulfide bonding.

Figure 46:
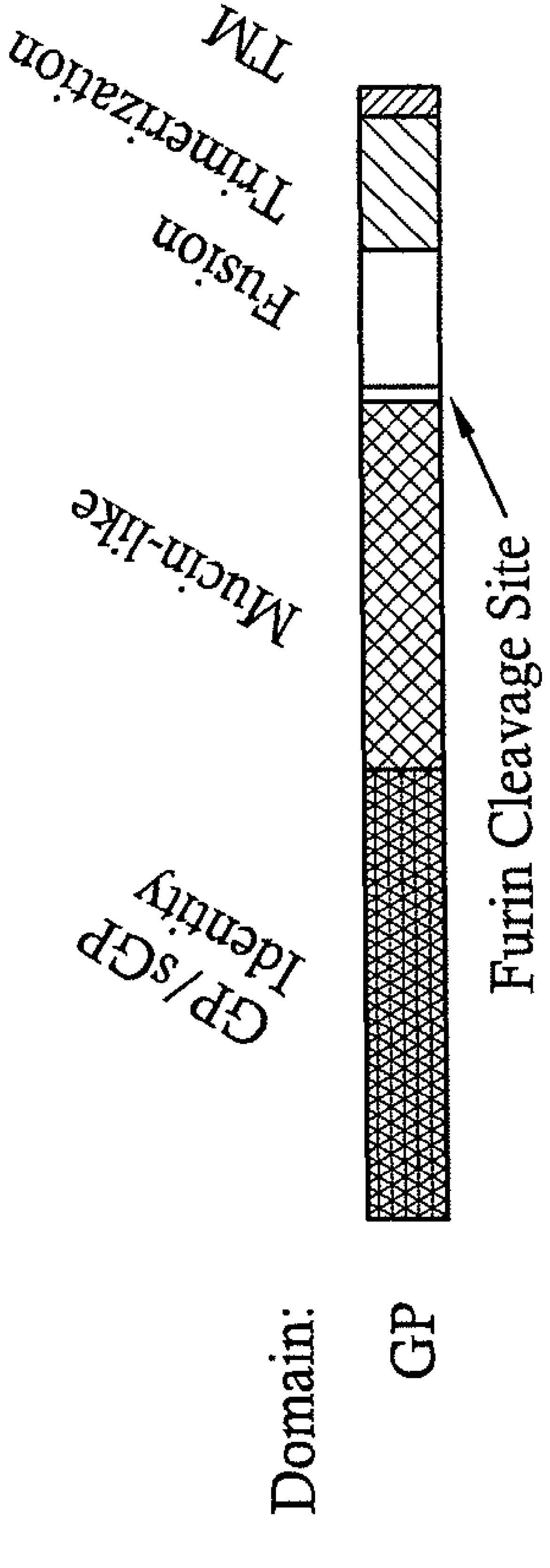
FIG. 46 shows induction of the cytopathic effects by Ebola virus glycoproteins and mapping of the molecular determinants of cytopathicity.

Referring to FIG. 46, investigators defined the main viral determinant of Ebola virus pathogenicity; synthesis of the virion glycoprotein (GP) of Ebola virus Zaire induced cytotoxic effects in human endothelial cells in vitro and in vivo. This effect mapped to a serine-threonine-rich, mucin-like domain of this type I transmembrane glycoprotein, one of seven gene products of the virus. Gene transfer of GP into explanted human or porcine blood vessels caused massive endothelial cell loss within 48 hours that led to a substantial increase in vascular permeability. Deletion of the mucin-like region of GP abolished these effects without affecting protein expression or function. GP derived from the Reston strain of virus, which causes disease in non-human primates but not in man, did not disrupt the vasculature of human blood vessels. In contrast, the Zaire GP induced endothelial cell disruption and cytotoxicity in both non-human primate and human blood vessels, and the mucin domain was required for this effect. These findings indicate that GP, through its mucin domain, is the viral determinant of Ebola pathogenicity and likely contributes to hemorrhage during infection.

Nucleic Acid Molecules

As indicated herein, nucleic acid molecules of the present invention may be in the form of RNA or in the form of DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By “isolated” nucleic acid molecule(s) is intended a nucleic acid molecule, DNA or RNA, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

Nucleic acid molecules of the present invention include DNA molecules comprising an open reading frame (ORF) encoding a wild-type filovirus structural gene product; and DNA molecules which comprise a sequence substantially different from those described above but which, due to the degeneracy of the genetic code, still encode an ORF of a wild-type filovirus structural gene product. Of course, the genetic code is well known in the art.

The present invention is further directed to fragments of the nucleic acid molecules described herein. By a fragment of a nucleic acid molecule having the nucleotide sequence of an ORF encoding a wild-type filovirus structural gene product is intended fragments at least about 15 nt., and more preferably at least about 20 nt., still more preferably at least about 30 nt., and even more preferably, at least about 40 nt. in length. Of course, larger fragments 50, 100, 150, 200, 250, 300, 350, 400, 450, or 500 nt. in length are also intended according to the present invention as are fragments corresponding to most, if not all, of the nucleotide sequence of the ORF encoding a wild-type filovirus structural gene product. By a fragment at least 20 nt. in length, for example, is intended fragments which include 20 or more contiguous bases from the nucleotide sequence of the ORF of a wild-type filovirus structural gene product.

Preferred nucleic acid fragments of the present invention include nucleic acid molecules encoding epitope-bearing portions of the filovirus structural protein. In particular, such nucleic acid fragments of the present invention include nucleic acid molecules encoding epitope-bearing domains of a filovirus structural protein, where the domain is the GP/SGP identity domain, the mucin-like domain, the furin cleavage site, the fusion peptide domain, the heptad repeat domain, the transmembrane anchor domain, and the intracellular domain, and any combination thereof, for example, a filovirus glycoprotein having a truncation at the carboxy terminus to delete the transmembrane anchor and intracellular domain, a filovirus glycoprotein having a truncation at the carboxy terminus to delete the heptad repeat domain and transmembrane anchor and intracellular domain, a filovirus glycoprotein having a truncation at the carboxy terminus to delete the fusion peptide domain, heptad repeat domain, and transmembrane anchor and intracellular domain, a filovirus glycoprotein having a truncation at the carboxy terminus to delete the furin cleavage site, fusion peptide domain, heptad repeat domain, and transmembrane anchor and intracellular domain, a filovirus glycoprotein having a truncation at the carboxy terminus to delete the mucin-like domain, furin cleavage site, fusion peptide domain, heptad repeat domain, and transmembrane anchor and intracellular domain. Another example is a filovirus glycoprotein having an amino, internal, or carboxy deletion to delete the mucin-like domain, the furin cleavage site, the fusion peptide domain, the heptad repeat domain, the transmembrane anchor domain, or the intracellular domain.

In another aspect, the invention provides a nucleic acid molecule comprising a polynucleotide which hybridizes under stringent hybridization conditions to a portion of the polynucleotide in a nucleic acid molecule of the invention described above. By “stringent hybridization conditions” is intended overnight incubation at 42° C. in a solution comprising: 50% formamide, 5×SSC (750 mM NaCl, 75 mM trisodium citrate), 50 mM sodium phosphate (pH 7.6), 5×Denhardt’s solution, 10% dextran sulfate, and 20 μg/ml denatured, sheared salmon sperm DNA, followed by washing the filters in 0.1×SSC at about 65° C.

By a polynucleotide which hybridizes to a “portion” of a polynucleotide is intended a polynucleotide (either DNA or RNA) hybridizing to at least about 15 nucleotides (nt.), and more preferably at least about 20 nt., still more preferably at least about 30 nt., and even more preferably about 30-70 nt. of the reference polynucleotide.

By a portion of a polynucleotide of “at least 20 nt. in length,” for example, is intended 20 or more contiguous nucleotides from the nucleotide sequence of the reference polynucleotide. Of course, a polynucleotide which hybridizes only to a poly A sequence or a complementary stretch of T (or U) residues, would not be included in a polynucleotide of the invention used to hybridize to a portion of a nucleic acid of the invention, since such a polynucleotide would hybridize to any nucleic acid molecule containing a poly A stretch or the complement thereof (e.g., practically any double-stranded cDNA clone).

As indicated herein, nucleic acid molecules of the present invention which encode a filovirus structural gene product may include, but are not limited to those encoding the amino acid sequence of the full-length polypeptide, by itself, the coding sequence for the full-length polypeptide and additional sequences, such as those encoding a leader or secretory sequence, such as a pre-, or pro- or prepro-protein sequence, the coding sequence of the full-length polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing, including splicing and polyadenylation signals, for example, ribosome binding and stability of mRNA; and additional coding sequence which codes for additional amino acids, such as those which provide additional functionalities.

The present invention further relates to variants of the nucleic acid molecules of the present invention, which encode portions, analogs or derivatives of the filovirus structural gene product. Variants may occur naturally, such as a natural allelic variant. By an "allelic variant" is intended one of several alternate forms of a gene occupying a given locus on a genome of an organism. (*Genes II*, Lewin, B., ed., John Wiley & Sons, 1985 New York). Non-naturally occurring variants may be produced using art-known mutagenesis techniques.

Such variants include those produced by nucleotide substitutions, deletions or additions, which may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the filovirus structural gene product or portions thereof. Also especially preferred in this regard are conservative substitutions.

Further embodiments of the invention include nucleic acid molecules comprising a polynucleotide having a nucleotide sequence at least 95% identical, and more preferably at least 96%, 97%, 98% or 99% identical to a nucleotide sequence encoding a polypeptide having the amino acid sequence of a wild-type filovirus structural gene product or fragment thereof or a nucleotide sequence complementary thereto.

By a polynucleotide having a nucleotide sequence at least, for example, 95% "identical" to a reference nucleotide sequence encoding a filovirus structural gene product is intended that the nucleotide sequence of the polynucleotide is identical to the reference sequence except that the polynucleotide sequence may include up to five point mutations per each 100 nucleotides of the reference nucleotide sequence encoding the Ebola virus structural gene product. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 95%, 96%, 97%, 98% or 99% identical to the reference nucleotide sequence can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, 1981 *Advances in Applied Mathematics* 2:482-489, to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

The present application is directed to nucleic acid molecules at least 95%, 96%, 97%, 98% or 99% identical to the nucleic acid sequences shown herein in the Sequence Listing which encode a polypeptide having Ebola, Marburg, or Lassa virus polypeptide activity. By "a polypeptide having Ebola, Marburg, or Lassa virus polypeptide activity" is intended polypeptides exhibiting Ebola, Marburg, or Lassa virus polypeptide activity in a particular biological assay. For example, GP, SGP or NP protein activity can be measured for changes in immunological character by an appropriate immunological assay.

Of course, due to the degeneracy of the genetic code, one of ordinary skill in the art will immediately recognize that a large number of the nucleic acid molecules having a sequence at least 95%, 96%, 97%, 98%, or 99% identical to a nucleic acid sequence shown herein in the Sequence Listing will encode a polypeptide "having Ebola, Marburg, or Lassa virus polypeptide activity". In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having Ebola, Marburg, or Lassa virus polypeptide activity. This is because the skilled artisan is fully aware of amino acid substitutions that are either less likely or not likely to significantly effect protein function (e.g., replacing one aliphatic amino acid with a second aliphatic amino acid).

For example, guidance concerning how to make phenotypically silent amino acid substitutions is provided in Bowie, J. U. et al. 1990 Science 247:1306-1310, wherein the authors indicate that proteins are surprisingly tolerant of amino acid substitutions.

Polypeptides and Fragments

The invention further provides a filovirus polypeptide having the amino acid sequence encoded by an open reading frame (ORF) of a wild-type filovirus structural gene, or a peptide or polypeptide comprising a portion thereof (e.g., SGP).

It will be recognized in the art that some amino acid sequences of the filovirus polypeptides can be varied without significant effect of the structure or function of the protein. If such differences in sequence are contemplated, it should be remembered that there will be critical areas on the protein which determine activity.

Thus, the invention further includes variations of the filovirus polypeptide which show substantial filovirus polypeptide activity or which include regions of filovirus protein such as the protein portions discussed below. Such mutants include deletions, insertions, inversions, repeats, and type substitutions. As indicated, guidance concerning which amino acid changes are likely to be phenotypically silent can be found in Bowie, J. U. et al. 1990 *Science* 247:1306-1310.

Thus, the fragment, derivative or analog of the polypeptide of the invention may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues include a substituent group, or (iii) one in which additional amino acids are fused to the mature polypeptide, such as an IgG Fc fusion region peptide or leader or secretory sequence or a sequence which is employed for purification of the mature polypeptide or a proprotein sequence. Such fragments, derivatives and analogs are deemed to be within the scope of those skilled in the art from the teachings herein.

As indicated, changes are preferably of a minor nature, such as conservative amino acid substitutions that do not significantly affect the folding or activity of the protein (see Table A).

TABLE A

| Conservative Amino Acid Substitutions | |
|---|---|
| Aromatic | Phenylalanine |
| | Tryptophan |
| | Tyrosine |
| Ionizable: Acidic | Aspartic Acid |
| | Glutamic Acid |
| Ionizable: Basic | Arginine |
| | Histidine |
| | Lysine |
| Nonionizable Polar | Asparagine |
| | Glutamine |
| | Selenocystine |
| | Serine |
| | Threonine |
| Nonpolar (Hydrophobic) | Alanine |
| | Glycine |
| | Isoleucine |
| | Leucine |
| | Proline |
| | Valine |
| Sulfur Containing | Cysteine |
| | Methionine |

Of course, the number of amino acid substitutions a skilled artisan would make depends on many factors, including those described above. Generally speaking, the number of amino acid substitutions for any given filovirus polypeptide will not be more than 50, 40, 30, 20, 10, 5 or 3.

Amino acids in the filovirus polypeptides of the present invention that are essential for function can be identified by methods known in the art, such as site-directed mutagenesis or alanine-scanning mutagenesis (Cunningham & Wells 1989 *Science* 244:1081-1085). The latter procedure introduces single alanine mutations at every residue in the molecule. The resulting mutant molecules are then tested for biological activity such as changes in immunological character.

The polypeptides of the present invention are conveniently provided in an isolated form. By "isolated polypeptide" is intended a polypeptide removed from its native environment. Thus, a polypeptide produced and/or contained within a recombinant host cell is considered isolated for purposes of the present invention. Also intended as an "isolated polypeptide" are polypeptides that have been purified, partially or substantially, from a recombinant host cell or a native source. For example, a recombinantly produced version of the filovirus polypeptide can be substantially purified by the one-step method described in Smith and Johnson 1988 *Gene* 67:31-40.

The polypeptides of the present invention include a polypeptide comprising a polypeptide having the amino acid sequence of a wild-type filovirus structural gene product or portion thereof or encoded by a nucleic acid sequence shown herein in the Sequence Listing; as well as polypeptides which are at least 95% identical, and more preferably at least 96%, 97%, 98%, or 99% identical to those described above.

By a polypeptide having an amino acid sequence at least, for example, 95% "identical" to a reference amino acid sequence of an filovirus polypeptide is intended that the amino acid sequence of the polypeptide is identical to the reference sequence except that the polypeptide sequence may include up to five amino acid alterations per each 100 amino acids of the reference amino acid of the filovirus polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 95%, 96%, 97%, 98%, or 99% identical to a reference amino acid sequence can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

In another aspect, the invention provides portions of the polypeptides described herein with at least 30 amino acids and more preferably at least 50 amino acids. Preferred portions of the present invention include polypeptides comprising an epitope-bearing portion of a filovirus structural protein. In particular, preferred portions of the present invention include polypeptides comprising an epitope-bearing domain of a filovirus structural protein, where the domain is the GP/SGP identity domain, the mucin-like domain, the furin cleavage site, the fusion peptide domain, the heptad repeat domain, the transmembrane anchor domain, and the intracellular domain, and any combination thereof, for example, a filovirus glycoprotein having a truncation at the carboxy terminus to delete the transmembrane anchor and intracellular domain, a filovirus glycoprotein having a truncation at the carboxy terminus to delete the heptad repeat domain and transmembrane anchor and intracellular domain, a filovirus glycoprotein having a truncation at the carboxy terminus to delete the fusion peptide domain, heptad repeat domain, and transmembrane anchor and intracellular domain, a filovirus glycoprotein having a truncation at the carboxy terminus to delete the furin cleavage site, fusion peptide domain, heptad repeat domain, and transmembrane anchor and intracellular domain, and a filovirus glycoprotein having a truncation at the carboxy terminus to delete the mucin-like domain, furin cleavage site, fusion peptide domain, heptad repeat domain, and transmembrane anchor and intracellular domain. Another example is a filovirus glycoprotein having an amino, internal, or carboxy deletion to delete the mucin-like domain, the furin cleavage site, the fusion peptide domain, the heptad repeat domain, the transmembrane anchor domain, or the intracellular domain.

The polypeptides of the invention may be produced by any conventional means (Houghten, R. A. 1985 *PNAS USA* 82:5131-5135). The "Simultaneous Multiple Peptide Synthesis (SMPS)" process is described in U.S. Pat. No. 4,631,211 to Houghten et al. (1986).

The present invention also relates to vectors which include the nucleic acid molecules of the present invention, host cells which are genetically engineered with the recombinant vectors, and the production of filovirus polypeptides or fragments thereof by recombinant techniques.

The present invention relates to "prime and boost" immunization regimes in which the immune response induced by administration of a priming composition is boosted by administration of a boosting composition. The present invention is based on the inventors' experimental demonstration that effective boosting can be achieved using replication-defective adenovirus vectors, following priming with any of a variety of different types of priming compositions. The present invention employs replication-deficient adenovirus which, as the experiments described below show, has been found to be an effective means for providing a boost to an immune response primed to antigen using any of a variety of different priming compositions.

Replication-deficient adenovirus derived from human serotype 5 has been developed as a live viral vector by Graham and colleagues (Graham & Prevec 1995 *Mol Biotechnol* 3:207-20; Bett et al. 1994 *PNAS USA* 91:8802-6). Adenoviruses are non-enveloped viruses containing a linear double-stranded DNA genome of around 3600 bp. Recombinant viruses can be constructed by in vitro recombination between an adenovirus genome plasmid and a shuttle vector containing the gene of interest together with a strong eukaryotic promoter, in a permissive cell line which allows viral replication. High viral titres can be obtained from the permissive cell line, but the resulting viruses, although capable of infecting a wide range of cell types, do not replicate in any cells other than the permissive line, and are therefore a safe antigen delivery system. Recombinant adenoviruses have been shown to elicit protective immune responses against a number of antigens including tick-borne encephalitis virus NS1 protein (Jacobs et al. 1992 *J Virol* 66:2086-95) and measles virus nucleoprotein (Fooks et al. 1995 *Virology* 210:456-65).

Remarkably, the experimental work described below demonstrates that use of embodiments of the present invention allows for recombinant replication-defective adenovirus expressing an antigen to boost an immune response primed by a DNA vaccine. The replication-defective adenovirus was found to induce an immune response after intramuscular immunization. In prime/boost vaccination regimes the replication-defective adenovirus is also envisioned as being able to prime a response that can be boosted by a different recombinant virus or recombinantly produced antigen.

Non-human primates immunized with plasmid DNA and boosted with replication-defective adenovirus were protected against challenge. Both recombinant replication-deficient adenovirus and plasmid DNA are vaccines that are safe for use in humans. Advantageously, the inventors found that a vaccination regime used intramuscular immunization for both prime and boost can be employed, constituting a general immunization regime suitable for inducing an immune response, e.g., in humans.

The present invention in various aspects and embodiments employs a replication-deficient adenovirus vector encoding an antigen for boosting an immune response to the antigen primed by previous administration of the antigen or nucleic acid encoding the antigen.

A general aspect of the present invention provides for the use of a replication-deficient adenoviral vector for boosting an immune response to an antigen.

One aspect of the present invention provides a method of boosting an immune response to an antigen in an individual, the method including provision in the individual of a replication-deficient adenoviral vector including nucleic acid encoding the antigen operably linked to regulatory sequences for production of antigen in the individual by expression from the nucleic acid, whereby an immune response to the antigen previously primed in the individual is boosted.

An immune response to an antigen may be primed by genetic immunization, by infection with an infectious agent, or by recombinantly produced antigen.

A further aspect of the invention provides a method of inducing an immune response to an antigen in an individual, the method comprising administering to the individual a priming composition comprising the antigen or nucleic acid encoding the antigen and then administering a boosting composition which comprises a replication-deficient adenoviral vector including nucleic acid encoding the antigen operably linked to regulatory sequences for production of antigen in the individual by expression from the nucleic acid.

A further aspect provides for use of a replication-deficient adenoviral vector, as disclosed, in the manufacture of a medicament for administration to a mammal to boost an immune response to an antigen. Such a medicament is generally for administration following prior administration of a priming composition comprising the antigen.

The priming composition may comprise any viral vector, including adenoviral, or other than adenoviral, such as a vaccinia virus vector such as a replication-deficient strain such as modified virus Ankara (MVA) (Mayr et al. 1978 *Zentralbl Bakteriol* 167:375-90; Sutter and Moss 1992 *PNAS USA* 89:10847-51; Sutter et al. 1994 *Vaccine* 12:1032-40) or NYVAC (Tartaglia et al. 1992 *Virology* 118:217-32), an avipox vector such as fowlpox or canarypox, e.g., the strain known as ALVAC (Kanapox, Paoletti et al. 1994 *Dev Biol Stand* 1994 82:65-9), or a herpes virus vector.

The priming composition may comprise DNA encoding the antigen, such DNA preferably being in the form of a circular plasmid that is not capable of replicating in mammalian cells. Any selectable marker should not be resistant to an antibiotic used clinically, so for example Kanamycin resistance is preferred to Ampicillin resistance. Antigen expression should be driven by a promoter which is active in mammalian cells, for instance the cytomegalovirus immediate early (CMV IE) promoter.

In particular embodiments of the various aspects of the present invention, administration of a priming composition is followed by boosting with first and second boosting compositions, the first and second boosting compositions being the same or different from one another, e.g., as exemplified below. Still further boosting compositions may be employed without departing from the present invention. In one embodiment, a triple immunization regime employs DNA, then adenovirus (Ad) as a first boosting composition, and then MVA as a second boosting composition, optionally followed by a further (third) boosting composition or subsequent boosting administration of one or other or both of the same or different vectors. Another option is DNA then MVA then Ad, optionally followed by subsequent boosting administration of one or other or both of the same or different vectors.

The antigen to be included in respective priming and boosting compositions (however many boosting compositions are employed) need not be identical, but should share epitopes. The antigen may correspond to a complete antigen in a target pathogen or cell, or a fragment thereof. Peptide epitopes or artificial strings of epitopes may be employed, more efficiently cutting out unnecessary protein sequence in the antigen and encoding sequence in the vector or vectors. One or more additional epitopes may be included, for instance epitopes which are recognized by T helper cells, especially epitopes recognized in individuals of different HLA types.

Within the replication-deficient adenoviral vector, regulatory sequences for expression of the encoded antigen will include a promoter. By "promoter" is meant a sequence of nucleotides from which transportation may be initiated of DNA operably linked downstream (i.e. in the 3' direction on the sense strand of double-stranded DNA). "Operably linked" means joined as part of the same nucleic acid molecule, suitably positioned and oriented for transcription to be initiated from the promoter. DNA operably linked to a promoter is "under transcriptional initiation regulation" of the promoter. Other regulatory sequences including terminator fragments, polyadenylation sequences, enhancer sequences, marker genes, internal ribosome entry site (IRES) and other sequences may be included as appropriate, in accordance with the knowledge and practice of the ordinary person skilled in the art: see, for example, *Molecular Cloning: a Laboratory Manual,* $2^{nd}$ edition, Sambrook et al. 1989 Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in *Current Protocols in Molecular Biology*, Ausubel et al. eds., John Wiley & Sons, 1994.

Suitable promoters for use in aspects and embodiments of the present invention include the cytomegalovirus immediate early (CMV IE) promoter, with or without intron A, and any other promoter that is active in mammalian cells.

Either or both of the priming and boosting compositions may include an adjuvant or cytokine, such as alpha-interferon, gamma-interferon, platelet-derived growth factor (PDGF), granulocyte macrophage-colony stimulating factor (GM-CSF) granulocyte-colony stimulating factor (gCSF), tumor necrosis factor (TNF), epidermal growth factor (EGF), IL-1, IL-2, IL-4, IL-6, IL-8, IL-10 and IL-12, or encoding nucleic acid therefor.

Administration of the boosting composition is generally weeks or months after administration of the priming composition, preferably about 2-3 weeks or 4 weeks, or 8 weeks, or 16 weeks, or 20 weeks, or 24 weeks, or 28 weeks, or 32 weeks.

Preferably, administration of priming composition, boosting composition, or both priming and boosting compositions, is intramuscular immunization.

Intramuscular administration of adenovirus vaccines or plasmid DNA may be achieved by using a needle to inject a suspension of the virus or plasmid DNA. An alternative is the use of a needless injection device to administer a virus or plasmid DNA suspension (using, e.g., Biojector™) or a freeze-dried powder containing the vaccine (e.g., in accordance with techniques and products of Powderject), providing for manufacturing individually prepared doses that do not need cold storage. This would be a great advantage for a vaccine that is needed in rural areas of Africa.

Adenovirus is a virus with an excellent safety record in human immunizations. The generation of recombinant viruses can be accomplished simply, and they can be manufactured reproducibly in large quantities. Intramuscular administration of recombinant replication-deficient adenovirus is therefore highly suitable for prophylactic or therapeutic vaccination of humans against diseases which can be controlled by an immune response.

The individual may have a disease or disorder such that delivery of the antigen and generation of an immune response to the antigen is of benefit or has a therapeutically beneficial effect.

Most likely, administration will have prophylactic aim to generate an immune response against a pathogen or disease before infection or development of symptoms.

Diseases and disorders that may be treated or prevented in accordance with the present invention include those in which an immune response may play a protective or therapeutic role.

Components to be administered in accordance with the present invention may be formulated in pharmaceutical compositions. These compositions may comprise a pharmaceutically acceptable excipient, carrier, buffer, stabilizer or other materials well known to those skilled in the art. Such materials should be non-toxic and should not interfere with the efficacy of the active ingredient. The precise nature of the carrier or other material may depend on the route of administration, e.g., intravenous, cutaneous or subcutaneous, intramucosal (e.g., gut), intranasal, intramuscular, or intraperitoneal routes.

As noted, administration is preferably intradermal, subcutaneous or intramuscular.

Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives may be included, as required.

A slow-release formulation may be employed.

Following production of replication-deficient adenoviral particles and optional formulation of such particles into compositions, the particles may be administered to an individual, particularly human or other primate.

Administration may be to another mammal, e.g., rodent such as mouse, rat or hamster, guinea pig, rabbit, sheep, goat, pig, horse, cow, donkey, dog or cat.

Administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g., decisions on dosage etc., is within the responsibility of general practitioners and other medical doctors, or in a veterinary context a veterinarian, and typically takes account of the disorder to be treated, the condition of the individual patient, the site of delivery, the method of administration and other factors known to practitioners. Examples of the techniques and protocols mentioned above can be found in *Remington's Pharmaceutical Sciences,* $16^{th}$ edition, Osol, A. ed., 1980.

In one preferred regimen, DNA is administered (preferably intramuscularly) at a dose of 10 micrograms to 50 milligrams/injection, followed by adenovirus (preferably intramuscularly) at a dose of $5\times10^{7}$-$1\times10^{12}$ particles/injection.

The composition may, if desired, be presented in a kit, pack or dispenser, which may contain one or more unit dosage forms containing the active ingredient. The kit, for example, may comprise metal or plastic foil, such as a blister pack. The kit, pack, or dispenser may be accompanied by instructions for administration.

A composition may be administered alone or in combination with other treatments, either simultaneously or sequentially dependent upon the condition to be treated.

Delivery to a non-human mammal need not be for a therapeutic purpose, but may be for use in an experimental context, for instance in investigation of mechanisms of immune responses to an antigen of interest, e.g., protection against disease.

Further aspects and embodiments of the present invention will be apparent to those of ordinary skill in the art, in view of the above disclosure and following experimental exemplification, included by way of illustration and not limitation, and with reference to the attached figures.

Development of a Preventive Vaccine for Ebola Virus Infection in Primates

Genetic immunization has been shown to influence both humoral and cellular immune activation pathways and to protect against infection by human pathogens (Tang, D. C. et al. 1992 *Nature* 356:152-154; Ulmer, J. B. et al. 1993 *Science* 259:1745-1749; Wang, B. et al. 1993 *PNAS USA* 90:4156-4160; Sedegah, M. et al. 1994 *PNAS USA* 91:9866-9870). The effectiveness of plasmid vaccines is thought to result from host cell protein synthesis and endogenous presentation of the immunogen, and possibly to immunostimulatory effects of plasmid DNA itself (Krieg, A. M. et al. 1995 *Nature* 374:546-549; Sato, Y. et al. 1996 *Science* 273:352-354). DNA vaccines have been shown to elicit specific immune responses to Ebola virus antigens and to protect guinea pigs (Xu, L. et al. 1998 *Nat Med* 4:7-42) and mice (Vanderzanden, L. et al. 1998 *Virology* 246:134-144) against challenge with Ebola virus adapted to produce lethal infection in rodents (Connolly, B. M. et al. 1999 *J Infect Dis* 179:S203-S217; Bray, M. et al. 1998 *J Infect Dis* 178:651-661). Although both cell-mediated and humoral immune responses were elicited, antibody titer correlated with the degree of protection in animals immunized with plasmids encoding proteins from the Zaire subtype of Ebola virus.

A broadly effective vaccine would need to provide immunity to the multiple Ebola subtypes isolated in human infections (Zaire, Sudan and Ivory Coast), but a multivalent vaccine might dilute the specific immune response demonstrated for the single subtype vaccine. To address this concern, we analyzed the efficacy of the original Ebola Zaire DNA vaccine in comparison to its use in combination with DNA from Ebola subtypes Sudan and Ivory Coast. As in a previous study (Xu, L. et al. 1998 *Nat Med* 4:7-42), immunization with a single plasmid encoding Zaire subtype virion glycoprotein, GP(Z), generated a substantial virus-specific antibody response and conferred protective immunity in guinea pigs (Table I). Inclusion of a plasmid expressing Ebola nucleoprotein, NP, did not affect the antibody titer to Ebola GP(Z) or diminish its protective efficacy. Further broadening of the vaccine components to include NP and three subtypes of Ebola glycoprotein, Zaire, Ivory Coast and Sudan, GP(Z,IC, S)+NP, yielded a pre-challenge immune response comparable to the single-plasmid vaccine. Moreover, complete protection from infection with Ebola Zaire was achieved in guinea pigs that received the multivalent vaccine (Table I, subjects 13-16). Anamnestic antibody was not induced by the virus challenge, indicating that the vaccine itself provided an immune response sufficient to efficiently clear the virus. These findings show that multivalent plasmid immunization did not substantially diminish glycoprotein (GP)-specific antibody production and its protective efficacy in a rodent model.

TABLE I

Multivalent genetic immunization in guinea pigs

| ID | Immunization | ELISA IgG | Survival |
|---|---|---|---|
| 1 | Plasmid | 0 | No |
| 2 | Plasmid | 0 | No |
| 3 | Plasmid | 0 | No |
| 4 | Plasmid | 0 | No |
| 5 | GP(Z) | 6400 | Yes |
| 6 | GP(Z) | 6400 | Yes |
| 7 | GP(Z) | 6400 | Yes |
| 8 | GP(Z) | 3200 | Yes |
| 9 | GP(Z) + NP | 6400 | Yes |
| 10 | GP(Z) + NP | 6400 | Yes |
| 11 | GP(Z) + NP | 6400 | Yes |
| 12 | GP(Z) + NP | 6400 | Yes |
| 13 | GP(Z, IC, S) + NP | 6400 | Yes |
| 14 | GP(Z, IC, S) + NP | 1600 | Yes |
| 15 | GP(Z, IC, S) + NP | 6400 | Yes |
| 16 | GP(Z, IC, S) + NP | 6400 | Yes |

Table I. Comparison of multivalent vs. monovalent genetic immunization in guinea pigs. Guinea pigs were immunized intramuscularly three times at two-week intervals with 100 μg of DNA (Plasmid, 100 μg p1012; GP(Z), 100 μg pGP(Z); GP(Z) + NP, 75 μg pGP(Z) and 25 μg pNP; GP(Z, IC, S) + NP, 25 μg each of pGP(Z), pGP(IC), pGP(S) and pNP). Serum was collected 6 weeks after the first injection and pre-challenge titers for antibody to Ebola GP (ELISA IgG) were measured by ELISA (Ksiazek, T. G. et al. 1992 J Clin Microbiol 30: 947-950) and are displayed as the reciprocal endpoint dilution. Three months after the final immunization the animals were challenged as described (Xu, L. et al. 1998 Nat Med 4: 37-42).

Figure 47:
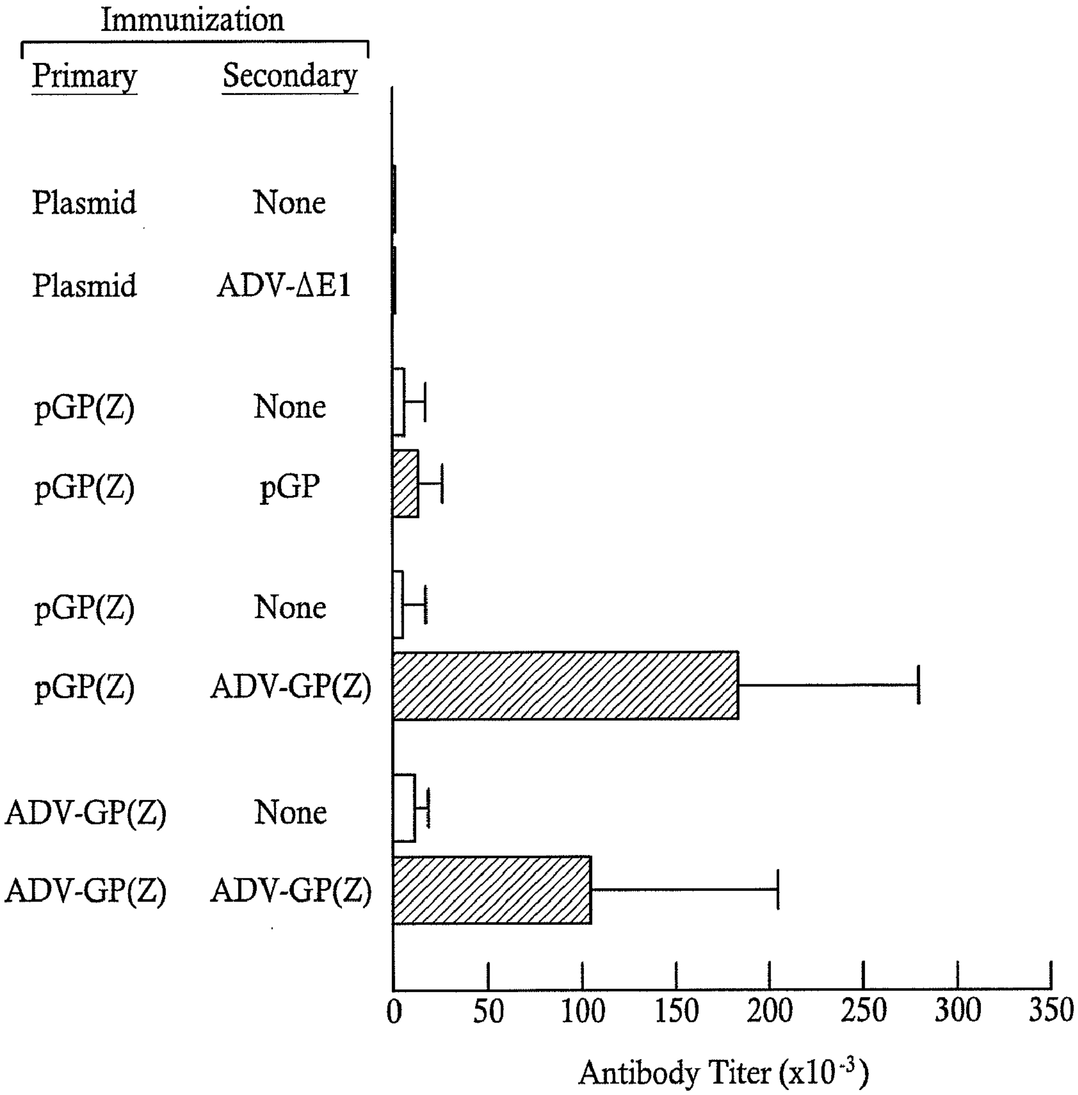
FIG. 47 shows Ebola-specific antibody responses generated by different DNA/adenovirus prime-boost combinations. Data are the means of the reciprocal endpoint dilution for each group of mice and error bars represent the standard deviation.

Because protection in the rodent model of Ebola virus infection correlated with antibody titers, and efficient humoral responses may influence clinical outcome in human disease (Baize, S. et al. 1999 *Nat Med* 5:423-426; Maruyama, T. et al. 1999 *J Virol* 73:6024-6030), we considered it important to elicit a strong humoral response for vaccines tested in primates, although cell-mediated immunity is coordinately induced and likely contributes to protection (Xu, L. et al. 1998 *Nat Med* 4:37-42). Recently, regimens of DNA priming followed by administration of viral vectors have demonstrated enhanced immune responses compared to vaccines using DNA alone (Sedegah, M. et al. 1998 *PNAS USA* 95:7648-7653; Hanke, T. et al. 1998 *Vaccine* 16:439-445; Robinson, H. L. et al. 1999 *Nat Med* 5:526-534; Schneider, J. et al. 1998 *Nat Med* 4:397-402). Recombinant, replication-deficient adenoviruses can be grown to high titer, infect antigen-presenting cells, and induce potent immune responses (Davis, A. R. et al. 1985 *PNAS USA* 82:7560-7564; Natuk, R. J. et al. 1992 *PNAS USA* 89:7777-7781; Xiang, Z. Q. et al. 1996 *Virology* 219: 220-227). Adenoviruses have shown a boosting effect in mice (Xiang, Z. Q. et al. 1999 *J Immunol* 162:6716-6723), but the combination of DNA and adenovirus has not been tested for efficacy in an infectious challenge model, and the success of this approach in primates is yet unknown. We therefore developed a recombinant adenoviral vector that directs high level GP expression ADV-GP(Z) and used this vector to test whether a modified prime-boost strategy would augment the antibody response to Ebola virus obtained with naked DNA alone. Mice were injected with DNA and adenovirus vectors either singly or in combinations, and cell-mediated and humoral immune responses were assessed. A 10- to 100-fold increase in antibody titer was found in mice injected with DNA followed by an adenovirus boost, compared to DNA immunization alone (FIG. 47). An increase in cytotoxic T cell responses was also observed with this combination. Immunization with ADV-GP(Z) alone yielded antibody titers that were not significantly different from those obtained with the DNA prime, adenovirus boost immunization. These data suggest that immunogenicity of the Ebola GP DNA vaccine in mice is improved by boosting with recombinant adenovirus and that this strategy might represent a useful approach to enhance immune responses in non-human primates.

Figure 48:
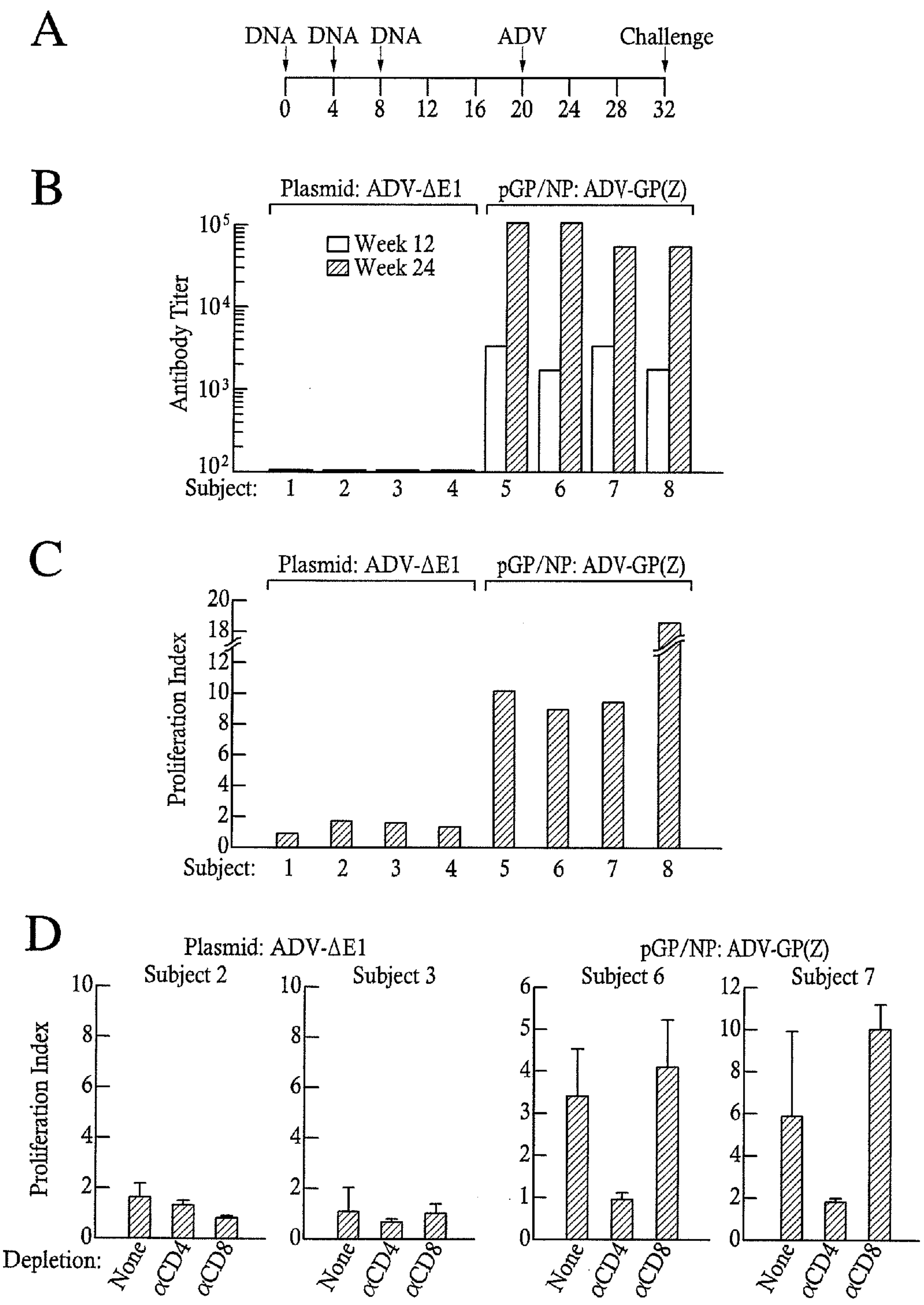
FIG. 48 (A-D) shows DNA-Adenovirus immunization of cynomolgus macaques. A) Immunization schedule for DNA and/or adenovirus injections, and challenge with the wild-type Mayinga strain of the Zaire subtype of Ebola virus. B) Elisa titers of Ebola-specific antibodies in serum. Serum was collected at week 12 (open bar) and 2 days before the immunization at week 24 (closed bar). C) Lymphoproliferative responses to Ebola-secreted glycoprotein (SGP) following immunization. Bars represent the average fold-proliferation of all four blood samples for each subject. The standard deviation is not shown because the baseline level of induction varied between experiments. However, PBMC from all 8 animals were assayed within the same experiment for each time point, and the averages displayed in the figure are representative of the results obtained for any single time point. D) Lymphoproliferative responses to Ebola SGP in bulk PBMC following depletion of lymphocyte subsets. PBMC from week 24 were treated with Dynal magnetic beads coated with the indicated antibody to deplete $CD4^+$ or $CD8^+$ cell subsets. Cells remaining after depletion were normalized for input cell number and stimulated as described in the Example. Results are shown for two control (Subjects 2 and 3) and two vaccinated (Subjects 6 and 7) monkeys.

Whereas the rodent model has been useful in the development of a vaccine strategy, Ebola virus isolated directly from humans must first be adapted by multiple, sequential passage in rodents in order to produce a lethal infection in mice or guinea pigs (Connolly, B. M. et al. 1999 *J Infect Dis* 179: S203-S217; Bray, M. et al. 1998 *J Infect Dis* 178:651-661). Primate models of Ebola infection are thought to have a stronger predictive value for human disease and immune protection. We therefore conducted studies in non-human primates using a bimodal DNA/ADV vaccine and the multiple plasmid strategy that correlated with protection in guinea pigs. Cynomolgus macaques (*Macaca fascicularis*) received 3 injections of naked DNA vectors at 4-week intervals (FIG. 48A) and, after several months of rest which has been shown to boost immune responses (Letvin, N. L. et al. 1997 *PNAS USA* 94:9378-9383), were boosted with recombinant adenovirus expressing only the Zaire glycoprotein (FIG. 48A). Control animals received empty vectors (plasmid DNA and ADV-ΔE1 recombinant adenovirus), and vaccinated animals received the multicomponent DNA vaccine containing NP and three subtypes of Ebola GP (pGP/NP), followed by ADV-GP(Z). As expected, anti-Ebola serum antibodies could not be detected in control animals, but in animals receiving the Ebola vaccine, an antigen-specific antibody response was detected at week 12, one month after the third DNA injection (FIG. 48B). After boosting with recombinant adenovirus, antibody titers increased 10- to 20-fold over the levels obtained with DNA alone. Three months after the final immunization, antibody levels remained high, except for one animal (subject 8) whose titer dropped slightly from $5\times10^4$ to $1.3\times10^4$.

Primate cellular responses to Ebola antigens were next examined with an in vitro lymphocyte proliferation assay. In control monkeys, antigen-specific lymphocyte proliferation, measured by $^3$H-thymidine uptake, was equivalent to that in matched, unstimulated cells, resulting in a proliferation index near 1.0 for each animal (FIG. 48C). In contrast, peripheral blood mononuclear cells (PBMC) from animals immunized with the multivalent vaccine showed 9- to 20-fold increased stimulation, demonstrating a robust immune response to Ebola antigen at the cellular level. Depletion of CD4-positive lymphocytes reduced the antigen-stimulated proliferative response of PBMC from vaccinated monkeys to the level observed in control animals (FIG. 48D). Depletion of CD8-positive lymphocytes, however, did not affect Ebola antigen-specific lymphocyte proliferation. Therefore, the CD4-positive subset of lymphocytes, which provide the T cell help required for high antibody titers, contributes to the vaccine-induced cellular immune response.

Figure 49:
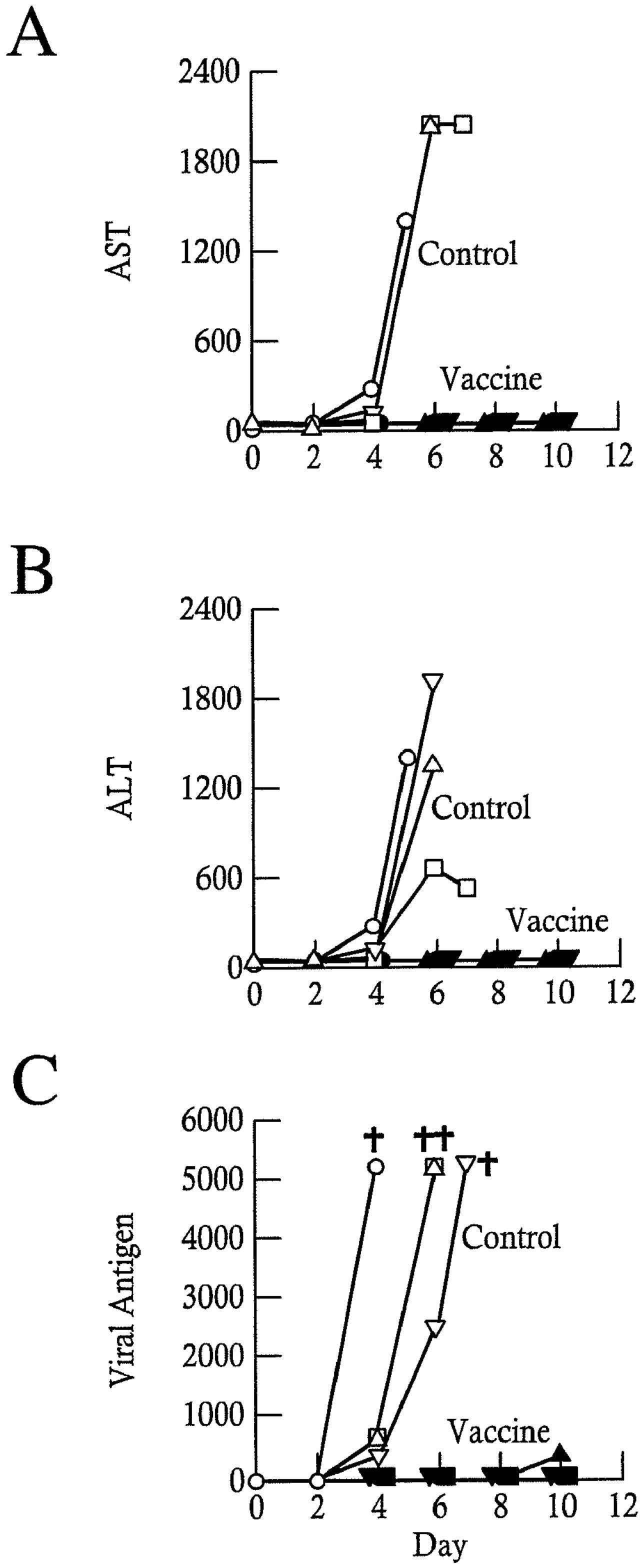
FIG. 49 (A-C) shows protection of cynomolgus macaques against lethal challenge with Ebola virus after DNA-adenovirus immunization. A, B) Hepatic enzyme levels in monkeys after challenge with Ebola virus. Liver enzymes [alanine aminotransferase (ALT) and aspartate aminotransferase (AST)] levels in the non-human primate sera were measured by standard recommended procedures using General chemistry 12 reagent disk for the Piccolo™ Analyzer (Abaxis, Inc., Sunnyvale, CA). Results are shown for four immunized (closed symbols) and four control (open symbols) monkeys. C) Plasma viraemia in monkeys following infection with Ebola virus. Crosses represent time of death in control animals [days 5 (subject 1) and 6 (subjects 2 and 4)]. One control animal, subject 3, was euthanized on day 7 when it was moribund. One vaccinated animal that was resistant to infection, subject 5, was euthanized on day 10 for histological examination of tissues. By day 17, none of the animals had detectable viraemia, and they remained aviraemic for the duration of the observation period (6 months). Data are the reciprocal endpoint dilution of serum for each monkey. Results are shown for four immunized (closed symbols) and four control (open symbols) monkeys.

To determine the protective efficacy of this vaccination regimen, monkeys were challenged with a lethal dose of the wild-type Maying a strain from the Zaire subtype of Ebola virus. In the control monkeys, blood chemistry revealed an increase in hepatic enzymes (FIGS. 49A, B) that is characteristic for Ebola virus infection (Fisher-Hoch, S. P. et al. 1985 *J Infect Dis* 152:887-894). No such increase was observed in vaccinated subjects. The elevation of serum alanine aminotransferase (ALT) and aspartate aminotransferase (AST) was parallel to a dramatic increase in viraemia in all of the control animals (FIG. 49C). In contrast, no substantial increase in viral load was observed in vaccinated monkeys. The kinetics of disease progression was similar among the control animals, and the disease incidence was 100% in this group. Death occurred between days 5 and 6 for 3 animals, and the last monkey, moribund, was euthanized on day 7. In contrast, 4 out of 4 monkeys immunized with the combination DNA-adenovirus vaccine survived this lethal challenge of Ebola virus, and sterilizing immunity was achieved in 3 out of 4 subjects. The remaining animal showed a small transient rise in viral antigen; however, when followed long-term, all vaccinated animals showed no signs or symptoms of infection, and there was no detectable viraemia for more than 6 months after infection, as measured by ELISA detection of viral antigen (FIG. 49A) and end point titration analysis of cultured virus. The vaccine recipient (subject 8) that exhibited a transient low level of viraemia on day 10 returned to undetectable levels by day 17.

As the natural reservoir for Ebola virus is unknown, the potential for traditional public health measures to prevent future outbreaks is limited, thus increasing the urgency for the development of a vaccine and therapeutics in humans. The present findings demonstrate that primates can be immunized against the lethal effects of Ebola virus infection, and that sterilizing immunity can be achieved using a heterologous prime-boost strategy. A multicomponent genetic vaccine expressing Ebola virus structural proteins from diverse geographic isolates generated a strong antigen-specific immune response and resulted in the survival of immunized primates after challenge with a lethal dose of Ebola Zaire, the subtype of this virus associated with the highest number of deaths in human infections. The results of this study suggest that T-cell mediated and humoral immunity contribute to virus clearance in non-human primates, consistent with previous studies in rodents (Xu, L. et al. 1998 *Nat Med* 4:37-42; Wilson, J. et al. 2000 *Science* 287:1664-1666). Two immune parameters, antibody titer (1:75,000 vs. <1:100, P=0.001) and the cellular proliferative response (~12-fold vs. 1.4-fold, P=0.0014), provided highly significant immune correlates of protection. Studies investigating the correlates of immune protection from Ebola virus infection in humans are hampered by the aggressive nature of the virus and necessarily high level of biosafety containment. With the model of primate immunity presented here, it is envisioned as now being possible to elucidate the mechanisms of immune protection from Ebola virus infection, to advance immune-based anti-viral therapies, and to develop a human vaccine for this pathogen and even other infectious causes of hemorrhagic fever.

DESCRIPTIONS OF EBOLA, MARBURG, AND LASSA CONSTRUCTS

VRC 6000 VRC6000 (pVR1012-GP(Z)).

Backbone, pVR1012 (#450) expressing Ebola Glycoprotein of Zaire Subtype. Orientation is BamHI/EcoRI/EcoRV/EcoRI/BglII)

VRC 6001 VRC6001 (pVR1012x/s-GP(Z)) No other description.

This is the same as 6000, with the addition of an Sfi restriction site to the pVR1012 backbone.

VRC 6002 VRC6002 (pVR1012-GP(Z) delta MUC).

The mucin-like domain of GP(Z) was deleted. 530 by in the backbone, pVR1012 GP(Z) were deleted from EarI (2844) to BfaI(3374). This mutant can bind to the Ebola receptor.

VRC 6003 VRC6003 (pVR1012-GP(Z) delta MUC delta FUR).

The mucin-like domain and furin-cleavage site of GP(Z) were deleted. 593 by in the backbone, pVR1012 GP (Z) were deleted, from EarI(2844) to EarI(3437). The protein has properties similar to pVR1012-GP(Z) delta MUC.

VRC 6004 VRC6004 (pVR1012-GP(Z) delta GP2).

A majority of the GP2 region in GP(Z) was deleted. 430 by from the backbone, pVR1012-GP (Z) were deleted from BclI(3414) to BspEI(3844). The TM (transmembrane) region was retained.

VRC 6005 VRC6005 (pVR1012-GP(Z) delta GP2 delta C-term A).

This is a C-terminal deletion of GP2. 267 by were deleted from the pVR1012-GP (Z) backbone, from MscI(3623) to BspMI(3890).

VRC 6006 VRC6006 (pVR1012-GP(Z) delta GP2 delta C-term B).

This is a smaller deletion of GP2 C-terminal. 110 by of backbone pVR1012-GP(Z) were deleted from BstXI (3780) to BspMI(3890).

VRC 6007 VRC6007 (pVR1012-GP(Z) delta GP2 delta FUS).

The fusion peptide in GP2 of GP(Z) was deleted in this mutant, using PCR. 47 by from the backbone, pVR1012-GP(Z), was deleted from (3508-3555).

VRC 6008 VRC6008 (pVR1012-GP(Z) delta TM).

The TM region of GP(Z) was truncated in this mutant. A stop codon (TGA) was added downstream of the BspMI site(3889). This protein is secreted and doesn't form a trimer.

VRC 6052 VRC 6052 (pVR1012-GP(Z) delta sGP).

The majority of the SGP/GP homology region was deleted. 687 by from the backbone, pVR1012-GP(Z), were deleted from HincII(2083) to HincII(2270).

VRC 6101 VRC 6101 (pVR1012x/s Ebola GP(R) (dTM)).

The vector expresses Ebola glycoprotein (subtype Reston) without its transmembrane and intracellular domains. Using PCR, a stop codon was generated downstream of a.a. 650 of GP(R), followed by an XbaI site. This protein can be secreted and is termed GP(R)(dTM).

VRC 6110 VRC 6110 (pAdApt Ebola GP(R) (dTM)).

An adenoviral shuttle vector expressing Ebola virus glycoprotein (Reston subtype) without its transmembrane and intracellular domains. Using PCR, a stop codon was generated downstream of a.a. 651 of GP(Reston), followed by an XbaI site. The resulting recombinant adenovirus expresses a 651a.a. secreted glycoprotein termed GP(R)(dTM).

VRC 6200 VRC6200 (pVR1012-GP(S)).

Backbone, pVR1012(#450), expressing Ebola Glycoprotein of the Sudan Subtype. Orientation is EcoRI/EcoRV/BamHI/BamHI/BamHI/XbaI.

VRC 6201 VRC 6201 (pVR1012x/s Ebola GP(S)).

No other description, but this is the same as 6200 with the addition of an Sfi site to the 1012 backbone.

VRC 6202 VRC6202 (pVR1012-GP(S) delta TM).

The TM region of GP(S) was truncated in this mutant. A stop codon (TGA) was added downstream of the BspMI site(xxx). This protein is secreted and doesn't form a trimer.

VRC 6300 VRC6300 (pVR1012-GP(IC)).

Backbone, pVR1012(#450), expressing Ebola Glycoprotein of the Ivory Coast Subtype. Orientation is EcoRI/EcoRV/BamHI/BamHI/BamHI/XbaI.

VRC 6301 VRC6301 (pVR1012x/s-GP(IC)).

No other description, but this is the same as 6300 with the addition of an Sfi site to the 1012 backbone.

VRC 6302 VRC6302 (pVR1012-GP(IC) delta TM).

The TM region of GP(IC) was truncated in this mutant. A stop codon (TGA) was added downstream of the BspMI site. This protein is secreted and doesn't form a trimer.

VRC 6303 VRC 6303 (pVR1012x/s Ebola GP (IC) (dTM)).

A pVRC2000 based vector expressing Ebola glycoprotein (Ivory Coast subtype) without transmembrane and intracellular domains. Using PCR, a stop codon was generated downstream of a.a. 650, followed by a BglII site. The vector expresses a 650 a.a. secreted glycoprotein (a.a. 1-a.a. 650).

VRC 6310 VRC 6310 (pAdApt Ebola GP (IC) (dTM)).

An adenoviral shuttle vector expressing Ebola glycoprotein (subtype Ivory Coast) without its transmembrane and intracellular domains. Using PCR, a stop codon was generated downstream of a.a. 651 of GP(IC). The resulting recombinant adenovirus expresses a 651a.a secreted glycoprotein termed as GP(IC)(dTM).

VRC 6351 VRC6351 (pVR1012x/s-sGP(IC)). No other description.

VRC 6400 VRC6400 (pVR1012-NP).

Backbone, pVR1012(#450) expressing Ebola Nucleoprotein of the Ivory Coast Subtype.

VRC 6401 VRC6401 (pVR1012x/s-NP).

No other description, but this is the same as 6400 with the addition of an Sfi site to the 1012 backbone.

VRC 6500 VRC6500 (pVR1012-VP35).

The backbone is pVR1012(#450). The insert is VP35 from Ebola cloned from pGEM 3Zf(+)VP35(#1213).

VRC 6600 VRC6600 (pAD/CMV-GP(dTM)(Z-CITE-S). No other description.

VRC 6601 VRC6601 (pAdApt Ebola GP(S)). No other description.

VRC 6602 VRC 6602 (pAdApt Ebola GP(S)(dTM)).

An adenoviral shuttle vector expressing Ebola glycoprotein (Sudan subtype) without its transmembrane and intracellular domains. A stop codon was fused downstream of a.a. 650 of GP(S). The resulting recombinant adenovirus expresses a 654 a.a. secreted glycoprotein, termed as GP(S)(dTM).

VRC 6603 VRC6603 (pAdApt Ebola GP(Z)). No other description.

VRC 6604 VRC 6604 (pAdApt Ebola GP(Z)(dTM)).

Adenoviral shuttle vector expressing Ebola glycoprotein (subtype Zaire) without its transmembrane and intracellular domains. A stop codon was fused downstream of a.a. 651 of GP(Z). The resulting recombinant adenovirus expresses a 655 a.a. secreted glycoprotein termed as GP(Z)(dTM).

VRC 6701 VRC6701 (pVR1012-Marburg).

Marburg glycoprotein (GP) open reading frame, Musoke strain. Marburg was cloned into backbone #450(Bam (blunt)/XbaI) from VRC6700 (Xba/PvuII).

VRC 6702 VRC 6702 (pVR1012x/s Marburg GP (dTM)).

This vector expresses the Marburg virus glycoprotein without its transmembrane and intracellular domains. Using PCR, a stop codon was generated downstream of a.a. 650 of GP(Marburg), followed by a BglII site. This protein can be secreted and termed as GP(Marburg) (dTM).

VRC 6710 VRC 6710 (pAdApt Marburg GP (dTM)).

Adenoviral shuttle vector (pVRC1290) expressing Marburg virus glycoprotein without transmembrane and intracellular domains. Using PCR, a terminator codon was generated downstream of a.a. 650, followed by a BglII site. The resulting recombinant adenovirus expresses a 650 a.a. secreted protein (a.a. 1-a.a. 650).

VRC 6800 VRC6800 (pVR1012x/s Lassa GP). No other description.

VRC 6801 VRC6801 (pVR1012x/s Lassa GP (dTM). No other description.

VRC 6810 VRC6810 (pAdApt Lassa GP). No other description.

VRC 6811 VRC6811 (pAdApt Lassa GP (dTM)). No other description.

EXAMPLE 1

Vector construction. The construction of DNA vectors expressing Ebola Zaire glycoprotein (GP), secreted GP (SGP), and nucleoprotein (NP) has been described in Xu, L. et al. 1998 *Nat Med* 4:37-42. The GP Sudan and Ivory Coast expression vectors were constructed similarly. Briefly, GP open reading frames were generated from polymerase chain reaction after reverse transcription of RNA (RT-PCR) products of infected cell RNA using the following primers: 5' ATC TTC AGG ATC TCG CCA TGG A 3' (Sudan GP gene; NcoI>ATG; SEQ ID NO: 44), 5' GAT ATT CAA CAA AGC AGC TTG CAG 3' (Sudan GP gene; C-terminus GP stop; SEQ ID NO: 45), 5' CTA ATC ACA GTC ACC ATG GGA 3' (Ivory Coast GP gene; NcoI>ATG; SEQ ID NO: 46), 5' AAA GTA TGA TGC TAT ATT AGT TCA 3' (Ivory Coast GP gene; C-terminus GP stop; SEQ ID NO: 47) yielding the TA clones PCR2.1 Sudan and PCR2.1 Ivory Coast. The Sudan glycoprotein was digested from plasmid PCR2.1 with XbaI/HindIII, Klenow treated, and cloned into the XbaI site of p1012 (Xu, L. et al. 1998 *Nat Med* 4:37-42). Ivory Coast GP was digested from plasmid PCR2.1 with EcoRI, Klenow treated, and cloned into the XbaI site of p1012 (Xu, L. et al. 1998 *Nat Med* 4:37-42).

To make ADV-GP, the BamHI/EcoRI fragment of GP(Z) was digested from pGEM-3Zf(−)-GP, treated with Klenow, and inserted into HindIII/XbaI/Kle/CIP treated pRc/CMV plasmid. The resulting plasmid (PRC/CMV-GP(Z)) was digested by NruI/DraIII and treated with Klenow. The NruI/DraIII/Kle fragment containing the CMV enhancer, GP(Z) DNA and bovine growth hormone polyadenylation signal was inserted into the BgtII site of the adenoviral shuttle plasmid pAdBgIII (Ohno, T. et al. 1994 Science 265:781-784). The adenovirus, a first generation dl 309-based Ad5 vector, contained a deletion in E1 to render the vector replication-defective and a partial deletion/substitution in E3, which disrupts the coding sequences for the E3 proteins with a relative molecular mass of 14.7 kD, 14.5 kD and 10.4 kD, respectively. The recombinant adenovirus expressing Zaire GP, ADV-GP(Z), was made according to previously published methods (Aoki, K. et al. 1999 *Mol Med* 5:224-231). The dose of adenovirus administered, $10^{10}$ plaque-forming units (PFU) per animal (approximately $3\times10^{9}$ PFU/kg), is within the range used safely in human gene therapy trials.

Animal study and safety. Eight cynomolgus macaques (*Macaca fascicularis*), 3 years of age and weighing 2-3 kg, obtained from Covance (Princeton, N.J.), were used for the immunization and challenge experiment. To obtain blood specimens and administer vaccines, the monkeys were anesthetized with Ketamine. The animals were housed singly and received regular enrichment according to the Guide for the Care and Use of Laboratory Animals (DHEW No. NIH 86-23). Just before the Ebola virus challenge and up to the end of the experiment, the animals were maintained in the Maximum Containment Laboratory (BSL-4) and fed and checked daily. One animal was euthanized that appeared moribund and was subsequently necropsied for pathologic examination. In addition, a single asymptomatic vaccinated animal was euthanized for pathologic and virologic analysis.

Mouse immunization. DNA and adenovirus vectors expressing Ebola Zaire GP or NP were constructed as described previously (Xu, L. et al. 1998 *Nat Med* 4:37-42; Ohno, T. et al. 1994 *Science* 265:781-784), with gene expression under the control of the cytomegalovirus enhancer and promoter. Mice were immunized intramuscularly with 100 μg of DNA (pGP or a p1012 plasmid control) or $10^{8}$ PFU of adenovirus (ADV-GP or ADV-ΔE1 control virus) on days 0, 14, and 28 and blood was collected on day 28. On day 42, mice received an intramuscular boost with DNA or adenovirus and titers were re-measured on day 56. ELISA IgG titers were determined using 96-well plates coated with a preparation of Ebola virus antigen derived from purified virions and enriched for membrane-associated proteins (GP, VP40 and VP24) (Ksiazek, T. G. et al. 1992 *J Clin Microbiol* 30:947-950). Specific antigen binding was detected using a goat anti-human IgG(H+L)-horseradish peroxidase conjugate and ABTS/Peroxide (substrate/indicator).

Macaque immunization. For the DNA immunizations, animals received 1 mg each of DNA expressing GP(Zaire) [GP (Z)], GP(Ivory Coast) [pGP(IC)], GP(Sudan) [pGP(S)] and NP(Zaire) administered as a mixture [pGP/NP], or 4 mg empty [pGP(Z)] control plasmid bilaterally (2 mg per side) in the deltoid muscle. Immunization at weeks 0 and 4 were by IM injection, and at week 8 by Biojector. For the adenovirus boost, animals received $10^{10}$ PFU of ADV-GP (Zaire subtype) or ADV-ΔE1 (empty vector) divided into two doses administered bilaterally in the deltoid muscle. At week 32, all animals received an intraperitoneal injection of approximately 6 PFUs of Ebola virus (Zaire 1976 isolate; Maying a strain) (Kiley, M. P. et al. 1980 *J Gen Virol* 49:333-341) in 1 ml Hanks' buffered salt solution. The virus was isolated directly from patient blood and used after a single passage in Vero cells.

ELISA IgG titers were determined as above for control (Plasmid: ADV-ΔE1) and immunized [pGP/NP: ADV-GP (Z)] monkeys. The reciprocal endpoint of dilution for each subject was at week 12 and week 24. Serum antibody levels were measured by ELISA as described (Ksiazek, T. G. et al. 1992 *J Clin Microbiol* 30:947-950).

Blood was collected from control (plasmid: ADV-ΔE1) or immunized [pGP/NP: ADV-GP(Z)] animals 1-3 days prior to the immunizations at weeks 4, 8 and 20, and at week 24. Blood was separated over a Percoll gradient to obtain the lymphocyte enriched population. Lymphocytes were stimulated as described (Xu, L. et al. 1998 *Nat Med* 4:37-42) for 5 days in vitro using supernatant from cells transfected with either Ebola secreted glycoprotein (SGP) or empty plasmid, and proliferation was measured by $^{3}$H-thymidine uptake. The proliferation index was calculated as the proliferation in wells receiving SGP divided by proliferation in wells receiving control supernatant.

Viral detection in macaques. The presence of circulating Ebola virus antigen was detected as described (Ksiazek, T. G. et al. 1992 *J Clin Microbiol* 30:947-950) by capturing VP40 protein from serial dilutions of monkey plasma. 96-well plates coated with antiVP40 mAb were used to capture antigen, and detection was with a rabbit anti-Ebola virus serum.

EXAMPLE 2

The amino acid sequences of Ebola GP(Zaire) and NP (Zaire) were obtained from Genbank: GP(Zaire), Genbank accession no. P87666; NP(Zaire), Genbank accession no. NC_002549; while GP(Sudan/Gulu) was obtained from the CDC. The amino acid sequences were then back-translated to DNA sequences using mammalian preferred codons. Serial 75 by oligos with 25 by overlapping were prepared to cover the entire gene. The oligos were then assembled into intact mammalian genes containing preferred codons using PCR. In the design, a stop codon was introduced in front of the predicted transmembrane domains of GP(Zaire) (a.a. 648-676) and GP (Sudan/Gulu) (a.a. 648-676) so that this region was excluded from these synthetically created genes. The deletions also led to the loss of a 4 a.a. cytoplasmic region in both constructs. Final sequencing of the Ebola GP (Zaire) sequence revealed 10 divergent amino acids from the laboratory GP sequence, which was used in our animal studies and these were corrected by site-directed mutagenesis. These inserts were cloned into p1012 x/s by XbaI/SalI.

Construction of CMV/R-GP(S/G)(ΔTM)/h

The codon-modified, transmembrane domain deleted form of the Ebola GP (Sudan/Gulu) gene was excised from p1012 (x/s)-GP(S/G)(ΔTM)/h using SalI/KpnI, and inserted into the SalI/KpnI digested CMV/R/MCS plasmid.

Construction of CMV/R GP(Z) (ΔTM)/h

The codon-modified, transmembrane domain deleted form of the Ebola GP (Zaire) gene was excised from p1012 x/s-GP (Z)(dTM)/h SalI/BglII sites and cloned into the SalI/BglII sites of the CMV/R plasmid.

Construction of CMV/R Ebola NP

The NotI-KpnI fragment from VRC6400 (pVR1012-NP) expressing Ebola nucleoprotein of Zaire Subtype was excised and cloned into the NotI/KpnI sites of the CMV/R plasmid.

EXAMPLE 3

Improved Non-Viral Mammalian Expression Vector

This invention provides an improved mammalian expression vector which generates a higher level of protein expression than vectors currently in use.

Initially, 3 new vectors, each containing a different enhancer, were developed and tested. The RSV enhancer, the mouse ubiquitin enhancer (mUBB), and the CMV enhancer (Xu et al. 1998 *Nature Med.* 4:37-42) were each combined with the HTLV-1 R region (Takebe et al. 1988 *Mol Cell Biol* 8:466-472) to create separate vectors. When these 3 vectors were compared to the backbone containing the CMV enhancer in combination with the CMV translational enhancer and intron (CMVint), which is currently the most effective vector, in vitro data showed that expression with the vector containing the CMV/R was increased 5-10 fold compared to CMV/int, and immunological studies showed induction of significantly higher CD4 and CD8 T cell responses compared to CMVint. Both in vivo and in vitro responses were markedly higher with this new vector. Neither of the other two vectors produced comparable results.

The expression vector is unique in that it uses a specific translational enhancer in combination with specific enhancer/promoters to yield high levels of expression and enhanced immunogenicity for DNA vaccines. This is particularly important because the potency of these vaccines in humans is marginal and generic improvements can serve as important platforms to make the technology practical for human use. The expression vector cassettes can be used in other gene based vaccines as well, or for production of recombinant proteins from eukaryotic expression vectors. The invention is useful in the production of genetic vaccines and gene therapies for a wide variety of diseases, including HIV and other viral diseases and cancer.

FIG. 50. Enhanced Expression of Modified CMV Expression Vector, CMV/R.

Mouse fibroblast 3T3 cells were transfected with (A) vector alone (lane 1), CMVint-gp-145(dCFI) (lane 2), CMV/R-gp145(dCFI) (lane 3) or (B) mUBB-gp145(dCFI) (lane 4), mUBB/R-gp145(dCFI) (lane 5) in 6-well tissue culture dishes with 0.5 ug of the corresponding plasmids using calcium phosphate. 24 hours after transfection, cells were harvested and lysed in lysis buffer (50 mM HEPES, 150 mM NaCl, 1% NP-40, Mini Complete protease inhibitor cocktail (Roche)). 10 μg of total protein of each sample were separated on a 4-15% gradient gel using SDS-PAGE, followed by protein transfer and Western blot analysis. Human HIV-IgG (1:5000) was used as the primary antibody, and HRP-conjugated goat anti-human IgG (1:5000) as the secondary antibody. The membrane was developed using the ECL Western blot developing system. The arrow indicates the specific band for the HIV Env gp145(ΔCFI) polyprotein.

Figure 51:
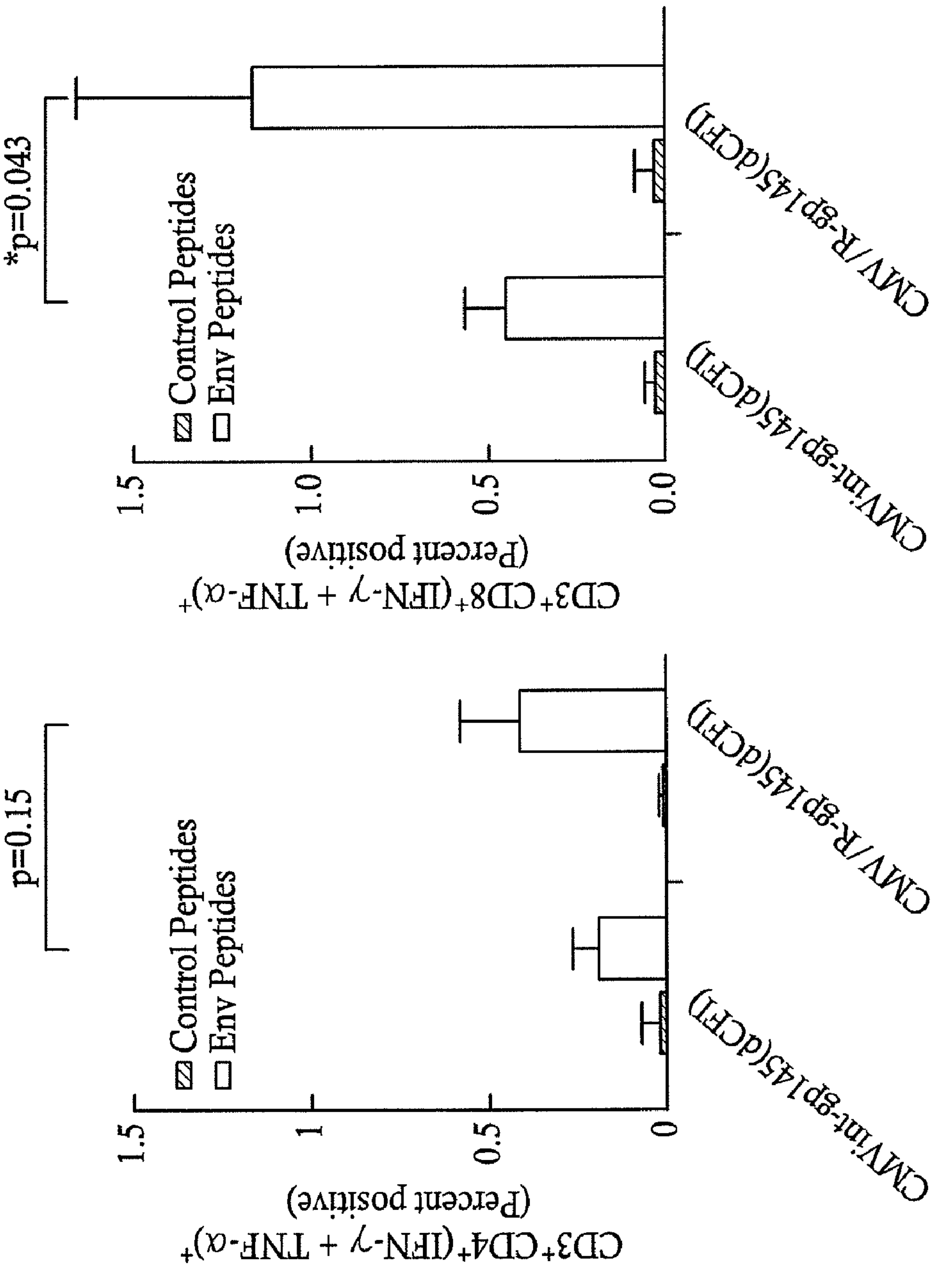
FIG. 51 shows enhanced immunogenicity of modified CMV expression vector, CMV/R, in mice.

FIG. 51. Enhanced immunogenicity of modified CMV expression vector, CMV/R, in Mice.

Five mice in each group were immunized with 50 μg of the indicated plasmid DNA at weeks 0, 2, and 6. 10 days after the last injection, splenocytes from each mouse were harvested and stimulated using a pool of control peptides (15 mer), or a pool of HIV Env peptides (15 mer) for 6 hours. The stimulated splenocytes were stained using a cocktail of antibodies containing PE-anti-mouse CD3, PerCP-anti-mouse CD4, APC-anti-mouse CD8, FITC-anti-mouse IFN-γ and FITC-anti-mouse TNF-α. The samples were analyzed by flow cytometry. CD3/CD4/IFN-γ/TNF-α and CD3/CD8/IFN-γ/TNF-α positive cell numbers were measured using FloJo software (Treestar).

The CMV Enhancer/Promoter, R Region (HTVL-1), CMV IE Splicing Acceptor sequence

```
(SEQ ID NO: 52):
CCATTGCATACGTTGTATCCATATCATAATATGTACATTTATATTGGC

TCATGTCCAACATTACCGCCATGTTGACATTGATTATTGACTAGTTAT

TAATAGTAATCAATTACGGGGTCATTAGTTCATAGCCCATATATGGAG

TTCCGCGTTACATAACTTACGGTAAATGGCCCGCCTGGCTGACCGCCC

AACGACCCCCGCCCATTGACGTCAATAATGACGTATGTTCCCATAGTA

ACGCCAATAGGGACTTTCCATTGACGTCAATGGGTGGAGTATTTACGG

TAAACTGCCCACTTGGCAGTACATCAAGTGTATCATATGCCAAGTACG

CCCCCTATTGACGTCAATGACGGTAAATGGCCCGCCTGGCATTATGCC

CAGTACATGACCTTATGGGACTTTCCTACTTGGCAGTACATCTACGTA

TTAGTCATCGCTATTACCATGGTGATGCGGTTTTGGCAGTACATCAAT

GGGCGTGGATAGCGGTTTGACTCACGGGGATTTCCAAGTCTCCACCCC

ATTGACGTCAATGGGAGTTTGTTTTGGCACCAAAATCAACGGGACTTT

CCAAAATGTCGTAACAACTCCGCCCCATTGACGCAAATGGGCGGTAGG

CGTGTACGGTGGGAGGTCTATATAAGCAGAGCTCGTTTAGTGAACCGT

CAGATCGCCTGGAGACGCCATCCACGCTGTTTTGACCTCCATAGAAGA

CACCGGGACCGATCCAGCCTCCATCGGCTCGCATCTCTCCTTCACGCG
```

-continued

CCCGCCGCCTTACCTGAGGCCGCCATCCACGCCGGTTGAGTCGCGTTC

TGCCGCCTCCCGCCTGTGGTGCCTCCTGAACTACGTCCGCCGTCTAGG

TAAGTTTAGAGCTCAGGTCGAGACCGGGCCTTTGTCCGGCGCTCCCTT

GGAGCCTACCTAGACTCAGCCGGCTCTCCACGCTTTGCCTGACCCTGC

TTGCTCAACTCTAGTTAACGGTGGAGGGCAGTGTAGTCTGAGCAGTAC

TCGTTGCTGCCGCGCGCGCCACCAGACATAATAGCTGACAGACTAACA

GACTGTTCCTTTCCATGGGTCTTTTCTGCAG 1-741: CMV Enhancer/Promoter

-continued 742-972: HTLV-1 R region 973-1095: CMV/IE Splicing Acceptor

* * * * *

While the present invention has been described in some detail for purposes of clarity and understanding, one skilled in the art will appreciate that various changes in form and detail can be made without departing from the true scope of the invention. All figures, tables, and appendices, as well as patents, applications and publications referred to above are hereby incorporated by reference.

What is claimed is:

1. A vaccine comprising an adenoviral vector comprising a sequence encoding Ebola Sudan glycoprotein being at least 95% identical to Ebola Sudan glycoprotein that is encoded in the construct VRC6601 (SEQ ID NO:26).

2. The vaccine of claim 1, wherein the sequence encoding Ebola Sudan glycoprotein is the sequence as present in the construct VRC6601 (SEQ ID NO:26).

3. A composition for boosting an immune response to a viral antigen in an individual, comprising an adenoviral vector comprising a sequence encoding Ebola Sudan glycoprotein being at least 95% identical to Ebola Sudan glycoprotein that is encoded in the construct VRC6601 (SEQ ID NO:26).

4. The composition of claim 3, wherein the sequence encoding Ebola Sudan glycoprotein is the sequence as present in the construct VRC6601 (SEQ ID NO:26).

5. A method for boosting an immune response to a viral antigen in an individual, comprising administering to the individual a composition comprising an adenoviral vector comprising a sequence encoding Ebola Sudan glycoprotein being at least 95% identical to Ebola Sudan glycoprotein that is encoded in the construct VRC6601 (SEQ ID NO:26).

6. The method of claim 5, wherein the sequence encoding Ebola Sudan glycoprotein is the sequence as present in the construct VRC6601 (SEQ ID NO:26).

7. The method of claim 5, wherein the viral antigen is an Ebola virus antigen.

8. The method of claim 5, wherein the administering is performed by injection.

9. The method of claim 8, wherein the administering is performed at a dose of $5\times10^7$ to $1\times10^{12}$ particles per injection.

* * * * *